United States Patent
Simons et al.

(10) Patent No.: US 12,365,726 B2
(45) Date of Patent: Jul. 22, 2025

(54) ANTI-VEGF ANTIBODY CONSTRUCTS

(71) Applicant: Akouos, Inc., Boston, MA (US)

(72) Inventors: Emmanuel John Simons, Brookline, MA (US); Robert Ng, Newton, MA (US); Michael McKenna, Boston, MA (US)

(73) Assignee: Akouos, Inc., Boston, MA (US)

( * ) Notice: Subject to any disclaimer, the term of this patent is extended or adjusted under 35 U.S.C. 154(b) by 0 days.

(21) Appl. No.: 18/134,095

(22) Filed: Apr. 13, 2023

(65) Prior Publication Data

US 2023/0295287 A1    Sep. 21, 2023

Related U.S. Application Data

(63) Continuation of application No. PCT/US2021/061205, filed on Nov. 30, 2021.

(60) Provisional application No. 63/152,832, filed on Feb. 23, 2021, provisional application No. 63/120,189, filed on Dec. 1, 2020.

(51) Int. Cl.
| | |
|---|---|
| C12N 15/86 | (2006.01) |
| A61K 48/00 | (2006.01) |
| A61P 27/16 | (2006.01) |
| C07K 14/005 | (2006.01) |
| C07K 14/55 | (2006.01) |
| C07K 16/22 | (2006.01) |

(52) U.S. Cl.
CPC .......... *C07K 16/22* (2013.01); *A61K 48/0066* (2013.01); *A61P 27/16* (2018.01); *C07K 14/005* (2013.01); *C07K 14/55* (2013.01); *C12N 15/86* (2013.01); *C07K 2317/24* (2013.01); *C07K 2317/55* (2013.01); *C07K 2317/76* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | |
|---|---|---|
| 4,797,368 A | 1/1989 | Carter et al. |
| 4,816,567 A | 3/1989 | Cabilly et al. |
| 5,122,458 A | 6/1992 | Post et al. |
| 5,139,941 A | 8/1992 | Muzyczka et al. |
| 5,168,062 A | 12/1992 | Stinski |
| 5,478,745 A | 12/1995 | Samulski et al. |
| 5,741,683 A | 4/1998 | Zhou et al. |
| 5,952,221 A | 9/1999 | Kurtzman et al. |
| 6,001,650 A | 12/1999 | Colosi |
| 6,054,297 A | 4/2000 | Carter et al. |
| 6,057,152 A | 5/2000 | Samulski et al. |
| 6,156,303 A | 12/2000 | Russell et al. |
| 6,204,059 B1 | 3/2001 | Samulski et al. |
| 6,268,213 B1 | 7/2001 | Samulski et al. |
| 6,407,213 B1 | 6/2002 | Carter et al. |
| 6,491,907 B1 | 12/2002 | Rabinowitz et al. |
| 6,660,514 B1 | 12/2003 | Zolotukhin et al. |
| 6,884,879 B1 | 4/2005 | Baca et al. |
| 6,951,753 B2 | 10/2005 | Shenk et al. |
| 7,060,269 B1 | 6/2006 | Baca et al. |
| 7,094,604 B2 | 8/2006 | Snyder et al. |
| 7,169,901 B2 | 1/2007 | Baca et al. |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,297,334 B2 | 11/2007 | Baca et al. |
| 7,365,166 B2 | 4/2008 | Baca et al. |
| 7,439,065 B2 | 10/2008 | Ferrari et al. |
| 7,485,291 B2 | 2/2009 | Fang et al. |
| 7,498,024 B2 | 3/2009 | Fang et al. |
| 7,588,772 B2 | 9/2009 | Kay et al. |
| 7,612,181 B2 | 11/2009 | Wu et al. |
| 7,662,623 B2 | 2/2010 | Fang et al. |
| 7,709,224 B2 | 5/2010 | Fang et al. |
| 7,714,119 B2 | 5/2010 | Fang et al. |
| 7,790,449 B2 | 9/2010 | Gao et al. |
| 8,258,268 B2 | 9/2012 | Wu et al. |
| 8,513,390 B2 | 8/2013 | Stagliano et al. |
| 8,586,714 B2 | 11/2013 | Ghayur et al. |

(Continued)

FOREIGN PATENT DOCUMENTS

| | | |
|---|---|---|
| CN | 102219859 A | 10/2011 |
| CN | 103143017 A | 6/2013 |

(Continued)

OTHER PUBLICATIONS

Landegger et al Nature Biotechnoloby, 35(3), 280-284 (Year: 2017).*
Wu et al Journal of Molecular Biology, 294, 151-162, (Year: 1999).*
Maccallum et al (Journal of Molecular Biology, 262, pp. 732-745 (Year: 1996).*
Skolnick et al Trends in Biotechnology vol. 18, pp. 34-39 (Year: 2000).*

(Continued)

*Primary Examiner* — Anoop K Singh
(74) *Attorney, Agent, or Firm* — Choate, Hall & Stewart LLP; Stephanie L. Schonewald

(57) ABSTRACT

The present disclosure provides a construct comprising a coding sequence operably linked to a promoter, wherein the coding sequence encodes a vascular endothelial growth factor (VEGF) binding agent or a portion thereof. In some embodiments, a construct is an AAV construct. In some embodiments, an AAV construct is a part of an AAV particle. Compositions comprising constructs and AAV particles described herein can be useful in treating hearing loss, for example, hearing loss associated with vestibular schwannoma.

14 Claims, 38 Drawing Sheets
Specification includes a Sequence Listing.

(56) References Cited

U.S. PATENT DOCUMENTS

| | | |
|---|---|---|
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,822,645 B2 | 9/2014 | Ghayur et al. |
| 8,962,804 B2 | 2/2015 | Williams et al. |
| 9,079,953 B2 | 7/2015 | Harding et al. |
| 9,453,241 B2 | 9/2016 | Pan |
| 9,522,949 B2 | 12/2016 | Fang et al. |
| 10,179,925 B2 | 1/2019 | Laird et al. |
| 10,647,758 B2 | 5/2020 | Wilson et al. |
| 10,799,566 B2 | 10/2020 | High et al. |
| 11,197,937 B2 | 12/2021 | Tretiakova et al. |
| 11,697,801 B2 | 7/2023 | Simons et al. |
| 11,766,489 B2 | 9/2023 | Kirn et al. |
| 12,077,783 B2 | 9/2024 | Simons et al. |
| 12,084,503 B2 | 9/2024 | Gastwirt et al. |
| 12,122,844 B2 | 10/2024 | Crystal et al. |
| 12,275,960 B2 | 4/2025 | Simons et al. |
| 2001/0034062 A1 | 10/2001 | Koenig |
| 2006/0018882 A1 | 1/2006 | Kaemmerer et al. |
| 2006/0040354 A1 | 2/2006 | O'Keefe |
| 2006/0110364 A1 | 5/2006 | Harding |
| 2006/0177819 A1 | 8/2006 | Smith et al. |
| 2007/0141029 A1 | 6/2007 | Brough |
| 2009/0215178 A1 | 8/2009 | Tang |
| 2009/0305344 A1 | 12/2009 | Polo et al. |
| 2010/0317096 A1 | 12/2010 | Fang et al. |
| 2010/0322931 A1 | 12/2010 | Harding et al. |
| 2011/0052576 A1 | 3/2011 | Ferrara et al. |
| 2011/0065779 A1 | 3/2011 | Fang et al. |
| 2013/0078260 A1 | 3/2013 | Cheeseman et al. |
| 2013/0090375 A1 | 4/2013 | Crystal et al. |
| 2015/0050243 A1 | 2/2015 | Kaczmarczyk et al. |
| 2015/0147317 A1 | 5/2015 | Robblee et al. |
| 2015/0182638 A1 | 7/2015 | Crystal et al. |
| 2015/0210771 A1 | 7/2015 | Crystal et al. |
| 2016/0024483 A1 | 1/2016 | Kim et al. |
| 2016/0243229 A1 | 8/2016 | Crystal et al. |
| 2016/0289314 A1 | 10/2016 | Shandilya et al. |
| 2017/0321214 A1 | 11/2017 | Zhang et al. |
| 2018/0311319 A1 | 11/2018 | Constable et al. |
| 2018/0369414 A1 | 12/2018 | Stankovic et al. |
| 2019/0060328 A1 | 2/2019 | Ibañez et al. |
| 2019/0060425 A1 | 2/2019 | Scheel et al. |
| 2019/0127455 A1 | 5/2019 | Simpson et al. |
| 2019/0211091 A1 | 7/2019 | Simpson et al. |
| 2019/0381194 A1 | 12/2019 | Tretiakova et al. |
| 2020/0277364 A1 | 9/2020 | Yoo et al. |
| 2020/0282077 A1 | 9/2020 | Kirn et al. |
| 2021/0071149 A1 | 3/2021 | Simons et al. |
| 2021/0171656 A1 | 6/2021 | Crystal et al. |
| 2021/0363499 A1 | 11/2021 | Simons et al. |
| 2022/0143221 A1 | 5/2022 | Danos et al. |
| 2022/0195462 A1 | 6/2022 | Danos et al. |
| 2022/0267739 A1* | 8/2022 | Simons ............... A61K 9/08 |
| 2022/0280608 A1 | 9/2022 | Pakola et al. |
| 2022/0288236 A1 | 9/2022 | Burns et al. |
| 2022/0288238 A1 | 9/2022 | Tretiakova et al. |
| 2023/0057380 A1 | 2/2023 | Gao et al. |
| 2023/0057519 A1 | 2/2023 | Simpson et al. |
| 2023/0075045 A1 | 3/2023 | Wang et al. |
| 2023/0295243 A1 | 9/2023 | Shi et al. |
| 2023/0372538 A1 | 11/2023 | Bee et al. |
| 2023/0414788 A1 | 12/2023 | Bee et al. |
| 2024/0024508 A1 | 1/2024 | Bee et al. |
| 2024/0101970 A1 | 3/2024 | Simons et al. |
| 2024/0335560 A1 | 10/2024 | Kirn et al. |
| 2024/0343791 A1 | 10/2024 | Dong et al. |
| 2025/0136673 A1 | 5/2025 | Simons et al. |

FOREIGN PATENT DOCUMENTS

| | | |
|---|---|---|
| CN | 103492574 A | 1/2014 |
| CN | 104994882 A | 10/2015 |
| CN | 106414487 A | 2/2017 |
| CN | 107074969 A | 8/2017 |
| EP | 2101807 B1 | 5/2016 |
| JP | 2017-510297 A | 4/2017 |
| WO | WO-92/022653 A1 | 12/1992 |
| WO | WO-96/037234 A1 | 11/1996 |
| WO | WO-9709442 A1 * | 3/1997 ............. A61K 48/00 |
| WO | WO-98/10088 A1 | 3/1998 |
| WO | WO-98/45331 A2 | 10/1998 |
| WO | WO-00/028004 A1 | 5/2000 |
| WO | WO-01/059142 A1 | 8/2001 |
| WO | WO-2003/042397 A2 | 5/2003 |
| WO | WO-2004/113493 A2 | 12/2004 |
| WO | WO-2005/017149 A1 | 2/2005 |
| WO | WO-2005/033321 A2 | 4/2005 |
| WO | WO-05/073384 A2 | 8/2005 |
| WO | WO-06/12414 A2 | 2/2006 |
| WO | WO-2006/017325 A2 | 2/2006 |
| WO | WO-2006/110689 A2 | 10/2006 |
| WO | WO-2008/077077 A2 | 6/2008 |
| WO | WO-2011/104307 A2 | 9/2011 |
| WO | WO-2012/115980 A1 | 8/2012 |
| WO | WO-2013/173129 A2 | 11/2013 |
| WO | WO-2014/043480 A1 | 3/2014 |
| WO | WO-2014/178078 A2 | 11/2014 |
| WO | WO-2015054653 A2 * | 4/2015 ............. A61K 39/00 |
| WO | WO-2015/123715 A1 | 8/2015 |
| WO | WO-2015/138616 A1 | 9/2015 |
| WO | WO-2015/142963 A1 | 9/2015 |
| WO | WO-2016/040441 A1 | 3/2016 |
| WO | WO-2017/040528 A1 | 3/2017 |
| WO | WO-2017/050825 A1 | 3/2017 |
| WO | WO-2017/075119 A1 | 5/2017 |
| WO | WO-2017/100791 A1 | 6/2017 |
| WO | WO-2017/117464 A1 | 7/2017 |
| WO | WO-2017/147265 A1 | 8/2017 |
| WO | WO-2017/180936 A1 | 10/2017 |
| WO | WO-2017/181021 A1 | 10/2017 |
| WO | WO-2017/218974 A2 | 12/2017 |
| WO | WO-2017/218981 A2 | 12/2017 |
| WO | WO-2019/067540 A1 | 4/2019 |
| WO | WO-2019/079496 A2 | 4/2019 |
| WO | WO-2019/104279 A1 | 5/2019 |
| WO | WO-2019/116349 A1 | 6/2019 |
| WO | WO-2019126329 A1 * | 6/2019 ......... A61K 39/3955 |
| WO | WO-2019/164854 A1 | 8/2019 |
| WO | WO-2020097372 A1 * | 5/2020 ......... A61K 48/0075 |
| WO | WO-2020/206098 A1 | 10/2020 |
| WO | WO-2020/219868 A1 | 10/2020 |
| WO | WO-2021/046245 A1 | 3/2021 |
| WO | WO-2021/071835 A1 | 4/2021 |
| WO | WO-2021/076794 A1 | 4/2021 |
| WO | WO-2021/108530 A1 | 6/2021 |
| WO | WO-2021/231808 A2 | 11/2021 |
| WO | WO-2021/255589 A1 | 12/2021 |
| WO | WO-2021/255590 A1 | 12/2021 |
| WO | WO-2022/018516 A1 | 1/2022 |
| WO | WO-2022/051537 A1 | 3/2022 |
| WO | WO-2022/076549 A1 | 4/2022 |
| WO | WO-2022/076591 A1 | 4/2022 |
| WO | WO-2022/076595 A1 | 4/2022 |
| WO | WO-2022/119839 A1 | 6/2022 |
| WO | WO-2022/240778 A1 | 11/2022 |
| WO | WO-2023/280157 A1 | 1/2023 |
| WO | WO-2023/284879 A1 | 1/2023 |
| WO | WO-2023/150142 A1 | 8/2023 |
| WO | WO-2023/155918 A1 | 8/2023 |
| WO | WO-2024/002076 A1 | 1/2024 |
| WO | WO-2024/222934 A1 | 10/2024 |

OTHER PUBLICATIONS

Casset et al Biochemical and Biophysical Research Communications vol. 307, pp. 198-205 (Year: 2003).*
Vajdos et al Journal of Molecular Biology vol. 320, pp. 415-428 (Year: 2002).*
Zinn Cell Rep. 12(6): 1056-1068 (Year: 2015).*
Suzuki Scientific Reports, 7: 45524, 1-11 (Year: 2017).*
Chen (Microorganisms 12, 310, 1-16 (Year: 2024).*
Earley Human Gene Therapy, 31, 2, 151-162 (Year: 2020).*

(56) References Cited

OTHER PUBLICATIONS

Adachi, K. et al., Drawing a high-resolution functional map of adeno-associated virus capsid by massively parallel sequencing, Nat Commun., 5:3075 (2014).

Ahn, S. et al., Intraocular pharmacokinetics of ranibizumab in vitrectomized versus nonvitrectomized eyes, *Invest Ophthalmol Vis Sci.*, 55(1):567-573 (2014).

Akil, O. et al., Dual AAV-mediated gene therapy restores hearing in a DFNB9 mouse model, *Proc Natl Acad Sci USA*, 116(10):4496-4501 (2019).

Akil, O. et al., Restoration of hearing in the VGLUT3 knockout mouse using virally mediated gene therapy, *Neuron*, 75(2):283-293 (2012).

Al-Moyed, H. et al., A dual-AAV approach restores fast exocytosis and partially rescues auditory function in deaf otoferlin knock-out mice, *EMBO Mol Med.*, 11(1):e9396 (2019).

Andersen, J. et al., Herpesvirus-Mediated Gene Delivery into the Rat Brain: Specificity and Efficiency of the Neuron-Specific Enolase Promoter, Cell Mol. Neurobiol., 13(5):503-515 (1993).

Andres-Mateos, E. et al., Optimized surgical approach leads to highly efficient AAV gene transfer to inner hair cells in rhesus macaque, *American Society of Gene and Cell Therapy Annual Meeting*, 22:676 (2019).

Ansari, S. et al., Surgery for vestibular schwannomas: a systematic review of complications by approach, *Neurosurg Focus*, 33(3):E14 (2012).

Arbuthnot, P et al., In vitro and in vivo hepatoma cell-specific expression of a gene transferred with an adenoviral vector, Hum Gene Ther., 7(13):1503-1514 (1996).

Askew, C. et al., Tmc gene therapy restores auditory function in deaf mice, *Sci Transl Med.*, 7(295):295ra108 (2015).

Asokan, A. et al., The AAV Vector Toolkit: Poised at the Clinical Crossroads, Molecular Therapy, 20(4):699-708 (2012).

AveXis. 2019. Zolgensma US prescribing information. US Food and Drug Administration. https://www.fda.gov/media/126109/download. Accessed Aug. 31, 2020.

Bakri, S. J. et al., Pharmacokinetics of Intravitreal Ranibizumab (Lucentis), American Academy of Ophthalmology, 14(12):2179-2182 (2007).

Banaszynski, L. A. et al., A rapid, reversible, and tunable method to regulate protein function in living cells using synthetic small molecules, Cell, 126(5): 995-1004 (2012).

Bankoti, K. et al., Advances and challenges in adeno-associated viral inner-ear gene therapy for sensorineural hearing loss, Molecular Therapy: Methods & Clinical Development, 21:209-236 (2021).

Bartoli. M. et al., Noninvasive Monitoring of Therapeutic Gene Transfer in Animal Models of Muscular Dystrophies, Gene Ther. 13:20-28 (2006).

Batt, D. and Carmichael, G., Characterization of the polyomavirus late polyadenylation signal, Mol Cell Biol., 15(9):4783-4790 (1995).

Batt, D. B. and Carmichael, G. G., Characterization of the polyomavirus late polyadenylation signal, Mol. Cell Biol., 15(9):4783-4790 (1995).

Bennett, J. et al., AAV2 gene therapy readministration in three adults with congenital blindness, *Sci Transl Med.*, 4(120):120ra15 (2012).

Bohne, B. and Harding, G., Degeneration in the cochlea after noise damage: primary versus secondary events, Am J Otol., 21(4):505-509 (2000).

Bonne, N. et al., An allograft mouse model for the study of hearing loss secondary to vestibular schwannoma growth, *J Neurooncol.*, 129(1):47-56 (2016).

Boshart, M. et al., A very strong enhancer is located upstream of an immediate early gene of human cytomegalovirus, Cell, 41(2):521-530 (1985).

Brastianos, P. and Batchelor, T., VEGF inhibitors in brain tumors, Clin Adv Hematol Oncol., 7(11):753-768 (2009).

Bulankina, A. and Moser, T., Neural circuit development in the mammalian cochlea, *Physiology (Bethesda)*, 27(2):100-112 (2012).

Carlson, M. et al., A cross-sectional survey of the North American Skull Base Society: current practice patterns of vestibular schwannoma evaluation and management in North America, *J Neurol Surg B Skull Base*, 79(3):289-296 (2018).

Carlson, M. et al., Long-term quality of life in patients with vestibular schwannoma: an international multicenter cross-sectional study comparing microsurgery, stereotactic radiosurgery, observation, and nontumor controls, *J Neurosurg.*, 122(4):833-842 (2015).

Carneiro, A. et al., Vascular endothelial growth factor plasma levels before and after treatment of neovascular age-related macular degeneration with bevacizumab or ranibizumab, *Acta Ophthalmol.*, 90(1):e25-e30 (2012).

Carvalho, L. et al., Synthetic adeno-associated viral vector efficiently targets mouse and nonhuman primate retina in vivo, *Hum Gene Ther.*, 29(7):771-784 (2018).

Casset, F. et al., A peptide mimetic of an anti-CD4 monoclonal antibody by rational design, Biochem. Biophys. Res. Commun., 307(1):198-205 (2003).

Caye-Thomasen, P. et al. Immunohistochemical demonstration of vascular endothelial growth factor in vestibular schwannomas correlates to tumor growth rate, *Laryngoscope*, 113(12):2129-2134 (2003).

Caye-Thomasen, P. et al., VEGF and VEGF receptor-1 concentration in vestibular schwannoma homogenates correlates to tumor growth rate, *Otol Neurotol.*, 26(1):98-101 (2005).

Chamney, S. et al., A mutation in the Norrie disease gene (NDP) associated with familial exudative vitreoretinopathy, Eye, 25(12):1658 (2011).

Chen, C. et al., mRNA decay mediated by two distinct AU-rich elements from c-fos and granulocyte-macrophage colony-stimulating factor transcripts: different deadenylation kinetics and uncoupling from translation, Mol Cell Biol., 15(10):5777-5788 (1995).

Chen, H. and Cleck, J., Adverse effects of anticancer agents that target the VEGF pathway, Nat Rev Clin Oncol., 6(8):465-477 (2009).

Chen, J. et al., A cerebellopontine angle mouse model for the investigation of tumor biology, hearing, and neurological function in NF2-related vestibular schwannoma, *Nat Protoc.*, 14(2):541-555 (2019).

Chen, J. et al., Expression of rat bone sialoprotein promoter in transgenic mice, J Bone Miner Res., 11(5):654-664 (1996).

Chen, Q. et al., An AU-rich element in the 3' untranslated region of the spinach chloroplast petD gene participates in sequence-specific RNA-protein complex formation, Mol Cell Biol., 15(4):2010-2018 (1995).

Chen, X. et al., HSV amplicon-mediated neurotrophin-3 expression protects murine spiral ganglion neurons from cisplatin-induced damage, *Mol Ther.*, 3(6):958-963 (2001).

Chen, Y. et al., Selection and Analysis of an Optimized Anti-VEGF Anitbody: Crystal Structure of an Affinity-matured Fab in Complex and Antigen, J. Mol. Biol., 293:865-881 (1999).

Chien, W. et al., Gene therapy restores hair cell stereocilia morphology in inner ears of deaf whirler mice, *Mol Ther.*, 24(1):17-25 (2016).

Christoforidis, J. et al., PET/CT imaging of I-124-radiolabeled bevacizumab and ranibizumab after intravitreal injection in a rabbit model, *Invest Ophthalmol Vis Sci.*, 52(8):5899-5903 (2011).

Clinicaltrials.gov. 2020a. NCT02132130: Safety, Tolerability and Efficacy for CGF166 in Patients with Unilateral or Bilateral Severe-to-profound Hearing Loss. National Institutes of Health. Accessed Aug. 31, 2020.

Clinicaltrials.gov. 2020b. NCT03066258: RGX-314 gene therapy for neovascular AMD trial. National Institutes of Health. Accessed Aug. 31, 2020.

Clinicaltrials.gov. 2020c. NCT03748784: ADVM-022 Intravitreal Gene Therapy for Wet AMD (Optic). National Institutes of Health. Accessed Aug. 31, 2020.

Clinicaltrials.gov. 2020d. NCT04418427: ADVM-022 Intravitreal Gene Therapy for DME (Infinity). National Institutes of Health. Accessed Aug. 31, 2020.

Colella, P. et al., Emerging issues in AAV-mediated in vivo gene therapy, Mol Ther Methods Clin Dev., 8:87-104 (2018).

Cotten, M. et al., High-efficiency receptor-mediated delivery of small and large (48 kilobase gene constructs using the endosome-

(56) References Cited

OTHER PUBLICATIONS disruption activity of defective or chemically inactivated adenovirus particles, P.N.A.S. U.S.A., 89(13):6094-98 (1992).
Cromie, K. et al., Nanobodies and their use in GPCR Drug Discovery, Curr. Top. Med. Chem., 15:2543-2557 (2016).
Curiel, D. T., High-efficiency gene transfer employing adenovirus-polylysine-DNA complexes, Nat Immun., 13(2-3):141-64 (1994).
Dai, C. et la., Rhesus cochlear and vestibular functions are preserved after inner ear injection of saline volume sufficient for gene therapy delivery, J Assoc Res Otolaryngol., 18(4):601-617 (2017).
De Felipe, P. and Izqierdo, M., Tricistronic and tetracistronic retroviral vectors for gene transfer, Hum Gene Ther, 11(13):1921-1931 (2000).
De Felipe, P. et al., Use of the 2A sequence from foot-and-mouth disease virus in the generation of retroviral vectors for gene therapy, Gene Ther., 6(2):198-208 (1999).
De Fougerolles, A., Delivery vehicles for small interfering RNA in vivo, Hum Gene Ther., 19(2):125-132 (2008).
De Genst, E. et al., Antibody repertoire development in camelids, Dev Comp Immunol., 30(1-2):187-198 (2006).
De Meyer., T. et al., Nanobody-based products as research and diagnostic tools, Trends Biotechnol., 32(5):263-270 (2014).
Digiammarino, E. et al., Design and generation of DVD-Ig™ molecules for dual-specific targeting, Methods Mol Biol., 899:145-156 (2012).
Dilwali, S. et al., Secreted factors from human vestibular schwannomas can cause cochlear damage, Sci Rep., 5:18599 (2015).
Dinh, C. et al., A xenograft model of vestibular schwannoma and hearing loss, Otol Neurotol., 39(5):e362-e369 (2018).
Dmitriev, I. et al., An adenovirus vector with genetically modified fibers demonstrates expanded tropism via utilization of a coxsackievirus and adenovirus receptor-independent cell entry mechanism, J Virol., 72(12):9706-9713 (1998).
Doherty, J. and Friedman, R., Controversies in building a management algorithm for vestibular schwannomas, Curr Opin Otolaryngol Head Neck Surg., 14(5):305-313 (2006).
Failla, C. et al., Positive and Negative Regulation of Angiogenesis by Soluble Vascular Endothelial Growth Factor Receptor-1, Int J Mol Sci., 19(5):1306 (2018).
Fath, S. et al., Multiparameter RNA and Codon Optimization: A Stardardized Tool to Access and Enhance Autologous Mammalian Gene Expression, PLoS One, 6(3):e17596, 14 pages (2011).
FDA, Applying human factors and usability engineering to medical devices—guidance for industry and Food and Drug Administration staff. In, edited by Food and Drug Administration and Center for Devices and Radiological Health, 49 pages (Feb. 2016).
FDA, Design and analysis of shedding studies for virus or bacteria-based gene therapy and oncolytic products—guidance for industry. In, edited by Food and Drug Administration and Center for Biologics Evaluation and Research, 19 pages (Aug. 2015).
FDA, Evaluation of devices used with Regenerative Medicine Advanced Therapies—guidance for industry. In, edited by Food and Drug Administration, Center for Biologics Evaluation and Research, Center for Devices and Radiological Health and Office of Combination Products, 14 pages (Feb. 2019).
FDA, Principles of premarket pathways for combination products guidance for industry and FDA staff—draft guidance. In, edited by Food and Drug Administration, Office of Combination Products, Center for Biologics Evaluation and Research, Center for Drug Evaluation and Research and Center for Devices and Radiological Health, 24 pages (Feb. 2019).
FDA, Use of International Standard ISO 10993-1, "Biological evaluation of medical devices—Part 1: Evaluation and testing within a risk management process"—guidance for industry and Food and Drug Administration staff. In, edited by Food and Drug Administration and Center for Devices and Radiological Health, 68 pages (Sep. 2020).
Ferrara, N. et al., Bevacizumab (Avastin), a humanized anti-VEGF monoclonal antibody for cancer therapy, Biochem Biophys Res Commun., 333(2):328-335 (2005).
Fisher, K. et al., Transduction with recombinant adeno-associated virus for gene therapy is limited by leading-strand synthesis, J Virol., 70(1):520-532 (1996).
Flotte, T. et al., A phase I study of an adeno-associated virus-CFTR gene vector in adult CF patients with mild lung disease, Hum Gene Ther., 7(9):1145-1159 (1996).
Flotte, Terence R., Birth of a new therapeutic platform: 47 years of adeno-associated virus biology from virus discovery to licensed gene therapy, Mol Ther., 21(11):1976-1981 (2013).
Francis, S. et al., The adeno-associated viral Anc80 vector efficiently transduces inner ear cells in cynomolgus macaques (Macaca fascicularis), Association for Research in Otolaryngology Midwinter Meeting, 43:685 (2020).
Fujioka, M. et al., Inflammatory and immune responses in the cochlea: potential therapeutic targets for sensorineural hearing loss, Front Pharmacol., 5:287 (2014).
Furler, S. et al., Recombinant AAV vectors containing the foot and mouth disease virus 2A sequence confer efficient bicistronic gene expression in cultured cells and rat substantia nigra neurons, Gene Ther., 8(11):864-873 (2001).
Gaffen, S.L. and Liu, K.D., Overview of interleukin-2 function, production and clinical applications, Cytokine, 28:109-123 (2004).
Gao, G. et al., Clades of Adeno-associated viruses are widely disseminated in human tissues, J. Virol.. 78(12): 6381-6388 (2004).
Gao, X. et al., Anti-VEGF treatment improves neurological function and augments radiation response in NF2 schwannoma model, Proc Natl Acad Sci USA, 112(47):14676-14681 (2015).
Gao, Y. et al., The adeno-associated viral AAVAnc80 vector efficiently transduces inner ear cells in olive baboons (Papio anubis), Association for Research in Otolaryngology Midwinter Meeting, 43:680 (2020).
Garber, K., Bispecific antibodies rise again, Nat Rev Drug Discov., 13(11):799-801 (2014).
Gaudreault, J. et al., Preclinical pharmacokinetics of ranibizumab (rhuFabV2) after a single intravitreal administration, Invest Ophthalmol Vis Sci., 46(2):726-733 (2005).
Gehlhausen, J. et al., A murine model of neurofibromatosis type 2 that accurately phenocopies human schwannoma formation, Hum Mol Genet., 24(1):1-8 (2015).
Genentech. 2017. Lucentis US prescribing information. US Food and Drug Administration. https://www.accessdata.fda.gov/drugsatfda_docs/label/2017/125156s114lbl.pdf., 7 pages, Accessed Aug. 31, 2020.
Giovannini, M. et al., Conditional biallelic Nf2 mutation in the mouse promotes manifestations of human neurofibromatosis type 2, Genes Dev., 14(13):1617-1630 (2000).
Giovannini, M. et al., Schwann cell hyperplasia and tumors in transgenic mice expressing a naturally occurring mutant NF2 protein, Genes Dev., 13(8):978-986 (1999).
Glasscock, M. et al., Twenty-five years of experience with stapedectomy, Laryngoscope, 105(9 Pt 1): 899-904 (1995).
Golfinos, J. et al., A matched cohort comparison of clinical outcomes following microsurgical resection or stereotactic radiosurgery for patients with small- and medium-sized vestibular schwannomas, J Neurosurg., 125(6):1472-1482 (2016).
Gossen, M. and Bujard, H., Tight control of gene expression in mammalian cells by tetracycline-responsive promoters, Proc Natl Acad Sci USA, 89(12):5547-5551 (1992).
Gossen, M. et al., Transcriptional activation by tetracyclines in mammalian cells, Science, 268(5218):1766-1769 (1995).
Gutmann, D. and Giovannini, M., Mouse models of neurofibromatosis 1 and 2, Neoplasia, 4(4):279-290 (2002).
Gyorgy, B. et al., Gene transfer with AAV9-PHP.B rescues hearing in a mouse model of Usher Syndrome 3A and transduces hair cells in a non-human primate, Mol Ther Methods Clin Dev., 13:1-13 (2019).
Halpin, C et al., Self-processing 2A-polyproteins—a system for co-ordinate expression of multiple proteins in transgenic plants, Plant J., 17(4):453-45 (1999).
Hamernik, R. et al., Anatomical correlates of impulse noise-induced mechanical damage in the cochlea, Hear Res., 13(3):229-247 (1984).

(56) References Cited

OTHER PUBLICATIONS

Hanna, R. et al., Nephrotoxicity induced by intravitreal vascular endothelial growth factor inhibitors: emerging evidence, *Kidney Int.*, 96(3):572-580 (2019).
Hansal, S. et al., Induction of antigen-specific hyporesponsiveness by transplantation of hemopoietic cells containing an MHC class I transgene regulated by a lymphocyte-specific promoter, J Immunol., 161(3):1063-1068 (1998).
Harvey, D. and Caskey, C., Inducible control of gene expression: prospects for gene therapy, Curr Opin Chem Biol., 2(4):512-518 (1998).
Haryadi, R. et al., Optimization of Heavy Chain and Light Chain Signal Peptides for High Level Expression of Therapeutic Antibodies in CHO Cells, PLOS One, 16 pages (2015).
Heidel, J. et al., Aministration in non-human primates of escalating intravenous doses of targeted nanoparticles containing ribonucleotide reductase subunit M2 siRNA, Proc Natl Acad Sci USA, 104(14):5715-5721 (2007).
Hellen, C. and Sarnow, P., Internal ribosome entry sites in eukaryotic mRNA molecules, Genes Dev., 15(13):1593-1612 (2001).
Huang, V. et al., Improvement in patient-reported hearing after treatment with bevacizumab in people with neurofibromatosis type 2, *Otol Neurotol.*, 39(5):632-638 (2018).
Huang, X. et al., Spontaneous tumour shrinkage in 1261 observed patients with sporadic vestibular schwannoma, *J Laryngol Otol.*, 127(8):739-743 (2013).
Hudry, E. et al., Efficient gene transfer to the central nervous system by single-stranded Anc80L65, *Mol Ther Methods Clin Dev.*, 10:197-209 (2018).
Hu-Lieskovan, S. et al., Sequence-specific knockdown of EWS-FLI1 by targeted, nonviral delivery of small interfering RNA inhibits tumor growth in a murine model of metastatic Ewing's sarcoma, Cancer Res., 65(19):8984-8992 (2005).
Husseman, J. and Raphael, Y., Gene Therapy in the Inner Ear Using Adenovirus Vectors, Adv. Otorhinolaryngol., 66:37-51 (2009).
Hutton-Smith, L. et al., A mechanistic model of the intravitreal pharmacokinetics of large molecules and the pharmacodynamic suppression of ocular vascular endothelial growth factor levels by ranibizumab in patients with neovascular age-related macular degeneration, *Mol Pharm.*, 13(9):2941-2950 (2016).
Ikeda, Y. et al., Efficient gene transfer to kidney mesenchymal cells using a synthetic adeno-associated viral vector, *J Am Soc Nephrol.*, 29(9):2287-2297 (2018).
International Search Report for PCT/US2018/066512 (AAV-Mediated Delivery of Therapeutic Antibodies to the Inner Ear, filed Dec. 19, 2018), received from ISA/KR, 7 pages (Apr. 17, 2019).
International Search Report for PCT/US2021/061205, 6 pages (Mar. 31, 2022).
Isgrig, K. et al., AAV2.7m8 is a powerful viral vector for inner ear gene therapy, Nat. Commun., 10(1):427 (2019).
Ito, T. et al., SLC26A4 mutation testing for hearing loss associated with enlargement of the vestibular aqueduct, World J. Otorhinolaryngol., 3(2):26-34 (2013).
Iwamoto, M. et al., A general chemical method to regulate protein stability in the mammalian central nervous system. Chem Biol., 17(9): 981-988 (2010).
Jakob, C. et al., Structure reveals function of the dual variable domain immunoglobulin (DVD-Ig™) molecule, Mabs, (3):358-363 (2013).
Jung, J. et al., Secretion of soluble vascular endothelial growth factor receptor 1 (sVEGFR1/sFlt1) requires Arf1, Arf6, and Rab11 GTPases, PLoS One, 7(9):e44572, 11 pages (2012).
Kanaan, N. M. et al., Rationally Engineered AAV Capsids Improve Transduction and Volumetric Spread in the CNS, Mol. Ther. Nucleic Acids, 8:184-197 (2017).
Kapurch, J. et al., Temporal lobe gliosarcoma after gamma knife radiosurgery for vestibular schwannoma, *Otol Neurotol.*, 37(8):1143-1147 (2016).

Karajannis, M. et al., Sustained imaging response and hearing preservation with low-dose bevacizumab in sporadic vestibular schwannoma, *Neuro Oncol.*, 21(6):822-824 (2019).
Karch-Georges, A. et al., MRI of endolymphatic hydrops in patients with vestibular schwannomas: a case-controlled study using non-enhanced T2-weighted images at 3 Teslas, *Eur Arch Otorhinolaryngol.*, 276(6):1591-1599 (2019).
Kaul, V. and Cosetti, M., Management of vestibular schwannoma (including NF2): facial nerve considerations, *Otolaryngol Clin North Am.*, 51(6):1193-1212 (2018).
Kelleher, Z. T. and Vos, J. M., Long-term episomal gene delivery in human lymphoid cells using human and avian adenoviral-assisted transfection, Biotechniques, 17(6):1110-17 (1994).
Kendall, R. et al,. Identification of a Natural Soluble Form of the Vascular Endothelial Growth Factor Receptor, FLT-1, and its Heterodimerization with KDR, Biochem Biophys Res Commun. 226:324-328 (1996).
Kendall., R. and Thomas, K., Inhibition of vascular endothelial cell growth factor activity by an endogenously encoded soluble receptor, Proc Natl Acad Sci USA, 90(22):10705-10709 (1993).
Kijanka, M. et al., Nanobody-based cancer therapy of solid tumors, Nanomedicine (Lond)., 10(1):161-174 (2015).
Killeen, D. et al., Long-term effects of bevacizumab on vestibular schwannoma volume in neurofibromatosis type 2 patients, *J Neurol Surg B Skull Base*, 80(5):540-546 (2019).
Kim, H. et al., FcRn receptor-mediated pharmacokinetics of therapeutic IgG in the eye, *Mol Vis.*, 15:2803-2812 (2009).
Kim, M. et al., Methionine sulfoxide reductase B3-targeted in utero gene therapy rescues hearing function in a mouse model of congenital sensorineural hearing loss, *Antioxid Redox Signal*, 24(11):590-602 (2016).
Kim, M. et al., Targeted gene delivery into the mammalian inner ear using synthetic serotypes of adeno-associated virus vectors, *Mol Ther Methods Clin Dev.*, 13:197-204 (2019).
Kirchmann, M. et al., Ten-year follow-up on tumor growth and hearing in patients observed with an intracanalicular vestibular schwannoma, *Neurosurgery*, 80(1):49-56 (2017).
Klettner, A. and Roider, J., Comparison of bevacizumab, ranibizumab, and pegaptanib in vitro: efficiency and possible additional pathways, *Invest Ophthalmol Vis Sci.*, 49(10):4523-4527 (2008).
Klump, H. et al., Retroviral vector-mediated expression of HoxB4 in hematopoietic cells using a novel coexpression strategy, Gene Ther., 8(10):811-817 (2001).
Koen, N. et al., Location of small intracanalicular vestibular schwannomas based on magnetic resonance imaging, *Otolaryngol Head Neck Surg.*, 162(2):211-214 (2020).
Kondziolka, D. et al., The newly diagnosed vestibular schwannoma: radiosurgery, resection, or observation?, *Neurosurg Focus*, 33(3):E8 (2012).
Konishi, T. et al., Effects of chemical alteration in the endolymph on the cochlear potentials, *Acta Otolaryngol.*, 62(4):393-404 (1966).
Koutsimpelas, D. et al., Expression of vascular endothelial growth factor and basic fibroblast growth factor in sporadic vestibular schwannomas correlates to growth characteristics, *Otol Neurotol.*, 28(8):1094-1099 (2007).
Koutsimpelas, D. et al., The VEGF/VEGF-R axis in sporadic vestibular schwannomas correlates with irradiation and disease recurrence, *ORL J Otorhinolaryngol Relat Spec.*, 74(6):330-338 (2012).
Kovaleva, M. et al., Shark variable new antigen receptor biologics—a novel technology platform for therapeutic drug development, Expert Opin Biol Ther., 14(10):1527-1539 (2014).
Krah, S. et al., Single-domain antibodies for biomedical applications, Immunopharmacol Immunotoxicol., 38(1):21-28 (2016).
Kshettry, V. et al., Incidence of vestibular schwannomas in the United States, *J Neurooncol.*, 124(2):223-228 (2015).
Kujawa, S. and Liberman, M. et al., Synaptopathy in the noise-exposed and aging cochlea: Primary neural degeneration in acquired sensorineural hearing loss, Hear Res., 330(Pt B):191-199 (2015).
Landegger, L. et al., A synthetic AAV vector enables safe and efficient gene transfer to the mammalian inner ear, *Nat Biotechnol.*, 35(3):280-284 (2017).

(56) References Cited

OTHER PUBLICATIONS

Leabman, M. et al., Effects of altered Fc?R binding on antibody pharmacokinetics in cynomolgus monkeys, Mabs, 5(6):896-903 (2013).
Lees, K. et al., Natural history of sporadic vestibular schwannoma: a volumetric study of tumor growth, Otolaryngol Head Neck Surg., 159(3):535-542 (2018).
Levitt, N. et al., Definition of an efficient synthetic poly(A) site, Genes Dev., 3(7):1019-1025 (1989).
Li, S. et al., Effective electrophoretic mobilities and charges of anti-VEGF proteins determined by capillary zone electrophoresis, J Pharm Biomed Anal., 55(3):603-607 (2011).
Li, W. et al., Engineering and selection of shuffled AAV genomes: a new strategy for producing targeted biological nanoparticles, Mol. Ther. 16(7):1252-1260 (2008).
Lichtenbeld, H. et al., Effect of local anti-VEGF antibody treatment on tumor microvessel permeability, Microvasc Res., 57(3):357-362 (1999).
Litovsky, Ruth, Development of the auditory system, Handb Clin Neurol., 129:55-72 (2015).
Littman, T. et al., The quinoxalinediones DNOX, CNOX and two related congeners suppress hair cell-to-auditory nerve transmission, Hear Res., 40(1-2):45-53 (1989).
Liu, H. et al., Current strategies for drug delivery to the inner ear, Acta Pharmaceutica Sinica B, 3(2):86-96 (2013).
Liu, Y. et al., AAV8-antiVEGFfab Ocular Gene Transfer for Neovascular Age-Related Macular Degeneration, Molecular Therapy, 26(2):542-549 (2017).
Liu, Y. et al., Promoter effects of adeno-associated viral vector for transgene expression in the cochlea in vivo, Experimental and Molecular Medicine, 39(2):170-175 (2007).
London, N.R. et al., The role of vascular endothelial growth factor and vascular stability in diseases of the ear, The Laryngoscope, 124:E340-E346 (2014).
Lu, V. et al., Efficacy and safety of bevacizumab for vestibular schwannoma in neurofibromatosis type 2: a systematic review and meta-analysis of treatment outcomes, J Neurooncol., 144(2):239-248 (2019).
Lysaght, A. et al., Proteome of human perilymph, J Proteome Res., 10(9):3845-3851 (2011).
MacCallum, R.M et al., Antibody-antigen interactions: contact analysis and binding site topography, J. Mol. Biol., 262(5):732-745 (1996).
MacKeith, S. et al., Trends in acoustic neuroma management: a 20-year review of the oxford skull base clinic, J Neurol Surg B Skull Base, 74(4):194-200 (2013).
Magari, S. et al., Pharmacologic control of a humanized gene therapy system implanted into nude mice, J Clin Invest., 100(11):2865-2872 (1997).
Mahmud, M. et al., Histopathology of the inner ear in unoperated acoustic neuroma, Ann Otol Rhinol Laryngol., 112(11):979-986 (2003).
Maier, P. et al., Retroviral vectors for gene therapy, Future Microbiol., 5(10):1507-1523 (2010).
Manley, Geoffrey A., Comparative auditory neuroscience: understanding the evolution and function of ears, J Assoc Res Otolaryngol., 18(1):1-24 (2017).
Mattion, N. et al., Foot-and-mouth disease virus 2A protease mediates cleavage in attenuated Sabin 3 poliovirus vectors engineered for delivery of foreign antigens, J Virol., 70(11):8124-8127 (1996).
McClatchey, A. et al., Mice heterozygous for a mutation at the Nf2 tumor suppressor locus develop a range of highly metastatic tumors, Genes Dev., 12(8):1121-1133 (1998).
McClatchey, A. et al., The Nf2 tumor suppressor gene product is essential for extraembryonic development immediately prior to gastrulation, Genes Dev., 11(10):1253-1265 (1997).
Miyazaki, J. et al., Expression vector system based on the chicken beta-actin promoter directs efficient production of interleukin-5, Gene, 79(2):269-277 (1989).
Morrison, S. et al., Chimeric human antibody molecules: mouse antigen-binding domains with human constant region domains, Proc Natl Acad Sci USA, 81(21):6851-6855 (1984).
Mujic-Delic, A. et al., GPCR-targeting nanobodies: attractive research tools, diagnostics, and therapeutics, Trends Pharmacol Sci., 35(5):247-255 (2014).
Murillo, O. et al., Liver expression of a miniATP7B gene results in long-term restoration of copper homeostasis in a Wilson disease model in mice, Hepatology, 70(1):108-126 (2019).
Muyldermans, S. et al., Recognition of antigens by single-domain antibody fragments: the superfluous luxury of paired domains, Trends Biochem Sci., 26(4):230-235 (2001).
Muyldermans, S., Nanobodies: natural single-domain antibodies, Ann. Rev. Biochem. 82:775-797 (2013).
Muyldermans, S., Single domain camel antibodies: current status, J. Biotechnol., 74(4):277-302 (2001).
Muzyczka, N., Use of adeno-associated virus as a general transduction vector for mammalian cells, Curr Top Microbiol Immunol, 158:97-129 (1992).
Naganawa, S. et al., Endolympathic hydrops in patients with vestibular schwannoma: visualization by non-contrast-enhanced 3D FLAIR, Neuroradiology, 53(12):1009-1015 (2011).
Niwa, H. et al., Efficient selection for high-expression transfectants with a novel eukaryotic vector, Gene, 108(2):193-199 (1991).
No Author Listed, High-dose AAV gene therapy deaths, Nat Biotechnol., 38(8):910 (2020).
No, D. et al., Ecdysone-inducible gene expression in mammalian cells and transgenic mice, Proc Natl Acad Sci USA, 93(8):3346-3351 (1996).
Nuttall, A. et al., Acute perilymphatic perfusion of the guinea pig cochlea, Hear Res., 6(2):207-221 (1982).
Omichi, R. et al., Hair cell transduction efficiency of single- and dual-AAV serotypes in adult murine cochleae, Mol Ther Methods Clin Dev., 17:1167-1177 (2020).
Orban, T. et al., Applying a "double-feature" promoter to identify cardiomyocytes differentiated from human embryonic stem cells following transposon-based gene delivery, Stem Cells, 27(5):1077-1087 (2009).
Orkin, S. et al., Thalassemia due to a mutation in the cleavage-polyadenylation signal of the human beta-globin gene, EMBO J., 4(2):453-456 (1985).
Ostrom, Q. et al., CBTRUS statistical report: primary brain and other central nervous system tumors diagnosed in the United States in 2011-2015, Neuro Oncol., 20(suppl_4):iv1-iv86 (2018).
Paldor, I. et al., Growth rate of vestibular schwannoma, J Clin Neurosci., 32:1-8 (2016).
Pan, B. et al., Gene therapy restores auditory and vestibular function in a mouse model of Usher syndrome type 1c, Nat Biotechnol., 35(3):264-272 (2017).
Papadopoulos, N. et al., Binding and neutralization of vascular endothelial growth factor (VEGF) and related ligands by VEGF Trap, ranibizumab and bevacizumab, Angiogenesis, 15(2):171-185 (2012).
Pararas, E. et al., Kinetics of reciprocating drug delivery to the inner ear, J Control Release, 152(2):270-277 (2011).
Parente, V. and Corti, S., Advances in spinal muscular atrophy therapeutics, Ther Adv Neurol Disord., 11:1-13 (2018).
Pedrosa, C. et al., Determinants and impact of headache after acoustic neuroma surgery, Am J Otol., 15(6):793-797 (1994).
Pelletier, J. et al., Cap-independent translation of poliovirus mRNA is conferred by sequence elements within the 5' noncoding region., Mol. Cell. Biol. 8(3):1103-1112 (1988).
Peris-Celda, M. et al., Main symptom that led to medical evaluation and diagnosis of vestibular schwannoma and patient-reported tumor size: cross-sectional study in 1,304 patients, J Neurol Surg B Skull Base, 80(3):316-322 (2019).
Peyre, M. et al., Conservative management of bilateral vestibular schwannomas in neurofibromatosis type 2 patients: hearing and tumor growth results, Neurosurgery, 72(6):907-914 (2013).
Piccioli, P. et al., Neuroantibodies: ectopic expression of a recombinant anti-substance P antibody in the central nervous system of transgenic mice, Neuron, 15(2):373-384 (1995).

(56) References Cited

OTHER PUBLICATIONS

Piccioli, P. et al., Neuroantibodies: molecular cloning of a monoclonal antibody against substance P for expression in the central nervous system, Proc Natl Acad Sci USA, 88(13):5611-5615 (1991).
Plotkin, S. et al., Bevacizumab for progressive vestibular schwannoma in neurofibromatosis type 2: a retrospective review of 31 patients, Otol Neurotol., 33(6):1046-1052 (2012).
Plotkin, S. et al., Hearing improvement after bevacizumab in patients with neurofibromatosis type 2, N Engl J Med., 361(4):358-367 (2009).
Plotkin, S. et al., Multicenter, prospective, phase II and biomarker study of high-dose bevacizumab as induction therapy in patients with neurofibromatosis type 2 and progressive vestibular schwannoma, J Clin Oncol., 37(35):3446-3454 (2019).
Poulin, K. et al., Retargeting of adenovirus vectors through genetic fusion of a single-chain or single-domain antibody to capsid protein IX, J Virol., 84(19):10074-10086 (2010).
Proudfoot, N. et al., Integrating mRNA processing with transcription, Cell, 108(4):501-512 (2002).
Pryadkina, M. et al., A Comparison of AAV Strategies Distinguishes Overlapping Vectors for Efficient Systemic Delivery of the 6.2 Kb Dysferlin Coding Sequence, Meth. Clin. Devel. 2:15009 (2015).
Quesnel, A. et al., Otosclerosis: temporal bone pathology, Otolaryngol Clin North Am., 51(2):291-303 (2018).
Rahbarizadeh, F. et al., Nanobody; an old concept and new vehicle for immunotargeting, Immunol Invest., 40(3):299-338 (2011).
Rask-Andersen, H. et al., Perilymph/modiolar communication routes in the human cochlea, Ear Hear., 27(5):457-465 (2006).
Reid, C. et al., Development of an inducible anti-VEGF rAAV gene therapy strategy for the treatment of wet AMD, Scientific Reports, 8(1): p. 11763 (2018).
Remenschneider, A. et al., Is the cause of sensorineural hearing loss in patients with facial schwannomas multifactorial?, Laryngoscope, 127(7):1676-1682 (2017).
Reznitsky, M. et al., Epidemiology of vestibular schwannomas—prospective 40-year data from an unselected national cohort, Clin Epidemiol., 11:981-986 (2019).
Roesch, S. et al., Functional Testing of SLC26A4 Variants-Clinical and Molecular Analysis of a Cohort with Enlarged Vestibular Aqueduct from Austria, Int. J. Mol. Sci. 19(1):209 (2018).
Ronzitti, G. et al., Human immune responses to adeno-associated virus (AAV) Vectors, Front Immunol., 11:670 (2020).
Roosli, C. et al., Dysfunction of the cochlea contributing to hearing loss in acoustic neuromas: an underappreciated entity, Otol Neurotol., 33(3):473-480 (2012).
Rozema, D. et al., Dymanic PolyConjugates for targeted in vivo delivery of siRNA to hepatocytes, Proc Natl Acad Sci USA, 104(32):12982-12987 (2007).
Rudikoff, S. et al., Single amino acid substitution altering antigen-binding specificity, Proc. Natl. Acad. Sci. USA, 79:1979-1983 (1982).
Russell, S. et al., Efficacy and safety of voretigene neparvovec (AAV2-hRPE65v2) in patients with RPE65-mediated inherited retinal dystrophy: a randomised, controlled, open-label, phase 3 trial, Lancet, 390(10097):849-860 (2017).
Ryan, A. et al., Cellular targeting for cochlear gene therapy, Adv Otorhinolaryngol., 66:99-115 (2009).
Ryan, M. and Drew, J., Foot-and-mouth disease virus 2A oligopeptide mediated cleavage of an artificial polyprotein, EMBO J., 13(4):928-933 (1994).
Saito, K. et al., Expression of Ki-67 antigen and vascular endothelial growth factor in sporadic and neurofibromatosis type 2-associated schwannomas, Clin Neuropathol., 22(1):30-34 (2003).
Sampath, P. et al., Facial nerve injury in acoustic neuroma (vestibular schwannoma) surgery: etiology and prevention, J Neurosurg., 87(1):60-66 (1997).
Sandig, V. et al., HBV-derived promoters direct liver-specific expression of an adenovirally transduced LDL receptor gene, Gene Ther., 3(11):1002-1009 (1996).
Sanofi-Aventis US. 2020. Zaltrap US prescribing information. US Food and Drug Administration. https://www.accessdata.fda.gov/drugsatfda_docs/label/2020/125418s047lbl.pdf. Accessed Aug. 31, 2020.
Sardhara, J. et al., Postoperative tinnitus after vestibular schwannoma surgery: a neglected entity, Neurol India, 68(2):333-339 (2020).
Schek, N. et al., Definition of the Upstream Efficiency Element of the Simian Virus 40 Late Polyadenylation Signal by Using in Vitro Analyses, Mol. Cell Biol., 12(12):5386-5393 (1992).
Schmidt-Erfurth, Ursula, Clinical safety of ranibizumab in age-related macular degeneration, Expert Opin Drug Saf., 9(1):149-165 (2010).
Schnurman, Z. et la., Volumetric growth rates of untreated vestibular schwannomas, J Neurosurg., 1-7 (2019).
Seol, H. et al., Optimal extent of resection in vestibular schwannoma surgery: relationship to recurrence and facial nerve preservation, Neurol Med Chir (Tokyo), 46(4):176-181 (2006).
Sharma, A. et al., Transduction efficiency of AAV 2/6, 2/8 and 2/9 vectors for delivering genes in human corneal fibroblasts, Brain Res Bull., 81(2-3):273 (2010).
Shepherd, R. et al., Cochlear pathology following reimplantation of a multichannel scala tympani electrode array in the macaque, Am J Otol., 16(2):186-199 (1995).
Shu, Y. et al., Adenovirus vectors target several cell subtypes of mammalian inner ear in vivo, Neural Plast., 2016:1-8 (2016).
Shu, Y. et al., Identification of Adeno-Associated Viral Vectors That Target Neonatal and Adult Mammalian Inner Ear Cell Subtypes, Hum Gene Ther., 27(9):687-99 (2016).
Skolnick, J. and Fetrow, U.S., From genes to protein structure and function: novel applications of computational approaches in the genomic era, Trends Biotechnol., 18(1):34-39 (2000).
Slattery, W. et al., Vestibular schwannoma growth rates in neurofibromatosis type 2 natural history consortium subjects, Otol Neurotol., 25(5):811-817 (2004).
Spark Therapeutics. 2017. Luxturna US prescribing information. US Food and Drug Administration. https://www.fda.gov/media/109906/download, 16 pages, Accessed Aug. 31, 2020.
Sridhar, T. et al., A novel cholinergic "slow effect" of efferent stimulation on cochlear potentials in the guinea pig, J Neurosci., 15(5 Pt 1):3667-3678 (1995).
Srinivasan, M. et al., Effect of fixatives and tissue processing on the content and integrity of nucleic acids, Am J Pathol., 161(6):1961-1971 (2002).
Stein, G. et al., The osteocalcin gene: a model for multiple parameters of skeletal-specific transcriptional control, Mol Biol Rep., 24(3):185-196 (1997).
Sullivan, J. et al., Convective forces increase rostral delivery of intrathecal radiotracers and antisense oligonucleotides in the cynomolgus monkey nervous system, J Transl Med., 18(1):309 (2020).
Suzuki, J. et al., Cochlear gene therapy with ancestral AAV in adult mice: complete transduction of inner hair cells without cochlear dysfunction, Sci Rep., 7:45524, pp. 1-11 (2017).
Suzuki, J. et al., Round-window delivery of neurotrophin 3 regenerates cochlear synapses after acoustic overexposure, Sci Rep., 6:24907, 11 pages (2016).
Szymanski, P. et al., Development and validation of a robust and versatile one-plasmid regulated gene expression system, Mol Ther., 15(7):1340-1347 (2007).
Talaei, S. et la., Dye tracking following posterior semicircular canal or round window membrane injections suggests a role for the cochlea aqueduct in modulating distribution, Front Cell Neurosci., 13:471, 16 pages (2019).
Tandon, V. et al., Microfabricated infuse-withdraw micropump component for an integrated inner-ear drug-delivery platform, Biomed Microdevices, 17(2):37 (2015).
Tandon, V. et al., Microfabricated reciprocating micropump for intracochlear drug delivery with integrated drug/fluid storage and electronically controlled dosing, Lab Chip., 16(5):829-846 (2016).
Tao, Y. et al., Delivery of adeno-associated virus vectors in adult mammalian inner-ear cell subtypes without auditory dysfunction, Hum Gene Ther., 29(4):492-506 (2018).

(56) References Cited

OTHER PUBLICATIONS

Thein, S. et al., The polyadenylation site mutation in the alpha-globin gene cluster, Blood, 71(2):313-319 (1988).
Tian, Y. et al., Creation of a transgenic mouse for hair-cell gene targeting by using a modified bacterial artificial chromosome containing Prestin, Dev Dyn., 231(1):199-203 (2004).
Timmers, A. et al., Ocular inflammatory response to intravitreal injection of adeno-associated virus vector: relative contribution of genome and capsid, *Hum Gene Ther.*, 31(1-2):80-89 (2020).
Torres Maldonado, S. et al., Recent trends in vestibular schwannoma management: an 11-year analysis of the National Cancer Database, *Otolaryngol Head Neck Surg.*, 161(1):137-143 (2019).
Trapani, I., et al., Effective delivery of large genes to the retina by dual AAV vectors, EMBO Mol Med., 6(2):194-211 (2014).
Tschudi, D. et al., Conservative management of unilateral acoustic neuromas, Am J Otol., 21(5):722-728 (2000).
Vajdos, F.F. et al., Comprehensive functional maps of the antigen-binding site of an anti-ErbB2 antibody obtained with shotgun scanning mutagenesis, *J. Mol. Biol.*, 320(2)415-428 (2002).
Van Audenhove, I. and Gettemans, J., Nanobodies as Versatile Tools to Understand, Diagnose, Visualize and Treat Cancer, EBioMedicine, 8:40-48 (2016).
Van Bockstaele, F. et al., The development of nanobodies for therapeutic applications, Curr Opin Investig Drugs, 10(11):1212-1224 (2009).
Vincke, C. and Muyldermans, S. Introduction to heavy chain antibodies and derived Nanobodies, Methods Mol Biol., 911:15-26 (2012).
Vitosevic, K. et al., Effect of formalin fixation on por amplification of DNA isolated from healthy autopsy tissues, *Acta Histochem*, 120(8):780-788 (2018).
Wang, D. et al., Adeno-associated virus vector as a platform for gene therapy delivery, *Nat Rev Drug Discov.*, 18(5):358-378 (2019).
Wang, L. et al., Single stranded adeno-associated virus achieves efficient gene transfer to anterior segment in the mouse eye, *PLoS One*, 12(8):e0182473, pp. 1-12 (2017).
Wang, Y. et al., Ligand-inducible and liver-specific target gene expression in transgenic mice, Nat Biotechnol., 15(3):239-243 (1997).
Wang, Y., et al., Positive and negative regulation of gene expression in eukaryotic cells with an inducible transcriptional regulator, Gene Ther., 4(5):432-441 (1997).
Wen, H. et al., Characterization of human sclera barrier properties for transscleral delivery of bevacizumab and ranibizumab, *J Pharm Sci.*, 102(3):892-903 (2013).
Wenzel, G. et al., Helper-dependent adenovirus-mediated gene transfer into the adult mouse cochlea, *Otol Neurotol.*, 28(8):1100-1108 (2007).
Wesolowski, J. et al., Single domain antibodies: promising experimental and therapeutic tools in infection and immunity, Med Microbiol Immunol., 198(3):157-174 (2009).
Wolf, A. et al., Risk of radiation-associated intracranial malignancy after stereotactic radiosurgery: a retrospective, multicentre, cohort study, *Lancet Oncol.*, 20(1):159-164 (2019).
Wong, H. et al., Anti-vascular endothelial growth factor therapies as a novel therapeutic approach to treating neurofibromatosis-related tumors, *Cancer Res.*, 70(9):3483-3493 (2010).
Woychik, R. et al., Requirement for the 3' flanking region of the bovine growth hormone gene for accurate polyadenylylation, Proc Natl Acad Sci USA, 81(13):3944-3948 (1984).
Wright, C. et al., Ototoxicity of neomycin and polymyxin B following middle ear application in the chinchilla and baboon, *Am J Otol.*, 8(6):495-499 (1987).
Written Opinion for PCT/US2018/066512 (AAV-Mediated Delivery of Therapeutic Antibodies to the Inner Ear, filed Dec. 19, 2018), received from ISA/KR, 19 pages (Apr. 17, 2019).
Written Opinion for PCT/US2021/061205, 10 pages (Mar. 31, 2022).

Wu, H. et al. Humanization of a Murine Monoclonal Antibody by Simultaneous Optimization of Framework and CDR Residues, J. Mol. Biol., 294:151-162 (1999).
Wu, H. et al., Humanization of a murine monoclonal antibody by simultaneous optimization of framework and CDR residues, J. Mol. Biol., 294(1): 151-162 (1999).
Xenaki, K. et al., Antibody or antibody fragments: implications for molecular imaging and targeted therapy of solid tumors, *Front Immunol.*, 8:1287 (2017).
Xiao, W. et al., Gene therapy vectors based on adeno-associated virus type 1, J. Virol., 73(5):3994-4003 (1999).
Yang, J. et al., Comparison of binding characteristics and in vitro activities of three inhibitors of vascular endothelial growth factor A, *Mol Pharm.*, 11(10):3421-3430 (2014).
Yoshimoto, Yuhei, Systematic review of the natural history of vestibular schwannoma, *J Neurosurg.*, 103(1):59-63 (2005).
Yoshimura, H. et al., Enhanced viral-mediated cochlear gene delivery in adult mice by combining canal fenestration with round window membrane inoculation, *Sci Rep.*, 8(1):2980, pp. 1-10 (2018).
Yuan, F. et al., Time-dependent vascular regression and permeability changes in established human tumor xenografts induced by an anti-vascular endothelial growth factor/vascular permeability factor antibody, *Proc Natl Acad Sci USA*, 93(25):14765-14770 (1996).
Zhang, H. et al., Adenovirus-adeno-associated virus hybrid for large-scale recombinant adeno-associated virus production, Human Gene Therapy, 20(9):922-929 (2009).
Zhang, L. et al., Alteration in the IL-2 signal peptide affects secretion of proteins in vitro and in vivo, J. Gene Med., 7(3):354-365 (2005).
Zhao, Y. et al., Targeting the cMET pathway augments radiation response without adverse effect on hearing in NF2 schwannoma models, *Proc Natl Acad Sci USA*, 115(9):E2077-E2084 (2018).
Zheng, J. et al., Prestin is the motor protein of cochlear outer hair cells, Nature, 405(6783):149-155 (2000).
Zinn, E. et al., In silico reconstruction of the viral evolutionary lineage yields a potent gene therapy vector, *Cell Rep.*, 12(6):1056-1068 (2015).
International Search Report for PCT/US2023/012083, filed Feb. 1, 2023, 7 pages, (mailed Jul. 18, 2023).
Valentini, C. et al., Inner Ear Gene Delivery: Vectors and Routes, Hearing Balance Commun., 18(4):278-285 (2020).
Written Opinion for PCT/US2023/012083, filed Feb. 1, 2023, 9 pages, (mailed Jul. 18, 2023).
GenBank: AOZ48529.1, Bevacizumab light chain [synthetic construct], 3 pages, (2016).
Mautner, V.F. et al., Bevacizumab induces regression of vestibular schwannomas in patients with neurofibromatosis type 2, Neuro. Oncol., 12(1):14-18 (2010).
Kang, T.H. and Jung, S.T., Boosting therapeutic potency of antibodies by taming Fc domain functions, Exp. Mol. Med., 51(11):1-9 (2019).
Sacheli, R. et al., Gene transfer in inner ear cells: a challenging race, Gene Ther., 20(3):237-247 (2013).
Yan, Z. et al., Inverted terminal repeat sequences are important for intermolecular recombination and circularization of adeno-associated virus genomes, J. Virol., 79(1):364-379 (2005).
Hoyng, S.A. et al., Gene delivery to rat and human Schwann cells and nerve segments: a comparison of AAV 1-9 and lentiviral vectors, Gene Ther., 22(10):767-780 (2015).
Lusby, E. et al., Nucleotide sequence of the Inverted Terminal Repetition in Adeno-Associated Virus DNA, J. Virol., 34(2):402-409 (1980).
Samulski, R.J. et al., A recombinant plasmid from which an infectious adeno-associated virus genome can be excised in vitro and its use to study viral replication, J. Virol., 61(10):3096-3101 (1987).
Samulski, R.J. et al., Rescue of Adeno-Associated Virus from Recombinant Plasmids: Gene Correction within the Terminal Repeats of AAV, Cell, 33(1):135-143 (1983).
Stone, I.M. et al., Adeno-associated virus-mediated gene transfer to hair cells and support cells of the murine cochlea, Mol. Ther., 11(6):843-848 (2005).

* cited by examiner

ANTI-VEGF ANTIBODY CONSTRUCTS

CROSS-REFERENCE TO RELATED APPLICATIONS

This application is a continuation of International Patent Application No. PCT/US21,61205, filed Nov. 30, 2021, which claims priority to U.S. Provisional Patent Applications 63/120,189 filed on Dec. 1, 2020, and 63/152,832 filed on Feb. 23, 2021, the entire contents of each of which is hereby incorporated by reference.

SEQUENCE LISTING

The instant application contains a Sequence Listing which has been submitted electronically in XML format and is hereby incorporated by reference in its entirety. Said sequence listing, created on Feb. 13, 2023, is named 2013615-0592.xml and is 276,644 bytes in size.

BACKGROUND

Hearing loss can be conductive (arising from the ear canal or middle ear), sensorineural (arising from the inner ear or auditory nerve), or mixed. Sensorineural hearing loss includes hearing loss that is caused by a malfunction of the cells (e.g., hair cells) in an inner ear of a mammal. Non-limiting causes of sensorineural hearing loss include exposure to loud noise, head trauma, viral infection, autoimmune inner ear disease, genetic hearing loss, aging, malformations in the inner ear, Meniere's disease, otosclerosis, and tumors. As discussed herein, another cause of hearing loss can be vestibular schwannoma (VS), which is, e.g., a tumor that develops on the nerves leading from the inner ear to the brain.

SUMMARY

The present disclosure provides the recognition that administration of anti-VEGF proteins (e.g., ranibizumab, bevacizumab, and/or aflibercept) to a subject can be useful in treating conditions, diseases, or disorders associated with neovascularization. The present disclosure further recognizes that administration of anti-VEGF proteins may not always be straightforward. For example, administration of anti-VEGF proteins should be achieved in such a way that provides the proper levels of anti-VEGF proteins locally at cells and tissues associated with neovascularization.

The present disclosure provides that administration of anti-VEGF constructs, which can express anti-VEGF proteins (e.g., ranibizumab, bevacizumab, and/or aflibercept) can be useful in treating conditions, diseases, or disorders associated with neovascularization. In particular, recombinant AAV (rAAV) constructs encoding anti-VEGF proteins (e.g., ranibizumab, bevacizumab, and/or aflibercept) can be particularly useful in treating conditions, diseases, or disorders associated with neovascularization in the ears and eyes, particularly when used with an rAAVAnc80 capsid to form an rAAVAnc80-antiVEGF particle.

Among other things, the present disclosure provides a construct comprising a coding sequence operably linked to a promoter, where the coding sequence encodes a vascular endothelial growth factor (VEGF) binding agent or portion thereof (also collectively referred to herein as an anti-VEGF protein).

In some embodiments, a promoter is an inducible promoter, a constitutive promoter, or a tissue-specific promoter. In some embodiments, a promoter is a CAG promoter, a CBA promoter, a CMV promoter, or a CB7 promoter. In some embodiments, a promoter comprises a nucleic acid sequence according to SEQ ID NO: 49 or 50, SEQ ID NO: 64, and/or SEQ ID NO: 65.

In some embodiments, a coding sequence is or comprises a primate coding sequence. In some embodiments, a coding sequence is or comprises a human coding sequence. In some embodiments, a coding sequence is or comprises an engineered coding sequence.

In some embodiments, a VEGF binding agent or portion thereof is a primate VEGF binding agent. In some embodiments, a VEGF binding agent is or comprises a human VEGF binding agent. In some embodiments, a VEGF binding agent is or comprises a humanized VEGF binding agent.

In some embodiments, a VEGF binding agent is capable of binding to at least one VEGF protein. In some embodiments, at least one VEGF protein is VEGF-A, VEGF-B, VEGF-C, VEGF-D, or a combination thereof. In some embodiments, at least one VEGF protein is VEGF-A.

In some embodiments, a VEGF binding agent comprises at least one polypeptide. In some embodiments, a VEGF binding agent is or comprises an antibody or fragment thereof. In some embodiments, an antibody fragment is a Fab fragment, a Fab' fragment, a F(ab')2 fragment, a Fd fragment, a Fd' fragment, a complementarity determining region (CDR), a single chain Fv, or an Fc domain. In some embodiments, a VEGF binding agent is or comprises an immunoglobulin heavy chain, an immunoglobulin light chain, or a combination thereof.

In some embodiments, a VEGF binding agent comprises a polypeptide that comprises an amino sequence according to SEQ ID NO: 16. In some embodiments, a VEGF binding agent comprises a polypeptide that comprises an amino sequence according to SEQ ID NO: 20. In some embodiments, a VEGF binding agent comprises a polypeptide that comprises an amino sequence according to SEQ ID NO: 16 and a polypeptide that comprises an amino sequence according to SEQ ID NO: 20.

In some embodiments, a VEGF binding agent is or comprises ranibizumab.

In some embodiments, a coding sequence comprises a nucleic acid sequence according to SEQ ID NO: 13. In some embodiments, a coding sequence comprises a nucleic acid sequence according to SEQ ID NO: 19. In some embodiments, a coding sequence comprises a nucleic acid sequence according to SEQ ID NO: 13 and a nucleic acid sequence according to SEQ ID NO: 19.

In some embodiments, a coding sequence is or comprises a nucleic acid sequence according to SEQ ID NO: 103.

In some embodiments, a VEGF binding agent comprises a polypeptide that comprises an amino sequence according to SEQ ID NO: 24. In some embodiments, a VEGF binding agent comprises a polypeptide that comprises an amino sequence according to SEQ ID NO: 25. In some embodiments, a VEGF binding agent comprises a polypeptide that comprises an amino sequence according to SEQ ID NO: 24 and a polypeptide that comprises an amino sequence according to SEQ ID NO: 25.

In some embodiments, a VEGF binding agent is or comprises bevacizumab.

In some embodiments, a coding sequence comprises a nucleic acid sequence according to SEQ ID NO: 108. In some embodiments, a coding sequence comprises a nucleic acid sequence according to SEQ ID NO: 109. In some embodiments, a coding sequence comprises a nucleic acid sequence according to SEQ ID NO: 108 and a nucleic acid sequence according to SEQ ID NO: 109.

In some embodiments, a coding sequence is or comprises a nucleic acid sequence according to SEQ ID NO: 22.

In some embodiments, a coding sequence comprises one or more nucleic acid sequences that each encode a signal peptide. In some embodiments, at least one nucleic acid sequence encodes an interleukin 2 (IL2) signal peptide.

In some embodiments, a coding sequence comprises one or more sequences encoding a self-cleaving peptide. In some embodiments, a self-cleaving peptide is a *Thosea asigna* virus 2A (T2A) peptide.

In some embodiments, a VEGF binding agent comprises a Fc domain. In some embodiments, an Fc domain comprises an amino acid sequence according to SEQ ID NO: 111.

In some embodiments, a coding sequence comprises a nucleic acid sequence according to SEQ ID NO: 110.

In some embodiments, a VEGF binding agent comprises one or more extracellular domains of VEGF receptors. In some embodiments, one or more extracellular domains of VEGF receptors comprise an extracellular domain comprising an amino sequence according to SEQ ID NO: 112.

In some embodiments, a VEGF binding agent comprises two extracellular domains of VEGF receptors.

In some embodiments, a coding sequence comprises one or more nucleic acid sequences each encoding a signal peptide. In some embodiments, at least one nucleic acid sequence encodes an IL2 signal peptide.

In some embodiments, a construct comprises two AAV inverted terminal repeats (ITRs). In some embodiments, two AAV ITRs flank a coding sequence and promoter.

In some embodiments, two AAV ITRs are or are derived from AAV2 ITRs.

In some embodiments, two AAV ITRs comprise a 5' ITR comprising a nucleic acid sequence according to SEQ ID NO: 45 or 47 and a 3' ITR comprising a nucleic acid sequence according to SEQ ID NO: 46 or 48.

In some embodiments, a construct comprises a nucleic acid sequence according to any of SEQ ID NOs: 90, 91, 92, 93, 94, 106, or 107.

In some embodiments, a construct comprises a nucleic acid sequence according to any of SEQ ID NOs: 95 or 96.

In some embodiments, a construct as described herein is for use in the treatment of an otological disease characterized by neovascularization and/or one or more symptoms associated with the otological disease. In some embodiments, use of a construct as described herein is provided for the manufacture of a medicament to treat an otological disease characterized by neovascularization and/or one or more symptoms associated with the otological disease. In some embodiments, one or more symptoms associated with the otological disease comprise hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, or death.

The present disclosure further provides an AAV particle comprising a construct as described herein.

In some embodiments, an rAAV particle comprises an rAAV capsid, where the rAAV capsid is or is derived from an AAV2, AAV3, AAV4, AAV5, AAV6, AAV7, AAV8, AAV9, AAV10, AAV-rh8, AAV-rh10, AAV-rh39, AAV-rh43 or AAV Anc80 capsid. In some embodiments, an rAAV capsid is an rAAV Anc80 capsid. In some embodiments, an rAAV Anc80 capsid is an rAAV Anc80L65 capsid.

In some embodiments, an AAV particle as described herein is for use in the treatment of an otological disease characterized by neovascularization and/or one or more symptoms associated with the otological disease. In some embodiments, use of an AAV particle as described herein for the manufacture of a medicament to treat an otological disease characterized by neovascularization and/or one or more symptoms associated with the otological disease. In some embodiments, one or more symptoms associated with the otological disease comprise hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, or death.

The present disclosure provides a composition comprising a construct as described herein and/or an AAV particle as described herein.

In some embodiments, a composition is a pharmaceutical composition. In some embodiments, a composition comprises a pharmaceutically acceptable carrier.

In some embodiments, a composition (e.g., a pharmaceutical composition) comprising an AAV particle described herein, e.g., rAAV-antiVEGF particle, is administered at a dose (e.g., amount) of about $1\times10^{11}$ vg/mL to about $1\times10^{15}$ vg/mL. In some embodiments, a composition (e.g., a pharmaceutical composition) comprising an AAV particle described herein, e.g., rAAV-antiVEGF particle, is administered at a dose (e.g., amount) of $2.5\times10^{12}$ vg/mL+/−10%. In some embodiments, a composition (e.g., a pharmaceutical composition) comprising an AAV particle described herein, e.g., rAAV-antiVEGF particle, is administered at a dose (e.g., amount) of $5\times10^{12}$ vg/mL+/−10%. In some embodiments, a composition (e.g., a pharmaceutical composition) comprising an AAV particle described herein, e.g., rAAV-antiVEGF particle, is administered at a dose (e.g., amount) of $1\times10^{13}$ vg/mL+/−10%.

In some embodiments, a composition (e.g., a pharmaceutical composition) comprising an AAV particle described herein, e.g., rAAV-antiVEGF particle, is administered at a dose of about $1\times10^{10}$ to about $1\times10^{13}$ vg/cochlea. In some embodiments, a composition (e.g., a pharmaceutical composition) comprising an AAV particle described herein, e.g., rAAV-antiVEGF particle, is administered at a dose of about $2.3\times10^{11}$ vg/cochlea. In some embodiments, a composition (e.g., a pharmaceutical composition) comprising an AAV particle described herein, e.g., rAAV-antiVEGF particle, is administered at a dose of about $4.5\times10^{11}$ vg/cochlea. In some embodiments, a composition (e.g., a pharmaceutical composition) comprising an AAV particle described herein, e.g., rAAV-antiVEGF particle, is administered at a dose of about $9\times10^{11}$ vg/cochlea.

In some embodiments, a composition (e.g., a pharmaceutical composition) comprising an AAV particle described herein, e.g., rAAV-antiVEGF particle, is administered to a subject at a volume of about 0.01 mL to 0.1 mL. In some embodiments, a composition (e.g., a pharmaceutical composition) comprising an AAV particle described herein, e.g., rAAV-antiVEGF particle, is administered to a subject at a volume of about 0.09 mL.

In some embodiments, a composition as described herein is for use in the treatment of an otological disease, e.g., in a mammal, which otological disease is characterized by neovascularization and/or one or more symptoms associated with the otological disease. In some embodiments, use of a construct as described herein is provided for the manufacture of a medicament to treat an otological disease, e.g., in a mammal, which otological disease is characterized by neovascularization and/or one or more symptoms associated with the otological disease. In some embodiments, one or more symptoms associated with the otological disease comprises hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, death, or a combination thereof.

In some embodiments, a composition as described herein is for use in the treatment of an inner ear disorder, e.g. in a mammal. In some embodiments, use of a construct as described herein is provided for the manufacture of a medicament to treat an inner ear disorder, e.g., in a mammal. In some embodiments, an inner ear disorder comprises acoustic neuroma, vestibular schwannoma, or neurofibromatosis type II. In some embodiments, an inner ear disorder is or comprises acoustic neuroma. In some embodiments, an inner ear disorder is or comprises vestibular schwannoma. In some embodiments, an inner ear disorder is or comprises neurofibromatosis type II.

In some embodiments, a composition as described herein is for use in the treatment of vestibular schwannoma, e.g. in a mammal. In some embodiments, use of a construct as described herein is provided for the manufacture of a medicament to treat vestibular schwannoma, e.g., in a mammal.

In some embodiments of any of the methods or uses disclosed herein, the mammal is a human.

The present disclosure also provides a cell. In some embodiments, a cell comprises a construct as described herein, an rAAV particle as described herein, and/or a composition as described herein.

In some embodiments, a cell is in vivo, ex vivo, or in vitro.

In some embodiments, a cell is a mammalian cell. In some embodiments, a cell is a human cell. In some embodiments, a human cell is in the ear of a subject.

In some embodiments, a cell is immortalized to generate a stable cell line.

The present disclosure provides a system. A system comprises a construct as described herein, an rAAV particle as described herein, a composition as described herein, and/or a cell as described herein.

The present disclosure provides a method. In some embodiments, a method comprises contacting a cell with a construct as described herein, an rAAV particle as described herein, and/or a composition as described herein.

In some embodiments, a cell is a cell of a subject.

In some embodiments, a cell is an ear cell. In some embodiments, a cell is an inner ear cell. In some embodiments, an inner ear cell is an outer hair cell. In some embodiments, an inner ear cell is an inner hair cell.

In some embodiments, an inner ear cell is in vitro or ex vivo.

In some embodiments, a method comprises introducing a construct as described herein, an rAAV particle as described herein, and/or a composition as described herein into the inner ear of a subject.

In some embodiments, a construct, rAAV particle, or composition is introduced into a cochlea of a subject. In some embodiments, a construct, rAAV particle, or composition is introduced via a round window membrane injection.

In some embodiments, a method comprises measuring a hearing level of a subject. In some embodiments, a hearing level is measured by performing an auditory brainstem response (ABR) test.

In some embodiments, a method comprises comparing a hearing level of a subject to a reference hearing level. In some embodiments, a reference hearing level is a published or historical reference hearing level.

In some embodiments, a hearing level of a subject is measured after a construct as described herein, an rAAV particle as described herein, and/or a composition as described herein is introduced, and a reference hearing level is a hearing level of a subject that was measured before a construct as described herein, an rAAV particle as described herein, and/or a composition as described herein was introduced.

In some embodiments, a method comprises measuring a level of a vascular endothelial growth factor (VEGF) binding agent or portion thereof in a subject.

In some embodiments, a level of a vascular endothelial growth factor (VEGF) binding agent or portion thereof is measured in an inner ear of a subject. In some embodiments, a level of a vascular endothelial growth factor (VEGF) binding agent or portion thereof is measured in a cochlea of a subject.

In some embodiments, a method comprises comparing a level of a vascular endothelial growth factor (VEGF) binding agent or portion thereof in a subject to a reference level of vascular endothelial growth factor (VEGF) binding agent or portion thereof.

In some embodiments, a reference level of vascular endothelial growth factor (VEGF) binding agent or portion thereof is a published or historical reference level of vascular endothelial growth factor (VEGF) binding agent or portion thereof.

In some embodiments, a level of the vascular endothelial growth factor (VEGF) binding agent or portion thereof in a subject is measured after a construct as described herein, an AAV particle as described herein, and/or a composition as described herein is introduced, and a reference level of vascular endothelial growth factor (VEGF) binding agent or portion thereof is a level a vascular endothelial growth factor (VEGF) binding agent or portion thereof in a subject that was measured before a construct as described herein, an AAV particle as described herein, and/or a composition as described herein was introduced.

In some embodiments, a method comprises measuring a dimension or volume of a tumor in a subject. In some embodiments, a dimension is a maximum diameter or length across a tumor.

In some embodiments, a method comprises comparing a dimension or volume of a tumor in the subject to a reference tumor dimension or volume, respectively.

In some embodiments, a reference tumor dimension or volume is a published or historical reference tumor dimension or volume.

In some embodiments, a dimension or volume of a tumor in a subject is measured after a construct as described herein, an AAV particle as described herein, and/or a composition as described herein is introduced, and a reference tumor dimension or volume is the dimension or volume of the tumor in the subject that was measured before a construct as described herein, an AAV particle as described herein, and/or a composition as described herein was introduced.

In some embodiments, a method is a method of treating hearing loss comprising administering a construct as described herein, an rAAV particle as described herein, and/or a composition as described herein to a subject in need thereof.

In some embodiments, a subject is suffering from or is at risk of an otological disease characterized by neovascularization. In some embodiments, an otological disease is or comprises an acoustic neuroma. In some embodiments, an otological disease is or comprises a vestibular schwannoma.

In some embodiments, a method is a method of treating an inner ear disorder comprising administering a construct as described herein, an rAAV particle as described herein, and/or a composition as described herein to a subject in need thereof. In some embodiments, an inner ear disorder is acoustic neuroma, vestibular schwannoma, or neurofibromatosis type II.

In some embodiments of any of the methods or uses disclosed herein, a subject is a human.

In some embodiments, one or more symptoms associated with an otological disease is alleviated or ameliorated following administration of a construct as described herein, an AAV particle as described herein, and/or a composition as described herein. In some embodiments, one or more symptoms comprise hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, or death.

In some embodiments, a method is a method of treating vestibular schwannoma.

In some embodiments, a method is a method of modulating the level of VEGF.

In some embodiments, a method is a method of modulating the level of active VEGF.

In some embodiments, a method is a method of decreasing the activity of VEGF.

The present disclosure provides a method comprising contacting a cell with a construct as described herein, and one or more constructs comprising an AAV Rep gene, AAV Cap gene, AAV VA gene, AAV E2a gene, and AAV E4 gene.

In some embodiments, a cell is an inner ear cell. In some embodiments, an inner ear cell is an outer hair cell. In some embodiments, an inner ear cell is an inner hair cell. In some embodiments, an inner ear cell is in an ear of a subject. In some embodiments, an inner ear cell is in vitro or ex vivo.

The present disclosure provides a population of cells comprising one or more cells as described herein, where the population is or comprises a stable cell line.

Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

The scope of the present disclosure is defined by the claims appended hereto and is not limited by certain embodiments described herein. Those skilled in the art, reading the present specification, will be aware of various modifications that may be equivalent to such described embodiments, or otherwise within the scope of the claims. In general, terms used herein are in accordance with their understood meaning in the art, unless clearly indicated otherwise. Explicit definitions of certain terms are provided below; meanings of these and other terms in particular instances throughout this specification will be clear to those skilled in the art from context.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an," as used herein, should be understood to include the plural referents unless clearly indicated to the contrary. Claims or descriptions that include "or" between one or more members of a group are considered satisfied if one, more than one, or all of the group members are present in, employed in, or otherwise relevant to a given product or process unless indicated to the contrary or otherwise evident from the context. In some embodiments, exactly one member of a group is present in, employed in, or otherwise relevant to a given product or process. In some embodiments, more than one, or all group members are present in, employed in, or otherwise relevant to a given product or process. It is to be understood that the present disclosure encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists (e.g., in Markush group or similar format), it is to be understood that each subgroup of the elements is also disclosed, and any element(s) can be removed from the group. It should be understood that, in general, where embodiments or aspects are referred to as "comprising" particular elements, features, etc., certain embodiments or aspects "consist," or "consist essentially of," such elements, features, etc. For purposes of simplicity, those embodiments have not in every case been specifically set forth in so many words herein. It should also be understood that any embodiment or aspect can be explicitly excluded from the claims, regardless of whether the specific exclusion is recited in the specification.

Throughout the specification, whenever a polynucleotide or polypeptide is represented by a sequence of letters (e.g., A, C, G, and T, which denote adenosine, cytidine, guanosine, and thymidine, respectively in the case of a polynucleotide), such polynucleotides or polypeptides are presented in 5' to 3' or N-terminus to C-terminus order, from left to right.

Administration: As used herein, the term "administration" typically refers to administration of a composition to a subject or system to achieve delivery of an agent to a subject or system. In some embodiments, an agent is, or is included in, a composition; in some embodiments, an agent is generated through metabolism of a composition or one or more components thereof. Those of ordinary skill in the art will be aware of a variety of routes that may, in appropriate circumstances, be utilized for administration to a subject, for example a human. For example, in some embodiments, administration may be systematic or local. In some embodiments, a systematic administration can be intravenous. In some embodiments, administration can be local. Local administration can involve delivery to cochlear perilymph via, e.g., injection through a round-window membrane or into scala-tympani, a scala-media injection through endolymph, perilymph and/or endolymph following canalostomy. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Allele: As used herein, the term "allele" refers to one of two or more existing genetic variants of a specific polymorphic genomic locus.

Amelioration: As used herein, the term "amelioration" refers to prevention, reduction or palliation of a state, or improvement of a state of a subject. Amelioration may include, but does not require, complete recovery or complete prevention of a disease, disorder or condition.

Amino acid: In its broadest sense, as used herein, the term "amino acid" refers to any compound and/or substance that can be incorporated into a polypeptide chain, e.g., through formation of one or more peptide bonds. In some embodiments, an amino acid has a general structure, e.g., $H_2N$—$C(H)(R)$—$COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than standard amino acids, regardless of whether it is prepared synthetically or obtained from a natural source. In some embodiments, an amino acid, including a carboxy- and/or amino-terminal amino acid in a polypeptide, can contain a structural modification as compared with general structure as shown above. For example, in some embodiments, an amino acid may be modified by methylation, amidation, acetylation, pegylation, glycosylation, phosphorylation, and/or substitution (e.g., of an amino group, a carboxylic acid group, one or more protons, and/or a hydroxyl group) as compared with a general structure. In some embodiments, such modification may, for example, alter circulating half-life of a polypeptide containing a modified amino acid as compared with one containing an otherwise identical unmodified amino acid. In some embodiments, such modification does not significantly alter a relevant activity of a polypeptide containing a modified amino acid, as compared with one containing an otherwise identical unmodified amino acid.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present invention is in a format selected from, but not limited to, intact IgA, IgG, IgE or IgM antibodies; bi- or multispecific antibodies (e.g., Zybodies®, etc); antibody fragments such as Fab fragments, Fab' fragments, F(ab')2 fragments, Fd' fragments, Fd fragments, and isolated CDRs or sets thereof;

single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody can include a heavy and/or light chain variable domain. In some embodiments, an antibody may not include a constant domain. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.].

Approximately or About: As used herein, the terms "approximately" or "about" may be applied to one or more values of interest, including a value that is similar to a stated reference value. In some embodiments, the term "approximately" or "about" refers to a range of values that fall within ±10% (greater than or less than) of a stated reference value unless otherwise stated or otherwise evident from context (except where such number would exceed 100% of a possible value). For example, in some embodiments, the term "approximately" or "about" may encompass a range of values that within 10%, 9%, 8%, 7%, 6%, 5%, 4%, 3%, 2%, 1%, or less of a reference value.

Associated: As used herein, the term "associated" describes two events or entities as "associated" with one another, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: As used herein, the term "biologically active" refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Characteristic portion: As used herein, the term "characteristic portion," in the broadest sense, refers to a portion of a substance whose presence (or absence) correlates with presence (or absence) of a particular feature, attribute, or activity of the substance. In some embodiments, a characteristic portion of a substance is a portion that is found in a given substance and in related substances that share a particular feature, attribute or activity, but not in those that do not share the particular feature, attribute or activity. In some embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to a sequence and/or structural identity specified above, shares at least one functional characteristic with the relevant intact substance. In some embodiments, a characteristic portion may be biologically active.

Characteristic sequence: As used herein, the term "characteristic sequence" is a sequence that is found in all members of a family of polypeptides or nucleic acids, and therefore can be used by those of ordinary skill in the art to define members of the family.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of a polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share a sequence element.

Combination therapy: As used herein, the term "combination therapy" refers to those situations in which a subject is simultaneously exposed to two or more therapeutic regimens (e.g., two or more therapeutic agents). In some embodiments, two or more agents may be administered simultaneously. In some embodiments, two or more agents may be administered sequentially. In some embodiments, two or more agents may be administered in overlapping dosing regimens.

Comparable: As used herein, the term "comparable" refers to two or more agents, entities, situations, sets of conditions, subjects, populations, etc., that may not be identical to one another but that are sufficiently similar to permit comparison therebetween so that one skilled in the art will appreciate that conclusions may reasonably be drawn based on differences or similarities observed. In some embodiments, comparable sets of agents, entities, situations, sets of conditions, subjects, populations, etc. are characterized by a plurality of substantially identical features and one or a small number of varied features. Those of ordinary skill in the art will understand, in context, what degree of identity is required in any given circumstance for two or more such agents, entities, situations, sets of conditions, subjects, populations, etc. to be considered comparable. For example, those of ordinary skill in the art will appreciate that sets of agents, entities, situations, sets of conditions, subjects, populations, etc. are comparable to one another when characterized by a sufficient number and type of substantially identical features to warrant a reasonable conclusion that differences in results obtained or phenomena observed under or with different sets of circumstances, stimuli, agents, entities, situations, sets of conditions, subjects, populations, etc. are caused by or indicative of the variation in those features that are varied.

Construct: As used herein, the term "construct" refers to a composition including a polynucleotide capable of carrying at least one heterologous polynucleotide. In some embodiments, a construct can be a plasmid, a transposon, a cosmid, an artificial chromosome (e.g., a human artificial chromosome (HAC), a yeast artificial chromosome (YAC), a bacterial artificial chromosome (BAC), or a P1-derived artificial chromosome (PAC)) or a viral construct, and any Gateway® plasmids. A construct can, e.g., include sufficient cis-acting elements for expression; other elements for expression can be supplied by the host primate cell or in an in-vitro expression system. A construct may include any genetic element (e.g., a plasmid, a transposon, a cosmid, an artificial chromosome, or a viral construct, etc.) that is capable of replicating when associated with proper control elements. Thus, in some embodiments, "construct" may include a cloning and/or expression construct and/or a viral construct (e.g., an adeno-associated virus (AAV) construct, an adenovirus construct, a lentivirus construct, or a retrovirus construct).

Conservative: As used herein, the term "conservative" refers to instances describing a conservative amino acid substitution, including a substitution of an amino acid residue by another amino acid residue having a side chain R group with similar chemical properties (e.g., charge or hydrophobicity). In general, a conservative amino acid substitution will not substantially change functional properties of interest of a protein, for example, ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, which is incorporated herein in its entirety by reference. In some embodiments, a substitution is a moderately conservative substitution wherein the substitution has a nonnegative value in the PAM250 log-likelihood matrix. One skilled in the art would appreciate that a change (e.g., substitution, addition, deletion, etc.) of amino acids that are not conserved between the same protein from different species is less likely to have an effect on the function of a protein and therefore, these amino acids should be selected for mutation. Amino acids that are conserved between the same protein from different species should not be changed (e.g., deleted, added, substituted, etc.), as these mutations are more likely to result in a change in function of a protein.

CONSERVATIVE AMINO ACID SUBSTITUTIONS

| For Amino Acid | Code | Replace With |
|---|---|---|
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. 4,511,390, incorporated herein in its entirety by reference) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |

-continued

| CONSERVATIVE AMINO ACID SUBSTITUTIONS | | |
|---|---|---|
| For Amino Acid | Code | Replace With |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Control: As used herein, the term "control" refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. For example, in one experiment, a "test" (i.e., a variable being tested) is applied. In a second experiment, a "control," the variable being tested is not applied. In some embodiments, a control is a historical control (e.g., of a test or assay performed previously, or an amount or result that is previously known). In some embodiments, a control is or comprises a printed or otherwise saved record. In some embodiments, a control is a positive control. In some embodiments, a control is a negative control.

Determining, measuring, evaluating, assessing, assaying and analyzing: As used herein, the terms "determining," "measuring," "evaluating," "assessing," "assaying," and "analyzing" may be used interchangeably to refer to any form of measurement, and include determining if an element is present or not. These terms include both quantitative and/or qualitative determinations. Assaying may be relative or absolute. For example, in some embodiments, "Assaying for the presence of" can be determining an amount of something present and/or determining whether or not it is present or absent.

Engineered: In general, as used herein, the term "engineered" refers to an aspect of having been manipulated by the hand of man. For example, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity. In some embodiments, "engineering" comprises "humanization" of a coding sequence. In some embodiments, "humanization" can include introducing human non-coding sequences, such as introns and regulatory elements, into a non-human sequence. In some embodiments, "humanization" can include codon optimizing a nucleotide sequence for human usage. In some embodiments, "humanization" can include replacing a portion of a polypeptide (such as a domain, e.g., a framework region or a complementarity domain region) or a nucleotide sequence (e.g., coding or non-coding) with a human polypeptide or nucleotide sequence.

Excipient: As used herein, the term "excipient" refers to an inactive (e.g., non-therapeutic) agent that may be included in a pharmaceutical composition, for example to provide or contribute to a desired consistency or stabilizing effect. In some embodiments, suitable pharmaceutical excipients may include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: As used herein, the term "expression" of a nucleic acid sequence refers to generation of any gene product (e.g., transcript, e.g., mRNA, e.g., polypeptide, etc.) from a nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, the term "functional" describes something that exists in a form in which it exhibits a property and/or activity by which it is characterized. For example, in some embodiments, a "functional" biological molecule is a biological molecule in a form in which it exhibits a property and/or activity by which it is characterized. In some such embodiments, a functional biological molecule is characterized relative to another biological molecule which is non-functional in that the "non-functional" version does not exhibit the same or equivalent property and/or activity as the "functional" molecule. A biological molecule may have one function, two functions (i.e., bifunctional) or many functions (i.e., multifunctional).

Gene: As used herein, the term "gene" refers to a DNA sequence in a chromosome that codes for a gene product (e.g., an RNA product, e.g., a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). As used herein, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid. In some embodiments, a gene may encode a polypeptide, but that polypeptide may not be functional, e.g., a gene variant may encode a polypeptide that does not function in the same way, or at all, relative to the wild-type gene. In some embodiments, a gene may encode a transcript which, in some embodiments, may be toxic beyond a threshold level. In some embodiments, a gene may encode a polypeptide, but that polypeptide may not be functional and/or may be toxic beyond a threshold level.

Hearing loss: As used herein, the term "hearing loss" may be used to a partial or total inability of a living organism to hear. In some embodiments, hearing loss may be acquired. In some embodiments, hearing loss may be hereditary. In some embodiments, hearing loss may be genetic. In some embodiments, hearing loss may be as a result of disease or trauma (e.g., physical trauma, treatment with one or more agents resulting in hearing loss, etc.). In some embodiments, hearing loss may be due to one or more known genetic causes and/or syndromes. In some embodiments, hearing loss may be of unknown etiology. In some embodiments, hearing loss may or may not be mitigated by use of hearing aids or other treatments.

Heterologous: As used herein, the term "heterologous" may be used in reference to one or more regions of a particular molecule as compared to another region and/or another molecule. For example, in some embodiments, heterologous polypeptide domains, refers to the fact that polypeptide domains do not naturally occur together (e.g., in the same polypeptide). For example, in fusion proteins generated by the hand of man, a polypeptide domain from one polypeptide may be fused to a polypeptide domain from a different polypeptide. In such a fusion protein, two polypeptide domains would be considered "heterologous" with respect to each other, as they do not naturally occur together.

Identity: As used herein, the term "identity" refers to overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of percent identity of two nucleic acid or polypeptide sequences, for example, can be performed by aligning two sequences for optimal comparison purposes (e.g., gaps can be introduced in one or both of a first and a second sequences for optimal alignment and non-identical sequences can be disregarded for comparison purposes). In some embodiments, a length of a sequence aligned for comparison purposes is at least 30%, at least 40%, at least 50%, at least 60%, at least 70%, at least 80%, at least 90%, at least 95%, or substantially 100% of length of a reference sequence; nucleotides at corresponding positions are then compared. When a position in the first sequence is occupied by the same residue (e.g., nucleotide or amino acid) as a corresponding position in the second sequence, then the two molecules (i.e., first and second) are identical at that position. Percent identity between two sequences is a function of the number of identical positions shared by the two sequences being compared, taking into account the number of gaps, and the length of each gap, which needs to be introduced for optimal alignment of the two sequences. Comparison of sequences and determination of percent identity between two sequences can be accomplished using a mathematical algorithm. For example, percent identity between two nucleotide sequences can be determined using the algorithm of Meyers and Miller (CABIOS, 1989, 4: 11-17, which is herein incorporated by reference in its entirety), which has been incorporated into the ALIGN program (version 2.0). In some embodiments, nucleic acid sequence comparisons made with the ALIGN program use a PAM120 weight residue table, a gap length penalty of 12 and a gap penalty of 4.

Improve, increase, enhance, inhibit or reduce: As used herein, the terms "improve," "increase," "enhance," "inhibit," "reduce," or grammatical equivalents thereof, indicate values that are relative to a baseline or other reference measurement. In some embodiments, a value is statistically significantly difference that a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment. In some embodiments, an appropriate reference is a negative reference; in some embodiments, an appropriate reference is a positive reference.

Nucleic acid: As used herein, the term "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in-vivo or in-vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments, a nucleic acid has a nucleotide sequence comprising at least one element that encodes, or is complementary to a sequence that encodes, a polypeptide. In some embodiments, a nucleic acid has enzymatic activity.

Operably linked: As used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with coding elements of interest; in some embodiments, control elements act in trans to or otherwise at a from the functional element of interest. In some embodiments, "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. In some embodiments, for example, a functional linkage may include transcriptional control. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

Pharmaceutical composition: As used herein, the term "pharmaceutical composition" refers to a composition in which an active agent is formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for, e.g., administration, for example, an injectable formulation that is, e.g., an aqueous or non-aqueous solution or suspension or a liquid drop designed to be administered into an ear canal. In some embodiments, a pharmaceutical composition may be formulated for administration via injection either in a particular organ or compartment, e.g., directly into an ear, or systemic, e.g., intravenously. In some embodiments, a formulation may be or comprise drenches (aqueous or non-aqueous solutions or suspensions), tablets, boluses, powders, granules, pastes, capsules, powders, etc. In some embodiments, an active agent may be or comprise an isolated, purified, or pure compound.

Pharmaceutically acceptable: As used herein, the term "pharmaceutically acceptable" which, for example, may be used in reference to a carrier, diluent, or excipient used to formulate a pharmaceutical composition as disclosed herein, means that a carrier, diluent, or excipient is compatible with other ingredients of a composition and not deleterious to a recipient thereof.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting a subject compound from one organ, or portion of a body, to another organ, or portion of a body. Each carrier must be is "acceptable" in the sense of being compatible with other ingredients of a formulation and not injurious to a patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Polyadenylation: As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. In some embodiments, a 3' poly(A) tail is a long sequence of adenine nucleotides (e.g., 50, 60, 70, 100, 200, 500, 1000, 2000, 3000, 4000, or 5000)(SEQ ID NO: 117) added to the pre-mRNA through the action of an enzyme, polyadenylate polymerase. In higher eukaryotes, a poly(A) tail can be added onto transcripts that contain a specific sequence, the polyadenylation signal or "poly(A) sequence." A poly(A) tail and proteins bound to it aid in protecting mRNA from degradation by exonucleases. Polyadenylation can be affect transcription termination, export of the mRNA from the nucleus, and translation. Typically, polyadenylation occurs in the nucleus immediately after transcription of DNA into RNA, but additionally can also occur later in the cytoplasm. After transcription has been terminated, the mRNA chain can be cleaved through the action of an endonuclease complex associated with RNA polymerase. The cleavage site can be characterized by the presence of the base sequence AAUAAA near the cleavage site. After mRNA has been cleaved, adenosine residues can be added to the free 3' end at the cleavage site. As used herein, a "poly(A) sequence" is a sequence that triggers the endonuclease cleavage of an mRNA and the additional of a series of adenosines to the 3' end of the cleaved mRNA.

Polypeptide: As used herein, the term "polypeptide" refers to any polymeric chain of residues (e.g., amino acids) that are typically linked by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may include one or more pendant groups or other modifications, e.g., modifying or attached to one or more amino acid side chains, at a polypeptide's N-terminus, at a polypeptide's C-terminus, or any combination thereof. In some embodiments, such pendant groups or modifications may be acetylation, amidation, lipidation, methylation, pegylation, etc., including combinations thereof. In some embodiments, polypeptides may contain L-amino acids, D-amino acids, or both and may contain any of a variety of amino acid modifications or analogs known in the art. In some embodiments, useful modifications may be or include, e.g., terminal acetylation, amidation, methylation, etc. In some embodiments, a protein may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, a protein is antibodies, antibody fragments, biologically active portions thereof, and/or characteristic portions thereof.

Polynucleotide: As used herein, the term "polynucleotide" refers to any polymeric chain of nucleic acids. In some embodiments, a polynucleotide is or comprises RNA; in some embodiments, a polynucleotide is or comprises DNA. In some embodiments, a polynucleotide is, comprises, or consists of one or more natural nucleic acid residues. In some embodiments, a polynucleotide is, comprises, or consists of one or more nucleic acid analogs. In some embodiments, a polynucleotide analog differs from a nucleic acid in that it does not utilize a phosphodiester backbone. Alternatively or additionally, in some embodiments, a polynucleotide has one or more phosphorothioate and/or 5'-N-phosphoramidite linkages rather than phosphodiester bonds. In some embodiments, a polynucleotide is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a polynucleotide is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, C-5 aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a polynucleotide comprises one or more modified sugars (e.g., 2'-fluororibose, ribose, 2'-deoxyribose, arabinose, and hexose) as compared with those in natural nucleic acids. In some embodiments, a polynucleotide has a nucleotide sequence that encodes a functional gene product such as an RNA or protein. In some embodiments, a polynucleotide includes one or more introns. In some embodiments, a polynucleotide is prepared by one or more of isolation from a natural source, enzymatic synthesis by polymerization based on a complementary template (in-vivo or in-vitro), reproduction in a recombinant cell or system, and chemical synthesis. In some embodiments, a polynucleotide is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a polynucleotide is partly or wholly single stranded; in some embodiments, a polynucleotide is partly or wholly double stranded. In some embodiments, a polynucleotide has a nucleotide sequence comprising at least one element that encodes, or is the complement of a sequence that encodes, a polypeptide. In some embodiments, a polynucleotide has enzymatic activity.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means.

Recombinant: As used herein, the term "recombinant" is intended to refer to polypeptides that are designed, engineered, prepared, expressed, created, manufactured, and/or or isolated by recombinant means, such as polypeptides expressed using a recombinant expression construct transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of a polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in-vivo or in-vitro) of a known sequence element, e.g., from a natural or synthetic source such as, for example, in the germline of a source organism of interest (e.g., of a human, a mouse, etc).

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference.

Regulatory Element: As used herein, the term "regulatory element" or "regulatory sequence" refers to non-coding regions of DNA that regulate, in some way, expression of one or more particular genes. In some embodiments, such genes are apposed or "in the neighborhood" of a given regulatory element. In some embodiments, such genes are located quite far from a given regulatory element. In some embodiments, a regulatory element impairs or enhances transcription of one or more genes. In some embodiments, a regulatory element may be located in cis to a gene being regulated. In some embodiments, a regulatory element may be located in trans to a gene being regulated. For example, in some embodiments, a regulatory sequence refers to a nucleic acid sequence which is regulates expression of a gene product operably linked to a regulatory sequence. In some such embodiments, this sequence may be an enhancer sequence and other regulatory elements which regulate expression of a gene product.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe (e.g., virus), a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to a qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. The term "substantially" is therefore used herein to capture a potential lack of completeness inherent in many biological and chemical phenomena.

Treatment: As used herein, the term "treatment" (also "treat" or "treating") refers to any administration of a therapy that partially or completely alleviates, ameliorates, eliminates, reverses, relieves, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively, or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of a given disease, disorder, and/or condition.

Tumor: As used herein, the term "tumor" refers to an abnormal growth of cells or tissue. In some embodiments, a tumor may comprise cells that are precancerous (e.g., benign), malignant, pre-metastatic, metastatic, and/or non-metastatic. In some embodiments, a tumor is associated with, or is a manifestation of, a cancer. In some embodiments, a tumor may be a disperse tumor or a liquid tumor. In some embodiments, a tumor may be a solid tumor.

Variant: As used herein, the term "variant" refers to a version of something, e.g., a gene sequence, that is different, in some way, from another version. To determine if something is a variant, a reference version is typically chosen and a variant is different relative to that reference version. In some embodiments, a variant can have the same or a different (e.g., increased or decreased) level of activity or functionality than a wild type sequence. For example, in some embodiments, a variant can have improved functionality as compared to a wild-type sequence if it is, e.g., codon-optimized to resist degradation, e.g., by an inhibitory nucleic acid, e.g., miRNA. Such a variant is referred to herein as a gain-of-function variant. In some embodiments, a variant has a reduction or elimination in activity or functionality or a change in activity that results in a negative outcome (e.g., increased electrical activity resulting in chronic depolarization that leads to cell death). Such a variant is referred to herein as a loss-of-function variant. For example, in some embodiments, a gene sequence is a wild-type sequence, which encodes a functional protein and exists in a majority of members of species with genomes containing the gene. In some such embodiments, a gain-offunction variant can be a gene sequence that contains one or more nucleotide differences relative to a wild-type gene sequence. In some embodiments, a gain-of-function variant is a codon-optimized sequence which encodes a transcript or polypeptide that may have improved properties (e.g., less susceptibility to degradation, e.g., less susceptibility to miRNA mediated degradation) than its corresponding wild type (e.g., non-codon optimized) version. In some embodiments, a loss-of-function variant has one or more changes that result in a transcript or polypeptide that is defective in some way (e.g., decreased function, non-functioning) relative to the wild type transcript and/or polypeptide.

VEGF inhibitor: As used herein, the term "VEGF inhibitor" is used interchangeably with the term "anti-VEGF protein".

BRIEF DESCRIPTION OF THE DRAWING

As shown in FIGS. 3A-3B of U.S. Provisional patent application 63/152,832 (the entire contents of which is incorporated herein by reference), perilymph is shown in light purple. FIG. 3A is a schematic of a coiled cochlea. The number of cochlear turns shown is representative of a mouse inner ear. FIG. 3B is a schematic showing a cross-section of the cochlea. In the schematic, scala tympani and scala vestibuli are filled with perilymph, while scala media is filled with endolymph (Talaei 2019, incorporated herein in its entirety by reference).

FIG. 4A includes an image of a delivery device as described herein (Appendix A, which is incorporated herein in its entirety by reference). A delivery device as shown is intended for intracochlear administration of injected fluid through the round window membrane, with a stopper to guide insertion depth. The stopper is shown in green in FIG. 4A of U.S. Provisional patent application 63/152,832, the entire contents of which is incorporated herein by reference. FIG. 4B includes an image showing an expected flow of injected fluid through scala tympani to scala vestibuli (via communication at the helicotrema at the cochlear apex) and then out of the cochlea through a vent placed in the stapes footplate of a delivery device within the oval window (Talei 2019, which is incorporated herein in its entirety by reference).

FIG. 6A is an exemplary rAAV-AntiVEGF construct that comprises, inter alia, sequences encoding an immunoglobulin heavy chain variable domain and an immunoglobulin light chain variable domain separated by a sequence encoding a self-cleaving peptide. Such a construct is referred to herein as a "$V_H/V_L$ construct," or an "rAAV-$V_H/V_L$ construct." Exemplary rAAV-$V_H/V_L$ include rAAV-ranibizumab and rAAV-ranibizumab-PC, which are rAAV-$V_H/V_L$s that encode ranibizumab. FIG. 6B is an exemplary rAAV-AntiVEGF construct that comprises, inter alia, sequences encoding an immunoglobulin heavy chain variable domain, an optional immunoglobulin heavy chain constant domain, an immunoglobulin light chain variable domain, an optional immunoglobulin light chain variable domain, and a green florescent protein (GFP). Each of these components may be separated by a sequence encoding a self-cleaving peptide. Such a construct may be referred to as an "ABGFP construct," or "rAAV-ABGFP construct." Exemplary rAAV-ABGFP include rAAV-ranibizumab-GFP and rAAV-bevacizumab-GFP, which are rAAV-ABGFPs that encode ranibizumab or bevacizumab. FIG. 6C is an exemplary rAAV-AntiVEGF construct that comprises, inter alia, sequences encoding an immunoglobulin heavy chain (comprising an immunoglobulin heavy chain variable domain and an immunoglobulin heavy chain constant domain), and immunoglobulin light chain (comprising an immunoglobulin light chain variable domain and an immunoglobulin light chain constant domain), with the chains separated by a sequence encoding a self-cleaving peptide. Such a construct is referred to herein as an "AB construct," or an "rAAV-AB construct." Exemplary rAAV-AB include rAAV-bevacizumab and rAAV-bevacizumab-PC, which are rAAV-ABs that encode bevacizumab. FIG. 6D is an exemplary rAAV construct that comprises, inter alia, sequences encoding a portion of VEGF Receptor Extracellular domain 1, VEGF Receptor Extracellular domain 2, and human immunoglobulin gamma (IgG) Fc. Such a construct may be referred to as a "VEGF TRAP construct," or "rAAV-TRAP construct." Exemplary rAAV-TRAP include rAAV-aflibercept and rAAV-aflibercept-PC, which are rAAV-TRAPs that encode aflibercept.

FIG. 8A is a graph showing the affinity of a control mouse anti-human VEGF monoclonal antibody (anti-hVEGF MmAb) in a buffer using recombinant human VEGF as the binding agent. In this assay, anti-hVEGF MmAb was prepared in CM at 100 µg/mL, then diluted to a final concentration of 10 µg/mL in 1× kinetics buffer. FIG. 8B is a graph showing the affinity of secreted proteins in culture medium from HEK cells transfected with rAAV-ranibizumab-PC construct corresponding to SEQ ID NO: 90 using recombinant human VEGF as the binding agent. FIG. 8C is a graph showing the affinity of secreted proteins in culture medium from HEK cells transfected with an rAAV-bevacizumab-PC construct corresponding to SEQ ID NO: 93 using recombinant human VEGF as the binding agent. FIG. 8D is a graph showing the affinity of secreted proteins in control culture medium (CM) from HEK cells that were not transfected with recombinant human VEGF as the binding agent.

As shown in FIG. 10 of U.S. Provisional patent application 63/152,832 (the entire contents of which is incorporated herein by reference), divergent residues are shown in blue, while ambiguous and dimorphic residues are shown in red.

FIG. 16A depicts RNA expression analysis, and demonstrates expression of the mRNA encoding ranibizumab and bevacizumab in cells of explants receiving rAAVAnc80-ranibizumab-PC or rAAVAnc80-bevacizumab-PC, respectively. No expression was detected in explants receiving vehicle. Results are presented as mean+SD. FIG. 16B depicts Meso Scale Discovery (MSD) mediated quantification of ranibizumab detected in the media of explants receiving various concentrations (1.4E10, 2.8E10, or 4.2E10 vg) of rAAVAnc80-ranibizumab-PC particles; ranibizumab was detected in the media of explants receiving rAAVAnc80-ranibizumab-PC particles but not of explants receiving vehicle. Open circles indicate ranibizumab concentration in individual samples (n=4/group), while bars represent the mean.

As shown in FIG. 17 of U.S. Provisional patent application 63/152,832 (the entire contents of which is incorporated herein by reference), phalloidin is shown in red and ranibizumab is shown in green. A human anti-ranibizumab antibody was used to detect the Fab segment of the proteins, which is shared between ranibizumab and bevacizumab. Clear labeling was detected in the IHCs and supporting cells lateral to the OHCs. Background staining was detected in the nerve fiber region of the cochlea (e.g., labeling of neuronal fibers was apparent for both the particle-injected and vehicle-injected cochleae), preventing reliable expression assessment in this particular area.

FIG. 20A depicts OHC counts for non-injected controls, vehicle injected controls, and test articles. FIG. 20B depicts IHC counts for non-injected controls, vehicle injected controls, and test articles. Counts for both FIGS. 20A and 20B were quantified and graphed as a function of treatment group and frequency region. The N for each group was either 9 or 10 animals, and the data are presented as mean+/−standard error of the mean (S.E.M). Control non-injected ear quantifications were from ears contralateral from control vehicle injected ears. *p<0.05, p<0.01, and *p<0.001 was made in comparison with the non-injected ear except for the bracket. p values were determined by a two-way ANOVA followed by a post-hoc Tukey's test.

FIG. 21A depicts hair cell (HC) counts for non-injected controls, vehicle injected controls, and test articles. FIG. 21B depicts non-hair cell (non-HC) counts for non-injected controls, vehicle injected controls, and test articles. Data are from Study 1, and are representative of populations of CBA/CaJ mice transduced with an rAAVAnc80-ranibizumab-PC (construct according to SEQ ID NO: 90) particles at 1.4E10 vg/cochlea, or rAAVAnc80-bevacizumab-PC (construct according to SEQ ID NO: 93) particles at 1.2E10 vg/cochlea. Quantification of transduced (Fab+) hair cells (FIG. 21A) and non-hair cells (FIG. 21B) are graphed as a function of treatment group and frequency region with data combined from both genders. The N for each group was either 9 or 10 animals, and the data are presented as mean+/−standard error of the mean (S.E.M). Control non-injected ear quantifications are from ears contralateral from control vehicle injected ears. No statistical comparisons were made due to the variability across samples.

FIG. 27A is a schematic of a computational modeling approach: depicting the three-dimensional diffusion of a constant source of anti-VEGF protein within a 90-µL sphere in relation to distance (in mm) from the surface of the sphere, e.g., the border of scala tympani/fundus. Distance from fundus to medial and lateral borders of tumors (<5 mm width) was estimated from data obtained from Koen 2020 which is incorporated herein in its entirety by reference (immediate FIG. 2). FIG. 27B represents a conservative modeling approach showing that perilymph anti-VEGF protein concentration decreases with diffusion distance, but remains within the reported biologically active range (area between 10-100% on the Y-axis and 0-11 mm on the X-axis) within the vicinity of the tumor in the internal auditory canal. Estimated anti-VEGF protein concentration varies with choice of diffusion coefficient, represented as a range (shaded area with solid dots) based on the three reported diffusion coefficients. A color image of FIG. 27B with shading is provided in FIG. 27B of U.S. Provisional patent application 63/152,832, the entire contents of which is incorporated herein by reference. The biologically active range, and predicted therapeutically-relevant range, was estimated as ~28 ng/mL; the concentration necessary to inhibit biological activity of VEGF-A by 50% in an in-vitro cellular proliferation assay is 11 to 27 ng/mL as described in Genentech 2017, incorporated herein in its entirety by reference).

DETAILED DESCRIPTION OF CERTAIN EMBODIMENTS

Figure 1:
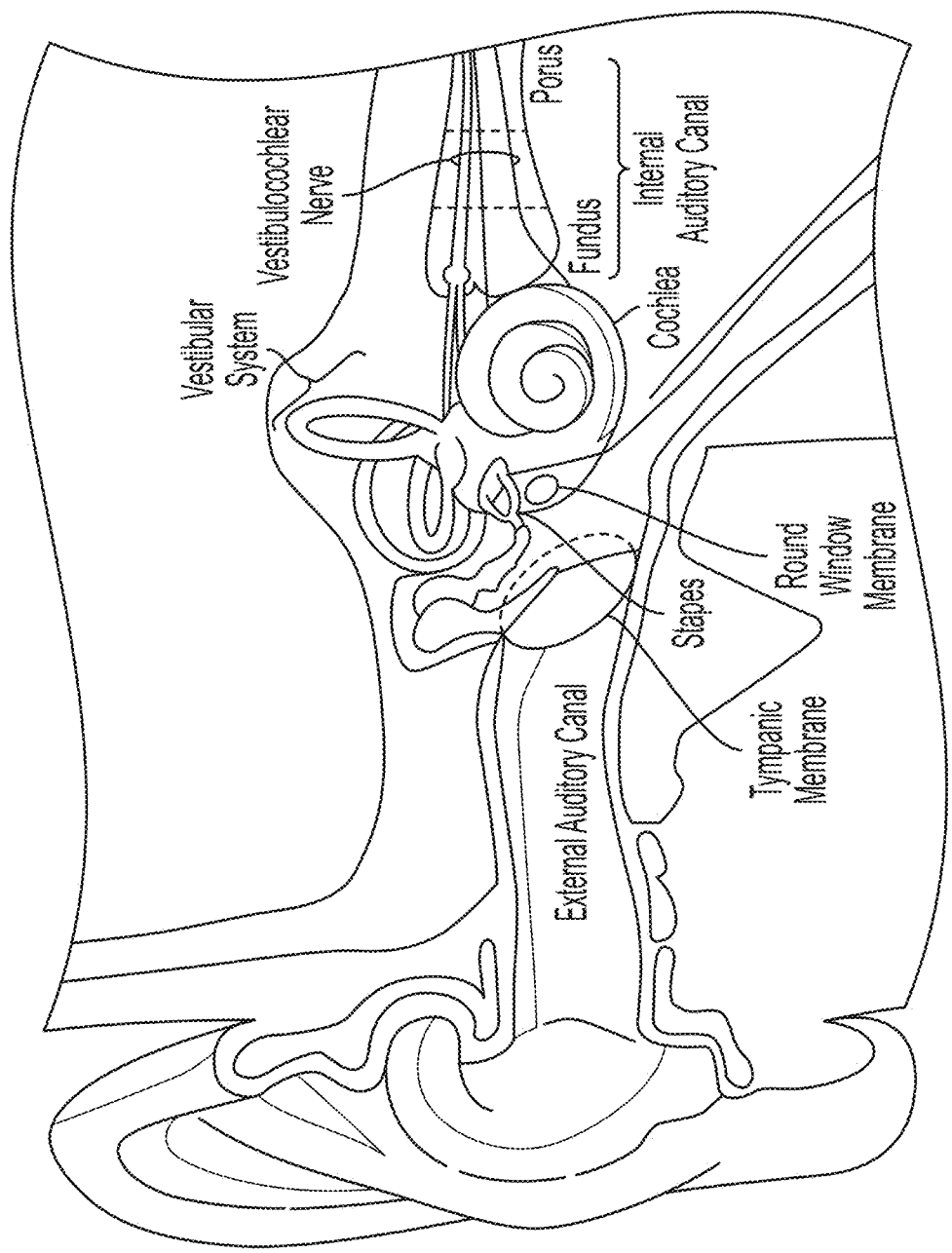
FIG. 1 is a schematic of a representative anatomy of the human ear, including common areas for vestibular schwannoma (VS) occurrence.

In certain embodiments, the present disclosure relates to an rAAV-antiVEGF particle intended for the treatment of subjects with otological diseases associated with neovascularization. In certain embodiments, such an otological disease associated with neovascularization is vestibular schwannoma (VS), or benign tumors that form in the cells around the vestibulocochlear nerve within the internal auditory canal. In certain embodiments, common symptoms associated with early VS include hearing loss, tinnitus, and dizziness; as tumors continue to grow, they can compress the brainstem, representing a significant concern for more serious morbidity and, in rare cases, mortality.

In certain embodiments, the present disclosure relates to an rAAV-antiVEGF particle intended for the treatment of subjects with an inner ear disorder, e.g., as described herein. In some embodiments, an inner ear disorder comprises acoustic neuroma, vestibular schwannoma, or neurofibromatosis type II. In some embodiments, an inner ear disorder is or comprises acoustic neuroma. In some embodiments, an inner ear disorder is or comprises vestibular schwannoma. In some embodiments, an inner ear disorder is or comprises neurofibromatosis type II.

In some embodiments, the present disclosure relates to an rAAV-antiVEGF particle intended for the treatment of subjects with vestibular schwannoma.

In certain cases, therapy with inhibitors of vascular endothelial growth factor (VEGF) offers an opportunity to attenuate progressive VS tumors, rather than using invasive alternatives such as surgical resection and/or radiation therapy, the current standard of care. In certain embodiments, clinical data support the use of a systemically administered VEGF inhibitor in patients with VS tumors from an efficacy perspective; however, long-term systemic administration of VEGF inhibitors is associated with significant safety concerns. In certain embodiments, rAAV-antiVEGF is designed and intended to treat individuals with VS by gene transfer to the inner ear to promote localized expression and secretion of an anti-VEGF protein. In certain embodiments, an objective is to provide local exposure of the therapeutic VEGF inhibitor (e.g., an anti-VEGF protein, e.g., bevacizumab, ranibizumab, and/or aflibercept) at the VS site, thereby limiting systemic exposure and minimizing the potential for the adverse effects associated with systemic administration.

In certain embodiments, cochlear and vestibular cells of the inner ear are transduced by rAAV-antiVEGF, and secrete anti-VEGF protein into perilymph: a cochlear fluid that is in diffusional continuity with the interstitial and perineural spaces of the vestibulocochlear nerve where VS tumors are located. In certain embodiments, a lack of barriers to diffusion along the internal auditory canal provides a potential path for therapeutic anti-VEGF protein expressed in perilymph to reach the intended VS target in the nerve interstitium. In certain embodiments, transduced cells of the cochlear modiolus are positioned to secrete the desired anti-VEGF protein directly into the interstitial fluid of the nerve.

In certain embodiments, escalating doses of compositions described herein (e.g., comprising an rAAV-antiVEGF) are administered via unilateral intracochlear injection to an individual (e.g., a mammal, e.g., a human patient in need thereof) with unilateral sporadic progressive VS. In certain embodiments, growth rates for these tumors are variable, and some VS tumors will not progress, in certain embodiments, an individual (e.g., a mammal, e.g., a human) may be limited to those individuals with tumors demonstrating clear evidence of progression, excluding those individuals with evidence of stable tumors on successive imaging evaluations. In certain embodiments, growth rates for these tumors are variable, and some VS tumors will not progress, in certain embodiments, an individual (e.g., a mammal, e.g., a human patient in need thereof) may be limited to those individuals with tumors demonstrating clear evidence of lack of progression, excluding those individuals with evidence of increasing tumor volume on successive imaging evaluations.

In certain embodiments, an individual (e.g., a mammal, e.g., a human patient in need thereof) with larger tumor(s) (e.g., tumors that have a greater potential to compress the brainstem) are excluded from treatment with compositions described herein, as in some embodiments, these individuals are at high risk for potentially life-threatening tumor-related sequelae that may potentially be avoided with the current standard of care of surgical resection and radiation therapy. In certain embodiments, individuals (e.g., a mammal, e.g., a human patient in need thereof) with larger tumors (e.g., tumors that have a greater potential to compress the brainstem) are expressly targeted for treatment with compositions described herein, as in some embodiments, these individuals are at high risk for potentially life-threatening tumor-related sequelae that may potentially be avoided using compositions as described herein in a less invasive manner and/or with greater or equal efficacy than the current standard of care of surgical resection and radiation therapy.

In certain embodiments, an individual (e.g., a mammal, e.g., a human) with growing tumors, where the tumor size is unlikely to impact brainstem, have the potential to derive greatest benefit from intervention with compositions as described herein (e.g., rAAV-antiVEGF therapy), while remaining candidates for future surgical resection and/or radiation as needed. In certain embodiments, an individual (e.g., a mammal, e.g., a human) with growing tumors, where the tumor size may impact the brainstem, have the potential to derive greatest benefit from intervention with compositions as described herein (e.g., rAAV-antiVEGF therapy), while remaining candidates for future surgical resection and/or radiation as needed.

In certain embodiment, provided herein are methods comprising introducing into an inner ear of an individual, e.g., a mammal, e.g., a human, an effective amount, e.g., a therapeutically effective amount, of an rAAV particle comprising a construct nucleotide sequence encoding: (a) a polypeptide comprising an antibody heavy chain variable domain operably linked to a signal peptide and a polypeptide comprising an antibody light chain variable domain operably linked to a signal peptide; or (b) a polypeptide comprising an antigen-binding antibody fragment (e.g., a Fab or a scFv) operably linked to a signal peptide.

In certain embodiments, compositions as described herein (e.g., rAAV-antiVEGF) may be administered in the surgical suite under controlled aseptic conditions by an otologic surgeon.

In some embodiments, provided herein are methods for increasing the level of an antibody, in an inner ear and/or internal auditory canal of an individual, e.g., a mammal, e.g., a human in need thereof, comprising: introducing into the inner ear of the mammal an effective amount, e.g., a therapeutically effective amount of an rAAV particle comprising a nucleotide sequence encoding: (a) a polypeptide comprising an antibody heavy chain variable domain operably linked to a signal peptide and a polypeptide comprising an antibody light chain variable domain operably linked to a signal peptide; or (b) a polypeptide comprising an antigen-binding antibody fragment (e.g., a Fab or a scFv) operably linked to a signal peptide; wherein the introducing results in an increase in the level of the antibody or the antigen binding antibody fragment in the inner ear of the individual, e.g., mammal, e.g., human.

In some embodiment, the disclosure provides methods for treating an inner ear disorder in an individual, e.g., a mammal, e.g., a human in need thereof, comprising introducing into the inner ear of the mammal an effective amount, e.g., a therapeutically effective amount, of an rAAV particle comprising a nucleotide sequence encoding: (a) a polypeptide comprising an antibody heavy chain variable domain operably linked to a signal peptide and a polypeptide comprising an antibody light chain variable domain operably linked to a signal peptide; or (b) a polypeptide comprising an antigen-binding antibody fragment linked to a signal peptide; where the introducing results in the treatment of the inner ear disorder in the mammal.

In some embodiments, provided herein are methods of reducing VEGF activity in an inner ear of an individual, e.g., a mammal, e.g., a human in need thereof, comprising introducing into the inner ear of the mammal an effective amount, e.g., a therapeutically effective amount, of an rAAV particle comprising a nucleotide sequence encoding (a) a polypeptide including an antibody heavy chain variable domain operably linked to a signal peptide and a polypeptide comprising an antibody light chain variable domain operably linked to a signal peptide; or (b) a polypeptide comprising an antigen-binding antibody fragment (e.g., a Fab or a scFv) operably linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; and wherein the introducing results in a reduction in VEGF activity in the inner ear of the individual, e.g., mammal or human.

In some embodiments, provided herein are methods of treating an otological disease associated with neovascularization, e.g., acoustic neuroma, VS, or neurofibromatosis type II in an inner ear of an individual (e.g., a mammal, e.g., a human) comprising: introducing into the inner ear of the individual an effective amount (e.g., a therapeutically effective amount) of an rAAV particle comprising a nucleotide sequence encoding (a) a polypeptide comprising an antibody heavy chain variable domain operably linked to a signal peptide and a polypeptide comprising an antibody light chain variable domain operably linked to a signal peptide; or (b) a polypeptide comprising an antigen-binding antibody fragment (e.g., a Fab or a scFv) operably linked to a signal peptide; wherein the polypeptide of (a) encodes an antibody that binds specifically to VEGF and reduces VEGF activity, the polypeptide of (b) encodes an antigen-binding antibody fragment that binds specifically to VEGF and reduces VEGF activity; and wherein the introducing results in treatment of the otological disease associated with neovascularization, e.g., acoustic neuroma or VS in the inner ear of the individual.

In some embodiment, provided herein are methods comprising introducing into an inner ear of an individual (e.g., a mammal, e.g., a human) an effective amount (e.g., a therapeutically effective amount) of an rAAV particle comprising a nucleotide sequence encoding a soluble VEGF receptor operably linked to a signal peptide.

In some embodiment, the disclosure provides methods for increasing the level of a soluble VEGF receptor in an inner ear of an individual (e.g., a mammal, e.g., a human) in need thereof, comprising introducing into the inner ear of the individual an effective amount (e.g., a therapeutically effective amount) of an rAAV particle comprising a nucleotide sequence encoding a soluble VEGF receptor operably linked to a signal peptide; wherein the introducing results in an increase in the level of the soluble VEGF receptor in the inner ear of the individual.

In some embodiment, provided herein are methods for treating an inner ear disorder in an individual (e.g., a mammal, e.g., a human) in need thereof comprising introducing into the inner ear of the individual an effective amount (e.g., a therapeutically effective amount) of an rAAV particle comprising a nucleotide sequence encoding at least a portion of a soluble VEGF receptor operably linked to a signal peptide; wherein the introducing results in the treatment of the inner ear disorder in the individual.

In some embodiment, provided herein are methods of reducing a VEGF activity in an inner ear of an individual (e.g., a mammal, e.g., a human) in need thereof comprising introducing into the inner ear of the individual an effective amount (e.g., a therapeutically effective amount) of an rAAV particle comprising a nucleotide sequence encoding at least a portion of a soluble VEGF receptor operably linked to a signal peptide; wherein the introducing results in a reduction in the VEGF activity in the inner ear of the individual.

In some embodiment, provided herein are methods of treating an otological disease associated with neovascularization, acoustic neuroma, VS, or neurofibromatosis type 2 in an inner ear (including e.g., the internal auditory canal) of an individual (e.g., a mammal, e.g., a human) that include introducing into the inner ear of the individual an effective amount (e.g., a therapeutically effective amount) of an rAAV particle comprising a nucleotide sequence encoding a nucleotide sequence encoding at least a portion of a VEGF receptor operably linked to a signal peptide; wherein the introducing results in treatment of the otological disease associated with neovascularization, acoustic neuroma, VS or neurofibromatosis type II, respectively, in the inner ear of the individual.

In other embodiments, the disclosure also provides kits comprising any of the rAAV particles described herein.

Additional non-limiting aspects of the compositions, kits, and methods are described herein and can be used in any combination without limitation.

Figure 2:
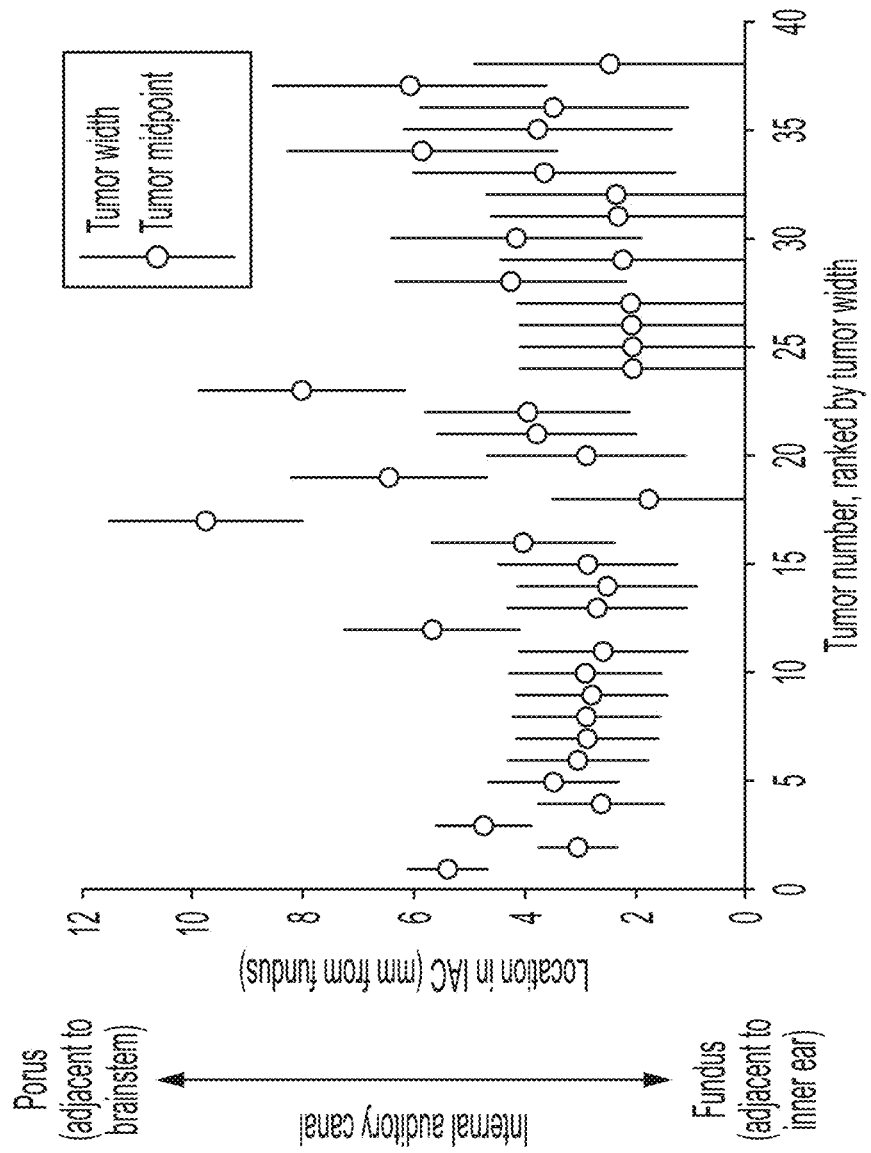
FIG. 2 is a graphical representation of VS (less than 5 mm width) locations within the internal auditory canal. In this analysis, the majority of small, intracanalicular VS (those located entirely in the internal auditory canal) were positioned close to the fundus of the internal auditory canal (e.g., within millimeters of the base of the cochlea), based on measurements from MRI scans (Koen 2020, incorporated herein in its entirety by reference). When the origin of these 38 tumors was localized to lateral, middle, and medial thirds of the internal auditory canal length, 60% originated within the lateral third (inner ear-adjacent) (Koen 2020, which is incorporated herein in its entirety by reference); when analyzing the distribution of these tumors as a function of percent of internal auditory canal length (normalized for modest internal auditory canal length [mm] variations between individuals), ~85% of the area under the curve was within the lateral (inner ear-adjacent) half of the internal auditory canal (Koen 2020, which is incorporated herein in its entirety by reference).
Figure 3B:
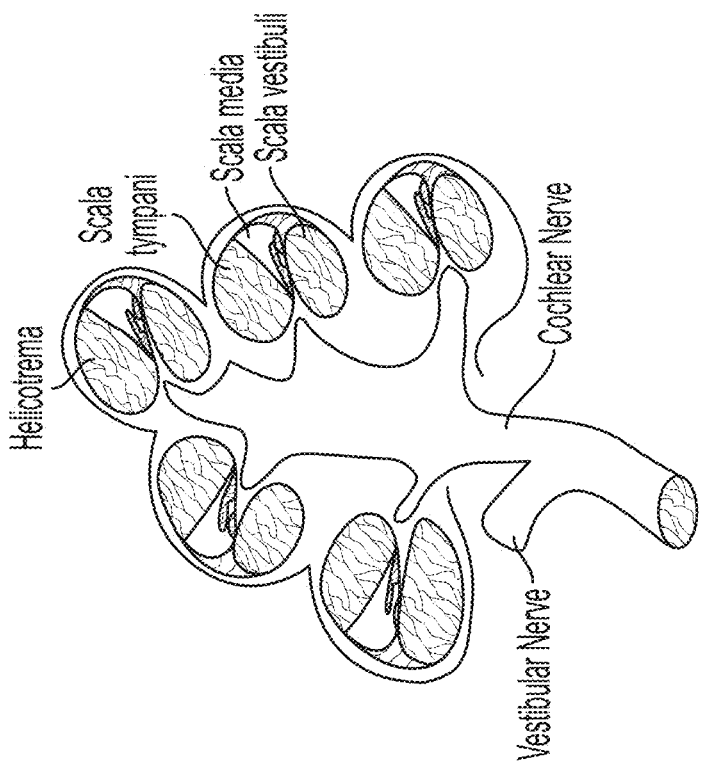
FIGS. 3A-3B is a schematic representation of an inner ear, indicating fluid continuity of perilymph between the vestibular system, on the left, and the cochlea (scala tympani, scala vestibuli), on the right.
Figure 3A:
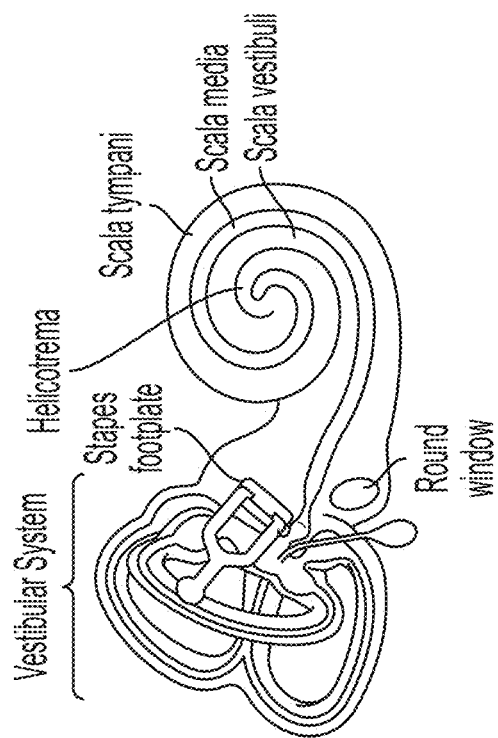

The present disclosure provides, inter alia, methods of gene therapy, e.g., using composition disclosed herein, to treat individuals with an otological disease associated with neovascularization, e.g., VS, by locally expressing secreted anti-VEGF protein in cells of the cochlea and vestibular system, in close proximity to and in diffusional continuity with the VS tumor environment in the internal auditory canal. In some embodiments, the method comprises gene transfer to the cochlea using an rAAV particle comprising a construct containing complimentary DNA (cDNA) encoding an anti-VEGF protein (rAAV-antiVEGF). Without wishing to be bound by theory, it is believed that in some embodiments, cochlear and vestibular cells of the inner ear transduced by an rAAV-antiVEGF (e.g., rAAVAnc80-antiVEGF) can secrete anti-VEGF protein into perilymph and the interstitial and perineural spaces of the vestibulocochlear nerve (comprised of the superior and inferior vestibular nerves and cochlear nerve). A majority of VS tumors originate in the lateral third, nearest the cochlea, of the internal auditory canal, which houses the vestibulocochlear nerve (FIGS. 1-3). The lack of barriers to diffusion along this canal results in the cochlear nerve being bathed in a continuum of fluid, with perilymph at its lateral end and CSF at its medial end; thus, diffusion from perilymph into the nerve interstitium provides a potential path for therapeutic anti-VEGF protein expressed in perilymph to reach the intended VS target. Although the precise mechanism by which VEGF inhibitors result in tumor control and regression is not fully understood, in some embodiments, mechanisms include decreasing vascular permeability and/or aberrant angiogenesis through inhibition of endothelial cell proliferation, as well as the normalization of tumor vasculature (Brastianos 2009, incorporated herein in its entirety by reference).

To date, there are no known gene transfer clinical trials comprising transfer to the inner ear using rAAV particles in humans; however, a clinical trial to evaluate an adenovirus particle comprising a construct encoding the complementary DNA (cDNA) for human Atonal transcription factor (Hath1) for the treatment of severe to profound hearing loss was initiated in 2014 and completed in 2019 (Clinicaltrials.gov 2020a [NCT02132130] which is incorporated herein in its entirety by reference).

In some embodiments, the delivery approach disclosed herein comprises a synthetic AAV capsid (e.g., AAVAnc80) for transduction of inner ear cells, and/or a device for targeted delivery directly to the cochlea.

The current standard of care for patients with VS includes several approaches and several treatment objectives (Doherty 2006; Kaul 2018, each of which is incorporated herein in its entirety by reference). Treatments include imaging/observation, surgery, and radiation therapy. Treatment objectives can include preservation of hearing, but often patients present with complete or partial deafness, and the size and growth of tumors can dictate more aggressive interventions that accept hearing loss as an inevitable consequence of therapy. Both surgery and radiation carry with them adverse effects; importantly, neither is associated with improvement in quality of life metrics compared to observation alone (Carlson 2015, incorporated herein in its entirety by reference), so there is a clear need for less invasive treatments that can mitigate the impact of tumor growth.

The clinical efficacy of systemically administered bevacizumab for controlling tumor growth and associated hearing loss in NF2 patients is not without significant risk, as the continued intravenous infusions required to maintain therapeutic benefit also increase the risk for serious complications; in a meta-analysis of studies using bevacizumab for NF2, the pooled incidence of serious toxicity (Grade 3 or 4) was 17%, based on a meta-analysis of five clinical trial populations comprising 125 patients (Lu 2019, incorporated herein in its entirety by reference). Hypertension, proteinuria, elevated liver enzymes, arterial thromboembolic events (ATE), venous thromboembolic events, hemorrhage, and surgery and wound healing complications have all been associated with high doses of bevacizumab therapy (Chen 2009; Hanna 2019, each of which is incorporated herein in its entirety by reference). Disclosed herein, inter alia, is an alternative approach to treating VS that, e.g., does not require high levels of circulating anti-VEGF protein (e.g., bevacizumab), and in some embodiments, can present lower risk to patients with respect to events related to systemic exposure to the therapeutic molecule.

In some embodiments, use of an intracochlear route of administration to deliver rAAV-antiVEGF to the inner ear, transduction of inner ear cells, and subsequent expression and/or secretion of an anti-VEGF protein (e.g., bevacizumab, ranibizumab, and/or aflibercept) can produce a sustained depot of the therapeutic drug in close proximity to the tumor. In some embodiments, cochlear and vestibular cells of the inner ear transduced by rAAV-antiVEGF can secrete anti-VEGF protein into nearby chambers (e.g., the perilymph, and cells of the cochlear modiolus, e.g., spiral ganglion neurons and satellite glial cells), and/or can secrete protein directly into the interstitial fluid of the cochlear nerve. In some embodiment, the lack of barriers to diffusion along the internal auditory canal results in the cochlear nerve being bathed in a continuum of fluid, with perilymph at its lateral end (nearest the cochlea, where the majority of VS tumors originate [FIGS. 1-3]) and CSF at its medial end. In some embodiments, diffusion from perilymph into the nerve interstitium provides a potential path for therapeutic anti-VEGF protein expressed in perilymph to reach the intended VS target.

In some embodiments, use of an intracochlear route of administration to deliver rAAV-antiVEGF to the inner ear, transduction of inner ear cells, and subsequent expression and/or secretion of an anti-VEGF protein (e.g., bevacizumab, ranibizumab, and/or aflibercept) results in non-therapeutically relevant or undetectable levels of anti-VEGF protein in non-cochlear tissue or fluid compartments. In some embodiments, an anti-VEGF protein is present at non-therapeutically relevant or undetectable levels in serum, CSF, liver, spleen, brainstem, auditory cortex, mandibular lymph nodes, or a combination thereof.

In some embodiments, local exposure to anti-VEGF proteins at the tumor surface can control tumor growth despite a different diffusion path to access and neutralize VEGF compared to extravasation of anti-VEGF proteins from the bloodstream. For example, Lichtenbeld et al., 1999 (incorporated herein in its entirety by reference) applied anti-VEGF proteins topically to tumors in mice and observed significantly reduced vascular permeability, notably at a 20-fold lower dose compared to a systemic dose that also achieved decreases in vascular permeability in mice to a similar degree (Yuan 1996, incorporated herein in its entirety by reference).

Without wishing to be bound by theory, it is believed in some embodiments that a low-level but sustained exposure to anti-VEGF protein in the fluid surrounding VS may stabilize and/or reduce tumor growth, through various mechanisms e.g., such as reducing permeability of tumor vessels and normalizing tumor vasculature. In some embodiments, by minimizing circulating levels of anti-VEGF proteins, local delivery of rAAV-antiVEGF to the ear and the resulting anti-VEGF protein exposure in the tumor microenvironment can provide a durable therapeutic benefit while minimizing risk of adverse events associated with systemic anti-VEGF protein administration.

Vestibular Schwannoma (VS)

VS (also called acoustic neuroma) is a benign, usually slow-growing tumor (or tumors) resulting from neoplasia of Schwann cells that ensheathe the vestibulocochlear nerve (also referred to as cranial nerve VIII). VS often originate on the superior or inferior vestibular branches of the vestibulocochlear nerve—the nerve responsible for transmitting information about sound and equilibrium from the inner ear to the brain (see e.g., FIGS. 1-3). These tumors often arise within the internal auditory canal (e.g., immediately adjacent to the inner ear) and can extend into the cerebellopontine angle; they can occur as sporadic unilateral tumors or, less commonly, as bilateral tumors, which generally occurs in the setting of neurofibromatosis type 2 (NF2). A common area for VS occurrence is along the vestibulocochlear nerve (see, e.g., FIGS. 1-3). Small, intracanalicular tumors (less than 5 mm width) can arise, e.g., within the lateral third of the internal auditory canal, nearest to the cochlea (Koen 2020, incorporated herein in its entirety by reference).

Common symptoms associated with VS include hearing loss, tinnitus, and dizziness. As tumors continue to grow and expand outside the internal auditory canal and into the cranial space, they can compress the brainstem, representing a significant concern for more serious morbidity and a threat to survival. In the current standard of care, small or non-growing tumors may be followed by observation only, while surgical resection and/or radiation therapy are indicated for larger and/or progressive tumors.

In certain embodiments, compositions and methods described herein may reduce and/or ameliorate symptoms associated with VS and/or current standard of care methods for treating VS. Such symptoms may include but are not limited to: hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, and/or death.

It is noteworthy that an increasing number of discovered VS tumors are asymptomatic and are identified in patients undergoing imaging for other indications (Reznitsky 2019, incorporated herein in its entirety by reference). In some cases, symptoms of VSs can arise from compression of the cochlear nerve and invasion of the vestibular branches of the vestibulocochlear nerve (cranial nerve VIII). While the facial nerve is often stretched and splayed by the tumor, facial paralysis is generally uncommon. In some cases, compression of the nearby trigeminal nerve, which is responsible for transmitting facial sensory information to the brain, can result in facial paresthesia. Although histologically benign, in some cases, large tumors can compress the brainstem and result in hydrocephalus, cerebellar herniation, and, in rare cases, death.

Hearing loss induced by VS is thought to be e.g., produced by compression of the cochlear nerve and/or by cochlear dysfunction, which is supported by the presence of cochlear pathology in most cases. The mechanisms of VS-induced hearing loss are hypothesized to include, e.g., degeneration of hair cells, alteration of biochemical milieu of inner ear fluids (e.g., toxic cytokines from the tumor), elevated intralabyrinthine protein, endolymphatic hydrops, cochlear aperture obstruction, intralabyrinthine hemorrhage, and/or disruption of cochlear vascular supply (Roosli 2012; Dilwali 2015; Remenschneider 2017, each of which is incorporated herein in its entirety by reference).

While current treatments may reduce risks associated with tumor growth, they are not associated with stabilization of hearing loss or tinnitus, and they can often result in adverse effects including unilateral loss of residual hearing, intractable headache, and facial nerve defects (Pedrosa 1994; Sampath 1997; Sardhara 2020, each of which is incorporated herein in its entirety by reference). While rare, radiation therapy also carries the additional risk of secondary malignancy (Kapurch 2016, incorporated herein in its entirety by reference). Estimates of hearing preservation following current treatment regimens for VS vary, but in a large-scale retrospective comparison of surgical resection procedures, Ansari reported a range of average post-operative hearing loss from 40.6 to 82.7%, depending on the surgical approach used, as well as tumor size and location; this included surgical approaches such as middle cranial fossa and retrosigmoid that, depending on tumor size, can be favored over a translabyrinthine approach specifically to facilitate greater hearing preservation (Ansari 2012, incorporated herein in its entirety by reference). Guidelines from the Congress of Neurological surgeons recommend counseling patients considering radiosurgery, microsurgery, or observation to expect a 50 to 75% chance of hearing loss within 10 years, as they describe only a moderately low probability (defined as >25 to 50%) of hearing preservation at 10 years with each of these treatment options (Carlson 2018, incorporated herein in its entirety by reference). No currently available standard treatment for VS carries with it the potential for hearing improvement.

Decision-making about treatment for sporadic VSs is complex. The presence of a tumor is generally confirmed via magnetic resonance imaging (MRI) and initial standard of care is based on the severity of symptoms and tumor size. At the time of diagnosis, approximately 20 to 30% of cases are less than 1 cm, approximately 30% of cases are 1 to 2 cm (inclusive), and the remainder of cases (approximately 40 to 50%) are greater 2 cm (Peris-Celda 2019, incorporated herein in its entirety by reference). With the increase in availability and utilization of MRI scanners, in general, these tumors are being discovered earlier (smaller) and more often at an asymptomatic stage (Reznitsky 2019, incorporated herein in its entirety by reference). In certain embodiments, the present disclosure provides compositions and methods that may be particularly amenable to halting or slowing the growth of and/or shrinking tumors that are less than 0.5 cm, less than 1 cm, less than 2 cm, less than 3 cm, less than 4 cm, or less than 5 cm.

In some cases, VS demonstrate variable and often unpredictable growth rates. This inherent behavior of the tumors is further complicated by variability in imaging modalities, tumor size estimates, and definitions of growth (Kondziolka 2012, incorporated herein in its entirety by reference). While overall tumor growth averages approximately 1 mm/year, between 30 and 60% of all tumors exhibit low or no apparent growth; for those that do grow, annual linear rates are between 2 and 3 mm/year (Paldor 2016; Lees 2018, each of which is incorporated herein in its entirety by reference). In some patients with small tumors, treatment comprises MRI scans alone, and additional treatment is considered only if the tumor displays measurable growth or if symptoms worsen (MacKeith 2013; Kirchmann 2017, each of which is incorporated in its entirety by reference herein). In some patients with tumors that continue to grow, and thus present a substantial increased risk for sequelae such as brainstem compression, current treatment options include surgical resection, radiation (Golfinos 2016, incorporated herein in its entirety by reference), or some combination of these approaches. While these treatments may reduce risks associated with tumor growth, they are not associated with long-term stabilization of hearing loss (Carlson 2018, incorporated herein in its entirety by reference) or improvement in tinnitus (Sardhara 2020, incorporated herein in its entirety by reference), and can often result in adverse effects including unilateral loss of residual hearing, intractable headache (Pedrosa 1994, incorporated herein in its entirety by reference), and facial nerve defects (Sampath 1997, incorporated herein in its entirety by reference). Currently, about half of all VS cases will eventually require surgical resection and/or radiation. In some embodiments, the present disclosure provides compositions and methods that reduce the risks associated with tumor growth, such as hearing loss, loss of speech understanding, tinnitus, loss of quality of life, brainstem compression, and/or death. In some embodiments, the present disclosure provides compositions and methods that reduce the risks associated, such as tumor growth, hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, and/or death.

Despite modern and recent improvements in both surgical and radiation therapies, in some embodiments, the more conservative approach of observation has gained favor; so long as the tumor is not growing, this represents the current best strategy to preserve remaining auditory function and minimize potential adverse impact of interventional treatments (MacKeith 2013; Kirchmann 2017; Torres Maldonado 2019, each of which is incorporated herein in its entirety by reference). In some embodiments, an improved treatment would be one that can promote VS stasis and/or regression, and thus circumvent the need for more invasive approaches including surgical resection or radiation therapy.

In the United States, the total incidence of VS is estimated to be 1.09 to 1.98 new cases per 100,000 population; thus, between 3300 and 6300 patients are diagnosed with VS in the US annually (Kshettry 2015; Ostrom 2018, each of which is incorporated herein in its entirety by reference). Increased reported incidence in recent years stems from the combination of an aging population and the continued enhancement of imaging technologies. The current standard of care for patients with VS includes several approaches and several treatment objectives (Doherty 2006; Kaul 2018, each of which is incorporated herein in its entirety by reference). Treatments include imaging/observation, surgery, and radiation therapy. Treatment objectives can include preservation of hearing, but often patients present with complete or partial deafness, and the size and growth of tumors can dictate more aggressive interventions that accept hearing loss as an inevitable consequence of therapy. Both surgery and radiation carry with them adverse effects; importantly, neither is associated with improvement in quality of life metrics compared to observation alone (Carlson 2015, incorporated herein in its entirety by reference), so there is a clear need for less invasive treatments that can mitigate the impact of tumor growth.

For many of these patients with growing tumors, or tumors that are compressing or may eventually compress the brainstem, observation alone may not be acceptable and surgical resection or radiation may be required to prevent impact to neurological function. In some cases, it is not possible to remove the whole tumor without certain injury to the facial nerve. In these cases, subtotal resection is often done to preserve facial nerve function; however, this treatment approach leaves residual tumor that can continue to grow. In some embodiments, compositions and methods described herein may be utilized as a combination therapy in conjunction with surgical resection and/or radiation therapy. In some embodiments, such combination therapy approaches reduce the risk of facial nerve injury, or residual tumor cell growth.

In some embodiments, therapeutic approaches described herein utilizing compositions described herein, e.g., rAAV-antiVEGF, attenuate tumor growth pharmacologically, while avoiding and/or minimizing adverse effects associated with current standard of care treatments such as surgical resection and/or radiation.

The current standard of care for VS has evolved over the past 2 to 3 decades, as imaging techniques have evolved and the ability to identify and track the growth of tumors has improved. There has been a progressive trend toward a conservative, observational "wait and rescan" approach, with a growing awareness that many tumors exhibit slow or low growth and may not impact hearing so long as the low growth rate is maintained (MacKeith 2013; Reznitsky 2019, each of which is incorporated herein in its entirety by reference).

In certain embodiments, interventions, methods, and/or compositions described herein comprise benefits, including the opportunity to augment conservative treatment approaches by, e.g., halting tumor growth, stabilizing hearing, and/or obviating the need for more invasive treatment approaches such as surgical resection and/or radiation therapy. While halting VS growth is likely to provide a substantial clinical benefit, it is also possible that in some embodiments, methods and therapies utilizing compositions described herein (e.g., rAAV-antiVEGF) could go beyond tumor stasis and drive shrinkage of tumors, restoration of speech understanding, and reduction in perceived difficulty of speech understanding, as demonstrated in studies of bevacizumab-treated VS tumors in NF2 patients (Huang 2018; Plotkin 2019, each of which is incorporated herein in its entirety by reference). In addition, studies with systemically administered VEGF inhibitor have shown improvements in NF2-related quality of life, including symptoms associated with VS in NF2 patients (Plotkin 2019, incorporated herein in its entirety by reference). However, these systemic administrations are often associated with negative side-effects. The results of these early studies may suggest that there is potential for anti-VEGF protein treatment to ameliorate and potentially combat the symptoms associated with VS. In certain embodiments, compositions described herein (e.g., rAAV-antiVEGF) may allow for less invasive treatment modalities, and sustained and localized expression of anti-VEGF protein in diffusional continuity with the tumor, potentially providing more concentrated and improved benefits of antiVEGF treatment without the systemic treatment associated side effects to patients with otological diseases associated with neovascularization (e.g., VS).

Vascular Endothelial Growth Factor (VEGF), and VEGF Inhibition in VS

New blood vessel development and vascularization have been found to be important factors in a number of tumor growth models, and may be important for VS growth. VEGF is one of the main regulators of angiogenesis. In certain cases, VEGF protein and its receptors are expressed in sporadic VS tumors (Cayé-Thomasen 2003; Plotkin 2009, each of which is incorporated herein in its entirety by reference), for instance all tumors examined in a study of 182 resected sporadic VS tumors expressed VEGF receptors (Koutsimpelas 2012, incorporated herein in its entirety by reference). In some cases, levels of VEGF protein and/or receptor expression in this type of schwannoma has been shown to correlate with tumor growth rates and/or growth indices determined by serial MRIs (Cayé-Thomasen 2005; Koutsimpelas 2007, each of which is incorporated herein in its entirety by reference) and with microvessel density (Koutsimpelas 2007, incorporated herein in its entirety by reference), suggesting a role for VEGF expression in VS growth. Additionally, systemic treatment with the VEGF inhibitor (bevacizumab) was effective in controlling growth and improving hearing in NF2 patients with VS. Without wishing to be bound by theory, it is believed that using VEGF inhibitors can result in the control of tumor growth, e.g., VS growth, by controlling vascular growth, e.g., tumor vascularization.

A VEGF gene encodes vascular endothelial growth factor (VEGF), formerly known as fms-like tyrosine kinase (Flt-1). A VEGF protein is a heparin-binding protein that induces migration and proliferation of vascular endothelial cells. Non-limiting examples of protein and nucleotide sequences encoding a wildtype VEGF protein are described herein.

In some embodiments, local exposure to anti-VEGF protein at the tumor surface has the potential to control tumor growth despite a different diffusion path to access and neutralize VEGF compared to extravasation of anti-VEGF protein from the bloodstream. For example, Lichtenbeld et al., 1999 (incorporated herein in its entirety by reference), applied anti-VEGF protein topically to tumors in mice and observed significantly reduced vascular permeability, notably at a 20-fold lower dose compared to a systemic dose that also achieved decreases in vascular permeability in mice to a similar degree (Yuan 1996, incorporated herein in its entirety by reference). Accordingly, in some embodiments, compositions as described herein (e.g., comprising rAAV-antiVEGF) deliver low-level but sustained exposure to anti-VEGF protein in the fluid surrounding VS, thus having the potential to stabilize and/or reduce tumor growth. In certain embodiments, compositions as described herein (e.g., comprising rAAV-antiVEGF) stabilize and/or reduce tumor growth by reducing permeability of tumor vessels and/or normalizing tumor vasculature.

In certain embodiments, anti-VEGF protein therapy, e.g., as described herein, for VS attenuates growing tumors without the need for invasive alternatives such as surgical resection and/or radiation therapy, thereby, e.g., avoiding the complications of surgical resection and/or radiation therapy. It has been suggested that systemically administered VEGF inhibitor (bevacizumab) may demonstrate efficacy in stabilizing or reducing VS growth and hearing loss sequelae in patients with neurofibromatosis type 2 (NF2), where tumors resulting from germline mutations in NF2 also highly express VEGF and its receptors (Plotkin 2009; Plotkin 2012; Lu 2019, each of which is incorporated herein in its entirety by reference). However, systemic administration of VEGF inhibitors for controlling VS growth in NF2 patients may also be associated with adverse effects, with a pooled incidence of serious toxicity (Grade 3 or 4) of 17% in a meta-analysis of five groups of clinical trial participants, comprising 125 patients (Lu 2019, incorporated herein in its entirety by reference).

In certain embodiments, compositions as described herein (e.g., rAAV-antiVEGF) can be used in a method of treating an individual (e.g., a mammal, e.g., a human) with VS by gene transfer to the inner ear to, e.g., promote expression and secretion of anti-VEGF protein. In certain embodiments, the compositions described herein, e.g., rAAV-antiVEGF, provide local exposure, e.g., in the inner ear, to the anti-VEGF protein. In certain embodiments, local exposure, e.g., in the inner ear, to the anti-VEGF protein at the VS site limits systemic exposure, and/or reduces, e.g., minimizes, potential adverse effects. In certain embodiments, compositions as described herein (e.g., rAAV-antiVEGF) comprise ranibizumab (48 kilodaltons [kDa]), a humanized monoclonal antibody fragment (Fab) derived from full-length murine anti-human VEGF monoclonal antibody. In certain embodiments, ranibizumab binds to VEGF and inhibits VEGF binding to its receptors VEGFR-1 and/or VEGFR-2, thereby reducing vascular leakage, aberrant angiogenesis, and/or tumor growth (Genentech 2017, incorporated herein in its entirety by reference).

In certain embodiments, cochlear and vestibular cells of the inner ear are transduced by compositions as described herein (e.g., comprising rAAV-antiVEGF). In certain embodiments, these cell types and/or others may secrete anti-VEGF protein into perilymph, which is an inner ear fluid that is in diffusional continuity with the interstitial and perineural spaces of the vestibulocochlear nerve, e.g., which is comprised of the superior and inferior vestibular nerves and the cochlear nerve, where the tumor is located. In some embodiments, a majority of VS tumors originate in the lateral third (nearest the cochlea) of the internal auditory canal, which houses the vestibulocochlear nerve. In some embodiments, lack of barriers to diffusion along this canal results in the cochlear nerve being bathed in a continuum of fluid, with perilymph at its lateral end and CSF at its medial end; thus, diffusion from perilymph into the nerve interstitium provides a potential path for therapeutic anti-VEGF protein expressed in perilymph to reach the intended VS target (Rask-Andersen 2006, incorporated herein in its entirety by reference). In some embodiments, spiral ganglion neurons and/or their satellite glial cells within the cochlear modiolus are transduced and/or transfected by compositions as described herein (e.g., comprising rAAV-antiVEGF), these cells are positioned to secrete protein directly into the interstitial fluid of the cochlear nerve.

In some embodiments, intracochlear administration of compositions described herein (e.g., rAAV-antiVEGF) has the potential to eliminate the need for future treatment and to preserve physiologic hearing in an individual (e.g., a mammal, e.g., a human) with an otological disease associated with neovascularization (e.g., VS), regardless of underlying etiology. In some embodiments, intracochlear administration of compositions described herein (e.g., rAAV-antiVEGF) has the potential to delay invasive treatment approaches, such as surgical resection and/or radiation therapy, and associated loss of physiologic hearing. In some embodiments, intracochlear administration of compositions described herein (e.g., rAAV-antiVEGF) is followed by subsequent standard of care treatments. In some embodiments, intracochlear administration of compositions described herein (e.g., rAAV-antiVEGF) occurs before and/or after radiation therapy. In some embodiments, administration of compositions described herein (e.g., rAAV-antiVEGF) may improve an individual's (e.g., a mammal's, e.g., a human's) response to radiotherapy by sensitizing the tumor and allowing for lower radiation dosing (Koutsimpelas 2012; Gao 2015, each of which is incorporated herein in its entirety by reference).

As described above, new blood vessel development and vascularization have been found to be important factors in VS growth (Koutsimpelas 2007; Wong 2010, each of which is incorporated herein in its entirety by reference), and VEGF is one of the main regulators of angiogenesis. In addition to the angiogenic effect, VEGF also provides cellular protection and resistance to apoptosis induced by irradiation (Koutsimpelas 2012, incorporated herein in its entirety by reference). Over the past decade, clinical data have emerged demonstrating that VEGF inhibitors can halt or reverse the growth of VS. Bevacizumab (Avastin®) is currently the only pharmacologic agent for which preliminary evidence of effectiveness, in the setting of NF2, has been demonstrated in patients with VS.

The initial clinical evidence was published more than ten years ago in a seminal paper by Plotkin et al. (Plotkin 2009, incorporated herein in its entirety by reference). In this study, ten NF2 patients (six men and four women with a median age of 25 years) with baseline tumor size of 2.2 to 38.7 cm$^3$ and baseline annual growth rates of 9 to 121%, and most presenting with hearing loss, were dosed with systemic bevacizumab 5 mg/kg every 2 weeks for an average of 12 months (3 to 19 months). After repeated bevacizumab dosing, tumors shrank in nine of ten patients, with six patients showing an MRI response of at least 20% reduction in tumor volume; responses were maintained in four of six patients during 11- to 16-month follow-up periods. The median best response to treatment for the nine of ten patients with smaller tumors was a volumetric reduction of 26%. Of the seven patients available for hearing testing, four demonstrated improvement, defined as a significant increase in word recognition score, two displayed stable hearing loss, and one demonstrated progressive hearing loss compared to baseline testing (Plotkin 2009, incorporated herein in its entirety by reference). Such results may suggest that this approach could potentially reverse progressive hearing loss observed in those with sustained tumor growth.

After this initial publication, a larger retrospective review of thirty-one NF2 patients treated systemically with intravenous bevacizumab (5 mg/kg every 2 weeks for 6 to 41 months; median duration 14 months) was reported (Plotkin 2012, incorporated herein in its entirety by reference). In this study of a similar patient population, 57% of evaluated patients demonstrated improvement in hearing, defined as increase in word recognition score from baseline, and 55% demonstrated a radiographic response, defined as at least a 20% decrease in tumor volume compared to baseline. When assessing long-term treatment response, 90% of patients had stable or improved hearing after one year and 61% of those patients continued that trend after three years. Additionally, 88% of patients had stable or decreased tumor size after one year of treatment and 54% of those patients remained stable at three years (Plotkin 2012, incorporated herein in its entirety by reference).

Most recently, Plotkin et al. published the results of a multicenter, prospective Phase 2 efficacy trial of systemic intravenous bevacizumab administration in NF2 patients with progressive VS (Plotkin 2019, incorporated herein in its entirety by reference). In this trial, patients (median age of 23 years) received bevacizumab systemically for six months at 10 mg/kg every two weeks, followed by eighteen months at 5 mg/kg every three weeks. Consistent with previous findings, interim trial results demonstrated that, six months into treatment, 41% of participants showed hearing improvement and 32% showed a radiographic response.

Preliminary efficacy and safety of systemically administered bevacizumab for NF2 patients with VS has also been reviewed in a meta-analysis of treatment outcomes from eight clinical trials conducted across the United States and Europe (Killeen 2019; Karajannis 2019; Lu 2019, each of which is incorporated herein in its entirety by reference). The treatment outcomes of 161 NF2 patients with 196 schwannomas across these eight studies, who received bevacizumab doses ranging from 5 to 10 mg/kg every 2 weeks (for an 11- to 22-month average range across the studies) were evaluated. Across these studies, the combined data demonstrate radiographic response (at least 20% volumetric reduction) in approximately 41% of schwannomas, tumor stability in approximately 47% of schwannomas, and tumor progression (at least 20% volumetric increase) in approximately 7% of schwannomas. In patients where audiometric data were available, these doses of bevacizumab were associated with improved hearing in approximately 20% of individuals, preserved hearing (stabilized hearing loss) in approximately 69% of individuals, and worsened hearing loss in approximately 6% of individuals. Subsequent surgical intervention was required in 11% of patients during the reported follow-up time. In addition, side effects of bevacizumab such as serious toxicity (including hypertension, proteinuria, and amenorrhea) were assessed. The pooled incidence of serious toxicity (Grade 3 or 4) was 17%, based on a meta-analysis of five groups of clinical trial participants, comprising 125 patients (Lu 2019, which is incorporated herein in its entirety by reference). In certain embodiments, the present disclosure provides methods and compositions suitable for fulfilling a long-met need of efficacious treatment of otological diseases associated with neovascularization while potentially avoiding negative consequences associated with systemic delivery of therapeutic anti-VEGF proteins.

The above described body of clinical data (showing from −30% to more than 60% response rates in tumor shrinkage) supports the systemic use of VEGF inhibitors to reduce VS growth and to improve associated symptoms of hearing loss despite the associated side-effects common with systemic use of VEGF inhibitors (Plotkin 2009; Plotkin 2012; Lu 2019; Plotkin 2019, each of which is incorporated herein in its entirety by reference). Without treatment, the mean growth rate of VS varies from 0.4 to 2.9 mm/year (Yoshimoto 2005, incorporated herein in its entirety by reference), with spontaneous tumor shrinkage reported to be from zero to 11% of tumors in studies of up to 212 patients (Tschudi 2000; Slattery 2004; Peyre 2013; Schnurman 2019, each of which is incorporated herein in its entirety by reference) or 3.8% of tumors in a large study of 1261 patients (Huang 2013, incorporated herein in its entirety by reference). The limitation to systemic anti-VEGF protein therapies, to date, has been the inevitability of adverse systemic effects. In certain embodiments, the disclosure provides methods of administering an anti-VEGF protein. In certain embodiments, methods and compositions are provided that utilize an Adeno-Associated Virus (AAV) delivery mechanism. In certain embodiments, such an AAV comprises a recombinant construct, and is referred to as a recombinant AAV (rAAV). Embodiments of such constructs are described in further detail below. In certain embodiments, compositions are provided to deliver localized anti-VEGF proteins, e.g., rAAV-antiVEGF, into the cochlea, e.g., in close proximity to the location of a tumor, e.g., VS. In some embodiments, administration of a VEGF inhibitor, e.g., rAAV-antiVEGF, into the cochlea reduces side effects associated with systemic delivery of VEGF inhibitors.

Despite their inadequacy in evaluating a biologically active dose range for a gene therapy particle delivered via an intracochlear route of administration for the treatment of VS, several mouse models have been utilized to generate data supporting the biological plausibility of VEGF inhibitors in reducing tumor vascular permeability. Using the cranial window model, Yuan et al. transplanted various human tumor cells lines and then administered an intravenous bolus of either neutralizing antibody against VEGF/VPF (vascular permeability factor) or phosphate-buffered saline control (Yuan 1996, incorporated herein in its entirety by reference). They showed that tumor vascular permeability to albumin in antibody-treated groups was lower than in the matched controls and that the tumor vessels became smaller in diameter and eventually disappeared after consecutive treatments. These data demonstrate that tumor vascular permeability can be reduced by neutralization of endogenous VEGF/VPF (Yuan 1996, incorporated herein in its entirety by reference). More recently, using both the sciatic nerve model and the intracranial window model, Gao et al. characterized the mechanism behind anti-VEGF protein treatment on bilateral VS (Gao 2015, incorporated herein in its entirety by reference). This group injected human HEI193 schwannoma cells into either the mouse sciatic nerve sheath or between the pia and arachnoid meninges of the right hemisphere of cranial window-implanted mice. After tumor size reached 4 mm in diameter, the VEGF inhibitor bevacizumab was administered 5 mg/kg/week via an intraperitoneal (IP) route. The resulting data demonstrated that bevacizumab alleviated tumor edema, improved neurological function, and transiently normalized tumor vasculature in the mouse.

These studies provide proof-of-concept data supporting the scientific rationale for the use of VEGF inhibitors to slow progression of schwannomas in the mouse, which is consistent with the preliminary clinical data in NF2 patients treated systemically with Avastin® (Plotkin 2009; Plotkin 2012; Lu 2019; Plotkin 2019, each of which is incorporated herein in its entirety by reference). One limitation of these prior studies is that they do not reflect the enduring exposure levels in a limited target location.

In certain embodiments, methods and compositions disclosed herein (e.g., comprising rAAV-antiVEGF), result in sustained levels of a VEGF inhibitor in a limited target location, e.g., in the inner ear. Without wishing to be bound by theory, it is believed that compositions disclosed herein, e.g., VEGF inhibitors, could enter VS tumor cells through direct uptake from the surrounding fluid bath, which is in continuity with the perilymphatic compartment of the inner ear through the nerve interstitium from which an inner ear supply of anti-VEGF protein may diffuse. In tumor-bearing mice, anti-VEGF protein applied topically to the tumor tissue, rather than through the bloodstream, resulted in beneficial effects such as reduced vascular permeability (Lichtenbeld 1999, incorporated herein in its entirety by reference).

In certain embodiments, the present disclosure provides methods and compositions suitable for delivery of VEGF inhibitors, e.g., rAAV-antiVEGF, locally to a tumor site. In some embodiments, these methods and compositions have the potential to maintain the benefit of anti-VEGF protein control of tumor growth while potentially minimizing the risk of serious toxicity that has been documented for systemic VEGF inhibitor administration. In certain embodiments, the present disclosure provides methods and compositions suitable for transduction of inner ear cells. In some embodiments, transduction of inner ear cells may enable long-lasting expression of anti-VEGF protein at and/or near the site of the tumor with minimal systemic exposure.

VEGF Polynucleotide Sequences

Among other things, the present disclosure provides polynucleotides, e.g., polynucleotides comprising a VEGF gene or characteristic portion thereof, as well as compositions including such polynucleotides and methods utilizing such polynucleotides and/or compositions.

In some embodiments, a polynucleotide comprising a VEGF gene or characteristic portion thereof can be DNA or RNA. In some embodiments, DNA can be genomic DNA or cDNA. In some embodiments, RNA can be an mRNA. In some embodiments, a polynucleotide comprises exons and/or introns of a VEGF gene.

In some embodiments, a gene product is expressed from a polynucleotide comprising a VEGF gene or characteristic portion thereof. In some embodiments, expression of such a polynucleotide can utilize one or more control elements (e.g., promoters, enhancers, splice sites, poly-adenylation sites, translation initiation sites, etc.). Thus, in some embodiments, a polynucleotide provided herein can include one or more control elements.

In some embodiments, a VEGF gene is a mammalian VEGF gene. In some embodiments, a VEGF gene is a murine VEGF gene. In some embodiments, a VEGF gene is a primate VEGF gene. In some embodiments, a VEGF gene is a human VEGF gene. In some embodiments, a VEGF gene is a genomic DNA sequence. In some embodiments, a VEGF gene is an RNA sequence which encodes a protein product. In some embodiments, a VEGF gene is a complementary DNA sequence which encodes the complement RNA sequence which encodes a protein product.

In some embodiments, an exemplary human VEGF gene is found at human Chromosomal location 6p21.1; location at NC_000006.12 (43770209 . . . 43786487) of the current 2020 assembly, and is known as VEGF-A with the NCBI Reference Sequence number: NG_008732.1. In some embodiments, an exemplary human VEGF gene is a cDNA sequence encompassed within the VEGF-A gene (e.g., VEGF-A transcript variant 1, transcript variant 2, transcript variant 3, etc.). In some embodiments, an exemplary human VEGF gene is one of the at least 9 known transcriptional isoforms of VEGF-A, one skilled in the art will understand these transcriptional isoforms may undergo alternative splicing to generate alternative translational isoforms. In some embodiments, an exemplary human VEGF-A gene is a cDNA sequence represented by transcript variant 1, encoding VEGF isoform A (NCBI Reference Sequence: NM_001025366.3). In some embodiments, an exemplary human VEGF-A gene is a cDNA sequence represented by transcript variant 2, encoding VEGF isoform B (NCBI Reference Sequence: NM_003376.6). In some embodiments, an exemplary human VEGF-A gene is a cDNA sequence represented by transcript variant 3, encoding VEGF isoform C (NCBI Reference Sequence: NM_001025367.3). In some embodiments, an exemplary human VEGF-A gene is a cDNA sequence represented by transcript variant 4, encoding VEGF isoform D (NCBI Reference Sequence: NM_001025368.3). In some embodiments, an exemplary human VEGF-A gene is a cDNA sequence represented by transcript variant 5, encoding VEGF isoform E (NCBI Reference Sequence: NM_001025369.3). In some embodiments, an exemplary human VEGF-A gene is a cDNA sequence represented by transcript variant 6, encoding VEGF isoform F (NCBI Reference Sequence: NM_001025370.3). In some embodiments, an exemplary human VEGF-A gene is a cDNA sequence represented by transcript variant 7, encoding VEGF isoform G (NCBI Reference Sequence: NM_001033756.3). In some embodiments, an exemplary human VEGF-A gene is a cDNA sequence represented by transcript variant 8, encoding VEGF isoform H (NCBI Reference Sequence: NM_001171622.2). In some embodiments, an exemplary human VEGF-A gene is a cDNA sequence represented by transcript variant, encoding VEGF isoform R (NCBI Reference Sequence: NM_001204385.2).

In some embodiments, an exemplary human VEGF gene is found at human Chromosomal location 11q13.1, at location NC_000011.10 (64234584 . . . 64239264), and is known as VEGF-B (NCBI Reference Sequence: NG_029823.1). In some embodiments, an exemplary human VEGF gene is a cDNA sequence encompassed within the VEGF-B gene e.g., VEGF-B transcript variant 167 (NCBI Reference Sequence: NM_001243733.2), and/or transcript variant 186 (NCBI Reference Sequence: NM_003377.5).

In some embodiments, an exemplary human VEGF gene is found at human Chromosomal location 4q34.1-q34.3, at location NC_000004.12 (176683538 . . . 176792922, complement), and is known as VEGF-C(NCBI Reference Sequence: NG_034216.1). In some embodiments, an exemplary human VEGF gene is a cDNA sequence encompassed within the VEGF-C gene, e.g., VEGF-C transcript variant 1 (NCBI Reference Sequence: NM_005429.5).

In some embodiments, an exemplary human VEGF gene is found at human Chromosomal location Xp22.2, at location NC_000023.11 (15345596 . . . 15384413, complement), and is known as VEGF-D (NCBI Reference Sequence: NG_012509.1). In some embodiments, an exemplary human VEGF gene is a genomic sequence or a cDNA sequence encompassed within the VEGF-D gene, e.g., VEGF-D transcript variant 1 (NCBI Reference Sequence: NM_004469.5).

VEGF Protein Sequences

In certain embodiments, proteins of interest are isoforms of the VEGF-A gene. This gene is a member of the PDGF (platelet-derived growth factor)/VEGF (vascular endothelial growth factor) family (PDGF/VEGF). It encodes a heparin-binding protein, which typically exists as a disulfide-linked homodimer. This growth factor induces proliferation and migration of vascular endothelial cells, and is essential for both physiological and pathological angiogenesis. Alternatively spliced transcript variants encoding different isoforms have been described. There is substantial evidence for alternative translation initiation from upstream non-AUG (CUG) codons resulting in additional isoforms. In some embodiments, proteins of interest are inhibitors of endogenous VEGF-A functions.

```
Exemplary Human VEGF-A isoform L-VEGF206
precursor (also known as Isoform A) amino
acid sequence
                                  (SEQ ID NO: 1)
MTDRQTDTAPSPSYHLLPGRRRTVDAAASRGQGPEPAPGGGVEGVGARGV

ALKLFVQLLGCSRFGGAVVRAGEAEPSGAARSASSGREEPQPEEGEEEEE

KEEERGPQWRLGARKPGSWTGEAAVCADSAPAARAPQALARASGRGGRVA

RRGAEESGPPHSPSRRGSASRAGPGRASETMNFLLSWVHWSLALLLYLHH

AKWSQAAPMAEGGGQNHHEVVKFMDVYQRSYCHPIETLVDIFQEYPDEIE

YIFKPSCVPLMRCGGCCNDEGLECVPTEESNITMQIMRIKPHQGQHIGEM

SFLQHNKCECRPKKDRARQEKKSVRGKGKGQKRKRKKSRYKSWSVYVGAR

CCLMPWSLPGPHPCGPCSERRKHLFVQDPQTCKCSCKNTDSRCKARQLEL

NERTCRCDKPRR

Exemplary Human VEGF-A isoform L-VEGF189
precursor (also known as Isoform B) amino
acid sequence
                                  (SEQ ID NO: 2)
MTDRQTDTAPSPSYHLLPGRRRTVDAAASRGQGPEPAPGGGVEGVGARGV

ALKLFVQLLGCSRFGGAVVRAGEAEPSGAARSASSGREEPQPEEGEEEEE

KEEERGPQWRLGARKPGSWTGEAAVCADSAPAARAPQALARASGRGGRVA

RRGAEESGPPHSPSRRGSASRAGPGRASETMNFLLSWVHWSLALLLYLHH

AKWSQAAPMAEGGGQNHHEVVKFMDVYQRSYCHPIETLVDIFQEYPDEIE

YIFKPSCVPLMRCGGCCNDEGLECVPTEESNITMQIMRIKPHQGQHIGEM

SFLQHNKCECRPKKDRARQEKKSVRGKGKGQKRKRKKSRYKSWSVPCGPC

SERRKHLFVQDPQTCKCSCKNTDSRCKARQLELNERTCRCDKPRR

Exemplary Human VEGF-A isoform VEGF111
precursor amino acid sequence
                                  (SEQ ID NO: 3)
MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHIGEMSFLQHNKCECRCDKPRR

Exemplary Human VEGF-A isoform VEGF121
precursor amino acid sequence
                                  (SEQ ID NO: 4)
MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHI GEMSFLQHNKCECRPKKDRARQEKCDKPRR

Exemplary Human VEGF-A isoform VEGF145
precursor amino acid sequence
                                  (SEQ ID NO: 5)
MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHIGEMSFLQHNKCECRPKKDRARQEKKSVRGKGKG

QKRKRKKSRYKSWSVCDKPRR

Exemplary Human VEGF-A isoform VEGF165A
precursor amino acid sequence
                                  (SEQ ID NO: 6)
MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHIGEMSFLQHNKCECRPKKDRARQENPCGPCSERR

KHLFVQDPQTCKCSCKNTDSRCKARQLELNERTCRCDKPRR

Exemplary Human VEGF-A isoform VEGF189
precursor amino acid sequence
                                  (SEQ ID NO: 7)
MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHIGEMSFLQHNKCECRPKKDRARQEKKSVRGKGKG

QKRKRKKSRYKSWSVPCGPCSERRKHLFVQDPQTCKCSCKNTDSRCKARQ

LELNERTCRCDKPRR

Exemplary Human VEGF-A isoform VEGF206
precursor amino acid sequence
                                  (SEQ ID NO: 8)
MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHIGEMSFLQHNKCECRPKKDRARQEKKSVRGKGKG

QKRKRKKSRYKSWSVYVGARCCLMPWSLPGPHPCGPCSERRKHLFVQDPQ

TCKCSCKNTDSRCKARQLELNERTCRCDKPRR
```

In certain embodiments, proteins of interest are isoforms of the VEGF-B gene. This gene encodes a member of the PDGF/VEGF. The VEGF family members regulate the formation of blood vessels and are involved in endothelial cell physiology. This member is a ligand for VEGFR-1 (vascular endothelial growth factor receptor 1) and NRP-1 (neuropilin-1). In some embodiments, proteins of interest are inhibitors of endogenous VEGF-B functions.

```
Exemplary Human VEGF-B isoform VEGFB-167
precursor amino acid sequence
                                  (SEQ ID NO: 9)
MSPLLRRLLLAALLQLAPAQAPVSQPDAPGHQRKVVSWIDVYTRATCQPR

EVVVPLTVELMGTVAKQLVPSCVTVQRCGGCCPDDGLECVPTGQHQVRMQ
```

ILMIRYPSSQLGEMSLEEHSQCECRPKKKDSAVKPDSPRPLCPRCTQHHQ

RPDPRTCRCRCRRRSFLRCQGRGLELNPDTCRCRKLRR

Exemplary Human VEGF-B isoform VEGFB-186
precursor amino acid sequence
(SEQ ID NO: 10)
MSPLLRRLLLAALLQLAPAQAPVSQPDAPGHQRKVVSWIDVYTRATCQPR

EVVVPLTVELMGTVAKQLVPSCVTVQRCGGCCPDDGLECVPTGQHQVRMQ

ILMIRYPSSQLGEMSLEEHSQCECRPKKKDSAVKPDRAATPHHRPQPRSV

PGWDSAPGAPSPADITHPTPAPGPSAHAAPSTTSALTPGPAAAAADAAAS

SVAKGGA

In certain embodiments, proteins of interest are isoforms of the VEGF-C gene. The protein encoded by this gene is a member of the PDGF/VEGF family. The encoded protein promotes angiogenesis and endothelial cell growth, and can also affect the permeability of blood vessels. The precursor protein is further cleaved into a fully processed form that can bind and activate VEGFR-2 and VEGFR-3 receptors. In some embodiments, proteins of interest are inhibitors of endogenous VEGF-C functions.

Exemplary Human VEGF-C precursor amino acid
sequence
(SEQ ID NO: 11)
MHLLGFFSVACSLLAAALLPGPREAPAAAAAFESGLDLSDAEPDAGEATAY

ASKDLEEQLRSVSSVDELMTVLYPEYWKMYKCQLRKGGWQHNREQANLNSR

TEETIKFAAAHYNTEILKSIDNEWRKTQCMPREVCIDVGKEFGVATNTFFK

PPCVSVYRCGGCCNSEGLQCMNTSTSYLSKTLFEITVPLSQGPKPVTISFA

NHTSCRCMSKLDVYRQVHSIIRRSLPATLPQCQAANKTCPTNYMWNNHICR

CLAQEDFMFSSDAGDDSTDGFHDICGPNKELDEETCQCVCRAGLRPASCGP

HKELDRNSCQCVCKNKLFPSQCGANREFDENTCQCVCKRTCPRNQPLNPGK

CACECTESPQKCLLKGKKFHHQTCSCYRRPCTNRQKACEPGFSYSEEVCRC

VPSYWKRPQMS

In certain embodiments, proteins of interest are isoforms of the VEGF-D gene. The protein encoded by this gene is a member of the PDGF/VEGF family and is active in angiogenesis, lymphangiogenesis, and endothelial cell growth. This secreted protein undergoes a complex proteolytic maturation, generating multiple processed forms which bind and activate VEGFR-2 and VEGFR-3 receptors. This protein is structurally and functionally similar to VEGF-C. In some embodiments, proteins of interest are inhibitors of endogenous VEGF-D functions.

Exemplary Human VEGF-D precursor amino acid
sequence
(SEQ ID NO: 12)
MYREWVVVNVFMMLYVQLVQGSSNEHGPVKRSSQSTLERSEQQIRAASSLE

ELLRITHSEDWKLWRCRLRLKSFTSMDSRSASHRSTRFAATFYDIETLKVI

DEEWQRTQCSPRETCVEVASELGKSTNTFFKPPCVNVFRCGGCCNEESLIC

MNTSTSYISKQLFEISVPLTSVPELVPVKVANHTGCKCLPTAPRHPYSIIR

RSIQIPEEDRCSHSKKLCPIDMLWDSNKCKCVLQEENPLAGTEDHSHLQEP

ALCGPHMMFDEDRCECVCKTPCPKDLIQHPKNCSCFECKESLETCCQKHKL

FHPDTCSCEDRCPFHTRPCASGKTACAKHCRFPKEKRAAQGPHSRKNP

VEGF, VEGF-R, and VEGF Binding Proteins

In some embodiments, proteins of interest are ones that can bind VEGF. In some embodiments, VEGF binding proteins can be or comprise antibodies, and/or fragments thereof. In some embodiments, VEGF binding proteins can be or comprise vascular endothelial growth factor receptor (VEGFR) proteins, and/or fragments thereof.

As described above, data has been generated that may support the biological plausibility of VEGF inhibitors in reducing tumor vascular permeability. In some embodiments, such data was generated using mouse models, which have been utilized to generate data supporting the biological plausibility of VEGF inhibitors in reducing tumor vascular permeability. In some embodiments, such mouse models are not ideal for evaluating biologically active dose ranges for gene therapy particles which are delivered via an intracochlear route of administration, e.g., for the treatment of VS. Using the cranial window model, Yuan et al. transplanted various human tumor cells lines and then administered an intravenous bolus of either neutralizing antibody against VEGF/VPF (vascular permeability factor) or phosphate-buffered saline control (Yuan 1996, incorporated herein in its entirety by reference). The Authors showed that tumor vascular permeability to albumin in antibody-treated groups was lower than in the matched controls and that the tumor vessels became smaller in diameter and eventually disappeared after consecutive treatments. These data demonstrate that tumor vascular permeability can be reduced by neutralization of endogenous VEGF/VPF (Yuan 1996, incorporated herein in its entirety by reference). More recently, using both the sciatic nerve model and the intracranial window model, Gao et al. sought to characterize the mechanism behind anti-VEGF protein treatment on bilateral VS (Gao 2015, incorporated herein in its entirety by reference). This group injected human HEI193 schwannoma cells into either the mouse sciatic nerve sheath or between the pia and arachnoid meninges of the right hemisphere of cranial window-implanted mice. After tumor size reached 4 mm in diameter, the VEGF inhibitor bevacizumab was administered 5 mg/kg/week via an intraperitoneal (IP) route. The resulting data demonstrate that bevacizumab alleviated tumor edema, improved neurological function, and transiently normalized tumor vasculature in the mouse.

Taken together, these studies provide proof-of-concept data supporting the scientific rationale for the use of VEGF inhibitors to slow progression of schwannomas in the mouse, which is consistent with the preliminary clinical data in NF2 patients treated systemically with Avastin® (Plotkin 2009; Plotkin 2012; Lu 2019; Plotkin 2019, each of which is incorporated herein in its entirety by reference). One limitation of these prior studies is that they do not reflect the enduring exposure levels in a limited target location.

In some embodiments, methods and compositions disclosed herein result in sustained levels of a VEGF inhibitor, e.g., rAAV-antiVEGF, at a limited target location, e.g., in the inner ear of an individual, e.g., mammal, e.g., human. Without wishing to be bound by theory, it is believed that in some embodiments, a VEGF inhibitor could enter VS tumor cells through direct uptake from the surrounding fluid bath, which is in continuity with the perilymphatic compartment of the inner ear through the nerve interstitium from which an inner ear supply of anti-VEGF protein may diffuse. In tumor-bearing mice, anti-VEGF protein applied topically to the tumor tissue, rather than through the bloodstream, resulted in beneficial effects such as reduced vascular permeability (Lichtenbeld 1999, incorporated herein in its entirety by reference).

Anti-VEGF Antibodies

In some embodiments of any of the antibodies described herein, said antibodies can bind to a VEGF antigen (e.g., any of the exemplary VEGF proteins described herein, e.g., one or more of mature human VEGF-A, mature human VEGF-B, mature human VEGF-C, and mature human VEGF-D) (e.g., any of the binding affinities described herein).

In some embodiments described herein, an antibody can decrease an activity of a VEGF (e.g., one or more of any of the exemplary VEGF proteins described herein, e.g., one or more of mature human VEGF-A, mature human VEGF-B, mature human VEGF-C, and mature human VEGF-D). In some embodiments, an antibody can block a VEGF (e.g., one or more of any of the exemplary VEGF proteins described herein, e.g., one or more of mature human VEGF-A, mature human VEGF-B, mature human VEGF-C, and mature human VEGF-D) from binding to one or more of its receptors (e.g., one or more VEGF receptors) See, e.g., WO 1998/045331, U.S. Pat. No. 9,079,953, US 2015/0147317, US 2016/0289314, Plotkin et al., Otology & Neurotology 33: 1046-1052 (2012); and Ferrara et al. (2005) Biochem Biophys Res Commun 333(2): 328-335, each of which is hereby incorporated in their entirety by reference. In some embodiments, an antibody can decrease downstream signaling (e.g., signaling downstream of a VEGF receptor, e.g., one or more of any of the exemplary VEGF receptors described herein, e.g., one or more of human VEGFR-1, human VEGFR-2, and human VEGFR-3). In some embodiments, a decrease in an activity of a VEGF can be detected indirectly, e.g., through VS tumor size, and/or alteration of VS associated symptoms described herein, e.g., through an increase in hearing (e.g., a 1% to about 400% increase (or any of the subranges of this range described herein) in hearing) or a decrease (e.g., a 1% to 99%, a 1% to 95%, a 1% to 90%, a 1% to 85%, a 1% to 80%, a 1% to 75%, a 1% to 70%, a 1% to 65%, a 1% to 60%, a 1% to 55%, a 1% to 50%, a 1% to 45%, a 1% to 40%, a 1% to 35%, a 1% to 30%, a 1% to 25%, a 1% to 20%, a 1% to 15%, a 1% to 10%, a 1% to 5%, a 5% to 99%, a 5% to 95%, a 5% to 90%, a 5% to 85%, a 5% to 80%, a 5% to 75%, a 5% to 70%, a 5% to 65%, a 5% to 60%, a 5% to 55%, a 5% to 50%, a 5% to 45%, a 5% to 40%, a 5% to 35%, a 5% to 30%, a 5% to 25%, a 5% to 20%, a 5% to 15%, a 5% to 10%, a 10% to 99%, a 10% to 95%, a 10% to 90%, a 10% to 85%, a 10% to 80%, a 10% to 75%, a 10% to 70%, a 10% to 65%, a 10% to 60%, a 10% to 55%, a 10% to 50%, a 10% to 45%, a 10% to 40%, a 10% to 35%, a 10% to 30%, a 10% to 25%, a 10% to 20%, a 10% to 15%, a 15% to 99%, a 15% to 95%, a 15% to 90%, a 15% to 85%, a 15% to 80%, a 15% to 75%, a 15% to 70%, a 15% to 65%, a 15% to 60%, a 15% to 55%, a 15% to 50%, a 15% to 45%, a 15% to 40%, a 15% to 35%, a 15% to 30%, a 15% to 25%, a 15% to 20%, a 20% to 99%, a 20% to 95%, a 20% to 90%, a 20% to 85%, a 20% to 80%, a 20% to 75%, a 20% to 70%, a 20% to 65%, a 20% to 60%, a 20% to 55%, a 20% to 50%, a 20% to 45%, a 20% to 40%, a 20% to 35%, a 20% to 30%, a 20% to 25%, a 25% to 99%, a 25% to 95%, a 25% to 90%, a 25% to 85%, a 25% to 80%, a 25% to 75%, a 25% to 70%, a 25% to 65%, a 25% to 60%, a 25% to 55%, a 25% to 50%, a 25% to 45%, a 25% to 40%, a 25% to 35%, a 25% to 30%, a 30% to 99%, a 30% to 95%, a 30% to 90%, a 30% to 85%, a 30% to 80%, a 30% to 75%, a 30% to 70%, a 30% to 65%, a 30% to 60%, a 30% to 55%, a 30% to 50%, a 30% to 45%, a 30% to 40%, a 30% to 35%, a 35% to 99%, a 35% to 95%, a 35% to 90%, a 35% to 85%, a 35% to 80%, a 35% to 75%, a 35% to 70%, a 35% to 65%, a 35% to 60%, a 35% to 55%, a 35% to 50%, a 35% to 45%, a 35% to 40%, a 40% to 99%, a 40% to 95%, a 40% to 90%, a 40% to 85%, a 40% to 80%, a 40% to 75%, a 40% to 70%, a 40% to 65%, a 40% to 60%, a 40% to 55%, a 40% to 50%, a 40% to 45%, a 45% to 99%, a 45% to 95%, a 45% to 90%, a 45% to 85%, a 45% to 80%, a 45% to 75%, a 45% to 70%, a 45% to 65%, a 45% to 60%, a 45% to 55%, a 45% to 50%, a 50% to 99%, a 50% to 95%, a 50% to 90%, a 50% to 85%, a 50% to 80%, a 50% to 75%, a 50% to 70%, a 50% to 65%, a 50% to 60%, a 50% to 55%, a 55% to 99%, a 55% to 95%, a 55% to 90%, a 55% to 85%, a 55% to 80%, a 55% to 75%, a 55% to 70%, a 55% to 65%, a 55% to 60%, a 60% to 99%, a 60% to 95%, a 60% to 90%, a 60% to 85%, a 60% to 80%, a 60% to 75%, a 60% to 70%, a 60% to 65%, a 65% to 99%, a 65% to 95%, a 65% to 90%, a 65% to 85%, a 65% to 80%, a 65% to 75%, a 65% to 70%, a 70% to 99%, a 70% to 95%, a 70% to 90%, a 70% to 85%, a 70% to 80%, a 70% to 75%, a 75% to 99%, a 75% to 95%, a 75% to 90%, a 75% to 85%, a 75% to 80%, a 80% to 99%, a 80% to 95%, a 80% to 90%, a 80% to 85%, a 85% to 99%, a 85% to 95%, a 85% to 90%, a 90% to 99%, a 90% to 95%, or a 95% to 99% decrease) in the size of a VS tumor and/or the severity of one or more symptoms of an acoustic neuroma, VS, or neurofibromatosis type II in a mammal as compared the severity of one or more symptoms of an acoustic neuroma (e.g., loss of hearing, tinnitus, vertigo, loss of quality of life etc.) and/or size of an acoustic neuroma, VS, or neurofibromatosis type II in the mammal, respectively, before administration of any rAAV particles described herein. In some embodiments, a decrease in a VEGF activity can be detected in an in-vitro assay.

In some embodiments, the antibody can be a humanized antibody, a chimeric antibody, or a multivalent antibody. In some embodiments, an antibody can be a scFv-Fc, a VHH domain, a VNAR domain, a (scFv)2, a minibody, or a BiTE. In some embodiments, an antibody can be a DVD-Ig, and a dual-affinity re-targeting antibody (DART), a triomab, kih IgG with a common LC, a crossmab, an ortho-Fab IgG, a 2-in-1-IgG, IgG-ScFv, scFv2-Fc, a bi-nanobody, tanden antibody, a DART-Fc, a scFv-HAS-scFv, DNL-Fab3, DAF (two-in-one or four-in-one), DutaMab, DT-IgG, knobs-in-holes common LC, knobs-in-holes assembly, charge pair antibody, Fab-arm exchange antibody, SEEDbody, Triomab, LUZ-Y, Fcab, kλ-body, orthogonal Fab, DVD-IgG, IgG(H)-scFv, scFv-(H)IgG, IgG(L)-scFv, scFv-(L)-IgG, IgG (L,H)-Fc, IgG(H)-V, V(H)-IgG, IgG(L)-V, V(L)-IgG, KIH IgG-scFab, 2scFv-IgG, IgG-2scFv, scFv4-Ig, Zybody, DVI-IgG, nanobody, nanobody-HSA, a diabody, a TandAb, scDiabody, scDiabody-CH3, Diabody-CH3, Triple Body, miniantibody, minibody, TriBi minibody, scFv-CH3 KIH, Fab-scFv, scFv-CH-CL-scFv, F(ab')2-scFV2, scFv-KIH, Fab-scFv-Fc, tetravalent HCAb, scDiabody-Fc, diabody-Fc, tandem scFv-Fc, intrabody, dock and lock bispecific antibody, ImmTAC, HSAbody, scDiabody-HAS, tandem scFv, IgG-IgG, Cov-X-Body, and scFv1-PEG-scFv2.

Additional examples of an antibody include an Fv fragment, a Fab fragment, a F(ab')2 fragment, and a Fab' fragment. Additional examples of an antibody include an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

In some embodiments, any of the antibodies described herein can bind specifically to VEGF. In some embodiments, any of the antibodies described herein can bind specifically to PDGF/VEGF.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., Curr. Top. Med. Chem. 15:2543-2557, 2016; De Genst et al., Dev. Comp. Immunol. 30:187-198, 2006; De Meyer et al., Trends Biotechnol. 32:263-270, 2014; Kijanka et al., Nanomedicine 10:161-174, 2015; Kovaleva et al., Expert. Opin. Biol. Ther. 14:1527-1539, 2014; Krah et al., Immunopharmacol. Immunotoxicol. 38:21-28, 2016; Mujic-Delic et al., Trends Pharmacol. Sci. 35:247-255, 2014; Muyldermans, J. Biotechnol. 74:277-302, 2001; Muyldermans et al., Trends Biochem. Sci. 26:230-235, 2001; Muyldermans, Ann. Rev. Biochem. 82:775-797, 2013; Rahbarizadeh et al., Immunol. Invest. 40:299-338, 2011; Van Audenhove et al., EBioMedicine 8:40-48, 2016; Van Bockstaele et al., Curr. Opin. Investig. Drugs 10:1212-1224, 2009; Vincke et al., Methods Mol. Biol. 911:15-26, 2012; and Wesolowski et al., Med. Microbiol. Immunol. 198:157-174, 2009, each of which is incorporated herein in its entirety by reference.

In some embodiments, a "Fv" fragment comprises a non-covalently-linked dimer of one heavy chain variable domain and one light chain variable domain.

In some embodiments, a "Fab" fragment comprises, the constant domain of the light chain and the first constant domain (CH1) of the heavy chain, in addition to the heavy and light chain variable domains of the Fv fragment.

In some embodiments, a "F(ab')2" fragment comprises two Fab fragments joined, near the hinge region, by disulfide bonds.

In some embodiments, a "dual variable domain immunoglobulin" or "DVD-Ig" refers to multivalent and multispecific binding proteins as described, e.g., in DiGiammarino et al., Methods Mol. Biol. 899:145-156, 2012; Jakob et al., MABs 5:358-363, 2013; and U.S. Pat. Nos. 7,612,181; 8,258,268; 8,586,714; 8,716,450; 8,722,855; 8,735,546; and 8,822,645, each of which are incorporated in its entirety herein by reference.

In some embodiments, Drug Affinity Responsive Target Stability (DARTS) assays are described and performed as found in e.g., Garber, Nature Reviews Drug Discovery 13:799-801, 2014; which is incorporated in its entirety herein by reference.

In some embodiments, any of the antibodies described herein has a dissociation constant (KD) of less than $1\times10^{-5}$ M (e.g., less than $0.5\times10^{-5}$ M, less than $1\times10^{-6}$ M, less than $0.5\times10^{-6}$ M, less than $1\times10^{-7}$ M, less than $0.5\times10^{-7}$ M, less than $1\times10^{-8}$ M, less than $0.5\times10^{-8}$ M, less than $1\times10^{-9}$ M, less than $0.5\times10^{-9}$ M, less than $1\times10^{-10}$ M, less than $0.5\times10^{-10}$ M, less than $1\times10^{-11}$ M, less than $0.5\times10^{-11}$ M, or less than $1\times10^{-12}$ M), e.g., as measured in phosphate buffered saline using surface plasmon resonance (SPR) for a VEGF protein (e.g., any of the VEGF proteins described herein, e.g., one or more of mature human VEGF-A, mature human VEGF-B, mature human VEGF-C, and mature human VEGF-D).

In some embodiments, any of the antibodies described herein has a KD of about $1\times10^{-12}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, about $0.5\times10^{-10}$ M, about $1\times10^{-11}$ M, or about $0.5\times10^{-11}$ M (inclusive); about $0.5\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, about $0.5\times10^{-10}$ M, or about $1\times10^{-11}$ M (inclusive); about $1\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, or about $0.5\times10^{-10}$ M (inclusive); about $0.5\times10^{-10}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, or about $1\times10^{-10}$ M (inclusive); about $1\times10^{-10}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, or about $0.5\times10^{-9}$ M (inclusive); about $0.5\times10^{-9}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, or about $1\times10^{-9}$ M (inclusive); about $1\times10^{-9}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, or about $0.5\times10^{-8}$ M (inclusive); about $0.5\times10^{-8}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, or about $1\times10^{-8}$ M (inclusive); about $1\times10^{-8}$ M to about $1\times10^{-5}$ M, about $0.5\times10^{-5}$ M, about $1\times10^{-6}$ M, about $0.5\times10^{-6}$ M, about $1\times10^{-7}$ M, or about $0.5\times10^{-7}$ M (inclusive); about $0.5\times10^{-7}$ M to about $1\times10^{-5}$ M, about $0.5\times10^{-5}$ M, about $1\times10^{-6}$ M, about $0.5\times10^{-6}$ M, or about $1\times10^{-7}$ M (inclusive); about $1\times10^{-7}$ M to about $1\times10^{-5}$ M, about $0.5\times10^{-5}$ M, about $1\times10^{-6}$ M, or about $0.5\times10^{-6}$ M (inclusive); about $0.5\times10^{-6}$ M to about $1\times10^{-5}$ M, about $0.5\times10^{-5}$ M, or about $1\times10^{-6}$ M (inclusive); about $1\times10^{-6}$ M to about $1\times10^{-5}$ M or about $0.5\times10^{-5}$ M (inclusive); or about $0.5\times10^{-5}$ M to about $1\times10^{-5}$ M (inclusive), e.g., as measured in phosphate buffered saline using surface plasmon resonance (SPR), for a VEGF protein (e.g., any of the VEGF proteins described herein, e.g., one or more of mature human VEGF-A, mature human VEGF-B, mature human VEGF-C, and mature human VEGF-D).

A variety of different methods known in the art can be used to determine the KD values of any of the antibodies described herein (e.g., an electrophoretic mobility shift assay, a filter binding assay, surface plasmon resonance, and a bimolecular binding kinetics assay, etc.).

In some embodiments of any of the antibodies described herein, the half-life of the antibody in a subject (e.g., a human) is decreased about 0.5-fold to about 4-fold (e.g., about 0.5-fold to about 3.5-fold, about 0.5-fold to about 3-fold, about 0.5-fold to about 2.5-fold, about 0.5-fold to about 2-fold, about 0.5-fold to about 1.5-fold, about 0.5-fold to about 1-fold, about 1-fold to about 4-fold, about 1-fold to about 3.5-fold, about 1-fold to about 3-fold, about 1-fold to about 2.5-fold, about 1-fold to about 2-fold, about 1.5-fold to about 4-fold, about 1.5-fold to about 3.5-fold, about 1.5-fold to about 3-fold, about 1.5-fold to about 2.5-fold, about 1.5-fold to about 2-fold, about 2-fold to about 4-fold, about 2-fold to about 3.5-fold, about 2-fold to about 3-fold, about 2-fold to about 2.5-fold, about 2.5-fold to about 4-fold, about 2.5-fold to about 3.5-fold, about 2.5-fold to about 3-fold, about 3-fold to about 4-fold, about 3-fold to about 3.5-fold, or about 3.5-fold to about 4-fold) as compared to the half-life of a control antibody (e.g., any of the control antibodies or conditions described herein) in a similar subject. See, e.g., Leabman et al., MAbs. 5(6): 896-903, 2013, incorporated herein in its entirety by reference. In some embodiments, an antibody described herein has one or more amino acid substitutions in the Fc region that decrease its half-life in a mammal, and a control antibody lacks at least one (e.g., lacks all) of these one or more amino acid substitutions in the Fc region.

In some embodiments, the antibody that specifically binds to a VEGF is bevacizumab (Avastatin®). Bevacizumab (full size antibody~150 kDa) inhibits all isoforms of VEGF-A. Bevacizumab received Food and Drug administration (FDA) approval in 2004 for colon cancer for intravenous (IV) dose of 4.0-7.5 mg/kg at 2-3 weeks (plasmatic half-life 21 days), for intravitreal (IVT) dose 1.25 mg in 0.05 mL (half-life 5.6 days). Bevacizumab has a $K_D$ for VEGF 165 (VEGF-A) of 58 pM. See, e.g., WO 2017/050825; which is incorporated in its entirety herein by reference.

In some embodiments, the antibody that specifically binds to a VEGF is ranibizumab (Lucentis®). Ranibizumab (~50 kDa) inhibits all isoforms of VEGF-A. Ranibizumab received FDA approval in 2006 for ocular use for intravenous (IV) dose of 4.0-7.5 mg/kg at 2-3 weeks (plasma half-life of 0.5 days), for intravitreal (IVT) dose 0.5 mg in 0.05 mL (half-life of 3.2 days). Ranibizumab has a $K_D$ for VEGF-$A_{165}$ (VEGF-A Isoform 165, as represented by SEQ ID NO: 6) of 46 pM. See, e.g., WO 2014/178078; which is incorporated in its entirety herein by reference.

In some embodiments, the antibody that specifically binds to VEGF is sevacizumab (APX003/SIM-BD0801), or a characteristic portion thereof.

In certain embodiments, an anti-VEGF protein coding sequence comprised within a composition as described herein (e.g., rAAV-antiVEGF) is selected from VEGF inhibitors approved for pathological vascularization in the retina, and in glioblastoma and other cancers, including for example: bevacizumab (Avastin®); aflibercept (Eylea®); ziv-aflibercept (Zaltrap®); brolucizumab (Beovu®); and/or ranibizumab (Lucentis®). In addition, in some embodiments, biosimilars of many of these products in various stages of nonclinical and clinical development, and a ranibizumab biosimilar, Razumab®, may be utilized.

Ranibizumab, aflibercept, and brolucizumab are each approved for repeated intravitreal administration for wet age-related macular degeneration (AMD); ranibizumab and aflibercept are additionally approved for repeated intravitreal administration for retinal vein occlusion (RVO), diabetic macular edema (DME), and diabetic retinopathy (DR). It has been observed that targeted local delivery, and associated reduction in systemic exposure, may result in improved safety profiles (including lower rates of thromboembolic events) over intravenous treatment regimens of VEGF inhibitors. Gene therapy versions of these therapeutics are currently in clinical development for AMD and DME (Clinicaltrials.gov 2020b, 2020c, and 2020d [NCT03066258, NCT03748784, and NCT04418427], each of which is incorporated herein in its entirety by reference). Aflibercept is a recombinant fusion protein (97 kDa) consisting of portions of human VEGF receptors 1 and 2 extracellular domains fused to the Fc portion of human IgG1 that has been shown to be effective in wet AMD and DME clinical trials when delivered locally to the eye through repeated intravitreal administration. Like bevacizumab, ziv-aflibercept is also approved for intravenous infusion and carries similar risks and warnings regarding hemorrhage and wound healing (Sanofi-Aventis US 2020, which is incorporated herein in its entirety by reference).

In a study of patients with wet age-related macular degeneration (AMD), localized delivery of clinical doses of anti-VEGF proteins such as bevacizumab and ranibizumab administered via intravitreal injection were associated with significant improvements in visual acuity at 4 months; however, at this same time point VEGF plasma levels were significantly reduced only for the cohort injected with bevacizumab (Carneiro 2012, incorporated herein in its entirety by reference), In certain embodiments, methods and compositions described in the present disclosure provide solutions to the reduction of plasma VEGF levels associated with systemic delivery and/or potentially associated with acute localized delivery of bevacizumab. Certain studies have demonstrated results consistent with findings in pharmacokinetic studies, e.g., that in rabbits, bevacizumab, but not ranibizumab, is detected in the serum following intravitreal injection (Bakri 2007, incorporated herein in its entirety by reference). Review of clinical safety data from pivotal trials in AMD suggests that repeated intravitreal administration of ranibizumab for up to two years is not associated with significant safety risks (Schmidt-Erfurth 2010, incorporated herein in its entirety by reference).

Ranibizumab

Ranibizumab is a humanized monoclonal antibody fragment (Fab) with similar clinical efficacy and an equivalent rate of thromboembolic events as aflibercept when delivered locally in the eye through intravitreal administration (Genentech 2017, incorporated herein in its entirety by reference). It is an IgG1 Fab that binds to and neutralizes VEGF. Ranibizumab is thought to bind to and inhibit biological activity all known isoforms of the human VEGF-A protein by preventing their interaction with the cognate receptors (VEGFR-1 and VEGFR-2). Ranibizumab has been marketed under the brand name Lucentis®. It is FDA approved for indications such as the treatment of macular edema after retinal vein occlusion, age-related macular degeneration (wet), and diabetic macular edema. Compared to bevacizumab, ranibizumab exhibits a more than 8-fold higher binding capacity and 66-fold higher binding affinity (Klettner 2008; Yang 2014, each of which incorporated herein in its entirety by reference). These differences yield an IC50 for VEGF-induced endothelial proliferation for ranibizumab that is 6-fold less than bevacizumab, with ranibizumab having a clinically relevant impact on VEGF activity down to 0.37 nanomolar (nM) (~17 nanograms per milliliter [ng/mL] ranibizumab; Yang 2014, incorporated herein in its entirety by reference). Importantly, ranibizumab also lacks an Fc region, allowing the molecule to avoid Fc recycling and making it significantly smaller (48 kDa) than the full-size antibody (149 kDa) (Meyer 2011, incorporated herein in its entirety by reference). In some embodiments, this smaller molecular size may be advantageous in improving diffusion to the target site, capacity to extravasate into the tumor interstitium, and/or efficiency to diffuse to target sites within the tumor (Xenaki 2017, incorporated herein in its entirety by reference). In some embodiments, compositions as described herein comprise a coding sequence of ranibizumab for development into an rAAV gene therapy product. In some embodiments, compositions as described herein (e.g., rAAV-antiVEGF) may be delivered into the cochlea, wherein intracochlear administration can result in low systemic exposure and thereby an improved safety profile compared to intravenous administration.

In certain embodiments, the present disclosure provides compositions comprising ranibizumab, an anti-VEGF protein that lacks the Fc region. An antibody Fc region as is found on bevacizumab, is thought to allow for bevacizumab's distribution across biological barriers through Fc-receptor mediated transport, as well as bevacizumab's activation of an immune response (Kim 2009; Meyer 2011, each of which is incorporated herein in its entirety by reference). Certain studies have suggested that compared to bevacizumab, ranibizumab may exhibit a 17-fold higher binding capacity and 6-fold higher binding affinity when highly diluted (Ferrara 2006; Klettner 2008, each of which is incorporated herein in its entirety by reference), suggesting greater specific activity in lower concentrations. In some embodiments, the smaller molecular size of ranibizumab (48 kDa, compared to 149 kDa for bevacizumab) may also be advantageous in improving diffusion to the target site, capacity to extravasate into the tumor interstitium, and/or efficiency to diffuse to target sites within the tumor (Xenaki 2017, incorporated herein in its entirety by reference).

In some embodiments, an anti-VEGF protein as described herein that specifically binds to VEGF and/or antigen-presenting fragments thereof, is an antibody. In some embodiments, such an antibody comprises an immunoglobulin light chain variable domain that is or comprises a sequence that is at least 80% identical (e.g., at least 82%, at least 84%, at least 86%, at least 88%, at least 90%, at least 92%, at least 94%, at least 96%, at least 98%, or at least 99%) identical to an immunoglobulin light chain variable domain of ranibizumab, and/or comprises an immunoglobulin heavy chain variable domain that is or comprises a sequence that is at least 80% identical (e.g., at least 82%, at least 84%, at least 86%, at least 88%, at least 90%, at least 92%, at least 94%, at least 96%, at least 98%, or at least 99%) identical to an immunoglobulin heavy chain variable domain of ranibizumab.

In some embodiments, an anti-VEGF protein as described herein that specifically binds to VEGF and/or antigen-presenting fragments thereof, is an antibody. In some embodiments, such an antibody comprises, inter alia, an immunoglobulin light chain variable domain that is or comprises an immunoglobulin light chain variable domain of ranibizumab, and/or an immunoglobulin heavy chain variable domain that is or comprises an immunoglobulin heavy chain variable domain of ranibizumab. In some embodiments, an antibody comprises an immunoglobulin light chain variable domain that is or comprises a sequence of an immunoglobulin light chain variable domain of ranibizumab (as represented by SEQ ID NO: 20), except that it comprises one, two, three, four, five, six, seven, eight, nine, ten, eleven, twelve, thirteen, fourteen, or fifteen amino acid substitutions, and/or comprises an immunoglobulin heavy chain variable domain that is or comprises a sequence of an immunoglobulin light chain variable domain of ranibizumab (as represented by SEQ ID NO: 16, 17, or 18), except that it comprises one, two, three, four, five, six, seven, eight, nine, ten, eleven, twelve, thirteen, fourteen, or fifteen amino acid substitutions. In some embodiments, an antigen-binding domain comprises three CDRs in an immunoglobulin light chain variable domain of ranibizumab, and/or three CDRs in an immunoglobulin heavy chain variable domain of ranibizumab.

```
Exemplary Ranibizumab Heavy Chain nucleotide sequence
                                             (SEQ ID NO: 13)
GAGGTGCAGCTGGTGGAATCTGGCGGCGGACTTGTTCAACCTGGCGGCTCTCTGAGA

CTGAGCTGTGCCGCTTCTGGCTACGACTTCACCCACTACGGCATGAACTGGGTCCGA

CAGGCCCCTGGCAAAGGCCTTGAATGGGTCGGATGGATCAACACCTACACCGGCGA

GCCAACATACGCCGCCGACTTCAAGCGGAGATTCACCTTCAGCCTGGACACCAGCA

AGAGCACCGCCTACCTGCAGATGAACAGCCTGAGAGCCGAGGACACCGCCGTGTAC

TACTGCGCCAAGTATCCCTACTACTACGGCACCAGCCACTGGTACTTTGACGTGTGG

GGACAGGGCACACTGGTCACAGTGTCTAGCGCCTCTACAAAGGGCCCCAGCGTTTTC

CCACTGGCTCCTAGCAGCAAGTCTACCAGCGGAGGAACAGCCGCTCTGGGCTGTCT

GGTCAAGGACTACTTTCCCGAGCCTGTGACCGTGTCCTGGAATTCTGGCGCTCTGAC

AAGCGGCGTGCACACCTTTCCAGCTGTGCTGCAAAGCAGCGGCCTGTACTCTCTGAG

CAGCGTCGTGACAGTGCCAAGCAGCTCTCTGGGCACCCAGACCTACATCTGCAATGT

GAACCACAAGCCTAGCAACACCAAGGTGGACAAGAAGGTGGAACCCAAGAGCTGC

GACAAGACCCACACCGGCAAG

Exemplary Ranibizumab Heavy Chain nucleotide sequence
                                             (SEQ ID NO: 14)
GAGGTGCAGCTGGTGGAATCTGGCGGCGGACTTGTTCAACCTGGCGGCTCTCTGAGA

CTGAGCTGTGCCGCTTCTGGCTACGACTTCACCCACTACGGCATGAACTGGGTCCGA

CAGGCCCCTGGCAAAGGCCTTGAATGGGTCGGATGGATCAACACCTACACCGGCGA

GCCAACATACGCCGCCGACTTCAAGCGGAGATTCACCTTCAGCCTGGACACCAGCA

AGAGCACCGCCTACCTGCAGATGAACAGCCTGAGAGCCGAGGACACCGCCGTGTAC
```

-continued

TACTGCGCCAAGTATCCCTACTACTACGGCACCAGCCACTGGTACTTTGACGTGTGG

GGACAGGGCACACTGGTCACAGTGTCTAGCGCCTCTACAAAGGGCCCCAGCGTTTTC

CCACTGGCTCCTAGCAGCAAGTCTACCAGCGGAGGAACAGCCGCTCTGGGCTGTCT

GGTCAAGGACTACTTTCCCGAGCCTGTGACCGTGTCCTGGAATTCTGGCGCTCTGAC

AAGCGGCGTGCACACCTTTCCAGCTGTGCTGCAAAGCAGCGGCCTGTACTCTCTGAG

CAGCGTCGTGACAGTGCCAAGCAGCTCTCTGGGCACCCAGACCTACATCTGCAATGT

GAACCACAAGCCTAGCAACACCAAGGTGGACAAGAAGGTGGAACCCAAGAGCTGC

GACAAGACCCACAAG

Exemplary Ranibizumab Heavy Chain nucleotide sequence
(SEQ ID NO: 15)
GAGGTGCAGCTGGTGGAATCTGGCGGCGGACTTGTTCAACCTGGCGGCTCTCTGAGA

CTGAGCTGTGCCGCTTCTGGCTACGACTTCACCCACTACGGCATGAACTGGGTCCGA

CAGGCCCCTGGCAAAGGCCTTGAATGGGTCGGATGGATCAACACCTACACCGGCGA

GCCAACATACGCCGCCGACTTCAAGCGGAGATTCACCTTCAGCCTGGACACCAGCA

AGAGCACCGCCTACCTGCAGATGAACAGCCTGAGAGCCGAGGACACCGCCGTGTAC

TACTGCGCCAAGTATCCCTACTACTACGGCACCAGCCACTGGTACTTTGACGTGTGG

GGACAGGGCACACTGGTCACAGTGTCTAGCGCCTCTACAAAGGGCCCCAGCGTTTTC

CCACTGGCTCCTAGCAGCAAGTCTACCAGCGGAGGAACAGCCGCTCTGGGCTGTCT

GGTCAAGGACTACTTTCCCGAGCCTGTGACCGTGTCCTGGAATTCTGGCGCTCTGAC

AAGCGGCGTGCACACCTTTCCAGCTGTGCTGCAAAGCAGCGGCCTGTACTCTCTGAG

CAGCGTCGTGACAGTGCCAAGCAGCTCTCTGGGCACCCAGACCTACATCTGCAATGT

GAACCACAAGCCTAGCAACACCAAGGTGGACAAGAAGGTGGAACCCAAGAGC

Exemplary Ranibizumab Heavy Chain amino acid sequence
(SEQ ID NO: 16)
EVQLVESGGGLVQPGGSLRLSCAASGYDFTHYGMNWVRQAPGKGLEWVGWINTYTGE

PTYAADFKRRFTFSLDTSKSTAYLQMNSLRAEDTAVYYCAKYPYYYGTSHWYFDVWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTGK

Exemplary Ranibizumab Heavy Chain amino acid sequence
(SEQ ID NO: 17)
EVQLVESGGGLVQPGGSLRLSCAASGYDFTHYGMNWVRQAPGKGLEWVGWINTYTGE

PTYAADFKRRFTFSLDTSKSTAYLQMNSLRAEDTAVYYCAKYPYYYGTSHWYFDVWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHL

Exemplary Ranibizumab Heavy Chain amino acid sequence
(SEQ ID NO: 18)
EVQLVESGGGLVQPGGSLRLSCAASGYDFTHYGMNWVRQAPGKGLEWVGWINTYTGE

PTYAADFKRRFTFSLDTSKSTAYLQMNSLRAEDTAVYYCAKYPYYYGTSHWYFDVWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKS

Exemplary Ranibizumab Light Chain nucleotide sequence
(SEQ ID NO: 19)
GACATCCAGCTGACACAGAGCCCCAGCAGCCTGTCTGCCTCTGTGGGAGACAGAGT

GACCATCACCTGTAGCGCCAGCCAGGACATCTCCAACTACCTGAACTGGTATCAGCA

AAAGCCCGGCAAGGCCCCTAAGGTGCTGATCTACTTCACAAGCAGCCTGCACTCCG

GCGTGCCCAGCAGATTTTCTGGCTCTGGCAGCGGCACCGACTTCACCCTGACCATAT

```
CTAGCCTGCAGCCTGAGGACTTCGCCACCTACTACTGCCAGCAGTACAGCACCGTGC

CTTGGACATTTGGCCAGGGCACAAAGGTGGAAATCAAGCGGACTGTGGCCGCTCCT

AGCGTGTTCATCTTTCCACCTAGCGACGAGCAGCTGAAGTCTGGCACAGCCTCTGTC

GTGTGCCTGCTGAACAACTTCTACCCCAGAGAAGCCAAGGTGCAGTGGAAAGTGGA

CAATGCCCTGCAGAGCGGCAACAGCCAAGAGAGCGTGACAGAGCAGGACTCCAAG

GATAGCACCTATAGCCTGAGCAGCACCCTGACACTGAGCAAGGCCGACTACGAGAA

GCACAAAGTGTACGCCTGCGAAGTGACCCACCAGGGCCTTTCTAGCCCTGTGACCA

AGAGCTTCAACCGGGGCGAATGT
```

Exemplary Ranibizumab Light Chain amino acid sequence
(SEQ ID NO: 20)
```
DIQLTQSPSSLSASVGDRVTITCSASQDISNYLNWYQQKPGKAPKVLIYFTSSLHSGVPSR

FSGSGSGTDFTLTISSLQPEDFATYYCQQYSTVPWTFGQGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC
```

Exemplary Cleavable polypeptide comprising Heavy and Light
Chain Ranibizumab, nucleotide sequence
(SEQ ID NO: 103)
```
ATGTACCGGATGCAGCTGCTGAGCTGTATCGCCCTGTCTCTGGCCCTGGTCACCAAT

TCTGAGGTGCAGCTGGTGGAATCTGGCGGCGGACTTGTTCAACCTGGCGGCTCTCTG

AGACTGAGCTGTGCCGCTTCTGGCTACGACTTCACCCACTACGGCATGAACTGGGTC

CGACAGGCCCCTGGCAAAGGCCTTGAATGGGTCGGATGGATCAACACCTACACCGG

CGAGCCAACATACGCCGCCGACTTCAAGCGGAGATTCACCTTCAGCCTGGACACCA

GCAAGAGCACCGCCTACCTGCAGATGAACAGCCTGAGAGCCGAGGACACCGCCGTG

TACTACTGCGCCAAGTATCCCTACTACTACGGCACCAGCCACTGGTACTTTGACGTG

TGGGGACAGGGCACACTGGTCACAGTGTCTAGCGCCTCTACAAAGGGCCCCAGCGT

TTTCCCACTGGCTCCTAGCAGCAAGTCTACCAGCGGAGGAACAGCCGCTCTGGGCTG

TCTGGTCAAGGACTACTTTCCCGAGCCTGTGACCGTGTCCTGGAATTCTGGCGCTCT

GACAAGCGGCGTGCACACCTTTCCAGCTGTGCTGCAAAGCAGCGGCCTGTACTCTCT

GAGCAGCGTCGTGACAGTGCCAAGCAGCTCTCTGGGCACCCAGACCTACATCTGCA

ATGTGAACCACAAGCCTAGCAACACCAAGGTGGACAAGAAGGTGGAACCCAAGAG

CTGCGACAAGACCCACACCGGCAAGCGGAAGAGAAGAGGCTCTGGCGAAGGCAGA

GGCAGCCTGCTTACATGTGGCGACGTGGAAGAGAACCCCGGACCTATGTATAGAAT

GCAGCTCCTGTCCTGCATTGCCCTGAGCCTGGCTCTCGTGACCAACAGCGACATCCA

GCTGACACAGAGCCCCAGCAGCCTGTCTGCCTCTGTGGGAGACAGAGTGACCATCA

CCTGTAGCGCCAGCCAGGACATCTCCAACTACCTGAACTGGTATCAGCAAAAGCCC

GGCAAGGCCCCTAAGGTGCTGATCTACTTCACAAGCAGCCTGCACTCCGGCGTGCCC

AGCAGATTTTCTGGCTCTGGCAGCGGCACCGACTTCACCCTGACCATATCTAGCCTG

CAGCCTGAGGACTTCGCCACCTACTACTGCCAGCAGTACAGCACCGTGCCTTGGACA

TTTGGCCAGGGCACAAAGGTGGAAATCAAGCGGACTGTGGCCGCTCCTAGCGTGTT

CATCTTTCCACCTAGCGACGAGCAGCTGAAGTCTGGCACAGCCTCTGTCGTGTGCCT

GCTGAACAACTTCTACCCCAGAGAAGCCAAGGTGCAGTGGAAAGTGGACAATGCCC

TGCAGAGCGGCAACAGCCAAGAGAGCGTGACAGAGCAGGACTCCAAGGATAGCAC

CTATAGCCTGAGCAGCACCCTGACACTGAGCAAGGCCGACTACGAGAAGCACAAAG
```

```
TGTACGCCTGCGAAGTGACCCACCAGGGCCTTTCTAGCCCTGTGACCAAGAGCTTCA

ACCGGGGCGAATGT
```

Exemplary Cleavable polypeptide comprising Heavy and Light Chain Ranibizumab (SEQ ID NO: 21)
```
MYRMQLLSCIALSLALVTNSEVQLVESGGGLVQPGGSLRLSCAASGYDFTHYGMNWV

RQAPGKGLEWVGWINTYTGEPTYAADFKRRFTFSLDTSKSTAYLQMNSLRAEDTAVYY

CAKYPYYYGTSHWYFDVWGQGTLVTVSSASTKGPSVFPLAPSSKSTSGGTAALGCLVK

DYFPEPVTVSWNSGALTSGVHTFPAVLQSSGLYSLSSVVTVPSSSLGTQTYICNVNHKPS

NTKVDKKVEPKSCDKTHTGKRKRRGSGEGRGSLLTCGDVEENPGPMYRMQLLSCIALS

LALVTNSDIQLTQSPSSLSASVGDRVTITCSASQDISNYLNWYQQKPGKAPKVLIYFTSSL

HSGVPSRFSGSGSGTDFTLTISSLQPEDFATYYCQQYSTVPWTFGQGTKVEIKRTVAAPS

VFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC
```

Bevacizumab

Bevacizumab is a humanized monoclonal full-length antibody against VEGF that is approved for intravenous infusion for the treatment of glioblastoma, colorectal, lung, kidney, cervical, and ovarian cancers. However, the main drawbacks to bevacizumab therapy are the need for continued regular intravenous infusions and the side effects associated with high doses in systemic circulation, which include hypertension, proteinuria, elevated liver enzymes, arterial thromboembolic events (ATE), venous thromboembolic events, hemorrhage, and surgery and wound healing complications. Currently, bevacizumab is the only pharmacologic agent for which preliminary clinical evidence of effectiveness in VS patients has been demonstrated.

In some embodiments, an anti-VEGF protein as described herein that specifically binds to VEGF and/or antigen-presenting fragments thereof, is an antibody. In some embodiments, such an antibody comprises an immunoglobulin light chain variable domain that is or comprises a sequence that is at least 80% identical (e.g., at least 82%, at least 84%, at least 86%, at least 88%, at least 90%, at least 92%, at least 94%, at least 96%, at least 98%, or at least 99%) identical to an immunoglobulin light chain variable domain of Bevacizumab, and/or comprises an immunoglobulin heavy chain variable domain that is or comprises a sequence that is at least 80% identical (e.g., at least 82%, at least 84%, at least 86%, at least 88%, at least 90%, at least 92%, at least 94%, at least 96%, at least 98%, or at least 99%) identical to an immunoglobulin heavy chain variable domain of Bevacizumab.

In some embodiments, an anti-VEGF protein as described herein that specifically binds to VEGF and/or antigen-presenting fragments thereof, is an antibody. In some embodiments, such an antibody comprises an immunoglobulin light chain variable domain that is or comprises an immunoglobulin light chain variable domain of Bevacizumab, and/or an immunoglobulin heavy chain variable domain that is or comprises an immunoglobulin heavy chain variable domain of Bevacizumab. In some embodiments, an antibody comprises an immunoglobulin light chain variable domain that is or comprises the sequence of an immunoglobulin light chain variable domain of Bevacizumab, except that it comprises one, two, three, four, five, six, seven, eight, nine, ten, eleven, twelve, thirteen, fourteen, or fifteen amino acid substitutions, and/or comprises an immunoglobulin heavy chain variable domain that is or comprises the sequence of an immunoglobulin heavy chain variable domain of Bevacizumab, except that it comprises one, two, three, four, five, six, seven, eight, nine, ten, eleven, twelve, thirteen, fourteen, or fifteen amino acid substitutions.

In some embodiments, an anti-VEGF protein as described herein that specifically binds to VEGF and/or antigen-presenting fragments thereof, is an antibody. In some embodiments, such an antibody comprises an immunoglobulin light chain (e.g., comprising an immunoglobulin light chain variable domain and an immunoglobulin light chain constant domain) that is or comprises an immunoglobulin light chain constant domain of Bevacizumab, and/or an immunoglobulin heavy chain (e.g., comprising an immunoglobulin heavy chain variable domain and an immunoglobulin heavy chain constant domain) that is or comprises an immunoglobulin heavy chain constant domain of Bevacizumab. In some embodiments, an antibody comprises an immunoglobulin light chain constant domain that is or comprises a sequence of an immunoglobulin light chain constant domain of Bevacizumab, except that it comprises one, two, three, four, five, six, seven, eight, nine, ten, eleven, twelve, thirteen, fourteen, or fifteen amino acid substitutions, and/or comprises an immunoglobulin heavy chain constant domain that is or comprises a sequence of an immunoglobulin heavy chain constant domain of Bevacizumab, except that it comprises one, two, three, four, five, six, seven, eight, nine, ten, eleven, twelve, thirteen, fourteen, or fifteen amino acid substitutions.

In some embodiments a first antigen-binding domain comprises three CDRs in an immunoglobulin light chain variable domain of Bevacizumab, and/or three CDRs in an immunoglobulin heavy chain variable domain of Bevacizumab. In some embodiments a second antigen-binding domain comprises three CDRs in an immunoglobulin light chain variable domain of Bevacizumab, and/or three CDRs in an immunoglobulin heavy chain variable domain of Bevacizumab.

Exemplary Bevacizumab nucleotide sequence
(SEQ ID NO: 22)
ATGTACCGGATGCAGCTGCTGAGCTGTATCGCCCTGTCTCTGGCCCTGGTCACCAAT
TCTGAGGTGCAGCTGGTGGAATCTGGCGGCGGACTTGTTCAACCTGGCGGCTCTCTG
AGACTGAGCTGTGCCGCTTCTGGCTACACCTTCACCAACTACGGCATGAACTGGGTC
CGACAGGCCCCTGGCAAAGGCCTTGAATGGGTCGGATGGATCAACACCTACACCGG
CGAGCCAACATACGCCGCCGACTTCAAGCGGAGATTCACCTTCAGCCTGGACACCA
GCAAGAGCACCGCCTACCTGCAGATGAACAGCCTGAGAGCCGAGGACACCGCCGTG
TACTACTGCGCCAAGTATCCCCACTACTACGGCAGCAGCCACTGGTACTTTGACGTG
TGGGGACAGGGCACACTGGTCACAGTGTCTAGCGCCTCTACAAAGGGCCCCAGCGT
TTTCCCACTGGCTCCTAGCAGCAAGTCTACCAGCGGAGGAACAGCCGCTCTGGGCTG
TCTGGTCAAGGACTACTTTCCCGAGCCTGTGACCGTGTCCTGGAATTCTGGCGCTCT
GACAAGCGGCGTGCACACCTTTCCAGCTGTGCTGCAAAGCAGCGGCCTGTACTCTCT
GAGCAGCGTCGTGACAGTGCCAAGCAGCTCTCTGGGCACCCAGACCTACATCTGCA
ATGTGAACCACAAGCCTAGCAACACCAAGGTGGACAAGAAGGTGGAACCCAAGAG
CTGCGACAAGACCCACACCTGTCCTCCATGTCCTGCTCCAGAACTGCTCGGCGGACC
TTCCGTGTTCCTGTTTCCTCCAAAGCCTAAGGACACCCTGATGATCAGCAGAACCCC
TGAAGTGACCTGCGTGGTGGTGGATGTGTCCCACGAGGATCCCGAAGTGAAGTTCA
ATTGGTACGTGGACGGCGTGGAAGTGCACAACGCCAAGACCAAGCCTAGAGAGGAA
CAGTACAACAGCACCTACAGAGTGGTGTCCGTGCTGACCGTGCTGCACCAGGATTG
GCTGAACGGCAAAGAGTACAAGTGCAAGGTGTCCAACAAGGCCCTGCCTGCTCCTA
TCGAGAAAACCATCAGCAAGGCCAAGGGCCAGCCTAGGGAACCCCAGGTTTACACA
CTGCCTCCAAGCCGGGAAGAGATGACCAAGAACCAGGTGTCCCTGACCTGCCTCGT
GAAGGGCTTCTACCCTTCCGATATCGCCGTGGAATGGGAGAGCAATGGCCAGCCAG
AGAACAACTACAAGACAACCCCTCCTGTGCTGGACAGCGACGGCTCATTCTTCCTGT
ACAGCAAGCTGACAGTGGACAAGTCCAGATGGCAGCAGGGCAACGTGTTCAGCTGC
AGCGTGATGCACGAGGCCCTGCACAACCACTACACCCAGAAGTCTCTGAGCCTGTCT
CCTGGCAAGCGGAAGAGAAGAGGCTCTGGCGAAGGCAGAGGCAGCCTGCTTACATG
TGGCGACGTGGAAGAGAACCCCGGACCTATGTATAGAATGCAGCTCCTGTCCTGCAT
TGCCCTGAGCCTGGCTCTCGTGACCAACAGCGACATCCAGATGACACAGAGCCCCA
GCAGCCTGTCTGCCTCTGTGGGAGACAGAGTGACCATCACCTGTAGCGCCAGCCAG
GACATCTCCAACTACCTGAACTGGTATCAGCAAAAGCCCGGCAAGGCCCCTAAGGT
GCTGATCTACTTCACAAGCAGCCTGCACTCCGGCGTGCCCAGCAGATTTTCTGGCTC
TGGCAGCGGCACCGACTTCACCCTGACCATATCTAGCCTGCAGCCTGAGGACTTCGC
CACCTACTACTGCCAGCAGTACAGCACCGTGCCTTGGACATTTGGCCAGGGCACAA
AGGTGGAAATCAAGCGGACTGTGGCCGCTCCTAGCGTGTTCATCTTTCCACCTAGCG
ACGAGCAGCTGAAGTCTGGCACAGCCTCTGTCGTGTGCCTGCTGAACAACTTCTACC
CCAGAGAAGCCAAGGTGCAGTGGAAAGTGGACAATGCCCTGCAGAGCGGCAACAG
CCAAGAGAGCGTGACAGAGCAGGACTCCAAGGATAGCACCTATAGCCTGAGCAGCA
CCCTGACACTGAGCAAGGCCGACTACGAGAAGCACAAAGTGTACGCCTGCGAAGTG
ACCCACCAGGGCCTTTCTAGCCCTGTGACCAAGAGCTTCAACCGGGGCGAATGT Exemplary Cleavable Polypeptide Comprising Heavy and Light -continued Chain Bevacizumab Amino Acid Sequence
(SEQ ID NO: 23)

MYRMQLLSCIALSLALVTNSEVQLVESGGGLVQPGGSLRLSCAASGYTFTNYGMNWVR

QAPGKGLEWVGWINTYTGEPTYAADFKRRFTFSLDTSKSTAYLQMNSLRAEDTAVYYC

AKYPHYYGSSHWYFDVWGQGTLVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSN

TKVDKKVEPKSCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVS

NKALPAPIEKTISKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEALHNHYTQKSLS

LSPGKRKRRGSGEGRGSLLTCGDVEENPGPMYRMQLLSCIALSLALVTNSDIQMTQSPSS

LSASVGDRVTITCSASQDISNYLNWYQQKPGKAPKVLIYFTSSLHSGVPSRFSGSGSGTD

FTLTISSLQPEDFATYYCQQYSTVPWTFGQGTKVEIKRTVAAPSVFIFPPSDEQLKSGTAS

VVCLLNNFYPREAKVQWKVDNALQSGNSQESVTEQDSKDSTYSLSSTLTLSKADYEKH

KVYACEVTHQGLSSPVTKSFNRGEC

Exemplary Bevacizumab Heavy Chain Nucleotide Sequence
(SEQ ID NO: 108)

ATGTACCGGATGCAGCTGCTGAGCTGTATCGCCCTGTCTCTGGCCCTGGTCACCAAT

TCTGAGGTGCAGCTGGTGGAATCTGGCGGCGGACTTGTTCAACCTGGCGGCTCTCTG

AGACTGAGCTGTGCCGCTTCTGGCTACACCTTCACCAACTACGGCATGAACTGGGTC

CGACAGGCCCCTGGCAAAGGCCTTGAATGGGTCGGATGGATCAACACCTACACCGG

CGAGCCAACATACGCCGCCGACTTCAAGCGGAGATTCACCTTCAGCCTGGACACCA

GCAAGAGCACCGCCTACCTGCAGATGAACAGCCTGAGAGCCGAGGACACCGCCGTG

TACTACTGCGCCAAGTATCCCCACTACTACGGCAGCAGCCACTGGTACTTTGACGTG

TGGGGACAGGGCACACTGGTCACAGTGTCTAGCGCCTCTACAAAGGGCCCCAGCGT

TTTCCCACTGGCTCCTAGCAGCAAGTCTACCAGCGGAGGAACAGCCGCTCTGGGCTG

TCTGGTCAAGGACTACTTTCCCGAGCCTGTGACCGTGTCCTGGAATTCTGGCGCTCT

GACAAGCGGCGTGCACACCTTTCCAGCTGTGCTGCAAAGCAGCGGCCTGTACTCTCT

GAGCAGCGTCGTGACAGTGCCAAGCAGCTCTCTGGGCACCCAGACCTACATCTGCA

ATGTGAACCACAAGCCTAGCAACACCAAGGTGGACAAGAAGGTGGAACCCAAGAG

CTGCGACAAGACCCACACCTGTCCTCCATGTCCTGCTCCAGAACTGCTCGGCGGACC

TTCCGTGTTCCTGTTTCCTCCAAAGCCTAAGGACACCCTGATGATCAGCAGAACCCC

TGAAGTGACCTGCGTGGTGGTGGATGTGTCCCACGAGGATCCCGAAGTGAAGTTCA

ATTGGTACGTGGACGGCGTGGAAGTGCACAACGCCAAGACCAAGCCTAGAGAGGAA

CAGTACAACAGCACCTACAGAGTGGTGTCCGTGCTGACCGTGCTGCACCAGGATTG

GCTGAACGGCAAAGAGTACAAGTGCAAGGTGTCCAACAAGGCCCTGCCTGCTCCTA

TCGAGAAAACCATCAGCAAGGCCAAGGGCCAGCCTAGGGAACCCCAGGTTTACACA

CTGCCTCCAAGCCGGGAAGAGATGACCAAGAACCAGGTGTCCCTGACCTGCCTCGT

GAAGGGCTTCTACCCTTCCGATATCGCCGTGGAATGGGAGAGCAATGGCCAGCCAG

AGAACAACTACAAGACAACCCCTCCTGTGCTGGACAGCGACGGCTCATTCTTCCTGT

ACAGCAAGCTGACAGTGGACAAGTCCAGATGGCAGCAGGGCAACGTGTTCAGCTGC

AGCGTGATGCACGAGGCCCTGCACAACCACTACACCCAGAAGTCTCTGAGCCTGTCT

CCTGGCAAG

```
Exemplary Bevacizumab Heavy Chain amino acid sequence
                                              (SEQ ID NO: 24)
EVQLVESGGGLVQPGGSLRLSCAASGYTFTNYGMNWVRQAPGKGLEWVGWINTYTGE

PTYAADFKRRFTFSLDTSKSTAYLQMNSLRAEDTAVYYCAKYPHYYGSSHWYFDVWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

Exemplary Bevacizumab Light Chain Nucleotide Sequence
                                              (SEQ ID NO: 109)
GACATCCAGATGACACAGAGCCCCAGCAGCCTGTCTGCCTCTGTGGGAGACAGAGT

GACCATCACCTGTAGCGCCAGCCAGGACATCTCCAACTACCTGAACTGGTATCAGCA

AAAGCCCGGCAAGGCCCCTAAGGTGCTGATCTACTTCACAAGCAGCCTGCACTCCG

GCGTGCCCAGCAGATTTTCTGGCTCTGGCAGCGGCACCGACTTCACCCTGACCATAT

CTAGCCTGCAGCCTGAGGACTTCGCCACCTACTACTGCCAGCAGTACAGCACCGTGC

CTTGGACATTTGGCCAGGGCACAAAGGTGGAAATCAAGCGGACTGTGGCCGCTCCT

AGCGTGTTCATCTTTCCACCTAGCGACGAGCAGCTGAAGTCTGGCACAGCCTCTGTC

GTGTGCCTGCTGAACAACTTCTACCCCAGAGAAGCCAAGGTGCAGTGGAAAGTGGA

CAATGCCCTGCAGAGCGGCAACAGCCAAGAGAGCGTGACAGAGCAGGACTCCAAG

GATAGCACCTATAGCCTGAGCAGCACCCTGACACTGAGCAAGGCCGACTACGAGAA

GCACAAAGTGTACGCCTGCGAAGTGACCCACCAGGGCCTTTCTAGCCCTGTGACCA

AGAGCTTCAACCGGGGCGAATGT

Exemplary Bevacizumab Light Chain amino acid sequence
                                              (SEQ ID NO: 25)
DIQMTQSPSSLSASVGDRVTITCSASQDISNYLNWYQQKPGKAPKVLIYFTSSLHSGVPS

RFSGSGSGTDFTLTISSLQPEDFATYYCQQYSTVPWTFGQGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC
```

VEGF TRAP

A soluble VEGF receptor (also referred to herein as a VEGF TRAP) is a polypeptide that comprises a portion of an extracellular region of one or more (e.g., two or three) mammalian VEGF receptor(s) (e.g., one or more of VEGFR-1, VEGFR-2, and VEGFR-3) operably linked to a signal peptide (e.g., any of the exemplary signal peptides described herein), where the soluble VEGF receptor is capable of specifically binding to one or more mammalian VEGF protein(s) (e.g., one or more (e.g., two, three, or four) of VEGF-A, VEGF-B, VEGF-C, and VEGF-D, e.g., one or more (e.g., two, three, or four) of human wildtype VEGF-A, human wildtype VEGF-B, human wildtype VEGF-C, and human wildtype VEGF-D).

In some examples, a soluble VEGF receptor comprises a portion (e.g., about 10 amino acids to about 732 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 250 amino acids, about 10 amino acids to about 200 amino acids, about 10 amino acids to about 150 amino acids, about 10 amino acids to about 100 amino acids, about 10 amino acids to about 50 amino acids, about 50 amino acids to about 732 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 250 amino acids, about 50 amino acids to about 200 amino acids, about 50 amino acids to about 150 amino acids, about 50 amino acids to about 100 amino acids, about 100 amino acids to about 732 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 250 amino acids, about 100 amino acids to about 200 amino acids, about 100 amino acids to about 150 amino acids, about 150 amino acids to about 732 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 250 amino acids, about 150 amino acids to about 200 amino acids, about 200 amino acids to about 732 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 250 amino acids, about 250 amino acids to about 732 amino acids, about 250 amino acids to about 700 amino acids, about 250 amino acids to about 650 amino acids, about 250 amino acids to about 600 amino acids, about 250 amino acids to about 550 amino acids, about 250 amino acids to about 500 amino acids, about 250 amino acids to about 450 amino acids, about 250 amino acids to about 400 amino acids, about 250 amino acids to about 350 amino acids, about 250 amino acids to about 300 amino acids, about 300 amino acids to about 732 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 732 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 732 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 732 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 732 amino acids, about 500 amino acids to about 700 amino acids, about 500 amino acids to about 650 amino acids, about 500 amino acids to about 600 amino acids, about 500 amino acids to about 550 amino acids, about 550 amino acids to about 732 amino acids, about 550 amino acids to about 700 amino acids, about 550 amino acids to about 650 amino acids, about 550 amino acids to about 600 amino acids, about 600 amino acids to about 732 amino acids, about 600 amino acids to about 700 amino acids, about 600 amino acids to about 650 amino acids, about 650 amino acids to about 732 amino acids, about 650 amino acids to about 700 amino acids, or about 700 amino acids to about 732 amino acids) of an extracellular region of VEGFR-1 (e.g., a contiguous sequence from wildtype human VEGFR-1 (e.g., a contiguous sequence including one or more (e.g., one, two, three, four, five, six, or seven) immunoglobulin-like domains in the extracellular region from wildtype human VEGFR-1 (e.g., SEQ ID NO: 27, 29, 31, or 33) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-1, e.g., a sequence that is at least 80% (e.g., least 82%, at least 84%, at least 86%, at least 88%, at least 90%, least 92%, at least 94%, at least 96%, at least 98%, or at least 99%) identical to a contiguous sequence in SEQ ID NO: 27, 29, 31, or 33.

In some examples, a soluble VEGF receptor comprises a portion (e.g., about 20 amino acids to about 745 amino acids, or any of the subranges of this range described herein) of an extracellular region of VEGFR-2 (e.g., a contiguous sequence from wildtype human VEGFR-2 (e.g., a contiguous sequence including one or more (e.g., one, two, three, four, five, six, or seven) immunoglobulin-like domains in the extracellular region from wildtype human VEGFR-2 (e.g., SEQ ID NO: 35) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-2, e.g., a sequence that is at least 80% (e.g., at least 82%, at least 84%, at least 86%, at least 88%, at least 90%, at least 92%, at least 94%, at least 96%, at least 98%, or at least 99%) identical to a contiguous sequence in SEQ ID NO: 35).

In some examples, a soluble VEGF receptor comprises a portion of an extracellular region of VEGFR-1 (e.g., any of the portions of an extracellular region of VEGFR-1 described herein) and a portion of an extracellular region of VEGFR-2 (e.g., any of the portions of an extracellular region of VEGFR-2 described herein). For example, a soluble VEGF receptor can include one or more (e.g., two, three, four, five, six, or seven) immunoglobulin-like domains in the extracellular region from wildtype human VEGFR-1 and one or more (e.g., two, three, four, five, six, or seven) immunoglobulin-like domains in the extracellular region from wildtype human VEGFR-2 (e.g., aflibercept).

In some examples, a soluble VEGF receptor comprises a portion (e.g., about 20 amino acids to about 751 amino acids, or any of the subranges of this range described herein) of an extracellular region of VEGFR-3 (e.g., a contiguous sequence from wildtype human VEGFR-3 (e.g., a contiguous sequence including one or more (e.g., one, two, three, four, five, six, or seven) immunoglobulin-like domains in the extracellular region from wildtype human VEGFR-3 (e.g., SEQ ID NO: 37, 39, or 41) or a sequence that is at least 80% (e.g., at least 82%, at least 84%, at least 86%, at least 88%, at least 90%, at least 92%, at least 94%, at least 96%, at least 98%, or at least 99%) identical to a contiguous sequence from wildtype human VEGFR-3, e.g., a sequence that is at least 80% (e.g., at least 82%, at least 84%, at least 86%, at least 88%, at least 90%, at least 92%, at least 94%, at least 96%, at least 98%, or at least 99%) identical to a contiguous sequence in SEQ ID NO: 37, 39, or 41).

Non-limiting examples of extracellular regions of different mammalian VEGFR-1, different mammalian VEGFR-2, and different mammalian VEGFR-3 are described herein. Non-limiting examples of protein and nucleotide sequences encoding a wildtype VEGF receptor protein are shown below. As one skilled in the art can appreciate, a substitution in an amino acid that is conserved between species is more likely to result in a change in the function of a protein, while a substitution in an amino acid position that is not conserved between species is less likely to have an effect on the function of a protein.

The VEGFR-1 gene found at human chromosomal position 13q12.3 encodes a 33 exon containing member of the vascular endothelial growth factor receptor (VEGFR) family. VEGFR family members are receptor tyrosine kinases (RTKs) which contain an extracellular ligand-binding region with seven immunoglobulin (Ig)-like domains, a transmembrane segment, and a tyrosine kinase (TK) domain within the cytoplasmic domain. This protein binds to VEGF-A, VEGF-B and placental growth factor and plays an important role in angiogenesis and vasculogenesis. Expression of this receptor is found in vascular endothelial cells, placental trophoblast cells and peripheral blood monocytes. Multiple transcript variants encoding different isoforms have been found for this gene. Isoforms include a full-length transmembrane receptor isoform and shortened, soluble isoforms.

```
Exemplary Human VEGFR-1 isoform 1 cDNA sequence
                                              (SEQ ID NO: 26)
ATCGAGGTCCGCGGGAGGCTCGGAGCGCGCCAGGCGGACACTCCTCTCGGCTCCTC

CCCGGCAGCGGCGGCGGCTCGGAGCGGGCTCCGGGGCTCGGGTGCAGCGGCCAGCG

GGCGCCTGGCGGCGAGGATTACCCGGGGAAGTGGTTGTCTCCTGGCTGGAGCCGCG

AGACGGGCGCTCAGGGCGCGGGGCCGGCGGCGGCGAACGAGAGGACGGACTCTGG

CGGCCGGGTCGTTGGCCGCGGGGAGCGCGGGCACCGGGCGAGCAGGCCGCGTCGCG

CTCACCATGGTCAGCTACTGGGACACCGGGGTCCTGCTGTGCGCGCTGCTCAGCTGT

CTGCTTCTCACAGGATCTAGTTCAGGTTCAAAATTAAAAGATCCTGAACTGAGTTTA

AAAGGCACCCAGCACATCATGCAAGCAGGCCAGACACTGCATCTCCAATGCAGGGG

GGAAGCAGCCCATAAATGGTCTTTGCCTGAAATGGTGAGTAAGGAAAGCGAAAGGC

TGAGCATAACTAAATCTGCCTGTGGAAGAAATGGCAAACAATTCTGCAGTACTTTAA

CCTTGAACACAGCTCAAGCAAACCACACTGGCTTCTACAGCTGCAAATATCTAGCTG

TACCTACTTCAAAGAAGAAGGAAACAGAATCTGCAATCTATATATTTATTAGTGATA

CAGGTAGACCTTTCGTAGAGATGTACAGTGAAATCCCCGAAATTATACACATGACTG

AAGGAAGGGAGCTCGTCATTCCCTGCCGGGTTACGTCACCTAACATCACTGTTACTT

TAAAAAAGTTTCCACTTGACACTTTGATCCCTGATGGAAAACGCATAATCTGGGACA

GTAGAAAGGGCTTCATCATATCAAATGCAACGTACAAAGAAATAGGGCTTCTGACC

TGTGAAGCAACAGTCAATGGGCATTTGTATAAGACAAACTATCTCACACATCGACA

AACCAATACAATCATAGATGTCCAAATAAGCACACCACGCCCAGTCAAATTACTTA

GAGGCCATACTCTTGTCCTCAATTGTACTGCTACCACTCCCTTGAACACGAGAGTTC

AAATGACCTGGAGTTACCCTGATGAAAAAAATAAGAGAGCTTCCGTAAGGCGACGA

ATTGACCAAAGCAATTCCCATGCCAACATATTCTACAGTGTTCTTACTATTGACAAA

ATGCAGAACAAAGACAAAGGACTTTATACTTGTCGTGTAAGGAGTGGACCATCATT

CAAATCTGTTAACACCTCAGTGCATATATATGATAAAGCATTCATCACTGTGAAACA

TCGAAAACAGCAGGTGCTTGAAACCGTAGCTGGCAAGCGGTCTTACCGGCTCTCTAT

GAAAGTGAAGGCATTTCCCTCGCCGGAAGTTGTATGGTTAAAAGATGGGTTACCTGC

GACTGAGAAATCTGCTCGCTATTTGACTCGTGGCTACTCGTTAATTATCAAGGACGT

AACTGAAGAGGATGCAGGGAATTATACAATCTTGCTGAGCATAAAACAGTCAAATG

TGTTTAAAAACCTCACTGCCACTCTAATTGTCAATGTGAAACCCCAGATTTACGAAA

AGGCCGTGTCATCGTTTCCAGACCCGGCTCTCTACCCACTGGGCAGCAGACAAATCC

TGACTTGTACCGCATATGGTATCCCTCAACCTACAATCAAGTGGTTCTGGCACCCCT
```

```
GTAACCATAATCATTCCGAAGCAAGGTGTGACTTTTGTTCCAATAATGAAGAGTCCT

TTATCCTGGATGCTGACAGCAACATGGGAAACAGAATTGAGAGCATCACTCAGCGC

ATGGCAATAATAGAAGGAAAGAATAAGATGGCTAGCACCTTGGTTGTGGCTGACTC

TAGAATTTCTGGAATCTACATTTGCATAGCTTCCAATAAAGTTGGGACTGTGGGAAG

AAACATAAGCTTTTATATCACAGATGTGCCAAATGGGTTTCATGTTAACTTGGAAAA

AATGCCGACGGAAGGAGAGGACCTGAAACTGTCTTGCACAGTTAACAAGTTCTTAT

ACAGAGACGTTACTTGGATTTTACTGCGGACAGTTAATAACAGAACAATGCACTACA

GTATTAGCAAGCAAAAAATGGCCATCACTAAGGAGCACTCCATCACTCTTAATCTTA

CCATCATGAATGTTTCCCTGCAAGATTCAGGCACCTATGCCTGCAGAGCCAGGAATG

TATACACAGGGGAAGAAATCCTCCAGAAGAAAGAAATTACAATCAGAGATCAGGA

AGCACCATACCTCCTGCGAAACCTCAGTGATCACACAGTGGCCATCAGCAGTTCCAC

CACTTTAGACTGTCATGCTAATGGTGTCCCCGAGCCTCAGATCACTTGGTTTAAAAA

CAACCACAAAATACAACAAGAGCCTGGAATTATTTTAGGACCAGGAAGCAGCACGC

TGTTTATTGAAAGAGTCACAGAAGAGGATGAAGGTGTCTATCACTGCAAAGCCACC

AACCAGAAGGGCTCTGTGGAAAGTTCAGCATACCTCACTGTTCAAGGAACCTCGGA

CAAGTCTAATCTGGAGCTGATCACTCTAACATGCACCTGTGTGGCTGCGACTCTCTT

CTGGCTCCTATTAACCCTCTTTATCCGAAAAATGAAAAGGTCTTCTTCTGAAATAAA

GACTGACTACCTATCAATTATAATGGACCCAGATGAAGTTCCTTTGGATGAGCAGTG

TGAGCGGCTCCCTTATGATGCCAGCAAGTGGGAGTTTGCCCGGGAGAGACTTAAACT

GGGCAAATCACTTGGAAGAGGGGCTTTTGGAAAAGTGGTTCAAGCATCAGCATTTG

GCATTAAGAAATCACCTACGTGCCGGACTGTGGCTGTGAAAATGCTGAAAGAGGGG

GCCACGGCCAGCGAGTACAAAGCTCTGATGACTGAGCTAAAAATCTTGACCCACAT

TGGCCACCATCTGAACGTGGTTAACCTGCTGGGAGCCTGCACCAAGCAAGGAGGGC

CTCTGATGGTGATTGTTGAATACTGCAAATATGGAAATCTCTCCAACTACCTCAAGA

GCAAACGTGACTTATTTTTTCTCAACAAGGATGCAGCACTACACATGGAGCCTAAGA

AAGAAAAAATGGAGCCAGGCCTGGAACAAGGCAAGAAACCAAGACTAGATAGCGT

CACCAGCAGCGAAAGCTTTGCGAGCTCCGGCTTTCAGGAAGATAAAAGTCTGAGTG

ATGTTGAGGAAGAGGAGGATTCTGACGGTTTCTACAAGGAGCCCATCACTATGGAA

GATCTGATTTCTTACAGTTTTCAAGTGGCCAGAGGCATGGAGTTCCTGTCTTCCAGA

AAGTGCATTCATCGGGACCTGGCAGCGAGAAACATTCTTTTATCTGAGAACAACGTG

GTGAAGATTTGTGATTTTGGCCTTGCCCGGGATATTTATAAGAACCCCGATTATGTG

AGAAAAGGAGATACTCGACTTCCTCTGAAATGGATGGCTCCTGAATCTATCTTTGAC

AAAATCTACAGCACCAAGAGCGACGTGTGGTCTTACGGAGTATTGCTGTGGGAAAT

CTTCTCCTTAGGTGGGTCTCCATACCCAGGAGTACAAATGGATGAGGACTTTTGCAG

TCGCCTGAGGGAAGGCATGAGGATGAGAGCTCCTGAGTACTCTACTCCTGAAATCTA

TCAGATCATGCTGGACTGCTGGCACAGAGACCCAAAAGAAAGGCCAAGATTTGCAG

AACTTGTGGAAAAACTAGGTGATTTGCTTCAAGCAAATGTACAACAGGATGGTAAA

GACTACATCCCAATCAATGCCATACTGACAGGAAATAGTGGGTTTACATACTCAACT

CCTGCCTTCTCTGAGGACTTCTTCAAGGAAAGTATTTCAGCTCCGAAGTTTAATTCAG

GAAGCTCTGATGATGTCAGATACGTAAATGCTTTCAAGTTCATGAGCCTGGAAAGAA

TCAAAACCTTTGAAGAACTTTTACCGAATGCCACCTCCATGTTTGATGACTACCAGG
```

-continued

```
GCGACAGCAGCACTCTGTTGGCCTCTCCCATGCTGAAGCGCTTCACCTGGACTGACA

GCAAACCCAAGGCCTCGCTCAAGATTGACTTGAGAGTAACCAGTAAAAGTAAGGAG

TCGGGGCTGTCTGATGTCAGCAGGCCCAGTTTCTGCCATTCCAGCTGTGGGCACGTC

AGCGAAGGCAAGCGCAGGTTCACCTACGACCACGCTGAGCTGGAAAGGAAAATCGC

GTGCTGCTCCCCGCCCCCAGACTACAACTCGGTGGTCCTGTACTCCACCCCACCCAT

CTAGAGTTTGACACGAAGCCTTATTTCTAGAAGCACATGTGTATTTATACCCCCAGG

AAACTAGCTTTTGCCAGTATTATGCATATATAAGTTTACACCTTTATCTTTCCATGGG

AGCCAGCTGCTTTTTGTGATTTTTTTAATAGTGCTTTTTTTTTTTGACTAACAAGAAT

GTAACTCCAGATAGAGAAATAGTGACAAGTGAAGAACACTACTGCTAAATCCTCAT

GTTACTCAGTGTTAGAGAAATCCTTCCTAAACCCAATGACTTCCCTGCTCCAACCCC

CGCCACCTCAGGGCACGCAGGACCAGTTTGATTGAGGAGCTGCACTGATCACCCAA

TGCATCACGTACCCCACTGGGCCAGCCCTGCAGCCCAAAACCCAGGGCAACAAGCC

CGTTAGCCCCAGGGATCACTGGCTGGCCTGAGCAACATCTCGGGAGTCCTCTAGCAG

GCCTAAGACATGTGAGGAGGAAAAGGAAAAAAAGCAAAAAGCAAGGGAGAAAAG

AGAAACCGGGAGAAGGCATGAGAAAGAATTTGAGACGCACCATGTGGGCACGGAG

GGGGACGGGGCTCAGCAATGCCATTTCAGTGGCTTCCCAGCTCTGACCCTTCTACAT

TTGAGGGCCCAGCCAGGAGCAGATGGACAGCGATGAGGGGACATTTTCTGGATTCT

GGGAGGCAAGAAAAGGACAAATATCTTTTTTGGAACTAAAGCAAATTTTAGAACTT

TACCTATGGAAGTGGTTCTATGTCCATTCTCATTCGTGGCATGTTTTGATTTGTAGCA

CTGAGGGTGGCACTCAACTCTGAGCCCATACTTTTGGCTCCTCTAGTAAGATGCACT

GAAAACTTAGCCAGAGTTAGGTTGTCTCCAGGCCATGATGGCCTTACACTGAAAATG

TCACATTCTATTTTGGGTATTAATATATAGTCCAGACACTTAACTCAATTTCTTGGTA

TTATTCTGTTTTGCACAGTTAGTTGTGAAAGAAAGCTGAGAAGAATGAAAATGCAGT

CCTGAGGAGAGGAGTTTTCTCCATATCAAAACGAGGGCTGATGGAGGAAAAAGGTC

AATAAGGTCAAGGGAAAACCCCGTCTCTATACCAACCAAACCAATTCACCAACACA

GTTGGGACCCAAAACACAGGAAGTCAGTCACGTTTCCTTTTCATTTAATGGGGATTC

CACTATCTCACACTAATCTGAAAGGATGTGGAAGAGCATTAGCTGGCGCATATTAAG

CACTTTAAGCTCCTTGAGTAAAAAGGTGGTATGTAATTTATGCAAGGTATTTCTCCA

GTTGGGACTCAGGATATTAGTTAATGAGCCATCACTAGAAGAAAAGCCCATTTTCAA

CTGCTTTGAAACTTGCCTGGGGTCTGAGCATGATGGGAATAGGGAGACAGGGTAGG

AAAGGGCGCCTACTCTTCAGGGTCTAAAGATCAAGTGGGCCTTGGATCGCTAAGCTG

GCTCTGTTTGATGCTATTTATGCAAGTTAGGGTCTATGTATTTATGATGTCTGCACCT

TCTGCAGCCAGTCAGAAGCTGGAGAGGCAACAGTGGATTGCTGCTTCTTGGGGAGA

AGAGTATGCTTCCTTTTATCCATGTAATTTAACTGTAGAACCTGAGCTCTAAGTAACC

GAAGAATGTATGCCTCTGTTCTTATGTGCCACATCCTTGTTTAAAGGCTCTCTGTATG

AAGAGATGGGACCGTCATCAGCACATTCCCTAGTGAGCCTACTGGCTCCTGGCAGC

GGCTTTTGTGGAAGACTCACTAGCCAGAAGAGAGGAGTGGGACAGTCCTCTCCACC

AAGATCTAAATCCAAACAAAAGCAGGCTAGAGCCAGAAGAGAGGACAAATCTTTGT

TCTTCCTCTTCTTTACATACGCAAACCACCTGTGACAGCTGGCAATTTTATAAATCAG

GTAACTGGAAGGAGGTTAAACACAGAAAAAAGAAGACCTCAGTCAATTCTCTACTT
```

-continued

```
TTTTTTTTTTTTCCAAATCAGATAATAGCCCAGCAAATAGTGATAACAAATAAAACC

TTAGCTATTCATGTCTTGATTTCAATAATTAATTCTTAATCATTAAGAGACCATAATA

AATACTCCTTTTCAAGAGAAAAGCAAAACCATTAGAATTGTTACTCAGCTCCTTCAA

ACTCAGGTTTGTAGCATACATGAGTCCATCCATCAGTCAAAGAATGGTTCCATCTGG

AGTCTTAATGTAGAAAGAAAAATGGAGACTTGTAATAATGAGCTAGTTACAAAGTG

CTTGTTCATTAAAATAGCACTGAAAATTGAAACATGAATTAACTGATAATATTCCAA

TCATTTGCCATTTATGACAAAAATGGTTGGCACTAACAAAGAACGAGCACTTCCTTT

CAGAGTTTCTGAGATAATGTACGTGGAACAGTCTGGGTGGAATGGGGCTGAAACCA

TGTGCAAGTCTGTGTCTTGTCAGTCCAAGAAGTGACACCGAGATGTTAATTTTAGGG

ACCCGTGCCTTGTTTCCTAGCCCACAAGAATGCAAACATCAAACAGATACTCGCTAG

CCTCATTTAAATTGATTAAAGGAGGAGTGCATCTTTGGCCGACAGTGGTGTAACTGT

ATGTGTGTGTGTGTGTGTGTGTGTGTGTGTGTGTGGGTGTATGTGTGTTTTGTGCA

TAACTATTTAAGGAAACTGGAATTTTAAAGTTACTTTTATACAAACCAAGAATATAT

GCTACAGATATAAGACAGACATGGTTTGGTCCTATATTTCTAGTCATGATGAATGTA

TTTTGTATACCATCTTCATATAATAAACTTCCAAAAACACA
```

Exemplary Human VEGFR-1 isoform 1 precursor amino acid sequence
(SEQ ID NO: 27)

```
MVSYWDTGVLLCALLSCLLLTGSSSGSKLKDPELSLKGTQHIMQAGQTLHLQCRGEAA

HKWSLPEMVSKESERLSITKSACGRNGKQFCSTLTLNTAQANHTGFYSCKYLAVPTSKK

KETESAIYIFISDTGRPFVEMYSEIPEIIHMTEGRELVIPCRVTSPNITVTLKKFPLDTLIPD

GKRIIWDSRKGFIISNATYKEIGLLTCEATVNGHLYKTNYLTHRQTNTIIDVQISTPRPVKLL

RGHTLVLNCTATTPLNTRVQMTWSYPDEKNKRASVRRRIDQSNSHANIFYSVLTIDKMQ

NKDKGLYTCRVRSGPSFKSVNTSVHIYDKAFITVKHRKQQVLETVAGKRSYRLSMKVK

AFPSPEVVWLKDGLPATEKSARYLTRGYSLIIKDVTEEDAGNYTILLSIKQSNVFKNLTA

TLIVNVKPQIYEKAVSSFPDPALYPLGSRQILTCTAYGIPQPTIKWFWHPCNHNHSEARC

DFCSNNEESFILDADSNMGNRIESITQRMAIIEGKNKMASTLVVADSRISGIYICIASNKVG

TVGRNISFYITDVPNGFHVNLEKMPTEGEDLKLSCTVNKFLYRDVTWILLRTVNNRTMH

YSISKQKMAITKEHSITLNLTIMNVSLQDSGTYACRARNVYTGEEILQKKEITIRDQEAPY

LLRNLSDHTVAISSSTTLDCHANGVPEPQITWFKNNHKIQQEPGIILGPGSSTLFIERVTEE

DEGVYHCKATNQKGSVESSAYLTVQGTSDKSNLELITLTCTCVAATLFWLLLTLFIRKM

KRSSSEIKTDYLSIIMDPDEVPLDEQCERLPYDASKWEFARERLKLGKSLGRGAFGKVVQ

ASAFGIKKSPTCRTVAVKMLKEGATASEYKALMTELKILTHIGHHLNVVNLLGACTKQG

GPLMVIVEYCKYGNLSNYLKSKRDLFFLNKDAALHMEPKKEKMEPGLEQGKKPRLDSV

TSSESFASSGFQEDKSLSDVEEEEDSDGFYKEPITMEDLISYSFQVARGMEFLSSRKCIHR

DLAARNILLSENNVVKICDFGLARDIYKNPDYVRKGDTRLPLKWMAPESIFDKIYSTKSD

VWSYGVLLWEIFSLGGSPYPGVQMDEDFCSRLREGMRMRAPEYSTPEIYQIMLDCWHR

DPKERPRFAELVEKLGDLLQANVQQDGKDYIPINAILTGNSGFTYSTPAFSEDFFKESISA

PKFNSGSSDDVRYVNAFKFMSLERIKTFEELLPNATSMFDDYQGDSSTLLASPMLKRFT

WTDSKPKASLKIDLRVTSKSKESGLSDVSRPSFCHSSCGHVSEGKRRFTYDHAELERKIA

CCSPPPDYNSVVLYSTPPI
```

This variant (2), also known as sFlt1 or sVEGFR-1, differs in the 3' coding region and 3' UTR, compared to variant 1. The encoded soluble protein (isoform 2) has a shorter, distinct C-terminus and lacks the transmembrane and cytoplasmic regions of isoform 1.

```
Exemplary Human VEGFR-1 isoform 2 (also known as sVEGFR-1)
cDNA sequence
                                                    (SEQ ID NO: 28)
ATCGAGGTCCGCGGGAGGCTCGGAGCGCGCCAGGCGGACACTCCTCTCGGCTCCTC

CCCGGCAGCGGCGGCGGCTCGGAGCGGGCTCCGGGGCTCGGGTGCAGCGGCCAGCG

GGCGCCTGGCGGCGAGGATTACCCGGGGAAGTGGTTGTCTCCTGGCTGGAGCCGCG

AGACGGGCGCTCAGGGCGCGGGGCCGGCGGCGGCGAACGAGAGGACGGACTCTGG

CGGCCGGGTCGTTGGCCGCGGGGAGCGCGGGCACCGGGCGAGCAGGCCGCGTCGCG

CTCACCATGGTCAGCTACTGGGACACCGGGGTCCTGCTGTGCGCGCTGCTCAGCTGT

CTGCTTCTCACAGGATCTAGTTCAGGTTCAAAATTAAAAGATCCTGAACTGAGTTTA

AAAGGCACCCAGCACATCATGCAAGCAGGCCAGACACTGCATCTCCAATGCAGGGG

GGAAGCAGCCCATAAATGGTCTTTGCCTGAAATGGTGAGTAAGGAAAGCGAAAGGC

TGAGCATAACTAAATCTGCCTGTGGAAGAAATGGCAAACAATTCTGCAGTACTTTAA

CCTTGAACACAGCTCAAGCAAACCACACTGGCTTCTACAGCTGCAAATATCTAGCTG

TACCTACTTCAAAGAAGAAGGAAACAGAATCTGCAATCTATATATTTATTAGTGATA

CAGGTAGACCTTTCGTAGAGATGTACAGTGAAATCCCCGAAATTATACACATGACTG

AAGGAAGGGAGCTCGTCATTCCCTGCCGGGTTACGTCACCTAACATCACTGTTACTT

TAAAAAAGTTTCCACTTGACACTTTGATCCCTGATGGAAAACGCATAATCTGGGACA

GTAGAAAGGGCTTCATCATATCAAATGCAACGTACAAAGAAATAGGGCTTCTGACC

TGTGAAGCAACAGTCAATGGGCATTTGTATAAGACAAACTATCTCACACATCGACA

AACCAATACAATCATAGATGTCCAAATAAGCACACCACGCCCAGTCAAATTACTTA

GAGGCCATACTCTTGTCCTCAATTGTACTGCTACCACTCCCTTGAACACGAGAGTTC

AAAATGACCTGGAGTTACCCTGATGAAAAAAATAAGAGAGCTTCCGTAAGGCGACGA

ATTGACCAAAGCAATTCCCATGCCAACATATTCTACAGTGTTCTTACTATTGACAAA

ATGCAGAACAAAGACAAAGGACTTTATACTTGTCGTGTAAGGAGTGGACCATCATT

CAAATCTGTTAACACCTCAGTGCATATATATGATAAAGCATTCATCACTGTGAAACA

TCGAAAACAGCAGGTGCTTGAAACCGTAGCTGGCAAGCGGTCTTACCGGCTCTCTAT

GAAAGTGAAGGCATTTCCCTCGCCGGAAGTTGTATGGTTAAAAGATGGGTTACCTGC

GACTGAGAAATCTGCTCGCTATTTGACTCGTGGCTACTCGTTAATTATCAAGGACGT

AACTGAAGAGGATGCAGGGAATTATACAATCTTGCTGAGCATAAAACAGTCAAATG

TGTTTAAAAACCTCACTGCCACTCTAATTGTCAATGTGAAACCCCAGATTTACGAAA

AGGCCGTGTCATCGTTTCCAGACCCGGCTCTCTACCCACTGGGCAGCAGACAAATCC

TGACTTGTACCGCATATGGTATCCCTCAACCTACAATCAAGTGGTTCTGGCACCCCT

GTAACCATAATCATTCCGAAGCAAGGTGTGACTTTTGTTCCAATAATGAAGAGTCCT

TTATCCTGGATGCTGACAGCAACATGGGAAACAGAATTGAGAGCATCACTCAGCGC

ATGGCAATAATAGAAGGAAAGAATAAGATGGCTAGCACCTTGGTTGTGGCTGACTC

TAGAATTTCTGGAATCTACATTTGCATAGCTTCCAATAAAGTTGGGACTGTGGGAAG

AAACATAAGCTTTTATATCACAGATGTGCCAAATGGGTTTCATGTTAACTTGGAAAA

AATGCCGACGGAAGGAGAGGACCTGAAACTGTCTTGCACAGTTAACAAGTTCTTAT
```

-continued

```
ACAGAGACGTTACTTGGATTTTACTGCGGACAGTTAATAACAGAACAATGCACTACA

GTATTAGCAAGCAAAAAATGGCCATCACTAAGGAGCACTCCATCACTCTTAATCTTA

CCATCATGAATGTTTCCCTGCAAGATTCAGGCACCTATGCCTGCAGAGCCAGGAATG

TATACACAGGGGAAGAAATCCTCCAGAAGAAAGAAATTACAATCAGAGGTGAGCAC

TGCAACAAAAAGGCTGTTTTCTCTCGGATCTCCAAATTTAAAAGCACAAGGAATGAT

TGTACCACACAAAGTAATGTAAAACATTAAAGGACTCATTAAAAAGTAACAGTTGT

CTCATATCATCTTGATTTATTGTCACTGTTGCTAACTTTCAGGCTCGGAGGAGATGCT

CCTCCCAAAATGAGTTCGGAGATGATAGCAGTAATAATGAGACCCCCGGGCCCCAG

CTCTGGGCCCCCCATTCAGGCCGAGGGGGCTGCTCCGGGGGGCCGACTTGGTGCAC

GTTTGGATTTGGAGGATCCCTGCACTGCCTTCTCTGTGTTTGTTGCTCTTGCTGTTTTC

TCCTGCCTGATAAACAACAACTTGGGATGATCCTTTCCTTCCATTTTGATGCCAACCT

CTTTTTATTTTTAAGTGTTGAAGCTGCACAAACTGAATAATTTAAACAAATGCTGGTT

TCTGCCAAAGATGGACACGAATAAGTTAATTTTCCAGCTCAGAATGAGTACAGTTGA

ATTTGAGACTCTGTCGGACTTCTGCCTGGTTTTATTTGGGACTATTTCATCTGCTCTT

GATTTGTAAATAGCACCTGGATAGCAAGTTATAATGCTTATTTATTTGAAAATGCTTT

TTTTTTTTTTACGTTAAGCACATTTATCTTGAACTGGAGCTTCTAAAATGGGCCCCAG

GGGTGCAAGATGTTGGTGTAATTCAGAGATAGTAAAGGTTTATCGCAGTGTGAATTA

TAAGAGTCCATCCAAATCAACGTCCCCTCCCTCCTCTCATGCGATCCAGGTAATTAT

GCAGTTAGTGCCACAGTAGACTAGCCTAGCAAAGGGTTTGCTCCTTGCTGTCTCTGA

CTGCACCACACAGCTATTGATGGCAGCTGAAAGAAAGTGGATCATGCCTTAATTTTA

AATATTCCTGTCCTCTGGTTATTATTTTAAGGAACTTCATCATGTTAAAATGACAGCA

TTCAAAGGTGTACCACAATCAATTTATCAAGGAAATAAAGGCTATTGTAACCAGAG

ATTTAATGCATTCTTCTAAATGTAAATTTAAAATTTGCCCTTTAAAAAAGTCCACTTT

CCCCATATGCAAATGTTAATAGGATTTTTATGGGGATTAAGAAGCGGCAAAACTACA

GAAGCAGAATTCAAAGTAATTTAAAAAATACACACCAGTTTTAAATCAAGAGAAGT

TGTAATCTCTTGTTTTAAGCTTGCGTTTGAGGGAAAATGACTTTTTCACCAATTTAAT

ATGCATTGTTCTGTTGTTTTTATTTATGATTGATCATTATATGTGACTTGCATAAACT

ATTTAAAAAAAAAAACTATAATGACCAAAATAGCCATGGCTGAGAAACACAGTGGC

TGGGCAGTTCAATAGGAGGTGACAATATGACAACTTCTCAAGCTTGGGAACTCACC

AGACTGTTTCCTCCTTTAGGTAACAGATTCTGTCCCACGGCTAAACTTGTCTTTCACG

TGGGAATTGCTTTTGTCAAACGTGAAAGAGTAAACAATAGCATTTCCCCAGAATGCC

AGTTTTATGGAGCCCCAAATGCTCTGAAAACAATTAGTAACCTGGAAGTTGTCAGCC

CAAAGGAAAGAAAAATCAATTGTATCTTGAAATTTTACCTATGGCTCTTTGGCCTGG

CTTCTTTGTTCATTATAAGTTAGTGTGTTCCTTCAGGAAACAATGCCTTAATACCATA

GAACATGGGGCCTTAATAGTTGCTAACATTAAAAAAGCAAACAGAATGATTGAGG

GATCCTTATGAAAACAAAATGGTGAATTGGACATGCAGAACCTACCATTTCCTTCCC

CTGTTTGCAATTTTTGTGGGGAGGGGAGGATGTTAGTATTTACAAAAGATGATTTA

AGAACTTCCAAGAGATGAGTTTAAGAATTCCATAGAGTATTAGTTGTTCACTGTGTA

ATTAATCCTTCCGGAGAGTCTTTTTTTTTTTTTAAAGAAACTTTTGGGTGGGTTTTG

TTTTTTATTAGTTACCCTAGGGGTATGTTACCCTGGGGTATGAAGGGAGGTGAAGAT
```

```
AACGGAGGGGGAGAAAAAAAAAGGAGAAAAAAGGAGCCTAAAATGGGGAATA
ATTGAAATGGAACAGGGGGTGTGAGGCTGGTTCCTCAGTCCCCATTCCAAACGGAG
GATAGAAGCTGTGTATTTATGTGACCTGGCAGATCTCTGGGGCCATAACACTGAAAA
GTGAAAGAACCTGGTGGGCAGCTATCTTTGGCTACTGATAACCAGCAGAAATGTCTG
TTAATTCTGATTTTCTCAATTTGAAGGGATCAGCTACACTGTTAAATTTTGGAAAGCC
ACTACCTACTTCCATCAAGTAACTTAGGTTTCGAAATATGGGTTCAACGCACCTCCC
TTATTCAAAATGTCAAAATAGATTATTATAATGTATAAAGTAAGAATTGACAAAATA
TGATTCTTGGGTTGATTGGTCATTTAGAAACTAGCCAAAAGTGAGACTTTTAATGTA
GAACATTTTTCAGAAATGGGTACAAAGAAAAATGCATATTACTGTATATTTCAGAGT
GTTTATGTGAACCTTGTATTTAATTGAGAGTCCCATGTACGTTCTGCAGCCTTTTTGC
TGCTTCTATCATCTGAAGTTTGTGTAGTACAAATAAGGCCTTTGGGATTCTTAATGAC
ATTTATGTTAAAATGTTCTCTTCTCTTTAAACACCGTTTTCCAATCCACCTGTCAGGG
AGTCCAAATCGTGTCTGTGTTGATGATGCTATACTTTGTAGCTAGAAAAACAATTTT
AGTGTTGTGGGCTCTGTATTCAGACTTCCTTTTTACAAGACCGATGGGCAGTGATAG
ATTATTTTATCATATTTAATGCATGGGAAATAGTGTGCTGAGGAAGCTATTAAAAGT
ATAACTCAGTGAATTGGGTCTGAGTTTTAAATGAGATATTTCAAAATTGGCTTGCCA
CTGTAAAAGCGACTAAATAATAATATGATACTGTTCTTTATGATCTTGTCATGTTTCA
CTGATATGTTTGGGGTCTTCACTATGTAAAAAATGTCAAAATTGTAATGAGCAAGCA
TGTACAAGTAGTCGTAAATCAAAGGTTTTAAACAGGACTGCATTTTCAATTAGGAAA
AGCTGTTTGGCAGATAGCATCCAATGCAAAAACAGAAATATCGTAACGTTCTGCTTA
GTGGGCAAGATAAGATAGGAAAGACATGCTCAAAGAGGCAAAAGAATCATTGCTAT
CATTCATTCTACACTAGTTTGAAGAAGTTTTTGTACATCAGAGCACTTCCTTCAGCAC
ACTTTTTTGCCTTCAGATTTCATTTTTTATAAAATGAGAAGACTAATGATAAACTGTA
GAAATCAAAATTTATTGAGAAATCTGTTTCTCCTAACAGATAGTAACCCTGCCATGA
TATACTACTTCAACAATGTTATAAAATTTATGTGATAATATACATTTTAACCTGGGAT
TTCTAAATTGCTTTAACAAATGCTAATCCTGAGAGTTGCCCTGCAGGACTCAAAAGG
GAAAGGTTTTGGGACGTGGCAGAACCCTGCAGGGACATGGAATTAAGGCCATTGCA
ATGTATCATCTTTGTAGCATTGTCATCACTCCTAAGCTGCCTTCACAGTTTTAGTACA
CTAAGATGAGGAAATCGAAAATGGGCAGAGAAAGCTCATACTGTATAATTGAAGAC
AGTGACAGAGAACGTGTCAGTTATGCCAAAACTCTTTTGATTTCTGTTCCAGGATTT
CCAACAAGAGGGGAAAGGAATGACTTGGGAGGGTGGGAAAGACATTAGGAGTTGT
TTTTATTTTTTACCTTGGAAGCTTTAGCTACCAATCCAGTACCCTCCTAACTAGAATG
TATACACATCAGCAGGACTGACTGACTACTTCATTAGAGATATACTGTACTCATTGG
GGGCCTTGGGGGTACTGCTGTTCTTATGTGGGATTTTAATGTTGTAATGTATTGCATC
TTAATGTATTGAATTCATTTTGTTGTACTATATTGGTTGGCATTTTATTAAAATAAAT
TGTATTGTATCATATTTGTATGTTTTAAGAGAAAATAATATAAAATACAATATTTGTA
CTATTATATAGTGCAAAAACTACAAATCTGTGCCTCTGCCTCTTGAATTAATTCTTTG
GTTGCTTGCATTTGGGAAGGGAATGGAGAAAGGAAAGAACCAATAAAGCTTTCAAA
GTTCAAGAAA

Exemplary Human VEGFR-1 isoform 2 (also known as sVEGFR-1)
precursor amino acid sequence
```

-continued (SEQ ID NO: 29)
MVSYWDTGVLLCALLSCLLLTGSSSGSKLKDPELSLKGTQHIMQAGQTLHLQCRGEAA

HKWSLPEMVSKESERLSITKSACGRNGKQFCSTLTLNTAQANHTGFYSCKYLAVPTSKK

KETESAIYIFISDTGRPFVEMYSEIPEIIHMTEGRELVIPCRVTSPNITVTLKKFPLDTLIPD

GKRIIWDSRKGFIISNATYKEIGLLTCEATVNGHLYKTNYLTHRQTNTIIDVQISTPRPVKLL

RGHTLVLNCTATTPLNTRVQMTWSYPDEKNKRASVRRRIDQSNSHANIFYSVLTIDKMQ

NKDKGLYTCRVRSGPSFKSVNTSVHIYDKAFITVKHRKQQVLETVAGKRSYRLSMKVK

AFPSPEVVWLKDGLPATEKSARYLTRGYSLIIKDVTEEDAGNYTILLSIKQSNVFKNLTA

TLIVNVKPQIYEKAVSSFPDPALYPLGSRQILTCTAYGIPQPTIKWFWHPCNHNHSEARC

DFCSNNEESFILDADSNMGNRIESITQRMAIIEGKNKMASTLVVADSRISGIYICIASNKVG

TVGRNISFYITDVPNGFHVNLEKMPTEGEDLKLSCTVNKFLYRDVTWILLRTVNNRTMH

YSISKQKMAITKEHSITLNLTIMNVSLQDSGTYACRARNVYTGEEILQKKEITIRGEHCNK

KAVFSRISKFKSTRNDCTTQSNVKH

This variant (3) differs in the 3' coding region and 3' UTR, compared to variant 1. The encoded soluble protein (isoform 3) has a shorter, distinct C-terminus and lacks the transmembrane and cytoplasmic regions of isoform 1.

Exemplary Human VEGFR-1 isoform 3 cDNA sequence (SEQ ID NO: 30)
ATCGAGGTCCGCGGGAGGCTCGGAGCGCGCCAGGCGGACACTCCTCTCGGCTCCTC

CCCGGCAGCGGCGGCGGCTCGGAGCGGGCTCCGGGGCTCGGGTGCAGCGGCCAGCG

GGCGCCTGGCGGCGAGGATTACCCGGGGAAGTGGTTGTCTCCTGGCTGGAGCCGCG

AGACGGGCGCTCAGGGCGCGGGGCCGGCGGCGGCGAACGAGAGGACGGACTCTGG

CGGCCGGGTCGTTGGCCGCGGGGAGCGCGGGCACCGGGCGAGCAGGCCGCGTCGCG

CTCACCATGGTCAGCTACTGGGACACCGGGGTCCTGCTGTGCGCGCTGCTCAGCTGT

CTGCTTCTCACAGGATCTAGTTCAGGTTCAAAATTAAAAGATCCTGAACTGAGTTTA

AAAGGCACCCAGCACATCATGCAAGCAGGCCAGACACTGCATCTCCAATGCAGGGG

GGAAGCAGCCCATAAATGGTCTTTGCCTGAAATGGTGAGTAAGGAAAGCGAAAGGC

TGAGCATAACTAAATCTGCCTGTGGAAGAAATGGCAAACAATTCTGCAGTACTTTAA

CCTTGAACACAGCTCAAGCAAACCACACTGGCTTCTACAGCTGCAAATATCTAGCTG

TACCTACTTCAAAGAAGAAGGAAACAGAATCTGCAATCTATATATTTATTAGTGATA

CAGGTAGACCTTTCGTAGAGATGTACAGTGAAATCCCCGAAATTATACACATGACTG

AAGGAAGGGAGCTCGTCATTCCCTGCCGGGTTACGTCACCTAACATCACTGTTACTT

TAAAAAAGTTTCCACTTGACACTTTGATCCCTGATGGAAAACGCATAATCTGGGACA

GTAGAAAGGGCTTCATCATATCAAATGCAACGTACAAAGAAATAGGGCTTCTGACC

TGTGAAGCAACAGTCAATGGGCATTTGTATAAGACAAACTATCTCACACATCGACA

AACCAATACAATCATAGATGTCCAAATAAGCACACCACGCCCAGTCAAATTACTTA

GAGGCCATACTCTTGTCCTCAATTGTACTGCTACCACTCCCTTGAACACGAGAGTTC

AAATGACCTGGAGTTACCCTGATGAAAAAAATAAGAGAGCTTCCGTAAGGCGACGA

ATTGACCAAAGCAATTCCCATGCCAACATATTCTACAGTGTTCTTACTATTGACAAA

ATGCAGAACAAAGACAAAGGACTTTATACTTGTCGTGTAAGGAGTGGACCATCATT

CAAATCTGTTAACACCTCAGTGCATATATATGATAAAGCATTCATCACTGTGAAACA

TCGAAAACAGCAGGTGCTTGAAACCGTAGCTGGCAAGCGGTCTTACCGGCTCTCTAT

-continued

```
GAAAGTGAAGGCATTTCCCTCGCCGGAAGTTGTATGGTTAAAAGATGGGTTACCTGC

GACTGAGAAATCTGCTCGCTATTTGACTCGTGGCTACTCGTTAATTATCAAGGACGT

AACTGAAGAGGATGCAGGGAATTATACAATCTTGCTGAGCATAAAACAGTCAAATG

TGTTTAAAAACCTCACTGCCACTCTAATTGTCAATGTGAAACCCCAGATTTACGAAA

AGGCCGTGTCATCGTTTCCAGACCCGGCTCTCTACCCACTGGGCAGCAGACAAATCC

TGACTTGTACCGCATATGGTATCCCTCAACCTACAATCAAGTGGTTCTGGCACCCCT

GTAACCATAATCATTCCGAAGCAAGGTGTGACTTTTGTTCCAATAATGAAGAGTCCT

TTATCCTGGATGCTGACAGCAACATGGGAAACAGAATTGAGAGCATCACTCAGCGC

ATGGCAATAATAGAAGGAAAGAATAAGATGGCTAGCACCTTGGTTGTGGCTGACTC

TAGAATTTCTGGAATCTACATTTGCATAGCTTCCAATAAAGTTGGGACTGTGGGAAG

AAACATAAGCTTTTATATCACAGATGTGCCAAATGGGTTTCATGTTAACTTGGAAAA

AATGCCGACGGAAGGAGAGGACCTGAAACTGTCTTGCACAGTTAACAAGTTCTTAT

ACAGAGACGTTACTTGGATTTTACTGCGGACAGTTAATAACAGAACAATGCACTACA

GTATTAGCAAGCAAAAAATGGCCATCACTAAGGAGCACTCCATCACTCTTAATCTTA

CCATCATGAATGTTTCCCTGCAAGATTCAGGCACCTATGCCTGCAGAGCCAGGAATG

TATACACAGGGGAAGAAATCCTCCAGAAGAAAGAAATTACAATCAGAGATCAGGA

AGCACCATACCTCCTGCGAAACCTCAGTGATCACACAGTGGCCATCAGCAGTTCCAC

CACTTTAGACTGTCATGCTAATGGTGTCCCCGAGCCTCAGATCACTTGGTTTAAAAA

CAACCACAAAATACAACAAGAGCCTGAACTGTATACATCAACGTCACCATCGTCAT

CGTCATCATCACCATTGTCATCATCATCATCATCGTCATCATCATCATCATAGCT

ATCATCATTATCATCATCATCATCATCATCATAGCTACCATTTATTGAAAACTAT

TATGTGTCAACTTCAAAGAACTTATCCTTTAGTTGGAGAGCCAAGACAATCATAACA

ATAACAAATGGCCGGGCATGGTGGCTCACGCCTGTAATCCCAGCACTTTGGGAGGC

CAAGGCAGGTGGATCATTTGAGGTCAGGAGTTCAAGACCAGCCTGACCAAGATGGT

GAAATGCTGTCTCTATTAAAAATACAAAATTAGCCAGGCATGGTGGCTCATGCCTGT

AATGCCAGCTACTCGGGAGGCTGAGACAGGAGAATCACTTGAACCCAGGAGGCAGA

GGTTGCAGGGAGCCGAGATCGTGTACTGCACTCCAGCCTGGGCAACAAGAGCGAAA

CTCCGTCTCAAAAAACAAATAAATAAATAAATAAATAAACAGACAAAATTCACTTT

TTATTCTATTAAACTTAACATACATGCATTAA
```

Exemplary Human VEGFR-1 isoform 3 cDNA sequence
(SEQ ID NO: 31)

```
MVSYWDTGVLLCALLSCLLLTGSSSGSKLKDPELSLKGTQHIMQAGQTLHLQCRGEAA

HKWSLPEMVSKESERLSITKSACGRNGKQFCSTLTLNTAQANHTGFYSCKYLAVPTSKK

KETESAIYIFISDTGRPFVEMYSEIPEIIHMTEGRELVIPCRVTSPNITVTLKKFPLDTLIPD

GKRIIWDSRKGFIISNATYKEIGLLTCEATVNGHLYKTNYLTHRQTNTIIDVQISTPRPVKLL

RGHTLVLNCTATTPLNTRVQMTWSYPDEKNKRASVRRRIDQSNSHANIFYSVLTIDKMQ

NKDKGLYTCRVRSGPSFKSVNTSVHIYDKAFITVKHRKQQVLETVAGKRSYRLSMKVK

AFPSPEVVWLKDGLPATEKSARYLTRGYSLIIKDVTEEDAGNYTILLSIKQSNVFKNLTA

TLIVNVKPQIYEKAVSSFPDPALYPLGSRQILTCTAYGIPQPTIKWFWHPCNHNHSEARC

DFCSNNEESFILDADSNMGNRIESITQRMAIIEGKNKMASTLVVADSRISGIYICIASNKVG

TVGRNISFYITDVPNGFHVNLEKMPTEGEDLKLSCTVNKFLYRDVTWILLRTVNNRTMH

YSISKQKMAITKEHSITLNLTIMNVSLQDSGTYACRARNVYTGEEILQKKEITIRDQEAPY
```

LLRNLSDHTVAISSSTTLDCHANGVPEPQITWFKNNHKIQQEPELYTSTSPSSSSSSPLSSS

SSSSSSSSS

This variant (4) differs in the 3' coding region and 3' UTR, compared to variant 1. The encoded soluble protein (isoform 4) has a shorter, distinct C-terminus and lacks the transmembrane and cytoplasmic regions of isoform 1.

```
Exemplary Human VEGFR-1 isoform 4 cDNA sequence
                                                         (SEQ ID NO: 32)
ATCGAGGTCCGCGGGAGGCTCGGAGCGCGCCAGGCGGACACTCCTCTCGGCTCCTC

CCCGGCAGCGGCGGCGGCTCGGAGCGGGCTCCGGGGCTCGGGTGCAGCGGCCAGCG

GGCGCCTGGCGGCGAGGATTACCCGGGGAAGTGGTTGTCTCCTGGCTGGAGCCGCG

AGACGGGCGCTCAGGGCGCGGGGCCGGCGGCGGCGAACGAGAGGACGGACTCTGG

CGGCCGGGTCGTTGGCCGCGGGGAGCGCGGGCACCGGGCGAGCAGGCCGCGTCGCG

CTCACCATGGTCAGCTACTGGGACACCGGGGTCCTGCTGTGCGCGCTGCTCAGCTGT

CTGCTTCTCACAGGATCTAGTTCAGGTTCAAAATTAAAAGATCCTGAACTGAGTTTA

AAAGGCACCCAGCACATCATGCAAGCAGGCCAGACACTGCATCTCCAATGCAGGGG

GGAAGCAGCCCATAAATGGTCTTTGCCTGAAATGGTGAGTAAGGAAAGCGAAAGGC

TGAGCATAACTAAATCTGCCTGTGGAAGAAATGGCAAACAATTCTGCAGTACTTTAA

CCTTGAACACAGCTCAAGCAAACCACACTGGCTTCTACAGCTGCAAATATCTAGCTG

TACCTACTTCAAAGAAGAAGGAAACAGAATCTGCAATCTATATATTTATTAGTGATA

CAGGTAGACCTTTCGTAGAGATGTACAGTGAAATCCCCGAAATTATACACATGACTG

AAGGAAGGGAGCTCGTCATTCCCTGCCGGGTTACGTCACCTAACATCACTGTTACTT

TAAAAAAGTTTCCACTTGACACTTTGATCCCTGATGGAAAACGCATAATCTGGGACA

GTAGAAAGGGCTTCATCATATCAAATGCAACGTACAAAGAAATAGGGCTTCTGACC

TGTGAAGCAACAGTCAATGGGCATTTGTATAAGACAAACTATCTCACACATCGACA

AACCAATACAATCATAGATGTCCAAATAAGCACACCACGCCCAGTCAAATTACTTA

GAGGCCATACTCTTGTCCTCAATTGTACTGCTACCACTCCCTTGAACACGAGAGTTC

AAATGACCTGGAGTTACCCTGATGAAAAAAATAAGAGAGCTTCCGTAAGGCGACGA

ATTGACCAAAGCAATTCCCATGCCAACATATTCTACAGTGTTCTTACTATTGACAAA

ATGCAGAACAAAGACAAAGGACTTTATACTTGTCGTGTAAGGAGTGGACCATCATT

CAAATCTGTTAACACCTCAGTGCATATATATGATAAAGCATTCATCACTGTGAAACA

TCGAAAACAGCAGGTGCTTGAAACCGTAGCTGGCAAGCGGTCTTACCGGCTCTCTAT

GAAAGTGAAGGCATTTCCCTCGCCGGAAGTTGTATGGTTAAAAGATGGGTTACCTGC

GACTGAGAAATCTGCTCGCTATTTGACTCGTGGCTACTCGTTAATTATCAAGGACGT

AACTGAAGAGGATGCAGGGAATTATACAATCTTGCTGAGCATAAAACAGTCAAATG

TGTTTAAAAACCTCACTGCCACTCTAATTGTCAATGTGAAACCCCAGATTTACGAAA

AGGCCGTGTCATCGTTTCCAGACCCGGCTCTCTACCCACTGGGCAGCAGACAAATCC

TGACTTGTACCGCATATGGTATCCCTCAACCTACAATCAAGTGGTTCTGGCACCCCT

GTAACCATAATCATTCCGAAGCAAGGTGTGACTTTTGTTCCAATAATGAAGAGTCCT

TTATCCTGGATGCTGACAGCAACATGGGAAACAGAATTGAGAGCATCACTCAGCGC

ATGGCAATAATAGAAGGAAAGAATAAGCTTCCACCAGCTAACAGTTCTTTCATGTTG
```

```
CCACCTACAAGCTTCTCTTCCAACTACTTCCATTTCCTTCCGTGA
```

Exemplary Human VEGFR-1 isoform 4 cDNA sequence
(SEQ ID NO: 33)
```
MVSYWDTGVLLCALLSCLLLTGSSSGSKLKDPELSLKGTQHIMQAGQTLHLQCRGEAA

HKWSLPEMVSKESERLSITKSACGRNGKQFCSTLTLNTAQANHTGFYSCKYLAVPTSKK

KETESAIYIFISDTGRPFVEMYSEIPEIIHMTEGRELVIPCRVTSPNITVTLKKFPLDTLIPDG

KRIIWDSRKGFIISNATYKEIGLLTCEATVNGHLYKTNYLTHRQTNTIIDVQISTPRPVKLL

RGHTLVLNCTATTPLNTRVQMTWSYPDEKNKRASVRRRIDQSNSHANIFYSVLTIDKMQ

NKDKGLYTCRVRSGPSFKSVNTSVHIYDKAFITVKHRKQQVLETVAGKRSYRLSMKVK

AFPSPEVVWLKDGLPATEKSARYLTRGYSLIIKDVTEEDAGNYTILLSIKQSNVFKNLTA

TLIVNVKPQIYEKAVSSFPDPALYPLGSRQILTCTAYGIPQPTIKWFWHPCNHNHSEARC

DFCSNNEESFILDADSNMGNRIESITQRMAIIEGKNKLPPANSSFMLPPTSFSSNYFHFLP
```

The VEGFR-2 gene found at human chromosomal position 4q12 encodes a 30 exon containing member of the vascular endothelial growth factor receptor family (VEGFR) and is one of two genes encoding receptors for VEGF-A. This receptor, known as kinase insert domain receptor, is a type III receptor tyrosine kinase. It functions as the main mediator of VEGF-A induced endothelial proliferation, survival, migration, tubular morphogenesis and sprouting. The signaling and trafficking of this receptor are regulated by multiple factors, including Rab GTPase, P2Y purine nucleotide receptor, integrin alphaVbeta3, T-cell protein tyrosine phosphatase, etc.

Exemplary Human VEGFR-2 cDNA sequence
(SEQ ID NO: 34)
```
ACTGAGTCCCGGGACCCCGGGAGAGCGGTCAATGTGTGGTCGCTGCGTTTCCTCTGC

CTGCGCCGGGCATCACTTGCGCGCCGCAGAAAGTCCGTCTGGCAGCCTGGATATCCT

CTCCTACCGGCACCCGCAGACGCCCCTGCAGCCGCGGTCGGCGCCCGGGCTCCCTAG

CCCTGTGCGCTCAACTGTCCTGCGCTGCGGGTGCCGCGAGTTCCACCTCCGCGCCT

CCTTCTCTAGACAGGCGCTGGGAGAAAGAACCGGCTCCCGAGTTCTGGGCATTTCGC

CCGGCTCGAGGTGCAGGATGCAGAGCAAGGTGCTGCTGGCCGTCGCCCTGTGGCTC

TGCGTGGAGACCCGGGCCGCCTCTGTGGGTTTGCCTAGTGTTTCTCTTGATCTGCCCA

GGCTCAGCATACAAAAAGACATACTTACAATTAAGGCTAATACAACTCTTCAAATTA

CTTGCAGGGACAGAGGGACTTGGACTGGCTTTGGCCCAATAATCAGAGTGGCAGT

GAGCAAAGGGTGGAGGTGACTGAGTGCAGCGATGGCCTCTTCTGTAAGACACTCAC

AATTCCAAAAGTGATCGGAAATGACACTGGAGCCTACAAGTGCTTCTACCGGGAAA

CTGACTTGGCCTCGGTCATTTATGTCTATGTTCAAGATTACAGATCTCCATTTATTGC

TTCTGTTAGTGACCAACATGGAGTCGTGTACATTACTGAGAACAAAAACAAAACTGT

GGTGATTCCATGTCTCGGGTCCATTTCAAATCTCAACGTGTCACTTTGTGCAAGATAC

CCAGAAAAGAGATTTGTTCCTGATGGTAACAGAATTTCCTGGGACAGCAAGAAGGG

CTTTACTATTCCCAGCTACATGATCAGCTATGCTGGCATGGTCTTCTGTGAAGCAAA

AATTAATGATGAAAGTTACCAGTCTATTATGTACATAGTTGTCGTTGTAGGGTATAG

GATTTATGATGTGGTTCTGAGTCCGTCTCATGGAATTGAACTATCTGTTGGAGAAAA

GCTTGTCTTAAATTGTACAGCAAGAACTGAACTAAATGTGGGGATTGACTTCAACTG

GGAATACCCTTCTTCGAAGCATCAGCATAAGAAACTTGTAAACCGAGACCTAAAAA

CCCAGTCTGGGAGTGAGATGAAGAAATTTTTGAGCACCTTAACTATAGATGGTGTAA

CCCGGAGTGACCAAGGATTGTACACCTGTGCAGCATCCAGTGGGCTGATGACCAAG

AAGAACAGCACATTTGTCAGGGTCCATGAAAAACCTTTTGTTGCTTTTGGAAGTGGC
```

```
ATGGAATCTCTGGTGGAAGCCACGGTGGGGGAGCGTGTCAGAATCCCTGCGAAGTA

CCTTGGTTACCCACCCCCAGAAATAAAATGGTATAAAAATGGAATACCCCTTGAGTC

CAATCACACAATTAAAGCGGGGCATGTACTGACGATTATGGAAGTGAGTGAAAGAG

ACACAGGAAATTACACTGTCATCCTTACCAATCCCATTTCAAAGGAGAAGCAGAGC

CATGTGGTCTCTCTGGTTGTGTATGTCCCACCCCAGATTGGTGAGAAATCTCTAATCT

CTCCTGTGGATTCCTACCAGTACGGCACCACTCAAACGCTGACATGTACGGTCTATG

CCATTCCTCCCCCGCATCACATCCACTGGTATTGGCAGTTGGAGGAAGAGTGCGCCA

ACGAGCCCAGCCAAGCTGTCTCAGTGACAAACCCATACCCTTGTGAAGAATGGAGA

AGTGTGGAGGACTTCCAGGGAGGAAATAAAATTGAAGTTAATAAAAATCAATTTGC

TCTAATTGAAGGAAAAAACAAAACTGTAAGTACCCTTGTTATCCAAGCGGCAAATG

TGTCAGCTTTGTACAAATGTGAAGCGGTCAACAAAGTCGGGAGAGGAGAGAGGGTG

ATCTCCTTCCACGTGACCAGGGGTCCTGAAATTACTTTGCAACCTGACATGCAGCCC

ACTGAGCAGGAGAGCGTGTCTTTGTGGTGCACTGCAGACAGATCTACGTTTGAGAAC

CTCACATGGTACAAGCTTGGCCCACAGCCTCTGCCAATCCATGTGGGAGAGTTGCCC

ACACCTGTTTGCAAGAACTTGGATACTCTTTGGAAATTGAATGCCACCATGTTCTCT

AATAGCACAAATGACATTTTGATCATGGAGCTTAAGAATGCATCCTTGCAGGACCAA

GGAGACTATGTCTGCCTTGCTCAAGACAGGAAGACCAAGAAAAGACATTGCGTGGT

CAGGCAGCTCACAGTCCTAGAGCGTGTGGCACCCACGATCACAGGAAACCTGGAGA

ATCAGACGACAAGTATTGGGGAAAGCATCGAAGTCTCATGCACGGCATCTGGGAAT

CCCCCTCCACAGATCATGTGGTTTAAAGATAATGAGACCCTTGTAGAAGACTCAGGC

ATTGTATTGAAGGATGGGAACCGGAACCTCACTATCCGCAGAGTGAGGAAGGAGGA

CGAAGGCCTCTACACCTGCCAGGCATGCAGTGTTCTTGGCTGTGCAAAAGTGGAGGC

ATTTTTCATAATAGAAGGTGCCCAGGAAAAGACGAACTTGGAAATCATTATTCTAGT

AGGCACGGCGGTGATTGCCATGTTCTTCTGGCTACTTCTTGTCATCATCCTACGGACC

GTTAAGCGGGCCAATGGAGGGGAACTGAAGACAGGCTACTTGTCCATCGTCATGGA

TCCAGATGAACTCCCATTGGATGAACATTGTGAACGACTGCCTTATGATGCCAGCAA

ATGGGAATTCCCCAGAGACCGGCTGAAGCTAGGTAAGCCTCTTGGCCGTGGTGCCTT

TGGCCAAGTGATTGAAGCAGATGCCTTTGGAATTGACAAGACAGCAACTTGCAGGA

CAGTAGCAGTCAAAATGTTGAAAGAAGGAGCAACACACAGTGAGCATCGAGCTCTC

ATGTCTGAACTCAAGATCCTCATTCATATTGGTCACCATCTCAATGTGGTCAACCTTC

TAGGTGCCTGTACCAAGCCAGGAGGGCCACTCATGGTGATTGTGGAATTCTGCAAAT

TTGGAAACCTGTCCACTTACCTGAGGAGCAAGAGAAATGAATTTGTCCCCTACAAGA

CCAAAGGGGCACGATTCCGTCAAGGGAAAGACTACGTTGGAGCAATCCCTGTGGAT

CTGAAACGGCGCTTGGACAGCATCACCAGTAGCCAGAGCTCAGCCAGCTCTGGATT

TGTGGAGGAGAAGTCCCTCAGTGATGTAGAAGAAGAGGAAGCTCCTGAAGATCTGT

ATAAGGACTTCCTGACCTTGGAGCATCTCATCTGTTACAGCTTCCAAGTGGCTAAGG

GCATGGAGTTCTTGGCATCGCGAAAGTGTATCCACAGGGACCTGGCGGCACGAAAT

ATCCTCTTATCGGAGAAGAACGTGGTTAAAATCTGTGACTTTGGCTTGGCCCGGGAT

ATTTATAAAGATCCAGATTATGTCAGAAAAGGAGATGCTCGCCTCCCTTTGAAATGG

ATGGCCCCAGAAACAATTTTTGACAGAGTGTACACAATCCAGAGTGACGTCTGGTCT
```

```
-continued
TTTGGTGTTTTGCTGTGGGAAATATTTTCCTTAGGTGCTTCTCCATATCCTGGGGTAA

AGATTGATGAAGAATTTTGTAGGCGATTGAAAGAAGGAACTAGAATGAGGGCCCCT

GATTATACTACACCAGAAATGTACCAGACCATGCTGGACTGCTGGCACGGGGAGCC

CAGTCAGAGACCCACGTTTTCAGAGTTGGTGGAACATTTGGGAAATCTCTTGCAAGC

TAATGCTCAGCAGGATGGCAAAGACTACATTGTTCTTCCGATATCAGAGACTTTGAG

CATGGAAGAGGATTCTGGACTCTCTCTGCCTACCTCACCTGTTTCCTGTATGGAGGA

GGAGGAAGTATGTGACCCCAAATTCCATTATGACAACACAGCAGGAATCAGTCAGT

ATCTGCAGAACAGTAAGCGAAAGAGCCGGCCTGTGAGTGTAAAAACATTTGAAGAT

ATCCCGTTAGAAGAACCAGAAGTAAAAGTAATCCCAGATGACAACCAGACGGACAG

TGGTATGGTTCTTGCCTCAGAAGAGCTGAAAACTTTGGAAGACAGAACCAAATTATC

TCCATCTTTTGGTGGAATGGTGCCCAGCAAAAGCAGGGAGTCTGTGGCATCTGAAGG

CTCAAACCAGACAAGCGGCTACCAGTCCGGATATCACTCCGATGACACAGACACCA

CCGTGTACTCCAGTGAGGAAGCAGAACTTTTAAAGCTGATAGAGATTGGAGTGCAA

ACCGGTAGCACAGCCCAGATTCTCCAGCCTGACTCGGGGACCACACTGAGCTCTCCT

CCTGTTTAAAAGGAAGCATCCACACCCCCAACTCCTGGACATCACATGAGAGGTGCT

GCTCAGATTTTCAAGTGTTGTTCTTTCCACCAGCAGGAAGTAGCCGCATTTGATTTTC

ATTTCGACAACAGAAAAAGGACCTCGGACTGCAGGGAGCCAGTCTTCTAGGCATAT

CCTGGAAGAGGCTTGTGACCCAAGAATGTGTCTGTGTCTTCTCCCAGTGTTGACCTG

ATCCTCTTTTTCATTCATTTAAAAAGCATTTATCATGCCCCCTGCTGCGGGTCTCACC

ATGGGTTTAGAACAAAGACGTTCAAGAAATGGCCCCATCCTCAAAGAAGTAGCAGT

ACCTGGGGAGCTGACACTTCTGTAAAACTAGAAGATAAACCAGGCAATGTAAGTGT

TCGAGGTGTTGAAGATGGGAAGGATTTGCAGGGCTGAGTCTATCCAAGAGGCTTTGT

TTAGGACGTGGGTCCCAAGCCAAGCCTTAAGTGTGGAATTCGGATTGATAGAAAGG

AAGACTAACGTTACCTTGCTTTGGAGAGTACTGGAGCCTGCAAATGCATTGTGTTTG

CTCTGGTGGAGGTGGGCATGGGGTCTGTTCTGAAATGTAAAGGGTTCAGACGGGGTT

TCTGGTTTTAGAAGGTTGCGTGTTCTTCGAGTTGGGCTAAAGTAGAGTTCGTTGTGCT

GTTTCTGACTCCTAATGAGAGTTCCTTCCAGACCGTTACGTGTCTCCTGGCCAAGCCC

CAGGAAGGAAATGATGCAGCTCTGGCTCCTTGTCTCCCAGGCTGATCCTTTATTCAG

AATACCACAAAGAAAGGACATTCAGCTCAAGGCTCCCTGCCGTGTTGAAGAGTTCT

GACTGCACAAACCAGCTTCTGGTTTCTTCTGGAATGAATACCCTCATATCTGTCCTGA

TGTGATATGTCTGAGACTGAATGCGGGAGGTTCAATGTGAAGCTGTGTGGTGTCA

AAGTTTCAGGAAGGATTTTACCCTTTTGTTCTTCCCCCTGTCCCCAACCCACTCTCAC

CCCGCAACCCATCAGTATTTTAGTTATTTGGCCTCTACTCCAGTAAACCTGATTGGGT

TTGTTCACTCTCTGAATGATTATTAGCCAGACTTCAAAATTATTTTATAGCCCAAATT

ATAACATCTATTGTATTATTTAGACTTTTAACATATAGAGCTATTTCTACTGATTTTT

GCCCTTGTTCTGTCCTTTTTTTCAAAAAAGAAAATGTGTTTTTTGTTTGGTACCATAG

TGTGAAATGCTGGGAACAATGACTATAAGACATGCTATGGCACATATATTTATAGTC

TGTTTATGTAGAAACAAATGTAATATATTAAAGCCTTATATATAATGAACTTTGTAC

TATTCACATTTTGTATCAGTATTATGTAGCATAACAAAGGTCATAATGCTTTCAGCA

ATTGATGTCATTTTATTAAAGAACATTGAAAAACTTGAAAAAAAAAAAAAAAA

Exemplary Human VEGFR-2 precursor amino acid sequence
```

-continued
(SEQ ID NO: 35)

MQSKVLLAVALWLCVETRAASVGLPSVSLDLPRLSIQKDILTIKANTTLQITCRGQRDLD

WLWPNNQSGSEQRVEVTECSDGLFCKTLTIPKVIGNDTGAYKCFYRETDLASVIYVYVQ

DYRSPFIASVSDQHGVVYITENKNKTVVIPCLGSISNLNVSLCARYPEKRFVPDGNRISW

DSKKGFTIPSYMISYAGMVFCEAKINDESYQSIMYIVVVVGYRIYDVVLSPSHGIELSVGE

KLVLNCTARTELNVGIDFNWEYPSSKHQHKKLVNRDLKTQSGSEMKKFLSTLTIDGVTR

SDQGLYTCAASSGLMTKKNSTFVRVHEKPFVAFGSGMESLVEATVGERVRIPAKYLGY

PPPEIKWYKNGIPLESNHTIKAGHVLTIMEVSERDTGNYTVILTNPISKEKQSHVVSLVVY

VPPQIGEKSLISPVDSYQYGTTQTLTCTVYAIPPPHHIHWYWQLEEECANEPSQAVSVTN

PYPCEEWRSVEDFQGGNKIEVNKNQFALIEGKNKTVSTLVIQAANVSALYKCEAVNKV

GRGERVISFHVTRGPEITLQPDMQPTEQESVSLWCTADRSTFENLTWYKLGPQPLPIHVG

ELPTPVCKNLDTLWKLNATMFSNSTNDILIMELKNASLQDQGDYVCLAQDRKTKKRHC

VVRQLTVLERVAPTITGNLENQTTSIGESIEVSCTASGNPPPQIMWFKDNETLVEDSGIVL

KDGNRNLTIRRVRKEDEGLYTCQACSVLGCAKVEAFFIIEGAQEKTNLEIIILVGTAVIAM

FFWLLLVIILRTVKRANGGELKTGYLSIVMDPDELPLDEHCERLPYDASKWEFPRDRLKL

GKPLGRGAFGQVIEADAFGIDKTATCRTVAVKMLKEGATHSEHRALMSELKILIHIGHH

LNVVNLLGACTKPGGPLMVIVEFCKFGNLSTYLRSKRNEFVPYKTKGARFRQGKDYVG

AIPVDLKRRLDSITSSQSSASSGFVEEKSLSDVEEEEAPEDLYKDFLTLEHLICYSFQVAK

GMEFLASRKCIHRDLAARNILLSEKNVVKICDFGLARDIYKDPDYVRKGDARLPLKWM

APETIFDRVYTIQSDVWSFGVLLWEIFSLGASPYPGVKIDEEFCRRLKEGTRMRAPDYTT

PEMYQTMLDCWHGEPSQRPTFSELVEHLGNLLQANAQQDGKDYIVLPISETLSMEEDSG

LSLPTSPVSCMEEEEVCDPKFHYDNTAGISQYLQNSKRKSRPVSVKTFEDIPLEEPEVKVI

PDDNQTDSGMVLASEELKTLEDRTKLSPSFGGMVPSKSRESVASEGSNQTSGYQSGYHS

DDTDTTVYSSEEAELLKLIEIGVQTGSTAQILQPDSGTTLSSPPV

The VEGFR-3 gene found at human chromosomal position 5q35.3 encodes a 35 exon containing member of the vascular endothelial growth factor receptor family (VEGFR) This gene encodes a tyrosine kinase receptor for vascular endothelial growth factors C and D. The protein is thought to be involved in lymphangiogenesis and maintenance of the lymphatic endothelium.

Exemplary Human VEGFR-3 Isoform 1 cDNA sequence
(SEQ ID NO: 36)
ACTTTCAGCCCCGAGCCGCGGCCGCTCGGGTCGGACCCACGCGCAGCGGCCGGAGA

TGCAGCGGGCGCCGCGCTGTGCCTGCGACTGTGGCTCTGCCTGGGACTCCTGGACG

GCCTGGTGAGTGGCTACTCCATGACCCCCCCGACCTTGAACATCACGGAGGAGTCAC

ACGTCATCGACACCGGTGACAGCCTGTCCATCTCCTGCAGGGGACAGCACCCCCTCG

AGTGGGCTTGGCCAGGAGCTCAGGAGGCGCCAGCCACCGGAGACAAGGACAGCGA

GGACACGGGGGTGGTGCGAGACTGCGAGGGCACAGACGCCAGGCCCTACTGCAAG

GTGTTGCTGCTGCACGAGGTACATGCCAACGACACAGGCAGCTACGTCTGCTACTAC

AAGTACATCAAGGCACGCATCGAGGGCACCACGGCCGCCAGCTCCTACGTGTTCGT

GAGAGACTTTGAGCAGCCATTCATCAACAAGCCTGACACGCTCTTGGTCAACAGGA

AGGACGCCATGTGGGTGCCCTGTCTGGTGTCCATCCCCGGCCTCAATGTCACGCTGC

-continued
```
GCTCGCAAAGCTCGGTGCTGTGGCCAGACGGGCAGGAGGTGGTGTGGGATGACCGG

CGGGGCATGCTCGTGTCCACGCCACTGCTGCACGATGCCCTGTACCTGCAGTGCGAG

ACCACCTGGGGAGACCAGGACTTCCTTTCCAACCCCTTCCTGGTGCACATCACAGGC

AACGAGCTCTATGACATCCAGCTGTTGCCCAGGAAGTCGCTGGAGCTGCTGGTAGG

GGAGAAGCTGGTCCTGAACTGCACCGTGTGGGCTGAGTTTAACTCAGGTGTCACCTT

TGACTGGGACTACCCAGGGAAGCAGGCAGAGCGGGGTAAGTGGGTGCCCGAGCGA

CGCTCCCAGCAGACCCACACAGAACTCTCCAGCATCCTGACCATCCACAACGTCAGC

CAGCACGACCTGGGCTCGTATGTGTGCAAGGCCAACAACGGCATCCAGCGATTTCG

GGAGAGCACCGAGGTCATTGTGCATGAAAATCCCTTCATCAGCGTCGAGTGGCTCA

AAGGACCCATCCTGGAGGCCACGGCAGGAGACGAGCTGGTGAAGCTGCCCGTGAAG

CTGGCAGCGTACCCCCCGCCCGAGTTCCAGTGGTACAAGGATGGAAAGGCACTGTC

CGGGCGCCACAGTCCACATGCCCTGGTGCTCAAGGAGGTGACAGAGGCCAGCACAG

GCACCTACACCCTCGCCCTGTGGAACTCCGCTGCTGGCCTGAGGCGCAACATCAGCC

TGGAGCTGGTGGTGAATGTGCCCCCCCAGATACATGAGAAGGAGGCCTCCTCCCCC

AGCATCTACTCGCGTCACAGCCGCCAGGCCCTCACCTGCACGGCCTACGGGGTGCCC

CTGCCTCTCAGCATCCAGTGGCACTGGCGGCCCTGGACACCCTGCAAGATGTTTGCC

CAGCGTAGTCTCCGGCGGCGGCAGCAGCAAGACCTCATGCCACAGTGCCGTGACTG

GAGGGCGGTGACCACGCAGGATGCCGTGAACCCCATCGAGAGCCTGGACACCTGGA

CCGAGTTTGTGGAGGGAAAGAATAAGACTGTGAGCAAGCTGGTGATCCAGAATGCC

AACGTGTCTGCCATGTACAAGTGTGTGGTCTCCAACAAGGTGGGCCAGGATGAGCG

GCTCATCTACTTCTATGTGACCACCATCCCCGACGGCTTCACCATCGAATCCAAGCC

ATCCGAGGAGCTACTAGAGGGCCAGCCGGTGCTCCTGAGCTGCCAAGCCGACAGCT

ACAAGTACGAGCATCTGCGCTGGTACCGCCTCAACCTGTCCACGCTGCACGATGCGC

ACGGGAACCCGCTTCTGCTCGACTGCAAGAACGTGCATCTGTTCGCCACCCCTCTGG

CCGCCAGCCTGGAGGAGGTGGCACCTGGGGCGCGCCACGCCACGCTCAGCCTGAGT

ATCCCCCGCGTCGCGCCCGAGCACGAGGGCCACTATGTGTGCGAAGTGCAAGACCG

GCGCAGCCATGACAAGCACTGCCACAAGAAGTACCTGTCGGTGCAGGCCCTGGAAG

CCCCTCGGCTCACGCAGAACTTGACCGACCTCCTGGTGAACGTGAGCGACTCGCTGG

AGATGCAGTGCTTGGTGGCCGGAGCGCACGCGCCCAGCATCGTGTGGTACAAAGAC

GAGAGGCTGCTGGAGGAAAAGTCTGGAGTCGACTTGGCGGACTCCAACCAGAAGCT

GAGCATCCAGCGCGTGCGCGAGGAGGATGCGGGACGCTATCTGTGCAGCGTGTGCA

ACGCCAAGGGCTGCGTCAACTCCTCCGCCAGCGTGGCCGTGGAAGGCTCCGAGGAT

AAGGGCAGCATGGAGATCGTGATCCTTGTCGGTACCGGCGTCATCGCTGTCTTCTTC

TGGGTCCTCCTCCTCCTCATCTTCTGTAACATGAGGAGGCCGGCCCACGCAGACATC

AAGACGGGCTACCTGTCCATCATCATGGACCCCGGGGAGGTGCCTCTGGAGGAGCA

ATGCGAATACCTGTCCTACGATGCCAGCCAGTGGGAATTCCCCCGAGAGCGGCTGC

ACCTGGGGAGAGTGCTCGGCTACGGCGCCTTCGGGAAGGTGGTGGAAGCCTCCGCT

TTCGGCATCCACAAGGGCAGCAGCTGTGACACCGTGGCCGTGAAAATGCTGAAAGA

GGGCGCCACGGCCAGCGAGCACCGCGCGCTGATGTCGGAGCTCAAGATCCTCATTC

ACATCGGCAACCACCTCAACGTGGTCAACCTCCTCGGGGCGTGCACCAAGCCGCAG

GGCCCCCTCATGGTGATCGTGGAGTTCTGCAAGTACGGCAACCTCTCCAACTTCCTG
```

-continued

```
CGCGCCAAGCGGGACGCCTTCAGCCCCTGCGCGGAGAAGTCTCCCGAGCAGCGCGG
ACGCTTCCGCGCCATGGTGGAGCTCGCCAGGCTGGATCGGAGGCGGCCGGGGAGCA
GCGACAGGGTCCTCTTCGCGCGGTTCTCGAAGACCGAGGGCGGAGCGAGGCGGGCT
TCTCCAGACCAAGAAGCTGAGGACCTGTGGCTGAGCCCGCTGACCATGGAAGATCT
TGTCTGCTACAGCTTCCAGGTGGCCAGAGGGATGGAGTTCCTGGCTTCCCGAAAGTG
CATCCACAGAGACCTGGCTGCTCGGAACATTCTGCTGTCGGAAAGCGACGTGGTGA
AGATCTGTGACTTTGGCCTTGCCCGGGACATCTACAAAGACCCCGACTACGTCCGCA
AGGGCAGTGCCCGGCTGCCCCTGAAGTGGATGGCCCCTGAAAGCATCTTCGACAAG
GTGTACACCACGCAGAGTGACGTGTGGTCCTTTGGGGTGCTTCTCTGGGAGATCTTC
TCTCTGGGGGCCTCCCCGTACCCTGGGGTGCAGATCAATGAGGAGTTCTGCCAGCGG
CTGAGAGACGGCACAAGGATGAGGGCCCCGGAGCTGGCCACTCCCGCCATACGCCG
CATCATGCTGAACTGCTGGTCCGGAGACCCCAAGGCGAGACCTGCATTCTCGGAGCT
GGTGGAGATCCTGGGGGACCTGCTCCAGGGCAGGGCCTGCAAGAGGAAGAGGAG
GTCTGCATGGCCCCGCGCAGCTCTCAGAGCTCAGAAGAGGGCAGCTTCTCGCAGGT
GTCCACCATGGCCCTACACATCGCCCAGGCTGACGCTGAGGACAGCCCGCCAAGCC
TGCAGCGCCACAGCCTGGCCGCCAGGTATTACAACTGGGTGTCCTTTCCCGGGTGCC
TGGCCAGAGGGCTGAGACCCGTGGTTCCTCCAGGATGAAGACATTTGAGGAATTC
CCCATGACCCCAACGACCTACAAAGGCTCTGTGGACAACCAGACAGACAGTGGGAT
GGTGCTGGCCTCGGAGGAGTTTGAGCAGATAGAGAGCAGGCATAGACAAGAAAGC
GGCTTCAGCTGTAAAGGACCTGGCCAGAATGTGGCTGTGACCAGGGCACACCCTGA
CTCCCAAGGGAGGCGGCGGCGGCCTGAGCGGGGGGCCCGAGGAGGCCAGGTGTTTT
ACAACAGCGAGTATGGGGAGCTGTCGGAGCCAAGCGAGGAGGACCACTGCTCCCCG
TCTGCCCGCGTGACTTTCTTCACAGACAACAGCTACTAAGCAGCATCGGACAAGACC
CCCAGCACTTGGGGGTTCAGGCCCGGCAGGGCGGGCAGAGGGCTGGAGGCCCAGGC
TGGGAACTCATCTGGTTGAACTCTGGTGGCACAGGAGTGTCCTCTTCCCTCTCTGCA
GACTTCCCAGCTAGGAAGAGCAGGACTCCAGGCCCAAGGCTCCCGGAATTCCGTCA
CCACGACTGGCCAGGGCCACGCTCCAGCTGCCCCGGCCCCTCCCCCTGAGATTCAGA
TGTCATTTAGTTCAGCATCCGCAGGTGCTGGTCCCGGGGCCAGCACTTCCATGGGAA
TGTCTCTTTGGCGACCTCCTTTCATCACACTGGGTGGTGGCCTGGTCCCTGTTTTCCC
ACGAGGAATCTGTGGGTCTGGGAGTCACACAGTGTTGGAGGTTAAGGCATACGAGA
GCAGAGGTCTCCCAAACGCCCTTTCCTCCTCAGGCACACAGCTACTCTCCCCACGAG
GGCTGGCTGGCCTCACCCACCCCTGCACAGTTGAAGGGAGGGCTGTGTTTCCATCT
CAAAGAAGGCATTTGCAGGGTCCTCTTCTGGGCCTGACCAAACAGCCAACTAGCCC
CTGGGGTGGCCACCAGTATGACAGTATTATACGCTGGCAACACAGAGGCAGCCCGC
ACACCTGCGCCTGGGTGTTGAGAGCCATCCTGCAAGTCTTTTTCAACAGAACTTCAC
AGACTGTTAGAGCTGCTGAGAAGAATTTGCTTTCCGAATTCAGCCTGGAAGGCGCCC
AGGGACAGCTGTACTGAGTCTAGATGACTCTGACCCCCGCCCCAGGTCAAGGCCAG
CAGAGCAGTCAGTGCCTCTGGAGAAGGCCCTTGCTCTCCCACCTGGCCCAGACTCCG
AGGAGCCTGGGTCTGGAGCTGCCGGTCTGGTTCTTCCCTTTAGAGCCCGGATCTGCC
ACCTGCGGCCCCTCCCAAGCCGTGAACCAGCTCATGAGAGATGAACACTGTGGGAT
```

```
                            -continued
CCACTCAGGAAGGCTCGGGGCTGGCACAAAGGACCACCCAGCATTGCCCTGTGCCA

CCCAGCACTCAGTGGACATTCTGGGGACCTGCCTTCAGCCTTTTCCTGCCCTGTGCCT

GACATCAGCACCCTGGCTGGTCAGAATGCCGCCCTCCCAGAGGAGCAGCCGAGAGA

TCCCCTGAAGGCTGGAGGCATTCTGCTCAGGACCCCTATCCCAGCTCACAGTGCCCA

ACCATCTCACCAGGAGAAAGAGCCACATCCCCACGTTAGGACCACGGAGACTGACC

ACCACCCTGACCCCCCAAACCCACGCACCAGACGCTTGCAGGACAGGCGCCGCGCA

GCGGGCAGGGGCTTGCCCGGCCGACCCTCCCCTCCCCACCTCCCCCACTGCGCGTTA

CTCCAGGATATGCCGAGTGCACGTATAAGGTCATCTTCGTCGTCCCCGTGGACCTCC

CCCTTCCTCTGCACGTCGTCCAACGTGGGACTGGCGTGTCAGGCTTCCCTGGGAGGA

TCTGGAGGTTGTTCTCTGCAGAGAACCAGCCTGGCTCCTGGCGCGCACCTCTGCTCC

CTTCTCCTCACTACCCACCCACGCATGTACCGGGAAAAAAACTACTATGCCCTTCTA

GACCATGTTCTGAGAAAAGATCGAAAATATTTAACAAGAGATAATAATAAATCTGA

TGCCGGTCTTTGTGTGTGTTGCGGA

Exemplary Human VEGFR-3 Isoform 1 precursor amino acid sequence
                                                (SEQ ID NO: 37)
MQRGAALCLRLWLCLGLLDGLVSGYSMTPPTLNITEESHVIDTGDSLSISCRGQHPLEW

AWPGAQEAPATGDKDSEDTGVVRDCEGTDARPYCKVLLLHEVHANDTGSYVCYYKYI

KARIEGTTAASSYVFVRDFEQPFINKPDTLLVNRKDAMWVPCLVSIPGLNVTLRSQSSVL

WPDGQEVVWDDRRGMLVSTPLLHDALYLQCETTWGDQDFLSNPFLVHITGNELYDIQL

LPRKSLELLVGEKLVLNCTVWAEFNSGVTFDWDYPGKQAERGKWVPERRSQQTHTELS

SILTIHNVSQHDLGSYVCKANNGIQRFRESTEVIVHENPFISVEWLKGPILEATAGDELVK

LPVKLAAYPPPEFQWYKDGKALSGRHSPHALVLKEVTEASTGTYTLALWNSAAGLRRN

ISLELVVNVPPQIHEKEASSPSIYSRHSRQALTCTAYGVPLPLSIQWHWRPWTPCKMFAQ

RSLRRRQQQDLMPQCRDWRAVTTQDAVNPIESLDTWTEFVEGKNKTVSKLVIQNANVS

AMYKCVVSNKVGQDERLIYFYVTTIPDGFTIESKPSEELLEGQPVLLSCQADSYKYEHLR

WYRLNLSTLHDAHGNPLLLDCKNVHLFATPLAASLEEVAPGARHATLSLSIPRVAPEHE

GHYVCEVQDRRSHDKHCHKKYLSVQALEAPRLTQNLTDLLVNVSDSLEMQCLVAGAH

APSIVWYKDERLLEEKSGVDLADSNQKLSIQRVREEDAGRYLCSVCNAKGCVNSSASV

AVEGSEDKGSMEIVILVGTGVIAVFFWVLLLLIFCNMRRPAHADIKTGYLSIIMDPGEVPL

EEQCEYLSYDASQWEFPRERLHLGRVLGYGAFGKVVEASAFGIHKGSSCDTVAVKMLK

EGATASEHRALMSELKILIHIGNHLNVVNLLGACTKPQGPLMVIVEFCKYGNLSNFLRA

KRDAFSPCAEKSPEQRGRFRAMVELARLDRRRPGSSDRVLFARFSKTEGGARRASPDQE

AEDLWLSPLTMEDLVCYSFQVARGMEFLASRKCIHRDLAARNILLSESDVVKICDFGLA

RDIYKDPDYVRKGSARLPLKWMAPESIFDKVYTTQSDVWSFGVLLWEIFSLGASPYPGV

QINEEFCQRLRDGTRMRAPELATPAIRRIMLNCWSGDPKARPAFSELVEILGDLLQGRGL

QEEEEVCMAPRSSQSSEEGSFSQVSTMALHIAQADAEDSPPSLQRHSLAARYYNWVSFP

GCLARGAETRGSSRMKTFEEFPMTPTTYKGSVDNQTDSGMVLASEEFEQIESRHRQESG

FSCKGPGQNVAVTRAHPDSQGRRRRPERGARGGQVFYNSEYGELSEPSEEDHCSPSARV

TFFTDNSY
```

This variant (2) contains an alternate 3' terminal exon compared to variant 1. This results in an isoform (2) with a shorter C-terminus compared to isoform 1.

Exemplary Human VEGFR-3 Isoform 2 cDNA sequence
(SEQ ID NO: 38)

ACTTTCAGCCCCGAGCCGCGGCCGCTCGGGTCGGACCCACGCGCAGCGGCCGGAGA

TGCAGCGGGGCGCCGCGCTGTGCCTGCGACTGTGGCTCTGCCTGGGACTCCTGGACG

GCCTGGTGAGTGGCTACTCCATGACCCCCCCGACCTTGAACATCACGGAGGAGTCAC

ACGTCATCGACACCGGTGACAGCCTGTCCATCTCCTGCAGGGGACAGCACCCCCTCG

AGTGGGCTTGGCCAGGAGCTCAGGAGGCGCCAGCCACCGGAGACAAGGACAGCGA

GGACACGGGGGTGGTGCGAGACTGCGAGGGCACAGACGCCAGGCCCTACTGCAAG

GTGTTGCTGCTGCACGAGGTACATGCCAACGACACAGGCAGCTACGTCTGCTACTAC

AAGTACATCAAGGCACGCATCGAGGGCACCACGGCCGCCAGCTCCTACGTGTTCGT

GAGAGACTTTGAGCAGCCATTCATCAACAAGCCTGACACGCTCTTGGTCAACAGGA

AGGACGCCATGTGGGTGCCCTGTCTGGTGTCCATCCCCGGCCTCAATGTCACGCTGC

GCTCGCAAAGCTCGGTGCTGTGGCCAGACGGGCAGGAGGTGGTGTGGGATGACCGG

CGGGGCATGCTCGTGTCCACGCCACTGCTGCACGATGCCCTGTACCTGCAGTGCGAG

ACCACCTGGGGAGACCAGGACTTCCTTTCCAACCCCTTCCTGGTGCACATCACAGGC

AACGAGCTCTATGACATCCAGCTGTTGCCCAGGAAGTCGCTGGAGCTGCTGGTAGG

GGAGAAGCTGGTCCTGAACTGCACCGTGTGGGCTGAGTTTAACTCAGGTGTCACCTT

TGACTGGGACTACCCAGGGAAGCAGGCAGAGCGGGGTAAGTGGGTGCCCGAGCGA

CGCTCCCAGCAGACCCACACAGAACTCTCCAGCATCCTGACCATCCACAACGTCAGC

CAGCACGACCTGGGCTCGTATGTGTGCAAGGCCAACAACGGCATCCAGCGATTTCG

GGAGAGCACCGAGGTCATTGTGCATGAAAATCCCTTCATCAGCGTCGAGTGGCTCA

AAGGACCCATCCTGGAGGCCACGGCAGGAGACGAGCTGGTGAAGCTGCCCGTGAAG

CTGGCAGCGTACCCCCCGCCCGAGTTCCAGTGGTACAAGGATGGAAAGGCACTGTC

CGGGCGCCACAGTCCACATGCCCTGGTGCTCAAGGAGGTGACAGAGGCCAGCACAG

GCACCTACACCCTCGCCCTGTGGAACTCCGCTGCTGGCCTGAGGCGCAACATCAGCC

TGGAGCTGGTGGTGAATGTGCCCCCCCAGATACATGAGAAGGAGGCCTCCTCCCCC

AGCATCTACTCGCGTCACAGCCGCCAGGCCCTCACCTGCACGGCCTACGGGGTGCCC

CTGCCTCTCAGCATCCAGTGGCACTGGCGGCCCTGGACACCCTGCAAGATGTTTGCC

CAGCGTAGTCTCCGGCGGCGGCAGCAGCAAGACCTCATGCCACAGTGCCGTGACTG

GAGGGCGGTGACCACGCAGGATGCCGTGAACCCCATCGAGAGCCTGGACACCTGGA

CCGAGTTTGTGGAGGGAAAGAATAAGACTGTGAGCAAGCTGGTGATCCAGAATGCC

AACGTGTCTGCCATGTACAAGTGTGTGGTCTCCAACAAGGTGGGCCAGGATGAGCG

GCTCATCTACTTCTATGTGACCACCATCCCCGACGGCTTCACCATCGAATCCAAGCC

ATCCGAGGAGCTACTAGAGGGCCAGCCGGTGCTCCTGAGCTGCCAAGCCGACAGCT

ACAAGTACGAGCATCTGCGCTGGTACCGCCTCAACCTGTCCACGCTGCACGATGCGC

ACGGGAACCCGCTTCTGCTCGACTGCAAGAACGTGCATCTGTTCGCCACCCCTCTGG

CCGCCAGCCTGGAGGAGGTGGCACCTGGGGCGCGCCACGCCACGCTCAGCCTGAGT

ATCCCCCGCGTCGCGCCCGAGCACGAGGGCCACTATGTGTGCGAAGTGCAAGACCG

GCGCAGCCATGACAAGCACTGCCACAAGAAGTACCTGTCGGTGCAGGCCCTGGAAG

CCCCTCGGCTCACGCAGAACTTGACCGACCTCCTGGTGAACGTGAGCGACTCGCTGG

AGATGCAGTGCTTGGTGGCCGGAGCGCACGCGCCCAGCATCGTGTGGTACAAAGAC

GAGAGGCTGCTGGAGGAAAAGTCTGGAGTCGACTTGGCGGACTCCAACCAGAAGCT

-continued

```
GAGCATCCAGCGCGTGCGCGAGGAGGATGCGGGACGCTATCTGTGCAGCGTGTGCA

ACGCCAAGGGCTGCGTCAACTCCTCCGCCAGCGTGGCCGTGGAAGGCTCCGAGGAT

AAGGGCAGCATGGAGATCGTGATCCTTGTCGGTACCGGCGTCATCGCTGTCTTCTTC

TGGGTCCTCCTCCTCCTCATCTTCTGTAACATGAGGAGGCCGGCCCACGCAGACATC

AAGACGGGCTACCTGTCCATCATCATGGACCCCGGGGAGGTGCCTCTGGAGGAGCA

ATGCGAATACCTGTCCTACGATGCCAGCCAGTGGGAATTCCCCCGAGAGCGGCTGC

ACCTGGGGAGAGTGCTCGGCTACGGCGCCTTCGGGAAGGTGGTGGAAGCCTCCGCT

TTCGGCATCCACAAGGGCAGCAGCTGTGACACCGTGGCCGTGAAAATGCTGAAAGA

GGGCGCCACGGCCAGCGAGCACCGCGCGCTGATGTCGGAGCTCAAGATCCTCATTC

ACATCGGCAACCACCTCAACGTGGTCAACCTCCTCGGGGCGTGCACCAAGCCGCAG

GGCCCCCTCATGGTGATCGTGGAGTTCTGCAAGTACGGCAACCTCTCCAACTTCCTG

CGCGCCAAGCGGGACGCCTTCAGCCCCTGCGCGGAGAAGTCTCCCGAGCAGCGCGG

ACGCTTCCGCGCCATGGTGGAGCTCGCCAGGCTGGATCGGAGGCGGCCGGGGAGCA

GCGACAGGGTCCTCTTCGCGCGGTTCTCGAAGACCGAGGGCGGAGCGAGGCGGGCT

TCTCCAGACCAAGAAGCTGAGGACCTGTGGCTGAGCCCGCTGACCATGGAAGATCT

TGTCTGCTACAGCTTCCAGGTGGCCAGAGGGATGGAGTTCCTGGCTTCCCGAAAGTG

CATCCACAGAGACCTGGCTGCTCGGAACATTCTGCTGTCGGAAAGCGACGTGGTGA

AGATCTGTGACTTTGGCCTTGCCCGGGACATCTACAAAGACCCCGACTACGTCCGCA

AGGGCAGTGCCCGGCTGCCCCTGAAGTGGATGGCCCCTGAAAGCATCTTCGACAAG

GTGTACACCACGCAGAGTGACGTGTGGTCCTTTGGGGTGCTTCTCTGGGAGATCTTC

TCTCTGGGGGCCTCCCCGTACCCTGGGGTGCAGATCAATGAGGAGTTCTGCCAGCGG

CTGAGAGACGGCACAAGGATGAGGGCCCCGGAGCTGGCCACTCCCGCCATACGCCG

CATCATGCTGAACTGCTGGTCCGGAGACCCCAAGGCGAGACCTGCATTCTCGGAGCT

GGTGGAGATCCTGGGGGACCTGCTCCAGGGCAGGGGCCTGCAAGAGGAAGAGGAG

GTCTGCATGGCCCCGCGCAGCTCTCAGAGCTCAGAAGAGGGCAGCTTCTCGCAGGT

GTCCACCATGGCCCTACACATCGCCCAGGCTGACGCTGAGGACAGCCCGCCAAGCC

TGCAGCGCCACAGCCTGGCCGCCAGGTATTACAACTGGGTGTCCTTTCCCGGGTGCC

TGGCCAGAGGGGCTGAGACCCGTGGTTCCTCCAGGATGAAGACATTTGAGGAATTC

CCCATGACCCCAACGACCTACAAAGGCTCTGTGGACAACCAGACAGACAGTGGGAT

GGTGCTGGCCTCGGAGGAGTTTGAGCAGATAGAGAGCAGGCATAGACAAGAAAGC

GGCTTCAGGTAGCTGAAGCAGAGAGAGAGAAGGCAGCATACGTCAGCATTTTCTTC

TCTGCACTTATAAGAAAGATCAAAGACTTTAAGACTTTCGCTATTTCTTCTACTGCTA

TCTACTACAAACTTCAAAGAGGAACCAGGAGGACAAGAGGAGCATGAAAGTGGAC

AAGGAGTGTGACCACTGAAGCACCACAGGGAGGGGTTAGGCCTCCGGATGACTGCG

GGCAGGCCTGGATAATATCCAGCCTCCCACAAGAAGCTGGTGGAGCAGAGTGTTCC

CTGACTCCTCCAAGGAAAGGGAGACGCCCTTTCATGGTCTGCTGAGTAACAGGTGCC

TTCCCAGACACTGGCGTTACTGCTTGACCAAAGAGCCCTCAAGCGGCCCTTATGCCA

GCGTGACAGAGGGCTCACCTCTTGCCTTCTAGGTCACTTCTCACAATGTCCCTTCAG

CACCTGACCCTGTGCCCACCAGTTATTCCTTGGTAATATGAGTAATACATCAAAGAG

TAGTATTAAAAGCTAATTAATCATGTTTATACTAA
```

-continued

```
Exemplary Human VEGFR-3 Isoform 1 precursor amino acid sequence
                                                    (SEQ ID NO: 39)
MQRGAALCLRLWLCLGLLDGLVSGYSMTPPTLNITEESHVIDTGDSLSISCRGQHPLEW

AWPGAQEAPATGDKDSEDTGVVRDCEGTDARPYCKVLLLHEVHANDTGSYVCYYKYI

KARIEGTTAASSYVFVRDFEQPFINKPDTLLVNRKDAMWVPCLVSIPGLNVTLRSQSSVL

WPDGQEVVWDDRRGMLVSTPLLHDALYLQCETTWGDQDFLSNPFLVHITGNELYDIQL

LPRKSLELLVGEKLVLNCTVWAEFNSGVTFDWDYPGKQAERGKWVPERRSQQTHTELS

SILTIHNVSQHDLGSYVCKANNGIQRFRESTEVIVHENPFISVEWLKGPILEATAGDELVK

LPVKLAAYPPPEFQWYKDGKALSGRHSPHALVLKEVTEASTGTYTLALWNSAAGLRRN

ISLELVVNVPPQIHEKEASSPSIYSRHSRQALTCTAYGVPLPLSIQWHWRPWTPCKMFAQ

RSLRRRQQQDLMPQCRDWRAVTTQDAVNPIESLDTWTEFVEGKNKTVSKLVIQNANVS

AMYKCVVSNKVGQDERLIYFYVTTIPDGFTIESKPSEELLEGQPVLLSCQADSYKYEHLR

WYRLNLSTLHDAHGNPLLLDCKNVHLFATPLAASLEEVAPGARHATLSLSIPRVAPEHE

GHYVCEVQDRRSHDKHCHKKYLSVQALEAPRLTQNLTDLLVNVSDSLEMQCLVAGAH

APSIVWYKDERLLEEKSGVDLADSNQKLSIQRVREEDAGRYLCSVCNAKGCVNSSASV

AVEGSEDKGSMEIVILVGTGVIAVFFWVLLLLIFCNMRRPAHADIKTGYLSIIMDPGEVPL

EEQCEYLSYDASQWEFPRERLHLGRVLGYGAFGKVVEASAFGIHKGSSCDTVAVKMLK

EGATASEHRALMSELKILIHIGNHLNVVNLLGACTKPQGPLMVIVEFCKYGNLSNFLRA

KRDAFSPCAEKSPEQRGRFRAMVELARLDRRRPGSSDRVLFARFSKTEGGARRASPDQE

AEDLWLSPLTMEDLVCYSFQVARGMEFLASRKCIHRDLAARNILLSESDVVKICDFGLA

RDIYKDPDYVRKGSARLPLKWMAPESIFDKVYTTQSDVWSFGVLLWEIFSLGASPYPGV

QINEEFCQRLRDGTRMRAPELATPAIRRIMLNCWSGDPKARPAFSELVEILGDLLQGRGL

QEEEEVCMAPRSSQSSEEGSFSQVSTMALHIAQADAEDSPPSLQRHSLAARYYNWVSFP

GCLARGAETRGSSRMKTFEEFPMTPTTYKGSVDNQTDSGMVLASEEFEQIESRHRQESG

FR
```

40

This variant (3) contains an alternate 3' terminal exon compared to variant 1. This results in an isoform (3) with a shorter C-terminus compared to isoform 1.

```
Exemplary Human VEGFR-3 Isoform 2 cDNA sequence
                                                    (SEQ ID NO: 40)
ACTTTCAGCCCCGAGCCGCGGCCGCTCGGGTCGGACCCACGCGCAGCGGCCGGAGA

TGCAGCGGGGCGCCGCGCTGTGCCTGCGACTGTGGCTCTGCCTGGGACTCCTGGACG

GCCTGGTGAGTGGCTACTCCATGACCCCCCCGACCTTGAACATCACGGAGGAGTCAC

ACGTCATCGACACCGGTGACAGCCTGTCCATCTCCTGCAGGGGACAGCACCCCCTCG

AGTGGGCTTGGCCAGGAGCTCAGGAGGCGCCAGCCACCGGAGACAAGGACAGCGA

GGACACGGGGGTGGTGCGAGACTGCGAGGGCACAGACGCCAGGCCCTACTGCAAG

GTGTTGCTGCTGCACGAGGTACATGCCAACGACACAGGCAGCTACGTCTGCTACTAC

AAGTACATCAAGGCACGCATCGAGGGCACCACGGCCGCCAGCTCCTACGTGTTCGT

GAGAGACTTTGAGCAGCCATTCATCAACAAGCCTGACACGCTCTTGGTCAACAGGA

AGGACGCCATGTGGGTGCCCTGTCTGGTGTCCATCCCCGGCCTCAATGTCACGCTGC

GCTCGCAAAGCTCGGTGCTGTGGCCAGACGGGCAGGAGGTGGTGTGGGATGACCGG

CGGGGCATGCTCGTGTCCACGCCACTGCTGCACGATGCCCTGTACCTGCAGTGCGAG
```

-continued

```
ACCACCTGGGGAGACCAGGACTTCCTTTCCAACCCCTTCCTGGTGCACATCACAGGC
AACGAGCTCTATGACATCCAGCTGTTGCCCAGGAAGTCGCTGGAGCTGCTGGTAGG
GGAGAAGCTGGTCCTGAACTGCACCGTGTGGGCTGAGTTTAACTCAGGTGTCACCTT
TGACTGGGACTACCCAGGGAAGCAGGCAGAGCGGGGTAAGTGGGTGCCCGAGCGA
CGCTCCCAGCAGACCCACACAGAACTCTCCAGCATCCTGACCATCCACAACGTCAGC
CAGCACGACCTGGGCTCGTATGTGTGCAAGGCCAACAACGGCATCCAGCGATTTCG
GGAGAGCACCGAGGTCATTGTGCATGAAAATCCCTTCATCAGCGTCGAGTGGCTCA
AAGGACCCATCCTGGAGGCCACGGCAGGAGACGAGCTGGTGAAGCTGCCCGTGAAG
CTGGCAGCGTACCCCCCGCCCGAGTTCCAGTGGTACAAGGATGGAAAGGCACTGTC
CGGGCGCCACAGTCCACATGCCCTGGTGCTCAAGGAGGTGACAGAGGCCAGCACAG
GCACCTACACCCTCGCCCTGTGGAACTCCGCTGCTGGCCTGAGGCGCAACATCAGCC
TGGAGCTGGTGGTGAATGTGCCCCCCCAGATACATGAGAAGGAGGCCTCCTCCCCC
AGCATCTACTCGCGTCACAGCCGCCAGGCCCTCACCTGCACGGCCTACGGGGTGCCC
CTGCCTCTCAGCATCCAGTGGCACTGGCGGCCCTGGACACCCTGCAAGATGTTTGCC
CAGCGTAGTCTCCGGCGGCGGCAGCAGCAAGACCTCATGCCACAGTGCCGTGACTG
GAGGGCGGTGACCACGCAGGATGCCGTGAACCCCATCGAGAGCCTGGACACCTGGA
CCGAGTTTGTGGAGGGAAAGAATAAGACTGTGAGCAAGCTGGTGATCCAGAATGCC
AACGTGTCTGCCATGTACAAGTGTGTGGTCTCCAACAAGGTGGGCCAGGATGAGCG
GCTCATCTACTTCTATGTGACCACCATCCCCGACGGCTTCACCATCGAATCCAAGCC
ATCCGAGGAGCTACTAGAGGGCCAGCCGGTGCTCCTGAGCTGCCAAGCCGACAGCT
ACAAGTACGAGCATCTGCGCTGGTACCGCCTCAACCTGTCCACGCTGCACGATGCGC
ACGGGAACCCGCTTCTGCTCGACTGCAAGAACGTGCATCTGTTCGCCACCCCTCTGG
CCGCCAGCCTGGAGGAGGTGGCACCTGGGGCGCGCCACGCCACGCTCAGCCTGAGT
ATCCCCCGCGTCGCGCCCGAGCACGAGGGCCACTATGTGTGCGAAGTGCAAGACCG
GCGCAGCCATGACAAGCACTGCCACAAGAAGTACCTGTCGGTGCAGGCCCTGGAAG
CCCCTCGGCTCACGCAGAACTTGACCGACCTCCTGGTGAACGTGAGCGACTCGCTGG
AGATGCAGTGCTTGGTGGCCGGAGCGCACGCGCCCAGCATCGTGTGGTACAAAGAC
GAGAGGCTGCTGGAGGAAAAGTCTGGAGTCGACTTGGCGGACTCCAACCAGAAGCT
GAGCATCCAGCGCGTGCGCGAGGAGGATGCGGGACGCTATCTGTGCAGCGTGTGCA
ACGCCAAGGGCTGCGTCAACTCCTCCGCCAGCGTGGCCGTGGAAGGCTCCGAGGAT
AAGGGCAGCATGGAGATCGTGATCCTTGTCGGTACCGGCGTCATCGCTGTCTTCTTC
TGGGTCCTCCTCCTCCTCATCTTCTGTAACATGAGGAGGCCGGCCCACGCAGACATC
AAGACGGGCTACCTGTCCATCATCATGGACCCCGGGGAGGTGCCTCTGGAGGAGCA
ATGCGAATACCTGTCCTACGATGCCAGCCAGTGGGAATTCCCCCGAGAGCGGCTGC
ACCTGGGGAGAGTGCTCGGCTACGGCGCCTTCGGGAAGGTGGTGGAAGCCTCCGCT
TTCGGCATCCACAAGGGCAGCAGCTGTGACACCGTGGCCGTGAAAATGCTGAAAGA
GGGCGCCACGGCCAGCGAGCACCGCGCGCTGATGTCGGAGCTCAAGATCCTCATTC
ACATCGGCAACCACCTCAACGTGGTCAACCTCCTCGGGGCGTGCACCAAGCCGCAG
GGCCCCCTCATGGTGATCGTGGAGTTCTGCAAGTACGGCAACCTCTCCAACTTCCTG
CGCGCCAAGCGGGACGCCTTCAGCCCCTGCGCGGAGAAGTCTCCCGAGCAGCGCGG
ACGCTTCCGCGCCATGGTGGAGCTCGCCAGGCTGGATCGGAGGCGGCCGGGGAGCA
```

```
GCGACAGGGTCCTCTTCGCGCGGTTCTCGAAGACCGAGGGCGGAGCGAGGCGGGCT

TCTCCAGACCAAGAAGCTGAGGACCTGTGGCTGAGCCCGCTGACCATGGAAGATCT

TGTCTGCTACAGCTTCCAGGTGGCCAGAGGGATGGAGTTCCTGGCTTCCCGAAAGTG

CATCCACAGAGACCTGGCTGCTCGGAACATTCTGCTGTCGGAAAGCGACGTGGTGA

AGATCTGTGACTTTGGCCTTGCCCGGGACATCTACAAAGACCCCGACTACGTCCGCA

AGGGCAGTGCCCGGCTGCCCCTGAAGTGGATGGCCCCTGAAAGCATCTTCGACAAG

GTGTACACCACGCAGAGTGACGTGTGGTCCTTTGGGGTGCTTCTCTGGGAGATCTTC

TCTCTGGGGGCCTCCCCGTACCCTGGGGTGCAGATCAATGAGGAGTTCTGCCAGCGG

CTGAGAGACGGCACAAGGATGAGGGCCCCGGAGCTGGCCACTCCCGCCATACGCCG

CATCATGCTGAACTGCTGGTCCGGAGACCCCAAGGCGAGACCTGCATTCTCGGAGCT

GGTGGAGATCCTGGGGGACCTGCTCCAGGGCAGGGCCTGCAAGAGGAAGAGGAG

GTCTGCATGGCCCCGCGCAGCTCTCAGAGCTCAGAAGAGGGCAGCTTCTCGCAGGT

GTCCACCATGGCCCTACACATCGCCCAGGCTGACGCTGAGGACAGCCCGCCAAGCC

TGCAGCGCCACAGCCTGGCCGCCAGGTATTACAACTGGGTGTCCTTTCCCGGGTGCC

TGGCCAGAGGGCTGAGACCCGTGGTTCCTCCAGGATGAAGACATTTGAGGAATTC

CCCATGACCCCAACGACCTACAAAGGCTCTGTGGACAACCAGACAGACAGTGGGAT

GGTGCTGGCCTCGGAGGAGTTTGAGCAGATAGAGAGCAGGCATAGACAAGAAAGC

GGCTTCAGAGGAACCAGGAGGACAAGAGGAGCATGAAAGTGGACAAGGAGTGTGA

CCACTGAAGCACCACAGGGAGGGGTTAGGCCTCCGGATGACTGCGGGCAGGCCTGG

ATAATATCCAGCCTCCCACAAGAAGCTGGTGGAGCAGAGTGTTCCCTGACTCCTCCA

AGGAAAGGGAGACGCCCTTTCATGGTCTGCTGAGTAACAGGTGCCTTCCCAGACACT

GGCGTTACTGCTTGACCAAAGAGCCCTCAAGCGGCCCTTATGCCAGCGTGACAGAG

GGCTCACCTCTTGCCTTCTAGGTCACTTCTCACAATGTCCCTTCAGCACCTGACCCTG

TGCCCACCAGTTATTCCTTGGTAATATGAGTAATACATCAAAGAGTAGTATTAAAAG

CTAATTAATCATGTTTATACTAA

Exemplary Human VEGFR-3 Isoform 1 precursor amino acid sequence
                                                    (SEQ ID NO: 41)
MQRGAALCLRLWLCLGLLDGLVSGYSMTPPTLNITEESHVIDTGDSLSISCRGQHPLEW

AWPGAQEAPATGDKDSEDTGVVRDCEGTDARPYCKVLLLHEVHANDTGSYVCYYKYI

KARIEGTTAASSYVFVRDFEQPFINKPDTLLVNRKDAMWVPCLVSIPGLNVTLRSQSSVL

WPDGQEVVWDDRRGMLVSTPLLHDALYLQCETTWGDQDFLSNPFLVHITGNELYDIQL

LPRKSLELLVGEKLVLNCTVWAEFNSGVTFDWDYPGKQAERGKWVPERRSQQTHTELS

SILTIHNVSQHDLGSYVCKANNGIQRFRESTEVIVHENPFISVEWLKGPILEATAGDELVK

LPVKLAAYPPPEFQWYKDGKALSGRHSPHALVLKEVTEASTGTYTLALWNSAAGLRRN

ISLELVVNVPPQIHEKEASSPSIYSRHSRQALTCTAYGVPLPLSIQWHWRPWTPCKMFAQ

RSLRRRQQQDLMPQCRDWRAVTTQDAVNPIESLDTWTEFVEGKNKTVSKLVIQNANVS

AMYKCVVSNKVGQDERLIYFVVTTIPDGFTIESKPSEELLEGQPVLLSCQADSYKYEHLR

WYRLNLSTLHDAHGNPLLLDCKNVHLFATPLAASLEEVAPGARHATLSLSIPRVAPEHE

GHYVCEVQDRRSHDKHCHKKYLSVQALEAPRLTQNLTDLLVNVSDSLEMQCLVAGAH

APSIVWYKDERLLEEKSGVDLADSNQKLSIQRVREEDAGRYLCSVCNAKGCVNSSASV

AVEGSEDKGSMEIVILVGTGVIAVFFWVLLLLIFCNMRRPAHADIKTGYLSIIMDPGEVPL
```

```
-continued
EEQCEYLSYDASQWEFPRERLHLGRVLGYGAFGKVVEASAFGIHKGSSCDTVAVKMLK

EGATASEHRALMSELKILIHIGNHLNVVNLLGACTKPQGPLMVIVEFCKYGNLSNFLRA

KRDAFSPCAEKSPEQRGRFRAMVELARLDRRRPGSSDRVLFARFSKTEGGARRASPDQE

AEDLWLSPLTMEDLVCYSFQVARGMEFLASRKCIHRDLAARNILLSESDVVKICDFGLA

RDIYKDPDYVRKGSARLPLKWMAPESIFDKVYTTQSDVWSFGVLLWEIFSLGASPYPGV

QINEEFCQRLRDGTRMRAPELATPAIRRIMLNCWSGDPKARPAFSELVEILGDLLQGRGL

QEEEEVCMAPRSSQSSEEGSFSQVSTMALHIAQADAEDSPPSLQRHSLAARYYNWVSFP

GCLARGAETRGSSRMKTFEEFPMTPTTYKGSVDNQTDSGMVLASEEFEQIESRHRQESG

FRGTRRTRGA
```

Fusion Proteins

Fusion proteins or chimeric proteins are proteins created through the joining of two or more genes that originally coded for separate proteins. Translation of a fusion gene results in creation of a single or multiple polypeptides with functional properties derived from each of the original proteins. Recombinant fusion proteins are created artificially, and resultant proteins may have underlying polypeptides with different functions and/or physico-chemical patterns. In some embodiments, anti-VEGF protein compositions as described herein comprise fusions of one or more VEGF-R proteins or characteristic portions thereof as described herein.

For example, antibody fusion proteins may combine an antibody that targets a specific antigen, with a protein that is able to modify an immune response or induce direct damage to a cancer cell. For example, cytolytic fusion proteins increase the potency of antibodies to eliminate cancer cells, by attaching them to a toxin. These so called "immunotoxins" derive their potency from the toxin and their specificity from the antibody or antibody fragment to which they are attached. In certain embodiments, such fusion proteins may comprise a polypeptide (e.g., antibody and/or characteristic portion thereof) fused to a cytokine, to create an "immunocytokines". Such a fusion protein may combine a tumor-targeting antibody (e.g., an anti-VEGF antibody) with a cytokine (an innate immune response mediator). In some such embodiments, this increases local activation of an immune system in a tumor microenvironment, potentially supporting elimination of a cancerous cell and/or tumor (e.g., VS).

In some embodiments, any of the anti-VEGF proteins described herein (e.g., an antibody, soluble VEGF receptor, and/or characteristic VEGF binding portion thereof) can include one or more (e.g., two, three, four, five, six, seven, eight, nine, or ten) amino acid substitutions in an Fc region that decrease the half-life of the antibody, and/or soluble VEGF receptor in a mammal, e.g., as compared to the half-life of an otherwise identical antibody, and/or soluble VEGF receptor not including at least one of the one or more amino acid substitutions. Methods for determining the half-life of an antibody, and/or soluble VEGF receptor in a mammal are well-known in the art. Non-limiting examples of point mutations in a Fc mutation that can decrease the half-life of an antibody, and/or soluble VEGF receptor are described in Leabman et al., MAbs 5(6):896-903, 2013; which is incorporated in its entirety herein by reference.

Aflibercept

In certain embodiments, an anti-VEGF protein as described herein is Aflibercept. Aflibercept is a recombinant fusion protein consisting of portions of human VEGF receptors 1 and 2 extracellular domains fused to the Fc portion of human IgG1. Aflibercept is a dimeric glycoprotein with a protein molecular weight of approximately 97 kilodaltons (kDa) and may contain post-translational glycosylation, which may constitute an additional 15% of the total molecular mass, resulting in a total molecular weight of 115 kDa. Aflibercept is FDA approved, and has been indicated for the treatment of Neovascular (Wet) Age-Related Macular Degeneration, Macular Edema Following Retinal Vein Occlusion, Diabetic Macular Edema, Metastatic Colorectal Cancer, and Diabetic Retinopathy.

In certain embodiments, Aflibercept functions as a VEGF-TRAP. In contrast to certain exemplary antibody-based VEGF binding strategies described herein, e.g., utilizing ranibizumab and/or bevacizumab, in some embodiments, the VEGF-TRAP incorporates the second binding domain of the VEGFR-1 receptor and the third domain of the VEGFR-2 receptor. By fusing these extracellular protein sequences to the Fc segment of a human IgG backbone a chimeric protein is produced with a very high VEGF binding affinity (Kd≈1 pM). Like ranibizumab and bevacizumab, a VEGF-TRAP such as aflibercept binds all isomers of the VEGF-A family, and also binds VEGF-B and placental growth factor. In certain embodiments, an Aflibercept protein is conjugated to a suitable secretion signal sequence, such as an IL2SS (described below). In certain embodiments, a VEGF-TRAP protein product is represented by SEQ ID NO: 43 or 44.

```
Exemplary Aflibercept nucleotide coding sequence
                                      (SEQ ID NO: 42)
ATGTACCGGATGCAGCTGCTGAGCTGTATCGCCCTGTCTCTGGCCCTGG

TCACCAATTCTAGCGATACCGGCAGACCCTTCGTGGAAATGTACAGCGA

GATCCCCGAGATCATCCACATGACCGAGGGCAGAGAGCTGGTCATCCCC

TGCAGAGTGACAAGCCCCAACATCACCGTGACTCTGAAGAAGTTCCCTC

TGGACACACTGATCCCCGACGGCAAGAGAATCATCTGGGACAGCCGGAA

GGGCTTCATCATCAGCAACGCCACCTACAAAGAGATCGGCCTGCTGACC

TGTGAAGCCACCGTGAATGGCCACCTGTACAAGACCAACTACCTGACAC

ACAGACAGACCAACACCATCATCGACGTGGTGCTGAGCCCTAGCCACGG

CATTGAACTGTCTGTGGGCGAGAAGCTGGTGCTGAACTGTACCGCCAGA

ACCGAGCTGAACGTGGGCATCGACTTCAACTGGGAGTACCCCAGCAGCA

AGCACCAGCACAAGAAACTGGTCAACCGGGACCTGAAAACCCAGAGCGG
```

-continued

CAGCGAGATGAAGAAATTCCTGAGCACCCTGACCATCGACGGCGTGACC

AGATCTGACCAGGGCCTGTACACATGTGCCGCCAGCTCTGGCCTGATGA

CCAAGAAAAACAGCACCTTCGTGCGGGTGCACGAGAAGGACAAGACCCA

CACCTGTCCTCCATGTCCTGCTCCAGAACTGCTCGGCGGACCTTCCGTG

TTCCTGTTTCCTCCAAAGCCTAAGGACACCCTGATGATCAGCAGAACCC

CTGAAGTGACCTGCGTGGTGGTGGATGTGTCCCACGAGGATCCCGAAGT

GAAGTTCAATTGGTACGTGGACGGCGTGGAAGTGCACAACGCCAAGACC

AAGCCTAGAGAGGAACAGTACAATAGCACCTACAGAGTGGTGTCCGTGC

TGACCGTGCTGCACCAGGATTGGCTGAACGGCAAAGAGTACAAGTGCAA

GGTGTCCAACAAGGCCCTGCCTGCTCCTATCGAGAAAACCATCTCCAAG

GCCAAGGGCCAGCCTAGGGAACCCCAGGTTTACACACTGCCTCCAAGCA

GGGACGAGCTGACAAAGAACCAGGTGTCCCTGACCTGCCTGGTCAAGGG

CTTCTACCCTTCCGATATCGCCGTGGAATGGGAGAGCAATGGCCAGCCT

GAGAACAACTACAAGACAACCCCTCCTGTGCTGGACAGCGACGGCTCAT

TCTTCCTGTACAGCAAGCTGACAGTGGACAAGAGCAGATGGCAGCAGGG

CAACGTGTTCAGCTGCAGCGTGATGCACGAGGCCCTGCACAACCACTAC

ACCCAGAAGTCCCTGAGCCTGTCTCCTGGA

Exemplary Aflibercept amino acid sequence
(SEQ ID NO: 43)
MYRMQLLSCIALSLALVTNSSDTGRPFVEMYSEIPEIIHMTEGRELVIP

CRVTSPNITVTLKKFPLDTLIPDGKRIIWDSRKGFIISNATYKEIGLLT

CEATVNGHLYKTNYLTHRQTNTIIDVVLSPSHGIELSVGEKLVLNCTAR

TELNVGIDFNWEYPSSKHQHKKLVNRDLKTQSGSEMKKFLSTLTIDGVT

RSDQGLYTCAASSGLMTKKNSTFVRVHEKDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQP

ENNYKTTPPVLDSDGSFFLYSKLTVDKSRWQQGNVFSCSVMHEALHNHY

TQKSLSLSPG

Exemplary Aflibercept Extracellular (EC) Domain
amino acid sequence
(SEQ ID NO: 112)
MYRMQLLSCIALSLALVTNSSDTGRPFVEMYSEIPEIIHMTEGRELVIP

CRVTSPNITVTLKKFPLDTLIPDGKRIIWDSRKGFIISNATYKEIGLLT

CEATVNGHLYKTNYLTHRQTNTIIDVVLSPSHGIELSVGEKLVLNCTAR

TELNVGIDENWEYPSSKHQHKKLVNRDLKTQSGSEMKKFLSTLTIDGVT

RSDQGLYTCAASSGLMTKKNSTFVRVHEK

Exemplary Aflibercept amino acid sequence
(SEQ ID NO: 44)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTIIDVVLSPSHGIELSVGEKLVLNCTARTELNVGIDENWEYPSSKHQH

KKLVNRDLKTQSGSEMKKFLSTLTIDGVTRSDQGLYTCAASSGLMTKKN

STFVRVHEKDKTHTCPPCPAPELLGGPSVFLFPPKPKDTLMISRTPEVT

CVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLY

SKLTVDKSRWQQGNVFSCSVMHEALHNHYTQKSLSLSPG

Exemplary Fragment, Crystallizable (Fc) Nucleo-
tide Sequence
(SEQ ID NO: 110)
GACAAGACCCACACCTGTCCTCCATGTCCTGCTCCAGAACTGCTCGGCG

GACCTTCCGTGTTCCTGTTTCCTCCAAAGCCTAAGGACACCCTGATGAT

CAGCAGAACCCCTGAAGTGACCTGCGTGGTGGTGGATGTGTCCCACGAG

GATCCCGAAGTGAAGTTCAATTGGTACGTGGACGGCGTGGAAGTGCACA

ACGCCAAGACCAAGCCTAGAGAGGAACAGTACAACAGCACCTACAGAGT

GGTGTCCGTGCTGACCGTGCTGCACCAGGATTGGCTGAACGGCAAAGAG

TACAAGTGCAAGGTGTCCAACAAGGCCCTGCCTGCTCCTATCGAGAAAA

CCATCAGCAAGGCCAAGGGCCAGCCTAGGGAACCCCAGGTTTACACACT

GCCTCCAAGCCGGGAAGAGATGACCAAGAACCAGGTGTCCCTGACCTGC

CTCGTGAAGGGCTTCTACCCTTCCGATATCGCCGTGGAATGGGAGAGCA

ATGGCCAGCCAGAGAACAACTACAAGACAACCCCTCCTGTGCTGGACAG

CGACGGCTCATTCTTCCTGTACAGCAAGCTGACAGTGGACAAGTCCAGA

TGGCAGCAGGGCAACGTGTTCAGCTGCAGCGTGATGCACGAGGCCCTGC

ACAACCACTACACCCAGAAGTCTCTGAGCCTGTCTCCTGGC

Exemplary Fragment, Crystallizable (Fc) Amino
Acid Sequence
(SEQ ID NO: 111)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPG

Constructs

Among other things, the present disclosure provides that some polynucleotides as described herein are polynucleotide constructs. Polynucleotide constructs according to the present disclosure include all those known in the art, including cosmids, plasmids (e.g., naked or contained in liposomes) and viral constructs (e.g., lentiviral, retroviral, adenoviral, and adeno-associated viral constructs) that incorporate a polynucleotide comprising an anti-VEGF protein, e.g., an anti-VEGF antibody, and/or a soluble VEGF Receptor (e.g., an anti-VEGF-TRAP protein (e.g., a fusion protein such as aflibercept)). Those of skill in the art will be capable of selecting suitable constructs, as well as cells, for making any of the polynucleotides described herein. In some embodiments, a construct is a plasmid (e.g., a circular DNA molecule that can autonomously replicate inside a cell). In some embodiments, a construct can be a cosmid (e.g., pWE or sCos series).

Figure 5A:
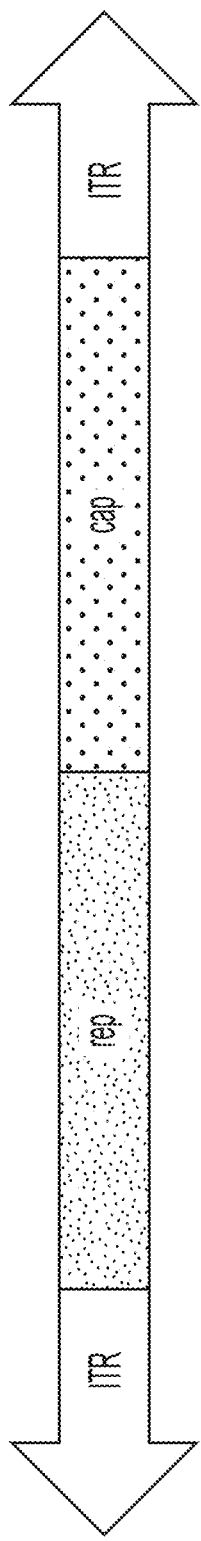
FIGS. 5A-5B are schematic representations of a simplified endogenous AAV construct (FIG. 5A) and a simplified recombinant AAV (rAAV) construct (FIG. 5B).
Figure 5B:
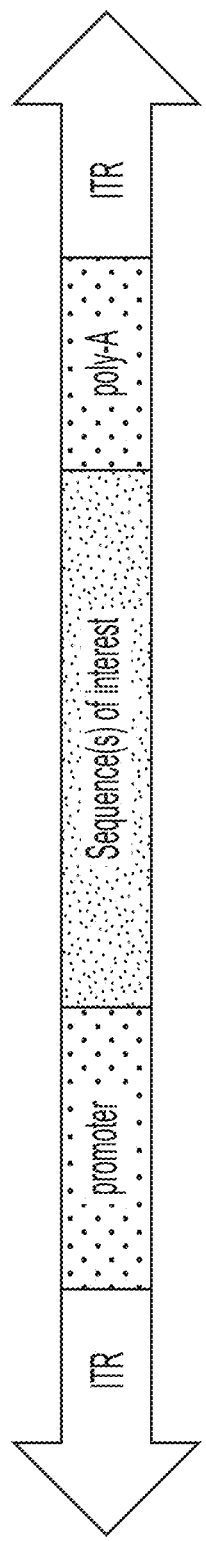
Figure 6A:
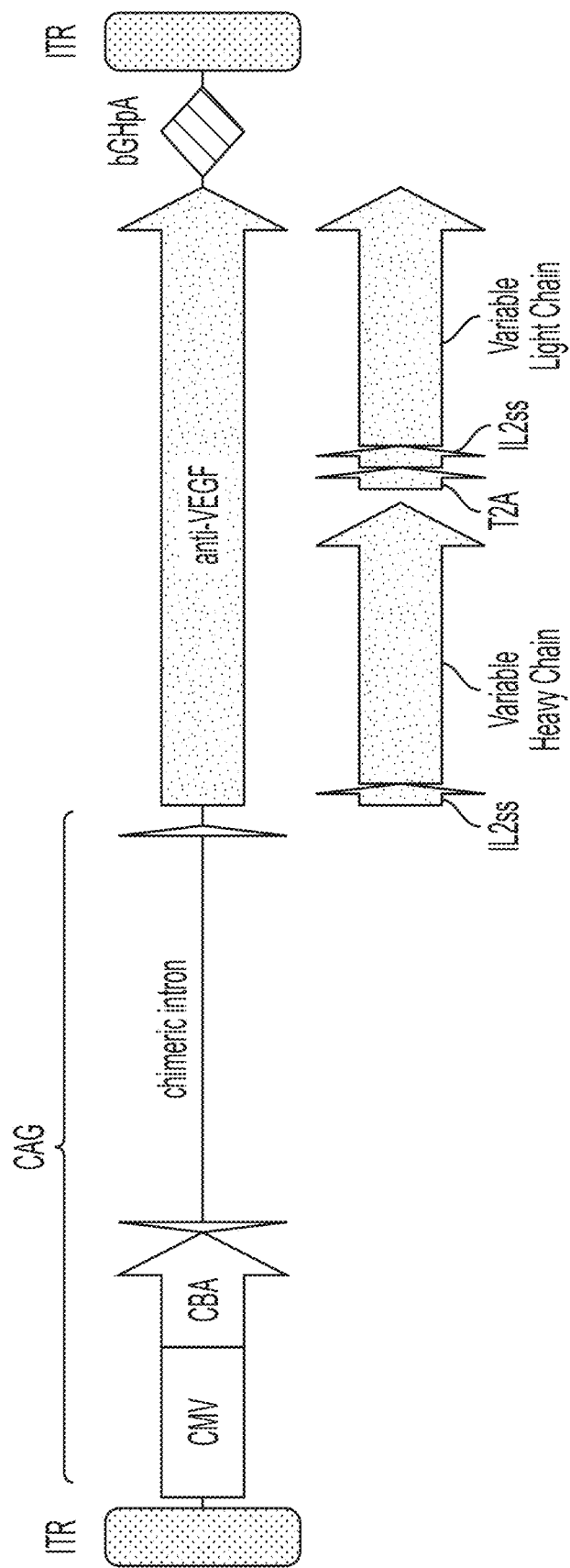
FIGS. 6A-6D are a series of schematic representations of exemplary rAAV constructs as described herein.
Figure 6B:
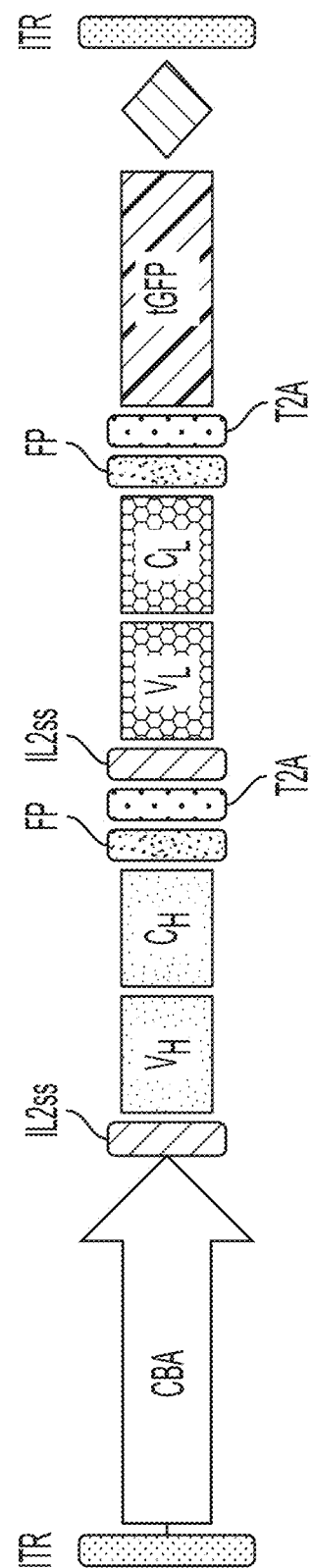
Figure 6C:
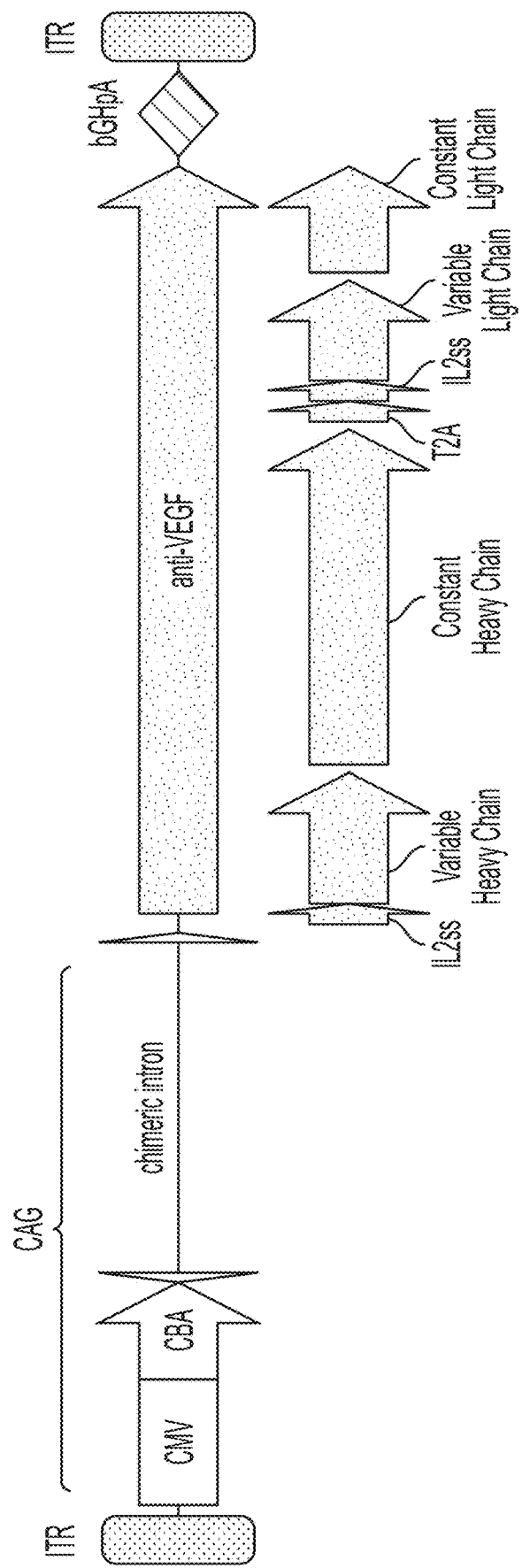
Figure 6D:
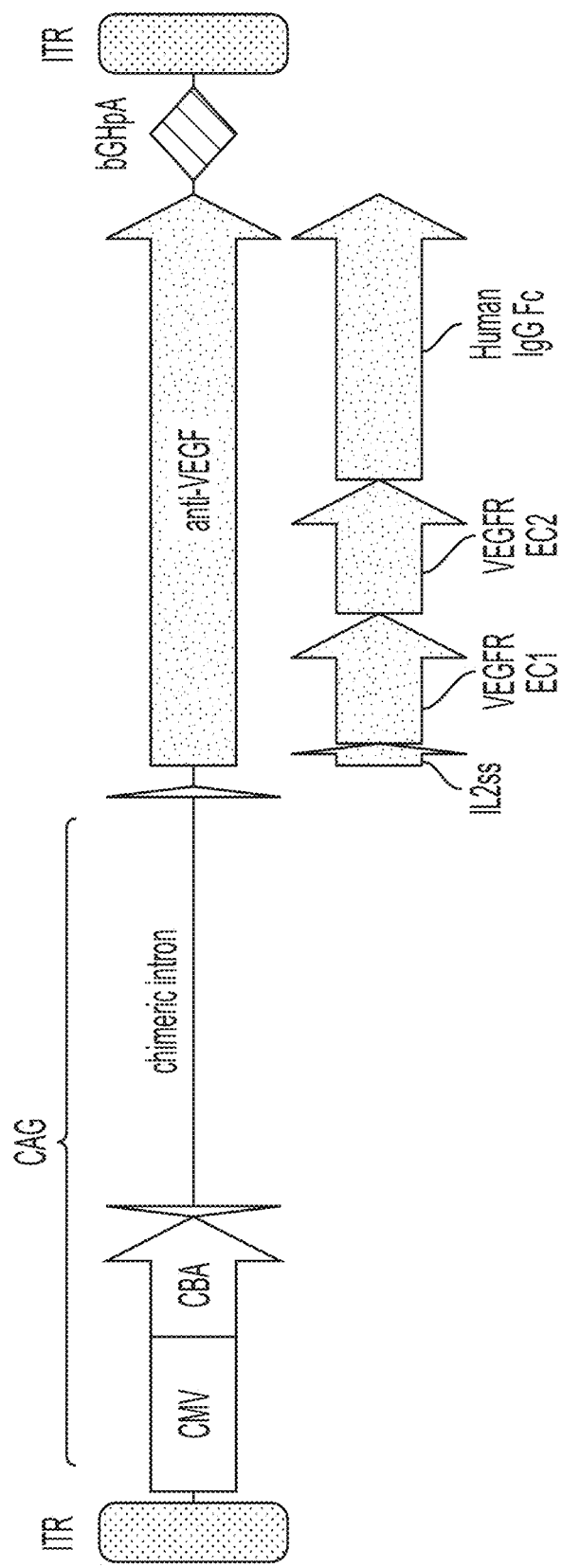

In some embodiments, a construct is a viral construct. In some embodiments, a viral construct is a lentivirus, retrovirus, adenovirus, or adeno-associated virus construct. In some embodiments, a construct is an adeno-associated virus (AAV) construct (see, e.g., Asokan et al., Mol. Ther. 20:

699-7080, 2012, which is incorporated in its entirety herein by reference). A simplified example of a WT AAV genome is represented in FIG. 5, Panel (A), while a simplified example of a recombinant AAV (rAAV) construct is represented in FIG. 5, Panel (B). In some embodiments, a viral construct is an adenovirus construct. In some embodiments, a viral construct may also be based on or derived from an alphavirus. Alphaviruses include Sindbis (and VEEV) virus, Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus, Southern elephant seal virus, Tonate virus, Trocara virus, Una virus, Venezuelan equine encephalitis virus, Western equine encephalitis virus, and Whataroa virus. Generally, the genome of such viruses encode nonstructural (e.g., replicon) and structural proteins (e.g., capsid and envelope) that can be translated in the cytoplasm of the host cell. Ross River virus, Sindbis virus, Semliki Forest virus (SFV), and Venezuelan equine encephalitis virus (VEEV) have all been used to develop viral constructs for coding sequence delivery. Pseudotyped viruses may be formed by combining alphaviral envelope glycoproteins and retroviral capsids. Examples of alphaviral constructs can be found in U.S. Publication Nos. 20150050243, 20090305344, and 20060177819; constructs and methods of their making are incorporated herein in its entirety by reference.

Constructs provided herein can be of different sizes. In some embodiments, a construct is a plasmid and can include a total length of up to about 1 kb, up to about 2 kb, up to about 3 kb, up to about 4 kb, up to about 5 kb, up to about 6 kb, up to about 7 kb, up to about 8 kb, up to about 9 kb, up to about 10 kb, up to about 11 kb, up to about 12 kb, up to about 13 kb, up to about 14 kb, or up to about 15 kb. In some embodiments, a construct is a plasmid and can have a total length in a range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 1 kb to about 11 kb, about 1 kb to about 12 kb, about 1 kb to about 13 kb, about 1 kb to about 14 kb, or about 1 kb to about 15 kb.

In some embodiments, a construct is a viral construct and can have a total number of nucleotides of up to 10 kb. In some embodiments, a viral construct can have a total number of nucleotides in the range of about 1 kb to about 2 kb, 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 2 kb to about 9 kb, about 2 kb to about 10 kb, about 3 kb to about 4 kb, about 3 kb to about 5 kb, about 3 kb to about 6 kb, about 3 kb to about 7 kb, about 3 kb to about 8 kb, about 3 kb to about 9 kb, about 3 kb to about 10 kb, about 4 kb to about 5 kb, about 4 kb to about 6 kb, about 4 kb to about 7 kb, about 4 kb to about 8 kb, about 4 kb to about 9 kb, about 4 kb to about 10 kb, about 5 kb to about 6 kb, about 5 kb to about 7 kb, about 5 kb to about 8 kb, about 5 kb to about 9 kb, about 5 kb to about 10 kb, about 6 kb to about 7 kb, about 6 kb to about 8 kb, about 6 kb to about 9 kb, about 6 kb to about 10 kb, about 7 kb to about 8 kb, about 7 kb to about 9 kb, about 7 kb to about 10 kb, about 8 kb to about 9 kb, about 8 kb to about 10 kb, or about 9 kb to about 10 kb.

In some embodiments, a construct is a lentivirus construct and can have a total number of nucleotides of up to 8 kb. In some examples, a lentivirus construct can have a total number of nucleotides of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 8 kb, about 6 kb to about 7 kb, or about 7 kb to about 8 kb In some embodiments, a construct is an adenovirus construct and can have a total number of nucleotides of up to 8 kb. In some embodiments, an adenovirus construct can have a total number of nucleotides in the range of about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 2 kb to about 3 kb, about 2 kb to about 4 kb, about 2 kb to about 5 kb, about 2 kb to about 6 kb, about 2 kb to about 7 kb, about 2 kb to about 8 kb, about 3 kb to about 4 kb, about 3 kb to about 5 kb, about 3 kb to about 6 kb, about 3 kb to about 7 kb, about 3 kb to about 8 kb, about 4 kb to about 5 kb, about 4 kb to about 6 kb, about 4 kb to about 7 kb, about 4 kb to about 8 kb, about 5 kb to about 6 kb, about 5 kb to about 7 kb, about 5 kb to about 8 kb, about 6 kb to about 7 kb, about 6 kb to about 8 kb, or about 7 kb to about 8 kb.

Any of the constructs described herein can further include a control sequence, e.g., a control sequence selected from the group of a transcription initiation sequence, a transcription termination sequence, a promoter sequence, an enhancer sequence, an RNA splicing sequence, a polyadenylation (poly(A)) sequence, a Kozak consensus sequence, and/or additional untranslated regions which may house pre- or post-transcriptional regulatory and/or control elements. In some embodiments, a promoter can be a native promoter, a constitutive promoter, an inducible promoter, and/or a tissue-specific promoter. Non-limiting examples of control sequences are described herein.

AAV Particles

Among other things, the present disclosure provides AAV particles that comprise an AAV capsid described herein containing a recombinant AAV (rAAV) construct encoding an anti-VEGF protein, e.g., an anti-VEGF antibody and/or an anti-VEGF-TRAP protein. In some embodiments, AAV particles can be described as having a serotype, which is a description of the construct strain and the capsid strain. For example, in some embodiments an AAV particle may be described as AAV2, wherein the particle has an AAV2 capsid and a construct that comprises characteristic AAV2 Inverted Terminal Repeats (ITRs). In some embodiments, an AAV particle may be described as a pseudotype, wherein the capsid and construct are derived from different AAV strains, for example, AAV2/9 would refer to an AAV particle that comprises a construct utilizing the AAV2 ITRs and an AAV9 capsid. This same nomenclature can also be used for rAAV capsids, constructs, and/or particles.

In certain embodiments, gene therapy using rAAV particles is a promising therapeutic modality for inner ear disorders for several reasons: (1) an inner ear, which contains the auditory and vestibular sensory epithelia, has modified immune surveillance, similar to that in the central nervous system (Fujioka 2014, incorporated herein in its entirety by reference); (2) sensory and supporting cells of the cochlear organ of Corti are post-mitotic, allowing for the possibility of long-term expression following a single administration of rAAV; and (3) aggregate clinical experience with rAAV delivery in both adults and children, via multiple routes of administration, suggests a strong safety profile for rAAV as a delivery vehicle, particularly in localized delivery and/or at low to moderate doses.

Clinical trials utilizing rAAV particles began more than two decades ago, and rAAV particles have been administered to hundreds of participants in dozens of clinical trials at doses of up to approximately 1E15 vg or more for systemic administration (Flotte 1996; Flotte 2013; Parente 2018; Wang 2019, each of which is incorporated herein in its entirety by reference). The number of trials in which rAAV particles have been used for in-vivo gene transfer has steadily increased. The safety profile, together with the high efficiency of transduction of a broad range of target tissues, has established rAAV particles as a platform of choice for in-vivo gene therapy (Wang 2019, incorporated herein in its entirety by reference). Successful application of rAAV technology has been achieved in the clinic for a variety of conditions, including coagulation disorders, inherited blindness, and neurodegenerative diseases (Colella 2018; Wang 2019, each of which is incorporated herein in its entirety by reference).

In certain embodiments, compositions comprising an rAAV particle comprising constructs encoding an anti-VEGF protein are referred to as rAAV-antiVEGF. In certain compositions, wherein Anc80 capsid is utilized, such a composition may be referred to as rAAVAnc80-antiVEGF. In some embodiments, these compositions may also be referred to as AK-antiVEGF. In some embodiments, an rAAVAnc80-antiVEGF particle comprises a specific rAAV construct, for example it may comprise a construct as represented by FIG. 6, Panel (A). Such a construct is referred to herein as a $V_H/V_L$ construct, and/or rAAVAnc80-$V_H/V_L$; an exemplary rAAVAnc80-$V_H/V_L$ construct encodes ranibizumab. In some embodiments, an rAAVAnc80-antiVEGF particle comprises a construct as represented by FIG. 6, Panel (B), wherein the construct may be referred to as an antibody GFP construct (ABGFP), and/or rAAVAnc80-ABGFP; an exemplary rAAVAnc80-ABGFP construct encodes ranibizumab or bevacizumab transcriptionally linked to GFP. In some embodiments, an rAAVAnc80-antiVEGF construct comprises a construct as represented by FIG. 6 Panel (C), wherein the construct may be referred to as an antibody (AB) construct, and/or rAAVAnc80-AB; an exemplary rAAVAnc80-AB construct encodes bevacizumab. In some embodiments, an rAAVAnc80-antiVEGF construct comprises a construct as represented by FIG. 6, Panel (D), wherein the construct may be referred to as anti-VEGF-TRAP (TRAP), and/or rAAVAnc80-TRAP; an exemplary rAAVAnc80-TRAP construct encodes aflibercept. In some embodiments, a compositions disclosed herein, e.g., rAAV-antiVEGF, is a gene therapy composition and is intended for the treatment of patients with VS. In some embodiments, a composition disclosed herein comprises AAVAnc80, a putative common ancestor of adeno-associated viral (AAV) particle serotypes 1, 2, 8, and 9 (Zinn 2015, incorporated herein in its entirety by reference), as a delivery vehicle for a transgene encoding the sequence for ranibizumab, an antibody fragment (Fab) previously optimized for inhibition of VEGF following intraocular administration (Genentech 2017, incorporated herein in its entirety by reference). In some embodiments, a composition disclosed herein is a non-enveloped icosahedral virion of approximately 26 nanometer (nm) in diameter. In some embodiments, adeno-associated viruses, on which a composition disclosed herein, e.g., synthetic AAVAnc80 capsid sequence, is based, are non-pathogenic, single-stranded DNA genome-containing, helper virus-dependent members of the Parvoviridae family.

Recombinant AAV (rAAV) particles, while retaining the same overall capsid structure as found in wild-type adeno-associated viruses, encapsidate genomes that are devoid of any viral protein-coding sequences and have therapeutic gene expression cassettes inserted in their place. The only sequences of viral origin are the inverted terminal repeat (ITR) sequences, which are necessary to guide genome replication and packaging during particle production. The removal of viral coding sequences maximizes the packaging capacity of rAAV particles and contributes to their low immunogenicity and cytotoxicity when delivered in-vivo (Wang 2019, incorporated herein in its entirety by reference).

AAVAnc80 is a rationally designed AAV capsid whose sequence was inferred by ancestral sequence reconstruction (Zinn 2015, incorporated herein in its entirety by reference). The first reported uses of AAVAnc80 in the mammalian inner ear revealed a high transduction efficiency in cochlear and vestibular hair cells and evidence for recovery of auditory, cochlear, and vestibular function in a knock-in mouse model (Landegger 2017; Pan 2017, each of which is incorporated herein in its entirety by reference). Subsequent studies have confirmed that cochlear- and vestibular cell transduction efficiency of AAVAnc80 is significantly higher than other AAV serotypes in mice (Landegger 2017; Tao 2018; Yoshimura 2018; Omichi 2020, each of which is incorporated herein in its entirety by reference) and in non-human primates (Andres-Mateos 2019, incorporated herein in its entirety by reference).

In some embodiments, a composition disclosed herein, e.g., rAAV-antiVEGF, comprises two components: AAVAnc80 (also referred to as Anc80L65; Zinn 2015, incorporated herein in its entirety by reference) capsid and a single-stranded rAAV DNA genome encoding an anti-VEGF protein, such as an rAAV-$V_H/V_L$ (e.g., ranibizumab), rAAV-AB (e.g., bevacizumab), rAAV-ABGFP (e.g., an antibody tagged with GFP, e.g., ranibizumab or bevacizumab tagged with GFP), and/or rAAV-TRAP (e.g., aflibercept) encapsidated by said AAVAnc80 capsid. In some embodiments, a composition disclosed herein, e.g., rAAV-anti-VEGF, comprises two components: AAVAnc80 (also referred to as Anc80L65; Zinn 2015, incorporated herein in its entirety by reference) capsid and a single-stranded DNA genome of 3000-5000 nucleotides, exclusive of ITR sequences (e.g., as shown by FIG. 6, Panels (A)-(D)), encapsidated by said AAVAnc80 capsid.

In some embodiments, a composition disclosed herein, e.g., a recombinant construct DNA genome is flanked by AAV2 ITR sequences and comprises a eukaryotic expression cassette encoding the following promoter and regulatory sequences: the cytomegalovirus (CMV) early enhancer element; the chicken beta actin (CβA) gene sequence located between the 5' flanking region and the proximal region of the second exon; and the 3' splice acceptor sequence derived from the rabbit beta globin (RβG) gene, commonly referred to as the CAG promoter (Miyazaki 1989; Niwa 1991; Orbán 2009, each of which is incorporated herein in its entirety by reference). In some embodiments, following this hybrid regulatory element is a bicistronic cassette encoding ranibizumab heavy and light chains, separated by furin and *Thosea asigna* virus-derived protease 2A (T2A) cleavage sites. In some embodiments, to facilitate protein secretion, a 20 amino-acid human interleukin-2 (IL-2) leader sequence is situated upstream of each Fab chain. In some embodiments of a composition disclosed herein, downstream of an anti-VEGF protein coding sequence is a bovine growth hormone polyadenylation site.

The current standard of care for VS has evolved over the past 2 to 3 decades, as imaging techniques have evolved and the ability to identify and track the growth of tumors has improved. There has been a progressive trend toward a conservative, observational "wait and rescan" approach, with a growing awareness that many tumors exhibit slow or low growth and may not impact hearing so long as the low growth rate is maintained (MacKeith 2013; Reznitsky 2019, each of which is incorporated herein in its entirety by reference). In some embodiments, a key potential benefit of a composition disclosed herein, e.g., rAAV-antiVEGF, is the opportunity, e.g., to augment this conservative treatment approach by halting tumor growth, stabilizing hearing, and/or obviating the need for more invasive treatment approaches, such as surgical resection and/or radiation therapy. Without wishing to be bound by theory, it is believed that in some embodiments, while halting VS growth is likely to provide a substantial clinical benefit, it is also possible that a composition disclosed herein, e.g., rAAV-antiVEGF therapy could go beyond tumor stasis and drive shrinkage of tumors, restoration of speech understanding, and/or reduction in perceived difficulty of speech understanding, as demonstrated in studies of bevacizumab-treated VS tumors in NF2 patients (Huang 2018; Plotkin 2019, each of which is incorporated herein in its entirety by reference). In addition, studies with systemically administered VEGF inhibitor have shown improvements in NF2-related quality of life, including symptoms associated with VS in NF2 patients (Plotkin 2019, incorporated herein in its entirety by reference). In some embodiments, these clinical data suggest that rAAV-antiVEGF administration, and sustained and localized expression of anti-VEGF protein in diffusional continuity with the tumor, has the potential to provide these additional benefits to patients with VS.

In some embodiments, intracochlear administration of a composition disclosed herein, e.g., rAAV-antiVEGF, has the potential to eliminate the need for future treatment and to preserve physiologic hearing in those with VS, regardless of underlying etiology. In some embodiments, a composition disclosed herein can result in a delay of invasive treatment approaches, such as surgical resection and/or radiation therapy, and associated loss of physiologic hearing. In some embodiments of any of the methods disclosed herein, the method further comprises administration of standard of care treatments. In some embodiments, there may also be potential benefit to subjects who subsequently undergo radiation therapy, as anti-VEGF protein treatment may improve a subject's response to radiotherapy by sensitizing the tumor and allowing for lower radiation dosing (Koutsimpelas 2012; Gao 2015, each of which is incorporated herein in its entirety by reference).

AAV Constructs

The present disclosure provides polynucleotide constructs that comprise an anti-VEGF antibody and/or a soluble VEGF receptor (e.g., an anti-VEGF TRAP protein, such as the fusion protein aflibercept). In some embodiments described herein, a polynucleotide comprising an anti-VEGF antibody and/or a soluble VEGF receptor is referred to as a construct, and can be encompassed within an AAV capsid, to create an rAAV particle. In certain embodiments, an rAAV construct may be referred to as a vector, and may be quantified as vector genomes (vg); for example, as vg per milliliter (mL). A simplified schematic representation of a WT AAV genome is depicted in FIG. 5, Panel (A), while a simplified schematic representation of an rAAV construct is depicted in FIG. 5, Panel (B).

In some embodiments, a polynucleotide construct comprises one or more components derived from or modified from a naturally occurring AAV genomic construct. In some embodiments, a sequence derived from an AAV construct is an AAV1 construct, an AAV2 construct, an AAV3 construct, an AAV4 construct, an AAV5 construct, an AAV6 construct, an AAV7 construct, an AAV8 construct, an AAV9 construct, an AAV2.7m8 construct, an AAV8BP2 construct, an AAV293 construct, or AAVAnc80 construct. Additional exemplary AAV constructs that can be used herein are known in the art. See, e.g., Kanaan et al., Mol. Ther. Nucleic Acids 8:184-197, 2017; Li et al., Mol. Ther. 16(7): 1252-1260, 2008; Adachi et al., Nat. Commun. 5: 3075, 2014; Isgrig et al., Nat. Commun. 10(1): 427, 2019; and Gao et al., J. Virol. 78(12): 6381-6388, 2004; each of which is incorporated herein in its entirety by reference.

In some embodiments, provided constructs comprise coding sequence, e.g., an anti-VEGF gene or a characteristic portion thereof, one or more regulatory and/or control sequences, and optionally 5' and 3' AAV derived inverted terminal repeats (ITRs). In some embodiments wherein a 5' and 3' AAV derived ITR is utilized, the polynucleotide construct may be referred to as a recombinant AAV (rAAV) construct. In some embodiments, provided rAAV constructs are packaged into an AAV capsid to form an rAAV particle.

In some embodiments, AAV derived sequences (which are comprised in a polynucleotide construct) typically include the cis-acting 5' and 3' ITR sequences (see, e.g., B. J. Carter, in "Handbook of Parvoviruses," ed., P. Tijsser, CRC Press, pp. 155 168, 1990, which is incorporated herein in its entirety by reference). Typical AAV2-derived ITR sequences are about 145 nucleotides in length. In some embodiments, at least 80% of a typical ITR sequence (e.g., at least 85%, at least 90%, or at least 95%) is incorporated into a construct provided herein. The ability to modify these ITR sequences is within the skill of the art (see, e.g., texts such as Sambrook et al., "Molecular Cloning. A Laboratory Manual", 2d ed., Cold Spring Harbor Laboratory, New York, 1989; and K. Fisher et al., J Virol. 70:520 532, 1996, each of which is incorporated herein in its entirety by reference). In some embodiments, any of the coding sequences and/or constructs described herein are flanked by 5' and 3' AAV ITR sequences. An AAV ITR sequences may be obtained from any known AAV, including presently identified AAV types.

In some embodiments, polynucleotide constructs described in accordance with this disclosure and in a pattern known to the art (see, e.g., Asokan et al., *Mol. Ther.* 20: 699-7080, 2012, which is incorporated herein in its entirety by reference) are typically comprised of, a coding sequence or a portion thereof, at least one and/or control sequence, and optionally 5' and 3' AAV inverted terminal repeats (ITRs). In some embodiments, provided constructs can be packaged into a capsid to create an rAAV particle. An rAAV particle may be delivered to a selected target cell. In some embodiments, provided constructs comprise an additional optional coding sequence that is a nucleic acid sequence (e.g., inhibitory nucleic acid sequence), heterologous to the construct sequences, which encodes a polypeptide, protein, functional RNA molecule (e.g., miRNA, miRNA inhibitor)

or other gene product, of interest. In some embodiments, a nucleic acid coding sequence is operatively linked to and/or control components in a manner that permits coding sequence transcription, translation, and/or expression in a cell of a target tissue.

As shown in FIG. 5, Panel (A), an unmodified AAV endogenous genome comprises two open reading frames, "cap" and "rep," which are flanked by ITRs. As shown in FIG. 5, Panel (B), exemplary rAAV constructs similarly include ITRs flanking a coding region, e.g., a coding sequence (e.g., an antiVEGF gene). In some embodiments, a rAAV construct also comprises conventional control elements that are operably linked to the coding sequence in a manner that permits its transcription, translation and/or expression in a cell transfected with the plasmid construct or infected with the virus produced by the disclosure. In some embodiments, a rAAV construct optionally comprises a promoter (shown in FIG. 5, Panel (B)), an enhancer, an untranslated region (e.g., a 5' UTR, 3' UTR), a Kozak sequence, an internal ribosomal entry site (IRES), splicing sites (e.g., an acceptor site, a donor site), a polyadenylation site (shown in FIG. 5, Panel (B)), or any combination thereof. Such additional elements are described further herein.

In some embodiments, a construct is a rAAV construct. In some embodiments, a rAAV construct can include at least 500 bp, at least 1 kb, at least 1.5 kb, at least 2 kb, at least 2.5 kb, at least 3 kb, at least 3.5 kb, at least 4 kb, or at least 4.5 kb. In some embodiments, an rAAV construct can include at most 7.5 kb, at most 7 kb, at most 6.5 kb, at most 6 kb, at most 5.5 kb, at most 5 kb, at most 4.5 kb, at most 4 kb, at most 3.5 kb, at most 3 kb, or at most 2.5 kb. In some embodiments, an rAAV construct can include about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5 kb, about 3 kb to about 4 kb, about 3 kb to about 5 kb, or about 4 kb to about 5 kb.

Any of the constructs described herein can further include regulatory and/or control sequences, e.g., a control sequence selected from the group of a transcription initiation sequence, a transcription termination sequence, a promoter sequence, an enhancer sequence, an RNA splicing sequence, a polyadenylation (poly(A)) sequence, a Kozak consensus sequence, and/or any combination thereof. In some embodiments, a promoter can be a native promoter, a constitutive promoter, an inducible promoter, and/or a tissue-specific promoter. Non-limiting examples of control sequences are described herein.

Exemplary Construct Components
Inverted Terminal Repeat Sequences (ITRs)

AAV derived sequences of a construct typically comprises the cis-acting 5' and 3' ITRs (See, e.g., B. J. Carter, in "Handbook of Parvoviruses", ed., P. Tijsser, CRC Press, pp. 155 168 (1990), which is incorporated in its entirety herein by reference). Generally, ITRs are able to form a hairpin. The ability to form a hairpin can contribute to an ITRs ability to self-prime, allowing primase-independent synthesis of a second DNA strand. ITRs can also aid in efficient encapsidation of an rAAV construct in an rAAV particle.

In some embodiments, a rAAV particle (e.g., an AAV2/Anc80 particle) of the present disclosure can comprise a rAAV construct comprising a coding sequence (e.g., an anti-VEGF gene) and associated elements flanked by a 5' and a 3' AAV ITR sequences. In some embodiments, an ITR is or comprises about 145 nucleic acids. In some embodiments, all or substantially all of a sequence encoding an ITR is used. An AAV ITR sequence may be obtained from any known AAV, including presently identified mammalian AAV types. In some embodiments an ITR is an AAV2 ITR.

An example of a construct molecule employed in the present disclosure is a "cis-acting" construct containing a transgene, in which the selected transgene sequence and associated regulatory elements are flanked by 5' or "left" and 3' or "right" AAV ITR sequences. 5' and left designations refer to a position of an ITR sequence relative to an entire construct, read left to right, in a sense direction. For example, in some embodiments, a 5' or left ITR is an ITR that is closest to a promoter (as opposed to a polyadenylation sequence) for a given construct, when a construct is depicted in a sense orientation, linearly. Concurrently, 3' and right designations refer to a position of an ITR sequence relative to an entire construct, read left to right, in a sense direction. For example, in some embodiments, a 3' or right ITR is an ITR that is closest to a polyadenylation sequence (as opposed to a promoter sequence) for a given construct, when a construct is depicted in a sense orientation, linearly. ITRs as provided herein are depicted in 5' to 3' order in accordance with a sense strand. Accordingly, one of skill in the art will appreciate that a 5' or "left" orientation ITR can also be depicted as a 3' or "right" ITR when converting from sense to antisense direction. Further, it is well within the ability of one of skill in the art to transform a given sense ITR sequence (e.g., a 5'/left AAV ITR) into an antisense sequence (e.g., 3'/right ITR sequence). One of ordinary skill in the art would understand how to modify a given ITR sequence for use as either a 5'/left or 3'/right ITR, or an antisense version thereof.

For example, an ITR (e.g., a 5' ITR) can have a sequence according to SEQ ID NO: 45. In some embodiments, an ITR (e.g., a 3' ITR) can have a sequence according to SEQ ID NO: 46. In some embodiments, an ITR comprises one or more modifications, e.g., truncations, deletions, substitutions or insertions, as is known in the art. In some embodiments, an ITR comprises fewer than 145 nucleotides, e.g., 127, 130, 134 or 141 nucleotides. For example, in some embodiments, an ITR comprises 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143 144, or 145 nucleotides. In some embodiments, an ITR (e.g., a 5' ITR) can have a sequence according to SEQ ID NO: 47. In some embodiments, an ITR (e.g., a 3' ITR) can have a sequence according to SEQ ID NO: 48.

A non-limiting example of a 5' AAV ITR sequence is SEQ ID NO: 45. A non-limiting example of a 3' AAV ITR sequence is SEQ ID NO: 46. A non-limiting example of a 5' AAV ITR sequence is SEQ ID NO: 47. A non-limiting example of a 3' AAV ITR sequence is SEQ ID NO: 48. In some embodiments, rAAV constructs of the present disclosure comprise a 5' AAV ITR and/or a 3' AAV ITR. In some embodiments, a 5' AAV ITR sequence is SEQ ID NO: 45. In some embodiments, a 3' AAV ITR sequence is SEQ ID NO: 46. In some embodiments, the 5' and a 3' AAV ITRs (e.g., SEQ ID NOs: 45 and 46, or 47 and 48) flank a portion of a coding sequence, e.g., all or a portion of an anti-VEGF gene (e.g., SEQ ID NOs: 13, 14, 15, 19, 22, 42 and/or 103). The ability to modify these ITR sequences is within the skill of the art. (See, e.g., texts such as Sambrook et al. "Molecular Cloning. A Laboratory Manual", 2d ed., Cold Spring Harbor Laboratory, New York (1989); and K. Fisher et al., J Virol., 70:520 532 (1996), each of which is incorporated in its entirety herein by reference). In some embodiments, a 5' ITR sequence is at least 85%, 90%, 95%, 98% or 99% identical to a 5' ITR sequence represented by SEQ ID NOs: 45 or 47. In some embodiments, a 3' ITR sequence is at least 85%, 90%, 95%, 98% or 99% identical to a 3' ITR sequence represented by SEQ ID NOs: 46 or 48.

```
Exemplary 5' AAV ITR
                                       (SEQ ID NO: 45)
TTGGCCACTCCCTCTCTGCGCGCTCGCTCGCTCACTGAGGCCGCCCGGG
CAAAGCCCGGGCGTCGGGCGACCTTTGGTCGCCCGGCCTCAGTGAGCGA
GCGAGCGCGCAGAGAGGGAGTGGCCAACTCCATCACTAGGGGTTCCT Exemplary 3' AAV ITR
                                       (SEQ ID NO: 46)
AGGAACCCCTAGTGATGGAGTTGGCCACTCCCTCTCTGCGCGCTCGCTC
GCTCACTGAGGCCGGGCGACCAAAGGTCGCCCGACGCCCGGGCTTTGCC
CGGGCGGCCTCAGTGAGCGAGCGAGCGCGCAGAGAGGGAGTGGCCAA Exemplary 5' AAV ITR
                                       (SEQ ID NO: 47)
CTGCGCGCTCGCTCGCTCACTGAGGCCGCCCGGGCGTCGGGCGACCTTT
GGTCGCCCGGCCTCAGTGAGCGAGCGAGCGCGCAGAGAGGGAGTGGCCA
ACTCCATCACTAGGGGTTCCT Exemplary 3' AAV ITR
                                       (SEQ ID NO: 48)
AGGAACCCCTAGTGATGGAGTTGGCCACTCCCTCTCTGCGCGCTCGCTC
GCTCACTGAGGCCGGGCGACCAAAGGTCGCCCGACGCCCGGGCTTTGCC
CGGGCGGCCTCAGTGAGCGAGCGAGCGCGCAG
```

Promoters

In some embodiments, a construct (e.g., an rAAV construct) comprises a promoter. The term "promoter" refers to a DNA sequence recognized by enzymes/proteins that can promote and/or initiate transcription of an operably linked gene (e.g., an anti-VEGF gene). For example, a promoter typically refers to, e.g., a nucleotide sequence to which an RNA polymerase and/or any associated factor binds and from which it can initiate transcription. Thus, in some embodiments, a construct (e.g., an rAAV construct) comprises a promoter operably linked to one of the non-limiting example promoters described herein.

In some embodiments, a promoter is an inducible promoter, a constitutive promoter, a mammalian cell promoter, a viral promoter, a chimeric promoter, an engineered promoter, a tissue-specific promoter, or any other type of promoter known in the art. In some embodiments, a promoter is a RNA polymerase II promoter, such as a mammalian RNA polymerase II promoter. In some embodiments, a promoter is a RNA polymerase III promoter, including, but not limited to, a HI promoter, a human U6 promoter, a mouse U6 promoter, or a swine U6 promoter. A promoter will generally be one that is able to promote transcription in an inner ear cell. In some embodiments, a promoter is a cochlea-specific promoter or a cochlea-oriented promoter. In some embodiments, a promoter is a hair cell specific promoter, or a supporting cell specific promoter.

A variety of promoters are known in the art, which can be used herein. Non-limiting examples of promoters that can be used herein include: human EF1α, human cytomegalovirus (CMV) (U.S. Pat. No. 5,168,062, which is incorporated in its entirety herein by reference), human ubiquitin C (UBC), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g., human T-cell leukemia virus HTLV), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene H-2$_K$b, HSP70, proliferin, tumor necrosis factor, thyroid stimulating hormone a gene, immunoglobulin light chain, T-cell receptor, HLA DQa and DQ, interleukin-2 receptor, MHC class II, MHC class II HLA-DRa, muscle creatine kinase, prealbumin (transthyretin), elastase I, albumin gene, c-fos, c-HA-ras, neural cell adhesion molecule (NCAM), H2B (TH2B) histone, rat growth hormone, human serum amyloid (SAA), troponin I (TN I), duchenne muscular dystrophy, human immunodeficiency virus, and Gibbon Ape Leukemia Virus (GALV) promoters. Additional examples of promoters are known in the art. See, e.g., Lodish, Molecular Cell Biology, Freeman and Company, New York 2007, each of which is incorporated in its entirety herein by reference. In some embodiments, a promoter is the CMV immediate early promoter. In some embodiments, the promoter is a CAG promoter or a CAG/CBA promoter. In some embodiments, the promoter comprises or consists of SEQ ID NO: 49. In some embodiments, a promoter comprises or consists of SEQ ID NO: 50. In certain embodiments, a promoter comprises a CMV/CBA enhancer/promoter construct exemplified in SEQ ID NO: 51. In certain embodiments, a promoter comprises a CMV/CBA enhancer/promoter construct exemplified in SEQ ID NO: 52. In certain embodiments, a promoter comprises a CAG promoter or CMV/CBA/SV-40 enhancer/promoter construct exemplified in SEQ ID NO: 53. In certain embodiments, a promoter comprises a CAG promoter or CMV/CBA/SV-40 enhancer/promoter construct exemplified in SEQ ID NO: 54. In some embodiments, a promoter sequence is at least 85%, 90%, 95%, 98% or 99% identical to the promoter sequences represented by SEQ ID NOs: 49 or 50. In some embodiments, an enhancer-promoter sequence is at least 85%, 90%, 95%, 98% or 99% identical to enhancer-promoter sequence represented by SEQ ID NOs: 51, 52, 53, or 54.

The term "constitutive" promoter refers to a nucleotide sequence that, when operably linked with a nucleic acid encoding a protein (e.g., an anti-VEGF protein), causes RNA to be transcribed from the nucleic acid in a cell under most or all physiological conditions.

Examples of constitutive promoters include, without limitation, the retroviral Rous sarcoma virus (RSV) LTR promoter, the cytomegalovirus (CMV) promoter (see, e.g., Boshart et al, Cell 41:521-530, 1985, which is incorporated in its entirety herein by reference), the SV40 promoter, the dihydrofolate reductase promoter, the beta-actin promoter, the phosphoglycerol kinase (PGK) promoter, and the EF1-alpha promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Additional examples of inducible promoters are known in the art.

Examples of inducible promoters regulated by exogenously supplied compounds include the zinc-inducible sheep metallothionein (MT) promoter, the dexamethasone (Dex)-inducible mouse mammary tumor virus (MMTV) promoter, the T7 polymerase promoter system (WO 98/10088, which is incorporated in its entirety herein by reference); the ecdysone insect promoter (No et al, Proc. Natl. Acad Sci. U.S.A. 93:3346-3351, 1996, which is incorporated in its entirety herein by reference), the tetracycline-repressible system (Gossen et al, Proc. Natl. Acad Sci.

U.S.A. 89:5547-5551, 1992, which is incorporated in its entirety herein by reference), the tetracycline-inducible system (Gossen et al, Science 268:1766-1769, 1995, see also Harvey et al, Curr. Opin. Chem. Biol. 2:512-518, 1998, each of which is incorporated in their entirety herein by reference), the RU486-inducible system (Wang et al, Nat. Biotech. 15:239-243, 1997, and Wang et al, Gene Ther. 4:432-441, 1997, each of which is incorporated in their entirety herein by reference), and the rapamycin-inducible system (Magari et al. J Clin. Invest. 100:2865-2872, 1997, which is incorporated in its entirety herein by reference).

The term "tissue-specific" promoter refers to a promoter that is active only in certain specific cell types and/or tissues (e.g., transcription of a specific gene occurs only within cells expressing transcription regulatory and/or control proteins that bind to the tissue-specific promoter). In some embodiments, regulatory and/or control sequences impart tissue-specific gene expression capabilities. In some cases, tissue-specific regulatory and/or control sequences bind tissue-specific transcription factors that induce transcription in a tissue-specific manner.

In some embodiments, a tissue-specific promoter is a cochlea-specific promoter. In some embodiments, a tissue-specific promoter is a cochlear hair cell-specific promoter. Non-limiting examples of cochlear hair cell-specific promoters include but are not limited to: a ATOH1 promoter, a POU4F3 promoter, a LHX3 promoter, a MYO7A promoter, a MYO6 promoter, a α9ACHR promoter, and a α10ACHR promoter. In some embodiments, a promoter is a cochlear hair cell-specific promoter such as a PRESTIN promoter or an ONCOMOD promoter. See, e.g., Zheng et al., Nature 405:149-155, 2000; Tian et al. Dev. Dyn. 23 1: 199-203, 2004; and Ryan et al., Adv. Otorhinolaryngol. 66: 99-115, 2009, each of which is incorporated in their entirety herein by reference.

In some embodiments, a tissue-specific promoter is an ear cell specific promoter. In some embodiments, a tissue-specific promoter is an inner ear cell specific promoter. Non-limiting examples of inner ear non-sensory cell-specific promoters include but are not limited to: GJB2, GJB6, SLC26A4, TECTA, DFNA5, COCH, NDP, SYN1, GFAP, PLP, TAK1, or SOX21. In some embodiments, a cochlear non-sensory cell specific promoter may be an inner ear supporting cell specific promoter. Non-limiting examples of inner ear supporting cell specific promoters include but are not limited to: SOX2, FGFR3, PROX1, GLAST1, LGR5, HES1, HES5, NOTCH1, JAG1, CDKN1A, CDKN1B, SOX10, P75, CD44, HEY2, LFNG, or S100b.

In some embodiments, provided rAAV constructs comprise a promoter sequence selected from a CAG, a CBA, a CMV, or a CB7 promoter. In some embodiments of any of the therapeutic compositions described herein, the first and/or sole rAAV construct further comprises at least one promoter sequence selected from Cochlea and/or inner ear specific promoters.

Exemplary CBA promoter
(SEQ ID NO: 49)
GTCGAGGTGAGCCCCACGTTCTGCTTCACTCTCCCCATCTCCCCCCCCT

CCCCACCCCCAATTTTGTATTTATTTATTTTTTAATTATTTTGTGCAGC

GATGGGGCGGGGGGGGGGGGGGCGCGCGCCAGGCGGGGCGGGGCGG

GGCGAGGGGCGGGGCGGGGCGAGGCGGAGAGGTGCGGCGGCAGCCAATC

AGAGCGGCGCGCTCCGAAAGTTTCCTTTTATGGCGAGGCGGCGGCGCG

GCGGCCCTATAAAAAGCGAAGCGCGCGGCGGGCG

Exemplary CBA promoter
(SEQ ID NO: 50)
GTCGAGGTGAGCCCCACGTTCTGCTTCACTCTCCCCATCTCCCCCCCCT

CCCCACCCCCAATTTTGTATTTATTTATTTTTTAATTATTTTGTGCAGC

GATGGGGCGGGGGGGGGGGGGGCGCGCGCCAGGCGGGGCGGGGCGGGG

CGAGGGGCGGGCGGGGCGAGGCGGAGAGGTGCGGCGGCAGCCAATCAG

AGCGGCGCGCTCCGAAAGTTTCCTTTTATGGCGAGGCGGCGGCGGCGGC

GGCCCTATAAAAAGCGAAGCGCGCGGCGGGCG

Exemplary CMV/CBA enhancer/promoter
(SEQ ID NO: 51)
GACATTGATTATTGACTAGTTATTAATAGTAATCAATTACGGGGTCATT

AGTTCATAGCCCATATATGGAGTTCCGCGTTACATAACTTACGGTAAAT

GGCCCGCCTGGCTGACCGCCCAACGACCCCCGCCCATTGACGTCAATAA

TGACGTATGTTCCCATAGTAACGCCAATAGGGACTTTCCATTGACGTCA

ATGGGTGGACTATTTACGGTAAACTGCCCACTTGGCAGTACATCAAGTG

TATCATATGCCAAGTACGCCCCCTATTGACGTCAATGACGGTAAATGGC

CCGCCTGGCATTATGCCCAGTACATGACCTTATGGGACTTTCCTACTTG

GCAGTACATCTACGTATTAGTCATCGCTATTACCATGGGTCGAGGTGAG

CCCCACGTTCTGCTTCACTCTCCCCATCTCCCCCCCCTCCCCACCCCCA

ATTTTGTATTTATTTATTTTTTAATTATTTTGTGCAGCGATGGGGCGG

GGGGGGGGGGGCGCGCGCCAGGCGGGGCGGGGCGGGGCGAGGGGCG

GGGCGGGGCGAGGCGGAGAGGTGCGGCGGCAGCCAATCAGAGCGGCGCG

CTCCGAAAGTTTCCTTTTATGGCGAGGCGGCGGCGGCGGCGGCCCTATA

AAAAGCGAAGCGCGCGGCGGGCG

Exemplary CMV/CBA enhancer/promoter
(SEQ ID NO: 52)
GACATTGATTATTGACTAGTTATTAATAGTAATCAATTACGGGGTCATT

AGTTCATAGCCCATATATGGAGTTCCGCGTTACATAACTTACGGTAAAT

GGCCCGCCTGGCTGACCGCCCAACGACCCCCGCCCATTGACGTCAATAA

TGACGTATGTTCCCATAGTAACGCCAATAGGGACTTTCCATTGACGTCA

ATGGGTGGACTATTTACGGTAAACTGCCCACTTGGCAGTACATCAAGTG

TATCATATGCCAAGTACGCCCCCTATTGACGTCAATGACGGTAAATGGC

CCGCCTGGCATTATGCCCAGTACATGACCTTATGGGACTTTCCTACTTG

GCAGTACATCTACGTATTAGTCATCGCTATTACCATGGGTCGAGGTGAG

CCCCACGTTCTGCTTCACTCTCCCCATCTCCCCCCCCTCCCCACCCCCA

ATTTTGTATTTATTTATTTTTTAATTATTTTGTGCAGCGATGGGGCGG

GGGGGGGGGGCGCGCGCCAGGCGGGGCGGGGCGGGGCGAGGGGCGGG

GCGGGGCGAGGCGGAGAGGTGCGGCGGCAGCCAATCAGAGCGGCGCGCT

CCGAAAGTTTCCTTTTATGGCGAGGCGGCGGCGGCGGCGGCCCTATAAA

AAGCGAAGCGCGCGGCGGGCG

Exemplary CAG enhancer/promoter
(SEQ ID NO: 53)
GACATTGATTATTGACTAGTTATTAATAGTAATCAATTACGGGGTCATT

```
AGTTCATAGCCCATATATGGAGTTCCGCGTTACATAACTTACGGTAAAT
GGCCCGCCTGGCTGACCGCCCAACGACCCCCGCCCATTGACGTCAATAA
TGACGTATGTTCCCATAGTAACGCCAATAGGGACTTTCCATTGACGTCA
ATGGGTGGACTATTTACGGTAAACTGCCCACTTGGCAGTACATCAAGTG
TATCATATGCCAAGTACGCCCCCTATTGACGTCAATGACGGTAAATGGC
CCGCCTGGCATTATGCCCAGTACATGACCTTATGGGACTTTCCTACTTG
GCAGTACATCTACGTATTAGTCATCGCTATTACCATGGGTCGAGGTGAG
CCCCACGTTCTGCTTCACTCTCCCCATCTCCCCCCCCTCCCCACCCCCA
ATTTTGTATTTATTTATTTTTTAATTATTTTGTGCAGCGATGGGGCGG
GGGGGGGGGGGGCGCGCGCCAGGCGGGGCGGGGCGGGGCGAGGGGCG
GGGCGGGGCGAGGCGGAGAGGTGCGGCGGCAGCCAATCAGAGCGGCGCG
CTCCGAAAGTTTCCTTTTATGGCGAGGCGGCGGCGGCGGCGGCCCTATA
AAAAGCGAAGCGCGCGGCGGGCGGGAGTCGCTGCGTTGCCTTCGCCCCG
TGCCCCGCTCCGCGCCGCCTCGCGCCGCCCGCCCCGGCTCTGACTGACC
GCGTTACTCCCACAGGTGAGCGGGCGGGACGGCCCTTCTCCTCCGGGCT
GTAATTAGCGCTTGGTTTAATGACGGCTCGTTTCTTTTCTGTGGCTGCG
TGAAAGCCTTAAAGGGCTCCGGGAGGGCCCTTTGTGCGGGGGGGAGCGG
CTCGGGGGGTGCGTGCGTGTGTGTGCGTGGGGAGCGCCGCGTGCGGC
CCGCGCTGCCCGGCGGCTGTGAGCGCTGCGGGCGCGGCGCGGGGCTTTG
TGCGCTCCGCGTGTGCGCGAGGGGAGCGCGGCCGGGGGCGGTGCCCCGC
GGTGCGGGGGGGCTGCGAGGGGAACAAAGGCTGCGTGCGGGGTGTGTGC
GTGGGGGGTGAGCAGGGGGTGTGGGCGCGGCGGTCGGGCTGTAACCCC
CCCCTGCACCCCCCTCCCCGAGTTGCTGAGCACGGCCCGGCTTCGGGTG
CGGGGCTCCGTGCGGGCGTGGCGCGGGGCTCGCCGTGCCGGGCGGGGG
GTGGCGGCAGGTGGGGGTGCCGGGCGGGGCGGGGCCGCCTCGGGCCGGG
GAGGGCTCGGGGAGGGGCGCGGCGGCCCCCGGAGCGCCGGCGGCTGTC
GAGGCGCGGCGAGCCGCAGCCATTGCCTTTTATGGTAATCGTGCGAGAG
GGCGCAGGGACTTCCTTTGTCCCAAATCTGTGCGGAGCCGAAATCTGGG
AGGCGCCGCCGCACCCCCTCTAGCGGGCGCGGGGCGAAGCGGTGCGGCG
CCGGCAGGAAGGAAATGGGCGGGAGGGCCTTCGTGCGTCGCCGCGCCG
CCGTCCCCTTCTCCCTCTCCAGCCTCGGGGCTGTCCGCGGGGGGACGGC
TGCCTTCGGGGGGGACGGGGCAGGGCGGGGTTCGGCTTCTGGCGTGTGA
CCGGCGGCTCTAGAGCCTCTGCTAACCATGTTCATGCCTTCTTCTTTTT
CCTACAG
```

Exemplary CAG enhancer/promoter
(SEQ ID NO: 54)
```
GACATTGATTATTGACTAGTTATTAATAGTAATCAATTACGGGTCATT
AGTTCATAGCCCATATATGGAGTTCCGCGTTACATAACTTACGGTAAAT
GGCCCGCCTGGCTGACCGCCCAACGACCCCCGCCCATTGACGTCAATAA
TGACGTATGTTCCCATAGTAACGCCAATAGGGACTTTCCATTGACGTCA
ATGGGTGGACTATTTACGGTAAACTGCCCACTTGGCAGTACATCAAGTG
TATCATATGCCAAGTACGCCCCCTATTGACGTCAATGACGGTAAATGGC
CCGCCTGGCATTATGCCCAGTACATGACCTTATGGGACTTTCCTACTTG
GCAGTACATCTACGTATTAGTCATCGCTATTACCATGGGTCGAGGTGAG
CCCCACGTTCTGCTTCACTCTCCCCATCTCCCCCCCCTCCCCACCCCCA
ATTTTGTATTTATTTATTTTTTAATTATTTTGTGCAGCGATGGGGCGG
GGGGGGGGGGGCGCGCGCCAGGCGGGGCGGGGCGGGGCGAGGGCGGG
GCGGGGCGAGGCGGAGAGGTGCGGCGGCAGCCAATCAGAGCGGCGCGCT
CCGAAAGTTTCCTTTTATGGCGAGGCGGCGGCGGCGGCGGCCCTATAAA
AGCGAAGCGCGCGGCGGGCGGGAGTCGCTGCGTTGCCTTCGCCCCGTG
CCCCGCTCCGCGCCGCCTCGCGCCGCCCGCCCCGGCTCTGACTGACCGC
GTTACTCCCACAGGTGAGCGGGCGGGACGGCCCTTCTCCTCCGGGCTGT
AATTAGCGCTTGGTTTAATGACGGCTCGTTTCTTTTCTGTGGCTGCGTG
AAAGCCTTAAAGGGCTCCGGGAGGGCCCTTTGTGCGGGGGGAGCGGCT
CGGGGGGTGCGTGCGTGTGTGTGCGTGGGGAGCGCCGCGTGCGGCCC
GCGCTGCCCGGCGGCTGTGAGCGCTGCGGGCGCGGCGCGGGGCTTTGTG
CGCTCCGCGTGTGCGCGAGGGGAGCGCGGCCGGGGGCGGTGCCCCGCGG
TGCGGGGGGCTGCGAGGGGAACAAAGGCTGCGTGCGGGGTGTGTGCGT
GGGGGGGTGAGCAGGGGGTGTGGGCGCGGCGGTCGGGCTGTAACCCCCC
CCTGCACCCCCTCCCCGAGTTGCTGAGCACGGCCCGGCTTCGGGTGCG
GGGCTCCGTGCGGGCGTGGCGCGGGGCTCGCCGTGCCGGGCGGGGGT
GGCGGCAGGTGGGGTGCCGGGCGGGGCGGGGCCGCCTCGGGCCGGGGA
GGGCTCGGGGAGGGGCGCGGCGGCCCCCGGAGCGCCGGCGGCTGTCGA
GGCGCGGCGAGCCGCAGCCATTGCCTTTTATGGTAATCGTGCGAGAGGG
CGCAGGGACTTCCTTTGTCCCAAATCTGTGCGGAGCCGAAATCTGGGAG
GCGCCGCCGCACCCCCTCTAGCGGGCGCGGGGCGAAGCGGTGCGGCGCC
GGCAGGAAGGAAATGGGCGGGAGGGCCTTCGTGCGTCGCCGCGCCGCC
GTCCCCTTCTCCCTCTCCAGCCTCGGGGCTGTCCGCGGGGGACGGCTG
CCTTCGGGGGGACGGGCAGGGCGGGGTTCGGCTTCTGGCGTGTGACC
GGCGGCTCTAGAGCCTCTGCTAACCATGTTCATGCCTTCTTCTTTTTCC
TACAG
```

In certain embodiments, a promoter is an endogenous human ATOH1 enhancer-promoter as set forth in SEQ ID NO: 55. In some embodiments, an enhancer-promoter sequence is at least 85%, 90%, 95%, 98% or 99% identical to enhancer-promoter sequence represented by SEQ ID NO: 55.

Exemplary Human ATOH1 enhancer-promoter
(SEQ ID NO: 55)
```
CTATGGAGTTTGCATAACAAACGTTTGGCAGCTCGCTCTCTTACACTCC
ATTAACAAGCTGTAACATATAGCTGCAGGTTGCTATAATCTCATTAATA
TTTTGGAAACTTGAATATTGAGTATTTCTGAGTGCTCATTCCCCATATG
CCAGCCACTTCTGCCATGCTGACTGGTTCCTTTCTCTCCATTATTAGCA
ATTAGCTTCTTACCTTCCAAAGTCAGATCCAAGGTATCCAAGATACTAG
```

-continued
CAAAGGAATCAACTATGTGTGCAAGTTAAGCATGCTTAATATCACCCAA

ACAAACAAAGAGGCAGCATTTCTTAAAGTAATGAAGATAGATAAATCGG

GTTAGTCCTTTGCGACACTGCTGGTGCTTTCTAGAGTTTTATATATTTT

AAGCAGCTTGCTTTATATTCTGTCTTTGCCTCCCACCCCACCAGCACTT

TTATTTGTGGAGGGTTTTGGCTCGCCACACTTTGGGAAACTTATTTGAT

TTCACGGAGAGCTGAAGGAAGATCATTTTTGGCAACAGACAAGTTTAAA

CACGATTTCTATGGGACATTGCTAACTGGGGCCCCTAAGGAGAAAGGGG

AAACTGAGCGGAGAATGGGTTAAATCCTTGGAAGCAGGGGAGAGGCAGG

GGAGGAGAGAAGTCGGAGGAGTATAAAGAAAAGGACAGGAACCAAGAAG

CGTGGGGGTGGTTTGCCGTAATGTGAGTGTTTCTTAATTAGAGAACGGT

TGACAATAGAGGGTCTGGCAGAGGCTCCTGGCCGCGGTGCGGAGCGTCT

GGAGCGGAGCACGCGCTGTCAGCTGGTGAGCGCACTCTCCTTTCAGGCA

GCTCCCCGGGGAGCTGTGCGGCCACATTTAACACCATCATCACCCCTCC

CCGGCCTCCTCAACCTCGGCCTCCTCCTCGTCGACAGCCTTCCTTGGCC

CCCACCAGCAGAGCTCACAGTAGCGAGCGTCTCTCGCCGTCTCCCGCAC

TCGGCCGGGCCTCTCTCCTCCCCAGCTGCGCAGCGGGAGCCGCCACT

GCCCACTGCACCTCCCAGCAACCAGCCCAGCACGCAAAGAAGCTGCGCA

AAGTTAAAGCCAAGCAATGCCAAGGGGAGGGGAAGCTGGAGGCGGGCTT

TGAGTGGCTTCTGGGCGCCTGGCGGGTCCAGAATCGCCCAGAGCCGCCC

GCGGTCGTGCACATCTGACCCGAGTCAGCTTGGGCACCAGCCGAGAGCC

GGCTCCGCACCGCTCCCGCACCCCAGCCGCCGGGGTGGTGACACACACC

GGAGTCGAATTACAGCCCTGCAATTAACATATGAATCTGACGAATTTAA

AAGAAGGAAAAAAAAAAAAAACCTGAGCAGGCTTGGGAGTCCTCTGCA

CACAAGAACTTTTCTCGGGGTGTAAAAACTCTTTGATTGGCTGCTCGCA

CGCGCCTGCCCGCGCCCTCCATTGGCTGAGAAGACACGCGACCGGCGCG

AGGAGGGGGTTGGGAGAGGAGCGGGGGGAGACTGAGTGGCGCGTGCCGC

TTTTTAAAGGGGCGCAGCGCCTTCAGCAACCGGAGAAGCATAGTTGCAC

GCGACCTGGTGTGTGATCTCCGAGTGGGTGGGGAGGGTCGAGGAGGGA

AAAAAAAATAAGACGTTGCAGAAGAGACCCGGAAAGGGCCTTTTTTTG

GTTGAGCTGGTGTCCCAGTGCTGCCTCCGATCCTGAGCCTCCGAGCCTT

TGCAGTGCAA

In certain embodiments, a promoter is an endogenous human SLC26A4 immediate promoter as set forth in SEQ ID NO: 56 or 57. In certain embodiments, a promoter is an endogenous human SLC26A4 enhancer-promoter as set forth in SEQ ID NO: 58, 59, or 60. In some embodiments, an enhancer-promoter sequence is at least 85%, 90%, 95%, 98% or 99% identical to a promoter or enhancer-promoter sequence represented by SEQ ID NO: 56, 57, 58, 59, or 60. In certain embodiments, a promoter is a human SLC26A4 endogenous enhancer-promoter sequence comprised within SEQ ID NO: 58, 59, or 60.

Exemplary Human SLC26A4 immediate promoter
(SEQ ID NO: 56)
CTGCCTTCTGAGAGCGCTATAAAGGCAGCGGAAGGGTAGTCCGCGGGC -continued
ATTCCGGGCGG Exemplary Human SLC26A4 immediate promoter
(SEQ ID NO: 57)
CTCTAGGCGGGCTCTGCTCTTCTTTAAGGAGTCCCACAGGGCCTGGCCC

GCCCCTGACCT

Exemplary Human SLC26A4 enhancer-promoter
(SEQ ID NO: 58)
TAAAGAGTTGTGAGTTGTGTAGGTGAGTTGCCATGGAGCTACAAATATG

AGTTGATATTCTGAAATCCTAGACAGCCATCTCCAAGGTTAAGAAAAAT

CCTTATGCACTCACTTGCAAAGATATCCACAGCATGCTCTTAATGGAGA

AAAACAAAGCCTTAGATCAAATATGTAAAGTAATTTTTAGTTTTTTGAA

AAGGTATGTTTGGGCTATAGATAAATCTGTTCAAAAAACATGAGAGAAG

ATAATAATGGTTGAAAGGAGACACAGTGCTTGCCCTCAAGAAGTTTTTG

TCTAGTGAGGGAGAGAGAACTTGTATGTAAATAAAATTGTGTTACTAAG

GTAGATAGTGAGAAGTAACTTAAGAGAGGATCAGATAAGGTATTAAGAG

AATACAGAAAAGGGTCTGGATTAATTCTGAACAGCATCAAAGAATGTTC

TTGCAAGAGATAGTGTTTTCACCAGATCTTGAAGGTATGGATGAGGGTA

TACAGAGTGAGTATATTCAGATTCTACTTTAAAACAAATACTTTCCTCT

GTTGTAGTGGAGTTGAGCTATACATCCAACAATAATGAAAAAATACACG

CATATATACATATATGGAGAGAGATACATATTTTAGTACATGTAGCAAT

TGATTAATAAATGTACAGTTTAAGTCGCATGCAAAACCTTGGAGTGATA

GCAAACTTCATTGTAGGATGTTTAGCAGCATCTCTGGTCTCTACTCACT

AGATCCCAATAGCATCTCCCTAGGTGTGACAACCAAAAATGTCTCCAGG

CATTGACCTCTGGAGGCAAAAAAAGCCCTTTATTAAGAACCAGTGGTAT

ACATAAGTAAAACATACACAAGAGATTCCTCCCCTCTTCTCTGTATGTG

AATAAAAATTGCAAAGTTCATGACCTGGATTTTCCTTTTAGGTTTCTTC

TTTAGTGGTTCTTAACTTCATTGGGTGAAGTAAGCCTTTGAAGATCTGT

TGAAAGCTGTTGACTCATTCACTTCTCAGGAAAACGCACATGCTGACTA

CCATTTCAGAGAATTTGCATCAGGGTTCTCTGGGGAGGAGTTCTGAGTT

CTGTTTCCAGGAGCTCGTAGAATTGTCATGGTCTGCATATGCAAGGCAG

GTGGATTACGGAAGGTTGATGTACAGAGGTCTGTATTTTGGAGCCTCTT

CTGTATTTACTTCAGAACACTAACAATCAGGCGAGAATGTTCTGGTTTA

TCAAACCCTTCCTTCTGCCTTTCATCTTAACCATGCATTAGTTTTAACA

AAGTTCATCCCAACAGAAGACAAAACACTGATGAGGTAGGATAGCTCCA

GCTCCTCCTCCCTCTCTTCTAGTCTTGATTTCCATGTAGTCCAGTTTAT

TCCTTCCCTGATTGTCCAGGAGAATGAGAAAAAGAAAAAACAGAGTCTA

GTGGGTAAGAAAGGGCCACCTGGACGGCTTGATTTGGATTGTGAAATAA

AACACACACACATGCACACGTAGAATAAGTGGCTAAAATCTGAGTAAAT

CGTGAACTCTCTGTATCCTCCACCCATTGAATACTCCTAAAAGACTTTC

TAGAAATTCAAGGACTTATTAATATAGAAACCTGGCCATTGTTCCTCTT

CTCCTCCCCATGTGGTATGAGAGCACCTGTGGCAGGCTCCCAGAGACCA

CGGACCTCTTCCTCTAGGCGGGCTCTGCTCTTCTTTAAGGAGTCCCACA

Exemplary Human SLC26A4 enhancer-promoter
(SEQ ID NO: 59)
GGCTGCTCGGAAAACAGGACGAGGGGAGAGACTTGCTCAATAAGCTGAA
AGTTCTGCCCCCGAGAGGGCTGCGACAGCTGCTGGAATGTGCCTGCAGC
GTCCGCCTCTTGGGGACCCGCGGAGCGCGCCCTGACGGTTCCACGCCTG
GCCCGGGGGTCTGCACCTCTCCTCCAGTGCGCACCTGGAGCTGCGTCCC
GGGTCAGGTGCGGGGAGGGAGGGAATCTCAGTGTCCCCTTCCAGCCTTG
CAAGCGCCTTTGGCCCCTGCCCCAGCCCCTCGGTTTGGGGGAGATTTCA
GAACGCGGACAGCGCCCTGGCTGCGGGCCATAGGGGACTGGGTGGAACT
CGGGAAGCCCCAGAGCAGGGGCTTACTCGCTTCAAGTTTGGGGAACCC
CGGGCAGCGGGTGCAGGCCACGAGACCCGAAGGTTCTCAGGTGCCCCCC
TGCAGGCTGGCCGTGCGCGCCGTGGGCGCTTGTCGCGAGCGCCGAGGG
CTGCAGGACGCGGACCAGACTCGCGGTGCAGGGGGGCCTGGCTGCAGCT
AACAGGTGATCCCGTTCTTTCTGTTCCTCGCTCTTCCCCTCCGATCGTC
CTCGCTTACCGCGTGTCCTCCCTCCTCGCTGTCCTCTGGCTCGCAGGTC
ATGGCAGCGCCAGGCGGCAGGTCGGAGCCGCCGCAGCTCCCCGAGTACA
GCTGCAGCTACATGGTGTCGCGGCCGGTCTACAGCGAGCTCGCTTTCCA
GCAACAGCACGAGCGGCGCCTGCAGGAGCGCAAGACGCTGCGGGAGAGC
CTGGCCAAGTGCTGCAGGTAGCGGCCGCGCGGGCCTGCGTAGAGAAG
CGGAGCGGGGCGTCCACGCCTTGGGGAGGGAAGGGCGTCCCCAGCGGGC
GAGAGTGGGGTGCGGCGGCGGAGCCCCTGGGCGCCAGCTGCTTCTCCC
AGAGGCCCGACTTTCGGTCTCCGGTCCTCCACGCGCCCTTCTGGTGGG
AGGGTGGCTCCATCAGTCTCGGGCCCGAAATGAACTTACCTGGGAAACT
CGCCTTTGGGGAGAGTGGGTTCTAGGAGCCCCGTCTCTCTTTTTCCTCT
CTGAAGGAAACTTGGAGTGCCTCTTGGGGTACAGTGGGTCCCTGTTGCC
TTCTTGGGAGCTTGTTTAAATGAAATGAATAGGGAAACCCAGCTCTTGA
CCAGGAGGAGTCCTTGAAACACTCAAGCTAAGTAGGCGGGCTACCATTC
AGTTAGAGACCAGGATGCAAGCTAGAACCCAGGGGAGCGCGGGGTGTGC
CAAGTACTTCATCAGCAGGCTGTGGGACCCCTGGGGAAAGCCACCCTCA
GTCTCTAAACCCAAACATGCCGTAACTAGATGTCACAAACATAAAGAAA
TTAGAGTTTCTAAAACCTTTCATTATAG Exemplary Human SLC26A4 enhancer-promoter
(SEQ ID NO: 60)
CGGAAGGTTGATGTACAGAGGTCTGTATTTTGGAGCCTCTTCTGTATTT
ACTTCAGAACACTAACAATCAGGCGAGAATGTTCTGGTTTATCAAACCC
TTCCTTCTGCCTTTCATCTTAACCATGCATTAGTTTTAACAAAGTTCAT
CCCAACAGAAGACAAAACACTGATGAGGTAGGATAGCTCCAGCTCCTCC
TCCCTCTCTTCTAGTCTTGATTTCCATGTAGTCCAGTTTATTCCTTCCC
TGATTGTCCAGGAGAATGAGAAAAAGAAAAAACAGAGTCTAGTGGGTAA
GAAAGGGCCACCTGGACGGCTTGATTTGGATTGTGAAATAAAACACACA
CACATGCACACGTAGAATAAGTGGCTAAAATCTGAGTAAATCGTGAACT
CTCTGTATCCTCCACCCATTGAATACTCCTAAAAGACTTTCTAGAAATT
CAAGGACTTATTAATATAGAAACCTGGCCATTGTTCCTCTTCTCCTCCC
CATGTGGTATGAGAGCACCTGTGGCAGGCTCCCAGAGACCACGGACCTC
TTCCTCTAGGCGGGCTCTGCTCTTCTTTAAGGAGTCCCACAGGGCCTGG
CCCGCCCCTGACCTCGCAACCCTTGAGATTAGTAACGGGATGAGTGAGG
ATCCGGGTGGCCCCTGCGTGGCAGCCAGTAAGAGTCTCAGCCTTCCCGG
TTCGGGAAAGGGGAAGAATGCAGGAGGGGTAGGATTTCTTTCCTGATAG
GATCGGTTGGGAAAGACCGCAGCCTGTGTGTGTCTTTCCCTTCGACCAA
GGTGTCTGTTGCTCCGTAAATAAAACGTCCCACTGCCTTCTGAGAGCGC
TATAAAGGCAGCGGAAGGGTAGTCCGCGGGGCATTCCGGGCGGGGCGCG
AGCAGAGACAGGTGAGTT In certain embodiments, a promoter is a human LGR5 enhancer-promoter as set forth in SEQ ID NO: 61. In some embodiments, an enhancer-promoter sequence is at least 85%, 90%, 95%, 98% or 99% identical to enhancer-promoter sequence represented by SEQ ID NO: 61. In some embodiments, a promoter is a human LGR5 endogenous enhancer-promoter sequence comprised within SEQ ID NO: 61.

Exemplary Human LGR5 enhancer-promoter
(SEQ ID NO: 61)
AGGGCTATTTGTACCTCAACGAGGGCTTCTCTCCAAGAAAGCCCTGAAT
CCTTTTCCTCCTTTTTCCTGCAGATTCACTATAGGACACTTTTTGAAGC
AAGAGCATGCATTTTCCCCCTGGCGCTCTGCAGCGGTTCTCAGAGCCCA
GTGTCACTCACATAGGTGGGACTGCTCTCAGTTCAGAGAGCGCTGGGAC
ACTTAAGATGAAAAGTCCCTGGAAGTTAGCAAACAGCCATCTGTCACTC
TGGCATCGATTTACTAAAAGTGACTTCTAGGGTATTCTAAACCACTTTT
AAAAAACAAATGAGTCACTTCGACTTCCTCACCCCGCAAGAGATAGGAA
GGCAGCAGTGGAGTGCTCGCTCAGGAGCTGTATTTGTTTAGCGATTAGC
CTAGAGCTTTGATTTTAGGGCAAAAGCGAGCCAGACAGTGCGGCAGACG
TAAGGATCAAAAAGGCCACCTATCATTCGCCGGGGACGCCTGCCTCCTT
ACCCTGATAACGTAACTATTTCTCTGCATAGGATTTTAGTTTTTGTGTT
TTTGTTTTGTTTTATTCTGTTTAATCACTTCAAGTATCTCATCCATTAT
TTGAAGCGGGCTCGGAGGAAACGTGCCGCATCCTCCAGTCCTTGTGCGT
CTGTTTAGGTCTCTCCGAAGCAGGTCCCTCTCGACTCTTAGATCTGGGT
CTCCAGCACGCATGAAGGGGTAAGGGTGGGGGGTCCCCTATTCCGGCG
CGCGGCGTTGAGCACTGAATCTTCCAGGCGGAGGCTCAGTGGGAGCGCC
GAGAACTCGCCAGTACCGCGCGCTGCCTGCTGCCTGCTGCCTCCCAGCC
CAGGACTTGGGAAAGGAGGGAGGGGACAAGTGGAGGGAAAGTGGGGCCG

```
GGCGGGGGGTGCCTGGGAAGCCAGGCTGCGCTGACGTCACTGGGCGCGC
AATTCGGGCTGGAGCGCTTTAAAAAACGAGCGTGCAAGCAGAGATGCTG
CTCCACACCGCTCAGGCCGCGAGCAGCAGCAAGGCGCACCGCCACTGTC
GCCGCTGCAGCCAGGGCTGCTCCGAAGGCCGGCGTGGCGGCAACCGGCA
CCTCTGTCCCCGCCGCGCTTCTCCTCGCCGCCCACGCCGTGGGGTCAGG
AACGCGGCGTCTGGCGCTGCAGACGCCCGCTGAGTTGCAGAAGCCCACG
GAGCGGCGCCCGGCGCGCCACGGCCCGTAGCAGTCCGGTGCTGCTCTCC
GCCCGCGTCCGGCTCGTGGCCCCCTACTTCGGGCACCGACCGGT
```

In certain embodiments, a promoter is a human SYN1 enhancer-promoter as set forth in SEQ ID NO: 62. In some embodiments, an enhancer-promoter sequence is at least 85%, 90%, 95%, 98% or 99% identical to enhancer-promoter sequence represented by SEQ ID NO: 62. In some embodiments, a promoter is a human SYN1 endogenous enhancer-promoter sequence comprised within SEQ ID NO: 62.

```
Exemplary Human SYN1 enhancer-promoter
                                    (SEQ ID NO: 62)
TGCGTATGAGTGCAAGTGGGTTTTAGGACCAGGATGAGGCGGGGTGGGG
GTGCCTACCTGACGACCGACCCCGACCCACTGGACAAGCACCCAACCCC
CATTCCCCAAATTGCGCATCCCCTATCAGAGAGGGGGAGGGGAAACAGG
ATGCGGCGAGGCGCGTGCGCACTGCCAGCTTCAGCACCGCGGACAGTGC
CTTCGCCCCCGCCTGGCGGCGCGCGCCACCGCCGCCTCAGCACTGAAGG
CGCGCTGACGTCACTCGCCGGTCCCCCGCAAACTCCCCTTCCCGGCCAC
CTTGGTCGCGTCCGCGCCGCCGCCGGCCCAGCCGGACCGCACCACGCGA
GGCGCGAGATAGGGGGGCACGGGCGCGACCATCTGCGCTGCGGCGCCGG
CGACTCAGCGCTGCCTCAGTCTGCGGTGGGCAGCGGAGGAGTCGTGTCG
TGCCTGAGAGCGCAGTCGAGAA
```

In certain embodiments, a promoter is a human GFAP enhancer-promoter as set forth in SEQ ID NO: 63. In some embodiments, an enhancer-promoter sequence is at least 85%, 90%, 95%, 98% or 99% identical to enhancer-promoter sequence represented by SEQ ID NO: 63. In some embodiments, a promoter is a human GFAP endogenous enhancer-promoter sequence comprised within SEQ ID NO: 63.

```
Exemplary Human GFAP enhancer-promoter
                                    (SEQ ID NO: 63)
CCCACCTCCCTCTCTGTGCTGGGACTCACAGAGGGAGACCTCAGGAGGC
AGTCTGTCCATCACATGTCCAAATGCAGAGCATACCCTGGGCTGGGCGC
AGTGGCGCACAACTGTAATTCCAGCACTTTGGGAGGCTGATGTGGAAGG
ATCACTTGAGCCCAGAAGTTCTAGACCAGCCTGGGCAACATGGCAAGAC
CCTATCTCTACAAAAAAAGTTAAAAAATCAGCCACGTGTGGTGACACAC
ACCTGTAGTCCCAGCTATTCAGGAGGCTGAGGTGAGGGGATCACTTAAG
GCTGGGAGGTTGAGGCTGCAGTGAGTCGTGGTTGCGCCACTGCACTCCA
GCCTGGGCAACAGTGAGACCCTGTCTCAAAAGACAAAAAAAAAAAAAAA
AAAAAAAGAACATATCCTGGTGTGGAGTAGGGGACGCTGCTCTGACAG
AGGCTCGGGGGCCTGAGCTGGCTCTGTGAGCTGGGGAGGAGGCAGACAG
CCAGGCCTTGTCTGCAAGCAGACCTGGCAGCATTGGGCTGGCCGCCCCC
CAGGGCCTCCTCTTCATGCCCAGTGAATGACTCACCTTGGCACAGACAC
AATGTTCGGGGTGGGCACAGTGCCTGCTTCCCGCCGCACCCCAGCCCCC
CTCAAATGCCTTCCGAGAAGCCCATTGAGCAGGGGGCTTGCATTGCACC
CCAGCCTGACAGCCTGGCATCTTGGGATAAAAGCAGCACAGCCCCCTAG
GGGCTGCCCTTGCTGTGTGGCGCCACCGGCGGTGGAGAACAAGGCTCTA
TTCAGCCTGTGCCCAGGAAAGGGGATCAGGGGATGCCCAGGCATGGACA
GTGGGTGGCAGGGGGGGAGAGGAGGGCTGTCTGCTTCCCAGAAGTCCAA
GGACACAAATGGGTGAGGGGACTGGGCAGGGTTCTGACCCTGTGGGACC
AGAGTGGAGGGCGTAGATGGACCTGAAGTCTCCAGGGACAACAGGGCCC
AGGTCTCAGGCTCCTAGTTGGGCCCAGTGGCTCCAGCGTTTCCAAACCC
ATCCATCCCCAGAGGTTCTTCCCATCTCTCCAGGCTGATGTGTGGGAAC
TCGAGGGAAATAAATCTCCAGTGGGAGACGGAGGGGTGGCCAGGGAAACG
GGGCGCTGCAGGAATAAAGACGAGCCAGCACAGCCAGCTCATGTGTAAC
GGCTTTGTGGAGCTGTCAAGGCCTGGTCTCTGGGAGAGAGGCACAGGGA
GGCCAGACAAGGAAGGGGTGACCTGGAGGGACAGATCCAGGGGCTAAAG
TCCTGATAAGGCAAGAGAGTGCCGGCCCCCTCTTGCCCTATCAGGACCT
CCACTGCCACATAGAGGCCATGATTGACCCTTAGACAAAGGGCTGGTGT
CCAATCCCAGCCCCCAGCCCCAGAACTCCAGGGAATGAATGGGCAGAGA
GCAGGAATGTGGGACATCTGTGTTCAAGGGAAGGACTCCAGGAGTCTGC
TGGGAATGAGGCCTAGTAGGAAATGAGGTGGCCCTTGAGGGTACAGAAC
AGGTTCATTCTTCGCCAAATTCCCAGCACCTTGCAGGCACTTACAGCTG
AGTGAGATAATGCCTGGGTTATGAAATCAAAAAGTTGGAAAGCAGGTCA
GAGGTCATCTGGTACAGCCCTTCCTTCCCTTTTTTTTTTTTTTTTTTGT
GAGACAAGGTCTCTCTCTGTTGCCCAGGCTGGAGTGGCGCAAACACAGC
TCACTGCAGCCTCAACCTACTGGGCTCAAGCAATCCTCCAGCCTCAGCC
TCCCAAAGTGCTGGGATTACAAGCATGAGCCACCCCACTCAGCCCTTTC
CTTCCTTTTTAATTGATGCATAATAATTGTAAGTATTCATCATGGTCCA
ACCAACCCTTTCTTGACCCACCTTCCTAGAGAGAGGGTCCTCTTGCTTC
AGCGGTCAGGGCCCCAGACCCATGGTCTGGCTCCAGGTACCACCTGCCT
CATGCAGGAGTTGGCGTGCCCAGGAAGCTCTGCCTCTGGGCACAGTGAC
CTCAGTGGGTGAGGGGAGCTCTCCCCATAGCTGGGCTGCGGCCCAACC
CCACCCCCTCAGGCTATGCCAGGGGGTGTTGCCAGGGGCACCCGGGCAT
CGCCAGTCTAGCCCACTCCTTCATAAAGCCCTCGCATCCCAGGAGCGAG
CAGAGCCAGAGCAGGTTGGAGAGGAGACGCATCACCTCCGCTGCTCGC
```

Enhancers

In some instances, a construct can include an enhancer sequence. The term "enhancer" refers to a nucleotide sequence that can increase the level of transcription of a nucleic acid encoding a protein of interest (e.g., an anti-VEGF protein). Enhancer sequences (generally 50-1500 bp in length) generally increase the level of transcription by providing additional binding sites for transcription-associated proteins (e.g., transcription factors). In some embodiments, an enhancer sequence is found within an intronic sequence. Unlike promoter sequences, enhancer sequences can act at much larger distance away from the transcription start site (e.g., as compared to a promoter). Non-limiting examples of enhancers include a RSV enhancer, a CMV enhancer, and/or a SV40 enhancer. In some embodiments, a construct comprises a CMV enhancer exemplified by SEQ ID NO: 64. In some embodiments, an enhancer sequence is at least 85%, 90%, 95%, 98% or 99% identical to the enhancer sequence represented by SEQ ID NO: 64. In some embodiments, an SV-40 derived enhancer is the SV-40 T intron sequence, which is exemplified by SEQ ID NO: 65. In some embodiments, a an enhancer sequence is at least 85%, 90%, 95%, 98% or 99% identical to the enhancer sequence represented by SEQ ID NO: 65.

```
Exemplary CMV enhancer
                                             (SEQ ID NO: 64)
GACATTGATTATTGACTAGTTATTAATAGTAATCAATTACGGGTCATT

AGTTCATAGCCCATATATGGAGTTCCGCGTTACATAACTTACGGTAAAT

GGCCCGCCTGGCTGACCGCCCAACGACCCCCGCCCATTGACGTCAATAA

TGACGTATGTTCCCATAGTAACGCCAATAGGGACTTTCCATTGACGTCA

ATGGGTGGACTATTTACGGTAAACTGCCCACTTGGCAGTACATCAAGTG

TATCATATGCCAAGTACGCCCCCTATTGACGTCAATGACGGTAAATGGC

CCGCCTGGCATTATGCCCAGTACATGACCTTATGGGACTTTCCTACTTG

GCAGTACATCTACGTATTAGTCATCGCTATTACCATGG

Exemplary SV-40 synthetic intron
                                             (SEQ ID NO: 65)
GGAGTCGCTGCGTTGCCTTCGCCCCGTGCCCCGCTCCGCGCCGCCTCGC

GCCGCCCGCCCCGGCTCTGACTGACCGCGTTACTCCCACAGGTGAGCGG

GCGGGACGGCCCTTCTCCTCCGGGCTGTAATTAGCGCTTGGTTTAATGA

CGGCTCGTTTCTTTTCTGTGGCTGCGTGAAAGCCTTAAAGGGCTCCGGG

AGGGCCCTTTGTGCGGGGGGGAGCGGCTCGGGGGGTGCGTGCGTGTGTG

TGTGCGTGGGGAGCGCCGCGTGCGGCCCGCGCTGCCCGGCGGCTGTGAG

CGCTGCGGGCGCGGCGCGGGGCTTTGTGCGCTCCGCGTGTGCGCGAGGG

GAGCGCGGCCGGGGCGGTGCCCCGCGGTGCGGGGGGCTGCGAGGGGA

ACAAAGGCTGCGTGCGGGGTGTGTGCGTGGGGGGTGAGCAGGGGGTGT

GGGCGCGGCGGTCGGGCTGTAACCCCCCCTGCACCCCCCTCCCCGAGT

TGCTGAGCACGGCCCGGCTTCGGGTGCGGGGCTCCGTGCGGGGCGTGGC

GCGGGGCTCGCCGTGCCGGGCGGGGGTGGCGGCAGGTGGGGGTGCCGG

GCGGGGCGGGCCGCCTCGGGCCGGGAGGGCTCGGGGGAGGGGCGCGG

CGGCCCCGGAGCGCCGGCGGCTGTCGAGGCGCGGCGAGCCGCAGCCAT

TGCCTTTTATGGTAATCGTGCGAGAGGGCGCAGGGACTTCCTTTGTCCC

AAATCTGTGCGGAGCCGAAATCTGGGAGGCGCCGCCGCACCCCCTCTAG

CGGGCGCGGGGCGAAGCGGTGCGGCGCCGGCAGGAAGGAAATGGGCGGG

GAGGGCCTTCGTGCGTCGCCGCGCCGCCGTCCCCTTCTCCCTCTCCAGC

CTCGGGGCTGTCCGCGGGGGACGGCTGCCTTCGGGGGGGACGGGGCAG
```

```
GGCGGGGTTCGGCTTCTGGCGTGTGACCGGCGGCTCTAGAGCCTCTGCT

AACCATGTTCATGCCTTCTTCTTTTTCCTACAG
```

Untranslated Regions: 5' UTRs and 3' UTRs

In some embodiments, any of the constructs described herein can include an untranslated region (UTR), such as a 5' UTR or a 3' UTR. UTRs of a gene are transcribed but not translated. A 5' UTR starts at the transcription start site and continues to the start codon but does not include the start codon. A 3' UTR starts immediately following the stop codon and continues until the transcriptional termination signal. The regulatory and/or control features of a UTR can be incorporated into any of the constructs, compositions, kits, or methods as described herein to enhance or otherwise modulate the expression of an anti-VEGF protein.

Natural 5' UTRs include a sequence that plays a role in translation initiation. In some embodiments, a 5' UTR can comprise sequences, like Kozak sequences, which are commonly known to be involved in the process by which the ribosome initiates translation of many genes. Kozak sequences have the consensus sequence CCR(A/G) CCAUGG, where R is a purine (A or G) three bases upstream of the start codon (AUG), and the start codon is followed by another "G". The 5' UTRs have also been known to form secondary structures that are involved in elongation factor binding.

In some embodiments, a 5' UTR is included in any of the constructs described herein. Non-limiting examples of 5' UTRs, including those from the following genes: albumin, serum amyloid A, Apolipoprotein A/B/E, transferrin, alpha fetoprotein, erythropoietin, and Factor VIII, can be used to enhance expression of a nucleic acid molecule, such as an mRNA.

In some embodiments, a 5' UTR from an mRNA that is transcribed by a cell in the cochlea can be included in any of the constructs, compositions, kits, and methods described herein. In some embodiments, a 5' UTR is derived from an endogenous gene loci and may include all or part of an endogenous sequence.

3' UTRs are found immediately 3' to the stop codon of the gene of interest. In some embodiments, a 3' UTR from an mRNA that is transcribed by a cell in the cochlea can be included in any of the constructs, compositions, kits, and methods described herein. In some embodiments, a 3' UTR is derived from an endogenous gene loci and may include all or part of an endogenous sequence.

3' UTRs are known to have stretches of adenosines and uridines (in the RNA form) or thymidines (in the DNA form) embedded in them. These AU-rich signatures are particularly prevalent in genes with high rates of turnover. Based on their sequence features and functional properties, the AU-rich elements (AREs) can be separated into three classes (Chen et al., Mal. Cell. Biol. 15:5777-5788, 1995; Chen et al., Mal. Cell Biol. 15:2010-2018, 1995, each of which is incorporated herein in its entirety by reference): Class I AREs contain several dispersed copies of an AUUUA motif within U-rich regions. For example, c-Myc and MyoD mRNAs contain class I AREs. Class II AREs possess two or more overlapping UUAUUUA(U/A) (U/A) nonamers. GM-CSF and TNF-alpha mRNAs are examples that contain class II AREs. Class III AREs are less well defined. These U-rich regions do not contain an AUUUA motif, two well-studied examples of this class are c-Jun and myogenin mRNAs.

Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in-vivo.

In some embodiments, the introduction, removal, or modification of 3' UTR AREs can be used to modulate the stability of an mRNA encoding an anti-VEGF protein. In other embodiments, AREs can be removed or mutated to increase the intracellular stability and thus increase translation and production of an anti-VEGF protein.

In other embodiments, non-ARE sequences may be incorporated into the 5' or 3' UTRs. In some embodiments, introns or portions of intron sequences may be incorporated into the flanking regions of the polynucleotides in any of the constructs, compositions, kits, and methods provided herein. Incorporation of intronic sequences may increase protein production as well as mRNA levels.

Internal Ribosome Entry Sites (IRES)

In some embodiments, a construct encoding an anti-VEGF protein can include an internal ribosome entry site (IRES). An IRES forms a complex secondary structure that allows translation initiation to occur from any position with an mRNA immediately downstream from where the IRES is located (see, e.g., Pelletier and Sonenberg, Mal. Cell. Biol. 8(3):1103-1112, 1988, incorporated herein in its entirety by reference).

There are several IRES sequences known to those in skilled in the art, including those from, e.g., foot and mouth disease virus (FMDV), encephalomyocarditis virus (EMCV), human rhinovirus (HRV), cricket paralysis virus, human immunodeficiency virus (HIV), hepatitis A virus (HAV), hepatitis C virus (HCV), and poliovirus (PV). See e.g., Alberts, Molecular Biology of the Cell, Garland Science, 2002; and Hellen et al., Genes Dev. 15(13):1593-612, 2001, each of which is incorporated in its entirety herein by reference.

In some embodiments, the IRES sequence that is incorporated into a construct that encodes an anti-VEGF protein, or a portion of an anti-VEGF protein is the foot and mouth disease virus (FMDV) 2A sequence. The Foot and Mouth Disease Virus 2A sequence is a small peptide (approximately 18 amino acids in length) that has been shown to mediate the cleavage of polyproteins (Ryan, M D et al., EMBO 4:928-933, 1994; Mattion et al., J Virology 70:8124-8127, 1996; Furler et al., Gene Therapy 8:864-873, 2001; and Halpin et al., Plant Journal 4:453-459, 1999, each of which is incorporated in its entirety herein by reference). The cleavage activity of the 2A sequence has previously been demonstrated in artificial systems including plasmids and gene therapy constructs (AAV and retroviruses) (Ryan et al., EMBO 4:928-933, 1994; Mattion et al., J Virology 70:8124-8127, 1996; Furler et al., Gene Therapy 8:864-873, 2001; and Halpin et al., Plant Journal 4:453-459, 1999; de Felipe et al., Gene Therapy 6:198-208, 1999; de Felipe et al., Human Gene Therapy I I: 1921-1931, 2000; and Klump et al., Gene Therapy 8:811-817, 2001, each of which is incorporated in its entirety herein by reference).

An IRES can be utilized in an rAAV construct. In some embodiments, a construct encoding a C-terminal portion of an anti-VEGF protein can include a polynucleotide internal ribosome entry site (IRES). In some embodiments, an IRES can be part of a composition comprising more than one construct. In some embodiments, an IRES is used to produce more than one polypeptide from a single gene transcript.

Secretion and Cleavage Signals

In some embodiments, any of the constructs provided herein can include secretion signals, cleavage sites, and/or linker sequences. In some embodiments, these sites are functional in a translated protein, and result in post-translational modifications and/or processing events. In some embodiments, constructs as described herein are translated into a relatively long precursor polypeptide, such a precursor polypeptide may then undergo post translational modifications and/or processing, which may involve endogenous cellular enzymatic. Such a processing step may produce multiple peptides, the biological function of such peptides may be accomplished either solely by one peptide, or by the function of multiple peptides acting in concert.

In some embodiments, constructs provided herein include a signal peptide. In some embodiments, a signal peptide may be a signal sequence, targeting signal, localization signal, localization sequence, transit peptide, leader sequence or leader peptide. In some embodiments, such a sequence is generally short (e.g., approximately 16-30 amino acids in length). In some embodiments, such a signal peptide is present at the N-terminus of a peptide of interest. In some embodiments, more than one signal peptide may exist in a translational product. In some embodiments, an exemplary signal peptide comprises a secretion signal from interleukin-2 (IL2SS). In some embodiments, an exemplary signal peptide is encoded by a nucleotide sequence represented by SEQ ID NO: 66 or 67. In some embodiments, such an amino acid sequence is represented by SEQ ID NO: 68, and can be 95%, 90%, 85%, 80%, or 75% identical to such a sequence. One skilled in the art will recognize that alternative secretion signal sequences exist, and may be incorporated into constructs as described herein.

In some embodiments, constructs provided herein include a linker peptide. In some embodiments, a linker peptide is utilized to join two or more functional peptides in a translational product. In some embodiments, such a linker peptide may include additional functional sequences, such as recognition sequences for endogenous peptidases. In some embodiments, such a linker sequence comprises a furin cleavage signal. In some embodiments, an exemplary linker sequence comprising a furin cleavage signal is encoded by a nucleotide sequence represented by SEQ ID NO: 71. In some embodiments, such a linker sequence comprises a furin cleavage signal and can be represented by SEQ ID NO: 72, or can be approximately 90%, 80%, 70%, or 60% similar to such a sequence. In some embodiments, a linker peptide sequence may be one amino acid in length, two amino acids in length, three amino acids in length, four amino acids in length, five amino acids in length, six amino acids in length, seven amino acids in length, eight amino acids in length, nine amino acids in length, ten amino acids in length, eleven amino acids in length, twelve amino acids in length, thirteen amino acids in length, fourteen amino acids in length, fifteen amino acids in length, sixteen amino acids in length, seventeen amino acids in length, eighteen amino acids in length, nineteen amino acids in length, or twenty amino acids in length. In some embodiments, a linker peptide sequence may be up to fifty amino acids in length. One skilled in the art will recognize that alternative linker sequences exist (functional or not), and may be incorporated into constructs as described herein.

In some embodiments, constructs provided herein include a peptide sequence that induces polypeptide cleavage and/or failure to form a peptide linkage during translation. In some embodiments, constructs as described herein may include a self-cleaving peptide, that in some embodiments may be a 2A self-cleaving peptide. In some embodiments, such a peptide is approximately 18 to 22 amino acids in length, e.g., 18 amino acids in length, 19 amino acids in length, 20 amino acids in length, 21 amino acids in length, or 22 amino acids in length. In some embodiments, such a peptide may induce ribosomal skipping during translation of a protein. In some embodiments, a 2A self-cleaving peptide is represented by a core sequence motif of DxExNPGP (SEQ ID NO: 115), and are found endogenously in a range of viral families. In some embodiments, a self-cleaving peptide generates polyproteins from a single transcript by causing the ribosome to fail at making a peptide bond. In some embodiments, a self-cleaving and/or cleavage signal is encoded by a nucleotide sequence represented by SEQ ID NO: 69. In some embodiments, a self-cleaving and/or cleavage signal is represented by SEQ ID NO: 70, or a sequence sharing approximately 95%, 90%, 80%, 75%, 70%, 65%, 60%, 55%, or 50% identity. One skilled in the art will recognize that alternative peptide cleavage sequences exist (self-cleaving or requiring the aid of endogenous cellular machinery), and may be incorporated into constructs as described herein.

```
Exemplary Signal Secretion nucleotide sequence
                                        (SEQ ID NO: 66)
ATGTACCGGATGCAGCTGCTGAGCTGTATCGCCCTGTCTCTGGCCCTGG
TCACCAATTCT Exemplary Signal Secretion nucleotide sequence
                                        (SEQ ID NO: 67)
ATGTATAGAATGCAGCTCCTGTCCTGCATTGCCCTGAGCCTGGCTCTCG
TGACCAACAGC Exemplary Signal Secretion amino acid sequence
                                        (SEQ ID NO: 68)
MYRMQLLSCIALSLALVTNS Exemplary Cleavage signal nucleotide sequence
                                        (SEQ ID NO: 69)
GGCTCTGGCGAAGGCAGAGGCAGCCTGCTTACATGTGGCGACGTGGAAG
AGAACCCCGGACCT Exemplary Cleavage signal amino acid sequence
                                        (SEQ ID NO: 70)
GSGEGRGSLLTCGDVEENPGP Exemplary Linker/Cleavage signal nucleotide
sequence
                                        (SEQ ID NO: 71)
GACAAGACCCACACCGGCAAGCGGAAGAGAAGA Exemplary Linker/Cleavage signal amino acid
sequence
                                        (SEQ ID NO: 72)
DKTHTGKRKRR
```

Splice Sites

In some embodiments, any of the constructs provided herein can include splice donor and/or splice acceptor sequences, which are functional during RNA processing occurring during transcription. In some embodiments, splice sites are involved in trans-splicing.

```
Exemplary splice donor intron
                                        (SEQ ID NO: 73)
GTAAGTATCAAGGTTACAAGACAGGTTTAAGGAGACCAATAGAAACTGG
GCTTGTCGAGACAGAGAAGACTCTTGCGTTTCT Exemplary splice acceptor intron
                                        (SEQ ID NO: 74)
GATAGGCACCTATTGGTCTTACTGACATCCACTTTGCCTTTCTCTCCAC
AG
```

Polyadenylation Sequences

In some embodiments, a construct provided herein can include a polyadenylation (poly(A)) signal sequence. Most nascent eukaryotic mRNAs possess a poly(A) tail at their 3' end, which is added during a complex process that comprises cleavage of the primary transcript and a coupled polyadenylation reaction driven by the poly(A) signal sequence (see, e.g., Proudfoot et al., Cell 108:501-512, 2002, which is incorporated herein in its entirety by reference). A poly(A) tail confers mRNA stability and transferability (Molecular Biology of the Cell, Third Edition by B. Alberts et al., Garland Publishing, 1994, which is incorporated herein in its entirety by reference). In some embodiments, a poly(A) signal sequence is positioned 3' to the coding sequence.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. A 3' poly(A) tail is a long sequence of adenine nucleotides (e.g., 50, 60, 70, 100, 200, 500, 1000, 2000, 3000, 4000, or 5000)(SEQ ID NO: 117) added to the pre-mRNA through the action of an enzyme, polyadenylate polymerase. In some embodiments, a poly(A) tail is added onto transcripts that contain a specific sequence, e.g., a poly(A) signal. A poly(A) tail and associated proteins aid in protecting mRNA from degradation by exonucleases. Polyadenylation also plays a role in transcription termination, export of the mRNA from the nucleus, and translation. Polyadenylation typically occurs in the nucleus immediately after transcription of DNA into RNA, but also can occur later in the cytoplasm. After transcription has been terminated, an mRNA chain is cleaved through the action of an endonuclease complex associated with RNA polymerase. A cleavage site is usually characterized by the presence of the base sequence AAUAAA near the cleavage site. After the mRNA has been cleaved, adenosine residues are added to the free 3' end at the cleavage site.

As used herein, a "poly(A) signal sequence" or "polyadenylation signal sequence" is a sequence that triggers the endonuclease cleavage of an mRNA and the addition of a series of adenosines to the 3' end of the cleaved mRNA.

There are several poly(A) signal sequences that can be used, including those derived from bovine growth hormone (bGH) (Woychik et al., Proc. Natl. Acad Sci. U.S.A. 81(13): 3944-3948, 1984; U.S. Pat. No. 5,122,458, each of which is incorporated herein in its entirety by reference), mouse-β-globin, mouse-α-globin (Orkin et al., EMBO J 4(2):453-456, 1985; Thein et al., Blood 71(2):313-319, 1988, each of which is incorporated herein in its entirety by reference), human collagen, polyoma virus (Batt et al., Mal. Cell Biol. 15(9):4783-4790, 1995, which is incorporated herein in its entirety by reference), the Herpes simplex virus thymidine kinase gene (HSV TK), IgG heavy-chain gene polyadenylation signal (US 2006/0040354, which is incorporated herein in its entirety by reference), human growth hormone (hGH) (Szymanski et al., Mal. Therapy 15(7):1340-1347, 2007, which is incorporated herein in its entirety by reference), the group consisting of SV40 poly(A) site, such as the SV40 late and early poly(A) site (Schek et al., Mal. Cell Biol. 12(12):5386-5393, 1992, which is incorporated herein in its entirety by reference).

The poly(A) signal sequence can be AATAAA. The AATAAA sequence may be substituted with other hexanucleotide sequences with homology to AATAAA and that are capable of signaling polyadenylation, including ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, or AATAAG (see, e.g., WO 06/12414, which is incorporated herein in its entirety by reference).

In some embodiments, a poly(A) signal sequence can be a synthetic polyadenylation site (see, e.g., the pCI-neo expression construct of Promega that is based on Levitt el al, Genes Dev. 3(7):1019-1025, 1989, which is incorporated herein in its entirety by reference). In some embodiments, a poly(A) signal sequence is the polyadenylation signal of soluble neuropilin-1 (sNRP) (AAATAAAATACGAAATG) (SEQ ID NO: 116) (see, e.g., WO 05/073384, which is incorporated herein in its entirety by reference). In some embodiments, a poly(A) signal sequence comprises or consists of the SV40 poly(A) site. In some embodiments, a poly(A) signal comprises or consists of SEQ ID NO: 76. In some embodiments, a poly(A) signal sequence comprises or consists of bGHpA. In some embodiments, a poly(A) signal comprises or consists of SEQ ID NO: 75. Additional examples of poly(A) signal sequences are known in the art. In some embodiments, a poly(A) sequence is at least 85%, 90%, 95%, 98% or 99% identical to the poly(A) sequence represented by SEQ ID NOs: 75 or 76.

```
Exemplary bGH poly(A) signal sequence
                                        (SEQ ID NO: 75)
CTGTGCCTTCTAGTTGCCAGCCATCTGTTGTTTGCCCCTCCCCCGTGCC

TTCCTTGACCCTGGAAGGTGCCACTCCCACTGTCCTTTCCTAATAAAAT

GAGGAAATTGCATCGCATTGTCTGAGTAGGTGTCATTCTATTCTGGGGG

GTGGGGTGGGGCAGGACAGCAAGGGGGAGGATTGGGAAGACAATAGCAG

GCATGCTGGGGATGCGGTGGGCTCTATGG

Exemplary SV40 poly(A) signal sequence
                                        (SEQ ID NO: 76)
AACTTGTTTATTGCAGCTTATAATGGTTACAAATAAAGCAATAGCATCA

CAAATTTCACAAATAAAGCATTTTTTTCACTGCATTCTAGTTGTGGTTT

GTCCAAACTCATCAATGTATCTTA
```

Additional Sequences

In some embodiments, constructs of the present disclosure may comprise one or more cloning sites. In some such embodiments, cloning sites may not be fully removed prior to manufacturing for administration to a subject. In some embodiments, cloning sites may have functional roles including as linker sequences, as nucleotide and/or peptide cleavage signals, and/or as portions of a Kozak site. As will be appreciated by those skilled in the art, cloning sites may vary significantly in primary sequence while retaining their desired function. In some embodiments, constructs may contain any combination of cloning sites, exemplary cloning sites are represented by SEQ ID NO: 77-82.

```
Exemplary cloning site A
                                        (SEQ ID NO: 77)
TTGTCGACGCGGCCGCACGCGT Exemplary cloning site B
                                        (SEQ ID NO: 78)
CTCCTGGGCAACGTGCTGGTTATTGTGACCGGTGCCACC Exemplary cloning site C
                                        (SEQ ID NO: 79)
TAAGAGCTCGCTGATCAGCCTCGA Exemplary cloning site D
                                        (SEQ ID NO: 80)
AAGCTTGAATTCAGCTGACGTGCCTCGGACCGCCTAGG Exemplary cloning site E
                                        (SEQ ID NO: 81)
GCGGCCGCACGCGT Exemplary cloning site F
                                        (SEQ ID NO: 82)
AAGCTTGAATTCAGCTGACGTGCCTCGGACCGCT
```

Destabilization Domains

In some embodiments, any of the constructs provided herein can optionally include a sequence encoding a destabilizing domain ("a destabilizing sequence") for temporal control of protein expression. Non-limiting examples of destabilizing sequences include sequences encoding a FK506 sequence, a dihydrofolate reductase (DHFR) sequence, or other exemplary destabilizing sequences.

In the absence of a stabilizing ligand, a protein sequence operatively linked to a destabilizing sequence is degraded by ubiquitination. In contrast, in the presence of a stabilizing ligand, protein degradation is inhibited, thereby allowing the protein sequence operatively linked to the destabilizing sequence to be actively expressed. As a positive control for stabilization of protein expression, protein expression can be detected by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry).

Additional examples of destabilizing sequences are known in the art. In some embodiments, the destabilizing sequence is a FK506- and rapamycin-binding protein (FKBP12) sequence, and the stabilizing ligand is Shield-1 (Shld1) (Banaszynski et al. (2012) Cell 126(5): 995-1004, which is incorporated in its entirety herein by reference). In some embodiments, a destabilizing sequence is a DHFR sequence, and a stabilizing ligand is trimethoprim (TMP) (Iwamoto et al. (2010) Chem Biol 17:981-988, which is incorporated in its entirety herein by reference).

In some embodiments, a destabilizing sequence is a FKBP12 sequence, and a presence of an rAAV construct carrying the FKBP12 gene in a subject cell (e.g., a supporting cochlear outer hair cell) is detected by western blotting. In some embodiments, a destabilizing sequence can be used to verify the temporally-specific activity of any of the rAAV constructs described herein.

```
Exemplary DHFR destabilizing amino acid sequence
                                        (SEQ ID NO: 83)
MISLIAALAVDYVIGMENAMPWNLPADLAWFKRNTLNKPVIMGRHTWES

IGRPLPGRKNIILSSQPSTDDRVTWVKSVDEAIAACGDVPEIMVIGGGR

VIEQFLPKAQKLYLTHIDAEVEGDTHFPDYEPDDWESVFSEFHDADAQN

SHSYCFEILERR

Exemplary DHFR destabilizing nucleotide sequence
                                        (SEQ ID NO: 84)
GGTACCATCAGTCTGATTGCGGCGTTAGCGGTAGATTACGTTATCGGCA

TGGAAAACGCCATGCCGTGGAACCTGCCTGCCGATCTCGCCTGGTTTAA

ACGCAACACCTTAAATAAACCCGTGATTATGGGCCGCCATACCTGGGAA

TCAATCGGTCGTCCGTTGCCAGGACGCAAAAATATTATCCTCAGCAGTC

AACCGAGTACGGACGATCGCGTAACGTGGGTGAAGTCGGTGGATGAAGC
```

```
                            -continued
CATCGCGGCGTGTGGTGACGTACCAGAAATCATGGTGATTGGCGGCGGT

CGCGTTATTGAACAGTTCTTGCCAAAAGCGCAAAAACTGTATCTGACGC

ATATCGACGCAGAAGTGGAAGGCGACACCCATTTCCCGGATTACGAGCC

GGATGACTGGGAATCGGTATTCAGCGAATTCCACGATGCTGATGCGCAG

AACTCTCACAGCTATTGCTTTGAGATTCTGGAGCGGCGATAA

Exemplary destabilizing domain
                                        (SEQ ID NO: 85)
ATCAGTCTGATTGCGGCGTTAGCGGTAGATTACGTTATCGGCATGGAAA

ACGCCATGCCGTGGAACCTGCCTGCCGATCTCGCCTGGTTTAAACGCAA

CACCTTAAATAAACCCGTGATTATGGGCCGCCATACCTGGGAATCAATC

GGTCGTCCGTTGCCAGGACGCAAAAATATTATCCTCAGCAGTCAACCGA

GTACGGACGATCGCGTAACGTGGGTGAAGTCGGTGGATGAAGCCATCGC

GGCGTGTGGTGACGTACCAGAAATCATGGTGATTGGCGGCGGTCGCGTT

ATTGAACAGTTCTTGCCAAAAGCGCAAAAACTGTATCTGACGCATATCG

ACGCAGAAGTGGAAGGCGACACCCATTTCCCGGATTACGAGCCGGATGA

CTGGGAATCGGTATTCAGCGAATTCCACGATGCTGATGCGCAGAACTCT

CACAGCTATTGCTTTGAGATTCTGGAGCGGCGA

Exemplary FKBP12 destabilizing peptide amino acid
sequence
                                        (SEQ ID NO: 86)
MGVEKQVIRPGNGPKPAPGQTVTVHCTGFGKDGDLSQKFWSTKDEGQKP

FSFQIGKGAVIKGWDEGVIGMQIGEVARLRCSSDYAYGAGGFPAWGIQP

NSVLDFEIEVLSVQ
```

Reporter Sequences or Elements

In some embodiments, constructs provided herein can optionally include a sequence encoding a reporter polypeptide and/or protein ("a reporter sequence"). Non-limiting examples of reporter sequences include DNA sequences encoding: a beta-lactamase, a beta-galactosidase (LacZ), an alkaline phosphatase, a thymidine kinase, a green fluorescent protein (GFP), a red fluorescent protein, an mCherry fluorescent protein, a yellow fluorescent protein, a chloramphenicol acetyltransferase (CAT), and a luciferase. Additional examples of reporter sequences are known in the art. When associated with control elements which drive their expression, the reporter sequence can provide signals detectable by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry).

In some embodiments, a reporter sequence is the LacZ gene, and the presence of a construct carrying the LacZ gene in a mammalian cell (e.g., a cochlear hair cell) is detected by assays for beta-galactosidase activity. When the reporter is a fluorescent protein (e.g., green fluorescent protein) or luciferase, the presence of a construct carrying the fluorescent protein or luciferase in a mammalian cell (e.g., a cochlear hair cell) may be measured by fluorescent techniques (e.g., fluorescent microscopy or FACS) or light production in a luminometer (e.g., a spectrophotometer or an IVIS imaging instrument). In some embodiments, a reporter sequence can be used to verify the tissue-specific targeting capabilities and tissue-specific promoter regulatory and/or control activity of any of the constructs described herein.

In some embodiments, a reporter sequence is a FLAG tag (e.g., a 3×FLAG tag), and the presence of a construct carrying the FLAG tag in a mammalian cell (e.g., an inner ear cell, e.g., a cochlear hair or supporting cell) is detected by protein binding or detection assays (e.g., Western blots, immunohistochemistry, radioimmunoassay (RIA), mass spectrometry). An exemplary 3×FLAG tag sequence is provided as SEQ ID NO: 87.

In some embodiments, a reporter sequence is an Enhanced Green Fluorescent Protein (eGFP) tag (e.g., an eGFP tag), and the presence of a construct carrying an eGFP tag in a mammalian cell (e.g., an inner ear cell, e.g., a cochlear hair or supporting cell) is detected by fluorescence, protein binding, or detection assays (e.g., Western blots, immunohistochemistry, radioimmunoassay (RIA), mass spectrometry). Exemplary eGFP tag sequences are provided as SEQ ID NO: 104 and 105.

```
Exemplary 3xFLAG tag sequence
                                        (SEQ ID NO: 87)
GGATCCCGGGCTGACTACAAAGACCATGACGGTGATTATAAAGATCATG

ACATCGACTACAAGGATGACGATGACAAG

Exemplary Enhanced Green Fluorescent Protein
(eGFP) nucleotide sequence
                                        (SEQ ID NO: 104)
MVSKGEELFTGVVPILVELDGDVNGHKFSVSGEGEGDATYGKLTLKFIC

TTGKLPVPWPTLVTTLTYGVQCFSRYPDHMKQHDFFKSAMPEGYVQERT

IFFKDDGNYKTRAEVKFEGDTLVNRIELKGIDFKEDGNILGHKLEYNYN

SHNVYIMADKQKNGIKVNFKIRHNIEDGSVQLADHYQQNTPIGDGPVLL

PDNHYLSTQSALSKDPNEKRDHMVLLEFVTAAGITLGMDELYK

Exemplary Enhanced Green Fluorescent Protein
(eGFP) Amino Acid sequence
                                        (SEQ ID NO: 105)
ATGGTGAGCAAGGGCGAGGAGCTGTTCACCGGGGTGGTGCCCATCCTGG

TCGAGCTGGACGGCGACGTAAACGGCCACAAGTTCAGCGTGTCCGGCGA

GGGCGAGGGCGATGCCACCTACGGCAAGCTGACCCTGAAGTTCATCTGC

ACCACCGGCAAGCTGCCCGTGCCCTGGCCCACCCTCGTGACCACCCTGA

CCTACGGCGTGCAGTGCTTCAGCCGCTACCCCGACCACATGAAGCAGCA

CGACTTCTTCAAGTCCGCCATGCCCGAAGGCTACGTCCAGGAGCGCACC

ATCTTCTTCAAGGACGACGGCAACTACAAGACCCGCGCCGAGGTGAAGT

TCGAGGGCGACACCCTGGTGAACCGCATCGAGCTGAAGGGCATCGACTT

CAAGGAGGACGGCAACATCCTGGGGCACAAGCTGGAGTACAACTACAAC

AGCCACAACGTCTATATCATGGCCGACAAGCAGAAGAACGGCATCAAGG

TGAACTTCAAGATCCGCCACAACATCGAGGACGGCAGCGTGCAGCTCGC

CGACCACTACCAGCAGAACACCCCCATCGGCGACGGCCCCGTGCTGCTG

CCCGACAACCACTACCTGAGCACCCAGTCCGCCCTGAGCAAAGACCCCA

ACGAGAAGCGCGATCACATGGTCCTGCTGGAGTTCGTGACCGCCGCCGG

GATCACTCTCGGCATGGACGAGCTGTACAAG
```

AAV Capsids

The present disclosure provides one or more polynucleotide constructs packaged into an AAV capsid. In some embodiments, an AAV capsid is from or derived from an AAV capsid of an AAV2, 3, 4, 5, 6, 7, 8, 9, 10, rh8, rh10, rh39, rh43 or Anc80 serotype, or one or more hybrids thereof. In some embodiments, an AAV capsid is from an AAV ancestral serotype. In some embodiments, an AAV capsid is an ancestral (Anc) AAV capsid. An Anc capsid is created from a construct sequence that is constructed using evolutionary probabilities and evolutionary modeling to determine a probable ancestral sequence. Thus, an Anc capsid/construct sequence is not known to have existed in nature. For example, in some embodiments, an AAV capsid is an Anc80 capsid (e.g., an Anc80L65 capsid). In some embodiments, an AAV capsid is created using a template nucleotide coding sequence comprising SEQ ID NO: 88. In some embodiments, the capsid comprises a polypeptide represented by SEQ ID NO: 89. In some embodiments, the capsid comprises a polypeptide with at least 85%, 90%, 95%, 98% or 99% sequence identity to the polypeptide represented by SEQ ID NO: 89. In some embodiments, the capsid comprises a polypeptide represented by SEQ ID NO: 113. In some embodiments, the capsid comprises a polypeptide with at least 85%, 90%, 95%, 98% or 99% sequence identity to the polypeptide represented by SEQ ID NO: 113. In some embodiments, the capsid comprises a polypeptide represented by SEQ ID NO: 114. In some embodiments, the capsid comprises a polypeptide with at least 85%, 90%, 95%, 98% or 99% sequence identity to the polypeptide represented by SEQ ID NO: 114.

As provided herein, any combination of AAV capsids and rAAV constructs (e.g., comprising AAV ITRs) may be used in recombinant AAV (rAAV) particles of the present disclosure. For example, wild type or variant AAV2 ITRs and Anc80 capsid, wild type or variant AAV2 ITRs and AAV6 capsid, etc. In some embodiments of the present disclosure, an AAV particle is comprised of AAV2 components (e.g., capsid and ITRs are AAV2 serotype). In some embodiments, an AAV particle is an AAV2/6, AAV2/8 or AAV2/9 particle (e.g., an AAV6, AAV8 or AAV9 capsid with an AAV construct having AAV2 ITRs). In some embodiments of the present disclosure, an AAV particle is an AAV2/Anc80 particle that comprises an Anc80 capsid (e.g., comprising a polypeptide of SEQ ID NO: 89, SEQ ID NO: 113 or SEQ ID NO: 114) that encapsidates an AAV construct with AAV2 ITRs (e.g., SEQ ID NOs: 45 and 46, or 47 and 48) flanking a portion of a coding sequence, for example, a sequence encoding an anti-VEGF protein (e.g., SEQ ID NO: 13, 14, 15, 19, 22, 42, and/or 103). Other AAV particles are known in the art and are described in, e.g., Sharma et al., Brain Res Bull. 2010 Feb. 15; 81(2-3): 273, which is incorporated herein in its entirety by reference. In some embodiments, a capsid sequence is at least 85%, 90%, 95%, 98% or 99% identical to a capsid nucleotide or amino acid sequence represented by SEQ ID NO: 88 or 89, respectively.

In some embodiments, a platform delivery approach disclosed herein combines a library of synthetic AAV capsids, known as ancestral AAV (AAVAnc) capsids that recreate the evolutionary lineage of current naturally occurring viruses. In some embodiments, these AAV capsids are coupled with a novel, minimally invasive administration procedure to deliver product candidates directly to the cochlea. In some embodiment, a delivery approach utilizes an AAVAnc80 capsid variant from this library (also known as Anc80L65). In some embodiments, such a capsid is utilized to create an rAAV particle, wherein such a particle is created through the addition of a construct as described herein, e.g., a construct comprising an anti-VEGF protein as described herein, to create an rAAVAnc80-antiVEGF. In some embodiments, such a particle can deliver cDNA for an inhibitor of VEGF, a protein that can cause abnormal blood vessel growth. In some embodiments, such a treatment is for an otological disorder characterized by neovascularization, e.g., for the treatment of VS, a tumor of the vestibulocochlear nerve, also referred to as the cranial nerve VIII.

Figure 9:
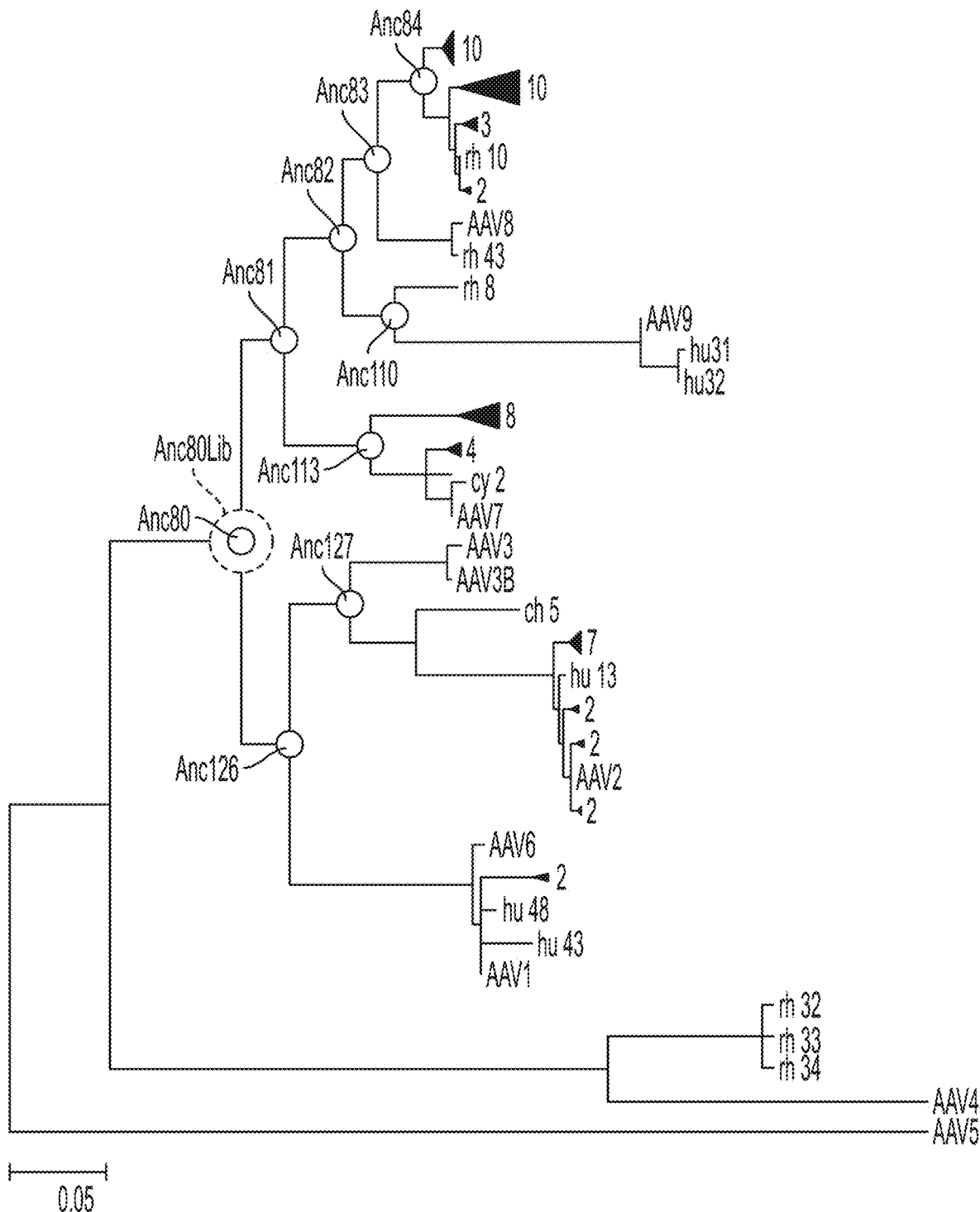
FIG. 9 is a graphical representation of the phylogeny and ancestral sequence reconstruction of the AAV evolutionary lineage. The dendrogram models the evolutionary path of AAVs with early specification of AAV4 and 5 serotypes, parallel to a single node named Anc80. Open circles with solid lines represent evolutionary intermediates reconstructed through ancestral sequence reconstruction. The open circle with a dotted line represents library of probabilistic sequence space around AAVAnc80 variant. Subclades are collapsed for clarity (Zinn 2015, incorporated herein in its entirety by reference).
Figure 10:
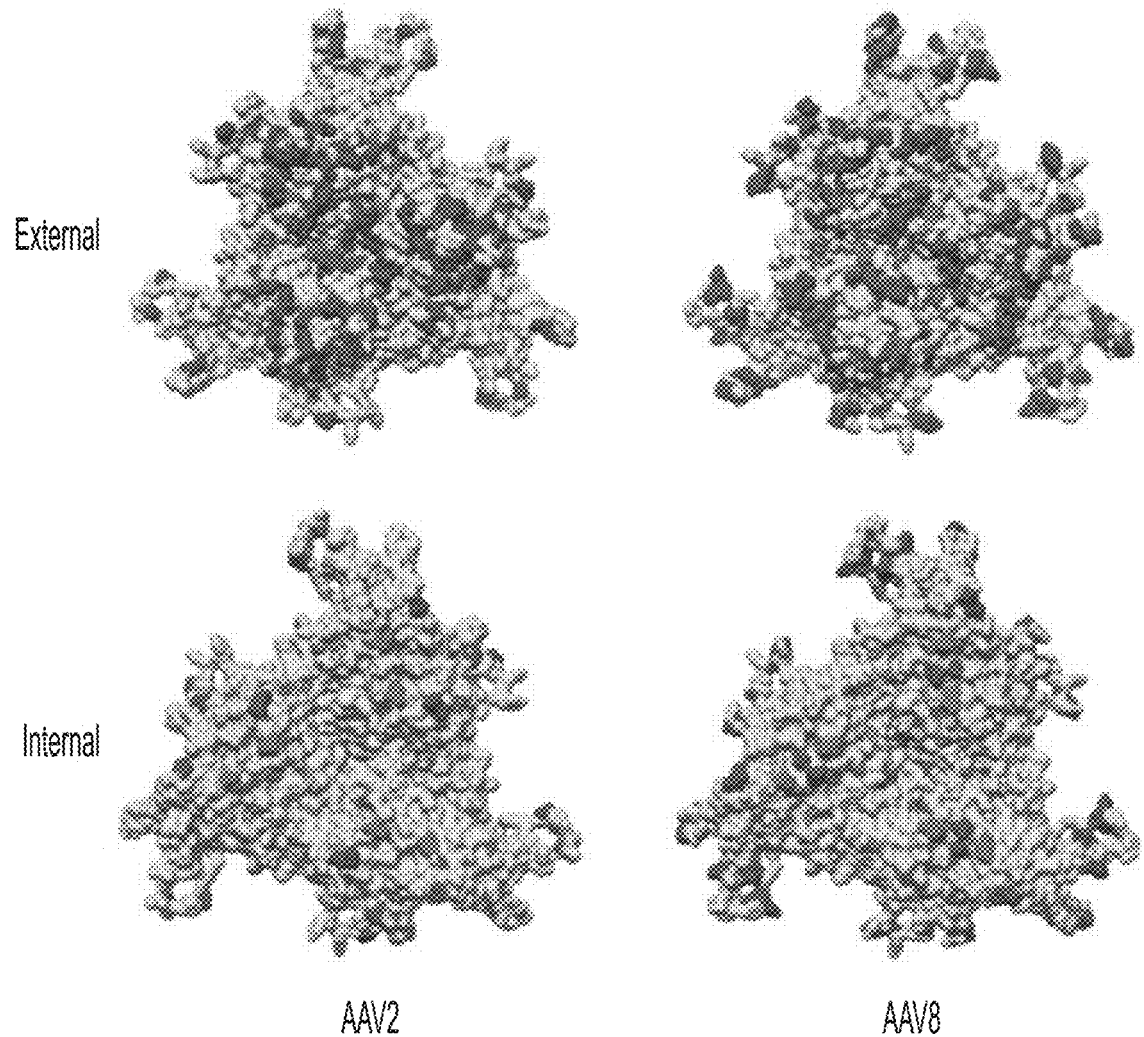
FIG. 10 is a schematic representation of a structural modeling of an AAVAnc80 capsid surface. Structural mapping of amino acid changes as compared to AAV2 (left) and AAV8 (right) on VP1 trimer visualizing the external (top) and internal (bottom) of the virion. There are some divergent residues in AAVAnc80, and some ambiguous and therefore dimorphic residues in Anc80Lib (Zinn 2015, incorporated herein in its entirety by reference).

In some embodiments, a composition disclosed herein comprises an AAVAnc80 capsid, which is a rationally designed, synthetic AAV capsid whose sequence was inferred by ancestral sequence reconstruction. Ancestral sequence reconstruction uses available sequence information from naturally occurring adeno-associated viruses and, as a result of phylogenetic and statistical prediction, identifies the ancestral state of a sequence at various intermediary evolutionary nodes (FIG. 9). During the creation of AAVAnc80, nine nodes were reconstructed, and in silico derived sequences across the AAV lineage were synthesized de novo and characterized. This led to the identification of the Anc80 Library node (Anc80Lib), the putative ancestor of the widely studied AAV serotypes 1, 2, 8, and 9. Anc80Lib protein sequences were subsequently reverse-translated and generated by gene synthesis, and individual clones were evaluated in isolation for packaging, infectivity, and biological properties. In some embodiments, and based on these results, AAVAnc80, the 65th Anc80Lib clone (Anc80L65), was selected for further characterization. An AAVAnc80 capsid variant has a distinctive composition; although the sequences of AAV8 and AAV2 differ by only approximately 9% and 12%, respectively, from AAVAnc80, structural modeling of AAVAnc80 has shown that around 20% of its particle external surface is divergent from known circulating AAVs (FIG. 9 and FIG. 10) in a manner that is distributed across the capsid surface (Zinn 2015, incorporated herein in its entirety by reference).

In some embodiments, AAVAnc80's performance as a gene therapy particle in-vivo has been characterized and rAAV particles comprising AAVAnc80 have demonstrated a potential to act as a broadly applicable gene therapy particle. In some embodiments, studies conducted in mice and non-human primates (NHPs) have shown that AAVAnc80 has a similar transduction efficiency to AAV8 when targeting the liver after intravenous injection, without obvious signs of systemic toxicity (Zinn 2015; Murillo 2019, each of which is incorporated herein in its entirety by reference). In addition, in some embodiments, AAVAnc80 has shown tropism for and efficient transduction of the mouse anterior segment of the eye (Wang 2017, incorporated herein in its entirety by reference), mouse and NHP retina (Zinn 2015; Carvalho 2018, each of which is incorporated herein in its entirety by reference), mouse skeletal muscle (Zinn 2015, incorporated herein in its entirety by reference), mouse central nervous system (CNS) by systemic and intraparenchymal delivery (Hudry 2018, incorporated herein in its entirety by reference), and murine kidney (Ikeda 2018, incorporated herein in its entirety by reference).

In some embodiments, compositions as described herein (e.g., comprising rAAV-antiVEGF) comprise an AAVAnc80 capsid. In some embodiments, AAVAnc80 capsid demonstrates high transduction efficiency for cochlear and vestibular cells. AAVAnc80 is a rationally designed AAV capsid whose sequence was inferred by ancestral sequence reconstruction (Zinn 2015, incorporated herein in its entirety by reference). Ancestral sequence reconstruction uses available sequence information from naturally occurring AAVs and, as a result of phylogenetic and statistical prediction, identifies the ancestral state of a sequence at various intermediary evolutionary nodes. As described in the literature, de novo synthesis and characterization of in silico derived sequences across the AAV lineage led to identification of the Anc80 Library (Anc80Lib) node, the putative ancestor of the widely studied AAV serotypes 1, 2, 8, and 9. Subsequent evaluation of Anc80Lib sequences led to the further characterization of AAVAnc80, the 65th Anc80Lib clone (Anc80L65). These studies indicated that the AAVAnc80 capsid variant has a distinctive composition with a divergent external surface particle distribution which yields a stable and functional AAV variant with a similar transduction efficiency to AAV8 (Zinn 2015, incorporated herein in its entirety by reference). The first reported use of AAVAnc80 in the mammalian inner ear revealed a high transduction efficiency in cochlear and vestibular hair cells (Landegger 2017, incorporated herein in its entirety by reference). Multiple subsequent, independent investigations have confirmed the increased cochlear and vestibular cell transduction efficiency of AAVAnc80 relative to other AAV serotypes; in mice of various ages (Landegger 2017; Tao 2018; Yoshimura 2018; Omichi 2020, each of which is incorporated herein in its entirety by reference) and in non-human primates (Andres-Mateos 2019, incorporated herein in its entirety by reference), AAVAnc80 has a higher transduction efficiency and broader tropism compared to a number of other AAV capsids.

Gene therapy using AAV particles is a promising therapeutic modality for inner ear disorders for several reasons, such as: (1) the inner ear, which contains the auditory and vestibular sensory epithelia, has modified immune surveillance, similar to that in the central nervous system (Fujioka 2014, incorporated herein in its entirety by reference); (2) the sensory and supporting cells of the cochlear organ of Corti are post-mitotic, allowing for the possibility of long-term expression following a single administration of AAV; and (3) the aggregate clinical experience with rAAV delivery in both adults and children, via multiple routes of administration, suggests a strong safety profile for AAV as a delivery vehicle, particularly in localized delivery and/or at low to moderate doses.

Beginning with initial clinical trials more than two decades ago, rAAV particles have been administered to hundreds of participants in dozens of clinical trials at doses of up to approximately 1E15 vg or more for systemic administration (Flotte 1996; Flotte 2013; Parente 2018; Wang 2019, each of which is incorporated herein in its entirety by reference). The number of trials in which AAV particles have been used for in-vivo gene transfer has steadily increased. The safety profile, together with the high efficiency of transduction of a broad range of target tissues, has established rAAV particles as the platform of choice for in-vivo gene therapy (Wang 2019, incorporated herein in its entirety by reference). Successful application of the rAAV technology has been achieved in the clinic for a variety of conditions, including coagulation disorders, inherited blindness, and neurodegenerative diseases (Colella 2018; Wang 2019, each of which is incorporated herein in its entirety by reference).

An rAAV particle product (alipogene tiparvovec; Glybera®) was first approved by the European Medicines Agency (EMA) for treatment of lipoprotein lipase deficiency in 2012. Subsequently, two rAAV products, voretigene neparvovec-rzyl (Luxturna®) for the treatment of confirmed biallelic RPE65 mutation-associated retinal dystrophy and onasemnogene abeparvovec-xioi (Zolgensma®) for the treatment of spinal muscular atrophy (SMA) with biallelic mutations in the SMN1 gene, were approved by the U.S. Food and Drug Administration (FDA) in 2017 and 2019, respectively; voretigene neparvovec-rzyl (Luxturna®) was also approved by the EMA for the treatment of loss of vision due to inherited retinal dystrophy, when the disease is caused by mutations in the gene RPE65.

In some embodiments, drugs and biologics, including rAAV particles, can reach many target cells in the inner ear by delivering them into the perilymph. Perilymph is a fluid very similar in composition to (Lysaght 2011, incorporated herein in its entirety by reference), and in diffusional continuity with, cerebrospinal fluid (CSF). Perilymph bathes most of the sensory, neural, and supporting cells of the cochlea and of the vestibular system, housed in the bony labyrinth of the inner ear (FIGS. 1 and 3). In some embodiments, perilymphatic space of cochlea, to which a composition disclosed herein, e.g., rAAV-antiVEGF, is delivered, comprises two scalae, or passages: scala tympani and scala vestibuli, which are continuous with one another at the apex of the cochlear spiral via the helicotrema. Many cells of the inner ear are in fluid continuity with perilymph through interstitial spaces in the tissue.

Figures 4A, 4B:
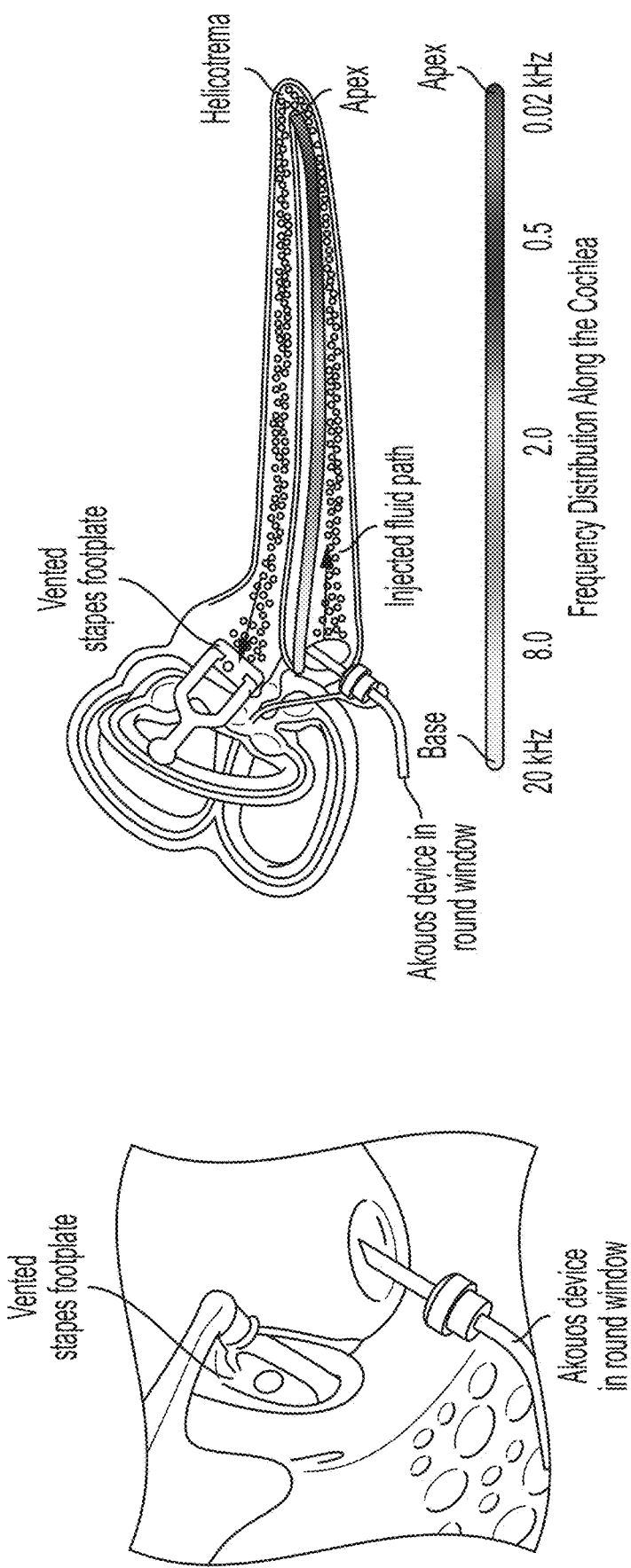
FIGS. 4A-4B is a schematic representation of an administration method as described herein.

In some embodiments, also disclosed herein is a sterile, one-time use delivery device for intracochlear administration, to deliver a composition disclosed herein, e.g., rAAV-antiVEGF to perilymph fluid of inner ear through a round window membrane with a vent located in a stapes footplate. In some embodiments, in this intracochlear administration approach, a composition disclosed herein, e.g., rAAV-antiVEGF, will be administered into the scala tympani through the round window membrane, with a vent in a stapes footplate within the oval window, such that composition is perfused through scala tympani, then through scala vestibuli via connection at the helicotrema, and follows the fluid path to a vent in a stapes footplate (FIG. 4). In some embodiments, presence of a vent distinct from the injection port allows for more even distribution of drug along the length of the cochlea and prevents the deleterious build-up of additional fluid pressure within the inner ear. In some embodiments, as evidenced by transduction of vestibular cells using this dual-fenestrae, injection plus venting technique, this delivery approach also permits diffusion of a composition disclosed herein, e.g., injectate, to a vestibular system. In some embodiments, the entire process can be accomplished in a subject with a relatively nontraumatic approach through an external auditory canal; see FIG. 1, and the Examples for additional information regarding the surgical administration procedure.

A number of studies on AAVAnc80 transduction in mice have been published. Different types of viral vectors (e.g., adenoviral vector, herpes simplex viral vectors) have been considered for gene delivery to the inner ear in animal models (Chen 2001; Wenzel 2007; Husseman 2009, each of which is incorporated herein in its entirety by reference); however, rAAV particles appear to be a promising tool for gene delivery directly to the cochlea given the acceptable safety profile and the long-lasting transgene expression, including recovery of auditory, cochlear, and vestibular function in knock-out and knock-in mouse models (Akil 2012; Kim 2016; Pan 2017; Akil 2019; Al-Moyed 2019; György 2019, each of which is incorporated herein in its entirety by reference). Several AAV serotypes have been delivered into the inner ear, using different surgical approaches and doses, in both neonatal and adult mice (Akil 2012; Askew 2015; Chien 2016; Landegger 2017; Suzuki 2017; Tao 2018; Yoshimura 2018; Akil 2019; Al-Moyed 2019; György 2019; Kim 2019; Omichi 2020, each of which is incorporated herein in its entirety by reference). Transduction efficiency, as assessed by GFP expression in different cell types of the cochlear and vestibular organs, differs depending on the mouse postnatal age, method use to deliver the particle, and serotype or capsid variant evaluated.

Figure 11:
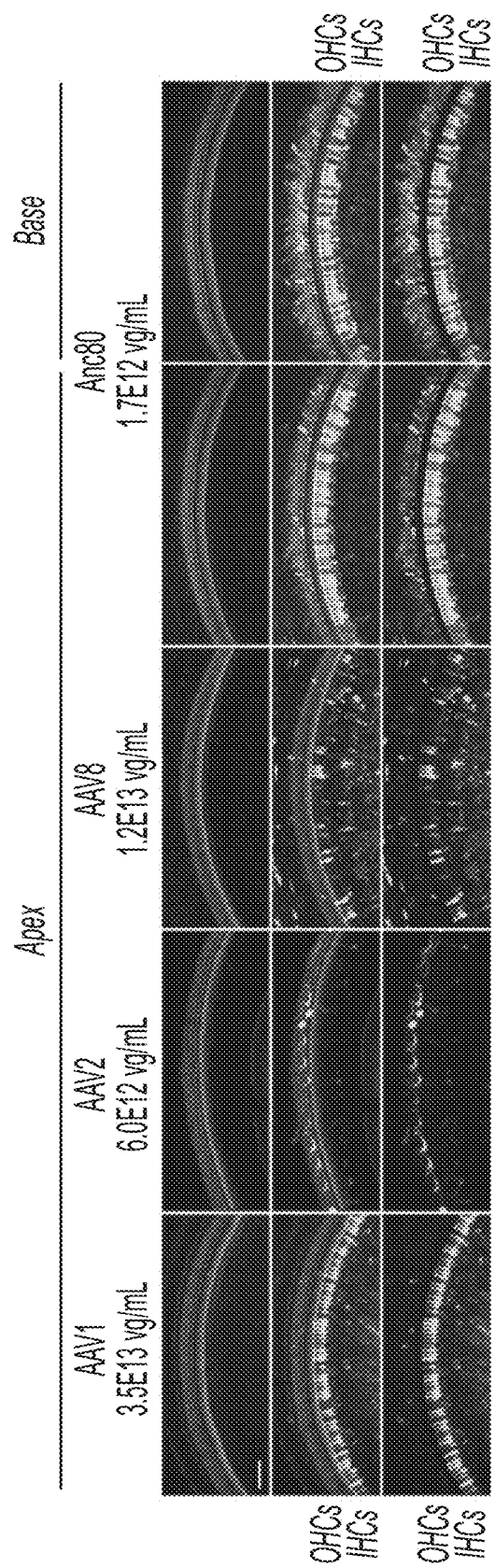
FIG. 11 includes representative fluorescent images depicting in-vivo cochlear transduction of naturally occurring AAV serotypes and an AAVAnc80 variant in neonatal mice via round window membrane delivery. Mice (P1) were injected with different AAV capsids (AAV1, AAV2, AAV8, AAV6 [not shown], and AAVAnc80) comprising a construct encoding enhanced GFP (eGFP). Phalloidin labeled actin and is shown in red in FIG. 11 of U.S. Provisional patent application 63/152,832, the entire contents of which is incorporated herein by reference. Quantification of eGFP-positive inner hair cells (IHCs) and outer hair cells (OHCs) showed transduction efficiency between approximately 90 to 100% from the base to the apex after delivery of rAAVAnc80 comprising a construct encoding enhanced GFP (rAAVAnc80-eGFP) (Landegger 2017, which is incorporated herein in its entirety by reference).
Figure 12:
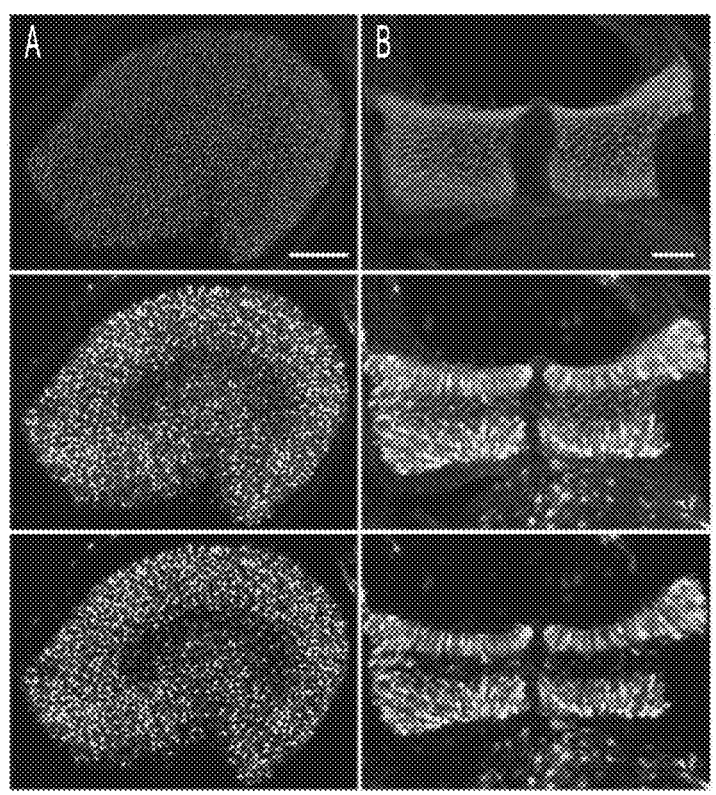
FIG. 12 includes representative fluorescent images depicting in-vivo vestibular transduction of rAAVAnc80 particles in neonatal mice via round window membrane delivery. Mice (P1) were injected with AAVAnc80-eGFP and phalloidin staining labeled actin. eGFP is shown in green and phalloidin is shown in red in FIG. 12 of U.S. Provisional patent application 63/152,832, the entire contents of which is incorporated herein by reference. Transduction was observed in both type I and type II hair cells of the utricle (Panel (A)), as well as cells of the semicircular canal cristate (Panel (B)) (Landegger 2017, which is incorporated herein in its entirety by reference).

In some embodiments, AAVAnc80 variant has shown high efficiency targeting of cochlear and vestibular sensory cells (hair cells) and accessory cells of cochlear and vestibular organs in neonatal and adult mice compared with other AAV capsids (Landegger 2017; Suzuki 2017; Omichi 2020, each of which is incorporated herein in its entirety by reference). Anc80 neonatal tropism and gene transfer efficiency was evaluated in-vivo in C57BL/6 mice injected at postnatal day 1 (P1) by round-window administration (Landegger 2017, incorporated herein in its entirety by reference). Consistent with prior studies, AAV2, AAV6, and AAV8 targeted a low percentage of IHCs, and AAV1 was able to transduce IHCs with higher efficiency, but OHC transduction was minimal; in contrast, AAVAnc80 (1.7E9 vg/cochlea) was able to transduce around 100% of IHCs and ~90% of OHCs (FIG. 11) without any deleterious effects to cochlear or auditory function (Landegger 2017, incorporated herein in its entirety by reference). In some embodiments, in the vestibular system, AAVAnc80 transduced type I and type II hair cells of the utricle as well as cells of the semicircular canal cristae (FIG. 12), without impacting vestibular function (Landegger 2017, incorporated herein in its entirety by reference).

Figure 13:
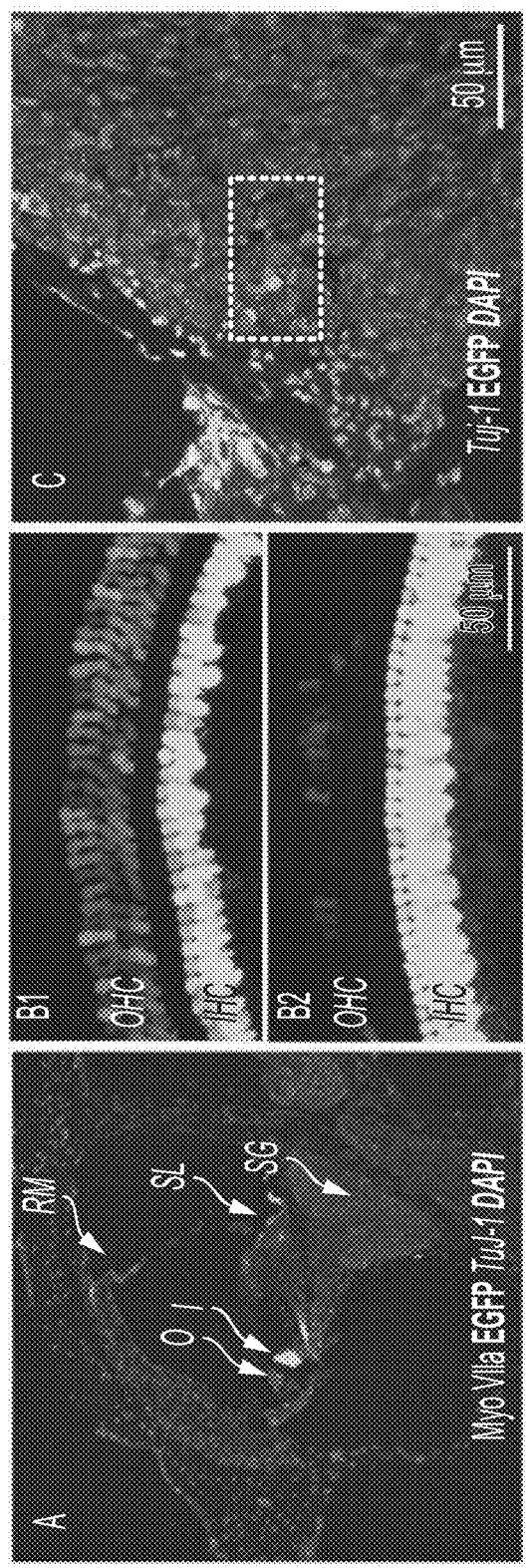
FIG. 13 includes representative fluorescent images depicting in-vivo cochlear transduction of rAAVAnc80 particles in adult mice via posterior semicircular canal delivery. Mice (7 weeks old) were injected with rAAVAnc80-eGFP particles. Panel (A) includes a low-magnification view of a midmodiolar section of an injected cochlea, showing eGFP signal in IHCs, referred to in the Panel as (I), OHCs, referred to in the Panel as (O), spiral limbus, referred to in the Panel as (SL), Reissner's membrane, referred to in the Panel as (RM), and spiral ganglion, referred to in the Panel as (SG). Panel (B1) and Panel (B2) include high-magnification views of the organ of Corti from apical (Panel (B1)) and mid (Panel (B2)) regions of the cochlea. Quantification of eGFP-positive cells showed that approximately 100% of the IHCs were transduced, whereas the OHC transduction decreased from apex to base. Panel (C) is a low magnification view showing that eGFP signal was detected in a subset of cells (neurons and satellite glial cells) in the spiral ganglion (Suzuki 2017, incorporated herein in its entirety by reference). Color images of the panels provided in this figure are shown in FIG. 13 of U.S. Provisional patent application 63/152,832, the entire contents of which is incorporated herein by reference.
Figure 14:
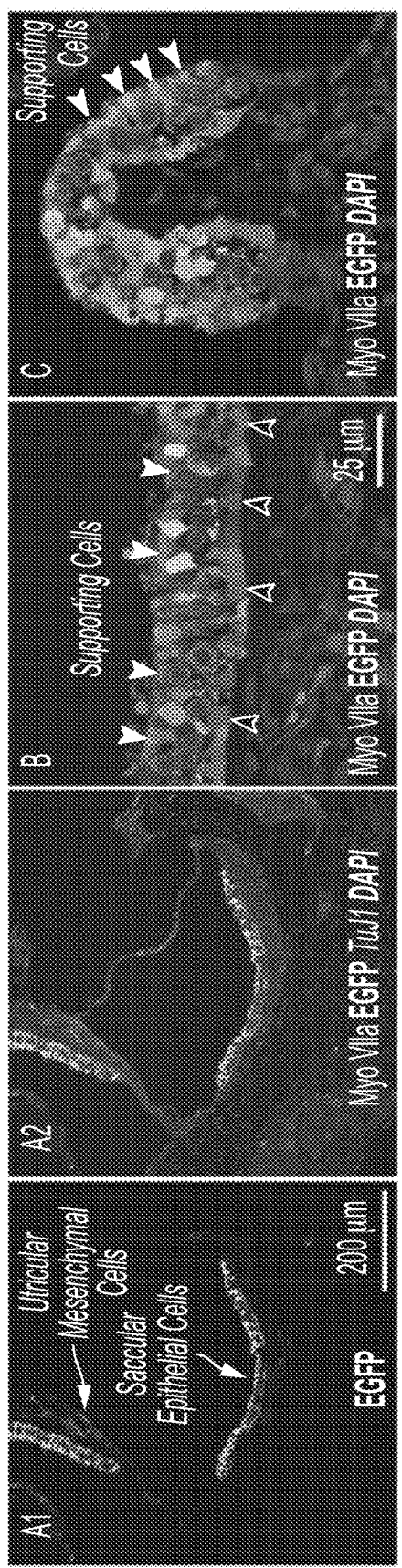
FIG. 14 includes representative fluorescent images depicting in-vivo vestibular transduction of rAAVAnc80-eGFP in adult mice via posterior semicircular canal delivery. Mice (7 weeks old) were injected with rAAVAnc80-eGFP. Panel (A1) and Panel (A2) include low-magnification view of a section through the vestibule, showing eGFP signal in both utricle and saccule. Panel (B) and Panel (C) include high-magnification views of sections through vestibular end-organs (Panel (B): utricle; Panel (C): crista ampularis), showing eGFP expression in supporting cells and hair cells. Filled arrowheads indicate example transduced supporting cells (hair cells not indicated) (Suzuki 2017, incorporated herein in its entirety by reference). Color images of the panels provided in this figure are shown in FIG. 14 of U.S. Provisional patent application 63/152,832, the entire contents of which is incorporated herein by reference.

Using a different route of administration via the posterior semicircular canal, AAVAnc80 tropism and gene transfer efficiency was evaluated in adult (7 wks) CBA/CaJ mice (Suzuki 2017, incorporated herein in its entirety by reference). AAVAnc80 (9.6E8 vg/cochlea) targeted sensory and accessory cells of the cochlea, including approximately 100% of IHCs throughout the cochlear length as well as a significant fraction of OHCs, cells of the spiral limbus and Reissner's membrane, and cells of the cochlear modiolus (e.g., spiral ganglion neurons and satellite glial cells) (FIG. 13) while maintaining normal cochlear and auditory function (Suzuki 2017, incorporated herein in its entirety by reference). Multiple cell types of the vestibular system were also transduced, including a subset of hair cells and virtually 100% of supporting cells in the utricle and semicircular canal cristae, as well as the saccule (FIG. 14), all without deleterious effects on vestibular function (Suzuki 2017, incorporated herein in its entirety by reference).

Figure 15:
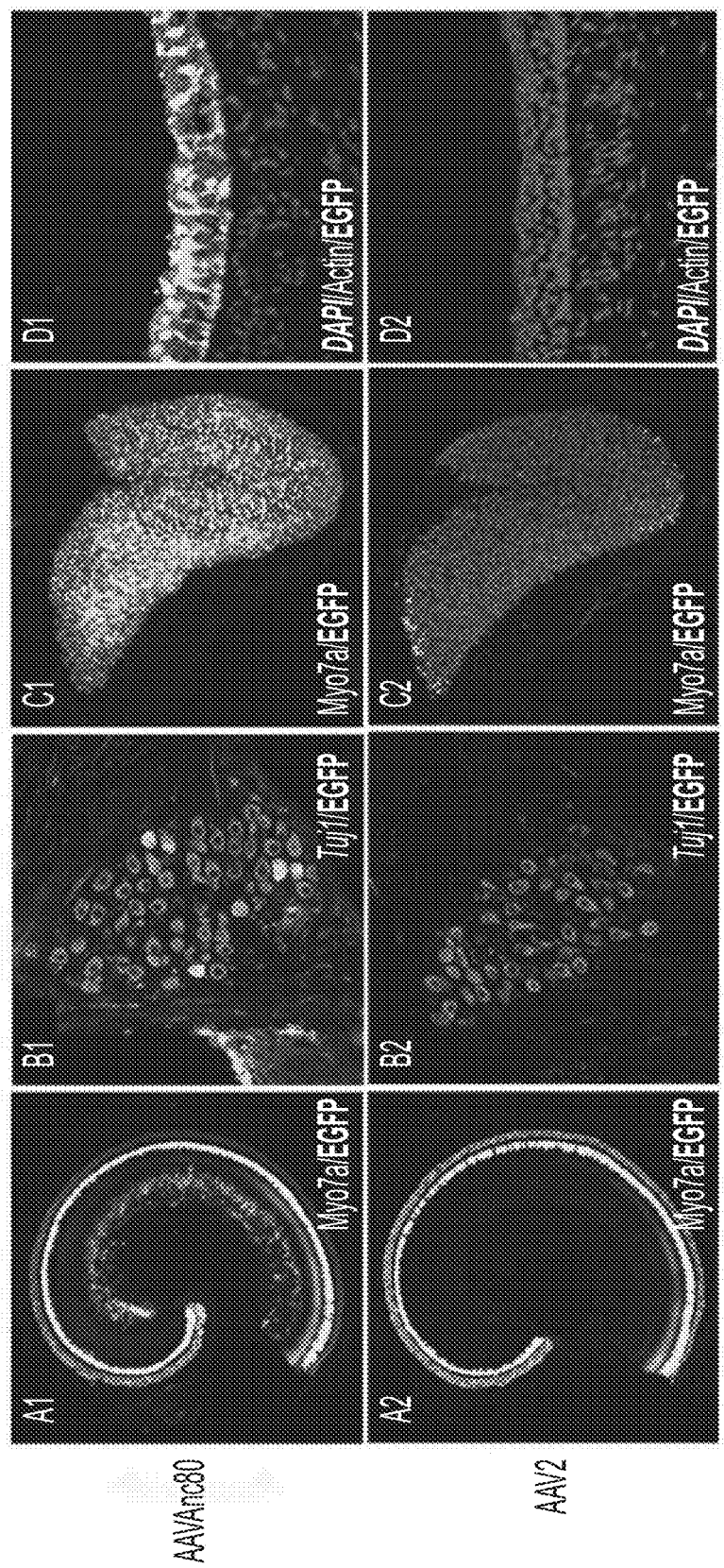
FIG. 15 includes representative fluorescent images depicting in-vivo cochlear and vestibular transduction of naturally occurring AAV2 serotype compared to rAAVAnc80 variant in adult mice via round window membrane delivery with canal fenestration. Mice (4 weeks old) were injected with different AAV particles (AAV2 and rAAVAnc80 shown here; AAV1, AAV8, and AAV9 not shown) encoding eGFP. Compared to AAV2, rAAVAnc80 mediated transduction showed comparable rates of IHC and OHC transduction (Panel (A1) vs. Panel (A2)) but broader transduction of spiral ganglion cells (Panel (B1) vs. Panel (B2)) and hair cells of the saccule (Panel (C1) vs. Panel (C2): whole mounts; Panel (D1) vs. Panel (D2): sections) (Omichi 2020, incorporated herein in its entirety by reference). Color images of the panels provided in this figure are shown in FIG. 15 of U.S. Provisional patent application 63/152,832, the entire contents of which is incorporated herein by reference.

More recently, AAVAnc80 in-vivo transduction in adult (4 wks) C3H/FeJ mice was evaluated using a route of delivery utilized herein (via round window membrane delivery with posterior semicircular canal fenestration) and directly compared to transduction by naturally occurring serotypes AAV1, AAV2, AAV8, and AAV9 (Omichi 2020, incorporated herein in its entirety by reference). All particles produced some degree of transduction without deleterious effects to auditory function, as demonstrated by control-like (uninjected) ABR thresholds. AAVAnc80 (5.5E9 vg/cochlea) transduced virtually 100% of IHCs along the cochlear length, and approximately 27 to 66% of OHCs depending on cochlear location (FIG. 15). Despite a slightly higher transduction efficiency for OHCs by AAV2 (3.68E9 vg/cochlea) compared to AAVAnc80, AAVAnc80 maintained a significantly broader tropism than AAV2 as evidenced by eGFP-positive hair cells of the saccule and spiral ganglion neurons in the cochlea; in these same cell types, AAV2 produced little-to-no transduction (FIG. 15) (Omichi 2020, incorporated herein in its entirety by reference).

In some embodiments, the ability of AAVAnc80 to target a wide range of inner ear cell types, including cochlear IHCs and OHCs, supporting cells, cells of the cochlear spiral ganglion, vestibular hair cells of utricle, saccule, and crista ampularis, and cochlear and vestibular supporting/accessory cells, in neonatal to adult mice, suggests, e.g., that AAVAnc80 could facilitate development of gene therapy approaches for disorders of the inner ear.

In certain embodiments, platform and supportive studies are conducted in non-human primates (NHPs) using reporter constructs to evaluate AAVAnc80 transduction in an inner ear. In some embodiments, exploratory platform and other supportive studies are performed in NHPs to evaluate AAVAnc80 tropism and dose-dependent effects of delivery of AAVAnc80 particles. In some embodiments, evaluation of AAVAnc80 capsid tropism for NHP inner ear cell types is facilitated using rAAVAnc80 particles comprising constructs encoding an enhanced GFP (eGFP) reporter transgene and delivered via intracochlear injection through the round window membrane. In some embodiments, such particles may also be useful for development of novel devices for efficient delivery directly to the cochlea as described herein.

In some embodiments, NHP ears were histologically evaluated for transduction efficiency of cochlear hair cells and dose-dependency of hair cell transduction. In some embodiments, such ears were also analyzed for breadth of cell-type transduction in cochlear and/or vestibular organs. In some embodiments, it is likely that increasing the populations of inner ear cells that are transduced with rAAV particles as described herein (e.g., comprising rAAVAnc80-antiVEGF) supports the likelihood that, in the case of rAAVAnc80-antiVEGF, the inner ear can maintain a sustained depot of secreted anti-VEGF protein; in turn, this protein has the potential to control VS growth via proximity and diffusional continuity with the site of the tumor in the adjacent internal auditory canal. In some embodiments, tolerability of a procedure on hair cell survival, transduction in the presence of pre-existing neutralizing antibodies (NAbs), and any potential transduction of the contralateral (uninjected) ear were also evaluated in NHP. Results are summarized in the Examples.

In some embodiments, the rationally designed, synthetic AAVAnc80L65 capsid variant (AAVAnc80) is highly efficient at transducing primate IHCs, in a dose-dependent manner, using a delivery device designed for round window membrane administration. In some embodiments, approximately 75 to 100% transduction of IHCs in an injected ear is achieved, using an AAVAnc80 particle comprising a construct encoding a transgene, at a dose of about $6.0 \times 10^{10}$ vg/cochlea or higher.

In some embodiments, pre-existing neutralizing antibodies against AAVAnc80, at least at moderate levels in serum, do not inhibit IHC or supporting cell transduction when particles are delivered via an intracochlear route of administration.

In some embodiments, qualitative assessments of injected ears demonstrates transduction across multiple cochlear and vestibular cell types, all of which are positioned to secrete anti-VEGF protein either into perilymph or directly into interstitial fluid of the cochlear nerve following transduction by rAAVAnc80-antiVEGF and thereby potentially control growth of VSs through diffusion in the vestibulocochlear nerve interstitium.

Exemplary AAV Anc80 Capsid DNA Sequence
(SEQ ID NO: 88)
ATGGCTGCCGATGGTTATCTTCCAGATTGGCTCGAGGACAACCTCTCTG

AGGGCATTCGCGAGTGGTGGGACTTGAAACCTGGAGCCCCGAAACCCAA

```
AGCCAACCAGCAAAAGCAGGACGACGGCCGGGGTCTGGTGCTTCCTGGC
TACAAGTACCTCGGACCCTTCAACGGACTCGACAAGGGGGAGCCCGTCA
ACGCGGCGGACGCAGCGGCCCTCGAGCACGACAAGGCCTACGACCAGCA
GCTCAAAGCGGGTGACAATCCGTACCTGCGGTATAACCACGCCGACGCC
GAGTTTCAGGAGCGTCTGCAAGAAGATACGTCTTTTGGGGGCAACCTCG
GGCGAGCAGTCTTCCAGGCCAAGAAGCGGGTTCTCGAACCTCTCGGTCT
GGTTGAGGAAGGCGCTAAGACGGCTCCTGGAAAGAAGAGACCGGTAGAG
CAATCACCCCAGGAACCAGACTCCTCTTCGGGCATCGGCAAGAAAGGCC
AGCAGCCCGCGAAGAAGAGACTCAACTTTGGGCAGACAGGCGACTCAGA
GTCAGTGCCCGACCCTCAACCACTCGGAGAACCCCCCGCAGCCCCCTCT
GGTGTGGGATCTAATACAATGGCAGCAGGCGGTGGCGCTCCAATGGCAG
ACAATAACGAAGGCGCCGACGGAGTGGGTAACGCCTCAGGAAATTGGCA
TTGCGATTCCACATGGCTGGGCGACAGAGTCATCACCACCAGCACCCGA
ACCTGGGCCCTCCCCACCTACAACAACCACCTCTACAAGCAAATCTCCA
GCCAATCGGGAGCAAGCACCAACGACAACACCTACTTCGGCTACAGCAC
CCCCTGGGGGTATTTTGACTTTAACAGATTCCACTGCCACTTCTCACCA
CGTGACTGGCAGCGACTCATCAACAACAACTGGGGATTCCGGCCCAAGA
GACTCAACTTCAAGCTCTTCAACATCCAGGTCAAGGAGGTCACGACGAA
TGATGGCACCACGACCATCGCCAATAACCTTACCAGCACGGTTCAGGTC
TTTACGGACTCGGAATACCAGCTCCCGTACGTCCTCGGCTCTGCGCACC
AGGGCTGCCTGCCTCCGTTCCCGGCGGACGTCTTCATGATTCCTCAGTA
CGGGTACCTGACTCTGAACAATGGCAGTCAGGCCGTGGGCCGTTCCTCC
TTCTACTGCCTGGAGTACTTTCCTTCTCAAATGCTGAGAACGGGCAACA
ACTTTGAGTTCAGCTACACGTTTGAGGACGTGCCTTTTCACAGCAGCTA
CGCGCACAGCCAAAGCCTGGACCGGCTGATGAACCCCCTCATCGACCAG
TACCTGTACTACCTGTCTCGGACTCAGACCACGAGTGGTACCGCAGGAA
ATCGGACGTTGCAATTTTCTCAGGCCGGGCCTAGTAGCATGGCGAATCA
GGCCAAAAACTGGCTACCCGGGCCCTGCTACCGGCAGCAACGCGTCTCC
AAGACAGCGAATCAAAATAACAACAGCAACTTTGCCTGGACCGGTGCCA
CCAAGTATCATCTGAATGGCAGAGACTCTCTGGTAAATCCCGGTCCCGC
TATGGCAACCCACAAGGACGACGAAGACAAATTTTTTCCGATGAGCGGA
GTCTTAATATTTGGGAAACAGGGAGCTGGAAATAGCAACGTGGACCTTG
ACAACGTTATGATAACCAGTGAGGAAGAAATTAAAACCACCAACCCAGT
GGCCACAGAACAGTACGGCACGGTGGCCACTAACCTGCAATCGTCAAAC
ACCGCTCCTGCTACAGGGACCGTCAACAGTCAAGGAGCCTTACCTGGCA
TGGTCTGGCAGAACCGGGACGTGTACCTGCAGGGTCCTATCTGGGCCAA
GATTCCTCACACGGACGGACACTTTCATCCCTCGCCGCTGATGGGAGGC
TTTGGACTGAAACACCCGCCTCCTCAGATCCTGATTAAGAATACACCTG
TTCCCGCGAATCCTCCAACTACCTTCAGTCCAGCTAAGTTTGCGTCGTT
CATCACGCAGTACAGCACCGGACAGGTCAGCGTGGAAATTGAATGGGAG
CTGCAGAAAGAAAACAGCAAACGCTGGAACCCAGAGATTCAATACACTT
CCAACTACAACAAATCTACAAATGTGGACTTTGCTGTTGACACAAATGG
CGTTTATTCTGAGCCTCGCCCCATCGGCACCCGTTACCTCACCCGTAAT
CTG
```

Exemplary AAV Anc80 Capsid Amino Acid Sequence
(SEQ ID NO: 89)
MAADGYLPDWLEDNLSEGIREWWDLKPGAPKPKANQQKQDDGRGLVLPG

YKYLGPFNGLDKGEPVNAADAAALEHDKAYDQQLKAGDNPYLRYNHADA

EFQERLQEDTSFGGNLGRAVFQAKKRVLEPLGLVEEGAKTAPGKKRPVE

QSPQEPDSSSGIGKKGQQPAKKRLNFGQTGDSESVPDPQPLGEPPAAPS

GVGSNTMAAGGGAPMADNNEGADGVGNASGNWHCDSTWLGDRVITTSTR

TWALPTYNNHLYKQISSQSGASTNDNTYFGYSTPWGYFDFNRFHCHFSP

RDWQRLINNNWGFRPKRLNFKLFNIQVKEVTTNDGTTTIANNLTSTVQV

FTDSEYQLPYVLGSAHQGCLPPFPADVFMIPQYGYLTLNNGSQAVGRSS

FYCLEYFPSQMLRTGNNFEFSYTFEDVPFHSSYAHSQSLDRLMNPLIDQ

YLYYLSRTQTTSGTAGNRTLQFSQAGPSSMANQAKNWLPGPCYRQQRVS

KTANQNNNSNFAWTGATKYHLNGRDSLVNPGPAMATHKDDEDKFFPMSG

VLIFGKQGAGNSNVDLDNVMITSEEEIKTTNPVATEQYGTVATNLQSSN

TAPATGTVNSQGALPGMVWQNRDVYLQGPIWAKIPHTDGHFHPSPLMGG

FGLKHPPPQILIKNTPVPANPPTTFSPAKFASFITQYSTGQVSVEIEWE

LQKENSKRWNPEIQYTSNYNKSTNVDFAVDTNGVYSEPRPIGTRYLTRN

L

Exemplary AAV Anc80 Capsid Amino Acid Sequence
(SEQ ID NO: 113)
MAADGYLPDWLEDNLSEGIREWWDLKPGAPKPKANQQKQDDGRGLVLPG

YKYLGPFNGLDKGEPVNAADAAALEHDKAYDQQLKAGDNPYLRYNHADA

EFQERLQEDTSFGGNLGRAVFQAKKRVLEPLGLVEEGAKTAPGKKRPVE

QSPQEPDSSSGIGKKGQQPAX$_1$KRLNFGQTGDSESVPDPQPLGEPPAAP

SGVGSNTMX$_2$AGGGAPMADNNEGADGVGNASGNWHCDSTWLGDRVITTS

TRTWALPTYNNHLYKQISSQSGX$_3$STNDNTYFGYSTPWGYFDFNRFHCH

FSPRDWQRLINNNWGFRPKX$_4$LNFKLFNIQVKEVTTNDGTTTIANNLTS

TVQVFTDSEYQLPYVLGSAHQGCLPPFPADVFMIPQYGYLTLNNGSQAV

GRSSFYCLEYFPSQMLRTGNNFX$_5$FSYTFEDVPFHSSYAHSQSLDRLMN

PLIDQYLYYLSRTQTTSGTAGNRX$_6$LQFSQAGPSSMANQAKNWLPGPCY

RQQRVSKTX$_7$NQNNNSNFAWTGATKYHLNGRDSLVNPGPAMATHKDDED

KFFPMSGVLIFGKQGAGNSNVDLDNVMITX$_8$EEEIKTTNPVATEX$_9$YGT

VATNLQSX$_{10}$NTAPATGTVNSQGALPGMVWQX$_{11}$RDVYLQGPIWAKIPHT

DGHFHPSPLMGGFGLKHPPPQILIKNTPVPANPPTTFSPAKFASFITQ

YSTGQVSVEIEWELQKENSKRWNPEIQYTSNYNKSTNVDFAVDTNGVY

SEPRPIGTRYLTRNL

| Symbol in SEQ ID NO: 113 | Corresponding Amino Acid |
|---|---|
| $X_1$ | K or R |
| $X_2$ | A or S |
| $X_3$ | A or G |
| $X_4$ | R or k |
| $X_5$ | E or Q |
| $X_6$ | T or E |
| $X_7$ | A or T |
| $X_8$ | S or N |
| $X_9$ | Q or E |
| $X_{10}$ | S or A |
| $X_{11}$ | N or D |

Exemplary AAV Anc80 Capsid Amino Acid Sequence
(SEQ ID NO: 114)

MAADGYLPDWLEDNLSEGIREWWDLKPGAPKPKANQQKQDDGRGLVLPG

YKYLGPFNGLDKGEPVNAADAAALEHDKAYDQQLKAGDNPYLRYNHADA

EFQERLQEDTSFGGNLGRAVFQAKKRVLEPLGLVEEGAKTAPGKKRPVE

QSPQEPDSSSGIGKKGQQPARKRLNFGQTGDSESVPDPQPLGEPPAAPS

GVGSNTMAAGGGAPMADNNEGADGVGNASGNWHCDSTWLGDRVITTSTR

TWALPTYNNHLYKQISSQSGGSTNDNTYFGYSTPWGYFDFNRFHCHFSP

RDWQRLINNNWGFRPKKLNFKLFNIQVKEVTTNDGTTTIANNLTSTVQV

FTDSEYQLPYVLGSAHQGCLPPFPADVFMIPQYGYLTLNNGSQAVGRSS

FYCLEYFPSQMLRTGNNFQFSYTFEDVPFHSSYAHSQSLDRLMNPLIDQ

YLYYLSRTQTTSGTAGNRTLQFSQAGPSSMANQAKNWLPGPCYRQQRVS

KTTNQNNNSNFAWTGATKYHLNGRDSLVNPGPAMATHKDDEDKFFPMSG

VLIFGKQGAGNSNVDLDNVMITNEEEIKTTNPVATEEYGTVATNLQSAN

TAPATGTVNSQGALPGMVWQDRDVYLQGPIWAKIPHTDGHFHPSPLMGG

FGLKHPPPQILIKNTPVPANPPTTFSPAKFASFITQYSTGQVSVEIEWE

LQKENSKRWNPEIQYTSNYNKSTNVDFAVDTNGVYSEPRPIGTRYLTRN

L

Exemplary AAV Particles

In certain embodiments, the present disclosure relates to an rAAV-antiVEGF composition comprising a particle comprising rAAV2/Anc80L65-CAG.ranibizumab.bGH. In certain embodiments, an rAAV-antiVEGF composition comprises: a) Anc80L65, a rationally designed, synthetic AAV capsid; b) Inverted terminal repeats derived from AAV2 (upstream and downstream); c) Cytomegalovirus (CMV) early enhancer element, the chicken beta actin (CβA) gene sequence located between the 5' flanking region and the proximal region of the second exon, and the 3' splice sequence derived from the rabbit beta globin (RβG) gene (Miyazaki 1989; Niwa 1991; and Orbán 2009, each of which is incorporated herein in its entirety by reference), which together are commonly referred to as the CAG promoter (upstream); d) Ranibizumab (antibody fragment [Fab]) coding sequence comprising, i) Bicistronic cassette encoding ranibizumab heavy and light chain variable regions, separated by furin and *Thosea asigna* virus-derived protease 2A (T2A) cleavage sites, and ii) A 20 amino-acid human interleukin-2 (IL-2) leader sequence cloned upstream of each Fab chain to facilitate protein secretion; and e) Bovine growth hormone (bGH) polyadenylation (pA) signal (downstream).

In certain embodiments, the present disclosure relates to an rAAVAnc80-antiVEGF composition comprising a particle comprising rAAV2/Anc80L65-CAG.bevacizumab.bGH. In certain embodiments, an rAAV-antiVEGF composition comprises: a) Anc80L65, a rationally designed, synthetic AAV capsid; b) Inverted terminal repeats derived from AAV2 (upstream and downstream); c) Cytomegalovirus (CMV) early enhancer element, the chicken beta actin (CβA) gene sequence located between the 5' flanking region and the proximal region of the second exon, and the 3' splice sequence derived from the rabbit beta globin (RβG) gene (Miyazaki 1989; Niwa 1991; Orbán 2009, each of which are incorporated herein in their entirety), which together are commonly referred to as the CAG promoter (upstream); d) bevacizumab coding sequence (antibody comprising Fab and Fc regions) comprising, i) Bicistronic cassette encoding heavy and light chain variable and constant regions, separated by furin and *Thosea asigna* virus-derived protease 2A (T2A) cleavage sites, and ii) A 20 amino-acid human interleukin-2 (IL-2) leader sequence cloned upstream of each Fab chain to facilitate protein secretion; and e) Bovine growth hormone (bGH) polyadenylation (pA) signal (downstream).

In certain embodiments, the present disclosure relates to an rAAVAnc80-antiVEGF composition comprising a particle comprising rAAV2/Anc80L65-CAG.aflibercept.bGH. In certain embodiments, an rAAV-antiVEGF composition comprises: a) Anc80L65, a rationally designed, synthetic AAV capsid; b) Inverted terminal repeats derived from AAV2 (upstream and downstream); c) Cytomegalovirus (CMV) early enhancer element, the chicken beta actin (CβA) gene sequence located between the 5' flanking region and the proximal region of the second exon, and the 3' splice sequence derived from the rabbit beta globin (R/3G) gene (Miyazaki 1989; Niwa 1991; Orbán 2009, each of which are incorporated herein in their entirety), which together are commonly referred to as the CAG promoter (upstream); d) aflibercept coding sequence comprising, i) an optional 20 amino-acid human interleukin-2 (IL-2) leader sequence, and ii) a recombinant fusion protein consisting of portions of human VEGF receptors 1 and 2 extracellular domains fused to the Fc portion of human IgG1; and e) Bovine growth hormone (bGH) polyadenylation (pA) signal (downstream).

Compositions

Among other things, the present disclosure provides compositions. In some embodiments, a composition comprises a construct as described herein. In some embodiments, a composition comprises one or more constructs as described herein. In some embodiments, a composition comprises a plurality of constructs as described herein. In some embodiments, when more than one construct is included in the composition, the constructs are each different.

In some embodiments, a composition comprises an rAAV particle as described herein. In some embodiments, a composition comprises one or more rAAV particles as described herein. In some embodiments, a composition comprises a plurality of rAAV particles. In come embodiments, when more than one rAAV particle is included in the composition, the rAAV particles are each different.

In some embodiments, a composition comprises an anti-VEGF protein. In some embodiments, a composition comprises a cell. In some embodiments, a composition is or comprises a pharmaceutical composition.

In some embodiments, an rAAVAnc80-antiVEGF particle is comprised of an AAVAnc80 capsid and a single-stranded DNA genome encoding ranibizumab, a 48 kilodalton (kDa) humanized monoclonal antibody fragment (Fab), which is used clinically to inhibit VEGF. In certain embodiments, rAAVAnc80-antiVEGF will be manufactured at a CRO or at an in-house operational GMP facility.

In some embodiments, rAAVAnc80-antiVEGF is produced through transient transfection of human embryonic kidney (HEK) 293 epithelial cells. In some embodiments, a clarified cell harvest is purified by affinity chromatography, followed by further purification and enrichment for full rAAVAnc80 particles by cesium chloride isopycnic gradient separation. In some embodiments, a formulation buffer is comprised of sterile water containing mono-potassium phosphate at a range of 0.1-5 mM (e.g., at 1.5 mM mono-potassium phosphate), sodium phosphate dibasic at a range of 1-20 mM (e.g., at 8.1 mM sodium phosphate dibasic), potassium chloride at a range of 0.1-10 mM (e.g., 2.7 mM potassium chloride), sodium chloride at a range of 100-1000 mM (e.g., at 172 mM sodium chloride), and Poloxamer at a range of 0.0001-0.001% (e.g., 0.001% Poloxamer 188). In some embodiments, once purified and formulated, an rAAVAnc80 particle comprising a construct is referred to as a drug substance. In some embodiments, a drug substance is subsequently sterile filtered (e.g., using a 0.2 micron [μm] filter) and aseptically filled for single use into sterile vials and stoppered. In some embodiments, these vialed aliquots constitute drug product and are stored at an appropriate temperature until the day of administration (e.g., from 4° C. to −100° C., e.g., at ≤−65° C.).

In some embodiments, a separate Diluent drug product can be created (e.g., an AAVAnc80 diluent), and can at or near equivalence in composition to the formulation buffer. In some embodiments, such a diluent can be sterile filtered (0.2 μm filter), aseptically filled for single use into sterile vials, and stored a at an appropriate temperature until the day of administration (e.g., from 4° C. to −100° C., e.g., at ≤−65° C.). In some embodiments, a Diluent drug product is utilized to prepare the concentration necessary for doses of drug substance described herein.

Dosing and Volume of Administration

In some embodiments, a composition disclosed herein, e.g., one or a plurality of AAV vectors disclosed herein, is administered as a single dose or as a plurality of doses.

In some embodiments, a composition disclosed herein is administered as a single dose. In some embodiments, a composition disclosed herein is administered as a plurality of doses, e.g., 2, 3, 4, 5, 6, 7, 8, 9 or 10 doses.

In some embodiments, a composition disclosed herein (e.g., a composition comprising one or a plurality of rAAV constructs disclosed herein) is administered at a volume of about 0.01 mL, about 0.02 mL, about 0.03 mL, about 0.04 mL, about 0.05 mL, about 0.06 mL, about 0.07 mL, about 0.08 mL, about 0.09 mL, about 1.00 mL, about 1.10 mL, about 1.20 mL, about 1.30 mL, about 1.40 mL, about 1.50 mL, about 1.60 mL, about 1.70 mL, about 1.80 mL, about 1.90 mL, or about 2.00 mL. In some embodiments, a composition disclosed herein is administered at a volume of about 0.01 mL. In some embodiments, a composition disclosed herein is administered at a volume of about 0.02 mL. In some embodiments, a composition disclosed herein is administered at a volume of about 0.03 mL. In some embodiments, a composition disclosed herein is administered at a volume of about 0.04 mL. In some embodiments, a composition disclosed herein is administered at a volume of about 0.05 mL. In some embodiments, a composition disclosed herein is administered at a volume of about 0.06 mL. In some embodiments, a composition disclosed herein is administered at a volume of about 0.07 mL. In some embodiments, a composition disclosed herein is administered at a volume of about 0.08 mL. In some embodiments, a composition disclosed herein is administered at a volume of about 0.09 mL. In some embodiments, a composition disclosed herein is administered at a volume of about 1.00 mL. In some embodiments, a composition disclosed herein is administered at a volume of about 1.10 mL. In some embodiments, a composition disclosed herein is administered at a volume of about 1.20 mL. In some embodiments, a composition disclosed herein is administered at a volume of about 1.30 mL. In some embodiments, a composition disclosed herein is administered at a volume of about 1.40 mL. In some embodiments, a composition disclosed herein is administered at a volume of about 1.50 mL. In some embodiments, a composition disclosed herein is administered at a volume of about 1.60 mL. In some embodiments, a composition disclosed herein is administered at a volume of about 1.70 mL. In some embodiments, a composition disclosed herein is administered at a volume of about 1.80 mL. In some embodiments, a composition disclosed herein is administered at a volume of about 1.90 mL. In some embodiments, a composition disclosed herein is administered at a volume of about 2.00 mL.

In some embodiments, a composition disclosed herein (e.g., a composition comprising one or a plurality of rAAV constructs disclosed herein) is administered at a volume of about 0.01 to 2.00 mL, about 0.02 to 1.90 mL, about 0.03 to 1.8 mL, about 0.04 to 1.70 mL, about 0.05 to 1.60 mL, about 0.06 to 1.50 mL, about 0.06 to 1.40 mL, about 0.07 to 1.30 mL, about 0.08 to 1.20 mL, or about 0.09 to 1.10 mL. In some embodiments a composition disclosed herein (e.g., a composition comprising one or a plurality of rAAV constructs disclosed herein) is administered at a volume of about 0.01 to 2.00 mL, about 0.02 to 2.00 mL, about 0.03 to 2.00 mL, about 0.04 to 2.00 mL, about 0.05 to 2.00 mL, about 0.06 to 2.00 mL, about 0.07 to 2.00 mL, about 0.08 to 2.00 mL, about 0.09 to 2.00 mL, about 0.01 to 1.90 mL, about 0.01 to 1.80 mL, about 0.01 to 1.70 mL, about 0.01 to 1.60 mL, about 0.01 to 1.50 mL, about 0.01 to 1.40 mL, about 0.01 to 1.30 mL, about 0.01 to 1.20 mL, about 0.01 to 1.10 mL, about 0.01 to 1.00 mL, about 0.01 to 0.09 mL.

In some embodiments, a composition disclosed herein (e.g., a composition comprising one or a plurality of rAAV constructs disclosed herein) is administered at a volume of about 0.01 mL to about 0.30 mL, about 0.01 mL to about 0.25 mL, about 0.01 mL to about 0.20 mL, about 0.01 mL to about 0.15 mL, about 0.01 mL to about 0.14 mL, about 0.01 mL to about 0.13 mL, about 0.01 mL to about 0.12 mL, about 0.01 mL to about 0.11 mL, about 0.01 mL to about 0.10 mL, about 0.01 mL to about 0.09 mL, about 0.01 mL to about 0.08 mL, about 0.01 mL to about 0.07 mL, about 0.01 mL to about 0.06 mL, about 0.01 mL to about 0.05 mL, about 0.01 mL to about 0.04 mL, about 0.01 mL to about 0.03 mL, or about 0.01 mL to about 0.02 mL.

In some embodiments, a composition disclosed herein (e.g., a composition comprising one or a plurality of rAAV constructs disclosed herein) is administered at a volume of about 0.02 mL to about 0.30 mL, 0.03 mL to about 0.30 mL, 0.04 mL to about 0.30 mL, 0.05 mL to about 0.30 mL, 0.06 mL to about 0.30 mL, 0.07 mL to about 0.30 mL, 0.08 mL to about 0.30 mL, 0.09 mL to about 0.30 mL, 0.10 mL to about 0.30 mL, 0.11 mL to about 0.30 mL, 0.12 mL to about 0.30 mL, 0.13 mL to about 0.30 mL, 0.14 mL to about 0.30 mL, 0.15 mL to about 0.30 mL, 0.16 mL to about 0.30 mL, 0.17 mL to about 0.30 mL, 0.18 mL to about 0.30 mL, 0.19 mL to about 0.30 mL, 0.20 mL to about 0.30 mL, or 0.25 mL to about 0.30 mL.

In some embodiments, a composition disclosed herein (e.g., a composition comprising one or a plurality of rAAV constructs disclosed herein) is administered at a volume of about 0.01 mL to about 0.03 mL, about 0.02 mL to about 0.25 mL, about 0.03 mL to about 0.20 mL, about 0.04 mL to about 0.18 mL, about 0.05 mL to about 0.16 mL, about 0.06 mL to about 0.14 mL, about 0.07 mL to about 0.12 mL, or about 0.08 mL to about 0.1 mL.

In some embodiments, a composition disclosed herein (e.g., a composition comprising one or a plurality of rAAV constructs disclosed herein) is administered at an amount of about $1\times10^{11}$ vg/mL to about $1\times10^{15}$ vg/mL, about $1\times10^{11}$ vg/mL to about $9\times10^{14}$ vg/mL, about $1\times10^{11}$ vg/mL to about $8\times10^{14}$ vg/mL, about $1\times10^{11}$ vg/mL to about $7\times10^{14}$ vg/mL, about $1\times10^{11}$ vg/mL to about $6\times10^{14}$ vg/mL, about $1\times10^{11}$ vg/mL to about $5\times10^{14}$ vg/mL, about $1\times10^{11}$ vg/mL to about $4\times10^{14}$ vg/mL, about $1\times10^{11}$ vg/mL to about $3\times10^{14}$ vg/mL, about $1\times10^{11}$ vg/mL to about $2\times10^{14}$ vg/mL, about $1\times10^{11}$ vg/mL to about $1\times10^{14}$ vg/mL, about $1\times10^{11}$ vg/mL to about $9\times10^{13}$ vg/mL, about $1\times10^{11}$ vg/mL to about $8\times10^{13}$ vg/mL, about $1\times10^{11}$ vg/mL to about $7\times10^{13}$ vg/mL, about $1\times10^{11}$ vg/mL to about $6\times10^{13}$ vg/mL, about $1\times10^{11}$ vg/mL to about $5\times10^{13}$ vg/mL, about $1\times10^{11}$ vg/mL to about $4\times10^{13}$ vg/mL, about $1\times10^{11}$ vg/mL to about $3\times10^{13}$ vg/mL, about $1\times10^{11}$ vg/mL to about $2\times10^{13}$ vg/mL, about $1\times10^{11}$ vg/mL to about $1\times10^{13}$ vg/mL, about $1\times10^{11}$ vg/mL to about $9\times10^{12}$ vg/mL, about $1\times10^{11}$ vg/mL to about $8\times10^{12}$ vg/mL, about $1\times10^{11}$ vg/mL to about $7\times10^{12}$ vg/mL, about $1\times10^{11}$ vg/mL to about $6\times10^{12}$ vg/mL, about $1\times10^{11}$ vg/mL to about $5\times10^{12}$ vg/mL, about $1\times10^{11}$ vg/mL to about $4\times10^{12}$ vg/mL, about $1\times10^{11}$ vg/mL to about $3\times10^{12}$ vg/mL, about $1\times10^{11}$ vg/mL to about $2\times10^{12}$ vg/mL, about $1\times10^{11}$ vg/mL to about $1\times10^{12}$ vg/mL, about $1\times10^{11}$ vg/mL to about $9.5\times10^{11}$ vg/mL, about $1\times10^{11}$ vg/mL to about $9\times10^{11}$ vg/mL, about $1\times10^{11}$ vg/mL to about $8.5\times10^{11}$ vg/mL, about $1\times10^{11}$ vg/mL to about $8\times10^{11}$ vg/mL, about $1\times10^{11}$ vg/mL to about $7.5\times10^{11}$ vg/mL, about $1\times10^{11}$ vg/mL to about $7\times10^{11}$ vg/mL, about $1\times10^{11}$ vg/mL to about $6.5\times10^{11}$ vg/mL, about $1\times10^{11}$ vg/mL to about $6\times10^{11}$ vg/mL, about $1\times10^{11}$ vg/mL to about $5.5\times10^{11}$ vg/mL, about $1\times10^{11}$ vg/mL to about $5\times10^{11}$ vg/mL, about $1\times10^{11}$ vg/mL to about $4.5\times10^{11}$ vg/mL, about $1\times10^{11}$ vg/mL to about $4\times10^{11}$ vg/mL, about $1\times10^{11}$ vg/mL to about $3.5\times10^{11}$ vg/mL, about $1\times10^{11}$ vg/mL to about $3\times10^{11}$ vg/mL, about $1\times10^{11}$ vg/mL to about $2.5\times10^{11}$ vg/mL, about $1\times10^{11}$ vg/mL to about $2\times10^{11}$ vg/mL, about $1\times10^{11}$ vg/mL to about $1.5\times10^{11}$ vg/mL.

In some embodiments, a composition disclosed herein (e.g., a composition comprising one or a plurality of rAAV constructs disclosed herein) is administered at an amount of about $1\times10^{11}$ vg/mL to about $1\times10^{15}$ vg/mL, about $2\times10^{11}$ vg/mL to about $1\times10^{15}$ vg/mL, about $3\times10^{11}$ vg/mL to about $1\times10^{15}$ vg/mL, about $4\times10^{11}$ vg/mL to about $1\times10^{15}$ vg/mL, about $5\times10^{11}$ vg/mL to about $1\times10^{15}$ vg/mL, about $6\times10^{11}$ vg/mL to about $1\times10^{15}$ vg/mL, about $7\times10^{11}$ vg/mL to about $1\times10^{15}$ vg/mL, about $8\times10^{11}$ vg/mL to about $1\times10^{15}$ vg/mL, about $9\times10^{11}$ vg/mL to about $1\times10^{15}$ vg/mL, about $1\times10^{12}$ vg/mL to about $1\times10^{15}$ vg/mL, about $2\times10^{12}$ vg/mL to about $1\times10^{15}$ vg/mL, about $3\times10^{12}$ vg/mL to about $1\times10^{15}$ vg/mL, about $4\times10^{12}$ vg/mL to about $1\times10^{15}$ vg/mL, about $5\times10^{12}$ vg/mL to about $1\times10^{15}$ vg/mL, about $6\times10^{12}$ vg/mL to about $1\times10^{15}$ vg/mL, about $7\times10^{12}$ vg/mL to about $1\times10^{15}$ vg/mL, about $8\times10^{12}$ vg/mL to about $1\times10^{15}$ vg/mL, about $9\times10^{12}$ vg/mL to about $1\times10^{15}$ vg/mL, about $1\times10^{13}$ vg/mL to about $1\times10^{15}$ vg/mL, about $2\times10^{13}$ vg/mL to about $1\times10^{15}$ vg/mL, about $3\times10^{13}$ vg/mL to about $1\times10^{15}$ vg/mL, about $4\times10^{13}$ vg/mL to about $1\times10^{15}$ vg/mL, about $5\times10^{13}$ vg/mL to about $1\times10^{15}$ vg/mL, about $6\times10^{13}$ vg/mL to about $1\times10^{15}$ vg/mL, about $7\times10^{13}$ vg/mL to about $1\times10^{15}$ vg/mL, about $8\times10^{13}$ vg/mL to about $1\times10^{15}$ vg/mL, about $9\times10^{13}$ vg/mL to about $1\times10^{15}$ vg/mL, about $1\times10^{14}$ vg/mL to about $1\times10^{15}$ vg/mL, about $2\times10^{14}$ vg/mL to about $1\times10^{15}$ vg/mL, about $3\times10^{14}$ vg/mL to about $1\times10^{15}$ vg/mL, about $4\times10^{14}$ vg/mL to about $1\times10^{15}$ vg/mL, about $5\times10^{14}$ vg/mL to about $1\times10^{15}$ vg/mL, about $6\times10^{14}$ vg/mL to about $1\times10^{15}$ vg/mL, about $7\times10^{14}$ vg/mL to about $1\times10^{15}$ vg/mL, about $8\times10^{14}$ vg/mL to about $1\times10^{15}$ vg/mL, or about $9\times10^{14}$ vg/mL to about $1\times10^{15}$ vg/mL.

In some embodiments, a composition disclosed herein (e.g., a composition comprising one or a plurality of rAAV constructs disclosed herein) is administered at an amount of at least $1\times10^{11}$, at least $5\times10^{11}$, at least $1\times10^{12}$, at least $1\times10^{12}$, at least $2\times10^{12}$, at least $3\times10^{12}$, at least $4\times10^{12}$, at least $5\times10^{12}$, at least $6\times10^{12}$, at least $7\times10^{12}$, at least $8\times10^{12}$, at least $9\times10^{12}$, at least $1\times10^{13}$, at least $2\times10^{13}$, at least $3\times10^{13}$, at least $4\times10^{13}$, at least $5\times10^{13}$, at least $6\times10^{13}$, at least $7\times10^{13}$, at least $8\times10^{13}$, at least $9\times10^{13}$, or at least $1\times10^{14}$ vector genomes (vg) per milliliter (mL) (vg/mL).

In some embodiments, a composition disclosed herein (e.g., a composition comprising one or a plurality of rAAV constructs disclosed herein) is administered at an amount of at most $1\times10^{15}$, at most $5\times10^{14}$, at most $1\times10^{14}$, at most $5\times10^{13}$, at most $1\times10^{13}$, at most $9\times10^{12}$, at most $8\times10^{12}$, at most $7\times10^{12}$, at most $6\times10^{12}$, at most $5\times10^{12}$, at most $4\times10^{12}$, at most $3\times10^{12}$, at most $2\times10^{12}$, or at most $1\times10^{12}$ vector genomes (vg) per milliliter (mL).

In some embodiments, a composition disclosed herein (e.g., a composition comprising one or a plurality of rAAV constructs disclosed herein) is administered at an amount of about $1\times10^{12}$ vg/mL, about $1.1\times10^{12}$ vg/mL, $1.2\times10^{12}$ vg/mL, about $1.3\times10^{12}$ vg/mL, about $1.4\times10^{12}$ vg/mL, about $1.5\times10^{12}$ vg/mL, about $1.6\times10^{12}$ vg/mL, about $1.7\times10^{12}$ vg/mL, about $1.8\times10^{12}$ vg/mL, about $1.9\times10^{12}$ vg/mL, about $2.0\times10^{12}$ vg/mL, about $2.1\times10^{12}$ vg/mL, about $2.2\times10^{12}$ vg/mL, about $2.3\times10^{12}$ vg/mL, about $2.4\times10^{12}$ vg/mL, about $2.5\times10^{12}$ vg/mL, about $2.6\times10^{12}$ vg/mL, about $2.7\times10^{12}$ vg/mL, about $2.8\times10^{12}$ vg/mL, about $2.9\times10^{12}$ vg/mL, about $3.0\times10^{12}$ vg/mL, about $3.1\times10^{12}$ vg/mL, about $3.2\times10^{12}$ vg/mL, about $3.3\times10^{12}$ vg/mL, about $3.4\times10^{12}$ vg/mL, about $3.5\times10^{12}$ vg/mL, about $3.6\times10^{12}$ vg/mL, about $3.7\times10^{12}$ vg/mL, about $3.8\times10^{12}$ vg/mL, about $3.9\times10^{12}$ vg/mL, about $4.0\times10^{12}$ vg/mL, about $4.1\times10^{12}$ vg/mL, about $4.2\times10^{12}$ vg/mL, about $4.3\times10^{12}$ vg/mL, about $4.4\times10^{12}$ vg/mL, about $4.5\times10^{12}$ vg/mL, about $4.6\times10^{12}$ vg/mL, about $4.7\times10^{12}$ vg/mL, about $4.8\times10^{12}$ vg/mL, about $4.9\times10^{12}$ vg/mL, about $5.0\times10^{12}$ vg/mL, about $5.1\times10^{12}$ vg/mL, about $5.2\times10^{12}$ vg/mL, about $5.3\times10^{12}$ vg/mL, about $5.4\times10^{12}$ vg/mL, about $5.5\times10^{12}$ vg/mL, about $5.6\times10^{12}$ vg/mL, about $5.7\times10^{12}$ vg/mL, about $5.8\times10^{12}$ vg/mL, about $5.9\times10^{12}$ vg/mL, about $6.0\times10^{12}$ vg/mL, about $7.0\times10^{12}$ vg/mL, about $8.0\times10^{12}$ vg/mL, about $9.0\times10^{12}$ vg/mL, about $9.1\times10^{12}$ vg/mL, $9.2\times10^{12}$ vg/mL, about $9.3\times10^{12}$ vg/mL, about $9.4\times10^{12}$ vg/mL, about $9.5\times10^{12}$ vg/mL, about $9.6\times10^{12}$ vg/mL, about $9.7\times10^{12}$ vg/mL, about $9.8\times10^{12}$ vg/mL, about $9.9\times10^{12}$ vg/mL, about $1\times10^{13}$ vg/mL, $1.1\times10^{13}$ vg/mL, $1.2\times10^{13}$ vg/mL, $1.3\times10^{13}$ vg/mL, $1.4\times10^{13}$ vg/mL, $1.5\times10^{13}$ vg/mL, $1.6\times10^{13}$ vg/mL, $1.7\times10^{13}$ vg/mL, $1.8\times10^{13}$ vg/mL, $1.9\times10^{13}$ vg/mL, $2\times10^{13}$ vg/mL, $5\times10^{13}$ vg/mL, or $1\times10^{14}$ vg/mL.

In some embodiments, a composition disclosed herein (e.g., a composition comprising one or a plurality of rAAV constructs disclosed herein) is administered at an amount of $2.5\times10^{12}$ vg/mL+/−10%. In some embodiments, a composition disclosed herein (e.g., a composition comprising one or a plurality of rAAV constructs disclosed herein) is administered at an amount of $2.5\times10^{12}$ vg/mL.

In some embodiments, a composition disclosed herein (e.g., a composition comprising one or a plurality of rAAV constructs disclosed herein) is administered at an amount of $5\times10^{12}$ vg/mL+/−10%. In some embodiments, a composition disclosed herein (e.g., a composition comprising one or a plurality of rAAV constructs disclosed herein) is administered at an amount of $5\times10^{12}$ vg/mL.

In some embodiments, a composition disclosed herein (e.g., a composition comprising one or a plurality of rAAV constructs disclosed herein) is administered at an amount of $1\times10^{13}$ vg/mL+/−10%. In some embodiments, a composition disclosed herein (e.g., a composition comprising one or a plurality of rAAV constructs disclosed herein) is administered at an amount of $1\times10^{13}$ vg/mL.

In some embodiments, a composition disclosed herein (e.g., a composition comprising one or a plurality of rAAV constructs disclosed herein) is administered at an amount of about $1\times10^{10}$ to about $1\times10^{13}$ vg/cochlea, about $2\times10^{10}$ to about $1\times10^{13}$ vg/cochlea, about $3\times10^{10}$ to about $1\times10^{13}$ vg/cochlea, about $4\times10^{10}$ to about $1\times10^{13}$ vg/cochlea, about $5\times10^{10}$ to about $1\times10^{13}$ vg/cochlea, about $6\times10^{10}$ to about $1\times10^{13}$ vg/cochlea, about $7\times10^{10}$ to about $1\times10^{13}$ vg/cochlea, about $8\times10^{10}$ to about $1\times10^{13}$ vg/cochlea, about $9\times10^{10}$ to about $1\times10^{13}$ vg/cochlea, about $1\times10^{11}$ to about $1\times10^{13}$ vg/cochlea, about $2\times10^{11}$ to about $1\times10^{13}$ vg/cochlea, about $3\times10^{11}$ to about $1\times10^{13}$ vg/cochlea, about $4\times10^{11}$ to about $1\times10^{13}$ vg/cochlea, about $5\times10^{11}$ to about $1\times10^{13}$ vg/cochlea, about $6\times10^{11}$ to about $1\times10^{13}$ vg/cochlea, about $7\times10^{11}$ to about $1\times10^{13}$ vg/cochlea, about $8\times10^{11}$ to about $1\times10^{13}$ vg/cochlea, about $9\times10^{11}$ to about $1\times10^{13}$ vg/cochlea, about $1\times10^{12}$ to about $1\times10^{13}$ vg/cochlea, about $2\times10^{12}$ to about $1\times10^{13}$ vg/cochlea, about $3\times10^{12}$ to about $1\times10^{13}$ vg/cochlea, about $4\times10^{12}$ to about $1\times10^{13}$ vg/cochlea, about $5\times10^{12}$ to about $1\times10^{13}$ vg/cochlea, about $6\times10^{12}$ to about $1\times10^{13}$ vg/cochlea, about $7\times10^{12}$ to about $1\times10^{13}$ vg/cochlea, about $8\times10^{12}$ to about $1\times10^{13}$ vg/cochlea, or about $9\times10^{12}$ to about $1\times10^{13}$ vg/cochlea.

In some embodiments, a composition disclosed herein (e.g., a composition comprising one or a plurality of rAAV constructs disclosed herein) is administered at an amount of about $1\times10^{10}$ to about $1\times10^{13}$ vg/cochlea, about $1\times10^{10}$ to about $9\times10^{12}$ vg/cochlea, about $1\times10^{10}$ to about $8\times10^{12}$ vg/cochlea, about $1\times10^{10}$ to about $7\times10^{12}$ vg/cochlea, about $1\times10^{10}$ to about $6\times10^{12}$ vg/cochlea, about $1\times10^{10}$ to about $5\times10^{12}$ vg/cochlea, about $1\times10^{10}$ to about $4\times10^{12}$ vg/cochlea, about $1\times10^{10}$ to about $3\times10^{12}$ vg/cochlea, about $1\times10^{10}$ to about $2\times10^{12}$ vg/cochlea, about $1\times10^{10}$ to about $1\times10^{12}$ vg/cochlea, about $1\times10^{10}$ to about $9\times10^{11}$ vg/cochlea, about $1\times10^{10}$ to about $8\times10^{11}$ vg/cochlea, about $1\times10^{10}$ to about $7\times10^{11}$ vg/cochlea, about $1\times10^{10}$ to about $6\times10^{11}$ vg/cochlea, about $1\times10^{10}$ to about $5\times10^{11}$ vg/cochlea, about $1\times10^{10}$ to about $4\times10^{11}$ vg/cochlea, about $1\times10^{10}$ to about $3\times10^{11}$ vg/cochlea, about $1\times10^{10}$ to about $2\times10^{11}$ vg/cochlea, about $1\times10^{10}$ to about $1\times10^{11}$ vg/cochlea, about $1\times10^{10}$ to about $9\times10^{10}$ vg/cochlea, about $1\times10^{10}$ to about $8\times10^{10}$ vg/cochlea, about $1\times10^{10}$ to about $7\times10^{10}$ vg/cochlea, about $1\times10^{10}$ to about $6\times10^{10}$ vg/cochlea, about $1\times10^{10}$ to about $5\times10^{10}$ vg/cochlea, about $1\times10^{10}$ to about $4\times10^{10}$ vg/cochlea, about $1\times10^{10}$ to about $3\times10^{10}$ vg/cochlea, to about $1\times10^{10}$ to about $2\times10^{10}$ vg/cochlea.

In some embodiments, a composition disclosed herein (e.g., a composition comprising one or a plurality of rAAV constructs disclosed herein) is administered at an amount of about $1\times10^{10}$ to about $1\times10^{13}$ vg/cochlea, about $5\times10^{10}$ to about $5\times10^{12}$ vg/cochlea, about $8\times10^{10}$ to about $1\times10^{12}$ vg/cochlea, about $1\times10^{11}$ to about $9\times10^{11}$ vg/cochlea, about $2\times10^{11}$ to about $8\times10^{11}$ vg/cochlea, about $2.5\times10^{11}$ to about $5\times10^{11}$ vg/cochlea, about $3\times10^{11}$ to about $4.5\times10^{11}$ vg/cochlea.

In some embodiments, a composition disclosed herein (e.g., a composition comprising one or a plurality of rAAV constructs disclosed herein) is administered at an amount of about $1\times10^{10}$ vg/cochlea, about $5\times10^{10}$ vg/cochlea, about $1\times10^{11}$ vg/cochlea, about $1.5\times10^{11}$ vg/cochlea, about $2\times10^{11}$ vg/cochlea, about $2.1\times10^{11}$ vg/cochlea, $2.2\times10^{11}$ vg/cochlea, $2.3\times10^{11}$ vg/cochlea, $2.4\times10^{11}$ vg/cochlea, about $2.5\times10^{11}$ vg/cochlea, $2.6\times10^{11}$ vg/cochlea, $2.7\times10^{11}$ vg/cochlea, $2.8\times10^{11}$ vg/cochlea, $2.9\times10^{11}$ vg/cochlea, about $3\times10^{11}$ vg/cochlea, $3.1\times10^{11}$ vg/cochlea, $3.2\times10^{11}$ vg/cochlea, $3.3\times10^{11}$ vg/cochlea, $3.4\times10^{11}$ vg/cochlea, about $3.5\times10^{11}$ vg/cochlea, $3.6\times10^{11}$ vg/cochlea, $3.7\times10^{11}$ vg/cochlea, $3.8\times10^{11}$ vg/cochlea, $3.9\times10^{11}$ vg/cochlea, about $4\times10^{11}$ vg/cochlea, $4.1\times10^{11}$ vg/cochlea, $4.2\times10^{11}$ vg/cochlea, $4.3\times10^{11}$ vg/cochlea, $4.4\times10^{11}$ vg/cochlea, about $4.5\times10^{11}$ vg/cochlea, $4.6\times10^{11}$ vg/cochlea, $4.7\times10^{11}$ vg/cochlea, $4.8\times10^{11}$ vg/cochlea, $4.9\times10^{11}$ vg/cochlea, about $5\times10^{11}$ vg/cochlea, about $5.5\times10^{11}$ vg/cochlea, about $6\times10^{11}$ vg/cochlea, about $6.5\times10^{11}$ vg/cochlea, about $7\times10^{11}$ vg/cochlea, about $7.5\times10^{11}$ vg/cochlea, about $8\times10^{11}$ vg/cochlea, about $8.5\times10^{11}$ vg/cochlea, about $9\times10^{11}$ vg/cochlea, about $9.5\times10^{11}$ vg/cochlea, about $1\times10^{12}$ vg/cochlea.

In some embodiments, a composition disclosed herein (e.g., a composition comprising one or a plurality of rAAV constructs disclosed herein) is administered at an amount of $2.3\times10^{11}$ vg/cochlea, +/−10%. In some embodiments, a composition disclosed herein (e.g., a composition comprising one or a plurality of rAAV constructs disclosed herein) is administered at an amount of $2.3\times10^{11}$ vg/cochlea.

In some embodiments, a composition disclosed herein (e.g., a composition comprising one or a plurality of rAAV constructs disclosed herein) is administered at an amount of $4.5\times10^{11}$ vg/cochlea, +/−10%. In some embodiments, a composition disclosed herein (e.g., a composition comprising one or a plurality of rAAV constructs disclosed herein) is administered at an amount of $4.5\times10^{11}$ vg/cochlea.

In some embodiments, a composition disclosed herein (e.g., a composition comprising one or a plurality of rAAV constructs disclosed herein) is administered at an amount of $9\times10^{11}$ vg/cochlea, +/−10%. In some embodiments, a composition disclosed herein (e.g., a composition comprising one or a plurality of rAAV constructs disclosed herein) is administered at an amount of $9\times10^{11}$ vg/cochlea.

Single AAV Construct Compositions

In some embodiments, the present disclosure provides compositions or systems comprising rAAV particles comprised of a single construct. In some such embodiments, a single construct may deliver a polynucleotide that encodes a functional (e.g., as previously described and/or otherwise functional, e.g., codon optimized) copy of an anti-VEGF gene. In some embodiments, a construct is or comprises a rAAV construct. In some embodiments described herein, a single rAAV construct is capable of expressing a full-length anti-VEGF messenger RNA (mRNA) or a characteristic protein thereof in a target cell (e.g., an inner ear cell). In some embodiments, a single construct (e.g., any of the constructs described herein) can include a sequence encoding a functional anti-VEGF protein (e.g., any construct that generates functional anti-VEGF protein). In some embodiments, a single construct (e.g., any of the constructs described herein) can include a sequence encoding a functional anti-VEGF protein (e.g., any construct that generates functional antiVEGF protein) and optionally additional polypeptide sequences (e.g., regulatory sequences, and/or reporter sequences).

In some embodiments, a single construct composition or system may comprise any or all of the exemplary construct components described herein. In some embodiments, an exemplary single construct is represented by SEQ ID NO: 90. In some embodiments, an exemplary single construct is represented by SEQ ID NO: 91. In some embodiments, an exemplary single construct is represented by SEQ ID NO: 92. In some embodiments, an exemplary single construct is represented by SEQ ID NO: 93. In some embodiments, an exemplary single construct is represented by SEQ ID NO: 94. In some embodiments, an exemplary single construct is represented by SEQ ID NO: 95. In some embodiments, an exemplary single construct is represented by SEQ ID NO: 96. In some embodiments, an exemplary single construct is represented by SEQ ID NO: 106. In some embodiments, an exemplary single construct is represented by SEQ ID NO: 107. In some embodiments, an exemplary single construct is at least 85%, 90%, 95%, 98% or 99% identical to the sequence represented by SEQ ID NO: 90, 91, 92, 93, 94, 95, 96, 106, or 107. One skilled in the art would recognize that constructs may undergo additional modifications including codon-optimization, introduction of novel but functionally equivalent (e.g., silent mutations), addition of reporter sequences, and/or other routine modification.

In some embodiments, a construct has a sequence according to SEQ ID NO: 90, this construct may be referred to as an rAAV-ranibizumab-PC construct, is an exemplary embodiment of the schematic shown in FIG. 6, Panel (A), and encodes for the anti-VEGF protein ranibizumab. In some embodiments, an exemplary construct comprises: a 5' ITR exemplified by SEQ ID NO: 47, optionally a cloning site exemplified by SEQ ID NO: 81, a CMV enhancer exemplified by SEQ ID NO: 64, a CBA promoter exemplified by SEQ ID NO: 50, a chimeric intron exemplified by SEQ ID NO: 65, optionally a cloning site exemplified by SEQ ID NO: 78, an anti-VEGF coding region exemplified by SEQ ID NO: 103, optionally a cloning site exemplified by SEQ ID NO: 79, a poly(A) site exemplified by SEQ ID NO: 75, optionally a cloning site exemplified by SEQ ID NO: 82, and a 3' ITR exemplified by SEQ ID NO: 48.

In some embodiments, a construct has a sequence according to SEQ ID NO: 91, this construct may be referred to as an rAAV-ranibizumab construct, is an exemplary embodiment of the schematic shown in FIG. 6, Panel (A), and encodes for the anti-VEGF protein ranibizumab. In some embodiments, an exemplary construct comprises: a 5' ITR exemplified by SEQ ID NO: 45, optionally a cloning site exemplified by SEQ ID NO: 77, a CMV enhancer exemplified by SEQ ID NO: 64, a CBA promoter exemplified by SEQ ID NO: 49, a chimeric intron exemplified by SEQ ID NO: 65, optionally a cloning site exemplified by SEQ ID NO: 78, an anti-VEGF coding region exemplified by SEQ ID NO: 103, optionally a cloning site exemplified by SEQ ID NO: 79, a poly(A) site exemplified by SEQ ID NO: 75, optionally a cloning site exemplified by SEQ ID NO: 80, and a 3' ITR exemplified by SEQ ID NO: 46.

In some embodiments, a construct has a sequence according to SEQ ID NO: 92, this construct may be referred to as an rAAV-ranibizumab.2 construct, is an exemplary embodiment of the schematic shown in FIG. 6, Panel (A), and encodes for the anti-VEGF protein ranibizumab. In some embodiments, an exemplary construct comprises: a 5' ITR exemplified by SEQ ID NO: 45, optionally a cloning site exemplified by SEQ ID NO: 77, a CMV enhancer exemplified by SEQ ID NO: 64, a CBA promoter exemplified by SEQ ID NO: 50, a chimeric intron exemplified by SEQ ID NO: 65, optionally a cloning site exemplified by SEQ ID NO: 78, an anti-VEGF coding region exemplified by SEQ ID NO: 103, optionally a cloning site exemplified by SEQ ID NO: 79, a poly(A) site exemplified by SEQ ID NO: 75, optionally a cloning site exemplified by SEQ ID NO: 80, and a 3' ITR exemplified by SEQ ID NO: 46.

In some embodiments, a construct has a sequence according to SEQ ID NO: 106, this construct may be referred to as an rAAV-ranibizumab-GFP construct, is an exemplary embodiment of the schematic shown in FIG. 6, Panel (B), and encodes for the anti-VEGF protein ranibizumab. In some embodiments, an exemplary construct comprises: a 5' ITR exemplified by SEQ ID NO: 47, optionally a cloning site exemplified by SEQ ID NO: 81, a CMV enhancer exemplified by SEQ ID NO: 64, a CBA promoter exemplified by SEQ ID NO: 50, a chimeric intron exemplified by SEQ ID NO: 65, optionally a cloning site exemplified by SEQ ID NO: 78, an anti-VEGF coding region exemplified by SEQ ID NO: 103, optionally a reporter sequence exemplified by SEQ ID NO: 104, optionally a cloning site exemplified by SEQ ID NO: 79, a poly(A) site exemplified by SEQ ID NO: 75, optionally a cloning site exemplified by SEQ ID NO: 82, and a 3' ITR exemplified by SEQ ID NO: 48.

In some embodiments, a construct has a sequence according to SEQ ID NO: 93, this construct may be referred to as an rAAV-bevacizumab-PC construct, is an exemplary embodiment of the schematic shown in FIG. 6, Panel (C), and encodes for the anti-VEGF protein bevacizumab. In some embodiments, an exemplary construct comprises: a 5' ITR exemplified by SEQ ID NO: 47, optionally a cloning site exemplified by SEQ ID NO: 81, a CMV enhancer exemplified by SEQ ID NO: 64, a CBA promoter exemplified by SEQ ID NO: 50, a chimeric intron exemplified by SEQ ID NO: 65, optionally a cloning site exemplified by SEQ ID NO: 78, an anti-VEGF coding region exemplified by SEQ ID NO: 22, optionally a cloning site exemplified by SEQ ID NO: 79, a poly(A) site exemplified by SEQ ID NO: 75, optionally a cloning site exemplified by SEQ ID NO: 82, and a 3' ITR exemplified by SEQ ID NO: 48.

In some embodiments, a construct has a sequence according to SEQ ID NO: 94, this construct may be referred to as an rAAV-bevacizumab construct, is an exemplary embodiment of the schematic shown in FIG. 6, Panel (C), and encodes for the anti-VEGF protein bevacizumab. In some embodiments, an exemplary construct comprises: a 5' ITR exemplified by SEQ ID NO: 45, optionally a cloning site exemplified by SEQ ID NO: 77, a CMV enhancer exemplified by SEQ ID NO: 64, a CBA promoter exemplified by SEQ ID NO: 49, a chimeric intron exemplified by SEQ ID NO: 65, optionally a cloning site exemplified by SEQ ID NO: 78, an anti-VEGF coding region exemplified by SEQ ID NO: 22, optionally a cloning site exemplified by SEQ ID NO: 79, a poly(A) site exemplified by SEQ ID NO: 75, optionally a cloning site exemplified by SEQ ID NO: 80, and a 3' ITR exemplified by SEQ ID NO: 46.

In some embodiments, a construct has a sequence according to SEQ ID NO: 107, this construct may be referred to as an rAAV-bevacizumab-GFP construct, is an exemplary embodiment of the schematic shown in FIG. 6, Panel (B), and encodes for the anti-VEGF protein bevacizumab. In some embodiments, an exemplary construct comprises: a 5' ITR exemplified by SEQ ID NO: 47, optionally a cloning site exemplified by SEQ ID NO: 81, a CMV enhancer exemplified by SEQ ID NO: 64, a CBA promoter exemplified by SEQ ID NO: 50, a chimeric intron exemplified by SEQ ID NO: 65, optionally a cloning site exemplified by SEQ ID NO: 78, an anti-VEGF coding region exemplified by SEQ ID NO: 22, optionally a reporter sequence exemplified by SEQ ID NO: 104, optionally a cloning site exemplified by SEQ ID NO: 79, a poly(A) site exemplified by SEQ ID NO: 75, optionally a cloning site exemplified by SEQ ID NO: 82, and a 3' ITR exemplified by SEQ ID NO: 48.

In some embodiments, a construct has a sequence according to SEQ ID NO: 95, this construct may be referred to as an rAAV-aflibercept-PC construct, is an exemplary embodiment of the schematic shown in FIG. 6, Panel (D), and encodes for the anti-VEGF protein aflibercept. In some embodiments, an exemplary construct comprises: a 5' ITR exemplified by SEQ ID NO: 47, optionally a cloning site exemplified by SEQ ID NO: 81, a CMV enhancer exemplified by SEQ ID NO: 64, a CBA promoter exemplified by SEQ ID NO: 50, a chimeric intron exemplified by SEQ ID NO: 65, optionally a cloning site exemplified by SEQ ID NO: 78, an anti-VEGF coding region exemplified by SEQ ID NO: 42, optionally a cloning site exemplified by SEQ ID NO: 79, a poly(A) site exemplified by SEQ ID NO: 75, optionally a cloning site exemplified by SEQ ID NO: 82, and a 3' ITR exemplified by SEQ ID NO: 48.

In some embodiments, a construct has a sequence according to SEQ ID NO: 96, this construct may be referred to as an rAAV-aflibercept construct, is an exemplary embodiment of the schematic shown in FIG. 6, Panel (D), and encodes for the anti-VEGF protein aflibercept. In some embodiments, an exemplary construct comprises: a 5' ITR exemplified by SEQ ID NO: 45, optionally a cloning site exemplified by SEQ ID NO: 77, a CMV enhancer exemplified by SEQ ID NO: 64, a CBA promoter exemplified by SEQ ID NO: 49, a chimeric intron exemplified by SEQ ID NO: 65, optionally a cloning site exemplified by SEQ ID NO: 78, an anti-VEGF coding region exemplified by SEQ ID NO: 42, optionally a cloning site exemplified by SEQ ID NO: 79, a poly(A) site exemplified by SEQ ID NO: 75, optionally a cloning site exemplified by SEQ ID NO: 80, and a 3' ITR exemplified by SEQ ID NO: 46.

In certain embodiments, rAAVAnc80 particles comprising constructs encoding anti-VEGF proteins were produced and used to evaluate biological activity and inner ear tolerability of said construct, in order to support the biological plausibility and reasonable safety of local anti-VEGF therapy for VS. In some embodiments, such evaluations were made through a series of studies using the following approaches/models: transduction and/or transfection of a cell line, transduction and/or transfection of cochlear explants; intracochlear administration and transduction of wildtype mice cells; and/or intracochlear administration and transduction of NHP cells. Summaries of certain anti-VEGF particles are shown in Table 1.

TABLE 1

Summary of Particles Used or Planned for Use in Certain Studies

| Capsid | Promoter | VEGF inhibitor coding sequence | pA Signal |
| --- | --- | --- | --- |
| AAVAnc80 | CAG | Bevacizumab | bGH |
| AAVAnc80 | CAG | Ranibizumab | bGH |
| AAVAnc80 | CAG | Aflibercept | bGH |

Abbreviations: bGH = bovine growth hormone;

CAG = cytomegalovirus (CMV) early enhancer element, the chicken beta actin (CβA) gene sequence located between the 5' flanking region and the proximal region of the second exon, and the 3' splice sequence derived from the rabbit beta globin (RβG) gene (Miyazaki 1989; Niwa 1991; Orbán 2009, each of which is incorporated herein in its entirety by reference), which together are commonly referred to as the CAG promoter;

GLP = Good Laboratory Practice;

pA = polyadenylation.

```
Exemplary rAAV-Ranibizumab-PC Construct Sequence
                                            (SEQ ID NO: 90)
CTGCGCGCTCGCTCGCTCACTGAGGCCGCCCGGGCGTCGGGCGACCTTTGGTCGCCC

GGCCTCAGTGAGCGAGCGAGCGCGCAGAGAGGGAGTGGCCAACTCCATCACTAGGG

GTTCCTGCGGCCGCACGCGTGACATTGATTATTGACTAGTTATTAATAGTAATCAAT

TACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGACT

ATTTACGGTAAACTGCCCACTTGGCAGTACATCAAGTGTATCATATGCCAAGTACGC

CCCCTATTGACGTCAATGACGGTAAATGGCCCGCCTGGCATTATGCCCAGTACATGA

CCTTATGGGACTTTCCTACTTGGCAGTACATCTACGTATTAGTCATCGCTATTACCAT

GGGTCGAGGTGAGCCCCACGTTCTGCTTCACTCTCCCCATCTCCCCCCCCTCCCCACC

CCCAATTTTGTATTTATTTATTTTTTAATTATTTTGTGCAGCGATGGGGGCGGGGGGG

GGGGGGCGCGCGCCAGGCGGGGCGGGCGGGCGAGGGGCGGGCGGGGCGAG

GCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGG

AGTCGCTGCGTTGCCTTCGCCCCGTGCCCGCTCCGCGCCGCCTCGCGCCGCCCGCC

CCGGCTCTGACTGACCGCGTTACTCCCACAGGTGAGCGGGCGGGACGGCCCTTCTCC
```

-continued

```
TCCGGGCTGTAATTAGCGCTTGGTTTAATGACGGCTCGTTTCTTTTCTGTGGCTGCGT

GAAAGCCTTAAAGGGCTCCGGGAGGGCCCTTTGTGCGGGGGGGAGCGGCTCGGGGG

GTGCGTGCGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGG

GGAGCGCGGCCGGGGGCGGTGCCCCGCGGTGCGGGGGGGCTGCGAGGGGAACAAA

GGCTGCGTGCGGGGTGTGTGCGTGGGGGGGTGAGCAGGGGGTGTGGGCGCGGCGGT

CGGGCTGTAACCCCCCCCTGCACCCCCCTCCCCGAGTTGCTGAGCACGGCCCGGCTT

CGGGTGCGGGGCTCCGTGCGGGGCGTGGCGCGGGGCTCGCCGTGCCGGGCGGGGGG

TGGCGGCAGGTGGGGGTGCCGGGCGGGGCGGGGCCGCCTCGGGCCGGGGAGGGCT

CGGGGGAGGGGCGCGGCGGCCCCCGGAGCGCCGGCGGCTGTCGAGGCGCGGCGAG

CCGCAGCCATTGCCTTTTATGGTAATCGTGCGAGAGGGCGCAGGGACTTCCTTTGTC

CCAAATCTGTGCGGAGCCGAAATCTGGGAGGCGCCGCCGCACCCCCTCTAGCGGGC

GCGGGGCGAAGCGGTGCGGCGCCGGCAGGAAGGAAATGGGCGGGGAGGGCCTTCG

TGCGTCGCCGCGCCGCCGTCCCCTTCTCCCTCTCCAGCCTCGGGGCTGTCCGCGGGG

GGACGGCTGCCTTCGGGGGGGACGGGGCAGGGCGGGGTTCGGCTTCTGGCGTGTGA

CCGGCGGCTCTAGAGCCTCTGCTAACCATGTTCATGCCTTCTTCTTTTTCCTACAGCT

CCTGGGCAACGTGCTGGTTATTGTGACCGGTGCCACCATGTACCGGATGCAGCTGCT

GAGCTGTATCGCCCTGTCTCTGGCCCTGGTCACCAATTCTGAGGTGCAGCTGGTGGA

ATCTGGCGGCGGACTTGTTCAACCTGGCGGCTCTCTGAGACTGAGCTGTGCCGCTTC

TGGCTACGACTTCACCCACTACGGCATGAACTGGGTCCGACAGGCCCCTGGCAAAG

GCCTTGAATGGGTCGGATGGATCAACACCTACACCGGCGAGCCAACATACGCCGCC

GACTTCAAGCGGAGATTCACCTTCAGCCTGGACACCAGCAAGAGCACCGCCTACCT

GCAGATGAACAGCCTGAGAGCCGAGGACACCGCCGTGTACTACTGCGCCAAGTATC

CCTACTACTACGGCACCAGCCACTGGTACTTTGACGTGTGGGGACAGGGCACACTG

GTCACAGTGTCTAGCGCCTCTACAAAGGGCCCCAGCGTTTTCCCACTGGCTCCTAGC

AGCAAGTCTACCAGCGGAGGAACAGCCGCTCTGGGCTGTCTGGTCAAGGACTACTTT

CCCGAGCCTGTGACCGTGTCCTGGAATTCTGGCGCTCTGACAAGCGGCGTGCACACC

TTTCCAGCTGTGCTGCAAAGCAGCGGCCTGTACTCTCTGAGCAGCGTCGTGACAGTG

CCAAGCAGCTCTCTGGGCACCCAGACCTACATCTGCAATGTGAACCACAAGCCTAG

CAACACCAAGGTGGACAAGAAGGTGGAACCCAAGAGCTGCGACAAGACCCACACC

GGCAAGCGGAAGAGAAGAGGCTCTGGCGAAGGCAGAGGCAGCCTGCTTACATGTG

GCGACGTGGAAGAGAACCCCGGACCTATGTATAGAATGCAGCTCCTGTCCTGCATTG

CCCTGAGCCTGGCTCTCGTGACCAACAGCGACATCCAGCTGACACAGAGCCCCAGC

AGCCTGTCTGCCTCTGTGGGAGACAGAGTGACCATCACCTGTAGCGCCAGCCAGGA

CATCTCCAACTACCTGAACTGGTATCAGCAAAAGCCCGGCAAGGCCCCTAAGGTGC

TGATCTACTTCACAAGCAGCCTGCACTCCGGCGTGCCCAGCAGATTTTCTGGCTCTG

GCAGCGGCACCGACTTCACCCTGACCATATCTAGCCTGCAGCCTGAGGACTTCGCCA

CCTACTACTGCCAGCAGTACAGCACCGTGCCTTGGACATTTGGCCAGGGCACAAAG

GTGGAAATCAAGCGGACTGTGGCCGCTCCTAGCGTGTTCATCTTTCCACCTAGCGAC

GAGCAGCTGAAGTCTGGCACAGCCTCTGTCGTGTGCCTGCTGAACAACTTCTACCCC
```

-continued

```
AGAGAAGCCAAGGTGCAGTGGAAAGTGGACAATGCCCTGCAGAGCGGCAACAGCC

AAGAGAGCGTGACAGAGCAGGACTCCAAGGATAGCACCTATAGCCTGAGCAGCACC

CTGACACTGAGCAAGGCCGACTACGAGAAGCACAAAGTGTACGCCTGCGAAGTGAC

CCACCAGGGCCTTTCTAGCCCTGTGACCAAGAGCTTCAACCGGGGCGAATGTTAAG

AGCTCGCTGATCAGCCTCGACTGTGCCTTCTAGTTGCCAGCCATCTGTTGTTTGCCCC

TCCCCCGTGCCTTCCTTGACCCTGGAAGGTGCCACTCCCACTGTCCTTTCCTAATAAA

ATGAGGAAATTGCATCGCATTGTCTGAGTAGGTGTCATTCTATTCTGGGGGGTGGGG

TGGGGCAGGACAGCAAGGGGGAGGATTGGGAAGACAATAGCAGGCATGCTGGGGA

TGCGGTGGGCTCTATGGAAGCTTGAATTCAGCTGACGTGCCTCGGACCGCTAGGAAC

CCCTAGTGATGGAGTTGGCCACTCCCTCTCTGCGCGCTCGCTCGCTCACTGAGGCCG

GGCGACCAAAGGTCGCCCGACGCCCGGGCTTTGCCCGGGCGGCCTCAGTGAGCGAG

CGAGCGCGCAG
```

Exemplary rAAV-Ranibizumab Construct Sequence
(SEQ ID NO: 91)

```
TTGGCCACTCCCTCTCTGCGCGCTCGCTCGCTCACTGAGGCCGCCCGGGCAAAGCCC

GGGCGTCGGGCGACCTTTGGTCGCCCGGCCTCAGTGAGCGAGCGAGCGCGCAGAGA

GGGAGTGGCCAACTCCATCACTAGGGGTTCCTTTGTCGACGCGGCCGCACGCGTGAC

ATTGATTATTGACTAGTTATTAATAGTAATCAATTACGGGGTCATTAGTTCATAGCCC

ATATATGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGACTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCT

GCTTCACTCTCCCCATCTCCCCCCCCTCCCCACCCCCAATTTTGTATTTATTTATTTTT

TAATTATTTTGTGCAGCGATGGGGGCGGGGGGGGGGGGGGGCGCGCGCCAGGCGG

GGCGGGGCGGGGCGAGGGGCGGGGCGGGGCGAGGCGGAGAGGTGCGGCGGCAGCC

AATCAGAGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGTTGCCTTCGCCCC

GTGCCCCGCTCCGCGCCGCCTCGCGCCGCCCGCCCCGGCTCTGACTGACCGCGTTAC

TCCCACAGGTGAGCGGGCGGGACGGCCCTTCTCCTCCGGGCTGTAATTAGCGCTTGG

TTTAATGACGGCTCGTTTCTTTTCTGTGGCTGCGTGAAAGCCTTAAAGGGCTCCGGG

AGGGCCCTTTGTGCGGGGGGGAGCGGCTCGGGGGTGCGTGCGTGTGTGTGCGT

GGGGAGCGCCGCGTGCGGCCCGCGCTGCCCGGCGGCTGTGAGCGCTGCGGGCGCGG

CGCGGGGCTTTGTGCGCTCCGCGTGTGCGCGAGGGGAGCGCGGCCGGGGGCGGTGC

CCCGCGGTGCGGGGGGGCTGCGAGGGGAACAAAGGCTGCGTGCGGGGTGTGTGCGT

GGGGGGGTGAGCAGGGGGTGTGGGCGCGGCGGTCGGGCTGTAACCCCCCCCTGCAC

CCCCCTCCCCGAGTTGCTGAGCACGGCCCGGCTTCGGGTGCGGGGCTCCGTGCGGGG

CGTGGCGCGGGGCTCGCCGTGCCGGGCGGGGGTGGCGGCAGGTGGGGGTGCCGG

GCGGGGCGGGGCCGCCTCGGGCCGGGGAGGGCTCGGGGAGGGGCGCGGCGGCCC

CCGGAGCGCCGGCGGCTGTCGAGGCGCGGCGAGCCGCAGCCATTGCCTTTTATGGT

AATCGTGCGAGAGGGCGCAGGGACTTCCTTTGTCCCAAATCTGTGCGGAGCCGAAA
```

-continued

```
TCTGGGAGGCGCCGCCGCACCCCCTCTAGCGGGCGCGGGGCGAAGCGGTGCGGCGC

CGGCAGGAAGGAAATGGGCGGGGAGGGCCTTCGTGCGTCGCCGCGCCGCCGTCCCC

TTCTCCCTCTCCAGCCTCGGGGCTGTCCGCGGGGGGACGGCTGCCTTCGGGGGGAC

GGGGCAGGGCGGGGTTCGGCTTCTGGCGTGTGACCGGCGGCTCTAGAGCCTCTGCTA

ACCATGTTCATGCCTTCTTCTTTTTCCTACAGCTCCTGGGCAACGTGCTGGTTATTGT

GACCGGTGCCACCATGTACCGGATGCAGCTGCTGAGCTGTATCGCCCTGTCTCTGGC

CCTGGTCACCAATTCTGAGGTGCAGCTGGTGGAATCTGGCGGCGGACTTGTTCAACC

TGGCGGCTCTCTGAGACTGAGCTGTGCCGCTTCTGGCTACGACTTCACCCACTACGG

CATGAACTGGGTCCGACAGGCCCCTGGCAAAGGCCTTGAATGGGTCGGATGGATCA

ACACCTACACCGGCGAGCCAACATACGCCGCCGACTTCAAGCGGAGATTCACCTTC

AGCCTGGACACCAGCAAGAGCACCGCCTACCTGCAGATGAACAGCCTGAGAGCCGA

GGACACCGCCGTGTACTACTGCGCCAAGTATCCCTACTACTACGGCACCAGCCACTG

GTACTTTGACGTGTGGGGACAGGGCACACTGGTCACAGTGTCTAGCGCCTCTACAAA

GGGCCCCAGCGTTTTCCCACTGGCTCCTAGCAGCAAGTCTACCAGCGGAGGAACAG

CCGCTCTGGGCTGTCTGGTCAAGGACTACTTTCCCGAGCCTGTGACCGTGTCCTGGA

ATTCTGGCGCTCTGACAAGCGGCGTGCACACCTTTCCAGCTGTGCTGCAAAGCAGCG

GCCTGTACTCTCTGAGCAGCGTCGTGACAGTGCCAAGCAGCTCTCTGGGCACCCAGA

CCTACATCTGCAATGTGAACCACAAGCCTAGCAACACCAAGGTGGACAAGAAGGTG

GAACCCAAGAGCTGCGACAAGACCCACACCGGCAAGCGGAAGAGAAGAGGCTCTG

GCGAAGGCAGAGGCAGCCTGCTTACATGTGGCGACGTGGAAGAGAACCCCGGACCT

ATGTATAGAATGCAGCTCCTGTCCTGCATTGCCCTGAGCCTGGCTCTCGTGACCAAC

AGCGACATCCAGCTGACACAGAGCCCCAGCAGCCTGTCTGCCTCTGTGGGAGACAG

AGTGACCATCACCTGTAGCGCCAGCCAGGACATCTCCAACTACCTGAACTGGTATCA

GCAAAAGCCCGGCAAGGCCCCTAAGGTGCTGATCTACTTCACAAGCAGCCTGCACT

CCGGCGTGCCCAGCAGATTTTCTGGCTCTGGCAGCGGCACCGACTTCACCCTGACCA

TATCTAGCCTGCAGCCTGAGGACTTCGCCACCTACTACTGCCAGCAGTACAGCACCG

TGCCTTGGACATTTGGCCAGGGCACAAAGGTGGAAATCAAGCGGACTGTGGCCGCT

CCTAGCGTGTTCATCTTTCCACCTAGCGACGAGCAGCTGAAGTCTGGCACAGCCTCT

GTCGTGTGCCTGCTGAACAACTTCTACCCCAGAGAAGCCAAGGTGCAGTGGAAAGT

GGACAATGCCCTGCAGAGCGGCAACAGCCAAGAGAGCGTGACAGAGCAGGACTCC

AAGGATAGCACCTATAGCCTGAGCAGCACCCTGACACTGAGCAAGGCCGACTACGA

GAAGCACAAAGTGTACGCCTGCGAAGTGACCCACCAGGGCCTTTCTAGCCCTGTGA

CCAAGAGCTTCAACCGGGGCGAATGTTAAGAGCTCGCTGATCAGCCTCGACTGTGC

CTTCTAGTTGCCAGCCATCTGTTGTTTGCCCCTCCCCCGTGCCTTCCTTGACCCTGGA

AGGTGCCACTCCCACTGTCCTTTCCTAATAAAATGAGGAAATTGCATCGCATTGTCT

GAGTAGGTGTCATTCTATTCTGGGGGGTGGGGTGGGCAGGACAGCAAGGGGGAGG

ATTGGGAAGACAATAGCAGGCATGCTGGGGATGCGGTGGGCTCTATGGAAGCTTGA

ATTCAGCTGACGTGCCTCGGACCGCCTAGGAGGAACCCCTAGTGATGGAGTTGGCC

ACTCCCTCTCTGCGCGCTCGCTCGCTCACTGAGGCCGGGCGACCAAAGGTCGCCCGA
```

-continued

CGCCCGGGCTTTGCCCGGGCGGCCTCAGTGAGCGAGCGAGCGCGCAGAGAGGGAGT

GGCCAA

Exemplary rAAV-Ranibizumab.2 Construct Sequence
(SEQ ID NO: 92)
TTGGCCACTCCCTCTCTGCGCGCTCGCTCGCTCACTGAGGCCGCCCGGGCAAAGCCC

GGGCGTCGGGCGACCTTTGGTCGCCCGGCCTCAGTGAGCGAGCGAGCGCGCAGAGA

GGGAGTGGCCAACTCCATCACTAGGGGTTCCTTTGTCGACGCGGCCGCACGCGTGAC

ATTGATTATTGACTAGTTATTAATAGTAATCAATTACGGGGTCATTAGTTCATAGCCC

ATATATGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGACTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA

GTACATCTACGTATTAGTCATCGCTATTACCATGGGTCGAGGTGAGCCCCACGTTCT

GCTTCACTCTCCCCATCTCCCCCCCCTCCCCACCCCCAATTTTGTATTTATTTATTTTT

TAATTATTTTGTGCAGCGATGGGGGCGGGGGGGGGGGGGCGCGCGCCAGGCGGGG

CGGGGCGGGGCGAGGGGCGGGGCGGGGCGAGGCGGAGAGGTGCGGCGGCAGCCAA

TCAGAGCGGCGCGCTCCGAAAGTTTCCTTTTATGGCGAGGCGGCGGCGGCGGCGGC

CCTATAAAAAGCGAAGCGCGCGGCGGGCGGGAGTCGCTGCGTTGCCTTCGCCCCGT

GCCCCGCTCCGCGCCGCCTCGCGCCGCCCGCCCCGGCTCTGACTGACCGCGTTACTC

CCACAGGTGAGCGGGCGGGACGGCCCTTCTCCTCCGGGCTGTAATTAGCGCTTGGTT

TAATGACGGCTCGTTTCTTTTCTGTGGCTGCGTGAAAGCCTTAAAGGGCTCCGGGAG

GGCCCTTTGTGCGGGGGGAGCGGCTCGGGGGTGCGTGCGTGTGTGTGCGTGG

GGAGCGCCGCGTGCGGCCCGCGCTGCCCGGCGGCTGTGAGCGCTGCGGGCGCGGCG

CGGGGCTTTGTGCGCTCCGCGTGTGCGCGAGGGGAGCGCGGCCGGGGCGGTGCCC

CGCGGTGCGGGGGGGCTGCGAGGGGAACAAAGGCTGCGTGCGGGGTGTGTGCGTGG

GGGGGTGAGCAGGGGGTGTGGGCGCGGCGGTCGGGCTGTAACCCCCCCCTGCACCC

CCCTCCCCGAGTTGCTGAGCACGGCCCGGCTTCGGGTGCGGGGCTCCGTGCGGGGC

GTGGCGCGGGGCTCGCCGTGCCGGGCGGGGGTGGCGGCAGGTGGGGGTGCCGGG

CGGGGCGGGGCCGCCTCGGGCCGGGGAGGGCTCGGGGGAGGGGCGCGGCGGCCCC

CGGAGCGCCGGCGGCTGTCGAGGCGCGGCGAGCCGCAGCCATTGCCTTTTATGGTA

ATCGTGCGAGAGGGCGCAGGGACTTCCTTTGTCCCAAATCTGTGCGGAGCCGAAATC

TGGGAGGCGCCGCCGCACCCCCTCTAGCGGGCGCGGGGCGAAGCGGTGCGGCGCCG

GCAGGAAGGAAATGGGCGGGAGGGCCTTCGTGCGTCGCCGCGCCGCCGTCCCCTT

CTCCCTCTCCAGCCTCGGGGCTGTCCGCGGGGGGACGGCTGCCTTCGGGGGGGACG

GGGCAGGGCGGGGTTCGGCTTCTGGCGTGTGACCGGCGGCTCTAGAGCCTCTGCTAA

CCATGTTCATGCCTTCTTCTTTTTCCTACAGCTCCTGGGCAACGTGCTGGTTATTGTG

ACCGGTGCCACCATGTACCGGATGCAGCTGCTGAGCTGTATCGCCCTGTCTCTGGCC

CTGGTCACCAATTCTGAGGTGCAGCTGGTGGAATCTGGCGGCGGACTTGTTCAACCT

GGCGGCTCTCTGAGACTGAGCTGTGCCGCTTCTGGCTACGACTTCACCCACTACGGC

ATGAACTGGGTCCGACAGGCCCCTGGCAAAGGCCTTGAATGGGTCGGATGGATCAA

```
-continued
CACCTACACCGGCGAGCCAACATACGCCGCCGACTTCAAGCGGAGATTCACCTTCA

GCCTGGACACCAGCAAGAGCACCGCCTACCTGCAGATGAACAGCCTGAGAGCCGAG

GACACCGCCGTGTACTACTGCGCCAAGTATCCCTACTACTACGGCACCAGCCACTGG

TACTTTGACGTGTGGGGACAGGGCACACTGGTCACAGTGTCTAGCGCCTCTACAAAG

GGCCCCAGCGTTTTCCCACTGGCTCCTAGCAGCAAGTCTACCAGCGGAGGAACAGC

CGCTCTGGGCTGTCTGGTCAAGGACTACTTTCCCGAGCCTGTGACCGTGTCCTGGAA

TTCTGGCGCTCTGACAAGCGGCGTGCACACCTTTCCAGCTGTGCTGCAAAGCAGCGG

CCTGTACTCTCTGAGCAGCGTCGTGACAGTGCCAAGCAGCTCTCTGGGCACCCAGAC

CTACATCTGCAATGTGAACCACAAGCCTAGCAACACCAAGGTGGACAAGAAGGTGG

AACCCAAGAGCTGCGACAAGACCCACACCGGCAAGCGGAAGAGAAGAGGCTCTGG

CGAAGGCAGAGGCAGCCTGCTTACATGTGGCGACGTGGAAGAGAACCCCGGACCTA

TGTATAGAATGCAGCTCCTGTCCTGCATTGCCCTGAGCCTGGCTCTCGTGACCAACA

GCGACATCCAGCTGACACAGAGCCCCAGCAGCCTGTCTGCCTCTGTGGGAGACAGA

GTGACCATCACCTGTAGCGCCAGCCAGGACATCTCCAACTACCTGAACTGGTATCAG

CAAAAGCCCGGCAAGGCCCCTAAGGTGCTGATCTACTTCACAAGCAGCCTGCACTC

CGGCGTGCCCAGCAGATTTTCTGGCTCTGGCAGCGGCACCGACTTCACCCTGACCAT

ATCTAGCCTGCAGCCTGAGGACTTCGCCACCTACTACTGCCAGCAGTACAGCACCGT

GCCTTGGACATTTGGCCAGGGCACAAAGGTGGAAATCAAGCGGACTGTGGCCGCTC

CTAGCGTGTTCATCTTTCCACCTAGCGACGAGCAGCTGAAGTCTGGCACAGCCTCTG

TCGTGTGCCTGCTGAACAACTTCTACCCCAGAGAAGCCAAGGTGCAGTGGAAAGTG

GACAATGCCCTGCAGAGCGGCAACAGCCAAGAGAGCGTGACAGAGCAGGACTCCA

AGGATAGCACCTATAGCCTGAGCAGCACCCTGACACTGAGCAAGGCCGACTACGAG

AAGCACAAAGTGTACGCCTGCGAAGTGACCCACCAGGGCCTTTCTAGCCCTGTGAC

CAAGAGCTTCAACCGGGGCGAATGTTAAGAGCTCGCTGATCAGCCTCGACTGTGCCT

TCTAGTTGCCAGCCATCTGTTGTTTGCCCCTCCCCCGTGCCTTCCTTGACCCTGGAAG

GTGCCACTCCCACTGTCCTTTCCTAATAAAATGAGGAAATTGCATCGCATTGTCTGA

GTAGGTGTCATTCTATTCTGGGGGGTGGGGTGGGGCAGGACAGCAAGGGGGAGGAT

TGGGAAGACAATAGCAGGCATGCTGGGGATGCGGTGGGCTCTATGGAAGCTTGAAT

TCAGCTGACGTGCCTCGGACCGCCTAGGAGGAACCCCTAGTGATGGAGTTGGCCAC

TCCCTCTCTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGAGAGGGAGTGG

CCAA

Exemplary rAAV-Ranibizumab-GFP Construct Sequence
                                            (SEQ ID NO: 106)
CTGCGCGCTCGCTCGCTCACTGAGGCCGCCCGGGCGTCGGGCGACCTTTGGTCGCCC

GGCCTCAGTGAGCGAGCGAGCGCGCAGAGAGGGAGTGGCCAACTCCATCACTAGGG

GTTCCTGCGGCCGCACGCGTGACATTGATTATTGACTAGTTATTAATAGTAATCAAT

TACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGACT

ATTTACGGTAAACTGCCCACTTGGCAGTACATCAAGTGTATCATATGCCAAGTACGC

CCCCTATTGACGTCAATGACGGTAAATGGCCCGCCTGGCATTATGCCCAGTACATGA
```

-continued

```
CCTTATGGGACTTTCCTACTTGGCAGTACATCTACGTATTAGTCATCGCTATTACCAT

GGGTCGAGGTGAGCCCCACGTTCTGCTTCACTCTCCCCATCTCCCCCCCCTCCCCACC

CCCAATTTTGTATTTATTTATTTTTTAATTATTTTGTGCAGCGATGGGGGCGGGGGGG

GGGGGGGCGCGCGCCAGGCGGGGCGGGGCGGGGCGAGGGGCGGGGCGGGGCGAG

GCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCCGCCCGCC

CCGGCTCTGACTGACCGCGTTACTCCCACAGGTGAGCGGGCGGGACGGCCCTTCTCC

TCCGGGCTGTAATTAGCGCTTGGTTTAATGACGGCTCGTTTCTTTTCTGTGGCTGCGT

GAAAGCCTTAAAGGGCTCCGGGAGGGCCCTTTGTGCGGGGGGGAGCGGCTCGGGGG

GTGCGTGCGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGG

GGAGCGCGGCCGGGGGCGGTGCCCCGCGGTGCGGGGGGGCTGCGAGGGGAACAAA

GGCTGCGTGCGGGGTGTGTGCGTGGGGGGGTGAGCAGGGGGTGTGGGCGCGGCGGT

CGGGCTGTAACCCCCCCCTGCACCCCCCTCCCCGAGTTGCTGAGCACGGCCCGGCTT

CGGGTGCGGGGCTCCGTGCGGGGCGTGGCGCGGGGCTCGCCGTGCCGGGCGGGGGG

TGGCGGCAGGTGGGGGTGCCGGGCGGGGCGGGGCCGCCTCGGGCCGGGGAGGGCT

CGGGGGAGGGGCGCGGCGGCCCCCGGAGCGCCGGCGGCTGTCGAGGCGCGGCGAG

CCGCAGCCATTGCCTTTTATGGTAATCGTGCGAGAGGGCGCAGGGACTTCCTTTGTC

CCAAATCTGTGCGGAGCCGAAATCTGGGAGGCGCCGCCGCACCCCCTCTAGCGGGC

GCGGGGCGAAGCGGTGCGGCGCCGGCAGGAAGGAAATGGGCGGGGAGGGCCTTCG

TGCGTCGCCGCGCCGCCGTCCCCTTCTCCCTCTCCAGCCTCGGGGCTGTCCGCGGGG

GGACGGCTGCCTTCGGGGGGGACGGGGCAGGGCGGGGTTCGGCTTCTGGCGTGTGA

CCGGCGGCTCTAGAGCCTCTGCTAACCATGTTCATGCCTTCTTCTTTTTCCTACAGCT

CCTGGGCAACGTGCTGGTTATTGTGACCGGTGCCACCATGTACCGGATGCAGCTGCT

GAGCTGTATCGCCCTGTCTCTGGCCCTGGTCACCAATTCTGAGGTGCAGCTGGTGGA

ATCTGGCGGCGGACTTGTTCAACCTGGCGGCTCTCTGAGACTGAGCTGTGCCGCTTC

TGGCTACGACTTCACCCACTACGGCATGAACTGGGTCCGACAGGCCCCTGGCAAAG

GCCTTGAATGGGTCGGATGGATCAACACCTACACCGGCGAGCCAACATACGCCGCC

GACTTCAAGCGGAGATTCACCTTCAGCCTGGACACCAGCAAGAGCACCGCCTACCT

GCAGATGAACAGCCTGAGAGCCGAGGACACCGCCGTGTACTACTGCGCCAAGTATC

CCTACTACTACGGCACCAGCCACTGGTACTTTGACGTGTGGGGACAGGGCACACTG

GTCACAGTGTCTAGCGCCTCTACAAAGGGCCCCAGCGTTTTCCCACTGGCTCCTAGC

AGCAAGTCTACCAGCGGAGGAACAGCCGCTCTGGGCTGTCTGGTCAAGGACTACTTT

CCCGAGCCTGTGACCGTGTCCTGGAATTCTGGCGCTCTGACAAGCGGCGTGCACACC

TTTCCAGCTGTGCTGCAAAGCAGCGGCCTGTACTCTCTGAGCAGCGTCGTGACAGTG

CCAAGCAGCTCTCTGGGCACCCAGACCTACATCTGCAATGTGAACCACAAGCCTAG

CAACACCAAGGTGGACAAGAAGGTGGAACCCAAGAGCTGCGACAAGACCCACACC

GGCAAGCGGAAGAGAAGAGGCTCTGGCGAAGGCAGAGGCAGCCTGCTTACATGTG

GCGACGTGGAAGAGAACCCCGGACCTATGTATAGAATGCAGCTCCTGTCCTGCATTG
```

```
CCCTGAGCCTGGCTCTCGTGACCAACAGCGACATCCAGCTGACACAGAGCCCCAGC

AGCCTGTCTGCCTCTGTGGGAGACAGAGTGACCATCACCTGTAGCGCCAGCCAGGA

CATCTCCAACTACCTGAACTGGTATCAGCAAAAGCCCGGCAAGGCCCCTAAGGTGC

TGATCTACTTCACAAGCAGCCTGCACTCCGGCGTGCCCAGCAGATTTTCTGGCTCTG

GCAGCGGCACCGACTTCACCCTGACCATATCTAGCCTGCAGCCTGAGGACTTCGCCA

CCTACTACTGCCAGCAGTACAGCACCGTGCCTTGGACATTTGGCCAGGGCACAAAG

GTGGAAATCAAGCGGACTGTGGCCGCTCCTAGCGTGTTCATCTTTCCACCTAGCGAC

GAGCAGCTGAAGTCTGGCACAGCCTCTGTCGTGTGCCTGCTGAACAACTTCTACCCC

AGAGAAGCCAAGGTGCAGTGGAAAGTGGACAATGCCCTGCAGAGCGGCAACAGCC

AAGAGAGCGTGACAGAGCAGGACTCCAAGGATAGCACCTATAGCCTGAGCAGCACC

CTGACACTGAGCAAGGCCGACTACGAGAAGCACAAAGTGTACGCCTGCGAAGTGAC

CCACCAGGGCCTTTCTAGCCCTGTGACCAAGAGCTTCAACCGGGGCGAATGTATGGT

GAGCAAGGGCGAGGAGCTGTTCACCGGGGTGGTGCCCATCCTGGTCGAGCTGGACG

GCGACGTAAACGGCCACAAGTTCAGCGTGTCCGGCGAGGGCGAGGGCGATGCCACC

TACGGCAAGCTGACCCTGAAGTTCATCTGCACCACCGGCAAGCTGCCCGTGCCCTGG

CCCACCCTCGTGACCACCCTGACCTACGGCGTGCAGTGCTTCAGCCGCTACCCCGAC

CACATGAAGCAGCACGACTTCTTCAAGTCCGCCATGCCCGAAGGCTACGTCCAGGA

GCGCACCATCTTCTTCAAGGACGACGGCAACTACAAGACCCGCGCCGAGGTGAAGT

TCGAGGGCGACACCCTGGTGAACCGCATCGAGCTGAAGGGCATCGACTTCAAGGAG

GACGGCAACATCCTGGGGCACAAGCTGGAGTACAACTACAACAGCCACAACGTCTA

TATCATGGCCGACAAGCAGAAGAACGGCATCAAGGTGAACTTCAAGATCCGCCACA

ACATCGAGGACGGCAGCGTGCAGCTCGCCGACCACTACCAGCAGAACACCCCCATC

GGCGACGGCCCCGTGCTGCTGCCCGACAACCACTACCTGAGCACCCAGTCCGCCCTG

AGCAAAGACCCCAACGAGAAGCGCGATCACATGGTCCTGCTGGAGTTCGTGACCGC

CGCCGGGATCACTCTCGGCATGGACGAGCTGTACAAGTAAGAGCTCGCTGATCAGC

CTCGACTGTGCCTTCTAGTTGCCAGCCATCTGTTGTTTGCCCCTCCCCCGTGCCTTCC

TTGACCCTGGAAGGTGCCACTCCCACTGTCCTTTCCTAATAAAATGAGGAAATTGCA

TCGCATTGTCTGAGTAGGTGTCATTCTATTCTGGGGGGTGGGGTGGGGCAGGACAGC

AAGGGGGAGGATTGGGAAGACAATAGCAGGCATGCTGGGGATGCGGTGGGCTCTAT

GGAAGCTTGAATTCAGCTGACGTGCCTCGGACCGCTAGGAACCCCTAGTGATGGAG

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAG

Exemplary rAAV-Bevacizumab-PC Construct Sequence
                                          (SEQ ID NO: 93)
CTGCGCGCTCGCTCGCTCACTGAGGCCGCCCGGGCGTCGGGCGACCTTTGGTCGCCC

GGCCTCAGTGAGCGAGCGAGCGCGCAGAGAGGGAGTGGCCAACTCCATCACTAGGG

GTTCCTGCGGCCGCACGCGTGACATTGATTATTGACTAGTTATTAATAGTAATCAAT

TACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGACT

ATTTACGGTAAACTGCCCACTTGGCAGTACATCAAGTGTATCATATGCCAAGTACGC

CCCCTATTGACGTCAATGACGGTAAATGGCCCGCCTGGCATTATGCCCAGTACATGA
```

```
CCTTATGGGACTTTCCTACTTGGCAGTACATCTACGTATTAGTCATCGCTATTACCAT

GGGTCGAGGTGAGCCCCACGTTCTGCTTCACTCTCCCCATCTCCCCCCCCTCCCCACC

CCCAATTTTGTATTTATTTATTTTTTAATTATTTTGTGCAGCGATGGGGGCGGGGGGG

GGGGGGGCGCGCGCCAGGCGGGGCGGGGCGGGGCGAGGGGCGGGGCGGGGCGAG

GCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCCGCCCGCC

CCGGCTCTGACTGACCGCGTTACTCCCACAGGTGAGCGGGCGGGACGGCCCTTCTCC

TCCGGGCTGTAATTAGCGCTTGGTTTAATGACGGCTCGTTTCTTTTCTGTGGCTGCGT

GAAAGCCTTAAAGGGCTCCGGGAGGGCCCTTTGTGCGGGGGGAGCGGCTCGGGGG

GTGCGTGCGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGG

GGAGCGCGGCCGGGGGCGGTGCCCCGCGGTGCGGGGGGGCTGCGAGGGGAACAAA

GGCTGCGTGCGGGGTGTGTGCGTGGGGGGGTGAGCAGGGGGTGTGGGCGCGGCGGT

CGGGCTGTAACCCCCCCCTGCACCCCCCTCCCCGAGTTGCTGAGCACGGCCCGGCTT

CGGGTGCGGGGCTCCGTGCGGGGCGTGGCGCGGGGCTCGCCGTGCCGGGCGGGGGG

TGGCGGCAGGTGGGGGTGCCGGGCGGGGCGGGGCCGCCTCGGGCCGGGGAGGGCT

CGGGGGAGGGGCGCGGCGGCCCCCGGAGCGCCGGCGGCTGTCGAGGCGCGGCGAG

CCGCAGCCATTGCCTTTTATGGTAATCGTGCGAGAGGGCGCAGGGACTTCCTTTGTC

CCAAATCTGTGCGGAGCCGAAATCTGGGAGGCGCCGCCGCACCCCCTCTAGCGGGC

GCGGGGCGAAGCGGTGCGGCGCCGGCAGGAAGGAAATGGGCGGGAGGGCCTTCG

TGCGTCGCCGCGCCGCCGTCCCCTTCTCCCTCTCCAGCCTCGGGGCTGTCCGCGGGG

GGACGGCTGCCTTCGGGGGGGACGGGGCAGGGCGGGGTTCGGCTTCTGGCGTGTGA

CCGGCGGCTCTAGAGCCTCTGCTAACCATGTTCATGCCTTCTTCTTTTTCCTACAGCT

CCTGGGCAACGTGCTGGTTATTGTGACCGGTGCCACCATGTACCGGATGCAGCTGCT

GAGCTGTATCGCCCTGTCTCTGGCCCTGGTCACCAATTCTGAGGTGCAGCTGGTGGA

ATCTGGCGGCGGACTTGTTCAACCTGGCGGCTCTCTGAGACTGAGCTGTGCCGCTTC

TGGCTACACCTTCACCAACTACGGCATGAACTGGGTCCGACAGGCCCCTGGCAAAG

GCCTTGAATGGGTCGGATGGATCAACACCTACACCGGCGAGCCAACATACGCCGCC

GACTTCAAGCGGAGATTCACCTTCAGCCTGGACACCAGCAAGAGCACCGCCTACCT

GCAGATGAACAGCCTGAGAGCCGAGGACACCGCCGTGTACTACTGCGCCAAGTATC

CCCACTACTACGGCAGCAGCCACTGGTACTTTGACGTGTGGGGACAGGGCACACTG

GTCACAGTGTCTAGCGCCTCTACAAAGGGCCCCAGCGTTTTCCCACTGGCTCCTAGC

AGCAAGTCTACCAGCGGAGGAACAGCCGCTCTGGGCTGTCTGGTCAAGGACTACTTT

CCCGAGCCTGTGACCGTGTCCTGGAATTCTGGCGCTCTGACAAGCGGCGTGCACACC

TTTCCAGCTGTGCTGCAAAGCAGCGGCCTGTACTCTCTGAGCAGCGTCGTGACAGTG

CCAAGCAGCTCTCTGGGCACCCAGACCTACATCTGCAATGTGAACCACAAGCCTAG

CAACACCAAGGTGGACAAGAAGGTGGAACCCAAGAGCTGCGACAAGACCCACACC

TGTCCTCCATGTCCTGCTCCAGAACTGCTCGGCGGACCTTCCGTGTTCCTGTTTCCTC

CAAAGCCTAAGGACACCCTGATGATCAGCAGAACCCCTGAAGTGACCTGCGTGGTG
```

-continued

```
GTGGATGTGTCCCACGAGGATCCCGAAGTGAAGTTCAATTGGTACGTGGACGGCGT

GGAAGTGCACAACGCCAAGACCAAGCCTAGAGAGGAACAGTACAACAGCACCTAC

AGAGTGGTGTCCGTGCTGACCGTGCTGCACCAGGATTGGCTGAACGGCAAAGAGTA

CAAGTGCAAGGTGTCCAACAAGGCCCTGCCTGCTCCTATCGAGAAAACCATCAGCA

AGGCCAAGGGCCAGCCTAGGGAACCCCAGGTTTACACACTGCCTCCAAGCCGGGAA

GAGATGACCAAGAACCAGGTGTCCCTGACCTGCCTCGTGAAGGGCTTCTACCCTTCC

GATATCGCCGTGGAATGGGAGAGCAATGGCCAGCCAGAGAACAACTACAAGACAA

CCCCTCCTGTGCTGGACAGCGACGGCTCATTCTTCCTGTACAGCAAGCTGACAGTGG

ACAAGTCCAGATGGCAGCAGGGCAACGTGTTCAGCTGCAGCGTGATGCACGAGGCC

CTGCACAACCACTACACCCAGAAGTCTCTGAGCCTGTCTCCTGGCAAGCGGAAGAG

AAGAGGCTCTGGCGAAGGCAGAGGCAGCCTGCTTACATGTGGCGACGTGGAAGAGA

ACCCCGGACCTATGTATAGAATGCAGCTCCTGTCCTGCATTGCCCTGAGCCTGGCTC

TCGTGACCAACAGCGACATCCAGATGACACAGAGCCCCAGCAGCCTGTCTGCCTCT

GTGGGAGACAGAGTGACCATCACCTGTAGCGCCAGCCAGGACATCTCCAACTACCT

GAACTGGTATCAGCAAAAGCCCGGCAAGGCCCCTAAGGTGCTGATCTACTTCACAA

GCAGCCTGCACTCCGGCGTGCCCAGCAGATTTTCTGGCTCTGGCAGCGGCACCGACT

TCACCCTGACCATATCTAGCCTGCAGCCTGAGGACTTCGCCACCTACTACTGCCAGC

AGTACAGCACCGTGCCTTGGACATTTGGCCAGGGCACAAAGGTGGAAATCAAGCGG

ACTGTGGCCGCTCCTAGCGTGTTCATCTTTCCACCTAGCGACGAGCAGCTGAAGTCT

GGCACAGCCTCTGTCGTGTGCCTGCTGAACAACTTCTACCCCAGAGAAGCCAAGGTG

CAGTGGAAAGTGGACAATGCCCTGCAGAGCGGCAACAGCCAAGAGAGCGTGACAG

AGCAGGACTCCAAGGATAGCACCTATAGCCTGAGCAGCACCCTGACACTGAGCAAG

GCCGACTACGAGAAGCACAAAGTGTACGCCTGCGAAGTGACCCACCAGGGCCTTTC

TAGCCCTGTGACCAAGAGCTTCAACCGGGGCGAATGTTAAGAGCTCGCTGATCAGC

CTCGACTGTGCCTTCTAGTTGCCAGCCATCTGTTGTTTGCCCCTCCCCCGTGCCTTCC

TTGACCCTGGAAGGTGCCACTCCCACTGTCCTTTCCTAATAAAATGAGGAAATTGCA

TCGCATTGTCTGAGTAGGTGTCATTCTATTCTGGGGGGTGGGGTGGGGCAGGACAGC

AAGGGGGAGGATTGGGAAGACAATAGCAGGCATGCTGGGGATGCGGTGGGCTCTAT

GGAAGCTTGAATTCAGCTGACGTGCCTCGGACCGCTAGGAACCCCTAGTGATGGAG

TTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAG

Exemplary rAAV-Bevacizumab Construct Sequence
                                          (SEQ ID NO: 94)
TTGGCCACTCCCTCTCTGCGCGCTCGCTCGCTCACTGAGGCCGCCCGGGCAAAGCCC

GGGCGTCGGGCGACCTTTGGTCGCCCGGCCTCAGTGAGCGAGCGAGCGCGCAGAGA

GGGAGTGGCCAACTCCATCACTAGGGGTTCCTTTGTCGACGCGGCCGCACGCGTGAC

ATTGATTATTGACTAGTTATTAATAGTAATCAATTACGGGGTCATTAGTTCATAGCCC

ATATATGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGACTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA
```

-continued

```
GTACATCTACGTATTAGTCATCGCTATTACCATGGGTCGAGGTGAGCCCCACGTTCT

GCTTCACTCTCCCCATCTCCCCCCCCTCCCCACCCCCAATTTTGTATTTATTTATTTTT

TAATTATTTTGTGCAGCGATGGGGGCGGGGGGGGGGGGGGCGCGCGCCAGGCGG

GGCGGGGCGGGGCGAGGGGCGGGGCGGGGCGAGGCGGAGAGGTGCGGCGGCAGCC

AATCAGAGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGTTGCCTTCGCCCC

GTGCCCCGCTCCGCGCCGCCTCGCGCCGCCCGCCCCGGCTCTGACTGACCGCGTTAC

TCCCACAGGTGAGCGGGCGGGACGGCCCTTCTCCTCCGGGCTGTAATTAGCGCTTGG

TTTAATGACGGCTCGTTTCTTTTCTGTGGCTGCGTGAAAGCCTTAAAGGGCTCCGGG

AGGGCCCTTTGTGCGGGGGGGAGCGGCTCGGGGGTGCGTGCGTGTGTGTGCGT

GGGGAGCGCCGCGTGCGGCCCGCGCTGCCCGGCGGCTGTGAGCGCTGCGGGCGCGG

CGCGGGGCTTTGTGCGCTCCGCGTGTGCGCGAGGGGAGCGCGGCCGGGGGCGGTGC

CCCGCGGTGCGGGGGGGCTGCGAGGGGAACAAAGGCTGCGTGCGGGGTGTGTGCGT

GGGGGGGGTGAGCAGGGGGTGTGGGCGCGGCGGTCGGGCTGTAACCCCCCCCTGCAC

CCCCCTCCCCGAGTTGCTGAGCACGGCCCGGCTTCGGGTGCGGGGCTCCGTGCGGGG

CGTGGCGCGGGGCTCGCCGTGCCGGGCGGGGGGTGGCGGCAGGTGGGGGTGCCGG

GCGGGGCGGGGCCGCCTCGGGCCGGGGAGGGCTCGGGGGAGGGGCGCGGCGGCCC

CCGGAGCGCCGGCGGCTGTCGAGGCGCGGCGAGCCGCAGCCATTGCCTTTTATGGT

AATCGTGCGAGAGGGCGCAGGGACTTCCTTTGTCCCAAATCTGTGCGGAGCCGAAA

TCTGGGAGGCGCCGCCGCACCCCCTCTAGCGGGCGCGGGGCGAAGCGGTGCGGCGC

CGGCAGGAAGGAAATGGGCGGGGAGGGCCTTCGTGCGTCGCCGCGCCGCCGTCCCC

TTCTCCCTCTCCAGCCTCGGGGCTGTCCGCGGGGGGACGGCTGCCTTCGGGGGGGAC

GGGGCAGGGCGGGGTTCGGCTTCTGGCGTGTGACCGGCGGCTCTAGAGCCTCTGCTA

ACCATGTTCATGCCTTCTTCTTTTTCCTACAGCTCCTGGGCAACGTGCTGGTTATTGT

GACCGGTGCCACCATGTACCGGATGCAGCTGCTGAGCTGTATCGCCCTGTCTCTGGC

CCTGGTCACCAATTCTGAGGTGCAGCTGGTGGAATCTGGCGGCGGACTTGTTCAACC

TGGCGGCTCTCTGAGACTGAGCTGTGCCGCTTCTGGCTACACCTTCACCAACTACGG

CATGAACTGGGTCCGACAGGCCCCTGGCAAAGGCCTTGAATGGGTCGGATGGATCA

ACACCTACACCGGCGAGCCAACATACGCCGCCGACTTCAAGCGGAGATTCACCTTC

AGCCTGGACACCAGCAAGAGCACCGCCTACCTGCAGATGAACAGCCTGAGAGCCGA

GGACACCGCCGTGTACTACTGCGCCAAGTATCCCCACTACTACGGCAGCAGCCACTG

GTACTTTGACGTGTGGGGACAGGGCACACTGGTCACAGTGTCTAGCGCCTCTACAAA

GGGCCCCAGCGTTTTCCCACTGGCTCCTAGCAGCAAGTCTACCAGCGGAGGAACAG

CCGCTCTGGGCTGTCTGGTCAAGGACTACTTTCCCGAGCCTGTGACCGTGTCCTGGA

ATTCTGGCGCTCTGACAAGCGGCGTGCACACCTTTCCAGCTGTGCTGCAAAGCAGCG

GCCTGTACTCTCTGAGCAGCGTCGTGACAGTGCCAAGCAGCTCTCTGGGCACCCAGA

CCTACATCTGCAATGTGAACCACAAGCCTAGCAACACCAAGGTGGACAAGAAGGTG

GAACCCAAGAGCTGCGACAAGACCCACACCTGTCCTCCATGTCCTGCTCCAGAACTG

CTCGGCGGACCTTCCGTGTTCCTGTTTCCTCCAAAGCCTAAGGACACCCTGATGATC

AGCAGAACCCCTGAAGTGACCTGCGTGGTGGTGGATGTGTCCCACGAGGATCCCGA
```

```
-continued
AGTGAAGTTCAATTGGTACGTGGACGGCGTGGAAGTGCACAACGCCAAGACCAAGC

CTAGAGAGGAACAGTACAACAGCCACCTACAGAGTGGTGTCCGTGCTGACCGTGCTG

CACCAGGATTGGCTGAACGGCAAAGAGTACAAGTGCAAGGTGTCCAACAAGGCCCT

GCCTGCTCCTATCGAGAAAACCATCAGCAAGGCCAAGGGCCAGCCTAGGGAACCCC

AGGTTTACACACTGCCTCCAAGCCGGGAAGAGATGACCAAGAACCAGGTGTCCCTG

ACCTGCCTCGTGAAGGGCTTCTACCCTTCCGATATCGCCGTGGAATGGGAGAGCAAT

GGCCAGCCAGAGAACAACTACAAGACAACCCCTCCTGTGCTGGACAGCGACGGCTC

ATTCTTCCTGTACAGCAAGCTGACAGTGGACAAGTCCAGATGGCAGCAGGGCAACG

TGTTCAGCTGCAGCGTGATGCACGAGGCCCTGCACAACCACTACACCCAGAAGTCTC

TGAGCCTGTCTCCTGGCAAGCGGAAGAGAAGAGGCTCTGGCGAAGGCAGAGGCAGC

CTGCTTACATGTGGCGACGTGGAAGAGAACCCCGGACCTATGTATAGAATGCAGCT

CCTGTCCTGCATTGCCCTGAGCCTGGCTCTCGTGACCAACAGCGACATCCAGATGAC

ACAGAGCCCCAGCAGCCTGTCTGCCTCTGTGGGAGACAGAGTGACCATCACCTGTA

GCGCCAGCCAGGACATCTCCAACTACCTGAACTGGTATCAGCAAAAGCCCGGCAAG

GCCCCTAAGGTGCTGATCTACTTCACAAGCAGCCTGCACTCCGGCGTGCCCAGCAGA

TTTTCTGGCTCTGGCAGCGGCACCGACTTCACCCTGACCATATCTAGCCTGCAGCCT

GAGGACTTCGCCACCTACTACTGCCAGCAGTACAGCACCGTGCCTTGGACATTTGGC

CAGGGCACAAAGGTGGAAATCAAGCGGACTGTGGCCGCTCCTAGCGTGTTCATCTTT

CCACCTAGCGACGAGCAGCTGAAGTCTGGCACAGCCTCTGTCGTGTGCCTGCTGAAC

AACTTCTACCCCAGAGAAGCCAAGGTGCAGTGGAAAGTGGACAATGCCCTGCAGAG

CGGCAACAGCCAAGAGAGCGTGACAGAGCAGGACTCCAAGGATAGCACCTATAGC

CTGAGCAGCACCCTGACACTGAGCAAGGCCGACTACGAGAAGCACAAAGTGTACGC

CTGCGAAGTGACCCACCAGGGCCTTTCTAGCCCTGTGACCAAGAGCTTCAACCGGG

GCGAATGTTAAGAGCTCGCTGATCAGCCTCGACTGTGCCTTCTAGTTGCCAGCCATC

TGTTGTTTGCCCCTCCCCCGTGCCTTCCTTGACCCTGGAAGGTGCCACTCCCACTGTC

CTTTCCTAATAAAATGAGGAAATTGCATCGCATTGTCTGAGTAGGTGTCATTCTATTC

TGGGGGGTGGGGTGGGGCAGGACAGCAAGGGGGAGGATTGGGAAGACAATAGCAG

GCATGCTGGGGATGCGGTGGGCTCTATGGAAGCTTGAATTCAGCTGACGTGCCTCGG

ACCGCCTAGGAGGAACCCCTAGTGATGGAGTTGGCCACTCCCTCTCTGCGCGCTCGC

TCGCTCACTGAGGCCGGGCGACCAAAGGTCGCCCGACGCCCGGGCTTTGCCCGGGC

GGCCTCAGTGAGCGAGCGAGCGCGCAGAGAGGGAGTGGCCAA

Exemplary rAAV-Bevacizumab-GFP Construct Sequence
                                              (SEQ ID NO: 107)
CTGCGCGCTCGCTCGCTCACTGAGGCCGCCCGGGCGTCGGGCGACCTTTGGTCGCCC

GGCCTCAGTGAGCGAGCGAGCGCGCAGAGAGGGAGTGGCCAACTCCATCACTAGGG

GTTCCTGCGGCCGCACGCGTGACATTGATTATTGACTAGTTATTAATAGTAATCAAT

TACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGACT

ATTTACGGTAAACTGCCCACTTGGCAGTACATCAAGTGTATCATATGCCAAGTACGC

CCCCTATTGACGTCAATGACGGTAAATGGCCCGCCTGGCATTATGCCCAGTACATGA

CCTTATGGGACTTTCCTACTTGGCAGTACATCTACGTATTAGTCATCGCTATTACCAT
```

-continued

```
GGGTCGAGGTGAGCCCCACGTTCTGCTTCACTCTCCCCATCTCCCCCCCCTCCCCACC
CCCAATTTTGTATTTATTTATTTTTTAATTATTTTGTGCAGCGATGGGGGCGGGGGGG
GGGGGGGCGCGCGCCAGGCGGGGCGGGGCGGGGCGAGGGGCGGGGCGGGGCGAG
GCGGAGAGGTGCGGCGGCAGCCAATCAGAGCGGCGCGCTCCGAAAGTTTCCTTTTA
TGGCGAGGCGGCGGCGGCGGCGGCCCTATAAAAAGCGAAGCGCGCGGCGGGCGGG
AGTCGCTGCGTTGCCTTCGCCCCGTGCCCCGCTCCGCGCCGCCTCGCGCCGCCCGCC
CCGGCTCTGACTGACCGCGTTACTCCCACAGGTGAGCGGGCGGGACGGCCCTTCTCC
TCCGGGCTGTAATTAGCGCTTGGTTTAATGACGGCTCGTTTCTTTTCTGTGGCTGCGT
GAAAGCCTTAAAGGGCTCCGGGAGGGCCCTTTGTGCGGGGGGGAGCGGCTCGGGGG
GTGCGTGCGTGTGTGTGCGTGGGGAGCGCCGCGTGCGGCCCGCGCTGCCCGGCG
GCTGTGAGCGCTGCGGGCGCGGCGCGGGGCTTTGTGCGCTCCGCGTGTGCGCGAGG
GGAGCGCGGCCGGGGCGGTGCCCCGCGGTGCGGGGGGGCTGCGAGGGGAACAAA
GGCTGCGTGCGGGGTGTGTGCGTGGGGGGGTGAGCAGGGGGTGTGGGCGCGGCGGT
CGGGCTGTAACCCCCCCCTGCACCCCCCTCCCCGAGTTGCTGAGCACGGCCCGGCTT
CGGGTGCGGGGCTCCGTGCGGGGCGTGGCGCGGGGCTCGCCGTGCCGGGCGGGGGG
TGGCGGCAGGTGGGGGTGCCGGGCGGGGCGGGGCCGCCTCGGGCCGGGGAGGGCT
CGGGGGAGGGGCGCGGCGGCCCCCGGAGCGCCGGCGGCTGTCGAGGCGCGGCGAG
CCGCAGCCATTGCCTTTTATGGTAATCGTGCGAGAGGGCGCAGGGACTTCCTTTGTC
CCAAATCTGTGCGGAGCCGAAATCTGGGAGGCGCCGCCGCACCCCCTCTAGCGGGC
GCGGGGCGAAGCGGTGCGGCGCCGGCAGGAAGGAAATGGGCGGGGAGGGCCTTCG
TGCGTCGCCGCGCCGCCGTCCCCTTCTCCCTCTCCAGCCTCGGGGCTGTCCGCGGGG
GGACGGCTGCCTTCGGGGGGGACGGGGCAGGGCGGGGTTCGGCTTCTGGCGTGTGA
CCGGCGGCTCTAGAGCCTCTGCTAACCATGTTCATGCCTTCTTCTTTTTCCTACAGCT
CCTGGGCAACGTGCTGGTTATTGTGACCGGTGCCACCATGTACCGGATGCAGCTGCT
GAGCTGTATCGCCCTGTCTCTGGCCCTGGTCACCAATTCTGAGGTGCAGCTGGTGGA
ATCTGGCGGCGGACTTGTTCAACCTGGCGGCTCTCTGAGACTGAGCTGTGCCGCTTC
TGGCTACACCTTCACCAACTACGGCATGAACTGGGTCCGACAGGCCCCTGGCAAAG
GCCTTGAATGGGTCGGATGGATCAACACCTACACCGGCGAGCCAACATACGCCGCC
GACTTCAAGCGGAGATTCACCTTCAGCCTGGACACCAGCAAGAGCACCGCCTACCT
GCAGATGAACAGCCTGAGAGCCGAGGACACCGCCGTGTACTACTGCGCCAAGTATC
CCCACTACTACGGCAGCAGCCACTGGTACTTTGACGTGTGGGGACAGGGCACACTG
GTCACAGTGTCTAGCGCCTCTACAAAGGGCCCCAGCGTTTTCCCACTGGCTCCTAGC
AGCAAGTCTACCAGCGGAGGAACAGCCGCTCTGGGCTGTCTGGTCAAGGACTACTTT
CCCGAGCCTGTGACCGTGTCCTGGAATTCTGGCGCTCTGACAAGCGGCGTGCACACC
TTTCCAGCTGTGCTGCAAAGCAGCGGCCTGTACTCTCTGAGCAGCGTCGTGACAGTG
CCAAGCAGCTCTCTGGGCACCCAGACCTACATCTGCAATGTGAACCACAAGCCTAG
CAACACCAAGGTGGACAAGAAGGTGGAACCCAAGAGCTGCGACAAGACCCACACC
TGTCCTCCATGTCCTGCTCCAGAACTGCTCGGCGGACCTTCCGTGTTCCTGTTTCCTC
CAAAGCCTAAGGACACCCTGATGATCAGCAGAACCCCTGAAGTGACCTGCGTGGTG
GTGGATGTGTCCCACGAGGATCCCGAAGTGAAGTTCAATTGGTACGTGGACGGCGT
```

-continued

```
GGAAGTGCACAACGCCAAGACCAAGCCTAGAGAGGAACAGTACAACAGCACCTAC
AGAGTGGTGTCCGTGCTGACCGTGCTGCACCAGGATTGGCTGAACGGCAAAGAGTA
CAAGTGCAAGGTGTCCAACAAGGCCCTGCCTGCTCCTATCGAGAAAACCATCAGCA
AGGCCAAGGGCCAGCCTAGGGAACCCCAGGTTTACACACTGCCTCCAAGCCGGGAA
GAGATGACCAAGAACCAGGTGTCCCTGACCTGCCTCGTGAAGGGCTTCTACCCTTCC
GATATCGCCGTGGAATGGGAGAGCAATGGCCAGCCAGAGAACAACTACAAGACAA
CCCCTCCTGTGCTGGACAGCGACGGCTCATTCTTCCTGTACAGCAAGCTGACAGTGG
ACAAGTCCAGATGGCAGCAGGGCAACGTGTTCAGCTGCAGCGTGATGCACGAGGCC
CTGCACAACCACTACACCCAGAAGTCTCTGAGCCTGTCTCCTGGCAAGCGGAAGAG
AAGAGGCTCTGGCGAAGGCAGAGGCAGCCTGCTTACATGTGGCGACGTGGAAGAGA
ACCCCGGACCTATGTATAGAATGCAGCTCCTGTCCTGCATTGCCCTGAGCCTGGCTC
TCGTGACCAACAGCGACATCCAGATGACACAGAGCCCCAGCAGCCTGTCTGCCTCT
GTGGGAGACAGAGTGACCATCACCTGTAGCGCCAGCCAGGACATCTCCAACTACCT
GAACTGGTATCAGCAAAAGCCCGGCAAGGCCCCTAAGGTGCTGATCTACTTCACAA
GCAGCCTGCACTCCGGCGTGCCCAGCAGATTTTCTGGCTCTGGCAGCGGCACCGACT
TCACCCTGACCATATCTAGCCTGCAGCCTGAGGACTTCGCCACCTACTACTGCCAGC
AGTACAGCACCGTGCCTTGGACATTTGGCCAGGGCACAAAGGTGGAAATCAAGCGG
ACTGTGGCCGCTCCTAGCGTGTTCATCTTTCCACCTAGCGACGAGCAGCTGAAGTCT
GGCACAGCCTCTGTCGTGTGCCTGCTGAACAACTTCTACCCCAGAGAAGCCAAGGTG
CAGTGGAAAGTGGACAATGCCCTGCAGAGCGGCAACAGCCAAGAGAGCGTGACAG
AGCAGGACTCCAAGGATAGCACCTATAGCCTGAGCAGCACCCTGACACTGAGCAAG
GCCGACTACGAGAAGCACAAAGTGTACGCCTGCGAAGTGACCCACCAGGGCCTTTC
TAGCCCTGTGACCAAGAGCTTCAACCGGGGCGAATGTATGGTGAGCAAGGGCGAGG
AGCTGTTCACCGGGGTGGTGCCCATCCTGGTCGAGCTGGACGGCGACGTAAACGGC
CACAAGTTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGC
ACGACTTCTTCAAGTCCGCCATGCCCGAAGGCTACGTCCAGGAGCGCACCATCTTCT
TCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCT
GGGGCACAAGCTGGAGTACAACTACAACAGCCACAACGTCTATATCATGGCCGACA
AGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGT
GCTGCTGCCCGACAACCACTACCTGAGCACCCAGTCCGCCCTGAGCAAAGACCCCA
ACGAGAAGCGCGATCACATGGTCCTGCTGGAGTTCGTGACCGCCGCCGGGATCACT
CTCGGCATGGACGAGCTGTACAAGTAAGAGCTCGCTGATCAGCCTCGACTGTGCCTT
CTAGTTGCCAGCCATCTGTTGTTTGCCCCTCCCCCGTGCCTTCCTTGACCCTGGAAGG
TGCCACTCCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGGAGGATT
GGGAAGACAATAGCAGGCATGCTGGGGATGCGGTGGGCTCTATGGAAGCTTGAATT
CAGCTGACGTGCCTCGGACCGCTAGGAACCCCTAGTGATGGAGTTGGCCACTCCCTC
```

-continued

TCTGCGCGCTCGCTCGCTCACTGAGGCCGGGCGACCAAAGGTCGCCCGACGCCCGG

GCTTTGCCCGGGCGGCCTCAGTGAGCGAGCGAGCGCGCAG

Exemplary rAAV-aflibercept-PC Construct Sequence
(SEQ ID NO: 95)
CTGCGCGCTCGCTCGCTCACTGAGGCCGCCCGGGCGTCGGGCGACCTTTGGTCGCCC

GGCCTCAGTGAGCGAGCGAGCGCGCAGAGAGGGAGTGGCCAACTCCATCACTAGGG

GTTCCTGCGGCCGCACGCGTGACATTGATTATTGACTAGTTATTAATAGTAATCAAT

TACGGGGTCATTAGTTCATAGCCCATATATGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGACT

ATTTACGGTAAACTGCCCACTTGGCAGTACATCAAGTGTATCATATGCCAAGTACGC

CCCCTATTGACGTCAATGACGGTAAATGGCCCGCCTGGCATTATGCCCAGTACATGA

CCTTATGGGACTTTCCTACTTGGCAGTACATCTACGTATTAGTCATCGCTATTACCAT

GGGTCGAGGTGAGCCCCACGTTCTGCTTCACTCTCCCCATCTCCCCCCCCTCCCCACC

CCCAATTTTGTATTTATTTATTTTTAATTATTTTGTGCAGCGATGGGGGCGGGGGGG

GGGGGGGCGCGCGCCAGGCGGGGCGGGGCGGGGCGAGGGCGGGGCGGGGCGAG

GCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCCGCCCGCC

CCGGCTCTGACTGACCGCGTTACTCCCACAGGTGAGCGGGCGGGACGGCCCTTCTCC

TCCGGGCTGTAATTAGCGCTTGGTTTAATGACGGCTCGTTTCTTTTCTGTGGCTGCGT

GAAAGCCTTAAAGGGCTCCGGGAGGGCCCTTTGTGCGGGGGGAGCGGCTCGGGGG

GTGCGTGCGTGTGTGTGCGTGGGGAGCGCCGCGTGCGGCCCGCGCTGCCCGGCG

GCTGTGAGCGCTGCGGGCGCGGCGCGGGGCTTTGTGCGCTCCGCGTGTGCGCGAGG

GGAGCGCGGCCGGGGCGGTGCCCCGCGGTGCGGGGGGGCTGCGAGGGGAACAAA

GGCTGCGTGCGGGGTGTGTGCGTGGGGGGGTGAGCAGGGGGTGTGGGCGCGGCGGT

CGGGCTGTAACCCCCCCCTGCACCCCCCTCCCCGAGTTGCTGAGCACGGCCCGGCTT

CGGGTGCGGGGCTCCGTGCGGGGCGTGGCGCGGGGCTCGCCGTGCCGGGCGGGGG

TGGCGGCAGGTGGGGGTGCCGGGCGGGGCGGGGCCGCCTCGGGCCGGGGAGGGCT

CGGGGGAGGGGCGCGGCGGCCCCCGGAGCGCCGGCGGCTGTCGAGGCGCGGCGAG

CCGCAGCCATTGCCTTTTATGGTAATCGTGCGAGAGGGCGCAGGGACTTCCTTTGTC

CCAAATCTGTGCGGAGCCGAAATCTGGGAGGCGCCGCCGCACCCCCTCTAGCGGGC

GCGGGGCGAAGCGGTGCGGCGCCGGCAGGAAGGAAATGGGCGGGAGGGCCTTCG

TGCGTCGCCGCCGCCGTCCCCTTCTCCCTCTCCAGCCTCGGGGCTGTCCGCGGGG

GGACGGCTGCCTTCGGGGGGGACGGGGCAGGGCGGGGTTCGGCTTCTGGCGTGTGA

CCGGCGGCTCTAGAGCCTCTGCTAACCATGTTCATGCCTTCTTCTTTTTCCTACAGCT

CCTGGGCAACGTGCTGGTTATTGTGACCGGTGCCACCATGTACCGGATGCAGCTGCT

GAGCTGTATCGCCCTGTCTCTGGCCCTGGTCACCAATTCTAGCGATACCGGCAGACC

CTTCGTGGAAATGTACAGCGAGATCCCCGAGATCATCCACATGACCGAGGGCAGAG

AGCTGGTCATCCCCTGCAGAGTGACAAGCCCCAACATCACCGTGACTCTGAAGAAG

TTCCCTCTGGACACACTGATCCCCGACGGCAAGAGAATCATCTGGGACAGCCGGAA

```
GGGCTTCATCATCAGCAACGCCACCTACAAAGAGATCGGCCTGCTGACCTGTGAAG

CCACCGTGAATGGCCACCTGTACAAGACCAACTACCTGACACACAGACAGACCAAC

ACCATCATCGACGTGGTGCTGAGCCCTAGCCACGGCATTGAACTGTCTGTGGGCGAG

AAGCTGGTGCTGAACTGTACCGCCAGAACCGAGCTGAACGTGGGCATCGACTTCAA

CTGGGAGTACCCCAGCAGCAAGCACCAGCACAAGAAACTGGTCAACCGGGACCTGA

AAACCCAGAGCGGCAGCGAGATGAAGAAATTCCTGAGCACCCTGACCATCGACGGC

GTGACCAGATCTGACCAGGGCCTGTACACATGTGCCGCCAGCTCTGGCCTGATGACC

AAGAAAAACAGCACCTTCGTGCGGGTGCACGAGAAGGACAAGACCCACACCTGTCC

TCCATGTCCTGCTCCAGAACTGCTCGGCGGACCTTCCGTGTTCCTGTTTCCTCCAAAG

CCTAAGGACACCCTGATGATCAGCAGAACCCCTGAAGTGACCTGCGTGGTGGTGGA

TGTGTCCCACGAGGATCCCGAAGTGAAGTTCAATTGGTACGTGGACGGCGTGGAAG

TGCACAACGCCAAGACCAAGCCTAGAGAGGAACAGTACAATAGCACCTACAGAGTG

GTGTCCGTGCTGACCGTGCTGCACCAGGATTGGCTGAACGGCAAAGAGTACAAGTG

CAAGGTGTCCAACAAGGCCCTGCCTGCTCCTATCGAGAAAACCATCTCCAAGGCCA

AGGGCCAGCCTAGGGAACCCCAGGTTTACACACTGCCTCCAAGCAGGGACGAGCTG

ACAAAGAACCAGGTGTCCCTGACCTGCCTGGTCAAGGGCTTCTACCCTTCCGATATC

GCCGTGGAATGGGAGAGCAATGGCCAGCCTGAGAACAACTACAAGACAACCCCTCC

TGTGCTGGACAGCGACGGCTCATTCTTCCTGTACAGCAAGCTGACAGTGGACAAGA

GCAGATGGCAGCAGGGCAACGTGTTCAGCTGCAGCGTGATGCACGAGGCCCTGCAC

AACCACTACACCCAGAAGTCCCTGAGCCTGTCTCCTGGATAAGAGCTCGCTGATCAG

CCTCGACTGTGCCTTCTAGTTGCCAGCCATCTGTTGTTTGCCCCTCCCCCGTGCCTTC

CTTGACCCTGGAAGGTGCCACTCCCACTGTCCTTTCCTAATAAAATGAGGAAATTGC

ATCGCATTGTCTGAGTAGGTGTCATTCTATTCTGGGGGGTGGGGTGGGGCAGGACAG

CAAGGGGGAGGATTGGGAAGACAATAGCAGGCATGCTGGGGATGCGGTGGGCTCTA

TGGAAGCTTGAATTCAGCTGACGTGCCTCGGACCGCTAGGAACCCCTAGTGATGGA

GTTGGCCACTCCCTCTCTGCGCGCTCGCTCGCTCACTGAGGCCGGGCGACCAAAGGT

CGCCCGACGCCCGGGCTTTGCCCGGGCGGCCTCAGTGAGCGAGCGAGCGCGCAG

Exemplary rAAV-Aflibercept Construct Sequence
                                              (SEQ ID NO: 96)
TTGGCCACTCCCTCTCTGCGCGCTCGCTCGCTCACTGAGGCCGCCCGGGCAAAGCCC

GGGCGTCGGGCGACCTTTGGTCGCCCGGCCTCAGTGAGCGAGCGAGCGCGCAGAGA

GGGAGTGGCCAACTCCATCACTAGGGGTTCCTTTGTCGACGCGGCCGCACGCGTGAC

ATTGATTATTGACTAGTTATTAATAGTAATCAATTACGGGGTCATTAGTTCATAGCCC

ATATATGGAGTTCCGCGTTACATAACTTACGGTAAATGGCCCGCCTGGCTGACCGCC

CAACGACCCCCGCCCATTGACGTCAATAATGACGTATGTTCCCATAGTAACGCCAAT

AGGGACTTTCCATTGACGTCAATGGGTGGACTATTTACGGTAAACTGCCCACTTGGC

AGTACATCAAGTGTATCATATGCCAAGTACGCCCCCTATTGACGTCAATGACGGTAA

ATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCT

GCTTCACTCTCCCCATCTCCCCCCCCTCCCCACCCCCAATTTTGTATTTATTTATTTTT

TAATTATTTTGTGCAGCGATGGGGGCGGGGGGGGGGGGGGGCGCGCGCCAGGCGG

GGCGGGGCGGGCGAGGGGCGGGGCGGGGCGAGGCGGAGAGGTGCGGCGGCAGCC
```

-continued

```
AATCAGAGCGGCGCGCTCCGAAAGTTTCCTTTTATGGCGAGGCGGCGGCGGCGG
GCCCTATAAAAGCGAAGCGCGCGGCGGGCGGGAGTCGCTGCGTTGCCTTCGCCCC
GTGCCCCGCTCCGCGCCGCCTCGCGCCGCCCGCCCCGGCTCTGACTGACCGCGTTAC
TCCCACAGGTGAGCGGGCGGGACGGCCCTTCTCCTCCGGGCTGTAATTAGCGCTTGG
TTTAATGACGGCTCGTTTCTTTTCTGTGGCTGCGTGAAAGCCTTAAAGGGCTCCGGG
AGGGCCCTTTGTGCGGGGGGGAGCGGCTCGGGGGGTGCGTGCGTGTGTGTGCGT
GGGGAGCGCCGCGTGCGGCCCGCGCTGCCCGGCGGCTGTGAGCGCTGCGGGCGCGG
CGCGGGCTTTGTGCGCTCCGCGTGTGCGCGAGGGGAGCGCGGCCGGGGGCGGTGC
CCCGCGGTGCGGGGGGGCTGCGAGGGGAACAAAGGCTGCGTGCGGGGTGTGTGCGT
GGGGGGGTGAGCAGGGGGTGTGGGCGCGGCGGTCGGGCTGTAACCCCCCCCTGCAC
CCCCCTCCCCGAGTTGCTGAGCACGGCCCGGCTTCGGGTGCGGGGCTCCGTGCGGGG
CGTGGCGCGGGGCTCGCCGTGCCGGGCGGGGGTGGCGGCAGGTGGGGGTGCCGG
GCGGGGCGGGCCGCCTCGGGCCGGGGAGGGCTCGGGGGAGGGGCGCGGCGGCCC
CCGGAGCGCCGGCGGCTGTCGAGGCGCGGCGAGCCGCAGCCATTGCCTTTTATGGT
AATCGTGCGAGAGGGCGCAGGGACTTCCTTTGTCCCAAATCTGTGCGGAGCCGAAA
TCTGGGAGGCGCCGCCGCACCCCCTCTAGCGGGCGCGGGGCGAAGCGGTGCGGCGC
CGGCAGGAAGGAAATGGGCGGGGAGGGCCTTCGTGCGTCGCCGCGCCGCCGTCCCC
TTCTCCCTCTCCAGCCTCGGGGCTGTCCGCGGGGGGACGGCTGCCTTCGGGGGGGAC
GGGGCAGGGCGGGGTTCGGCTTCTGGCGTGTGACCGGCGGCTCTAGAGCCTCTGCTA
ACCATGTTCATGCCTTCTTCTTTTTCCTACAGCTCCTGGGCAACGTGCTGGTTATTGT
GACCGGTGCCACCATGTACCGGATGCAGCTGCTGAGCTGTATCGCCCTGTCTCTGGC
CCTGGTCACCAATTCTAGCGATACCGGCAGACCCTTCGTGGAAATGTACAGCGAGAT
CCCCGAGATCATCCACATGACCGAGGGCAGAGAGCTGGTCATCCCCTGCAGAGTGA
CAAGCCCCAACATCACCGTGACTCTGAAGAAGTTCCCTCTGGACACACTGATCCCCG
ACGGCAAGAGAATCATCTGGGACAGCCGGAAGGGCTTCATCATCAGCAACGCCACC
TACAAAGAGATCGGCCTGCTGACCTGTGAAGCCACCGTGAATGGCCACCTGTACAA
GACCAACTACCTGACACACAGACAGACCAACACCATCATCGACGTGGTGCTGAGCC
CTAGCCACGGCATTGAACTGTCTGTGGGCGAGAAGCTGGTGCTGAACTGTACCGCCA
GAACCGAGCTGAACGTGGGCATCGACTTCAACTGGGAGTACCCCAGCAGCAAGCAC
CAGCACAAGAAACTGGTCAACCGGGACCTGAAAACCCAGAGCGGCAGCGAGATGA
AGAAATTCCTGAGCACCCTGACCATCGACGGCGTGACCAGATCTGACCAGGGCCTG
TACACATGTGCCGCCAGCTCTGGCCTGATGACCAAGAAAAACAGCACCTTCGTGCG
GGTGCACGAGAAGGACAAGACCCACACCTGTCCTCCATGTCCTGCTCCAGAACTGCT
CGGCGGACCTTCCGTGTTCCTGTTTCCTCCAAAGCCTAAGGACACCCTGATGATCAG
CAGAACCCCTGAAGTGACCTGCGTGGTGGTGGATGTGTCCCACGAGGATCCCGAAG
TGAAGTTCAATTGGTACGTGGACGGCGTGGAAGTGCACAACGCCAAGACCAAGCCT
AGAGAGGAACAGTACAATAGCACCTACAGAGTGGTGTCCGTGCTGACCGTGCTGCA
CCAGGATTGGCTGAACGGCAAAGAGTACAAGTGCAAGGTGTCCAACAAGGCCCTGC
CTGCTCCTATCGAGAAAACCATCTCCAAGGCCAAGGGCCAGCCTAGGGAACCCCAG
GTTTACACACTGCCTCCAAGCAGGGACGAGCTGACAAAGAACCAGGTGTCCCTGAC
```

-continued
```
CTGCCTGGTCAAGGGCTTCTACCCTTCCGATATCGCCGTGGAATGGGAGAGCAATGG

CCAGCCTGAGAACAACTACAAGACAACCCCTCCTGTGCTGGACAGCGACGGCTCAT

TCTTCCTGTACAGCAAGCTGACAGTGGACAAGAGCAGATGGCAGCAGGGCAACGTG

TTCAGCTGCAGCGTGATGCACGAGGCCCTGCACAACCACTACACCCAGAAGTCCCT

GAGCCTGTCTCCTGGATAAGAGCTCGCTGATCAGCCTCGACTGTGCCTTCTAGTTGC

CAGCCATCTGTTGTTTGCCCCTCCCCCGTGCCTTCCTTGACCCTGGAAGGTGCCACTC

CCACTGTCCTTTCCTAATAAAATGAGGAAATTGCATCGCATTGTCTGAGTAGGTGTC

ATTCTATTCTGGGGGGTGGGGTGGGGCAGGACAGCAAGGGGGAGGATTGGGAAGAC

AATAGCAGGCATGCTGGGGATGCGGTGGGCTCTATGGAAGCTTGAATTCAGCTGAC

GTGCCTCGGACCGCCTAGGAGGAACCCCTAGTGATGGAGTTGGCCACTCCCTCTCTG

CGCGCTCGCTCGCTCACTGAGGCCGGGCGACCAAAGGTCGCCCGACGCCCGGGCTT

TGCCCGGGCGGCCTCAGTGAGCGAGCGAGCGCGCAGAGAGGGAGTGGCCAA
```

Multiple AAV Construct Compositions

The present disclosure recognizes that some coding sequences encoding a protein (e.g., an anti-VEGF protein) may be delivered by dividing the coding sequence into multiple portions, which are each included in a different construct. In some embodiments, provided herein are compositions or systems comprising at least two different constructs (e.g., two, three, four, five, or six). In some embodiments, each of the at least two different constructs comprises a coding sequence that encodes a different portion of a coding region (e.g., encoding a target protein, e.g., an inner ear target protein, e.g., an anti-VEGF protein), each of the encoded portions being at least 10 amino acids (e.g., at least about 10 amino acids, at least about 20 amino acids, at least about 30 amino acids, at least about 60 amino acids, at least about 70 amino acids, at least about 80 amino acids, at least about 90 amino acids, at least about 100 amino acids, at least about 110 amino acids, at least about 120 amino acids, at least about 130 amino acids, at least about 140 amino acids, at least about 150 amino acids, at least about 160 amino acids, at least about 170 amino acids, at least about 180 amino acids, at least about 190 amino acids, at least about 200 amino acids, at least about 210 amino acids, at least about 220 amino acids, at least about 230 amino acids, at least about 240 amino acids, at least about 250 amino acids, at least about 260 amino acids, at least about 270 amino acids, at least about 280 amino acids, at least about 290 amino acids, at least about 300 amino acids, at least about 310 amino acids, at least about 320 amino acids, at least about 330 amino acids, at least about 340 amino acids, at least about 350 amino acids, at least about 360 amino acids, at least about 370 amino acids, at least about 380 amino acids, at least about 390 amino acids, at least about 400 amino acids, at least about 410 amino acids, at least about 420 amino acids, at least about 430 amino acids, at least about 440 amino acids, at least about 450 amino acids, at least about 460 amino acids, at least about 470 amino acids, at least about 480 amino acids, at least about 490 amino acids, at least about 500 amino acids, at least about 510 amino acids, at least about 520 amino acids, at least about 530 amino acids, at least about 540 amino acids, at least about 550 amino acids, at least about 560 amino acids, at least about 570 amino acids, at least about 580 amino acids, at least about 590 amino acids, at least about 600 amino acids, at least about 610 amino acids, at least about 620 amino acids, at least about 630 amino acids, at least about 640 amino acids, at least about 650 amino acids, at least about 660 amino acids, at least about 670 amino acids, at least about 680 amino acids, at least about 690 amino acids, at least about 700 amino acids, at least about 710 amino acids, at least about 720 amino acids, at least about 730 amino acids, at least about 740 amino acids, at least about 750 amino acids, at least about 760 amino acids, at least about 770 amino acids, at least about 780 amino acids, at least about 790 amino acids, at least about 800 amino acids, at least about 810 amino acids, or at least about 820 amino acids) where the amino acid sequence of each of the encoded portions may optionally partially overlap with the amino acid sequence of a different one of the encoded portions; no single construct of the at least two different constructs encodes the active target protein; and, when introduced into a subject cell (e.g., an animal cell, e.g., a primate cell, e.g., a human cell), the at least two different may undergo homologous recombination with each other, where the recombined nucleic acid encodes an active target protein (e.g., an anti-VEGF protein). In some embodiments, one of the nucleic acid constructs can include a coding sequence that encodes a portion of a target protein (e.g., an anti-VEGF protein), where the encoded portion is at most about 820 amino acids (e.g., at most about 10 amino acids, at most about 20 amino acids, at most about 30 amino acids, at most about 60 amino acids, at most about 70 amino acids, at most about 80 amino acids, at most about 90 amino acids, at most about 100 amino acids, at most about 110 amino acids, at most about 120 amino acids, at most about 130 amino acids, at most about 140 amino acids, at most about 150 amino acids, at most about 160 amino acids, at most about 170 amino acids, at most about 180 amino acids, at most about 190 amino acids, at most about 200 amino acids, at most about 210 amino acids, at most about 220 amino acids, at most about 230 amino acids, at most about 240 amino acids, at most about 250 amino acids, at most about 260 amino acids, at most about 270 amino acids, at most about 280 amino acids, at most about 290 amino acids, at most about 300 amino acids, at most about 310 amino acids, at most about 320 amino acids, at most about 330 amino acids, at most about 340 amino acids, at most about 350 amino acids, at most about 360 amino acids, at most about 370 amino acids, at most about 380 amino acids, at most about 390 amino acids, at most about 400 amino acids, at most about 410 amino acids, at most about 420 amino acids, at most about 430 amino acids, at most about 440 amino acids, at most about 450 amino acids, at most about 460 amino acids, at most about 470 amino acids, at most about 480 amino acids, at most about 490 amino acids, at most about 500 amino acids, at most about 510 amino acids, at most about 520 amino acids, at most about 530 amino acids, at most about 540 amino acids, at most about 550 amino acids, at most about 560 amino acids, at most about 570 amino acids, at most about 580 amino acids, at most about 590 amino acids, at most about 600 amino acids, at most about 610 amino acids, at most about 620 amino acids, at most about 630 amino acids, at most about 640 amino acids, at most about 650 amino acids, at most about 660 amino acids, at most about 670 amino acids, at most about 680 amino acids, at most about 690 amino acids, at most about 700 amino acids, at most about 710 amino acids, at most about 720 amino acids, at most about 730 amino acids, at most about 740 amino acids, at most about 750 amino acids, at most about 760 amino acids, at most about 770 amino acids, at most about 780 amino acids, at most about 790 amino acids, at most about 800 amino acids, at most about 810 amino acids, or at most about 820 amino acids).

In some embodiments, an amino acid sequence of an encoded portion of each of the constructs does not overlap, even in part, with an amino acid sequence of a different one of the encoded portions. In some embodiments, an amino acid sequence of an encoded portion of a construct partially overlaps with an amino acid sequence of an encoded portion of a different construct. In some embodiments, an amino acid sequence of an encoded portion of each construct partially overlaps with an amino acid sequence of an encoded portion of at least one different construct. In some embodiments, an overlapping amino acid sequence is between about 10 amino acid residues to about 820 amino acids, or any of the subranges of this range (e.g., about 10 amino acids, about 20 amino acids, about 30 amino acids, about 60 amino acids, about 70 amino acids, about 80 amino acids, about 90 amino acids, about 100 amino acids, about 110 amino acids, about 120 amino acids, about 130 amino acids, about 140 amino acids, about 150 amino acids, about 160 amino acids, about 170 amino acids, about 180 amino acids, about 190 amino acids, about 200 amino acids, about 210 amino acids, about 220 amino acids, about 230 amino acids, about 240 amino acids, about 250 amino acids, about 260 amino acids, about 270 amino acids, about 280 amino acids, about 290 amino acids, about 300 amino acids, about 310 amino acids, about 320 amino acids, about 330 amino acids, about 340 amino acids, about 350 amino acids, about 360 amino acids, about 370 amino acids, about 380 amino acids, about 390 amino acids, about 400 amino acids, about 410 amino acids, about 420 amino acids, about 430 amino acids, about 440 amino acids, about 450 amino acids, about 460 amino acids, about 470 amino acids, about 480 amino acids, about 490 amino acids, about 500 amino acids, about 510 amino acids, about 520 amino acids, about 530 amino acids, about 540 amino acids, about 550 amino acids, about 560 amino acids, about 570 amino acids, about 580 amino acids, about 590 amino acids, about 600 amino acids, about 610 amino acids, about 620 amino acids, about 630 amino acids, about 640 amino acids, about 650 amino acids, about 660 amino acids, about 670 amino acids, about 680 amino acids, about 690 amino acids, about 700 amino acids, about 710 amino acids, about 720 amino acids, about 730 amino acids, about 740 amino acids, about 750 amino acids, about 760 amino acids, about 770 amino acids, about 780 amino acids, about 790 amino acids, about 800 amino acids, about 810 amino acids, or about 820 amino acids in length).

In some examples, a desired gene product (e.g., a therapeutic gene product) is encoded by at least two different constructs. In some embodiments, each of at least two different constructs comprises a different segment of a potentially coding region, wherein the coding region may or may not comprise non-coding sequences such as introns and/or regulatory regions. In some embodiments, the at least two different constructs transduce the same cell. In some embodiments, the transduced cell transcribes and translates the two distinct constructs. In some embodiments, the translated polypeptides may then combine at the tertiary and/or quaternary structure level to create a functional anti-VEGF protein. For example, in some embodiments, a ranibizumab light chain, and a ranibizumab heavy chain, are encoded on at least two different constructs, and following translation combine to form a ranibizumab protein in the manner described herein and known in the art.

In some embodiments, compositions described herein comprising an anti-VEGF gene include naturally occurring and/or synthetic intron sequences. An intron may include a nucleotide sequence of an intron that is present in an endogenous genomic DNA sequence (e.g., an inner ear cell target genomic DNA (e.g., a VEGF and/or VEGF-R genomic DNA sequence). In some embodiments, different intron segments overlap. In some embodiments, different intron segments overlap in sequence by at most about 12,000 nucleotides (e.g., at most about 100 nucleotides, at most about 200 nucleotides, at most about 300 nucleotides, at most about 600 nucleotides, at most about 700 nucleotides, at most about 800 nucleotides, at most about 900 nucleotides, at most about 1,000 nucleotides, at most about 1,100 nucleotides, at most about 1,200 nucleotides, at most about 1,300 nucleotides, at most about 1,400 nucleotides, at most about 1,500 nucleotides, at most about 1,600 nucleotides, at most about 1,700 nucleotides, at most about 1,800 nucleotides, at most about 1,900 nucleotides, at most about 2,000 nucleotides, at most about 2,100 nucleotides, at most about 2,200 nucleotides, at most about 2,300 nucleotides, at most about 2,400 nucleotides, at most about 2,500 nucleotides, at most about 2,600 nucleotides, at most about 2,700 nucleotides, at most about 2,800 nucleotides, at most about 2,900 nucleotides, at most about 3,000 nucleotides, at most about 3,100 nucleotides, at most about 3,200 nucleotides, at most about 3,300 nucleotides, at most about 3,400 nucleotides, at most about 3,500 nucleotides, at most about 3,600 nucleotides, at most about 3,700 nucleotides, at most about 3,800 nucleotides, at most about 3,900 nucleotides, at most about 4,000 nucleotides, at most about 4,100 nucleotides, at most about 4,200 nucleotides, at most about 4,300 nucleotides, at most about 4,400 nucleotides, at most about 4,500 nucleotides, at most about 4,600 nucleotides, at most about 4,700 nucleotides, at most about 4,800 nucleotides, at most about 4,900 nucleotides, at most about 5,000 nucleotides, at most about 5,100 nucleotides, at most about 5,200 nucleotides, at most about 5,300 nucleotides, at most about 5,400 nucleotides, at most about 5,500 nucleotides, at most about 5,600 nucleotides, at most about 5,700 nucleotides, at most about 5,800 nucleotides, at most about 5,900 nucleotides, at most about 6,000 nucleotides, at most about 6,100 nucleotides, at most about 6,200 nucleotides, at most about 6,300 nucleotides, at most about 6,400 nucleotides, at most about 6,500 nucleotides, at most about 6,600 nucleotides, at most about 6,700 nucleotides, at most about 6,800 nucleotides, at most about 6,900 nucleotides, at most about 7,000 nucleotides, at most about 7,100 nucleotides, at most about 7,200 nucleotides, at most about 7,300 nucleotides, at most about 7,400 nucleotides, at most about 7,500 nucleotides, at most about 7,600 nucleotides, at most about 7,700 nucleotides, at most about 7,800 nucleotides, at most about 7,900 nucleotides, at most about 8,000 nucleotides, at most about 8,100 nucleotides, at most about 8,200 nucleotides, at most about 8,300 nucleotides, at most about 8,400 nucleotides, at most about 8,500 nucleotides, at most about 8,600 nucleotides, at most about 8,700 nucleotides, at most about 8,800 nucleotides, at most about 8,900 nucleotides, at most about 9,000 nucleotides, at most about 9,100 nucleotides, at most about 9,200 nucleotides, at most about 9,300 nucleotides, at most about 9,400 nucleotides, at most about 9,500 nucleotides, at most about 9,600 nucleotides, at most about 9,700 nucleotides, at most about 9,800 nucleotides, at most about 9,900 nucleotides, at most about 10,000 nucleotides, at most about 10,100 nucleotides, at most about 10,200 nucleotides, at most about 10,300 nucleotides, at most about 10,400 nucleotides, at most about 10,500 nucleotides, at most about 10,600 nucleotides, at most about 10,700 nucleotides, at most about 10,800 nucleotides, at most about 10,900 nucleotides, at most about 11,000 nucleotides, at most about 11,100 nucleotides, at most about 11,200 nucleotides, at most about 11,300 nucleotides, at most about 11,400 nucleotides, at most about 11,500 nucleotides, at most about 11,600 nucleotides, at most about 11,700 nucleotides, at most about 11,800 nucleotides, at most about 11,900 nucleotides, or at most about 12,000 nucleotides) in length. In some embodiments, the overlapping nucleotide sequence in any two of the different constructs can include part or all of one or more exons of a target gene (e.g., anti-VEGF gene).

In some embodiments, a composition or system is or comprises two, three, four, or five different constructs. In compositions where the number of different constructs in the composition is two, the first of the two different constructs can include a coding sequence that encodes an N-terminal portion of a protein (e.g., an anti-VEGF protein), which may be referred to as a lead portion, a first construct, or a 5' portion (e.g., one of at least two antibody chains, e.g., a sequence encoding a heavy chain variable region and/or a light chain variable region). In some examples, an N-terminal portion of the target gene is at least about 10 amino acids (e.g., at least about 10 amino acids, at least about 20 amino acids, at least about 30 amino acids, at least about 60 amino acids, at least about 70 amino acids, at least about 80 amino acids, at least about 90 amino acids, at least about 100 amino acids, at least about 110 amino acids, at least about 120 amino acids, at least about 130 amino acids, at least about 140 amino acids, at least about 150 amino acids, at least about 160 amino acids, at least about 170 amino acids, at least about 180 amino acids, at least about 190 amino acids, at least about 200 amino acids, at least about 210 amino acids, at least about 220 amino acids, at least about 230 amino acids, at least about 240 amino acids, at least about 250 amino acids, at least about 260 amino acids, at least about 270 amino acids, at least about 280 amino acids, at least about 290 amino acids, at least about 300 amino acids, at least about 310 amino acids, at least about 320 amino acids, at least about 330 amino acids, at least about 340 amino acids, at least about 350 amino acids, at least about 360 amino acids, at least about 370 amino acids, at least about 380 amino acids, at least about 390 amino acids, at least about 400 amino acids, at least about 410 amino acids, at least about 420 amino acids, at least about 430 amino acids, at least about 440 amino acids, at least about 450 amino acids, at least about 460 amino acids, at least about 470 amino acids, at least about 480 amino acids, at least about 490 amino acids, at least about 500 amino acids, at least about 510 amino acids, at least about 520 amino acids, at least about 530 amino acids, at least about 540 amino acids, at least about 550 amino acids, at least about 560 amino acids, at least about 570 amino acids, at least about 580 amino acids, at least about 590 amino acids, at least about 600 amino acids, at least about 610 amino acids, at least about 620 amino acids, at least about 630 amino acids, at least about 640 amino acids, at least about 650 amino acids, at least about 660 amino acids, at least about 670 amino acids, at least about 680 amino acids, at least about 690 amino acids, at least about 700 amino acids, at least about 710 amino acids, at least about 720 amino acids, at least about 730 amino acids, at least about 740 amino acids, at least about 750 amino acids, at least about 760 amino acids, at least about 770 amino acids, at least about 780 amino acids, at least about 790 amino acids, at least about 800 amino acids, at least about 810 amino acids, or at least about 820 amino acids) in length. In some examples, a first construct comprises one or both of a promoter (e.g., any of the promoters described herein or known in the art) and a Kozak sequence (e.g., any of the exemplary Kozak sequences described herein or known in the art). In some examples, a first construct comprises a promoter that is an inducible promoter, a constitutive promoter, or a tissue-specific promoter. In some examples, a second of the two different constructs comprises a coding sequence that encodes a C-terminal portion of the protein, which may be referred to as a terminal portion, a second construct, or a 3' portion (e.g., one of at least two antibody chains, e.g., a sequence encoding a heavy chain variable region and/or a light chain variable region). In some examples, a C-terminal portion of the target protein is at least about 10 amino acids (e.g., at least about 10 amino acids, at least about 20 amino acids, at least about 30 amino acids, at least about 60 amino acids, at least about 70 amino acids, at least about 80 amino acids, at least about 90 amino acids, at least about 100 amino acids, at least about 110 amino acids, at least about 120 amino acids, at least about 130 amino acids, at least about 140 amino acids, at least about 150 amino acids, at least about 160 amino acids, at least about 170 amino acids, at least about 180 amino acids, at least about 190 amino acids, at least about 200 amino acids, at least about 210 amino acids, at least about 220 amino acids, at least about 230 amino acids, at least about 240 amino acids, at least about 250 amino acids, at least about 260 amino acids, at least about 270 amino acids, at least about 280 amino acids, at least about 290 amino acids, at least about 300 amino acids, at least about 310 amino acids, at least about 320 amino acids, at least about 330 amino acids, at least about 340 amino acids, at least about 350 amino acids, at least about 360 amino acids, at least about 370 amino acids, at least about 380 amino acids, at least about 390 amino acids, at least about 400 amino acids, at least about 410 amino acids, at least about 420 amino acids, at least about 430 amino acids, at least about 440 amino acids, at least about 450 amino acids, at least about 460 amino acids, at least about 470 amino acids, at least about 480 amino acids, at least about 490 amino acids, at least about 500 amino acids, at least about 510 amino acids, at least about 520 amino acids, at least about 530 amino acids, at least about 540 amino acids, at least about 550 amino acids, at least about 560 amino acids, at least about 570 amino acids, at least about 580 amino acids, at least about 590 amino acids, at least about 600 amino acids, at least about 610 amino acids, at least about 620 amino acids, at least about 630 amino acids, at least about 640 amino acids, at least about 650 amino acids, at least about 660 amino acids, at least about 670 amino acids, at least about 680 amino acids, at least about 690 amino acids, at least about 700 amino acids, at least about 710 amino acids, at least about 720 amino acids, at least about 730 amino acids, at least about 740 amino acids, at least about 750 amino acids, at least about 760 amino acids, at least about 770 amino acids, at least about 780 amino acids, at least about 790 amino acids, at least about 800 amino acids, at least about 810 amino acids, or at least about 820 amino acids) in length. In some examples, a second construct further comprises a poly(A) sequence.

In some examples where the number of different constructs in the composition is two, an N-terminal portion encoded by one of the two constructs can include a portion including amino acid position 1 to about amino acid position 820, or any subrange of this range (e.g., amino acid 1 to at least about amino acid 10, amino acid 1 to at least about amino acid 20, amino acid 1 to at least about amino acid 30, amino acid 1 to at least about amino acid 60, amino acid 1 to at least about amino acid 70, amino acid 1 to at least about amino acid 80, amino acid 1 to at least about amino acid 90, amino acid 1 to at least about amino acid 100, amino acid 1 to at least about amino acid 110, amino acid 1 to at least about amino acid 120, amino acid 1 to at least about amino acid 130, amino acid 1 to at least about amino acid 140, amino acid 1 to at least about amino acid 150, amino acid 1 to at least about amino acid 160, amino acid 1 to at least about amino acid 170, amino acid 1 to at least about amino acid 180, amino acid 1 to at least about amino acid 190, amino acid 1 to at least about amino acid 200, amino acid 1 to at least about amino acid 210, amino acid 1 to at least about amino acid 220, amino acid 1 to at least about amino acid 230, amino acid 1 to at least about amino acid 240, amino acid 1 to at least about amino acid 250, amino acid 1 to at least about amino acid 260, amino acid 1 to at least about amino acid 270, amino acid 1 to at least about amino acid 280, amino acid 1 to at least about amino acid 290, amino acid 1 to at least about amino acid 300, amino acid 1 to at least about amino acid 310, amino acid 1 to at least about amino acid 320, amino acid 1 to at least about amino acid 330, amino acid 1 to at least about amino acid 340, amino acid 1 to at least about amino acid 350, amino acid 1 to at least about amino acid 360, amino acid 1 to at least about amino acid 370, amino acid 1 to at least about amino acid 380, amino acid 1 to at least about amino acid 390, amino acid 1 to at least about amino acid 400, amino acid 1 to at least about amino acid 410, amino acid 1 to at least about amino acid 420, amino acid 1 to at least about amino acid 430, amino acid 1 to at least about amino acid 440, amino acid 1 to at least about amino acid 450, amino acid 1 to at least about amino acid 460, amino acid 1 to at least about amino acid 470, amino acid 1 to at least about amino acid 480, amino acid 1 to at least about amino acid 490, amino acid 1 to at least about amino acid 500, amino acid 1 to at least about amino acid 510, amino acid 1 to at least about amino acid 520, amino acid 1 to at least about amino acid 530, amino acid 1 to at least about amino acid 540, amino acid 1 to at least about amino acid 550, amino acid 1 to at least about amino acid 560, amino acid 1 to at least about amino acid 570, amino acid 1 to at least about amino acid 580, amino acid 1 to at least about amino acid 590, amino acid 1 to at least about amino acid 600, amino acid 1 to at least about amino acid 610, amino acid 1 to at least about amino acid 620, amino acid 1 to at least about amino acid 630, amino acid 1 to at least about amino acid 640, amino acid 1 to at least about amino acid 650, amino acid 1 to at least about amino acid 660, amino acid 1 to at least about amino acid 670, amino acid 1 to at least about amino acid 680, amino acid 1 to at least about amino acid 690, amino acid 1 to at least about amino acid 700, amino acid 1 to at least about amino acid 710, amino acid 1 to at least about amino acid 720, amino acid 1 to at least about amino acid 730, amino acid 1 to at least about amino acid 740, amino acid 1 to at least about amino acid 750, amino acid 1 to at least about amino acid 760, amino acid 1 to at least about amino acid 770, amino acid 1 to at least about amino acid 780, amino acid 1 to at least about amino acid 790, amino acid 1 to at least about amino acid 800, amino acid 1 to at least about amino acid 810, or amino acid 1 to at least about amino acid 820) of an anti-VEGF protein (e.g., SEQ ID NOs: 16, 17, 18, 20, 21, 23, and/or 43). In some examples where the number of different constructs in the composition is two, an N-terminal portion of the precursor anti-VEGF protein can include a portion including at most amino acid position 1 to amino acid position 820 or any subrange of this range (e.g., amino acid 1 to at most about amino acid 10, amino acid 1 to at most about amino acid 20, amino acid 1 to at most about amino acid 30, amino acid 1 to at most about amino acid 60, amino acid 1 to at most about amino acid 70, amino acid 1 to at most about amino acid 80, amino acid 1 to at most about amino acid 90, amino acid 1 to at most about amino acid 100, amino acid 1 to at most about amino acid 110, amino acid 1 to at most about amino acid 120, amino acid 1 to at most about amino acid 130, amino acid 1 to at most about amino acid 140, amino acid 1 to at most about amino acid 150, amino acid 1 to at most about amino acid 160, amino acid 1 to at most about amino acid 170, amino acid 1 to at most about amino acid 180, amino acid 1 to at most about amino acid 190, amino acid 1 to at most about amino acid 200, amino acid 1 to at most about amino acid 210, amino acid 1 to at most about amino acid 220, amino acid 1 to at most about amino acid 230, amino acid 1 to at most about amino acid 240, amino acid 1 to at most about amino acid 250, amino acid 1 to at most about amino acid 260, amino acid 1 to at most about amino acid 270, amino acid 1 to at most about amino acid 280, amino acid 1 to at most about amino acid 290, amino acid 1 to at most about amino acid 300, amino acid 1 to at most about amino acid 310, amino acid 1 to at most about amino acid 320, amino acid 1 to at most about amino acid 330, amino acid 1 to at most about amino acid 340, amino acid 1 to at most about amino acid 350, amino acid 1 to at most about amino acid 360, amino acid 1 to at most about amino acid 370, amino acid 1 to at most about amino acid 380, amino acid 1 to at most about amino acid 390, amino acid 1 to at most about amino acid 400, amino acid 1 to at most about amino acid 410, amino acid 1 to at most about amino acid 420, amino acid 1 to at most about amino acid 430, amino acid 1 to at most about amino acid 440, amino acid 1 to at most about amino acid 450, amino acid 1 to at most about amino acid 460, amino acid 1 to at most about amino acid 470, amino acid 1 to at most about amino acid 480, amino acid 1 to at most about amino acid 490, amino acid 1 to at most about amino acid 500, amino acid 1 to at most about amino acid 510, amino acid 1 to at most about amino acid 520, amino acid 1 to at most about amino acid 530, amino acid 1 to at most about amino acid 540, amino acid 1 to at most about amino acid 550, amino acid 1 to at most about amino acid 560, amino acid 1 to at most about amino acid 570, amino acid 1 to at most about amino acid 580, amino acid 1 to at most about amino acid 590, amino acid 1 to at most about amino acid 600, amino acid 1 to at most about amino acid 610, amino acid 1 to at most about amino acid 620, amino acid 1 to at most about amino acid 630, amino acid 1 to at most about amino acid 640, amino acid 1 to at most about amino acid 650, amino acid 1 to at most about amino acid 660, amino acid 1 to at most about amino acid 670, amino acid 1 to at most about amino acid 680, amino acid 1 to at most about amino acid 690, amino acid 1 to at most about amino acid 700, amino acid 1 to at most about amino acid 710, amino acid 1 to at most about amino acid 720, amino acid 1 to at most about amino acid 730, amino acid 1 to at most about amino acid 740, amino acid 1 to at most about amino acid 750, amino acid 1 to at most about amino acid 760, amino acid 1 to at most about amino acid 770, amino acid 1 to at most about amino acid 780, amino acid 1 to at most about amino acid 790, amino acid 1 to at most about amino acid 800, amino acid 1 to at most about amino acid 810, or amino acid 1 to at most about amino acid 820) of an anti-VEGF protein (e.g., SEQ ID NOs: 16, 17, 18, 20, 21, 23, and/or 43)

In some examples where the number of different constructs in the composition is two, a C-terminal portion encoded by one of the two constructs can include a portion including the final amino acid (e.g., about amino acid position 820) to about amino acid position 1, or any subrange of this range (e.g., amino acid 820 to at least about amino acid 10, amino acid 820 to at least about amino acid 20, amino acid 820 to at least about amino acid 30, amino acid 820 to at least about amino acid 60, amino acid 820 to at least about amino acid 70, amino acid 820 to at least about amino acid 80, amino acid 820 to at least about amino acid 90, amino acid 820 to at least about amino acid 100, amino acid 820 to at least about amino acid 110, amino acid 820 to at least about amino acid 120, amino acid 820 to at least about amino acid 130, amino acid 820 to at least about amino acid 140, amino acid 820 to at least about amino acid 150, amino acid 820 to at least about amino acid 160, amino acid 820 to at least about amino acid 170, amino acid 820 to at least about amino acid 180, amino acid 820 to at least about amino acid 190, amino acid 820 to at least about amino acid 200, amino acid 820 to at least about amino acid 210, amino acid 820 to at least about amino acid 220, amino acid 820 to at least about amino acid 230, amino acid 820 to at least about amino acid 240, amino acid 820 to at least about amino acid 250, amino acid 820 to at least about amino acid 260, amino acid 820 to at least about amino acid 270, amino acid 820 to at least about amino acid 280, amino acid 820 to at least about amino acid 290, amino acid 820 to at least about amino acid 300, amino acid 820 to at least about amino acid 310, amino acid 820 to at least about amino acid 320, amino acid 820 to at least about amino acid 330, amino acid 820 to at least about amino acid 340, amino acid 820 to at least about amino acid 350, amino acid 820 to at least about amino acid 360, amino acid 820 to at least about amino acid 370, amino acid 820 to at least about amino acid 380, amino acid 820 to at least about amino acid 390, amino acid 820 to at least about amino acid 400, amino acid 820 to at least about amino acid 410, amino acid 820 to at least about amino acid 420, amino acid 820 to at least about amino acid 430, amino acid 820 to at least about amino acid 440, amino acid 820 to at least about amino acid 450, amino acid 820 to at least about amino acid 460, amino acid 820 to at least about amino acid 470, amino acid 820 to at least about amino acid 480, amino acid 820 to at least about amino acid 490, amino acid 820 to at least about amino acid 500, amino acid 820 to at least about amino acid 510, amino acid 820 to at least about amino acid 520, amino acid 820 to at least about amino acid 530, amino acid 820 to at least about amino acid 540, amino acid 820 to at least about amino acid 550, amino acid 820 to at least about amino acid 560, amino acid 820 to at least about amino acid 570, amino acid 820 to at least about amino acid 580, amino acid 820 to at least about amino acid 590, amino acid 820 to at least about amino acid 600, amino acid 820 to at least about amino acid 610, amino acid 820 to at least about amino acid 620, amino acid 820 to at least about amino acid 630, amino acid 820 to at least about amino acid 640, amino acid 820 to at least about amino acid 650, amino acid 820 to at least about amino acid 660, amino acid 820 to at least about amino acid 670, amino acid 820 to at least about amino acid 680, amino acid 820 to at least about amino acid 690, amino acid 820 to at least about amino acid 700, amino acid 820 to at least about amino acid 710, amino acid 820 to at least about amino acid 720, amino acid 820 to at least about amino acid 730, amino acid 820 to at least about amino acid 740, amino acid 820 to at least about amino acid 750, amino acid 820 to at least about amino acid 760, amino acid 820 to at least about amino acid 770, amino acid 820 to at least about amino acid 780, amino acid 820 to at least about amino acid 790, amino acid 820 to at least about amino acid 800, amino acid 820 to at least about amino acid 810, or amino acid 820 to at least about amino acid 820) of an anti-VEGF protein (e.g., SEQ ID NOs: 16, 17, 18, 20, 21, 23, and/or 43). In some examples where the number of different constructs in the composition is two, a C-terminal portion of the precursor anti-VEGF protein can include a portion including the final amino acid (e.g., about amino acid position 820) to at most about amino acid position 1, or any subrange of this range (e.g., amino acid 820 to at most about amino acid 10, amino acid 820 to at most about amino acid 20, amino acid 820 to at most about amino acid 30, amino acid 820 to at most about amino acid 60, amino acid 820 to at most about amino acid 70, amino acid 820 to at most about amino acid 80, amino acid 820 to at most about amino acid 90, amino acid 820 to at most about amino acid 100, amino acid 820 to at most about amino acid 110, amino acid 820 to at most about amino acid 120, amino acid 820 to at most about amino acid 130, amino acid 820 to at most about amino acid 140, amino acid 820 to at most about amino acid 150, amino acid 820 to at most about amino acid 160, amino acid 820 to at most about amino acid 170, amino acid 820 to at most about amino acid 180, amino acid 820 to at most about amino acid 190, amino acid 820 to at most about amino acid 200, amino acid 820 to at most about amino acid 210, amino acid 820 to at most about amino acid 220, amino acid 820 to at most about amino acid 230, amino acid 820 to at most about amino acid 240, amino acid 820 to at most about amino acid 250, amino acid 820 to at most about amino acid 260, amino acid 820 to at most about amino acid 270, amino acid 820 to at most about amino acid 280, amino acid 820 to at most about amino acid 290, amino acid 820 to at most about amino acid 300, amino acid 820 to at most about amino acid 310, amino acid 820 to at most about amino acid 320, amino acid 820 to at most about amino acid 330, amino acid 820 to at most about amino acid 340, amino acid 820 to at most about amino acid 350, amino acid 820 to at most about amino acid 360, amino acid 820 to at most about amino acid 370, amino acid 820 to at most about amino acid 380, amino acid 820 to at most about amino acid 390, amino acid 820 to at most about amino acid 400, amino acid 820 to at most about amino acid 410, amino acid 820 to at most about amino acid 420, amino acid 820 to at most about amino acid 430, amino acid 820 to at most about amino acid 440, amino acid 820 to at most about amino acid 450, amino acid 820 to at most about amino acid 460, amino acid 820 to at most about amino acid 470, amino acid 820 to at most about amino acid 480, amino acid 820 to at most about amino acid 490, amino acid 820 to at most about amino acid 500, amino acid 820 to at most about amino acid 510, amino acid 820 to at most about amino acid 520, amino acid 820 to at most about amino acid 530, amino acid 820 to at most about amino acid 540, amino acid 820 to at most about amino acid 550, amino acid 820 to at most about amino acid 560, amino acid 820 to at most about amino acid 570, amino acid 820 to at most about amino acid 580, amino acid 820 to at most about amino acid 590, amino acid 820 to at most about amino acid 600, amino acid 820 to at most about amino acid 610, amino acid 820 to at most about amino acid 620, amino acid 820 to at most about amino acid 630, amino acid 820 to at most about amino acid 640, amino acid 820 to at most about amino acid 650, amino acid 820 to at most about amino acid 660, amino acid 820 to at most about amino acid 670, amino acid 820 to at most about amino acid 680, amino acid 820 to at most about amino acid 690, amino acid 820 to at most about amino acid 700, amino acid 820 to at most about amino acid 710, amino acid 820 to at most about amino acid 720, amino acid 820 to at most about amino acid 730, amino acid 820 to at most about amino acid 740, amino acid 820 to at most about amino acid 750, amino acid 820 to at most about amino acid 760, amino acid 820 to at most about amino acid 770, amino acid 820 to at most about amino acid 780, amino acid 820 to at most about amino acid 790, amino acid 820 to at most about amino acid 800, amino acid 820 to at most about amino acid 810, or amino acid 820 to at most about amino acid 820, or any length sequence there between of an anti-VEGF protein (e.g., SEQ ID NO: 16, 17, 18, 20, 21, 23, and/or 43).

In some embodiments, splice sites are involved in trans-splicing. In some embodiments, a splice donor site (Trapani et al. EMBO Mol. Med. 6(2):194-211, 2014, which is incorporated herein in its entirety by reference) follows the coding sequence in the N-terminal construct. In the C-terminal construct, a splice acceptor site may be subcloned just before the coding sequence for a second portion of an anti-VEGF gene. In some embodiments, within the coding sequence, a silent mutation can be introduced, generating an additional site for restriction digestion.

In some embodiments, any of the constructs provided herein can be included in a composition suitable for administration to an animal for the amelioration of symptoms associated with an otological disease characterized by neovascularization (e.g., VS).

Pharmaceutical Compositions

In certain embodiments, a composition of the present disclosure relates to a separate diluent drug product (AAV diluent drug product), at or near equivalence in composition to an rAAV-antiVEGF formulation buffer. In certain embodiments, a diluent drug product will be manufactured, sterile filtered (0.2 µm filter), and aseptically filled into single-use vials. In certain embodiments, the formulation buffer comprises sterile water containing 1.5 mM monopotassium phosphate, 8.1 mM sodium phosphate dibasic, 2.7 mM potassium chloride, 172 mM sodium chloride, and 0.001% Poloxamer 188. In certain embodiments, diluent drug product will be utilized to prepare the concentrations necessary for the doses described for use in a mammal of interest (e.g., a human in need thereof).

Among other things, the present disclosure provides pharmaceutical compositions. In some embodiments compositions provided herein are suitable for administration to an animal for the amelioration of symptoms associated with an otological disease characterized by neovascularization (e.g., VS).

In some embodiments, pharmaceutical compositions of the present disclosure may comprise, e.g., a polynucleotide, e.g., one or more constructs, as described herein. In some embodiments, a pharmaceutical composition may comprise one or more AAV particles, e.g., one or more rAAV construct encapsidated by one or more AAV serotype capsids, as described herein.

In some embodiments, a pharmaceutical composition comprises one or more pharmaceutically or physiologically acceptable carriers, diluents or excipients. As used herein, the term "pharmaceutically acceptable carrier" comprises solvents, dispersion media, coatings, antibacterial agents, antifungal agents, and the like that are compatible with pharmaceutical administration. Supplementary active compounds can also be incorporated into any of the compositions described herein. Such compositions may include one or more buffers, such as neutral-buffered saline, phosphate-buffered saline, and the like; one or more carbohydrates, such as glucose, mannose, sucrose, and dextran; mannitol; one or more proteins, polypeptides, or amino acids, such as glycine; one or more antioxidants; one or more chelating agents, such as EDTA or glutathione; and/or one or more preservatives. In some embodiments, formulations are in a dosage forms, such as injectable solutions, injectable gels, drug-release capsules, and the like.

In some embodiments, compositions of the present disclosure are formulated for intravenous administration. In some embodiments compositions of the present disclosure are formulated for intra-cochlear administration. In some embodiments, a therapeutic composition is formulated to comprise a lipid nanoparticle, a polymeric nanoparticle, a mini-circle DNA and/or a CELiD DNA.

In some embodiments, a therapeutic composition is formulated to comprise a synthetic perilymph solution. For example, in some embodiments, a synthetic perilymph solution comprises 20-200 mM NaCl; 1-5 mM KCl; 0.1-10 mM $CaCl_2$; 1-10 mM glucose; and 2-50 mM HEPES, with a pH between about 6 and about 9. In some embodiments, a therapeutic composition is formulated at appropriate dilutions in a physiologically acceptable solution (e.g., artificial perilymph comprising NaCl, 120 mM; KCl, 3.5 mM; CaCl2, 1.5 mM; glucose, 5.5 mM; HEPES, 20 mM which is titrated with NaOH to adjust its pH to 7.5 (total $Na^+$ concentration of 130 mM) as described in Chen et al., J Controlled Rel. 110:1-19, 2005, which is incorporated in its entirety herein by reference). In some embodiments, a therapeutic composition is formulated to comprise a physiologically suitable solution. For example, in some embodiments, a physiologically suitable solution comprises commercially available 1×PBS with pluronic acid F68, prepared to a final concentration of: 8.10 mM Sodium Phosphate Dibasic, 1.5 mM Monopotassium Phosphate, 2.7 mM Potassium Chloride, 172 mM Sodium Chloride, and 0.001% Pluronic Acid F68). In some embodiments, alternative pluronic acids are utilized. In some embodiments, alternative ion concentrations are utilized.

In some embodiments, any of the pharmaceutical compositions described herein may further comprise one or more agents that promote the entry of a nucleic acid or any of the constructs described herein into a mammalian cell (e.g., a liposome or cationic lipid). In some embodiments, any of the constructs described herein can be formulated using natural and/or synthetic polymers. Non-limiting examples of polymers that may be included in any of the compositions described herein can include, but are not limited to, DYNAMIC POLYCONJUGATE® (Arrowhead Research Corp., Pasadena, Calif.), formulations from Mirus Bio (Madison, Wis.) and Roche Madison (Madison, Wis.), PhaseRX polymer formulations such as, without limitation, SMARTT POLYMER TECHNOLOGY® (PhaseRX, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly (lactic-co-glycolic acid) (PLGA) polymers, RONDEL™ (RNAi/Oligonucleotide Nanoparticle Delivery) polymers (Arrowhead Research Corporation, Pasadena, Calif.), and pH responsive co-block polymers, such as, but not limited to, those produced by PhaseRX (Seattle, Wash.). Many of these polymers have demonstrated efficacy in delivering oligonucleotides in-vivo into a mammalian cell (see, e.g., deFougerolles, Human Gene Ther. 19:125-132, 2008; Rozema et al., Proc. Natl. Acad. Sci. U.S.A. 104:12982-12887, 2007; Rozema et al., Proc. Natl. Acad. Sci. U.S.A. 104:12982-12887, 2007; Hu-Lieskovan et al., Cancer Res. 65:8984-8982, 2005; Heidel et al., Proc. Natl. Acad. Sci. U.S.A. 104:5715-5721, 2007, each of which is incorporated in its entirety herein by reference).

In some embodiments, a composition comprises a pharmaceutically acceptable carrier (e.g., phosphate buffered saline, saline, or bacteriostatic water). Upon formulation, in some embodiments, solutions can be administered in a manner compatible with a dosage formulation and in such amount as is therapeutically effective. In some embodiments, formulations are administered in a variety of dosage forms such as injectable solutions, injectable gels, drug-release capsules, and the like.

In some embodiments, a composition provided herein can be formulated to be compatible with their intended route of administration. A non-limiting example of an intended route of administration is local administration (e.g., intra-cochlear administration).

In some embodiments, a provided composition comprises one nucleic acid construct. In some embodiments, a provided composition comprises two or more different constructs. In some embodiments, a composition that include a single nucleic acid construct comprising a coding sequence that encodes an anti-VEGF protein and/or a functional characteristic portion thereof. In some embodiments, compositions comprise a single nucleic acid construct comprising a coding sequence that encodes an anti-VEGF protein and/or a functional characteristic portion thereof, which, when introduced into a mammalian cell, that coding sequence is integrated into the genome of the mammalian cell. In some embodiments, a composition comprising at least two different constructs, e.g., constructs comprise coding sequences that encode a different portion of an anti-VEGF protein, the constructs can be combined to generate a sequence encoding an active anti-VEGF protein (e.g., a full-length ranibizumab, bevacizumab, or aflibercept protein) in a mammalian cell, and thereby treat associated VS and/or other otology associated diseases characterized by neovascularization and amenable to anti-VEGF protein treatment as described herein.

Also provided are kits including any of the compositions described herein. In some embodiments, a kit can include a solid composition (e.g., a lyophilized composition including the at least two different constructs described herein) and a liquid for solubilizing the lyophilized composition. In some embodiments, a kit can include a pre-loaded syringe including any of the compositions described herein.

In some embodiments, a kit comprises a vial comprising any of the compositions described herein (e.g., formulated as an aqueous composition, e.g., an aqueous pharmaceutical composition). In some embodiments, a kit can include instructions for performing any of the methods described herein.

Genetically Modified Cells

The present disclosure also provides a cell (e.g., an animal cell, e.g., a mammalian cell, e.g., a primate cell, e.g., a human cell) that comprises any of the nucleic acids, constructs or compositions described herein. In some embodiments, an animal cell is a human cell (e.g., a human supporting cell or a human hair cell). In other embodiments, an animal cell is a non-human mammal (e.g., Simian cell, Felidae cell, Canidae cell etc.). A person skilled in the art will appreciate that the nucleic acids and constructs described herein can be introduced into any animal cell (e.g., the supporting or hair cells of any animal suitable for veterinary intervention). Non-limiting examples of constructs and methods for introducing constructs into animal cells are described herein.

In some embodiments, an animal cell can be any cell of the inner ear, including hair and/or supporting cells. Non-limiting examples such cells include: Hensen's cells, Deiters' cells, cells of the endolymphatic sac and duct, transitional cells in the saccule, utricle, and ampulla, inner and outer hair cells, spiral ligament cells, spiral ganglion cells, spiral prominence cells, external saccule cells, marginal cells, intermediate cells, basal cells, inner pillar cells, outer pillar cells, Claudius cells, inner border cells, inner phalangeal cells, or cells of the stria vascularis.

In some embodiments, an animal cell is a specialized cell of the cochlea. In some embodiments, an animal cell is a hair cell. In some embodiments, an animal cell is a cochlear inner hair cell or a cochlear outer hair cell. In some embodiments, an animal cell is a cochlear inner hair cell. In some embodiments, an animal cell is a cochlear outer hair cell.

In some embodiments, an animal cell is in-vitro. In some embodiments, an animal cell is of a cell type which is endogenously present in an animal, e.g., in a primate and/or human. In some embodiments, an animal cell is an autologous cell obtained from an animal and cultured ex-vivo.

Methods

Among other things, the present disclosure provides methods for treating a subject having an otological disease associated with vascularization, e.g., VS. In some embodiments, a method comprises introducing a composition as described herein into an inner ear (e.g., a cochlea) of a subject. For example, provided herein are methods that in some embodiments include administering to an inner ear (e.g., cochlea) of a subject (e.g., an animal, e.g., a mammal, e.g., a primate, e.g., a human) an effective amount, e.g., a therapeutically effective amount, of any composition described herein. In some embodiments of any of the methods disclosed herein, a subject has been previously identified as having a defective inner ear cell target gene (e.g., a supporting and/or hearing cell target gene having a mutation that results in a decrease in expression and/or activity of a supporting and/or hearing cell target protein encoded by the gene, e.g., a mutation in NF2). Some embodiments of any of the methods disclosed herein further include, prior to the introducing or administering step, determining that a subject has a defective inner ear cell target gene. Some embodiments of any of the methods disclosed herein can further include detecting a mutation in an inner ear cell target gene in a subject. Some embodiments of any of the methods disclosed herein can further include identifying or diagnosing a subject as having nonsyndromic or syndromic sensorineural hearing loss.

In some embodiments, a method disclosed herein comprises administering a composition disclosed herein, e.g., rAAV-antiVEGF, for the treatment of a subject, e.g., mammal, e.g., human, e.g., patient, with VS. In some embodiments, a composition disclosed herein is delivered via surgical delivery, e.g., to a cochlea.

In some embodiments, a subject has a progressive tumor, e.g., a tumor that has a growth rate of at least 5%, at least 10%, at least 20%, at least 30%, at least 40%, or at least 50% in successive scans, e.g., a tumor that has evidence of progression. In some embodiments, a subject has a progressive tumor, e.g., a tumor that has a growth rate of at least 5%, at least 10%, at least 20%, at least 30%, at least 40%, or at least 50% in consecutive scans, e.g., a tumor that has evidence of progression.

In some embodiments, a subject has a stable tumor, e.g., a tumor that has a growth rate that is less than 5%, less than 10%, less than 20%, or less than 30% in successive scans, e.g., a tumor that lacks evidence of substantive progression. In some embodiments, a subject has a stable tumor, e.g., a tumor that has a growth rate that is less than 5%, less than 10%, less than 20%, or less than 30% in consecutive scans, e.g., a tumor that lacks evidence of substantive progression.

In some embodiments, a subject does not have a tumor that is 2 cm or more maximum dimension (e.g., a tumor that is likely to invade a cerebellopontine angle and potentially compress the brainstem). In some embodiments, a subject is not at high risk for potentially life-threatening tumor-related sequelae that may be avoided with the current standard of care of surgical resection and radiation therapy. In some embodiments, a method disclosed herein further comprises administering surgical resection or radiation.

In some embodiments, a subject has a tumor that is 2 cm or more maximum dimension (e.g., a tumor that is likely to invade a cerebellopontine angle and potentially compress a brainstem). In some embodiments, a subject is at high risk for potentially life-threatening tumor-related sequelae that may be avoided through administration of methods and compositions as described herein. In some embodiments, methods and compositions as described herein are utilized as a combination therapy with current standard of care methods, e.g., in some embodiments a method disclosed herein further comprises administering surgical resection or radiation.

In some embodiments, a subject does not have profound deafness in the contralateral ear. In some embodiment, a subject has auditory function in the contralateral ear. In some embodiments, a subject can maintain access to important auditory domains such as speech reception and environmental awareness. In some embodiments, a subject having NF2 is not administered a composition disclosed herein. In some embodiments, safety and tolerability of a composition disclosed herein can be assessed in unilateral sporadic progressive VS. In some embodiments of any of the methods disclosed herein, a subject has progressive growth of small (less than 2 cm maximum dimension), and/or unilateral sporadic tumors. In some embodiments, safety and tolerability of a composition disclosed herein, e.g., rAAV-anti-VEGF, can be assessed in a subject disclosed herein.

In some embodiments, a composition disclosed herein, e.g., rAAV-antiVEGF, is formulated as a sterile suspension for intracochlear administration. In some embodiments, a composition comprises constructs in an amount of at least $1 \times 10^{11}$, at least $5 \times 10^{11}$, at least $1 \times 10^{12}$, at least $1 \times 10^{12}$, at least $2 \times 10^{12}$, at least $3 \times 10^{12}$, at least $4 \times 10^{12}$, at least $5 \times 10^{12}$, at least $6 \times 10^{12}$, at least $7 \times 10^{12}$, at least $8 \times 10^{12}$, at least $9 \times 10^{12}$, at least $1 \times 10^{13}$, at least $2 \times 10^{13}$, at least $3 \times 10^{13}$, at least $4 \times 10^{13}$, at least $5 \times 10^{13}$, at least $6 \times 10^{13}$, at least $7 \times 10^{13}$, at least $8 \times 10^{13}$, at least $9 \times 10^{13}$, or at least $1 \times 10^{14}$ vector genomes (vg) per milliliter (mL) (vg/mL). In some embodiments, a composition comprises constructs in an amount of at most $1 \times 10^{15}$, at most $5 \times 10^{14}$, at most $1 \times 10^{14}$, at most $5 \times 10^{13}$, at most $1 \times 10(13)$, at most $9 \times 10^{12}$, at most $8 \times 10^{12}$, at most $7 \times 10^{12}$, at most $6 \times 10^{12}$, at most $5 \times 10^{12}$, at most $4 \times 10(12)$, at most $3 \times 10^{12}$, at most $2 \times 10^{12}$, or at most $1 \times 10^{12}$ vector genomes (vg) per milliliter (mL). In some embodiments, a composition comprises constructs in an amount of about $1 \times 10^{12}$ vg/mL to $1 \times 10^{13}$ vg/mL, about $5 \times 10(12)$ vg/mL to $5 \times 10^{13}$ vg/mL, or about $1 \times 10^{13}$ vg/mL to $2 \times 10^{13}$ vg/mL.

In some embodiments, a composition comprises constructs in an amount of about $1 \times 10^{12}$ vg/mL, about $1.1 \times 10^{12}$ vg/mL, $1.2 \times 10^{12}$ vg/mL, about $1.3 \times 10^{12}$ vg/mL, about $1.4 \times 10^{12}$ vg/mL, about $1.5 \times 10^{12}$ vg/mL, about $1.6 \times 10^{12}$ vg/mL, about $1.7 \times 10^{12}$ vg/mL, about $1.8 \times 10^{12}$ vg/mL, about $1.9 \times 10^{12}$ vg/mL, about $2.0 \times 10^{12}$ vg/mL, about $2.1 \times 10^{12}$ vg/mL, about $2.2 \times 10^{12}$ vg/mL, about $2.3 \times 10^{12}$ vg/mL, about $2.4 \times 10^{12}$ vg/mL, about $2.5 \times 10^{12}$ vg/mL, about $2.6 \times 10^{12}$ vg/mL, about $2.7 \times 10^{12}$ vg/mL, about $2.8 \times 10^{12}$ vg/mL, about $2.9 \times 10^{12}$ vg/mL, about $3.0 \times 10^{12}$ vg/mL, about $3.1 \times 10^{12}$ vg/mL, about $3.2 \times 10^{12}$ vg/mL, about $3.3 \times 10^{12}$ vg/mL, about $3.4 \times 10^{12}$ vg/mL, about $3.5 \times 10^{12}$ vg/mL, about $3.6 \times 10^{12}$ vg/mL, about $3.7 \times 10^{12}$ vg/mL, about $3.8 \times 10^{12}$ vg/mL, about $3.9 \times 10^{12}$ vg/mL, about $4.0 \times 10^{12}$ vg/mL, about $4.1 \times 10^{12}$ vg/mL, about $4.2 \times 10^{12}$ vg/mL, about $4.3 \times 10^{12}$ vg/mL, about $4.4 \times 10^{12}$ vg/mL, about $4.5 \times 10^{12}$ vg/mL, about $4.6 \times 10^{12}$ vg/mL, about $4.7 \times 10^{12}$ vg/mL, about $4.8 \times 10^{12}$ vg/mL, about $4.9 \times 10^{12}$ vg/mL, about $5.0 \times 10^{12}$ vg/mL, about $5.1 \times 10^{12}$ vg/mL, about $5.2 \times 10^{12}$ vg/mL, about $5.3 \times 10^{12}$ vg/mL, about $5.4 \times 10^{12}$ vg/mL, about $5.5 \times 10^{12}$ vg/mL, about $5.6 \times 10^{12}$ vg/mL, about $5.7 \times 10^{12}$ vg/mL, about $5.8 \times 10^{12}$ vg/mL, about $5.9 \times 10^{12}$ vg/mL, about $6.0 \times 10^{12}$ vg/mL, about $7.0 \times 10^{12}$ vg/mL, about $8.0 \times 10^{12}$ vg/mL, about $9.0 \times 10^{12}$ vg/mL, about $9.1 \times 10^{12}$ vg/mL, about $9.2 \times 10^{12}$ vg/mL, about $9.3 \times 10^{12}$ vg/mL, about $9.4 \times 10^{12}$ vg/mL, about $9.5 \times 10^{12}$ vg/mL, about $9.6 \times 10^{12}$ vg/mL, about $9.7 \times 10^{12}$ vg/mL, about $9.8 \times 10^{12}$ vg/mL, about $9.9 \times 10^{12}$ vg/mL, about $1 \times 10^{13}$ vg/mL, $1.1 \times 10^{13}$ vg/mL, $1.2 \times 10^{13}$ vg/mL, $1.3 \times 10^{13}$ vg/mL, $1.4 \times 10^{13}$ vg/mL, $1.5 \times 10^{13}$ vg/mL, $1.6 \times 10^{13}$ vg/mL, $1.7 \times 10^{13}$ vg/mL, $1.8 \times 10^{13}$ vg/mL, $1.9 \times 10^{13}$ vg/mL, $2 \times 10^{13}$ vg/mL, $5 \times 10^{13}$ vg/mL, or $1 \times 10^{14}$ vg/mL.

In some embodiments, a composition comprises constructs in an amount of $2.5 \times 10^{12}$ vg/mL+/−10%.

In some embodiments, a composition comprises constructs in an amount of $5 \times 10^{12}$ vg/mL+/−10%.

In some embodiments, a composition comprises constructs in an amount of $1 \times 10^{13}$ vg/mL+/−10%.

In some embodiments, a composition disclosed herein, e.g., rAAV-antiVEGF, is administered in the surgical suite under controlled aseptic conditions by a board-certified surgeon experienced in performing otologic surgery. In some embodiments, an administration procedure is a microscope- or endoscope-assisted transcanal exploratory tympanotomy and laser-assisted microstapedotomy, followed by a round window injection to deliver, e.g., about 0.09 mL, of a solution containing a composition disclosed herein, e.g., rAAV-antiVEGF particles. Transcanal exploratory tympanotomy is a common procedure used to expose the structures of the middle ear; transcanal exploratory tympanotomy is often accompanied by laser-assisted stapedectomy (removal of the stapes footplate) or stapedotomy (creating a hole in the stapes footplate), e.g., for patients with otosclerosis. In some embodiments, the approximately 0.25 mm vent hole in the stapes footplate (made using an otologic laser) serves to prevent a potential deleterious rise in intralabyrinthine pressure.

In some embodiments, disclosed herein is a sterile, one-time use delivery device to administer a composition disclosed herein to the perilymph fluid of an inner ear through a round window membrane with a vent located in a stapes footplate. In some embodiments, this custom device affords advantages over available materials, e.g., both with respect to the potential for safety and efficacy of a therapeutic agent, as it was specifically designed for an intracochlear route of administration. In some embodiments, design elements of a delivery device include: maintenance of sterility of injected fluid; minimization of air bubbles introduced to the inner ear; ability to precisely deliver small volumes at a controlled flow rate (coupled with the use of a standard pump); allowance for visualization of round window membrane and delivery through the external auditory canal by the surgeon; minimization of damage to the round window membrane, or to cochlear structures beyond the round window membrane; and/or minimization of efflux back out through round window membrane.

In some embodiments, any of the methods disclosed herein comprise a dose-escalation study to assess safety and tolerability in subjects, e.g., mammals, e.g., humans, e.g., patients, e.g., with unilateral progressive sporadic VS. In some embodiments, a composition disclosed herein, e.g., rAAV-antiVEGF, is administered at a dosing regimen disclosed herein. In some embodiments, the dosing regimen comprises either unilateral or bilateral intracochlear administrations of a dose, e.g., as described herein, of a composition disclosed herein, e.g., rAAV-antiVEGF. In some embodiments, a dosing regimen comprises delivery in a volume of at least 0.01 mL, at least 0.02 mL, at least 0.03 mL, at least 0.04 mL, at least 0.05 mL, at least 0.06 mL, at least 0.07 mL, at least 0.08 mL, at least 0.09 mL, at least 0.10 mL, at least 0.11 mL, at least 0.12 mL, at least 0.13 mL, at least 0.14 mL, at least 0.15 mL, at least 0.16 mL, at least 0.17 mL, at least 0.18 mL, at least 0.19 mL, or at least 0.20 mL per cochlea. In some embodiments, a dosing regimen comprises delivery in a volume of at most 0.30 mL, at most 0.25 mL, at most 0.20 mL, at most 0.15 mL, at most 0.14 mL, at most 0.13 mL, at most 0.12 mL, at most 0.11 mL, at most 0.10 mL, at most 0.09 mL, at most 0.08 mL, at most 0.07 mL, at most 0.06 mL, or at most 0.05 mL per cochlea. In some embodiments, a dosing regimen comprises delivery in a volume of about 0.05 mL, about 0.06 mL, about 0.07 mL, about 0.08 mL, about 0.09 mL, about 0.10 mL, about 0.11 mL, about 0.12 mL, about 0.13 mL, about 0.14 mL, or about 0.15 mL per cochlea, e.g., depending on the population.

In some embodiments, a dosing regimen comprises delivery in a volume of about 0.01 mL to about 0.30 mL, about 0.01 mL to about 0.25 mL, about 0.01 mL to about 0.20 mL, about 0.01 mL to about 0.15 mL, about 0.01 mL to about 0.14 mL, about 0.01 mL to about 0.13 mL, about 0.01 mL to about 0.12 mL, about 0.01 mL to about 0.11 mL, about 0.01 mL to about 0.10 mL, about 0.01 mL to about 0.09 mL, about 0.01 mL to about 0.08 mL, about 0.01 mL to about 0.07 mL, about 0.01 mL to about 0.06 mL, about 0.01 mL to about 0.05 mL, about 0.01 mL to about 0.04 mL, about 0.01 mL to about 0.03 mL, or about 0.01 mL to about 0.02 Ml.

In some embodiments, a dosing regimen comprises delivery in a volume of about 0.02 mL to about 0.30 mL, 0.03 mL to about 0.30 mL, 0.04 mL to about 0.30 mL, 0.05 mL to about 0.30 mL, 0.06 mL to about 0.30 mL, 0.07 mL to about 0.30 mL, 0.08 mL to about 0.30 mL, 0.09 mL to about 0.30 mL, 0.10 mL to about 0.30 mL, 0.11 mL to about 0.30 mL, 0.12 mL to about 0.30 mL, 0.13 mL to about 0.30 mL, 0.14 mL to about 0.30 mL, 0.15 mL to about 0.30 mL, 0.16 mL to about 0.30 mL, 0.17 mL to about 0.30 mL, 0.18 mL to about 0.30 mL, 0.19 mL to about 0.30 mL, 0.20 mL to about 0.30 mL, or 0.25 mL to about 0.30 mL.

In some embodiments, a dosing regimen comprises delivery in a volume of about 0.01 mL to about 0.03 mL, about 0.02 mL to about 0.25 mL, about 0.03 mL to about 0.20 mL, about 0.04 mL to about 0.18 mL, about 0.05 mL to about 0.16 mL, about 0.06 mL to about 0.14 mL, about 0.07 mL to about 0.12 mL, or about 0.08 mL to about 0.1 mL.

In some embodiments, a subject having sporadic progressive VS typically presents unilaterally. In some embodiments, a subject having unilateral sporadic progressive VS is administered unilateral administration of a composition disclosed herein. In some embodiments, a subject having NF2 typically experiences bilateral VSs. In some embodiments, a subject having NF2 is administered either unilateral or bilateral administration of a composition disclosed herein.

In some embodiments, a method disclosed herein evaluates the safety and tolerability of escalating doses of a composition disclosed herein, e.g., rAAV-antiVEGF, administered via unilateral intracochlear injection to a subject, e.g., 18 to 80 years of age, with unilateral sporadic progressive VS. In some embodiments, a composition disclosed herein, e.g., rAAV-antiVEGF, inhibits growth of a tumor.

In some embodiments, any of the methods disclosed herein comprise an evaluation of the safety and tolerability of a composition disclosed herein, e.g., rAAV-antiVEGF. In some embodiments, evaluation of the efficacy of a composition disclosed herein, e.g., rAAV-antiVEGF to treat sporadic progressive VS, is performed in a randomized, controlled setting (using a concurrent, non-intervention observation arm).

In some embodiments, any of the methods disclosed herein comprise a determination of an optimal dose of a composition disclosed herein, e.g., rAAV anti-VEGF. In some embodiments, any of the methods disclosed herein comprise evaluation of efficacy of a composition disclosed herein, e.g., rAAV-antiVEGF in a broader VS population. In some embodiments, any of the methods disclosed herein comprise determination of an optimal dosing regimen, e.g., including for bilateral VS tumors (in the setting of NF2).

In some embodiments of any of the methods disclosed herein, the method further comprises administration of the current standard of care, e.g., surgical resection of the tumor and/or radiation therapy.

In some embodiments, of any of the methods disclosed herein, pre-existing neutralizing antibodies (NAb), as detected in serum, do not substantially impact transduction of rAAV particles delivered by an intracochlear route of administration. In some embodiments, a subject administered a composition disclosed herein has pre-existing neutralizing antibodies (NAb), e.g., as described herein. In some embodiments, a subject administered a composition disclosed herein does not have pre-existing neutralizing antibodies (NAb), e.g., as described herein.

In some embodiments, provided herein are methods of ameliorating and/or treating a disease characterized by neovascularization (e.g., VS) by expressing an anti-VEGF protein (e.g., a ranibizumab, bevacizumab, and/or aflibercept protein) in an inner ear of a subject, e.g., an animal, e.g., a mammal, e.g., a primate, e.g., a human. In some embodiments, methods include administering to the inner ear of a subject an effective amount, e.g., a therapeutically effective amount of any of the compositions described herein, wherein the administering ameliorates and/or treats a disease characterized by neovascularization by expression an anti-VEGF protein. In some embodiments, the inner ear target cell that produces an anti-VEGF protein may be a sensory cell, e.g., a hair cell, and/or a non-sensory cell, e.g., a supporting cell, and/or all or any subset of inner ear cells.

Also provided herein are methods of increasing the expression level of an anti-VEGF protein in any subset of inner ear cells of a subject (e.g., an animal, e.g., a mammal, e.g., a primate, e.g., a human,) that include: administering to the inner ear of the subject an effective amount, e.g., a therapeutically effective amount of any of the compositions described herein, wherein the administering results in an increase in the expression level of an anti-VEGF protein (e.g., ranibizumab, bevacizumab, and/or aflibercept) in any cell subset of the inner ear of a subject. In some embodiments, the inner ear target cell may be a sensory cell, e.g., a hair cell, and/or a non-sensory cell, e.g., a supporting cell, and/or all or any subset of inner ear cells.

Also provided herein are methods of treating VS associated symptoms (e.g., hearing loss, tinnitus, vertigo, dizziness, a feeling of fullness in the ear, facial numbness, facial paresthesia, headaches, clumsy gait, and/or mental confusion etc.) in a subject (e.g., an animal, e.g., a mammal, e.g., a primate, e.g., a human) identified as having an otology related disease characterized by neovascularization, comprising: administering to the inner ear of the subject an effective amount, e.g., a therapeutically effective amount of any of the compositions described herein. Also provided herein are methods that include administering to an inner ear of a subject an effective amount, e.g., a therapeutically effective amount of any of the compositions described herein.

Also provided herein are surgical methods for treatment of VS. In some embodiments, the methods include the steps of: introducing into a cochlea of a subject an incision, e.g., a first incision, at a first incision point; and administering intra-cochlearly an effective amount, e.g., a therapeutically effective amount of any of the compositions provided herein. In some embodiments, the composition is administered to the subject at the incision point, e.g., the first incision point. In some embodiments, the composition is administered to the subject into or through the first incision.

In some embodiments of any of the methods described herein, any composition described herein is administered to the subject into or through the cochlea oval window membrane. In some embodiments of any of the methods described herein, any of the compositions described herein is administered to the subject into or through the cochlea round window membrane. In some embodiments of any of the methods described herein, the composition is administered using a medical device capable of creating a plurality of incisions in the round window membrane. In some embodiments, the medical device comprises a plurality of micro-needles. In some embodiments, the medical device comprises a plurality of micro-needles including a generally circular first aspect, where each micro-needle has a diameter of at least about 10 microns. In some embodiments, the medical device comprises a base and/or a reservoir capable of holding the composition. In some embodiments, the medical device comprises a plurality of hollow micro-needles individually including a lumen capable of transferring the composition. In some embodiments, the medical device comprises a means for generating at least a partial vacuum.

In some embodiments, technologies of the present disclosure are used to treat subjects with or at risk of hearing loss. In some embodiments, technologies of the present disclosure are used to treat subjects with or at risk of tinnitus. In some embodiments, technologies of the present disclosure are used to treat subjects with or at risk of vertigo. In some embodiments, technologies of the present disclosure are used to treat subjects with or at risk of VS tumor growth. In some embodiments, technologies of the present disclosure are used to treat subjects with or at risk of myriad symptoms associated with VS and/or standard of care VS treatment options. For example, in some embodiments, a subject has symptoms attributed to at least one pathogenic variant of NF2. It will be understood by those in the art that many different mutations in NF2 can result in a pathogenic variant. In some such embodiments, a pathogenic variant causes or is at risk of causing hearing loss, tinnitus, vertigo, tumor growth etc. by increasing the likelihood of disease characterized by neovascularization.

In some embodiments, a subject experiencing VS associated symptoms (e.g., hearing loss, tinnitus, vertigo, dizziness, a feeling of fullness in the ear, facial numbness, facial paralysis, headaches, clumsy gait, and/or mental confusion etc.) will be evaluated to determine if and where one or more mutations may exist that may be causing said VS associated symptoms. In some such embodiments, the status of certain gene products or function (e.g., via protein or sequencing analyses) will be evaluated. In some embodiments of any of the methods described herein, the subject or animal is a mammal, in some embodiments the mammal is a domestic animal, a farm animal, a zoo animal, a non-human primate, or a human. In some embodiments of any of the methods described herein, the animal, subject, or mammal is an adult, a teenager, a juvenile, a child, a toddler, an infant, or a newborn. In some embodiments of any of the methods described herein, the animal, subject, or mammal is 1-5, 1-10, 1-20, 1-30, 1-40, 1-50, 1-60, 1-70, 1-80, 1-90, 1-100, 1-110, 2-5, 2-10, 10-20, 20-30, 30-40, 40-50, 50-60, 60-70, 70-80, 80-90, 90-100, 100-110, 10-30, 10-40, 10-50, 10-60, 10-70, 10-80, 10-90, 10-100, 10-110, 20-40, 20-50, 20-60, 20-70, 20-80, 20-90, 20-100, 20-110, 30-50, 30-60, 30-70, 30-80, 30-90, 30-100, 40-60, 40-70, 40-80, 40-90, 40-100, 50-70, 50-80, 50-90, 50-100, 60-80, 60-90, 60-100, 70-90, 70-100, 70-110, 80-100, 80-110, or 90-110 years of age. In some embodiments of any of the methods described herein, the subject or mammal is 1, 2, 3, 4, 5, 6, 7, 8, 9, 10, or 11 months of age.

In some embodiments, any of the methods and/or compositions described herein, may result in improvement(s) in VS associated symptoms (e.g., hearing loss, tinnitus, vertigo, dizziness, a feeling of fullness in the ear, facial numbness, facial paresthesia, headaches, clumsy gait, and/or mental confusion etc.). In some embodiments, such a symptom is measured and determined (e.g., using any of the metrics for determining improvement in such a symptom as described herein or known in the art) in a subject in need thereof for at least 10 days, at least 15 days, at least 20 days, at least 25 days, at least 30 days, at least 35 days, at least 40 days, at least 45 days, at least 50 days, at least 55 days, at least 60 days, at least 65 days, at least 70 days, at least 75 days, at least 80 days, at least 85 days, at least 100 days, at least 105 days, at least 110 days, at least 115 days, at least 120 days, at least 5 months, at least 6 months, at least 7 months, at least 8 months, at least 9 months, at least 10 months, at least 11 months, or at least 12 months.

In some embodiments a subject (e.g., an animal, e.g., a mammal, e.g., a human) has or is at risk of developing VS associated symptoms (e.g., hearing loss, tinnitus, vertigo, dizziness, a feeling of fullness in the ear, facial numbness, facial paresthesia, headaches, clumsy gait, and/or mental confusion etc.). In some embodiments a subject (e.g., an animal, e.g., a mammal, e.g., a human) has been previously identified as having a mutation in an NF2 gene. In some embodiments a subject (e.g., an animal, e.g., a mammal, e.g., a human) has any of the mutations in an NF2 gene that are known in the art to be associated with a disease characterized by neovascularization, e.g., VS. In some such embodiments, a subject (e.g., an animal, e.g., a mammal, e.g., a human) has been identified as being a carrier of a mutation in a gene associated with VS (e.g., via genetic testing) that has not previously been identified. In some such embodiments, identified mutations may be novel (e.g., not previously described in the literature), and methods of treatment for a subject suffering from or susceptible to VS will be personalized to the mutation(s) of the particular patient.

In some embodiments, a subject (e.g., an animal, e.g., a mammal, e.g., a human) has been identified as being a carrier of a mutation in an NF2 gene (e.g., via genetic testing). In some embodiments, a subject (e.g., an animal, e.g., a mammal, e.g., a human) has been identified as having a mutation in an NF2 gene and has been diagnosed with VS associated symptom(s) (e.g., hearing loss, tinnitus, vertigo, dizziness, a feeling of fullness in the ear, facial numbness, facial paresthesia, headaches, clumsy gait, and/or mental confusion etc.). In some embodiments, a subject (e.g., an animal, e.g., a mammal, e.g., a human) has been identified as having symptoms associated with a disease characterized by neovascularization.

In some embodiments, successful treatment of VS and VS associated symptom(s) (e.g., hearing loss, tinnitus, vertigo, dizziness, a feeling of fullness in the ear, facial numbness, facial paresthesia, headaches, clumsy gait, and/or mental confusion etc.) can be determined in a subject using any of the conventional methods known in the art, including but not limited to: hearing tests, tinnitus tests, gait tests, cognitive tests, imaging techniques, and/or diagnostic biomarker sampling. For example, non-limiting examples of functional hearing tests are various types of audiometric assays (e.g., pure-tone testing, speech testing, test of the middle ear, auditory brainstem response, and optoacoustic emissions).

In some embodiments of any method provided herein, two or more doses of any composition described herein are introduced or administered into a cochlea of a subject. Some embodiments of any of these methods can include introducing or administering a first dose of a composition into a cochlea of a subject, assessing hearing function of the subject following introduction or administration of a first dose, and administering an additional dose of a composition into the cochlea of the subject found not to have a hearing function within a normal range (e.g., as determined using any test for hearing known in the art).

In some embodiments of any method provided herein, the composition can be formulated for intra-cochlear administration. In some embodiments of any of the methods described herein, the compositions described herein can be administered via intra-cochlear administration or local administration. In some embodiments of any of the methods described herein, the compositions are administered through the use of a medical device (e.g., any of the exemplary medical devices described herein).

In some embodiments, intra-cochlear administration can be performed using any of the methods described herein or known in the art. For example, in some embodiments, a composition can be administered or introduced into the cochlea using the following surgical technique: first using visualization with a 0 degree, 2.5-mm rigid endoscope, the external auditory canal is cleared and a round knife is used to sharply delineate an approximately 5-mm tympanomeatal flap. The tympanomeatal flap is then elevated and the middle ear is entered posteriorly. The chorda tympani nerve is identified and divided, and a curette is used to remove the scutal bone, exposing the round window membrane. To enhance apical distribution of the administered or introduced composition, a surgical laser may be used to make a small 2-mm fenestration in the oval window to allow for perilymph displacement during trans-round window membrane infusion of the composition. The microinfusion device is then primed and brought into the surgical field. The device is maneuvered to the round window, and the tip is seated within the bony round window overhang to allow for penetration of the membrane by the microneedle(s). The footpedal is engaged to allow for a measured, steady infusion of the composition. The device is then withdrawn and the round window and stapes foot plate are sealed with a gelfoam patch.

In some embodiments of any method provided herein, a subject has or is at risk of developing VS and/or VS associated symptoms. In some embodiments of any method provided herein, a subject has been previously identified as having a mutation in a gene implicated in VS development, such a gene may be expressed in supporting cells and/or hair cells.

In some embodiments, a subject cell is in-vitro. In some embodiments, a subject cell is originally obtained from a subject and is cultured ex-vivo. In some embodiments, a subject cell is considered otherwise healthy, and is cultured and expanded ex-vivo. In some embodiments, a subject cell has previously been determined to have a defective inner ear cell target gene. In some embodiments, a subject cell has previously been determined to have a defective hair cell target gene. In some embodiments, a subject cell has previously been determined to have a defective supporting cell target gene.

Devices, Administration, and Surgical Methods

Provided herein are therapeutic delivery systems for treating hearing loss (e.g., nonsyndromic sensorineural hearing loss or syndromic sensorineural hearing loss). In some embodiments, a therapeutic delivery system includes: i) a medical device capable of creating one or a plurality of incisions in a round window membrane of an inner ear of a subject in need thereof, and ii) an effective dose of a composition (e.g., any of the compositions described herein). In some embodiments, a medical device includes a plurality of micro-needles.

In some embodiments of any of the methods disclosed herein, a subject will receive a treatment comprising dosing with a composition disclosed herein, e.g., rAAV-antiVEGF. In some embodiments, a subject may receive at least one additional treatment comprising dosing with a composition disclosed herein. In some embodiments, a subject will be monitored for at least 30 days between each test article composition (e.g., solution comprising rAAV particles) administration.

In certain embodiments, methods and compositions as described herein are utilized as a combination therapy with certain current treatment options, such as continual observation by MRI with no additional active intervention, stereotactic radiosurgery (SRS), fractionated radiotherapy (FRT), and/or Microsurgery (MS).

In some embodiments, methods and compositions as described herein are utilized as a combination therapy with continual observation using MRI. In certain embodiments, MRI measurements may identify tumor growth, tumor stasis, or tumor regression. In certain embodiments, methods as described herein coupled with continual observation without additional intervention increases hearing preservation rate when compared to methods utilizing continual MRI based observation alone.

In some embodiments, methods and compositions as described herein are utilized as a combination therapy with radiosurgery (e.g., gamma knife surgery) as is known in the art. In some embodiments, a single effective dose of radiation is delivered to the tumor (e.g., from 5 to 10 gy of radiation, from 7 to 12 gy of radiation, from 9 to 14 gy of radiation, from 11 to 16 gy of radiation, from 13 to 18 gy of radiation, or from 12 to 17 gy of radiation) before, or after treatment with compositions and methods as described herein. In some embodiments, combination therapy utilizing methods and compositions as described herein reduces necessary radiation dose profiles, reducing the chance that radiation profiles may overlap structures adjacent to a tumor. In some embodiments, this combination therapy approach reduces the potential of radiosurgery induced dysfunction of the cranial nerve or brainstem structures. In some embodiments, combination therapy approaches reduce post-operative hearing loss associated with increased radiation dose to the cochlea or associated brainstem nuclei. In some embodiments, combination therapy approaches reduce the possibility of post-operative hydrocephalus. In some embodiments, combination therapy approaches reduce the possibility of post-operative secondary malignancy. In some embodiments, combination therapy approaches slow tumor growth, arrest tumor growth, and/or shrink tumor size. In some embodiments, combination therapy approaches increase the efficacy of radiosurgery, for instance, increasing the chances of tumor growth arrest, reducing the requirements for additional treatments, increasing the odds of hearing preservation, reducing the odds of permanent facial neuropathy, reducing the odds of trigeminal neuropathy, and/or reducing the odds of hydrocephalus.

In some embodiments, methods and compositions as described herein are utilized as a combination therapy with fractionated radiotherapy as is known in the art. In some embodiments, an effective dose of radiation is delivered to the tumor through multiple micro doses (e.g., ~5 micro doses, ~10 micro doses, ~15 micro doses, ~20 micro doses, ~25 micro doses, or ~30 micro doses) over a period of weeks (e.g., 1 week, 2 weeks, 3 weeks, 4 weeks, 5 weeks, 6 weeks, 7 weeks, 8 weeks, 9 weeks, 10 weeks, 11 weeks, 12 weeks, or greater than 12 weeks) which together culminate in one large dose of radiation to the tumor (e.g., ~30 gy, ~40 gy, ~50 gy ~60 gy, or ~70 gy of radiation), that is administered before, during, or after treatment with compositions and methods as described herein. In some embodiments, combination therapy approaches as described herein result in continual damage the tumor, with the inhibition of neovascularization, while allowing the surrounding tissues to heal between doses. In some embodiments, combination therapy approaches as described herein increase the efficacy of fractionated radiotherapy, for instance, increasing the mean rate of tumor arrest, increasing the 5-year actuarial rate, reducing the chances for additional treatments being required, increasing hearing preservation, decreasing the odds of developing facial neuropathy, decreasing the odds of developing trigeminal neuropathy, and/or decreasing the odds of hydrocephalus.

In some embodiments, methods and compositions as described herein are utilized as a combination therapy with surgical interventions as are known in the art. In some embodiments, such a combination therapy approach increases the efficacy of surgical intervention while reducing the chances of additional surgical complications such as damage to cranial nerves, cerebrospinal fluid (CSF) leaks, and/or post-operative infection. In some embodiments, such a combination approach reduces the odds of additional treatments being required, increases the odds of hearing preservation, reduces the odds of permanent facial neuropathy, reduces the odds of acute morbidity associated with CSF patients, and/or reduces the odds of mortality.

Also provided herein are surgical methods for treatment of hearing loss (e.g., nonsyndromic sensorineural hearing loss or syndromic sensorineural hearing loss). In some embodiments, a method includes the steps of: introducing into a cochlea of a subject a first incision at a first incision point; and administering intra-cochlearly a therapeutically effective amount of any of the compositions provided herein. In some embodiments, a composition is administered to a subject at the first incision point. In some embodiments, a composition is administered to a subject into or through the first incision.

In some embodiments, systemic administration of VEGF inhibitors has been evaluated for the treatment of VS in NF2 patients and the results of these studies provide preliminary clinical evidence for the use of VEGF inhibitors to treat VS. In some embodiments, NF2 patients are at heightened risk for administration of a composition disclosed herein, as they generally present with bilateral schwannomas resulting in compromised hearing in both ears. In some embodiments, a subject having NF2 is not administered a composition disclosed herein. In some embodiments, a subject having NF2 is administered a composition disclosed herein, e.g., based on safety and efficacy of a composition disclosed herein, e.g., rAAV-antiVEGF, delivered via unilateral or bilateral intracochlear administration.

In some embodiments, sporadic VS tumors express VEGF (Saito 2003; Cayé-Thomasen 2003, each of which is incorporated herein in its entirety by reference), and the level of VEGF expression, e.g., correlates with the growth rate of the tumor (Cayé-Thomasen 2003; Cayé-Thomasen 2005, each of which is incorporated herein in its entirety by reference). In some embodiments of any of the methods disclosed herein, a subject has progressive sporadic VS (e.g., defined as a single tumor with a growth rate of at least 20% over successive scans), but whose tumors are still small enough where an additional observation period of one year would not put them at high risk for further tumor-related sequelae (apart from hearing loss). In some embodiments, the subject is an adult who is receiving or will be receiving invasive surgical resection and/or radiation therapy. In some embodiments of any of the methods disclosed herein, the method comprises evaluating a safe dose, e.g., a starting dose (8-fold below the anticipated NOAEL). In some embodiments, the starting dose results in VEGF inhibitor exposure levels in tissues and fluids in close proximity to the tumor location.

In some embodiments, compositions as described herein (e.g., rAAV-antiVEGF) may reach many target cells in the inner ear through delivery into the perilymph. Perilymph is a fluid very similar in composition to, and in diffusional continuity with, cerebrospinal fluid (CSF) (Lysaght 2011, incorporated herein in its entirety by reference). Perilymph bathes most of the sensory, neural, and supporting cells of the cochlea and of the vestibular system, housed in the bony labyrinth of the inner ear. The perilymphatic space of the cochlea, to which in some embodiments, compositions as described herein (e.g., comprising rAAV-antiVEGF) will be delivered, comprises two scalae, or passages: the scala tympani and the scala vestibuli, which are continuous with one another at the apex of the cochlear spiral via the helicotrema. Many cells of the inner ear are in fluid continuity with perilymph through interstitial spaces in the tissue.

Intracochlear administration of an rAAV-antiVEGF composition with a delivery device as described herein typically will occur through the round window membrane (see FIG. 1). In some embodiments, compositions as described herein are delivered to an individual (e.g., a mammal, e.g., a human) using a sterile, one-time use delivery device for intracochlear administration. In certain embodiments, compositions as described herein are delivered to the perilymph fluid of the inner ear through the round window membrane with a vent located in the stapes footplate. In certain embodiments, an intracochlear administration approach comprises administration of compositions as described herein into the scala tympani through the round window membrane, with a vent in the stapes footplate within the oval window, such that rAAV particles are perfused through scala tympani, then through scala vestibuli via connection at the helicotrema, and follows the fluid path to the vent in the stapes footplate. In some embodiments, presence of a vent distinct from the injection port allows for a more even and/or controlled distribution of drug along the length of the cochlea and/or prevents the potentially deleterious build-up of additional fluid pressure within the inner ear. In some embodiments, this delivery approach also permits diffusion of the injectate to the vestibular system. In some embodiments, a process such as that described herein can be accomplished in patients with a relatively nontraumatic approach through the external auditory canal.

In some embodiments of any method provided herein, any of the compositions described herein is administered to the subject into or through the cochlea oval window membrane. In some embodiments of any method provided herein, any of the compositions described herein is administered to the subject into or through the cochlea round window membrane. In some embodiments of any method provided herein, the composition is administered using a medical device capable of creating a plurality of incisions in the round window membrane. In some embodiments, a medical device includes a plurality of micro-needles. In some embodiments, a medical device includes a plurality of micro-needles including a generally circular first aspect, where each micro-needle has a diameter of at least about 10 microns. In some embodiments, a medical device includes a base and/or a reservoir capable of holding a composition. In some embodiments, a medical device includes a plurality of hollow micro-needles individually including a lumen capable of transferring a composition. In some embodiments, a medical device includes a means for generating at least a partial vacuum.

In some embodiments, disclosed herein is a sterile, one-time use delivery device to administer a composition disclosed herein to the perilymph fluid of the inner ear through the round window membrane with a vent located in the stapes footplate. In some embodiments, this custom device affords advantages over available materials and general-purpose surgical instruments, both with respect to safety and the potential for efficacy of a therapeutic agent, as it was specifically designed for the intracochlear route of administration. Important design elements of the delivery device include: maintenance of sterility of injected fluid; minimization of air bubbles introduced to the inner ear; ability to precisely deliver small volumes at a controlled flow rate (coupled with the use of a standard pump); allowance for visualization of round window membrane and delivery through the external auditory canal by the surgeon; minimization of damage to the round window membrane, or to cochlear structures beyond the round window membrane; and minimization of efflux back out through round window membrane. In some embodiments, a custom, dedicated device will be removed from the ear following delivery of about 0.09 mL of a composition disclosed herein, e.g., rAAV-antiVEGF into the perilymph of the cochlea.

Delivery to the inner ear is challenging as a result of the frailty and inaccessibility of the sensory cells and non-sensory supporting cells/structures, limiting the type of surgical approaches without unintended damage. In some embodiments, appropriate venting of the fluid-filled cochlear space prevents damage in the inner ear due to the increased fluid volume.

The structure and function of the mammalian inner ear is highly conserved across mammals (Manley 2017, incorporated herein in its entirety by reference), albeit with differences in timing of cochlear development relative to gestation and birth between primates and other mammals. Cochlear development in the mouse is still ongoing at the time of birth, with hearing onset at around postnatal day 12 (P12; Bulankina 2012, incorporated herein in its entirety by reference). Humans, in contrast, undergo complete cochlear development in utero, and experience hearing onset by gestational week 25 to 28 (Litovsky 2015, incorporated herein in its entirety by reference). Two significant structural aspects of the mature inner ear that must be taken into consideration in the development of potential therapies and their delivery in the ear are: 1) size differences of the inner ear among species; and 2) patency of the cochlear aqueduct that runs between the cochlear perilymph and the cerebrospinal fluid (CSF). In some embodiments of any of the methods disclosed herein, cochlear volume is used for dose extrapolation, e.g., from animals to humans.

In some embodiments, when the subject is a rodent, e.g., a mouse, a surgical approach described in Yoshimura et al., 2018, which comprises delivery through the round window membrane with fenestration of the posterior semicircular canal, which has demonstrated robust and reliable transduction, independent of the age of the animal at the time of injection is used (Yoshimura 2018, incorporated herein in its entirety by reference). A postauricular incision is made to access the temporal bone. A portion of the sternocleidomastoid muscle is divided to expose the otic bulla. A 0.5 to 0.6 mm diameter otologic drill is used to make a small hole in the bulla; the hole is then widened to visualize the stapedial artery and the round window membrane. Fenestration of the posterior semicircular canal is performed with the otologic drill (0.5 to 0.6 mm diameter) to serve as a vent the inner ear during cochlear administration. The round window membrane is penetrated with the mouse delivery device, which consists of a borosilicate capillary pipette and a 10 uL Hamilton syringe, and 1 µL of solution comprising viral particles (approximately 40 to 50% of the total inner ear volume) is delivered through the round window membrane, into the scala tympani, at rate of 300 nL/min.

In some embodiments, when the subject is a NHP, a postauricular incision is made and dissection of the soft tissue is performed down to the level of the periosteum. In some embodiments, the periosteum is incised and elevated to expose the mastoid bone. A cortical mastoidectomy is performed with a combination of high-speed cutting and diamond drill burs. The facial recess is then opened, allowing for adequate round window and oval window (OW) visualization. Fenestration of the stapes footplate in the OW is performed using a Rosen needle. As with other models, the fenestration allows for injection of a larger volume without damage to the inner ear; additionally, venting allows solution comprising rAAV particles to flow toward the apex of the cochlea. Thirty µL of solution comprising rAAV particles (approximately 40 to 50% of the total inner ear volume) is delivered through the round window membrane at rate 30 µL/min.

In some embodiments, when the subject is a mammal, e.g., a human, a less invasive approach through the external auditory canal is used, e.g., since the relevant structures are relatively large, even at birth. In some embodiments, the clinical administration procedure is a transcanal exploratory tympanotomy and laser-assisted microstapedotomy (using a potassium titanyl phosphate [KTP] or $CO_2$ otologic laser to place a small vent hole [approximately 0.25 mm] in the stapes footplate), followed by a round window injection to deliver about 0.09 mL (or 90 µL, approximately 40 to 50% of the total inner ear volume) of solution comprising a composition disclosed herein, e.g., rAAV-antiVEGF particles, through the round window membrane within a three-minute period. In some embodiments, venting serves to prevent a potential deleterious rise in intralabyrinthine pressure. Transcanal exploratory tympanotomy is a common procedure used to expose the structures of the middle ear; transcanal exploratory tympanotomy is often accompanied by laser-assisted stapedectomy (removal of the stapes footplate) or stapedotomy (creating a hole in the stapes footplate), e.g., for patients with otosclerosis.

In some embodiments, the present disclosure describes a delivery approach that utilizes a minimally invasive, well-accepted surgical technique for accessing the middle ear and/or inner ear through the external auditory canal. The procedure includes opening one of the physical barriers between the middle and inner ear at the oval window, and subsequently using a device disclosed herein, e.g., as shown in FIGS. 33-36 (or microcatheter) to deliver a composition disclosed herein at a controlled flow rate and in a fixed volume, via the round window membrane.

Figure 28:
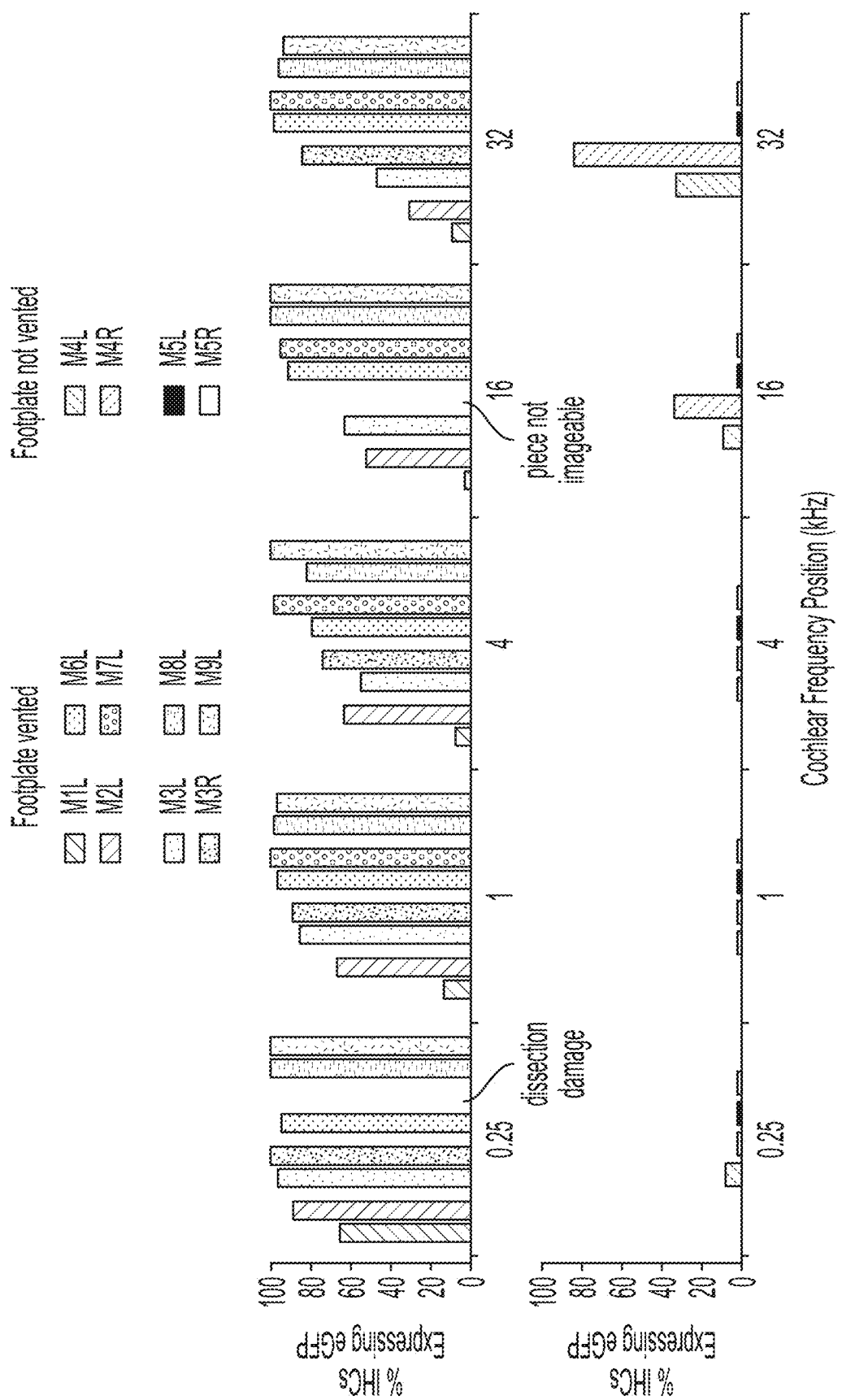
FIG. 28 depicts inner hair cell (IHC) transduction events for seven NHPs that underwent intracochlear (RWM) administration of AAVAnc80-eGFP with venting of the stapes footplate (6 unilateral, 1 bilateral), and two NHPs that underwent intracochlear (RWM) administration of AAVAnc80-eGFP without venting of the stapes footplate (bilateral). Cochleae were analyzed for eGFP expression in IHCs following a 3-week in-life duration. Transduction efficiency of ~80% to 100% can be achieved in macaque IHCs at higher doses (as seen with NHPs M6-M9), while at lower doses (as seen with NHPs M1-M3), an apex-to-base gradient in eGFP expression is observed. Only sporadic transduction at cochlear regions in the apical 75% of the cochlea were observed for animals that underwent surgery without venting of the stapes footplate.

In some embodiments, surgical procedures for mammals (e.g., rodents (e.g., mice, rats, hamsters, or rabbits), primates (e.g., NHP (e.g., macaque, chimpanzees, monkeys, or apes) or humans) may include venting to increase AAV vector transduction rates along the length of the cochlea. In some embodiments, absence of venting during surgery may result in lower AAV vector cochlear cell transduction rates when compared to AAV vector cochlear cell transduction rates following surgeries performed with venting. In some embodiments, venting facilitates transduction rates of about 75-100% of IHCs throughout the cochlea. In some embodiments, venting permits IHC transduction rates of about 50-70%, about 60-80%, about 70-90%, or about 80-100% at the base of the cochlea (see FIG. 28). In some embodiments, venting permits IHC transduction rates of about 50-70%, about 60-80%, about 70-90%, or about 80-100% at the apex of the cochlea (see FIG. 28).

A delivery device described herein may be placed in a sterile field of an operating room and the end of a tubing may be removed from the sterile field and connected to a syringe that has been loaded with a composition disclosed herein (e.g., one or more AAV vectors) and mounted in the pump. After appropriate priming of the system in order to remove any air, a needle may then be passed through the middle ear under visualization (surgical microscope, endoscope, and/or distal tip camera). A needle (or microneedle) may be used to puncture the RWM. The needle may be inserted until a stopper contacts the RWM. The device may then be held in that position while a composition disclosed herein is delivered at a controlled flow rate to the inner ear, for a selected duration of time. In some embodiments, the flow rate (or infusion rate) may include a rate of about 30 µL/min, or from about 25 µL/min to about 35 µL/min, or from about 20 µL/min to about 40 µL/min, or from about 20 µL/min to about 70 µL/min, or from about 20 µL/min to about 90 µL/min, or from about 20 µL/min to about 100 µL/min. In some embodiments, the flow rate is about 20 µL/min, about 30 µL/min, about 40 µL/min, about 50 µL/min, about 60 µL/min, about 70 µL/min, about 80 µL/min, about 90 µL/min or about 100 µL/min. In some embodiments, the selected duration of time (that is, the time during which a composition disclosed herein is flowing) may be about 3 minutes, or from about 2.5 minutes to about 3.5 minutes, or from about 2 minutes to about 4 minutes, or from about 1.5 minutes to about 4.5 minutes, or from about 1 minute to about 5 minutes. In some embodiments, the total volume of a composition disclosed herein that flows to the inner ear may be about 0.09 mL, or from about 0.08 mL to about 0.10 mL, or from about 0.07 mL to about 0.11 mL. In some embodiments, the total volume of a composition disclosed herein equates to from about 40% to about 50% of the volume of the inner ear.

Once the delivery has been completed, the device may be removed. In some embodiments, a device described herein, may be configured as a single-use disposable product. In other embodiments, a device described herein may be configured as a multi-use, sterilizable product, for example, with a replaceable and/or sterilizable needle sub-assembly. Single use devices may be appropriately discarded (for example, in a biohazard sharps container) after administration is complete.

In some embodiments, a composition disclosed herein comprises one or a plurality of rAAV constructs. In some embodiments, when more than one rAAV construct is included in the composition, the rAAV constructs are each different. In some embodiments, an rAAV construct comprises an anti-VEGF coding region, e.g., as described herein. In some embodiments, a composition comprises an rAAV particle comprising an AAV construct described herein. In some embodiments, the rAAV particle is encapsidated by an Anc80 capsid. In some embodiment, an Anc80 capsid comprises a polypeptide of SEQ ID NO: 89. In some embodiment, an Anc80 capsid comprises a polypeptide of SEQ ID NO: 113. In some embodiment, an Anc80 capsid comprises a polypeptide of SEQ ID NO: 114.

In some embodiments, a composition disclosed herein can be administered to a subject with a surgical procedure. In some embodiments, administration, e.g., via a surgical procedure, comprises injecting a composition disclosed herein via a delivery device as described herein into the inner ear. In some embodiments, a surgical procedure disclosed herein comprises performing a transcanal tympanotomy; performing a laser-assisted micro-stapedotomy; and injecting a composition disclosed herein via a delivery device as described herein into the inner ear.

In some embodiments, a surgical procedure comprises performing a transcanal tympanotomy; performing a laser-assisted micro-stapedotomy; injecting a composition disclosed herein via a delivery device as described herein into the inner ear; applying sealant around the round window and/or an oval window of the subject; and lowering a tympanomeatal flap of the subject to the anatomical position.

In some embodiments, a surgical procedure comprises performing a transcanal tympanotomy; preparing a round window of the subject; performing a laser-assisted micro-stapedotomy; preparing both a delivery device as described herein and a composition disclosed herein for delivery to the inner ear; injecting a composition disclosed herein via the delivery device into the inner ear; applying sealant around the round window and/or an oval window of the subject; and lowering a tympanomeatal flap of the subject to the anatomical position.

In some embodiments, performing a laser-assisted microstapedotomy includes using a KTP otologic laser and/or a CO2 otologic laser.

As another example, a composition disclosed herein is administered using a device and/or system specifically designed for intracochlear route of administration. In some embodiments, design elements of a device described herein may include: maintenance of sterility of injected fluid; minimization of air bubbles introduced to the inner ear; ability to precisely deliver small volumes at a controlled rate; delivery through the external auditory canal by the surgeon; minimization of damage to the round window membrane (RWM), or to inner ear, e.g., cochlear structures beyond the RWM; and/or minimization of injected fluid leaking back out through the RWM.

The devices, systems, and methods provided herein also describe the potential for delivering a composition safely and efficiently into the inner ear, in order to treat conditions and disorders that would benefit from delivery of a composition disclosed herein to the inner ear, including, but not limited to, hearing disorders, e.g., as described herein. As another example, by placing a vent in the stapes footplate and injecting through the RWM, a composition disclosed herein is dispersed throughout the cochlea with minimal dilution at the site of action. The development of the described devices allows the surgical administration procedure to be performed through the external auditory canal in humans. The described devices can be removed from the ear following infusion of an amount of fluid into the perilymph of the cochlea. In subjects, the device may be advanced through the external auditory canal, either under surgical microscopic control or along with an endoscope.

Figure 29:
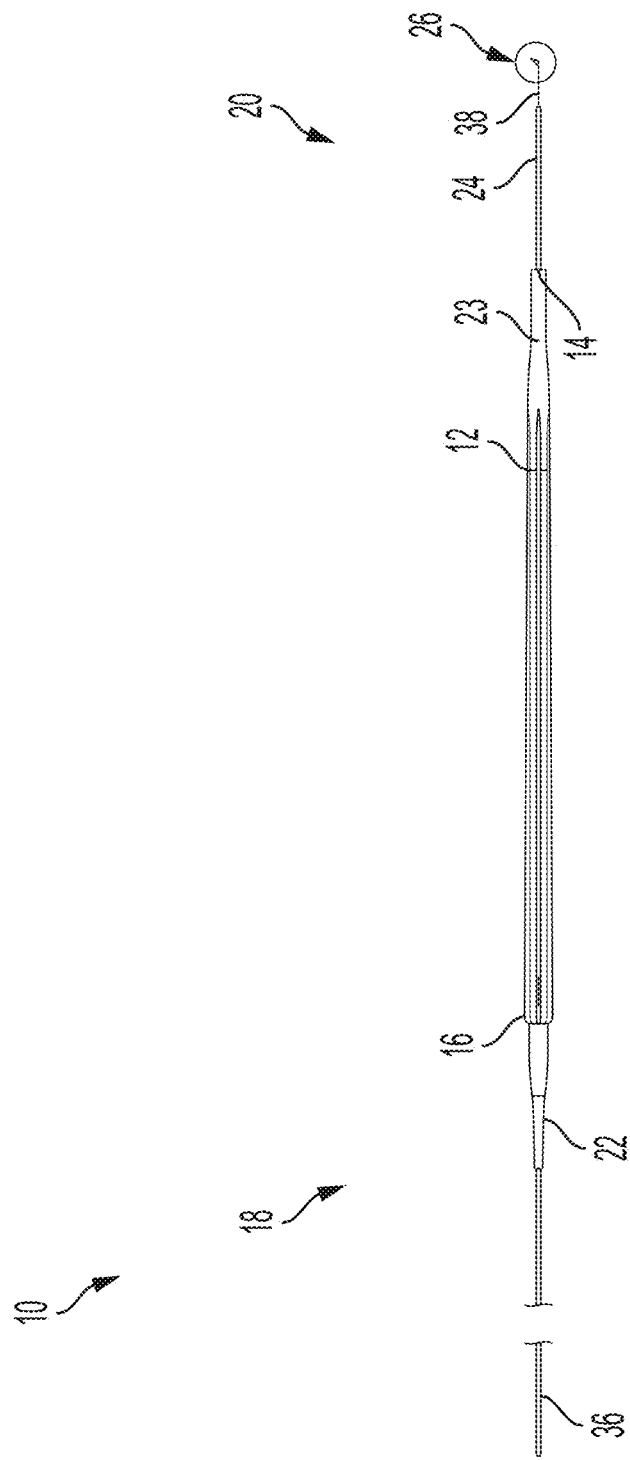
FIG. 29 illustrates a perspective of a device for delivering fluid to an inner ear, according to aspects of the present disclosure.

An exemplary device for use in any of the methods disclosed herein is described in FIGS. 29-32. FIG. 29 illustrates an exemplary device 10 for delivering fluid to an inner ear. Device 10 includes a knurled handle 12, and a distal handle adhesive 14 (for example, an epoxy such as Loctite 4014) that couples to a telescoping hypotube needle support 24. The knurled handle 12 (or handle portion) may include kurling features and/or grooves to enhance the grip. The knurled handle 12 (or handle portion) may be from about 5 mm to about 15 mm thick or from about 5 mm to about 12 mm thick, or from about 6 mm to about 10 mm thick, or from about 6 mm to about 9 mm thick, or from about 7 mm to about 8 mm thick. The knurled handle 12 (or handle portion) may be hollow such that fluid may pass through the device 10 during use. The device 10 may also include a proximal handle adhesive 16 at a proximal end 18 of the knurled handle 12, a needle sub-assembly 26 (shown in FIG. 30) with stopper 28 (shown in FIG. 30) at a distal end 20 of the device 10, and a strain relief feature 22. Strain relief feature 22 may be composed of a Santoprene material, a Pebax material, a polyurethane material, a silicone material, a nylon material, and/or a thermoplastic elastomer. The telescoping hypotube needle support 24 surrounds and supports a bent needle 38 (shown in FIG. 30) disposed therewithin.

Referring still to FIG. 29, the stopper 28 may be composed of a thermoplastic material or plastic polymer (such as a UV-cured polymer), as well as other suitable materials, and may be used to prevent the bent needle 38 from being inserted too far into the ear canal (for example, to prevent insertion of bent needle 38 into the lateral wall or other inner ear structure). Device 10 also may include a tapered portion 23 disposed between the knurled handle 12 and the distal handle adhesive 14 that is coupled to the telescoping hypotube needle support 24. The knurled handle 12 (or handle portion) may include the tapered portion 23 at the distal end of the handle portion 12. Device 10 may also include tubing 36 fluidly connected to the proximal end 16 the device 10 and acts as a fluid inlet line connecting the device to upstream components (for example, a pump, a syringe, and/or upstream components which, in some embodiments, may be coupled to a control system and/or power supply (not shown)). In some embodiments, the bent needle 38 (shown in FIG. 30) extends from the distal end 20, through the telescoping hypotube needle support 24, through the tapered portion 23, through the knurled handle 12, and through the strain relief feature 22 and fluidly connects directly to the tubing 36. In other embodiments, the bent needle 38 fluidly connects with the hollow interior of the knurled handle (for example, via the telescoping hypotube needle support 24) which in turn fluidly connects at a proximal end 16 with tubing 36. In embodiments where the bent needle 38 does not extend all the way through the interior of the device 10, the contact area (for example, between overlapping nested hypotubes 42), the tolerances, and/or sealants between interfacing components must be sufficient to prevent therapeutic fluid from leaking out of the device 10 (which operates at a relatively low pressure (for example, from about 1 Pascal to about 50 Pa, or from about 2 Pa to about 20 Pa, or from about 3 Pa to about 10 Pa)).

Figure 30:
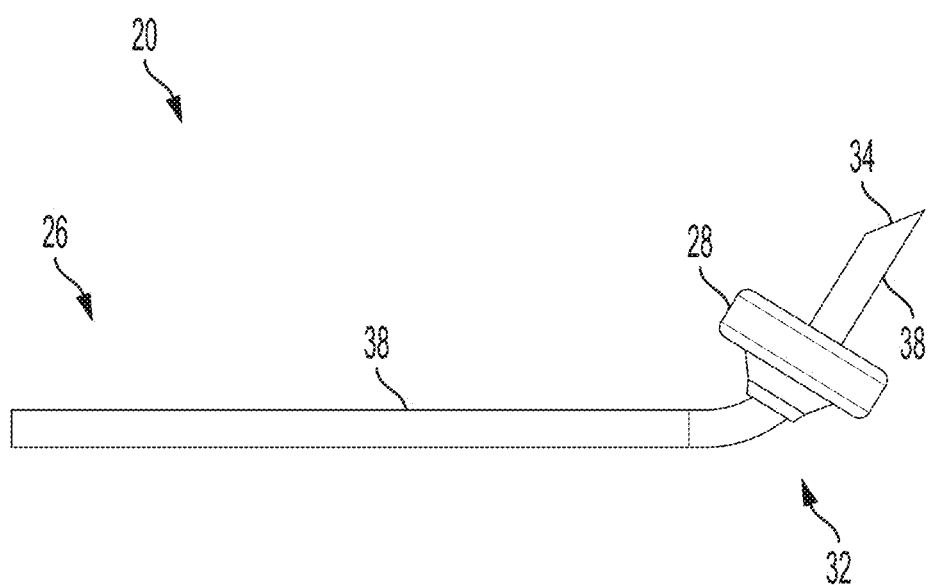
FIG. 30 illustrates a sideview of a bent needle sub-assembly, according to aspects of the present disclosure.

FIG. 30 illustrates a sideview of the bent needle sub-assembly 26, according to aspects of the present disclosed embodiments. Bent needle sub-assembly 26 includes a needle 38 that has a bent portion 32. Bent needle sub-assembly 26 may also include a stopper 28 coupled to the bent portion 32. The bent portion 32 includes an angled tip 34 at the distal end 20 of the device 10 for piercing a membrane of the ear (for example, the RWM). The needle 38, bent portion 32, and angled top 34 are hollow such that fluid may flow therethrough. The angle 46 (as shown in FIG. 33) of the bent portion 32 may vary. A stopper 28 geometry may be cylindrical, disk-shaped, annulus-shaped, dome-shaped, and/or other suitable shapes. Stopper 28 may be molded into place onto bent portion 32. For example, stopper 28 may be positioned concentrically around the bent portion 32 using adhesives or compression fitting. Examples of adhesives include an UV cure adhesive (such as Dymax 203A-CTH-F-T), elastomer adhesives, thermoset adhesives (such as epoxy or polyurethane), or emulsion adhesives (such as polyvinyl acetate). Stopper 28 fits concentrically around the bent portion 32 such that angled tip 34 is inserted into the ear at a desired insertion depth. The bent needle 38 may be formed from a straight needle using incremental forming, as well as other suitable techniques.

Figure 31:
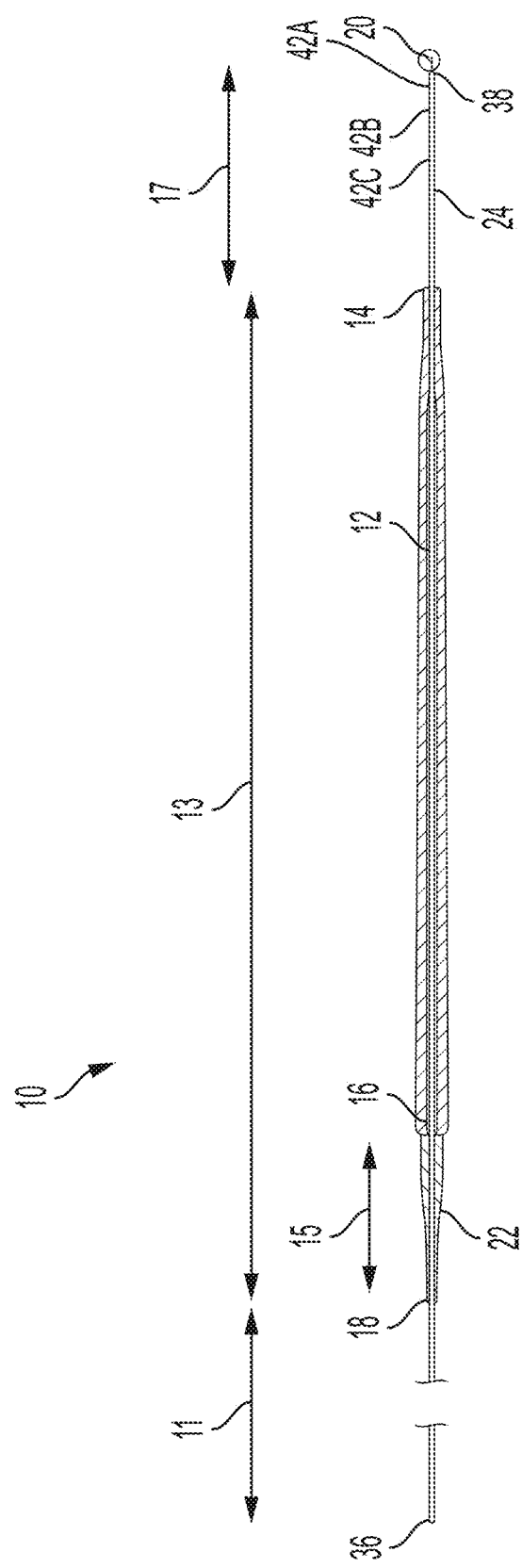
FIG. 31 illustrates a perspective view of a device for delivering fluid to an inner ear, according to aspects of the present disclosure.

FIG. 31 illustrates a perspective view of exemplary device 10 for delivering fluid to an inner ear. Tubing 36 may be from about 1300 mm in length (dimension 11 in FIG. 31) to about 1600 mm, or from about 1400 mm to about 1500 mm, or from about 1430 mm to about 1450 mm. Strain release feature 22 may be from about 25 mm to about 30 mm in length (dimension 15 in FIG. 31), or from about 20 mm to about 35 mm in length. Handle 12 may be about 155.4 mm in length (dimension 13 in FIG. 31), or from about 150 mm to about 160 mm, or from about 140 mm to about 170 mm. The telescoping hypotube needle support 24 may have two or more nested hypotubes, for example three nested hypotubes 42A, 42B, and 42C, or four nested hypotubes 42A, 42B, 42C, and 42D. The total length of hypotubes 42A, 42B, 42C and tip assembly 26 (dimension 17 in FIG. 31) may be from about 25 mm to about 45 mm, or from about 30 mm to about 40 mm, or about 35 mm. In addition, telescoping hypotube needle support 24 may have a length of about 36 mm, or from about 25 mm to about 45 mm, or form about 30 mm to about 40 mm. The three nested hypotubes 42A, 42B, and 42C each may have a length of 3.5 mm, 8.0 mm, and 19.8 mm, respectively, plus or minus about 20%. The inner-most nested hypotube (or most narrow portion) of the telescoping hypotube needle support 24 may be concentrically disposed around needle 38.

Figure 32:
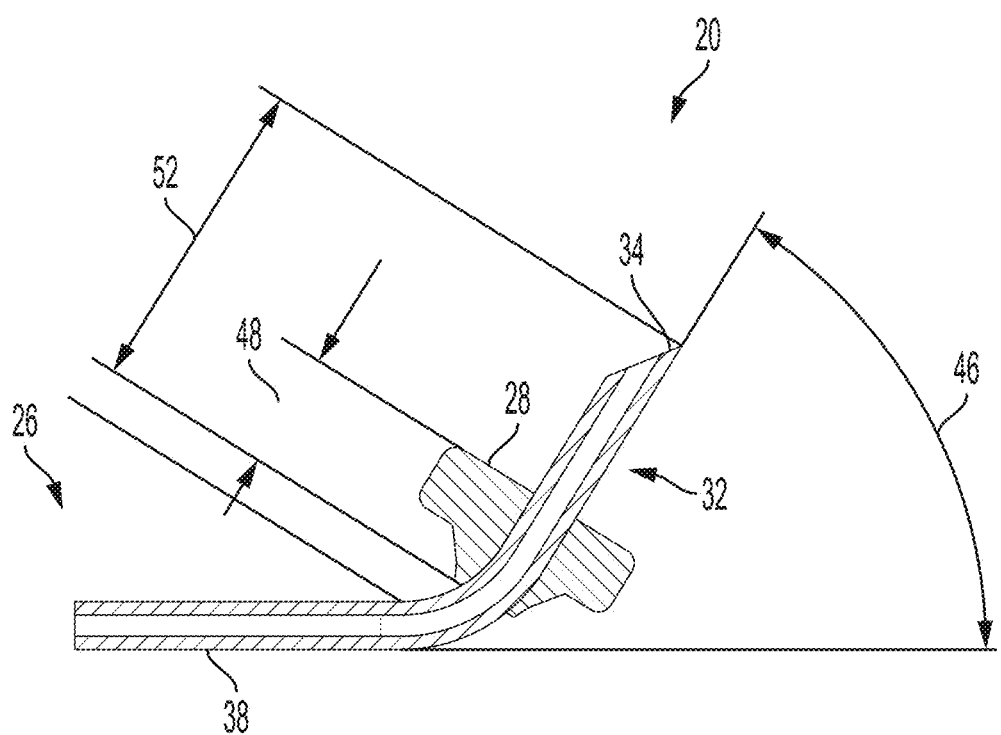
FIG. 32 illustrates a perspective view of a bent needle sub-assembly coupled to the distal end of a device, according to aspects of the present disclosure.

FIG. 32 illustrates a perspective view of bent needle sub-assembly 26 coupled to the distal end 20 of device 10, according to aspects of the present disclosed embodiments. As shown in FIG. 32, bent needle sub-assembly 26 may include a needle 38 coupled to a bent portion 32. In other embodiments, the bent needle 38 may be a single needle (for example, a straight needle that is then bent such that it includes the desired angle 46). Needle 38 may be a 33-gauge needle, or may include a gauge from about 32 to about 34, or from about 31 to 35. At finer gauges, care must be taken to ensure tubing 36 is not kinked or damaged. Needle 38 may be attached to handle 12 for safe and accurate placement of needle 38 into the inner ear. As shown in FIG. 32, bent needle sub-assembly 26 may also include a stopper 28 disposed around bent portion 32. FIG. 32 also shows that bent portion 32 may include an angled tip 34 for piercing a membrane of the ear (for example, the RWM). Stopper 28 may have a height 48 of about 0.5 mm, or from about 0.4 mm to about 0.6 mm, or from about 0.3 mm to about 0.7 mm. Bent portion 32 may have a length 52 of about 1.45 mm, or from about 1.35 mm to about 1.55 mm, or from about 1.2 mm to about 1.7 mm. In other embodiments, the bent portion 32 may have a length greater than 2.0 mm such that the distance between the distal end of the stopper 28 and the distal end of the angled tip 34 is from about 0.5 mm to about 1.7 mm, or from about 0.6 mm to about 1.5 mm, or from about 0.7 mm to about 1.3 mm, or from about 0.8 mm to about 1.2 mm. FIG. 32 shows that stopper 28 may have a geometry that is cylindrical, disk-shaped, and/or dome-shaped. A person of ordinary skill will appreciate that other geometries could be used.

Methods of Treating a Subject

The present disclosure provides, among other things, that technologies described herein may be used to treat an underlying disease and/or symptoms in a subject suffering from or at risk of an otological disease characterized by neovascularization (e.g., acoustic neuromas, e.g., VS).

In some embodiments, a method comprises administering a construct (e.g., an rAAV construct) described herein, a particle (e.g., an rAAV particle), or a composition described herein to a subject. In some embodiments, a method is a method of treatment. In some embodiments, a subject is a subject suffering from or at risk of an otological disease characterized by neovascularization (e.g., acoustic neuromas, e.g., VS).

In some embodiments, administering a construct (e.g., an rAAV construct) described herein, a particle (e.g., an rAAV particle), or a composition described herein to a subject may alleviate and/or ameliorate one or more symptoms associated with an otological disease characterized by neovascularization (e.g., acoustic neuromas, e.g., VS). Symptoms can include, for example, hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, and/or death.

In some embodiments, an otological disease characterized by neovascularization (e.g., acoustic neuromas, e.g., VS) is associated with a gene mutation (e.g., a deletion mutation, a frameshift mutation, a nonsense mutation, a hypomorphic mutation, a hypermorphic mutation, a neomorphic mutation, aberrant over expression, aberrant under expression, etc.). In some embodiments, a subject suffering from or at risk of an otological disease characterized by neovascularization (e.g., acoustic neuromas, e.g., VS) may have a mutation in a gene related to otological tumor progression, which may be characterized as described herein.

In some embodiments, a subject is genetically and/or symptomatically characterized prior to, during, and/or after treatment with technologies described herein (e.g. real-time PCR, quantitative real-time PCR, Western blotting, immunoprecipitation, immunohistochemistry, mass spectrometry, or immunofluorescence, indirect phenotypic determination of expression of a gene and/or protein (e.g., through functional hearing tests, ABRs, DPOAEs, etc.), etc.). In some embodiments, a subject suffering from or at risk of an otological disease characterized by neovascularization (e.g., acoustic neuromas, e.g., VS) may have their associated disease state characterized through tissue sampling (e.g., comprising one or more inner ear cells, e.g., comprising one or more hair cells and/or one or more supporting cells). In some embodiments, tissues are evaluated via morphological analysis to determine morphology of hair cells and/or support cells before, during, and/or after administration of any technologies (e.g., methodologies, e.g., compositions, e.g., compositions comprising constructs, and/or particles, etc.) as described herein. In some such embodiments, standard immunohistochemical or histological analyses may be performed. In some embodiments, if cells are used in-vitro or ex-vivo, additional immunocytochemical or immunohistochemical analyses may be performed. In some embodiments, one or more assays of one or more proteins or transcripts (e.g., western blot, ELISA, polymerase chain reactions) may be performed on one or more samples from a subject or in-vitro cell populations.

In some embodiments, administering a construct (e.g., an rAAV construct) described herein, a particle (e.g., an rAAV particle), or a composition described herein to a subject improves a subject's immunohistochemical evaluation (e.g., tests as described above) when compared to immunohistochemical tests performed prior to treatment with technologies described herein or when compared to a control population.

Treating a Subject to Improve Symptoms of Hearing Loss, Tinnitus, Dizziness, and/or Speech In some embodiments, a subject suffering from or at risk of an otological disease characterized by neovascularization (e.g., acoustic neuromas, e.g., VS) may receive a treatment regimen that is characterized by hearing function. In some embodiments, functionality of a treatment regimen is characterized through hearing function, wherein such hearing function is determined in an individual using auditory brainstem response measurements (ABR) before, after, and/or during treatment with compositions and methods described herein. In some embodiments, functionality of a treatment regimen is characterized through hearing function, wherein such hearing function is determined in an individual by measuring distortion product optoacoustic emissions (DPOAEs) before, after, and/or during treatment with compositions and methods described herein. In some such embodiments, hearing measurements are taken from one or both ears of a subject. In some such embodiments, recordings are compared to prior recordings for the same subject and/or known thresholds on such response measurements used to define, e.g., hearing loss versus acceptable hearing ranges to be defined as normal hearing. In some embodiments, a subject has ABR and/or DPOAE measurements recorded prior to receiving any treatment. In some embodiments, a subject treated with one or more technologies described herein will have improvements on ABR and/or DPOAE measurements after treatment as compared to before treatment. In some embodiments, ABR and/or DPOAE measurements are taken after treatment is administered and at regular follow-up intervals post-treatment. In some embodiments, treatment with technologies described herein improve a subject's test evaluation (e.g., tests as described above) when compared to tests performed prior to treatment with technologies described herein or when compared to a control population.

In some embodiments, a subject suffering from or at risk of an otological disease characterized by neovascularization (e.g., acoustic neuromas, e.g., VS) may have a treatment regimen that is characterized by hearing function as a function of speech, speech understanding, and/or tone recognition. In some embodiments, functionality of a treatment regimen is characterized through determination of speech pattern recognition and/or is determined by a speech therapist. In some embodiments, functionality of a therapeutic treatment regimen with technologies described herein is determined by pure tone testing. In some embodiments, functionality of a therapeutic treatment regimen with technologies described herein is determined by bone conduction testing. In some embodiments, functionality of a therapeutic treatment regimen with technologies described herein is determined by acoustic reflex testing. In some embodiments, functionality of a therapeutic treatment regimen with technologies described herein is determined by tympanometry. In some embodiments, functionality of a therapeutic treatment regimen with technologies described herein is determined by any combination of hearing analysis known in the art. In some embodiments, functionality of a therapeutic treatment regimen with technologies described herein is measured holistically, and/or from one or both ears of a subject. In some embodiments, functionality of a therapeutic treatment regimen with technologies described herein utilizes recordings and/or professional analysis taken post-regime compared to prior recordings and/or analysis for the same subject and/or known thresholds on such response measurements used to define, e.g., hearing loss versus acceptable hearing ranges to be defined as normal hearing. In some embodiments, a treatment subject has speech pattern recognition, pure tone testing, bone conduction testing, acoustic reflex testing and/or tympanometry measurements and/or analysis conducted prior to receiving any treatment. In some embodiments a subject treated with one or more technologies described herein will have improvements on speech pattern recognition, pure tone testing, bone conduction testing, acoustic reflex testing and/or tympanometry measurements after treatment as compared to before treatment. In some embodiments, speech pattern recognition, pure tone testing, bone conduction testing, acoustic reflex testing and/or tympanometry measurements are taken after treatment is administered and at regular follow-up intervals post-treatment. In some embodiments, treatment with technologies described herein improve a subject's test evaluation (e.g., tests as described above) when compared to tests performed prior to treatment with technologies described herein or when compared to a control population.

In some embodiments, a subject suffering from or at risk of an otological disease characterized by neovascularization (e.g., acoustic neuromas, e.g., VS) may undergo treatment functionality evaluation through a method comprising behavioral audiometry evaluation. In some embodiments, behavioral audiometry evaluation comprises pure-tone audiometry with air and bone curves with appropriate masking, Speech audiometry, Words in quiet, or words in noise analysis. In some embodiments, behavioral audiometry evaluation comprises electrophysiologic audiometry by auditory brainstem response testing. In some embodiments, behavioral audiometry evaluation comprises standardized questionnaires: HHIA: Hearing Handicap Inventory for Adults, DHI: Dizziness Handicap Inventory, THI: Tinnitus Handicap Inventory, PANQOL: Penn Acoustic Neuroma Quality of Life (QoL). In some embodiments, treatment with technologies described herein improve a subject's test evaluation (e.g., tests as described above) when compared to tests performed prior to treatment with technologies described herein or when compared to a control population.

In some embodiments, a subject suffering from or at risk of an otological disease characterized by neovascularization (e.g., acoustic neuromas, e.g., VS) may be monitored by evaluation of otologic, vestibular, and/or systemic adverse events, as well as hematology, clinical chemistry, and/or urinalysis parameters. In some embodiments, a subject undergoing treatment with technologies described herein may be assessed for anti-VEGF protein levels in blood and construct DNA in ear swabs, nasal swabs, saliva, and blood. In some embodiments, a subject undergoing treatment with technologies described herein may have blood collected for evaluation of potential humoral immune responses to the capsid and/or secreted transgene product.

In some embodiments, a subject suffering from or at risk of an otological disease characterized by neovascularization (e.g., acoustic neuromas, e.g., VS) may have their treatment functionality analyzed through ABR tests. In some embodiments, an ABR test measures whether the subject's cochlea, cochlear nerve, and brainstem responds to each sound stimulus, such tests are often used as a measure of the health of the ear. In some embodiments, in addition to measuring the lowest intensity of each stimulus frequency that the subject's brainstem could reliably process (threshold), the amplitude of Wave I in response to suprathreshold stimuli can be measured in order to assess the integrity of the afferent flow of information from the cochlear hair cells to the auditory nerve. In some embodiments, ABR thresholds can provide important information about the lowest level of sound that a subject's ear passes along to and is processed by the brainstem, the suprathreshold responses in the amplitude of the ABR Wave I has increasingly been used as a proxy for the integrity of the ribbon synapse connection between the base of the inner hair cells and the auditory nerve dendrites. In some embodiments, treatment with technologies described herein improve a subject's ABR evaluation when compared to tests performed prior to treatment with technologies described herein or when compared to a control population.

In some embodiments, a subject suffering from or at risk of an otological disease characterized by neovascularization (e.g., acoustic neuromas, e.g., VS) may have their treatment functionality analyzed through DPOAE based tests. In some embodiments, DPOAEs are sounds created by movement of the cochlear outer hair cells and are non-invasively measured in the ear canal with a transducer & microphone combination. In some embodiments, a size of evoked DPOAEs is a useful measure of outer hair cell function. In some embodiments, two primary tones (f1 and f2) are presented to an ear producing mechanical vibrations that causes pressure changes in cochlear fluids at stimulus and distortion frequencies. In some embodiments, these pressure changes drive the ear in reverse, activating the middle ear and then eardrum to produce sound in the ear canal. In some embodiments, DPOAEs are collected at the same test frequencies used in ABRs (8, 16, 32 kHz) and may be performed while a subject is under anesthesia for ABRs. In some embodiments, an f2 is centered at 8, 16, and 32 kHz while an f1=f2*0.8+10 dB. In some embodiments, at each frequency, tones are presented from 10-80 dB SPL in 5-dB ascending increments. In some embodiments, DPOAEs assess outer hair cell function and are therefore typically used as a suprathreshold assessment of the strength of the response, measured as an amplitude of the distortion product emission response. In some embodiments, all three test frequencies are used. In some embodiments, reliable distortion product responses may not be obtainable for each frequency tested, in such cases, analyses may be done as appropriate. In some embodiments, treatment with technologies described herein improve a subject's BPOAE evaluation when compared to tests performed prior to treatment with technologies described herein or when compared to a control population.

Treating a Subject to Reduce Tumor Size and/or Vasculature

In some embodiments, a subject suffering from or at risk of an otological disease characterized by neovascularization (e.g., acoustic neuromas, e.g., VS) may have their treatment functionality analyzed through imaging based techniques. In some embodiments, efficacy of treatment of an individual with compositions and methods described herein may be measured using radiographic methods. In some embodiments, such radiographic methods may comprise but are not limited to computed tomography (CT) (also known as a computerized axial tomography (CAT) scan), X-ray, magnetic resonance imaging (MRI), three-dimensional fluid-attenuated inversion recovery (3D-FLAIR) MRI, positron emission tomography (PET), and/or PET-CT scans. Additional radiographic techniques and methods that may be suitable are known in the art. In some embodiments, treatment with technologies described herein improve a subject's imaging based evaluation when compared to tests performed prior to treatment with technologies described herein or when compared to a control population.

In some embodiments, treatment(s) of a subject with technologies described herein are associated with a decrease in VS size as measured by a radiographic technique. In some embodiments, treatment(s) of a subject with technologies described herein are associated with a stasis of VS size as measured by a radiographic technique. In some embodiments, treatment(s) of a subject with technologies described herein are associated with a slowing of VS size growth as measured by a radiographic technique.

In some embodiments, treatment(s) of a subject with technologies described herein are associated with a decreased signal intensity of the fluid on three-dimensional fluid-attenuated inversion recovery (3D-FLAIR) MRI. In certain embodiments, there is a correlation between a higher cochlear signal on 3D FLAIR images and hearing loss in patients with VS. In certain embodiments, treatment(s) of a subject with technologies described herein reduce concentration of proteins in the perilymphatic space associated with enhanced cochlear signal on FLAIR images in subjects with VS.

Treating a Subject to Improve Neurological Function

In some embodiments, treatment(s) of a subject with technologies described herein are associated with an improvement in neurological function. In some embodiments, treatment(s) of a subject with technologies described herein alleviates tumor edema. In some embodiments, treatment(s) of a subject with technologies described herein transiently and/or stably normalizes tumor vasculature in an individual.

In some embodiments, treatment(s) of a subject with technologies described herein are associated with an improvement and/or restoration of speech understanding. In some embodiments, treatment(s) of a subject with technologies described herein are associated with a patient perceived reduction in the difficulty of speech understanding. In some embodiments, treatment(s) of a subject with technologies described herein are associated with an improvement and/or restoration of an individual's reported quality of life.

Methods of Characterizing a Disease State

Among other things, the present disclosure provides methods of characterizing a disease state of a subject, e.g., a subject suffering from or at risk of VS. In some embodiments, a disease state can be characterized by determining the presence (or absence) of a mutation in a gene. The term "mutation in a gene" refers to a modification in a known consensus functional gene that results in the production of a protein having one or more of: a deletion in one or more amino acids, one or more amino acid substitutions, and one or more amino acid insertions as compared to the consensus functional protein, and/or results in a decrease in the expressed level of the encoded protein in a mammalian cell as compared to the expressed level of the encoded protein in a mammalian cell not having a mutation. In some embodiments, a mutation can result in the production of a protein having a deletion in one or more amino acids (e.g., 2, 3, 4, 5, 6, 7, 8, 9, 10, 11, 12, 13, 14, 15 16, 17, 18, 19, 20, or more amino acids). In some embodiments, the mutation can result in a frameshift in the gene. The term "frameshift" is known in the art to encompass any mutation in a coding sequence that results in a shift in the reading frame of the coding sequence. In some embodiments, a frameshift can result in a nonfunctional protein. In some embodiments, a point mutation can be a nonsense mutation (e.g., result in a premature stop codon in an exon of the gene). A nonsense mutation can result in the production of a truncated protein (as compared to a corresponding consensus functional protein) that may or may not be functional. In some embodiments, the mutation can result in the loss (or a decrease in the level) of expression of mRNA or protein or both the mRNA and protein. In some embodiments, the mutation can result in the production of an altered protein having a loss or decrease in one or more biological activities (functions) as compared to a consensus functional protein.

In some embodiments, the mutation is an insertion of one or more nucleotides into a gene. In some embodiments, the mutation is in a regulatory and/or control sequence of the gene, e.g., a portion of the gene that is not coding sequence. In some embodiments, a mutation in a regulatory and/or control sequence may be in a promoter or enhancer region and prevent or reduce the proper transcription of the gene. In some embodiments, a mutation is in a known heterologous gene known to interact with a protein.

Methods of genotyping and/or detecting expression or activity of a gene mRNA and/or protein are known in the art (see e.g., Ito et al., World J Otorhinolaryngol. 2013 May 28; 3(2): 26-34, and Roesch et al., Int J Mol Sci. 2018 January; 19(1): 209, each of which is incorporated in its entirety herein by reference). In some embodiments, level of expression of mRNA or protein may be detected directly (e.g., detecting a protein, detecting an mRNA etc.). Non-limiting examples of techniques that can be used to detect expression and/or activity of a gene directly include, e.g., real-time PCR, quantitative real-time PCR, Western blotting, immunoprecipitation, immunohistochemistry, mass spectrometry, or immunofluorescence. In some embodiments, expression of a gene and/or protein can be detected indirectly (e.g., through functional hearing tests, ABRs, DPOAEs, etc.).

In some embodiments, tissue samples (e.g., comprising one or more inner ear cells, e.g., comprising one or more hair cells and/or one or more supporting cells) may be evaluated via morphological analysis to determine morphology of hair cells and/or support cells before and after administration of any agents (e.g., compositions, e.g., compositions comprising constructs, and/or particles, etc.) as described herein. In some such embodiments, standard immunohistochemical or histological analyses may be performed. In some embodiments, if cells are used in-vitro or ex-vivo, additional immunocytochemical or immunohistochemical analyses may be performed. In some embodiments, one or more assays of one or more proteins or transcripts (e.g., western blot, ELISA, polymerase chain reactions) may be performed on one or more samples from a subject or in-vitro cell populations.

Evaluating Hearing Loss, Tinnitus, Dizziness, and Symptom Recovery

In some embodiments, hearing function is determined in an individual using auditory brainstem response measurements (ABR) before, after, and/or during treatment with compositions and methods described herein. In some embodiments, hearing function is determined in an individual by measuring distortion product optoacoustic emissions (DPOAEs) before, after, and/or during treatment with compositions and methods described herein. In some such embodiments, measurements are taken from one or both ears of a subject. In some such embodiments, recordings are compared to prior recordings for the same subject and/or known thresholds on such response measurements used to define, e.g., hearing loss versus acceptable hearing ranges to be defined as normal hearing. In some embodiments, a subject has ABR and/or DPOAE measurements recorded prior to receiving any treatment. In some embodiments, a subject treated with one or more technologies described herein will have improvements on ABR and/or DPOAE measurements after treatment as compared to before treatment. In some embodiments, ABR and/or DPOAE measurements are taken after treatment is administered and at regular follow-up intervals post-treatment.

In some embodiments, hearing function is determined using speech pattern recognition or is determined by a speech therapist. In some embodiments, hearing function is determined by pure tone testing. In some embodiments, hearing function is determined by bone conduction testing. In some embodiments, hearing function is determined by acoustic reflex testing. In some embodiments hearing function is determined by tympanometry. In some embodiments, hearing function is determined by any combination of hearing analysis known in the art. In some such embodiments, measurements are taken holistically, and/or from one or both ears of a subject. In some such embodiments, recordings and/or professional analysis are compared to prior recordings and/or analysis for the same subject and/or known thresholds on such response measurements used to define, e.g., hearing loss versus acceptable hearing ranges to be defined as normal hearing. In some embodiments, a subject has speech pattern recognition, pure tone testing, bone conduction testing, acoustic reflex testing and/or tympanometry measurements and/or analysis conducted prior to receiving any treatment. In some embodiments a subject treated with one or more technologies described herein will have improvements on speech pattern recognition, pure tone testing, bone conduction testing, acoustic reflex testing and/or tympanometry measurements after treatment as compared to before treatment. In some embodiments, speech pattern recognition, pure tone testing, bone conduction testing, acoustic reflex testing and/or tympanometry measurements are taken after treatment is administered and at regular follow-up intervals post-treatment.

In some embodiments, any of the methods disclosed herein comprise behavioral audiometry evaluation. In some embodiments, behavioral audiometry evaluation comprises pure-tone audiometry with air and bone curves with appropriate masking, Speech audiometry, Words in quiet, or words in noise. In some embodiments, behavioral audiometry evaluation comprises electrophysiologic audiometry by auditory brainstem response testing. In some embodiments, behavioral audiometry evaluation comprises standardized questionnaires: HHIA: Hearing Handicap Inventory for Adults, DHI: Dizziness Handicap Inventory, THI: Tinnitus Handicap Inventory, PANQOL: Penn Acoustic Neuroma Quality of Life (QoL).

In some embodiments of any of the methods disclosed herein, safety and efficacy may be monitored by evaluation of otologic, vestibular, and systemic adverse events, as well as hematology, clinical chemistry, and/or urinalysis parameters. In some embodiments of any of the methods disclosed herein, additional parameters to be assessed will include anti-VEGF protein levels in blood and construct DNA in ear swabs, nasal swabs, saliva, and blood. In some embodiments of any of the methods disclosed herein, blood may also be collected for evaluation of potential humoral immune responses to the capsid and secreted transgene product.

The ABR test measures whether the animal's cochlea, cochlear nerve, and brainstem responds to each sound stimulus and is often used as a measure of the health of the ear. This same basic test is commonly used to test hearing of newborn humans in hospitals and it is a standard hearing test used in lab animals. In some embodiments, an ABR test involves injecting mice with an IP dose of ketamine/xylazine anesthetic to minimize movement and muscle artifacts and to aid in the placement of measurement electrodes. In some embodiments, an ABR test (when done with the DPOAE at the same time, and in both ears) takes approximately 45 minutes to complete, so a booster dose of anesthetic is sometimes required. In some embodiments, an initial dose of anesthetic consists of ketamine (100 mg/kg) and xylazine (10 mg/kg) IP and if needed, a ketamine only booster which consists of ¼-½ of the original ketamine dose. In some embodiments, no redosing of xylazine is performed based on veterinarian recommendations. In some embodiments, transdermal recording electrodes through the skin surface are placed at three standard locations (at vertex of the skull equidistant between the ears, over the mastoid behind the pinna on the test-ear, and over the mastoid behind the pinna for the opposite ear for the grounding electrode). In some embodiments, stimuli consists of low (8 kHz), middle (16 kHz), and high (32 kHz) frequency pure tone pip stimuli (0.1 ms rise fall, 1.5 ms duration) from 10-80 dB SPL in ascending 5-dB steps. In some embodiments, stimuli will be presented at a rate of 30/sec, and 512 artifact-free averages are acquired at each stimulus level. In some embodiments, ABRs were collected at 2-3 separate time points, depending upon the group; baseline and at terminal week 4-6 with a subset of animals also tested at 3 weeks post-surgery. In some embodiments, in addition to measuring the lowest intensity of each stimulus frequency that the animal's brainstem could reliably process (threshold), the amplitude of Wave I in response to suprathreshold stimuli can be measured in order to assess the integrity of the afferent flow of information from the cochlear hair cells to the auditory nerve. In some embodiments, ABR thresholds can provide important information about the lowest level of sound that an animal's ear passes along to and is processed by the brainstem, the suprathreshold responses in the amplitude of the ABR Wave I has increasingly been used as a proxy for the integrity of the ribbon synapse connection between the base of the inner hair cells and the auditory nerve dendrites.

DPOAEs are sounds created by movement of the cochlear outer hair cells and are non-invasively measured in the ear canal with a transducer & microphone combination. In some embodiments, a size of evoked DPOAEs is a useful measure of outer hair cell function. This same basic test is also commonly used to test hearing of newborn humans in hospitals and it is a standard hearing test used in lab animals. In some embodiments, two primary tones (f1 and f2) are presented to an ear producing mechanical vibrations that causes pressure changes in cochlear fluids at stimulus and distortion frequencies. In some embodiments, these pressure changes drive the ear in reverse, activating the middle ear and then eardrum to produce sound in the ear canal. In some embodiments, DPOAEs are collected at the same test frequencies used in ABRs (8, 16, 32 kHz) and while under anesthesia for ABRs. In some embodiments, an f2 is centered at 8, 16, and 32 kHz while an f1=f2*0.8+10 dB. In some embodiments, at each frequency, tones are presented from 10-80 dB SPL in 5-dB ascending increments. In some embodiments, DPOAEs assess outer hair cell function and are therefore typically used as a suprathreshold assessment of the strength of the response, measured as an amplitude of the distortion product emission response. In some embodiments, all three test frequencies are used. In some embodiments, reliable distortion product responses may not be obtainable for each frequency tested, in such cases, analyses may be done as appropriate.

Evaluating Tumor Size and Vasculature

In some embodiments, efficacy of treatment of an individual with compositions and methods described herein may be measured using radiographic methods. In some embodiments, such radiographic methods may comprise computed tomography (CT) (also known as a computerized axial tomography (CAT) scan), X-ray, magnetic resonance imaging (MRI), three-dimensional fluid-attenuated inversion recovery (3D-FLAIR) MRI, positron emission tomography (PET), and/or PET-CT scans. Additional radiographic techniques and methods that may be suitable are known in the art.

In some embodiments, treatment of an individual with methods and/or compositions described herein are associated with a decrease in VS size as measured by a radiographic technique. In some embodiments, treatment of an individual with methods and/or compositions described herein are associated with a stasis of VS size as measured by a radiographic technique. In some embodiments, treatment of an individual with methods and/or compositions described herein are associated with a slowing of VS size growth as measured by a radiographic technique.

In some embodiments, treatment of an individual with methods and/or compositions described herein are associated with a decreased signal intensity of the fluid on three-dimensional fluid-attenuated inversion recovery (3D-FLAIR) MRI. In certain embodiments, there is a correlation between a higher cochlear signal on 3D FLAIR images and hearing loss in patients with VS. In certain embodiments, methods and/or compositions as described herein reduce concentration of proteins in the perilymphatic space associated with enhanced cochlear signal on FLAIR images in subjects with VS.

Evaluating Neurological Function

In some embodiments, treatment of an individual with methods and/or compositions described herein are associated with an improvement in neurological function. In some embodiments, treatment of an individual with methods and/or compositions alleviates tumor edema. In some embodiments, treatment of an individual with methods and/or compositions transiently and/or stably normalizes tumor vasculature in an individual.

In some embodiments, treatment of an individual with methods and/or compositions described herein are associated with an improvement and/or restoration of speech understanding. In some embodiments, treatment of an individual with methods and/or compositions described herein are associated with a patient perceived reduction in the difficulty of speech understanding. In some embodiments, treatment of an individual with methods and/or compositions described herein are associated with an improvement and/or restoration of an individual's reported quality of life.

Evaluating Anti-VEGF Protein Concentration in Biological Samples

In some embodiments, methods described herein include evaluating anti-VEGF protein concentrations in one or more biological samples form an individual before, during, and/or after treatment with compositions described herein.

In some embodiments of these methods, following treatment e.g., one or two or more administrations of compositions described herein, there is an increase in expression of an anti-VEGF protein. In some embodiments, an increase in expression of an active anti-VEGF protein as described herein when compared relative to a control level, e.g., as compared to the level of expression of an anti-VEGF protein prior to introduction of the compositions comprising any construct(s) as described herein.

Methods of detecting expression and/or activity of a target RNA and/or protein are known in the art. In some embodiments, a level of expression of an inner ear cell target protein can be detected directly (e.g., detecting inner ear cell target protein or target mRNA). Non-limiting examples of techniques that can be used to detect expression and/or activity of a target RNA or protein directly include: real-time PCR, Western blotting, immunoprecipitation, immunohistochemistry, mass spectrometry, or immunofluorescence. In some embodiments, expression of an inner ear cell target protein can be detected indirectly (e.g., through functional hearing tests).

In some embodiments, biodistribution and/or shedding analysis of rAAV particles is performed. In some embodiments, disclosed herein is a composition comprising an rAAV-antiVEGF replication-defective, rAAV particle for delivering a cDNA, e.g., to express an anti-VEGF protein. In some embodiments, an rAAV particle as described herein is used to treat a subject, e.g., a human, e.g., a patient, with VS or at risk of developing VS. In some embodiments, a composition disclosed herein is administered via an intracochlear route. In some embodiments, a composition disclosed herein is administered at a dose of rAAV particles described herein (e.g., as measured by vector genome qPCR analysis). In some embodiments, a composition disclosed herein is administered to a localized area of the body. In some embodiments, a composition disclosed herein results in detectable expression of construct sequences at a localized area of the body, e.g., a cochlea and/or perilymph. In some embodiments, a composition disclosed herein, is expected to result in limited vascular spread and systemic exposure. In some embodiments, a composition disclosed herein results in higher levels of construct sequences in the cochlea, but not in non-cochlear tissue or fluid compartments, e.g., liver, spleen, lymph nodes, brainstem, auditory cortex, serum and/or CSF. In some embodiments, a composition disclosed herein results in lower but detectable levels of construct sequences in non-cochlear tissues and fluids collected. In some embodiments, expression of construct sequences in non-cochlear tissue is at a level that is not therapeutically relevant. In some embodiments, levels of construct sequences were generally decreased overall by six months. In some embodiments, levels of construct sequences decrease over time in blood samples, e.g., one month following intracochlear administration of a composition disclosed herein.

In some embodiments of any of the methods disclosed herein, relevant fluids for biodistribution and shedding (e.g., blood, serum, urine, saliva, nasal and ear swabs, and CSF fluid) are collected and/or evaluated. In some embodiments of any of the methods disclosed herein, non-target tissues are collected and/or evaluated. In some embodiments, capsid variant is expected to determine tropism. In some embodiments, a composition disclosed herein comprises a capsid variant, e.g., AAVAnc80 capsid variant. In some embodiments, delivery of a composition disclosed herein comprising a capsid variant, e.g., via the same route of administration, in the same particle formulation, and/or at equivalent or lower particle doses, is not expected to result in differences in biodistribution and shedding patterns.

In some embodiments, a composition disclosed herein, e.g., rAAV-antiVEGF, is dosed at a level less than about 5×10(12) total vg/cochlea. In some embodiments, a composition disclosed herein, e.g., rAAV-antiVEGF, is dosed at a level less than about $5 \times 10^{13}$ vg/mL. In some embodiments, a dose of a composition disclosed herein is a function of, e.g., limitations of volume and rAAV particle concentration.

In contrast, clinical trials using rAAV particles have delivered more than $1 \times 10^{14}$ vg/kg via systemic routes of administration, in some cases to participants younger than 6 months of age (AveXis 2019, incorporated herein in its entirety by reference).

Other localized deliveries with relatively low doses of rAAV particles have not reported extensive biodistribution beyond the target area, e.g., throughout the body, or extensive rAAV particle shedding (excretion/secretion; generally measuring underlying construct DNA concentration through methods such as qPCR). For example, low levels of distribution beyond the ocular target area (specifically in the optic nerve of the particle-injected eye, optic chiasm, spleen and liver, and sporadically in the lymph nodes of study animals) have been reported for Luxturna® delivered bilaterally at a dose of $7.5 \times 10^{11}$ vg/eye. Similarly, in the Phase 3 clinical trial, rAAV particle was shed transiently and at low levels in tears of 45% of the participants; it was detected, also at low levels, in serum (but not whole blood) samples of 10% of the participants in the days immediately following subretinal administration of Luxturna® delivered bilaterally at a dose of $1.5 \times 10^{11}$ vg/eye (Russell 2017; Spark Therapeutics 2017, each of which is incorporated herein in its entirety by reference).

In some embodiments, any of the methods disclosed herein comprise evaluating a distribution of rAAV particle sequences in blood (e.g., serum and whole blood) over a time course following unilateral administration to the cochlea using, e.g., a validated qPCR method. In some embodiments, additional specimens (e.g., external auditory canal swabs, nasal swabs, saliva, and urine) will be collected for evaluation of shedding from the subject. In some embodiments, a specimen is collected from a subject until at least three consecutive negative samples are obtained.

In some embodiments, proteins correlating with VS associated hearing loss are measured before, during, and/or after treatment with compositions and/or methods described herein. In certain embodiments, such VS associated hearing loss associated proteins include: µ-Crystallin (CRYM), low density lipoprotein receptor-related protein 2 (LRP2), immunoglobulin (Ig) γ-4 chain C region, Ig κ-chain C region, complement C3, immunoglobulin heavy constant γ 3, and/or chemokine receptor-4 (CXCR4).

In some embodiments, immunogenicity to AAV capsids and/or particles are measured. Immunogenicity to AAV capsids and/or particles delivered to localized areas, and in relatively low doses compared to systemic applications, have generally not yielded specific patterns of immune responses; importantly, responses observed through both humoral and cell-mediated immunological monitoring (e.g., through enzyme-linked immunosorbent assay [ELISA]/neutralizing antibody [NAb] and enzyme-linked immunosorbent spot [ELISPOT] assays, respectively) have predominantly been without clinical correlate for route(s) of administration (ROA) that afford some immunological protection (e.g., direct administration to the brain).

In some embodiments of any of the methods disclosed herein, an intracochlear ROA, e.g., in species with a non-patent cochlear aqueduct (e.g., NHPs and humans), is expected to provide a similar level of protection. In some embodiments of any of the methods disclosed herein, a subject will receive a short, peri-operative course of an immunomodulatory regimen, e.g., systemic oral corticosteroids, for approximately 17 days, beginning 3 days before administration of a compositions disclosed herein, e.g., rAAV-antiVEGF. In some embodiments, an immunomodulatory regimen reduces inflammation related to the surgical administration procedure. In some embodiments, an immunomodulatory regimen can also further reduce the potential for an immune reaction to either a capsid (e.g., AAVAnc80) or the underlying construct (e.g., a transgene product, e.g., an anti-VEGF protein).

In some embodiments, any method disclosed herein further comprise evaluating humoral immunity (e.g., antibody responses) in response to administration of a composition disclosed herein. In some embodiments, effect of pre-existing immunity, measured e.g., by serum NAb levels, on the transduction of a compositions disclosed herein when delivered via the intracochlear ROA is evaluated. In some embodiments, pre-existing NAb levels do not inhibit transduction of AAV particles delivered by an intracochlear route of administration. In some embodiments, any method disclosed herein further comprise evaluating serum for potential systemic humoral responses to both the AAV capsid and/or the transgene product (e.g., a secreted protein). In some embodiments, responsive to the evaluation of systemic humoral responses, a treatment interval for bilateral intracochlear administration of a composition disclosed herein, e.g., rAAV-antiVEGF can be developed.

In some embodiments, any method disclosed herein does not result in cytotoxic T cell responses, e.g., to either an AAV particle, capsid, and/or construct (e.g. underlying transgene) product from rAAV particles delivered via a localized route of administration (ROA), such as intracochlear administration. For example, the labeling for Luxturna® notes that no subject had a clinically significant, cytotoxic T cell response (Spark Therapeutics 2017, incorporated herein in its entirety by reference); isolated positive interferon-gamma (IFN-gamma) ELISPOT assay results were obtained during the clinical development program (Bennett 2012, incorporated herein in its entirety by reference), but the significance of these isolated results is unknown, as no clinical inflammatory response was observed and no dose limiting toxicity was seen in the clinical program.

In certain embodiments, pharmacokinetics of any of the compositions or products of compositions described herein are measured and collected. In certain embodiments, anti-VEGF protein is secreted; prior art has described high doses of systemic anti-VEGF protein as associated with hypertension, proteinuria, elevated liver enzymes, arterial thromboembolic events, venous thromboembolic events, hemorrhage, and surgery and wound healing complications when delivered systemically at high doses over time (5 to 15 mg/kg every 2 to 3 weeks). In some embodiments of any of the methods disclosed herein, a composition disclosed herein is administered locally. In some embodiments, local delivery of a composition disclosed herein results in a decrease in likelihood of any one or more detrimental off-target effects. In some embodiments, local delivery of a composition disclosed herein does not result in any detrimental off-target effects. In some embodiments of any of the methods disclosed herein, a subject is followed-up by monitoring anti-VEGF protein in serum (e.g., using an electrochemiluminescence assay), vital signs, urinalysis, and/or clinical chemistry. In some embodiments, monitoring of a subject administered a composition disclosed herein allows for early intervention and/or minimization of any off-target effects.

In some embodiments, following administration of a composition as described herein, serum can be collected and analyzed for anti-VEGF protein measurement. In some embodiments, such measurements can take place prior to composition administration (Baseline), at week 2 following administration, and monthly for an appropriate duration (e.g., 3 months, 6 months, 1 year, 2 years, 3 years, 4 years, or greater than 5 years). In some embodiments, anti-VEGF protein will not be detected in an individual's serum at baseline, or at any timepoint post-administration in individuals that received intracochlear delivery of either vehicle or a dose of rAAV-antiVEGF particles described herein.

In some embodiments of any method disclosed herein, a method comprises collection and/or evaluation of serum for presence of an anti-VEGF protein using, (e.g., an electrochemiluminescence assay as described herein).

Production Methods

AAV systems are generally well known in the art (see, e.g., Kelleher and Vos, Biotechniques, 17(6):1110-17 (1994); Cotten et al., P.N.A.S. U.S.A., 89(13):6094-98 (1992); Curiel, Nat Immun, 13(2-3):141-64 (1994); Muzyczka, Curr Top Microbiol Immunol, 158:97-129 (1992); and Asokan A, et al., Mol. Ther., 20(4):699-708 (2012), each of which is incorporated in its entirety herein by reference). Methods for generating and using AAV constructs are described, for example, in U.S. Pat. Nos. 5,139,941, 4,797,368 and PCT filing application US2019/060328, each of which is incorporated in its entirety herein by reference.

Methods for obtaining viral constructs are known in the art. For example, to produce AAV constructs, the methods typically involve culturing a host cell which contains a nucleic acid sequence encoding an AAV capsid protein or fragment thereof; a functional rep gene; a recombinant AAV construct composed of AAV inverted terminal repeats (ITRs) and a coding sequence; and/or sufficient helper functions to permit packaging of the recombinant AAV construct into the AAV capsid proteins.

In some embodiments, components to be cultured in a host cell to package an AAV construct in an AAV capsid may be provided to the host cell in trans. Alternatively, any one or more components (e.g., recombinant AAV construct, rep sequences, cap sequences, and/or helper functions) may be provided by a stable host cell that has been engineered to contain one or more such components using methods known to those of skill in the art. In some embodiments, such a stable host cell contains such component(s) under the control of an inducible promoter. In some embodiments, such component(s) may be under the control of a constitutive promoter. In some embodiments, a selected stable host cell may contain selected component(s) under the control of a constitutive promoter and other selected component(s) under the control of one or more inducible promoters. For example, a stable host cell may be generated that is derived from HEK293 cells (which contain E1 helper functions under the control of a constitutive promoter), but that contain the rep and/or cap proteins under the control of inducible promoters. Other stable host cells may be generated by one of skill in the art using routine methods.

Recombinant AAV construct, rep sequences, cap sequences, and helper functions required for producing an AAV of the disclosure may be delivered to a packaging host cell using any appropriate genetic element (e.g., construct). A selected genetic element may be delivered by any suitable method known in the art, e.g., to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y., which is incorporated in its entirety herein by reference). Similarly, methods of generating AAV particles are well known and any suitable method can be used with the present disclosure (see, e.g., K. Fisher et al, J. Virol., 70:520-532 (1993) and U.S. Pat. No. 5,478,745, which are incorporated in their entirety herein by reference).

In some embodiments, recombinant AAVs may be produced using a triple transfection method (e.g., as described in U.S. Pat. No. 6,001,650, which is incorporated in its entirety herein by reference). In some embodiments, recombinant AAVs are produced by transfecting a host cell with a recombinant AAV construct (comprising a coding sequence) to be packaged into AAV particles, an AAV helper function construct, and an accessory function construct. An AAV helper function construct encodes "AAV helper function" sequences (e.g., rep and cap), which function in trans for productive AAV replication and encapsidation. In some embodiments, the AAV helper function construct supports efficient AAV construct production without generating any detectable wild type AAV particles (e.g., AAV particles containing functional rep and cap genes). Non-limiting examples of constructs suitable for use with the present disclosure include pHLP19 (see, e.g., U.S. Pat. No. 6,001,650, which is incorporated in its entirety herein by reference) and pRep6cap6 construct (see, e.g., U.S. Pat. No. 6,156,303, which is incorporated in its entirety herein by reference). An accessory function construct encodes nucleotide sequences for non-AAV derived viral and/or cellular functions upon which AAV is dependent for replication (e.g., "accessory functions"). Accessory functions may include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any known helper viruses such as adenovirus, herpesvirus (other than herpes simplex virus type-1), and vaccinia virus.

Additional methods for generating and isolating AAV viral constructs suitable for delivery to a subject are described in, e.g., U.S. Pat. Nos. 7,790,449; 7,282,199; WO 2003/042397; WO 2005/033321, WO 2006/110689; and U.S. Pat. No. 7,588,772, each of which is incorporated in its entirety herein by reference. In one system, a producer cell line is transiently transfected with a construct that encodes a coding sequence flanked by ITRs and a construct(s) that encodes rep and cap. In another system, a packaging cell line that stably supplies rep and cap is transiently transfected with a construct encoding a coding sequence flanked by ITRs. In each of these systems, AAV particles are produced in response to infection with helper adenovirus or herpesvirus, and AAVs are separated from contaminating virus. Other systems do not require infection with helper virus to recover the AAV—the helper functions (e.g., adenovirus E1, E2a, VA, and E4 or herpesvirus UL5, UL8, UL52, and UL29, and herpesvirus polymerase) are also supplied, in trans, by the system. In such systems, helper functions can be supplied by transient transfection of the cells with constructs that encode the helper functions, or the cells can be engineered to stably contain genes encoding the helper functions, the expression of which can be controlled at the transcriptional or posttranscriptional level.

In some embodiments, viral construct titers post-purification are determined. In some embodiments, titers are determined using quantitative PCR. In certain embodiments, a TaqMan probe specific to a construct is utilized to determine construct levels. In certain embodiments, the TaqMan probe is represented by SEQ ID NO: 97, while forward and reverse amplifying primers are exemplified by SEQ ID NO: 98 and 99, respectively.

Exemplary TaqMan Probe for Quantification of Constructs (SEQ ID NO: 97)
/56-FAM/TAATTCCAA/ZEN/
CCAGCAGAGTCAGGGC/3IABkFQ/
Exemplary Forward qPCR Primer for Quantification of Constructs (SEQ ID NO: 98)
GATACAGCTAGAGTCCTGATTGC
Exemplary Reverse qPCR Primer for Quantification of Constructs (SEQ ID NO: 99)
GATCTGCCAAGTACCTCACTATG As described herein, in some embodiments, a viral construct of the present disclosure is an adeno-associated virus (AAV) construct. Several AAV serotypes have been characterized, including AAV1, AAV2, AAV3 (e.g., AAV3B), AAV4, AAV5, AAV6, AAV7, AAV8, AAV9, AAV10, AAV11, and AAV Anc80, as well as variants thereof. In some embodiments, an AAV particle is an AAV2/6, AAV2/8, AAV2/9, or AAV2/Anc80 particle (e.g., with AAV6, AAV8, AAV9 or Anc80 capsid and construct with AAV2 ITR). Other AAV particles and constructs are described in, e.g., Sharma et al., Brain Res Bull. 2010 Feb. 15; 81(2-3): 273, which is incorporated in its entirety herein by reference. Generally, any AAV particle may be used to deliver a coding sequence described herein. However, the serotypes have different tropisms, e.g., they preferentially infect different tissues. In some embodiments, an AAV construct is a self-complementary AAV construct.

The present disclosure provides, among other things, methods of making AAV-based constructs. In some embodiments, such methods include use of host cells. In some embodiments, a host cell is a mammalian cell. A host cell may be used as a recipient of an AAV helper construct, an AAV minigene plasmid, an accessory function construct, and/or other transfer DNA associated with the production of recombinant AAVs. The term includes the progeny of an original cell that has been transfected. Thus, a "host cell" as used herein may refer to a cell that has been transfected with an exogenous DNA sequence. It is understood that the progeny of a single parental cell may not necessarily be completely identical in morphology or in genomic or total DNA complement as the original parent, due to natural, accidental, or deliberate mutation.

Additional methods for generating and isolating AAV particles suitable for delivery to a subject are described in, e.g., U.S. Pat. Nos. 7,790,449; 7,282,199; WO 2003/042397; WO 2005/033321, WO 2006/110689; and U.S. Pat. No. 7,588,772, each of which is incorporated in its entirety herein by reference. In one system, a producer cell line is transiently transfected with a construct that encodes a coding sequence flanked by ITRs and a construct(s) that encodes rep and cap. In another system, a packaging cell line that stably supplies rep and cap is transiently transfected with a construct encoding a coding sequence flanked by ITRs. In each of these systems, AAV particles are produced in response to infection with helper adenovirus or herpesvirus, and AAV particles are separated from contaminating virus. Other systems do not require infection with helper virus to recover the AAV particles—the helper functions (e.g., adenovirus E1, E2a, VA, and E4 or herpesvirus UL5, UL8, UL52, and UL29, and herpesvirus polymerase) are also supplied, in trans, by the system. In such systems, helper functions can be supplied by transient transfection of cells with constructs that encode helper functions, or cells can be engineered to stably contain genes encoding helper functions, expression of which can be controlled at the transcriptional or posttranscriptional level.

In yet another system, a coding sequence flanked by ITRs and rep/cap genes are introduced into insect host cells by infection with baculovirus-based constructs. Such production systems are known in the art (see generally, e.g., Zhang et al., 2009, Human Gene Therapy 20:922-929, which is incorporated in its entirety herein by reference). Methods of making and using these and other AAV production systems are also described in U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065, each of which is incorporated in its entirety herein by reference.

In some embodiments of any of the methods disclosed herein, a focused set of analytical testing and a shorter stability testing protocol is used for a composition disclosed herein, e.g., rAAV-antiVEGF, e.g., AAV-anti VEGF drug substance (DS). In some embodiments, the DS and the drug product (DP) for a composition disclosed herein, e.g., rAAV-antiVEGF, are quite similar, with, e.g., only an additional filtration step and vialing constituting the DP manufacture from the DS. In some embodiments, DP undergoes a more comprehensive analytical testing and a longer stability testing protocol. In some embodiments, DS is not stored long-term, e.g., DS is moved promptly from DS to DP manufacture. In some embodiments, DS is stored, e.g., held at ≤−65° C. prior to the fill/finish process.

In some embodiments of any of the methods disclosed herein, stability of a composition disclosed herein, e.g., rAAV-antiVEGF DS and DP, is evaluated using assays that are, e.g., indicative of stability of the product including Appearance, Vector Genome Titer (ddPCR), Potency, and/or Bioburden (DS) or Sterility (DP). In some embodiments, a potency assay comprises a specification once sufficient data have been generated to support the establishment of a specification. In some embodiments, DS and DP will be placed on 2-8° C. stability for about 6 weeks. In some embodiments, DS is not stored at 2-8° C. for extended periods of time. In some embodiments, DP is stored for 60 months at the target storage temperature (≤−65° C.). In some embodiments, DS is stored, e.g., placed on stability, for about 12 months.

In some embodiments, potency and strength of a composition disclosed herein, e.g., rAAV-antiVEGF is evaluated using an assay, e.g., a matrix of assays as described herein. In some embodiments, the assays comprise evaluating multiple product characteristics, and will be used to assess product functional activity, consistency, stability, and/or to provide evidence of comparability after any changes are introduced to the manufacturing process. In some embodiments, ddPCR titer assay are qualified for suitability prior to administering a composition disclosed herein to a subject. In some embodiments, expression of anti-VEGF protein is assessed in a mammalian cell line in-vitro. In some embodiments, protein expression is assessed across several multiplicities of infection (MOIs) and compared relative to a reference standard. In some embodiments, a functional bioassay is used in a method disclosed herein, e.g., including commercially available kits and published methods for determining anti-VEGF activity. In some embodiments, a functional bioassay that assesses potency is used, e.g., a sensitive and quantitative measure of the bioactivity of expressed anti-VEGF protein.

In some embodiments, a manufacturing method as disclosed herein is utilized. In some embodiments a manufacturing method is not expected to impact quality attributes of an rAAV particle, or to affect the interpretation of the associated studies.

In some embodiments, a composition disclosed herein comprises a recombinant particle, e.g., rAAV-antiVEGF, which comprises two components, e.g., an AAVAnc80 capsid (Zinn 2015, which is incorporated herein in its entirety by reference) and single-stranded DNA genome of 3555 nucleotides, exclusive of inverted terminal repeat (ITR) sequences (an example of a construct represented by FIG. 6, Panel (A), and represented by SEQ ID NO: 92), encapsidated by the AAVAnc80 capsid. In some embodiments, a composition disclosed herein, e.g., an rAAV-antiVEGF particle, expresses ranibizumab, a 48 kDa humanized monoclonal Fab (derived from full-length murine anti-human VEGF monoclonal antibody A.4.6.1) which is used, e.g., clinically to inhibit VEGF.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather should be construed to encompass any and all variations that become evident as a result of the teaching provided herein.

It is believed that one or ordinary skill in the art can, using the preceding description and following Examples, as well as what is known in the art, to make and utilize technologies of the present disclosure.

Example 1: Construction of Viral Constructs

This example provides a description of generating exemplary viral constructs encoding an anti-VEGF protein, as described herein. Those of ordinary skill in the art will readily understand that similar constructs can be made in accordance with this example. For instance, rAAV constructs that express mammalian, primate, or human derived anti-VEGF proteins under single, dual, or multi construct strategies can be generated. AAV serotypes 1, 2, 3, 4, 5, 6, 7, 8, 9, rh8, rh10, rh39, rh43, and Anc80 can each be prepared to encapsulate anti-VEGF protein constructs, and form rAAV particles. Among other things, the rAAV particles can be utilized to test (i) a concatemerization-transplicing strategy, (ii) a hybrid intronic-homologous recombination-transplicing strategy, (iii) an exonic homologous recombination strategy, as summarized by Pryadkina et al., Meth. Clin. Devel. 2:15009, 2015, which is incorporated in its entirety herein by reference, and/or (iv) a single construct strategy.

Example 1.1: Construction of rAAV-Ranibizumab, rAAV-Ranibizumab-PC, and rAAV-Bevacizumab-PC Constructs This example provides a description of generating rAAV-ranibizumab, rAAV-ranibizumab-GFP, and rAAV-bevacizumab-PC constructs, as described herein. A first recombinantly generated construct had a sequence according to SEQ ID NO: 90. This construct is referred to throughout the Examples as an "rAAV-ranibizumab-PC construct." An rAAV-ranibizumab-PC construct is an exemplary embodiment of an rAAV-$V_H/V_L$ construct represented by the schematic shown in FIG. 6, Panel (A), and comprises a sequence that encodes for ranibizumab. A second recombinantly generated construct had a sequence according to SEQ ID NO: 91. This construct is referred to throughout the Examples as an "rAAV-ranibizumab construct." An rAAV-ranibizumab construct is an exemplary embodiment of an rAAV-$V_H/V_L$ construct represented by the schematic shown in FIG. 6, Panel (A), and comprises a sequence that encodes for ranibizumab. A third recombinantly generated construct had a sequence according to SEQ ID NO: 106. This construct is referred to throughout the Examples as an "rAAV-ranibizumab-GFP construct." An rAAV-ranibizumab-GFP construct is an exemplary embodiment of an rAAV-ABGFP construct represented by the schematic shown in FIG. 6, Panel (B), and comprises a sequence that encodes for ranibizumab. A fourth recombinantly generated construct had a sequence according to SEQ ID NO: 93. This construct is referred to throughout the Examples as an "rAAV-bevacizumab-PC construct." An rAAV-bevacizumab-PC construct is an exemplary embodiment of an rAAV-AB construct represented by the schematic shown in FIG. 6, Panel (C), and comprises a sequence that encodes for the anti-VEGF protein bevacizumab.

Certain constructs as described above, a trans plasmid with AAV Rep and Cap genes, and a helper plasmid with an essential region from an adenovirus genome were co-transfected in HEK293 cells. An AAVAnc80 capsid was then generated with an rAAV construct above to form either rAAVAnc80-ranibizumab, rAAVAnc80-ranibizumab-PC, and rAAVAnc80-bevacizumab-PC particles.

Example 1.2: Construction of rAAV-Bevacizumab, rAAV-Bevacizumab-GFP, rAAV-Aflibercept-PC, and rAAV-Aflibercept Constructs This example provides a description of generating rAAV-bevacizumab, rAAV-bevacizumab-GFP, rAAV-aflibercept-PC, and rAAV-aflibercept constructs, as described herein. One construct has a sequence according to SEQ ID NO: 94. This construct is referred to throughout the Examples as an "rAAV-bevacizumab construct." An rAAV-bevacizumab construct is an exemplary embodiment of an rAAV-AB construct represented by the schematic shown in FIG. 6, Panel (C), and comprises a sequence that encodes for the anti-VEGF protein bevacizumab. Another construct has a sequence according to SEQ ID NO: 107. This construct is referred to throughout the Examples as an "rAAV-bevacizumab-GFP construct." An rAAV-bevacizumab-GFP construct is an exemplary embodiment of an rAAV-ABGFP construct represented by the schematic shown in FIG. 6, Panel (B), and comprises a sequence that encodes for the anti-VEGF protein bevacizumab. Another construct has a sequence according to SEQ ID NO: 95. This construct is referred to throughout the examples as an "rAAV-aflibercept-PC construct." An rAAV-aflibercept-PC construct is an exemplary embodiment of an rAAV-TRAP construct represented by the schematic shown in FIG. 6, Panel (D), and comprises a sequence that encodes for the anti-VEGF protein aflibercept. Another construct has a sequence according to SEQ ID NO: 96. This construct is referred to throughout the examples as an "rAAV-aflibercept construct." An rAAV-aflibercept construct is an exemplary embodiment of an rAAV-TRAP construct represented by the schematic shown in FIG. 6, Panel (D), and comprises a sequence that encodes for the anti-VEGF protein aflibercept. rAAV particles are generated by transfection with an adenovirus-free method as described by Xiao et al. J Virol. 73(5):3994-4003, 1999, which is incorporated in its entirety herein by reference. An individual rAAV-bevacizumab-PC, rAAV-bevacizumab-GFP, rAAV-aflibercept-PC, or rAAV-aflibercept construct as described above, a trans plasmid with AAV Rep and Cap genes, and a helper plasmid with an essential region from an adenovirus genome are co-transfected in HEK293 cells. An AAVnc80 capsid is then generated with an rAAV construct described above to form either an rAAVAnc80-bevacizumab, rAAVAnc80-bevacizumab-PC, rAAV-Anc80-ranibizumab-GFP, rAAVAnc80-aflibercept-PC, and rAAVAnc80-aflibercept particles.

Example 2: Purifying Viral Particles

This example provides a description of methods that can be used to purify constructs encoding anti-VEGF proteins, as described herein.

Example 2.1: Purifying rAAVAnc80-Ranibizumab, rAAVAnc80-Ranibizumab-PC, and rAAVAnc80-Bevacizumab-PC Particles This example provides a description of methods that can be used to purify rAAV particles encoding anti-VEGF proteins, e.g., those formed in Example 1. rAAVAnc80-ranibizumab, rAAVAnc80-ranibizumab, and rAAVAnc80-bevacizumab-PC particles produced in Example 1.1 were each independently purified by two sequential cesium chloride (CsCl) density gradients, as described by Pryadkina et al., Mol. Ther. 2:15009, 2015, which is incorporated in its entirety herein by reference. Following the second CsCl density gradient centrifugation step, 11 fractions of 500 μL were recovered from the CsCl density gradient tube and purified through dialysis in 1×PBS. The fractions were analyzed by dot blot to determine those particles containing rAAV genomes. The viral genome number (vg) of each preparation was determined by a quantitative real-time PCR-based titration method using primers and probes corresponding to the ITR region of the AAV construct genome (see, e.g., Bartoli et al. Gene. Ther. 13:20-28, 2006, which is incorporated in its entirety herein by reference).

Example 2.2: Purifying rAAVAnc80-Ranibizumab-GFP, rAAVAnc80-Bevacizumab, rAAVAnc80-Bevacizumab-GFP, rAAVAnc80-Aflibercept, and rAAVAnc80-Aflibercept-PC Particles This example also provides a description of methods that can be used to purify rAAV particles encoding anti-VEGF proteins, e.g., those formed in Example 1. rAAVAnc80-ranibizumab particles produced in Example 1.1, and rAAVAnc80-bevacizumab, rAAVAnc80-bevacizumab-GFP, rAAVAnc80-aflibercept-PC, and rAAVAnc80-aflibercept particles produced in Example 1.2 are each independently purified by two sequential cesium chloride (CsCl) density gradients, as described by Pryadkina et al., Mol. Ther. 2:15009, 2015, which is incorporated in its entirety herein by reference. Following the second CsCl density gradient centrifugation step, 11 fractions of 500 μL are recovered from the CsCl density gradient tube and purified through dialysis in 1×PBS. The fractions are analyzed by dot blot to determine those containing rAAV genomes. The viral genome number (vg) of each preparation is determined by a quantitative real-time PCR-based titration method using primers and probes corresponding to the ITR region of the AAV construct genome (see, e.g., Bartoli et al. Gene. Ther. 13:20-28, 2006, which is incorporated in its entirety herein by reference).

Example 2.3: Purifying rAAVAnc80 Particles

This example also provides a description of additional methods that can be used to purify rAAV particles encoding anti-VEGF proteins, e.g., those formed in Example 1. rAAV-antiVEGF particles are purified in the following manner 72 hours post transfection. 10% Triton is added to the solution (for a final concentration of 2%) and the cell-culture is incubated for 1 hour at 37° C. on a cell-shaker. Subsequently, 100 U/mL benzonase and 2 uM MgCl2 are added, and the cells are incubated for 2 hours at 37° C. on a cell-shaker. Next, NaCl (150 uM) is added and the cells are incubated for 20 minutes at 37° C. on a cell-shaker. The samples are centrifuged at 2000×g for 10 minutes. The supernatant is transferred to a clean container and stored at −80° C., or immediately subjected to Tangential Flow Filtration (TFF). The filtered supernatant is then loaded into AVB columns to undergo AVB column chromatography and rAAV filtration. Filtered eluate is then subjected to CsCl density gradient centrifugation (RI=1.3905-1.3915, spin speed=65,000 RPM for ≥16 h at 15° C.). The purified full-particle sample is then subjected to a final round of TFF and formulations are vialed for later use.

Example 3: Formulation of rAAVAnc80-antiVEGF Particles

This example relates to the preparation of compositions comprising viral particles including constructs encoding an anti-VEGF protein, as described herein.

Example 3.1: Formulation of rAAVAnc80-Ranibizumab, rAAVAnc80-Ranibizumab-PC, and rAAVAnc80-Bevacizumab-PC Particles rAAVAnc80 particles including constructs rAAV-ranibizumab, rAAV-ranibizumab-PC, or rAAV-bevacizumab-PC, each encoding an anti-VEGF protein, as described herein were produced and purified, as set forth in the Examples above, to an appropriate titer as determined by quantitative digital droplet (dd) PCR (e.g., of approximately $1.39^{13}$ vg/mL). Purified particles were then prepared at known dilutions (e.g., at $6 \times 10^4$, $1.3 \times 10^5$, $1.8 \times 10^5$, $4.5 \times 10^9$, and $1.3 \times 10^{10}$ vg/mL) in physiologically acceptable solution. The physiologically acceptable solution used included a commercially available 1×PBS with pluronic acid F68, prepared to a final concentration of: 8.10 mM Sodium Phosphate Dibasic, 1.5 mM Monopotassium Phosphate, 2.7 mM Potassium Chloride, 172 mM Sodium Chloride, and 0.001% pluronic Acid F68). A titer quantification of rAAVAnc80-ranibizumab particles, rAAVAnc80-ranibizumab-PC particles, or rAAVAnc80-bevacizumab-PC particles, was performed using a forward primer sequence: CCGATTTCGGCCTATTGGTTA (SEQ ID NO: 100), a reverse primer sequence CTGTGGAGAGAAAGGCAAAGT (SEQ ID NO: 101), and a probe sequence GGCACCTATTGGTCTTACTGACATCC (SEQ ID NO: 102) with an appropriate fluorophore (FAM).

Example 3.2: Formulation of rAAVAnc80-Ranibizumab, rAAVAnc80-Ranibizumab-PC, and rAAVAnc80-Bevacizumab-PC Particles rAAVAnc80 particles including constructs rAAV-ranibizumab-GFP, rAAV-bevacizumab, rAAV-bevacizumab-GFP, rAAV-aflibercept, or rAAV-aflibercept-PC, each encoding an anti-VEGF protein, as described herein are produced and purified, as set forth in the Examples above, to an appropriate titer as determined by quantitative digital droplet (dd) PCR (e.g., of approximately $1.39^{13}$ vg/mL). Purified particles are then prepared at known dilutions (e.g., at $6 \times 10^4$, $1.3 \times 10^5$, $1.8 \times 10^5$, $4.5 \times 10^9$, and $1.3 \times 10^{10}$ vg/mL) in physiologically acceptable solution. The physiologically acceptable solution can include a commercially available 1×PBS with pluronic acid F68, and can be prepared to a final concentration of: 8.10 mM Sodium Phosphate Dibasic, 1.5 mM Monopotassium Phosphate, 2.7 mM Potassium Chloride, 172 mM Sodium Chloride, and 0.001% pluronic Acid F68). A titer quantification of rAAVAnc80-ranibizumab-GFP particles, rAAVAnc80-bevacizumab particles, rAAVAnc80-bevacizumab-GFP particles, rAAVAnc80-aflibercept particles, or rAAVAnc80-aflibercept-PC particles, is performed using a forward primer sequence: CCGATTTCGGCCTATTGGTTA (SEQ ID NO: 100), a reverse primer sequence CTGTGGAGAGAAAGGCAAAGT (SEQ ID NO: 101), and a probe sequence GGCACCTATTGGTCTTACTGACATCC (SEQ ID NO: 102) with an appropriate fluorophore (e.g., FAM).

Example 4: Device Description

This example relates to a device suitable for the delivery of rAAV particles, including the rAAV particles comprising constructs encoding anti-VEGF proteins described herein, to the inner ear. A specialized microcatheter designed for consistent and safe penetration of the round window membrane can be used to deliver a composition as provided herein to the cochlea of a subject (e.g., as depicted in FIG. 4). The microcatheter is shaped such that a surgeon performing the delivery procedure can enter the middle ear cavity via the external auditory canal and contact the end of the microcatheter with the round window membrane. The distal end of the microcatheter may include at least one microneedle with a diameter from about 10 microns to about 1,000 microns, which produces perforations in the round window membrane that are sufficient to allow rAAV particles comprising constructs as described herein (e.g., comprising a coding sequence for an anti-VEGF protein) to enter the cochlear perilymph of the scala tympani at a rate which does not damage the inner ear (e.g., a physiologically acceptable rate, e.g., a rate of approximately 30 μL/min to approximately 90 μL/min), but small enough to heal without surgical repair. The remaining portion of the microcatheter, proximal to the microneedle(s), is loaded with the rAAV/artificial perilymph formulation at a defined titer (e.g., approximately $1 \times 10^{12}$ to $5 \times 10^{13}$ vg/mL). The proximal end of the microcatheter is connected to a micromanipulator that allows for precise, low volume infusions of approximately 30 μL to approximately 100 μL.

Example 5: Expression and Secretion of Anti-VEGF Proteins Produced from Cell Lines This example relates to the transduction and/or transfection of exemplary constructs, and expression and secretion of exemplary proteins described herein.

Figure 7:
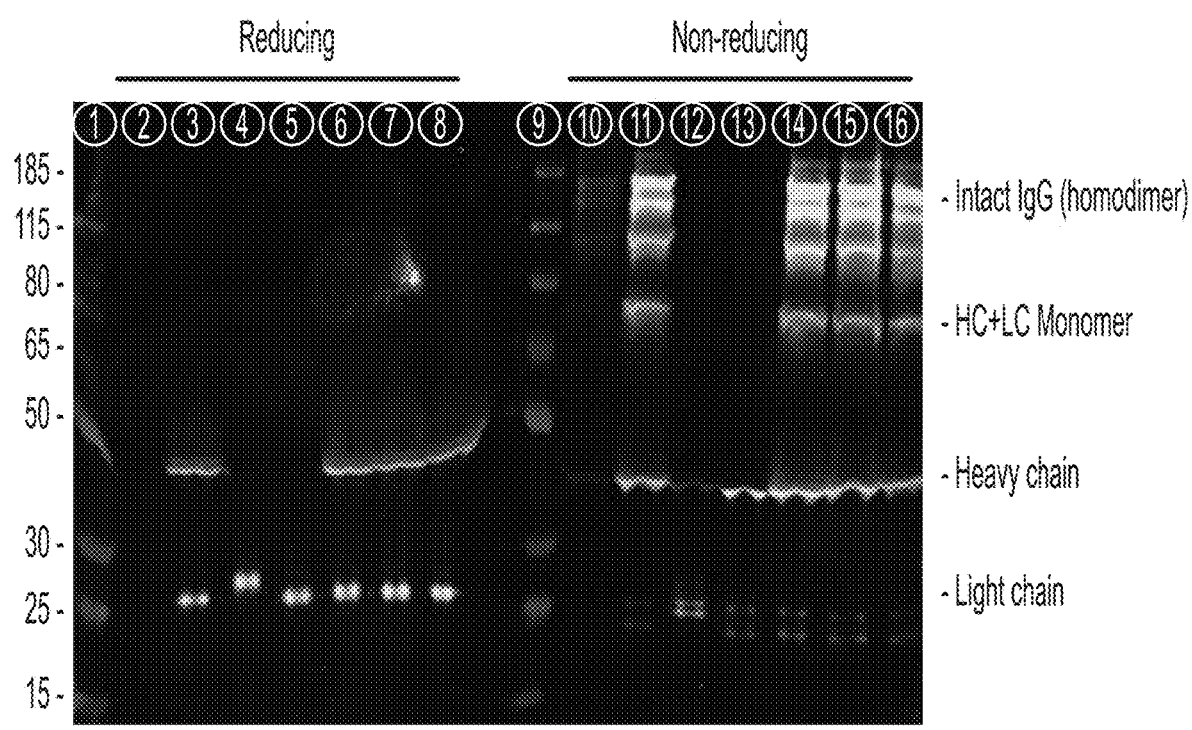
FIG. 7 includes a Western blot showing HEK cell expression of different anti-VEGF proteins, ranibizumab and bevacizumab, using transfection or transduction of exemplary rAAV-AntiVEGF constructs described herein. Lanes are noted along the top of the figure, with predicted protein sizes noted on the left of the figure. Lanes 2-8 contain reduced proteins, while lanes 10-16 contain non-reduced proteins. Lane 1: pre-stained PageRuler™ protein ladder. Lane 2: untransfected/negative control. Lane 3: transfection with an rAAV-bevacizumab-PC construct. Lane 4: transfection with an rAAV-ranibizumab-GFP construct. Lane 5: transfection with rAAV-ranibizumab-PC construct. Lane 6: transduction with an rAAVAnc80-bevacizumab-PC particle with a multiplicity of infection (MOI) of $7.5 \times 10^4$. Lane 7: transduction with an rAAVAnc80-bevacizumab-PC particle with a MOI of $2.2 \times 10^5$. Lane 8: transduction with an rAAVAnc80-bevacizumab-PC particle with an MOI of $5.5 \times 10^5$. Lane 9: prestained PageRuler™ protein ladder. Lane 10: untransfected/negative control. Lane 11: transfection with an rAAV-bevacizumab-PC construct. Lane 12: transfection with an rAAV-ranibizumab-GFP construct. Lane 13: transfection with rAAV-ranibizumab-PC construct. Lane 14: transduction with an rAAVAnc80-bevacizumab-PC particle with a MOI of $7.5\times10^4$. Lane 15: transduction with an rAAVAnc80-bevacizumab-PC particle with a MOI of $2.2\times10^5$. Lane 16: transduction with an rAAVAnc80-bevacizumab-PC particle with a MOI of $5.5\times10^5$.
Figure 8A:
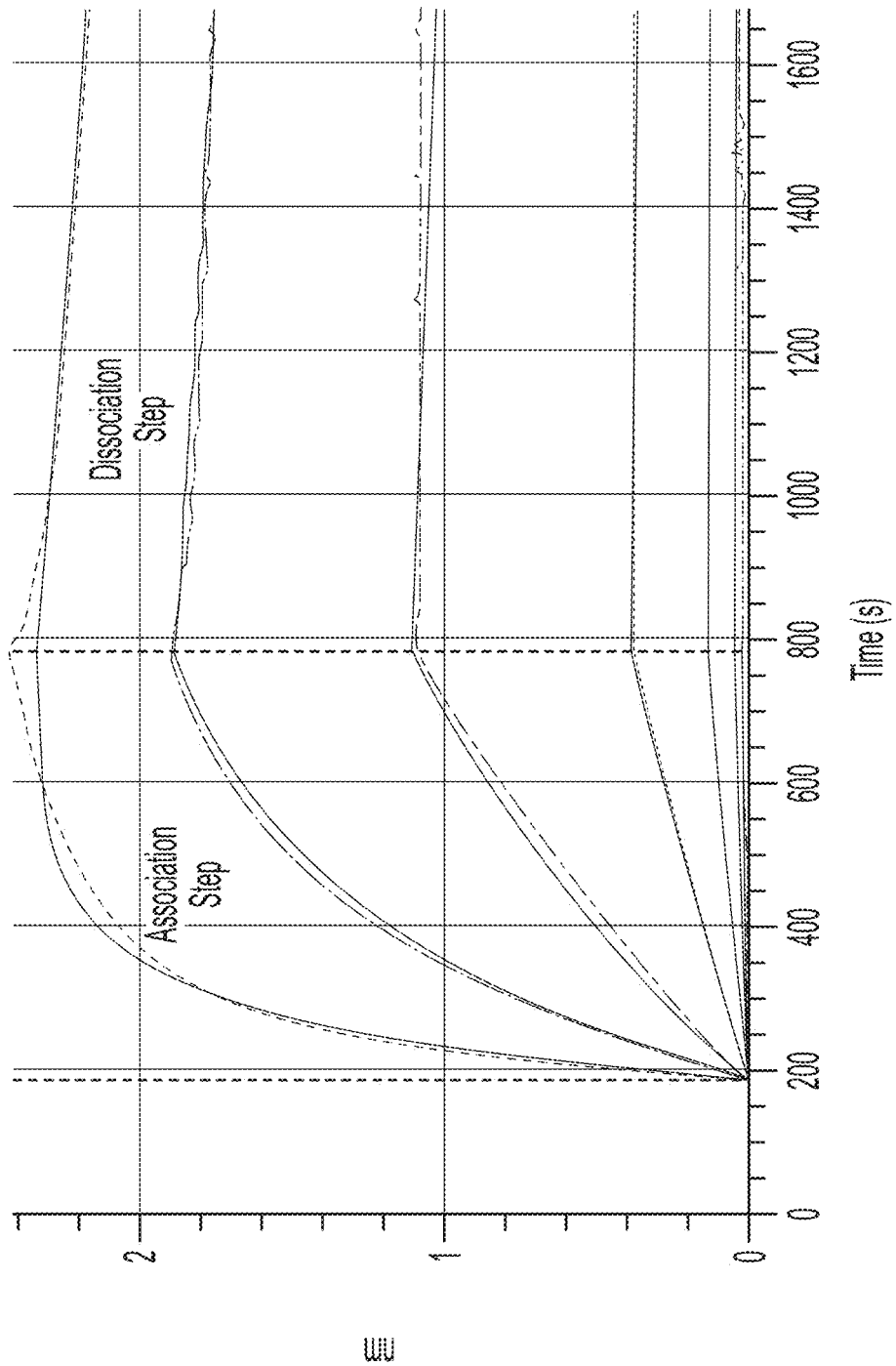
FIGS. 8A-8D are a series of graphs showing affinity of certain anti-VEGF proteins described herein as measured by Octet® HTX biosensor instrument using the Octet® analysis software, Data Analysis HT10.0.
Figure 8B:
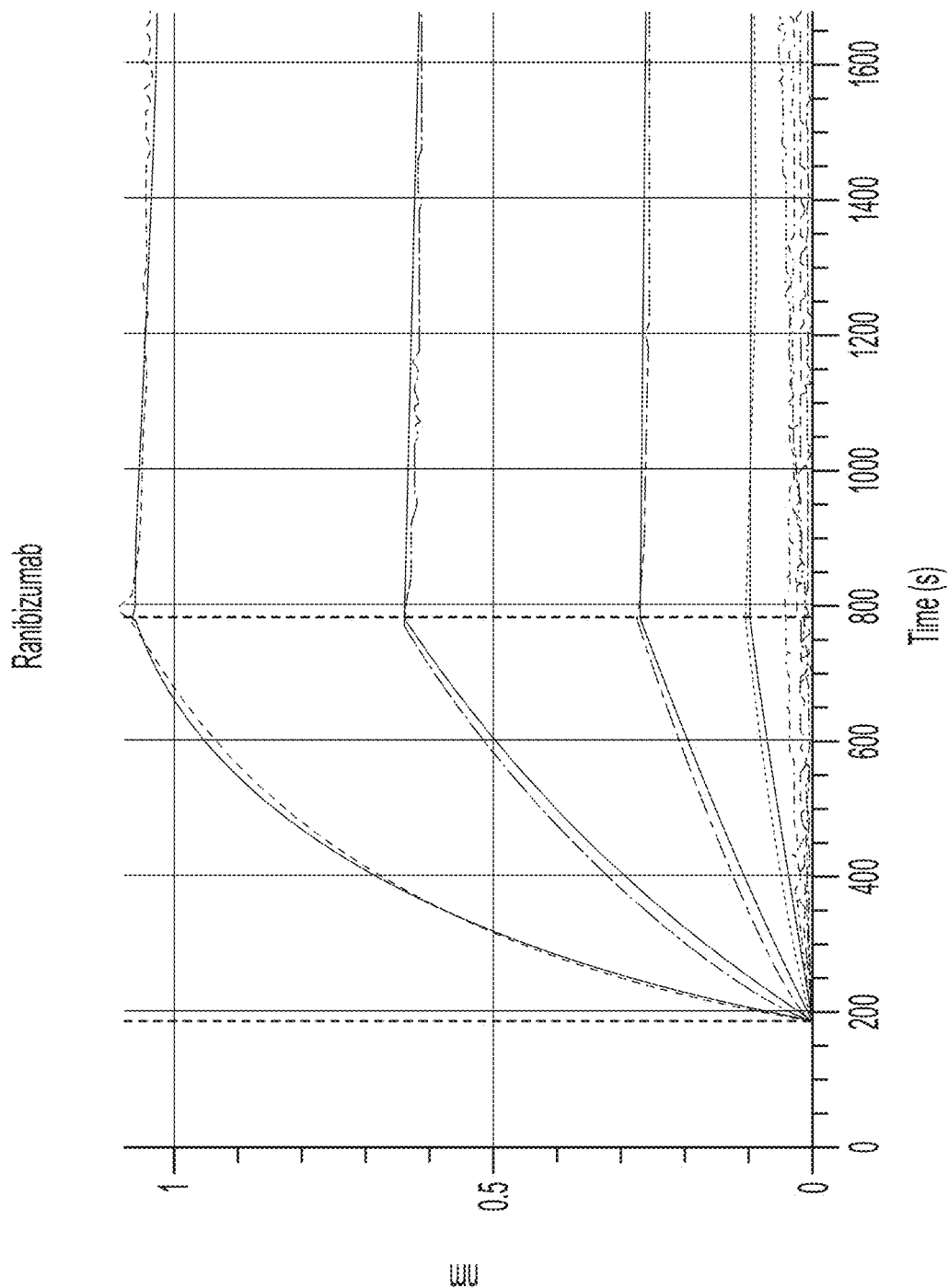
Figure 8C:
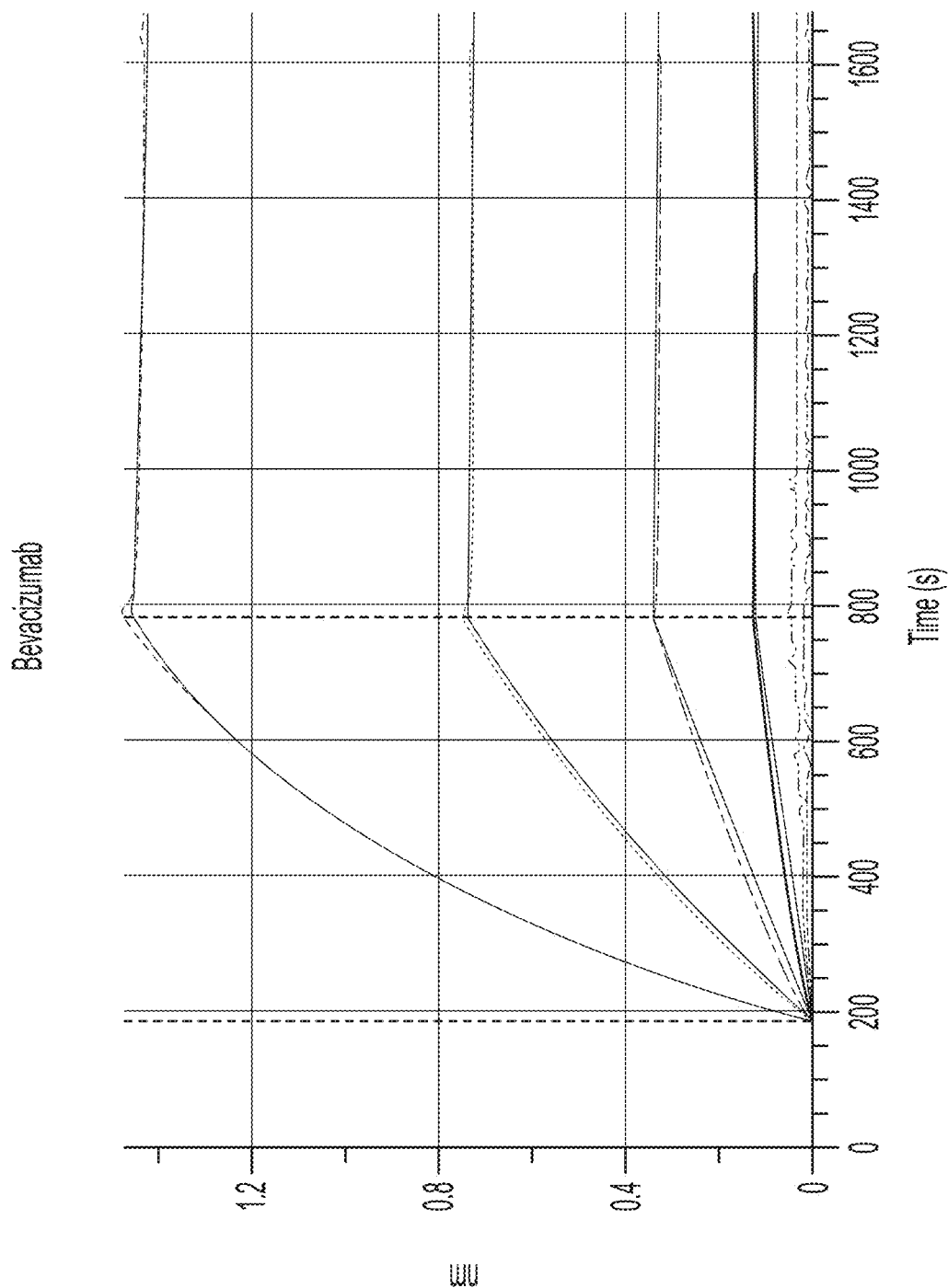
Figure 8D:
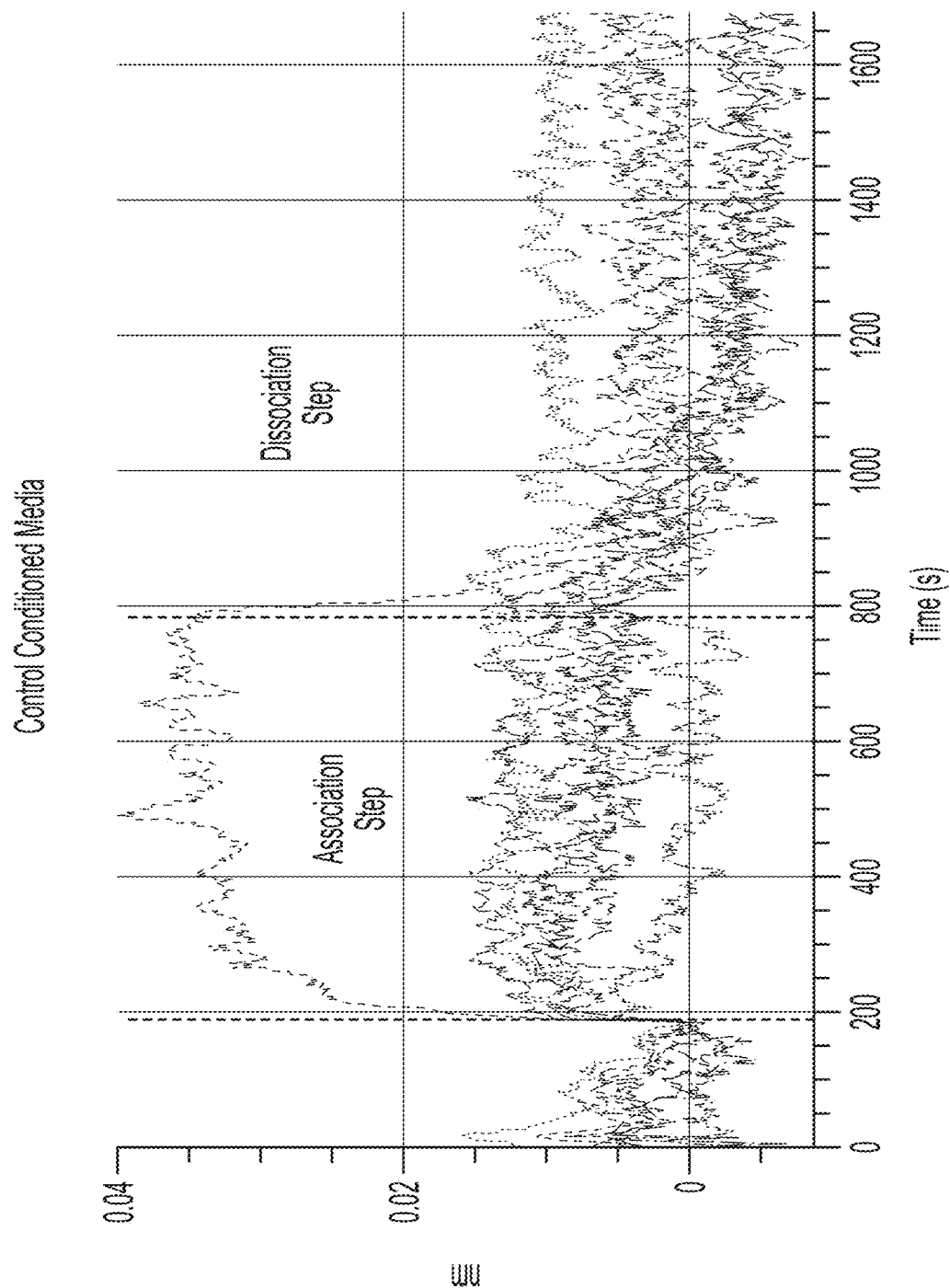

Example 5.1: Expression and Secretion of Proteins from rAAV-Ranibizumab-PC, rAAV-Ranibizumab-GFP, and rAAV-Bevacizumab-PC Constructs Cell lines (e.g., HEK239FT) were transfected with exemplary rAAV-antiVEGF constructs or transduced with exemplary rAAVAnc80-antiVEGF particles as described herein. For transfection events, HEK293FT cells were seeded overnight at $7 \times 10^4$ cells/well in a 24-well plate format with a culture volume of 400 μL. Approximately 800 ng of anti-VEGF constructs rAAV-ranibizumab-PC, rAAV-bevacizumab-PC, or rAAV-ranibizumab-GFP (as described in Example 1) were transfected into cells using jetprime transfection reagent (Polyplus-Transfection® SA). For transduction events, HEK293FT cells were seeded for 6 hours at $4 \times 10^4$ cells/well in a 96-well plate format with a culture volume of 50 μL in the presence of 2 μM etoposide (Fisher Scientific 34120525MG), exemplary rAAVAnc80-bevacizumab-PC particles (as described in Example 1) were added into the media at an MOI of $7.5 \times 10^4$, $2.2 \times 10^5$, and $5.5 \times 10^5$ respectively. For cells either transfected or transduced, supernatant was harvested at 72 hours post treatment for each sample. For protein expression analysis, 30 μL of samples were loaded into individual wells in a 4-12% Bis-Tris protein gel and standard western blotting procedures as known in the art were conducted. Banding patterns were determined using a fluorescent reader, with test anti-ranibizumab antibody (targeted at the Fab epitope; supplied by Abcam, ab168684-25UG) as the primary detection probe, and anti-human IgG as the secondary detection probe (see FIG. 7).

Example 5.2: Expression and Secretion of Proteins from rAAV-Ranibizumab, and rAAV-Bevacizumab, rAAV-Bevacizumab-GFP, rAAV-Aflibercept, and rAAV-Aflibercept-PC Constructs Cell lines (e.g., HEK239FT) are transfected with exemplary anti-VEGF constructs or transduced with exemplary rAAVAnc80-antiVEGF particles as described herein. For transfection events, HEK293FT cells are seeded overnight at approximately 7×104 cells/well in a 24-well plate format with a culture volume of 400 µL. Approximately 800 ng of rAAV-Ranibizumab, rAAV-Bevacizumab, rAAV-Bevacizumab-GFP, rAAV-Aflibercept-PC, or rAAV-Aflibercept constructs (e.g., as described in Example 1) are transfected into cells using jetprime transfection reagent (Polyplus-Transfection® SA). For transduction events, HEK293FT cells are seeded for 6 hours at $4 \times 10^4$ cells/well in a 96-well plate format with a culture volume of 50 µL in the presence of 2 µM etoposide (Fisher Scientific 34120525MG). rAAVAnc80-ranibizumab, rAAVAnc80-ranibizumab-PC, rAAVAnc80-ranibizumab-GFP, rAAVAnc80-bevacizumab, rAAVAnc80-bevacizumab-GFP, rAAVAnc80-aflibercept-PC, or rAAVAnc80-aflibercept (e.g., as described in Example 1) are added to the cell media at an MOI of approximately $7.5 \times 10^4$, $2.2 \times 10^5$, and/or $5.5 \times 10^5$. For cells either transfected or transduced, supernatant is harvested at approximately 72 hours post treatment for each sample. For protein expression analysis, 30 µL of samples are loaded into individual wells in a 4-12% Bis-Tris protein gel and standard western blotting procedures as known in the art are conducted. Banding patterns are determined using a fluorescent reader, with test anti-ranibizumab (targeted at the Fab epitope; supplied by Abcam, ab168684-25UG) and test anti-aflibercept antibodies as the primary detection probe, and anti-human IgG as the secondary detection probe.

Example 6: Binding Activity of Anti-VEGF Proteins Produced from Cell Lines

This example describes how to determine a binding activity of exemplary anti-VEGF proteins produced as described in Example 5 above.

Example 6.1: Binding Activity of Anti-VEGF Proteins Ranibizumab and Bevacizumab

Binding activity of exemplary anti-VEGF proteins ranibizumab or bevacizumab produced through transfection as described in Example 5 above were analyzed using Octet® HTX biosensor instruments. A first set of control experiments were performed to calibrate the plasmon surface resonance instrumentation, e.g., using a mouse anti-human VEGF monoclonal antibody (anti-hVEGF MmAb; R&D Systems, MAB293-100) added into control cell conditioned medium using recombinant human VEGF as the binding agent (FIG. 8, Panel (A)). A second set of experiments were performed to determine the VEGF-binding activity of particles comprised in conditioned medium from HEK293TF cells following transfection of exemplary constructs rAAV-ranibizumab-PC, or rAAV-bevacizumab-PC as described in Example 1, or control non-transfected cell conditioned medium. Graphical results for test materials are presented in FIG. 8, Panel (B) or Panel (C), with control media represented in FIG. 8, Panel (D).

Test samples included soluble ranibizumab and bevacizumab secreted and present in medium from HEK293TF cells transfected with constructs rAAV-ranibizumab-PC, or rAAV-bevacizumab-PC as described in Example 1. Samples were prepared by diluting cell conditioned media 1:10 in 1× kinetics buffer (Fortebio, 18-1105) and aliquoted into a 384-well sample plate. Anti-hVEGF MmAb (R&D Systems, MAB293-100) was diluted at a concentration of 10 µg/mL as a positive control. The capture agent, recombinant human VEGF (R&D Systems, 293-VE-010) was diluted in a series of 1:2 dilution ratio from 200 nM to 3.125 nM.

The binding affinities of the conditioned medium samples and mouse anti-human VEGF antibody (R&D Systems) samples were measured in 1× kinetics buffer in Octet® HTX biosensor instrument. The binding features and values were generated by the Octet® analysis software, Data Analysis HT10.0. Data collected is represented in Table 2, where the respective $K_D$, equilibrium association constant ($k_a$), and the dissociation ($k_{dis}$), are listed.

The anti-hVEGF mouse antibody (R&D Systems) showed high binding affinity. Similarly, rAAV construct encoded ranibizumab or bevacizumab showed high binding affinity to human VEGF. No $K_D$ value could be extrapolated from the binding data of control conditioned medium sample. Together, these data show that the constructs as provided herein can result in expression and secretion of anti-VEGF proteins ranibizumab or bevacizumab, and that constructs as provided herein may be used to express anti-VEGF proteins in the inner ear of a mammal.

TABLE 2

Binding kinetics of recombinant anti-VEGF proteins

| Sample ID | KD (M)* | ka (1/Ms) | kdis (1/s) | Full R^2 |
|---|---|---|---|---|
| Bevacizumab | 3.30E−10 | 8.49E+04 | 2.80E−05 | 0.9998 |
| Ranibizumab | 1.68E−10 | 2.45E+05 | 4.11E−05 | 0.9991 |
| MmAb-R&D | 2.29E−10 | 3.40E+05 | 7.77E−05 | 0.9993 |

Secreted ranibizumab was capable of binding biotinylated recombinant human VEGF (Acro Biosystems, VE5-H8210) with a KD of 168 pM and secreted bevacizumab was capable of binding with a KD of 330 pM (KD=229 pM for positive control mouse anti-human VEGF recombinant antibody [R&D Systems, MAB293-100]). Compared to the binding affinity for ranibizumab and bevacizumab to VEGF-A165, 20.6 and 35.1 pM, respectively (Papadopoulos 2012, incorporated herein in its entirety by reference), these data suggest that rAAV constructs in plasmid form comprising an anti-VEGF protein coding sequence are capable of producing a protein in-vitro with an acceptable binding affinity.

Example 6.2: Binding Activity of Anti-VEGF Proteins Ranibizumab, Bevacizumab, and Aflibercept Binding activity of exemplary anti-VEGF binding agents as described herein are analyzed using Octet® HTX biosensor instruments. anti-VEGF proteins are produced in cell lines (e.g., HEK293FT cells) following transfection of exemplary constructs rAAV-ranibizumab, rAAV-bevacizumab, rAAV-ranibizumab-GFP, rAAV-bevacizumab-GFP, rAAV-aflibercept-PC, or rAAV-aflibercept as described in Example 1, or transduction with the same constructs comprised within an AAV Anc80 capsid to form an rAAV particle, e.g., rAAVAnc80-ranibizumab particle, rAAVAnc80-bevacizumab particle, rAAVAnc80-ranibizumab-GFP particle, rAAVAnc80-bevacizumab-GFP particle, rAAVAnc80-aflibercept-PC particle, or rAAVAnc80-aflibercept particle. A first set of control experiments are performed to calibrate the plasmon surface resonance instrumentation, e.g., using a mouse anti-human VEGF monoclonal antibody (anti-hVEGF MmAb; R&D Systems, MAB293-100) in control conditioned medium using recombinant human VEGF as the binding agent. A second set of experiments are performed to determine the human VEGF-binding activity of conditioned medium from HEK293TF cells following transfection or transduction of exemplary constructs or rAAV particles as described herein, or control conditioned medium. Graphical results depict exemplary binding activity of transgenic anti-VEGF proteins.

Test samples include soluble ranibizumab, bevacizumab, and/or aflibercept secreted and present in medium from HEK293TF cells transduced or transfected with constructs as described herein (e.g., as described in Example 1). Samples are prepared by diluting cell conditioned media 1:10 in 1× kinetics buffer (Fortebio, 18-1105) and aliquoting into a 384-well sample plate. Anti-hVEGF MmAb (R&D Systems, MAB293-100) is diluted at a concentration of 10 µg/mL as a positive control. The capture agent, recombinant human VEGF (R&D Systems, 293-VE-010) is diluted in a series of 1:2 dilution ratio from 200 nM to 3.125 nM.

The binding affinities of the conditioned medium samples and mouse anti-human VEGF antibody (R&D Systems) samples are measured in 1× kinetics buffer in Octet® HTX biosensor instrument. The binding features and values are generated by the Octet® analysis software, Data Analysis HT10.0. Data collected is represented as $K_D$, equilibrium association constant ($k_a$), and the dissociation rate ($k_{dis}$).

Example 7: Ex-Vivo Demonstration of Anti-VEGF Protein Production

This example relates to the introduction, and expression analysis of rAAV constructs expressing an anti-VEGF protein in mammalian cochlear explants grown in-vitro or ex-vivo. Cochlear explant culture models can provide a reliable experimental system to mimic the morphology and molecular characteristics of sensory hair cells and non-sensory supporting cells of the cochlea to study transduction and expression of rAAV particles within the intrinsic cellular environment found in-vivo.

Example 7.1: Ex-Vivo Production of Anti-VEGF Proteins Ranibizumab and Bevacizumab Described herein are ex-vivo evaluations of anti-VEGF protein expression and secretion from newborn (P2) wild type (WT) mice cochlear explants transduced by rAAV (e.g., rAAVAnc80) particles comprising constructs rAAV-$V_H$/$V_L$ or rAAV-AB, exemplified by rAAV-ranibizumab-PC or rAAV-bevacizumab-PC (as described in Example 1). In these experiments, an organ of Corti was dissected and mounted on coverslips, followed by incubation for three to four days with either vehicle or a range of doses of rAAV particles—rAAVAnc80-ranibizumab-PC particles or rAAVAnc80-bevacizumab-PC particles. An rAAVAnc80-bevacizumab-PC particle was transduced at 1.2E10, 2.4E10, and 3.5E10 vg/explant, while an rAAVAnc80-ranibizumab-PC particle was transduced at 1.4E10, 2.8E10, and 4.2E10 vg/explant.

The media surrounding the explants was harvested and analyzed using an MSD immunoassay, a platform employing an electrochemiluminescent detection technology to quantify analytes with higher sensitivity and larger dynamic range than traditional ELISA analysis. Streptavidin-coated MSD assay plates were blocked and coated with biotinylated VEGF ligand before incubation with the sample. Anti-VEGF proteins bound to the assay plate were then detected with a tagged goat polyclonal anti-κ light-chain (pAb) antibody (FIG. 16, Panel (B)). The explants were lysed for ribonucleic acid (RNA) expression analysis using quantitative real-time polymerase chain reaction (qRT-PCR) with Taqman primer-probes for GAPDH (housekeeping control) and for anti-VEGF protein encoding nucleotides (mRNA products encoding bevacizumab or ranibizumab) (FIG. 16, Panel (A)).

Figure 16B:
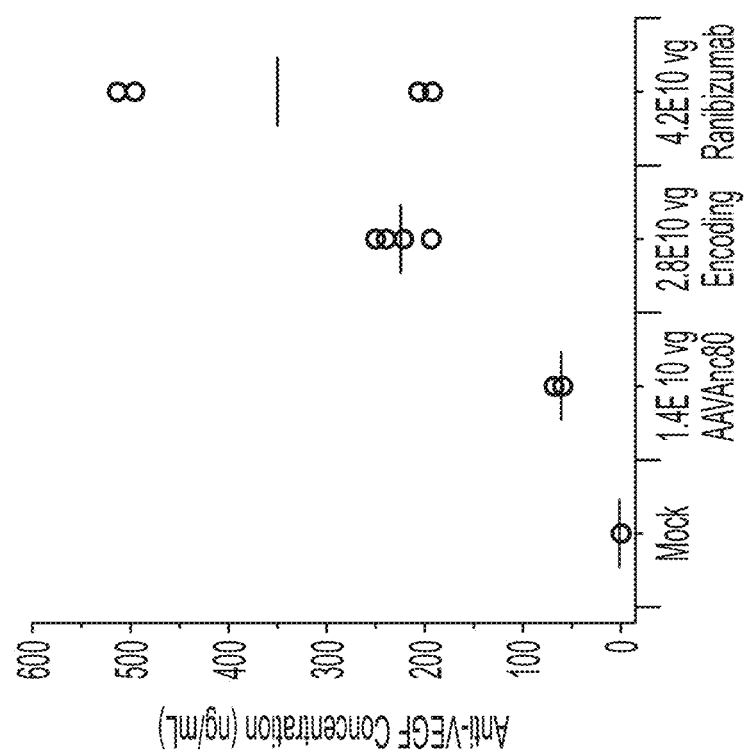
FIGS. 16A-16B are graphical representations of RNA expression in cochlear explants and secreted protein expression in cochlear explant media following transduction of WT newborn (P2) mice cochlear explants with rAAVAnc80 particles comprising anti-VEGF proteins as disclosed herein (rAAVAnc80-antiVEGF). rAAVAnc80-bevacizumab-PC particles (construct according to SEQ ID NO: 93) or rAAVAnc80-ranibizumab-PC particles (construct according to SEQ ID NO: 90) transduced cells in cochlear explants of WT mice and drove expression and secretion of mRNA encoding the anti-VEGF proteins.
Figure 16A:
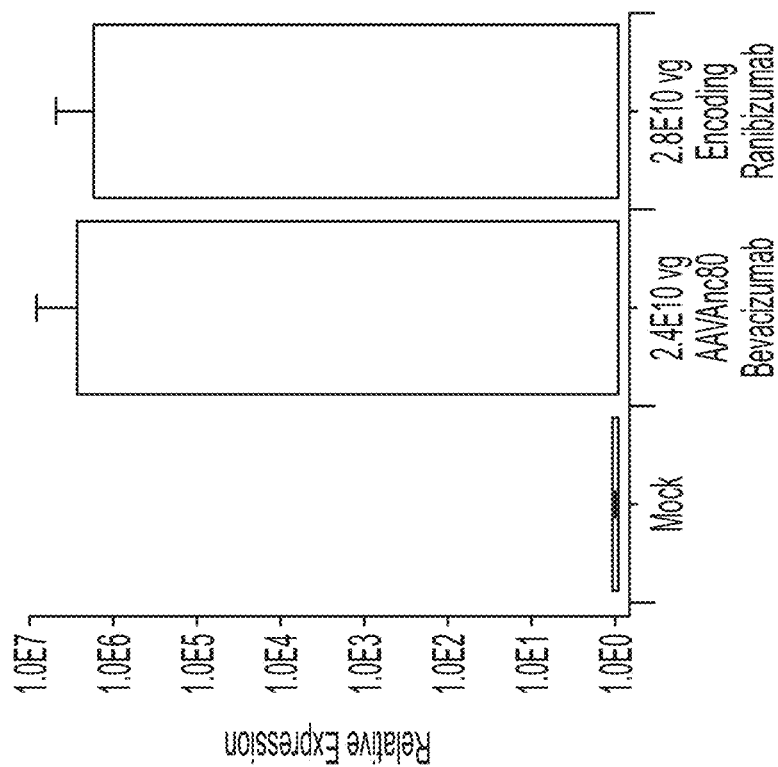
Figure 17:
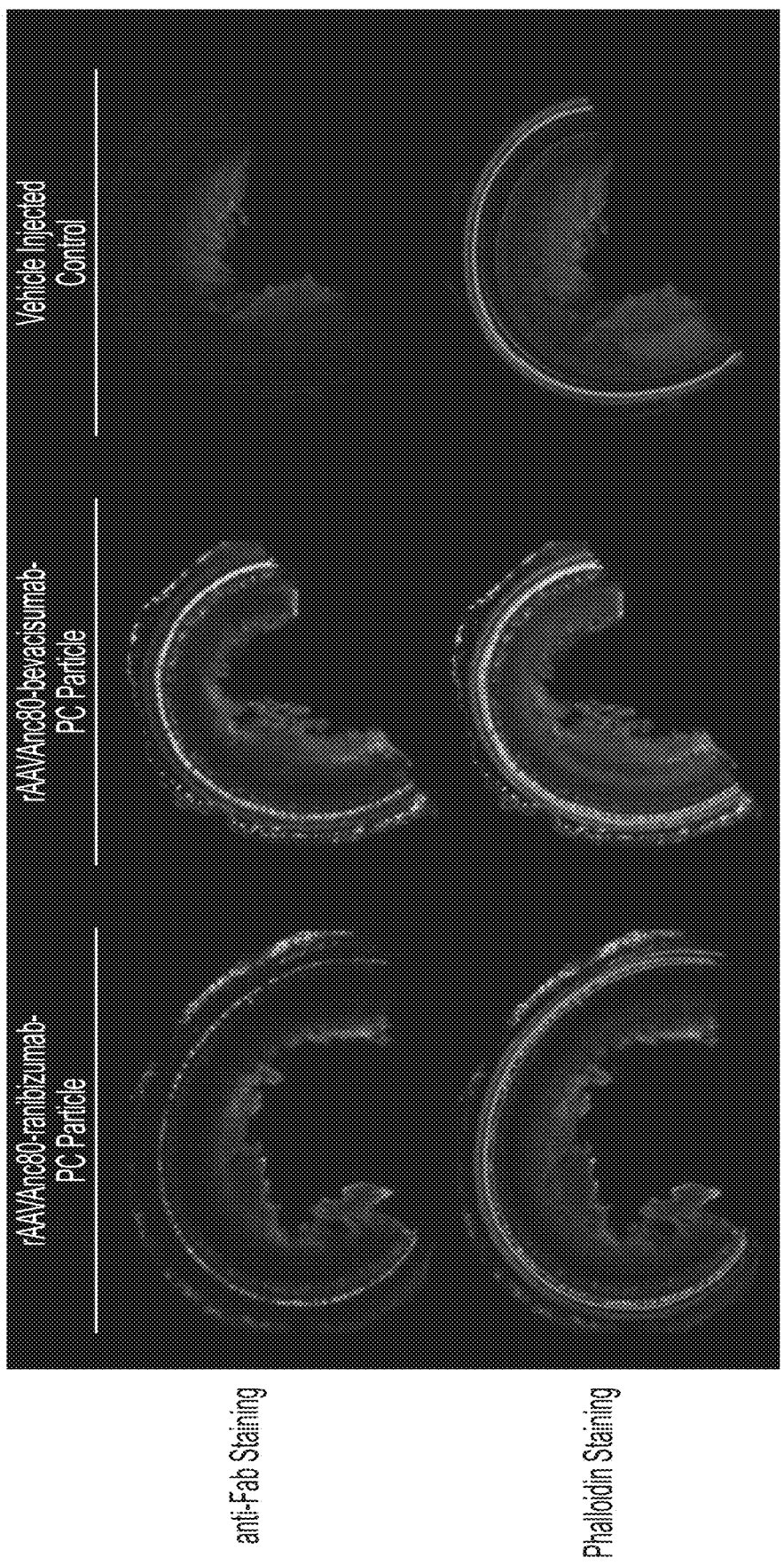
FIG. 17 includes representative low-magnification florescent staining images from a first study (referred to herein as "Study 1"), depicting the inner ear of CBA/CaJ mice transduced with rAAVAnc80-antiVEGF particles as described herein. Images are representative cochlear micrographs of the middle turn of microdissected cochleae after intracochlear administration of either rAAVAnc80-ranibizumab-PC (construct according to SEQ ID NO: 90) particles at 1.4E10 vg/cochlea, rAAVAnc80-bevacizumab-PC (construct according to SEQ ID NO: 93) particles at 1.2E10 vg/cochlea, or vehicle control. The sensory epithelium was immunostained with primary antibodies against phalloidin, a hair-cell marker (which also shows faint non-specific labeling of the spiral limbus in these micrographs), and ranibizumab ("anti-Fab staining"), to detect anti-VEGF protein expression.

Anti-VEGF RNA was detected in the explants receiving rAAVanc80-antiVEGF particles, but not those receiving vehicle (FIG. 16, Panel (A)), and secreted anti-VEGF protein was detected in the media of the explants receiving rAAVAnc80-antiVEGF particles, but not those receiving vehicle (FIG. 16, Panel (B)). These data suggest that administration of rAAVAnc80-antiVEGF particles comprising constructs encoding anti-VEGF proteins to WT mouse cochlea ex-vivo yields expression and secretion of the target protein from transduced cells. Cochlear explant results support in-vivo testing of intracochlear injection of WT mice with rAAVAnc80-antiVEGF particles to determine at least tolerability in-vivo, as well as to assess in-vivo secreted levels of anti-VEGF protein.

Example 7.2: Ex-Vivo Production of Anti-VEGF Proteins Ranibizumab, Bevacizumab, and Aflibercept Mock rAAV particles or rAAV particles rAAVAnc80-ranibizumab, rAAVAnc80-ranibizumab-GFP, rAAVAnc80-bevacizumab, rAAVAnc80-bevacizumab-GFP, rAAVAnc80-aflibercept-PC, or rAAVAnc80-aflibercept (e.g., as described in Example 1) are prepared and transduced into newborn (P2) wild type (WT) mice cochlear explants at a suitable MOI (e.g., at 1.2E10, 1.4E10, 2.4E10, 2.8E10, 3.5E10, and/or 4.2E10 vg/explant, etc.) In these experiments, an organ of Corti is dissected and mounted on coverslips, followed by incubation for three to four days with either vehicle or a range of doses of rAAVAnc80-ranibizumab particles, rAAVAnc80-ranibizumab-GFP particles, rAAVAnc80-bevacizumab particles, rAAVAnc80-bevacizumab-GFP particles, rAAVAnc80-aflibercept-PC particles, or rAAVAnc80-aflibercept particles, as described in Example 1. Media surrounding the explants is harvested and analyzed using an MSD immunoassay. Streptavidin-coated MSD assay plates are blocked and coated with biotinylated VEGF ligand before incubation with the sample. Anti-VEGF proteins (e.g., ranibizumab, bevacizumab, and/or aflibercept) bound to the assay plate are then detected with a tagged goat polyclonal anti-κ light-chain (pAb) antibody.

Optionally, experiments are conducted to determine the mRNA expression level from rAAV-antiVEGF constructs transduced into wild type explants (ex-vivo). Mock rAAV particles or rAAV particles comprising rAAV constructs (e.g., as described in Example 1) encapsidated by Anc80 capsids are prepared and transduced into explants at a suitable MOI (e.g., at those described above, and/or at an MOI of approximately $4.5\times10^9$ vg/cochlea or $1.5\times10^{10}$ vg/cochlea). Supernatant is collected, and cells are harvested 72 hours post transduction using 350 µL RLT Plus RNA lysis buffer (Qiagen), and RNA samples are prepared using the RNeasy Micro Kit (Qiagen). Relative mRNA expression levels are determined using quantitative real-time PCR with anti-VEGF protein encoding nucleotide specific amplifying primers (e.g., primers specific for bevacizumab, ranibizumab, and/or aflibercept encoding nucleotides) and a TaqMan probe and are compared relative to an appropriate control (e.g., mouse GAPDH probe as control (Life Technologies)). Robust and dose dependent anti-VEGF protein encoding mRNA production is observed. Soluble and secreted anti-VEGF protein levels are determined as described above.

Example 8: Surgical Methods and rAAV Particle Analysis in Model Animals

The current example relates to the introduction of technologies (e.g., constructs, particles, and/or compositions) described herein to the inner ear of aged mice. rAAV particles comprising a construct encoding an anti-VEGF protein are prepared in formulation buffer (e.g., artificial perilymph, or 1×PBS with pluronic acid F68) and then administered to the scala tympani in mice as described by Shu et al. (Human Gene Therapy, doi.10 1089/hum.2016 053, June 2016, which is incorporated in its entirety herein by reference). Male and female mice older than P15 are anesthetized using an intraperitoneal injection of xylazine (approximately 5-10 mg/kg) and ketamine (approximately 90-120 mg/kg). Body temperature is maintained at 37° C. using an electric heating pad. An incision is made from the right post-auricular region and the tympanic bulla and posterior semicircular canal are exposed. The bulla is perforated with a surgical needle and the small hole is expanded to provide access to the cochlea. The bone of the cochlear lateral wall of the scala tympani is thinned with a dental drill so that the membranous lateral wall is left intact. A small hole is then drilled in the posterior semicircular canal. Patency of the canalostomy is confirmed by visualization of a slow leak of perilymph. A Nanoliter Microinjection System in conjunction with glass micropipette is used to deliver a total of approximately 1 µL of construct containing buffer (e.g., rAAV constructs described herein at approximately $4.5\times10^9$ to $5\times10^{10}$ vg/per cochlea in artificial perilymph or 1×PBS with pluronic acid F68) to the scala tympani at a rate of 2 nL/second. The glass micropipette is left in place for 5 minutes post-injection. Following cochleostomy and injection, the opening in the tympanic bulla and the posterior semicircular canal are sealed with small pieces of fat, and the muscle and skin are sutured. The mice are allowed to awaken from anesthesia and their pain is controlled with 0.15 mg/kg buprenorphine hydrochloride for 3 days.

Studies such as those described in the present example are conducted in preparation for first-in-human safety and dose escalation trials in adult participants with unilateral progressive sporadic VS. Intracochlear delivery of rAAV (e.g., AAVAnc80, e.g., AAVAnc80-antiVEGF) can be used to transduce cochlear and vestibular cells of the inner ear, which are then expected to secrete anti-VEGF protein into perilymph or directly into the interstitial fluid of the cochlear nerve. The lack of barriers to diffusion along the internal auditory canal results in the cochlear nerve being bathed in a continuum of fluid, with perilymph at its lateral end (nearest the cochlea, where the majority of VS tumors originate (FIGS. 1 and 3) and CSF at its medial end; thus, diffusion from perilymph into the nerve interstitium provides a path for therapeutic anti-VEGF protein expressed in perilymph to reach the intended VS target.

In mice, a surgical approach, e.g., that described in Yoshimura et al., 2018, can be utilized for the delivery of rAAV particles as described herein (Yoshimura 2018, incorporated herein in its entirety by reference). Specifically, delivery through the round window membrane with fenestration of the posterior semicircular canal, which has demonstrated robust and reliable transduction, independent of the age of the animal at the time of injection (Yoshimura 2018, incorporated herein in its entirety by reference). A postauricular incision is made to access the temporal bone. A portion of the sternocleidomastoid muscle is divided to expose the otic bulla. A 0.5 to 0.6 mm diameter otologic drill is used to make a small hole in the bulla; the hole is then widened to visualize the stapedial artery and the round window membrane. Fenestration of the posterior semicircular canal is performed with the otologic drill (0.5 to 0.6 mm diameter) to serve as a vent the inner ear during cochlear administration. The round window membrane is penetrated with the mouse delivery device, which comprises a borosilicate capillary pipette and a 10 uL Hamilton syringe, and 1 µL of solution comprising viral particles (approximately 40 to 50% of the total inner ear volume) is delivered through the round window membrane, into the scala tympani, at rate of 300 nL/min. Studies of AAVAnc80 particles comprising constructs encoding an anti-VEGF protein are performed in mice with mature cochleae.

Example 9: Transgenic Expression, Analysis, and Imaging of Anti-VEGF Proteins in Mice This example relates to the transgenic expression of anti-VEGF proteins in mice, and the subsequent imaging and phenotypic analysis of said animals.

Example 9.1: In-Vivo Expression, and Imaging of Anti-VEGF Proteins Ranibizumab and Bevacizumab in Mice Biological tolerability and/or exposure to compositions comprising anti-VEGF proteins described herein were evaluated, including measuring anti-VEGF levels in CSF and serum, after intracochlear delivery of rAAV particles as described herein comprising constructs encoding antiVEGF. rAAVAnc80-ranibizumab-PC particles or rAAVAnc80-bevacizumab-PC particles (as described in Example 1) were injected into P30 WT CBA/CaJ mice. An outline of Study 1 groups can be found in Table 3. An additional study (referred to herein as "Study 2") described herein was also performed, results of which are described below, an outline of the study groups can be found in Table 4. These studies captured data related to surgical introduction, rAAV particle transduction, and subsequent expression of—and exposure to—secreted anti-VEGF proteins. These results are summarized below and their details can be found in FIGS. 17-26. In these studies, rAAVAnc80-ranibizumab-PC particles or rAAVAnc80-bevacizumab-PC particles (as described in Example 1) were administered via unilateral intracochlear injection through the round window membrane with posterior semicircular canal fenestration (as described herein). Vehicle-control animals were injected with formulation buffer.

CAB/CaJ wild type mice were anesthetized to prepare for introduction of compositions described herein. Vehicle controls, rAAVAnc80-ranibizumab-PC particles, or rAAVAnc80-bevacizumab-PC particles (as described in Example 1) were prepared and introduced to the mouse inner ear through the round window membrane. Introduction of rAAV particles was performed through the following steps: A) preauricular incision to expose the cochlear bulla, B) glass micropipettes (cat #4878—WPI) pulled with a micropipette puller (cat #P87—Sutter instruments) to a final OD of about 10 µm were used to manually deliver (micropipettes held by a Nanoliter 2000 micromanipulator—WPI) compositions containing rAAV particles into the scala tympanic, which allows access to inner ear cells, C) 1 µL of a composition described herein at a suitable concentration in suitable buffer (described in Example 1, rAAVAnc80-ranibizumab-PC particles at approximately $1.4 \times 10^{10}$ vg/per cochlea, or rAAVAnc80-bevacizumab-PC particles at approximately $1.2 \times 10^{10}$ vg/per cochlea; each diluted in in 1×PBS with pluronic acid F68) was injected into each tested cochlea at a release rate of 0.3 µL/min (controlled by MICRO4 microinjection controller—WPI). Sham surgeries were performed as above with vehicle as a negative control. Mice were allowed to recover from surgery without additional intervention. At 5 weeks post-injection, animals were euthanized, cerebrospinal fluid (CSF) samples, serum samples, and inner ear sections for immunofluorescence analysis were collected.

TABLE 3

Study 1 Group Assignments

| Group | Number of Animals* | Test Article | Concentration (vector genome [vg]/mL) | Dose (vg/ cochlea) | Survival Period |
|---|---|---|---|---|---|
| 1 | 10 | rAAVAnc80-ranibizumab-PC particles | 1.4E13 | 1.4E10 | 4 to 5 weeks |
| 2 | 10 | rAAVAnc80-bevacizumab-PC particles | 1.2E13 | 1.2E10 | 4 to 5 weeks |
| 3** | 10 | Vehicle | n/a | n/a | 4 to 5 weeks |

*Combined males and females (4 to 6 males per group).
**Uninjected, contralateral ears from Vehicle-control group used as histological controls.
Abbreviations: n/a = not applicable.

Figure 18:
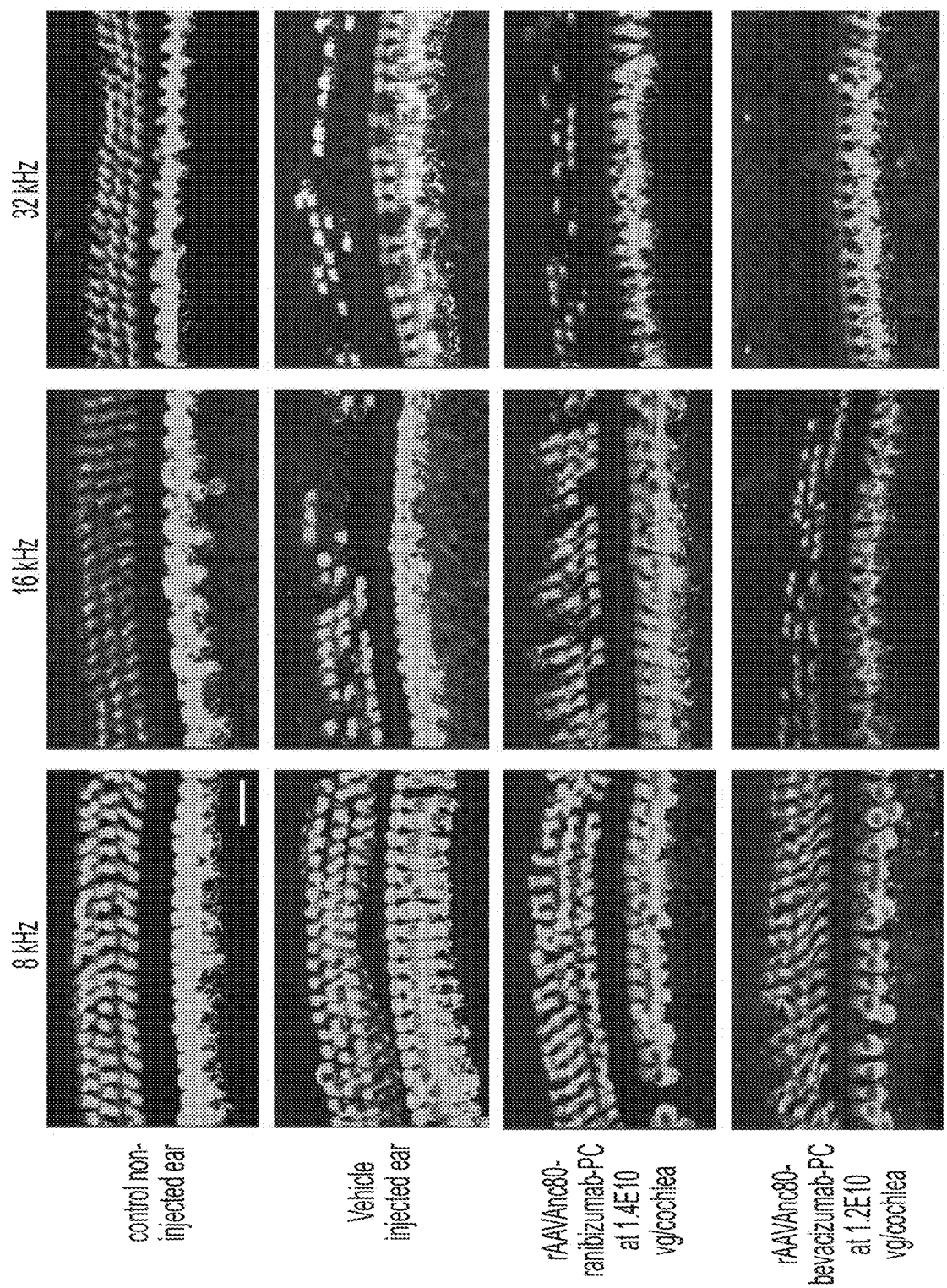
FIG. 18 includes representative florescent staining images from Study 1, depicting the inner ear of CBA/CaJ mice transduced with rAAVAnc80-ranibizumab-PC (construct according to SEQ ID NO: 90) particles at 1.4E10 vg/cochlea or rAAVAnc80-bevacizumab-PC (construct according to SEQ ID NO: 93) particles at 1.2E10 vg/cochlea, compared with non-injected and/or vehicle injected controls. IHCs and OHCs were immunostained with anti-myosin VIIa antibodies and imaged at the 8, 16, and 32 kHz regions using a published cochleogram (Viberg and Canlon, 2004, which is incorporated in its entirety herein by reference). Control non-injected ear images are from ears contralateral from control vehicle injected ears. Scale bar=20 μM. Color images of the panels provided in this figure are shown in FIG. 18 of U.S. Provisional patent application 63/152,832, the entire contents of which is incorporated herein by reference.
Figure 19:
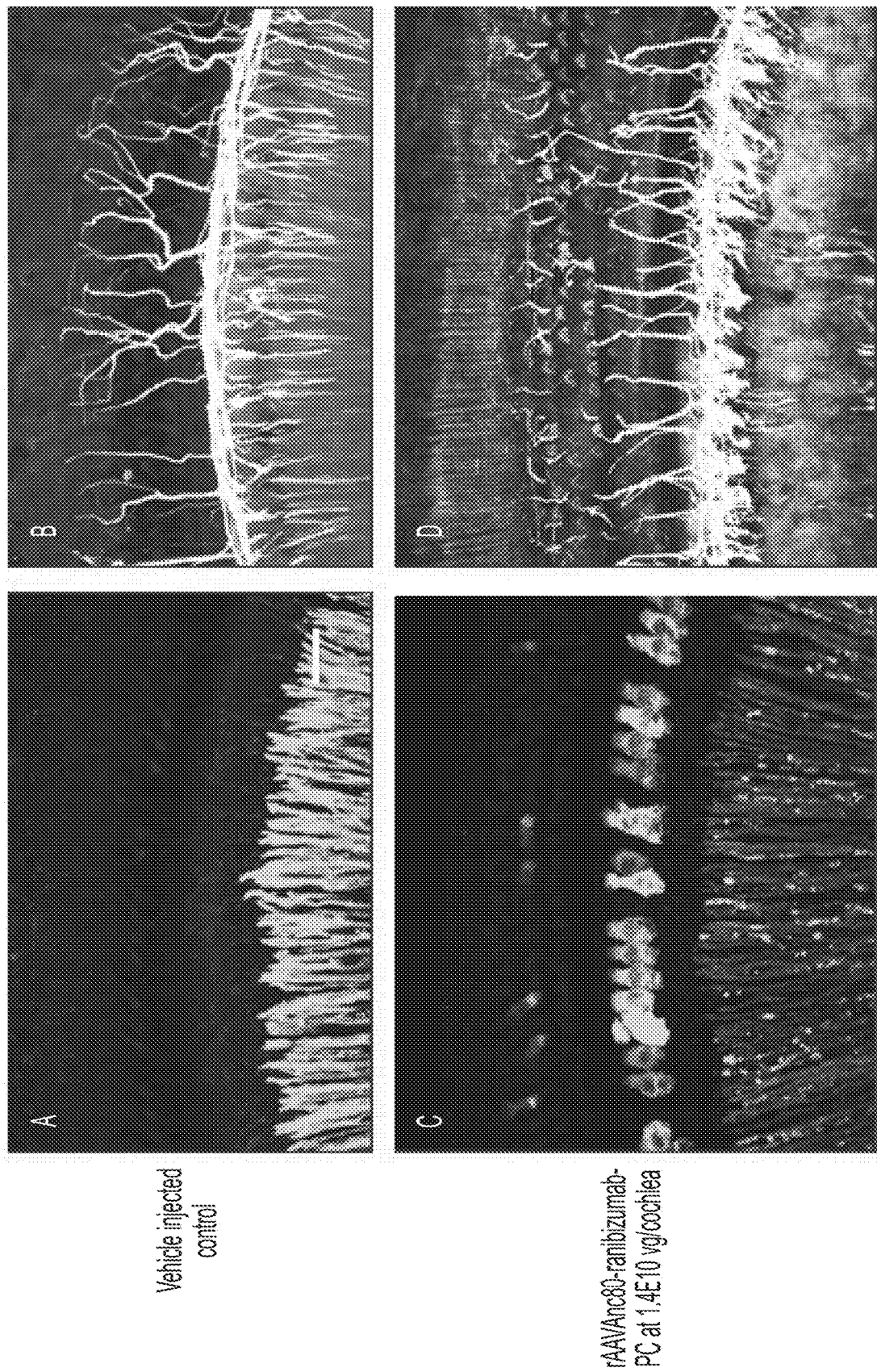
FIG. 19 includes representative confocal images from Study 1, depicting transduced hair cells and neurons for populations of CBA/CaJ mice transduced with rAAVAnc80-ranibizumab-PC (construct according to SEQ ID NO: 90). Panel (A) and Panel (C) represent transduced cells immunostained with anti-Fab antibodies. Panel (B) and Panel (D) represent neuronal projections immunostained with anti-Neurofilament 200. Both the vehicle injected samples (Panels (A) and (B)) and rAAVAnc80-ranibizumab-PC particle injected samples (Panels (C) and (D)) have transduced neuronal projections in the inner sulcus region, but not in the organ of Corti. Only the rAAVAnc80-ranibizumab-PC particle injected samples have transduced inner and outer hair cells. Scale bar=20 μM. Color images of the panels provided in this figure are shown in FIG. 19 of U.S. Provisional patent application 63/152,832, the entire contents of which is incorporated herein by reference.
Figure 20B:
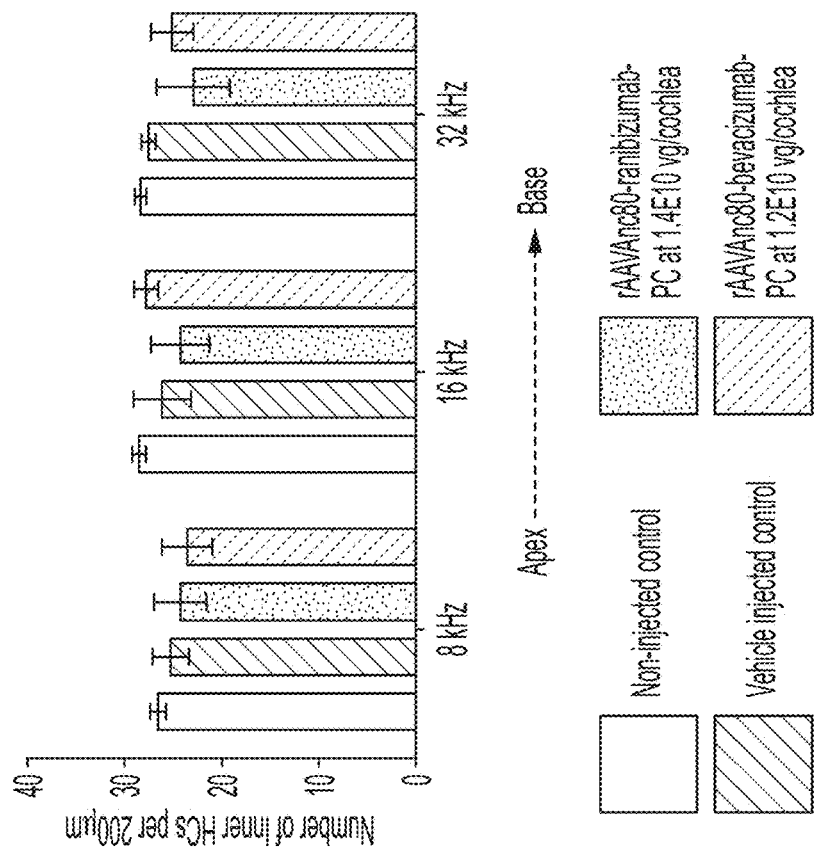
FIGS. 20A-20B are graphical representations from Study 1, depicting IHC and OHC count histograms from CBA/CaJ mice transduced with an rAAVAnc80-ranibizumab-PC (construct according to SEQ ID NO: 90) particles at 1.4E10 vg/cochlea, or rAAVAnc80-bevacizumab-PC (construct according to SEQ ID NO: 93) particles at 1.2E10 vg/cochlea, as compared with non-injected and/or vehicle injected controls. A representative population of the data sets utilized in this analysis are shown in FIG. 18.
Figure 20A:
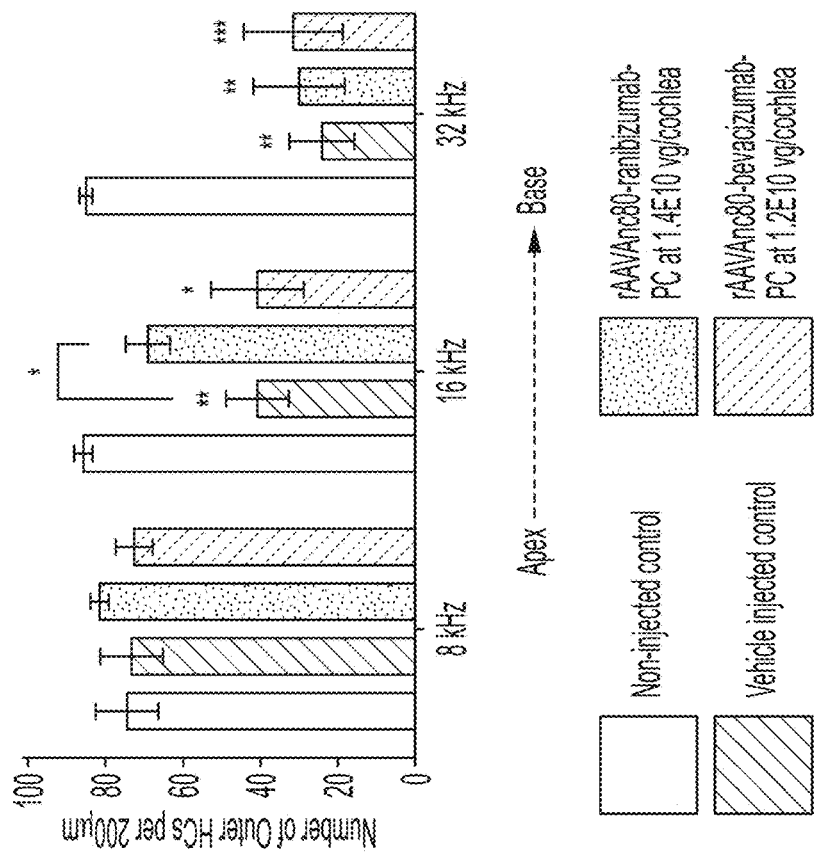
Figure 21B:
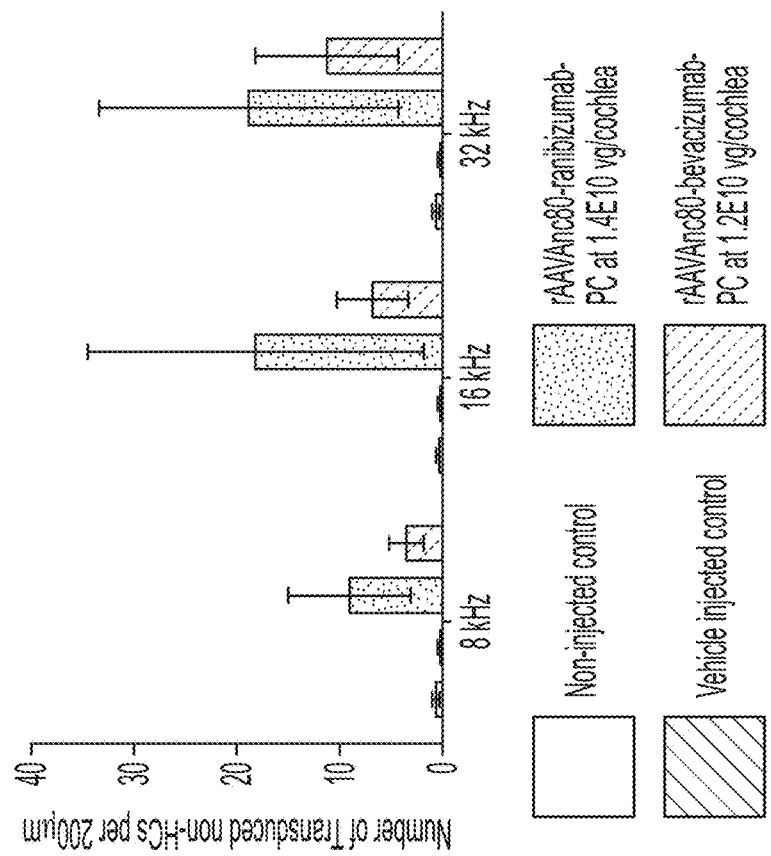
FIGS. 21A-21B are graphical representations of the transduction frequency of hair cells (HCs) and non-hair cells (non-HCs). A representative population of the data sets utilized in this analysis are shown in FIG. 18.
Figure 21A:
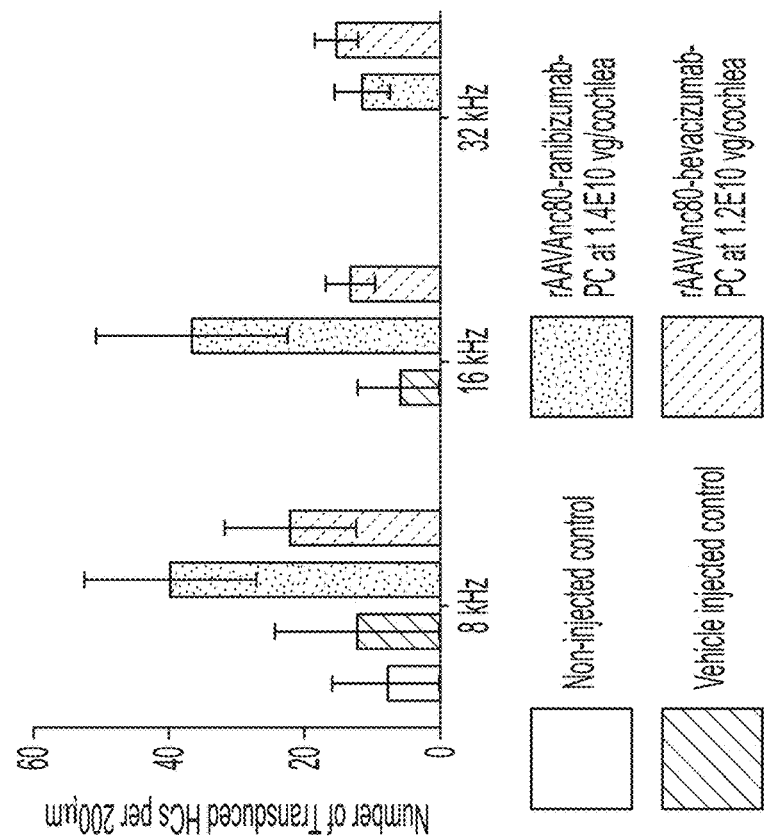

To evaluate anti-VEGF protein exposure as a result of inner ear transduction by rAAV particles as described herein (rAAVAnc80-antiVEGF particles), blood and CSF were collected upon termination at 4 to 5 weeks following intracochlear delivery, and anti-VEGF protein levels in CSF and serum were measured using an MSD immunoassay (e.g., as described in Example 7). Levels of soluble anti-VEGF protein (ranibizumab or bevacizumab) within the CSF was measured and ranged from 2.71-19.29 ng/mL. Following collection of these fluids, mice were transcardially perfused and cochleae were harvested and submersion-fixed for histological assessment. Cochlear samples were decalcified and microdissected. Dissected organ of Corti whole-mounts and cross-sections were stained with anti-ranibizumab (Abcam, ab168684-25UG, mAb) determine transgenic expression of constructs as described herein, and anti-Phalloidin (Thermo Fisher A12381) staining was used to characterize different inner ear cell types (FIG. 17) and anti-Myosin VIIa staining was used to label hair cells (depicted in FIG. 18 and quantified in FIG. 20). Half of the samples were also stained with anti-Sox2 to label supporting cells and the other half with anti-neurofilament 200 to label neuronal projections (FIG. 19). Confocal analysis of immunostained tissue was used to identify transduction efficiency/anti-VEGF expression, and cell survival (FIGS. 20 and 21).

Anti-VEGF protein expression was evaluated based on the appearance of a signal and not the intensity. Without wishing to be bound to any particular theory, one reason for this could be that the polyclonal secondary antibody could potentially bind a larger number of epitopes on the humanized mouse antibody bevacizumab when conjugated to the mouse monoclonal primary anti-ranibizumab antibody (MmAb described above) as compared to the corresponding smaller sized humanized mouse antibody ranibizumab when conjugated to the monoclonal primary anti-ranibizumab antibody. Inner hair cells robustly expressed a transgene in a majority of cochleae (17 of 19 ears) receiving rAAVAnc80-ranibizumab-PC particles or rAAVAnc80-bevacizumab-PC particles (as described in Example 1, results depicted in FIG. 17 and quantified in FIG. 21). Of these 17 cochleae, 14 also showed expression in a subset of OHCs and/or non-hair cells. No substantial difference was detected in the cell identity and expression pattern between ears receiving rAAVAnc80-ranibizumab-PC particles compared to those receiving rAAVAnc80-bevacizumab-PC particles.

Figure 23:
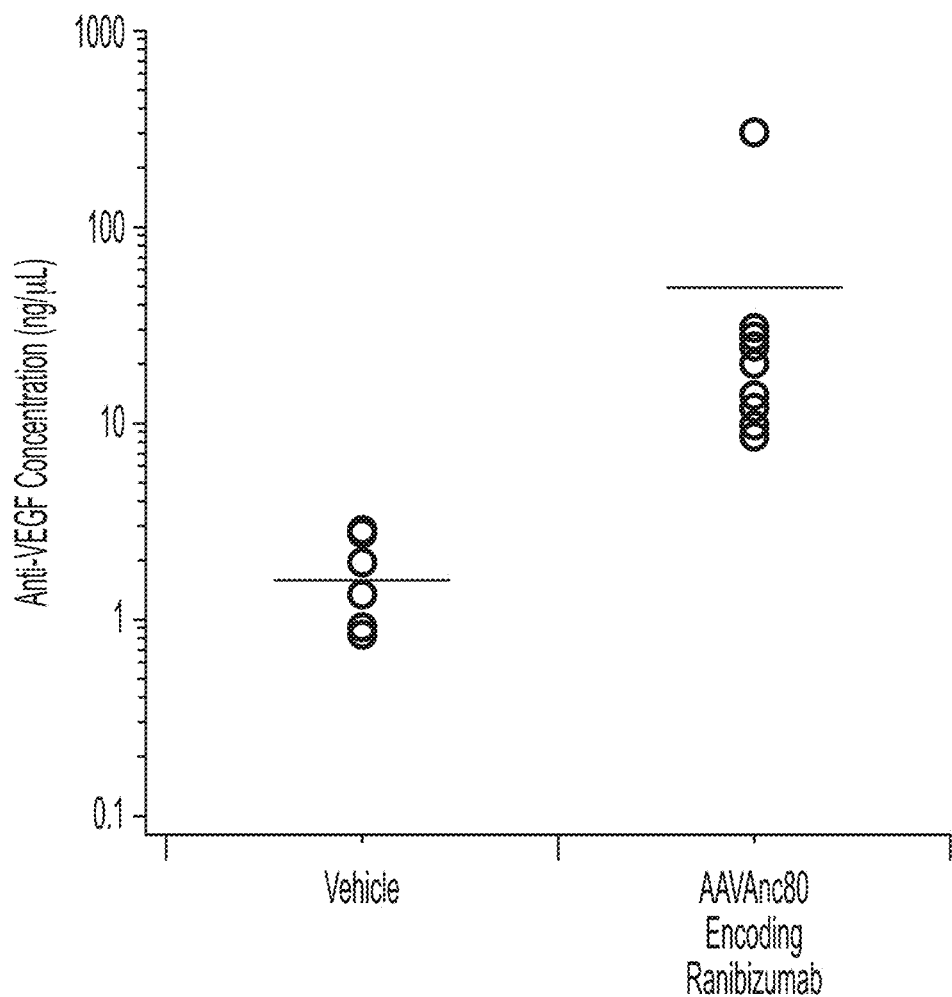
FIG. 23 is a graphical representation of the detection and quantification of secreted anti-VEGF protein in serum from Study 2, and is following intracochlear delivery of rAAVAnc80-ranibizumab-PC (construct according to SEQ ID NO: 90) particles at 1.4E10 vg/cochlea. Anti-VEGF protein was detected using meso scale discovery in the serum of mice injected with rAAVAnc80-ranibizumab-PC particles at a higher level than in the serum of mice injected with vehicle. Open circles indicate anti-VEGF protein concentration in individual samples (vehicle, n=7; ranibizumab, n=9), while bars represent the mean.
Figure 24:
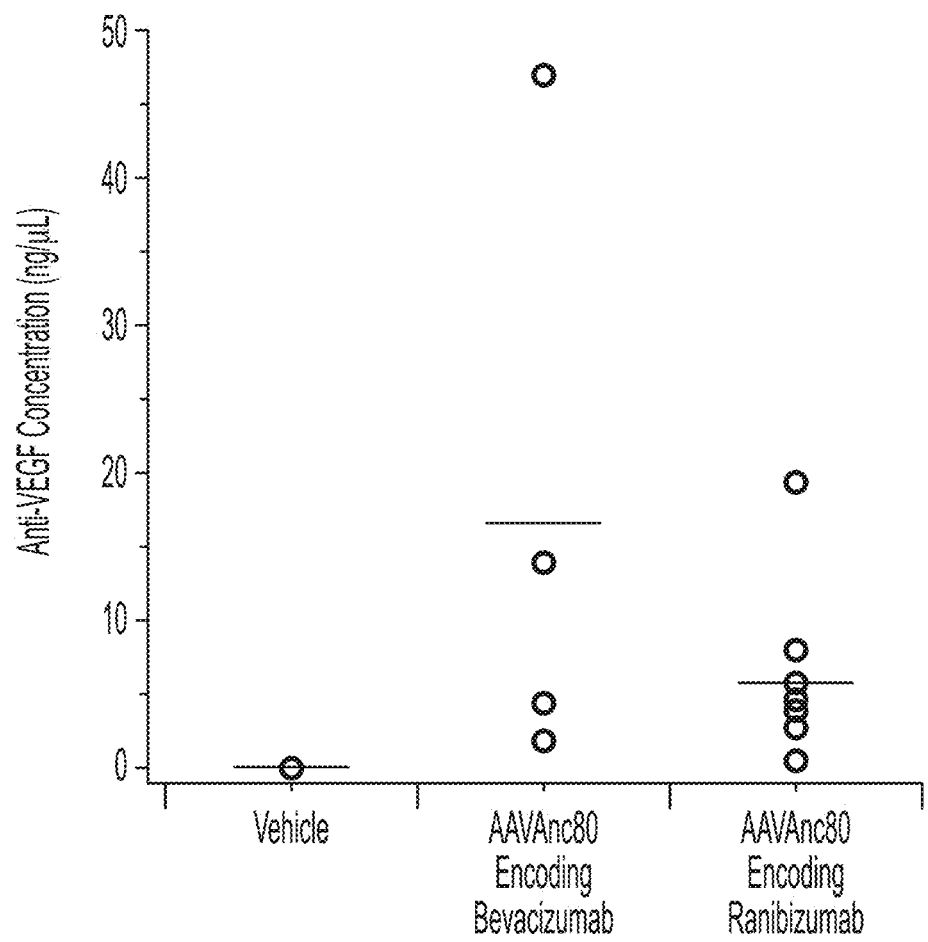
FIG. 24 is a graphical representation of the detection and quantification of secreted anti-VEGF protein in mouse cerebral spinal fluid (CSF) from Study 1, and is following intracochlear delivery of rAAVAnc80-ranibizumab-PC (construct according to SEQ ID NO: 90) particles at 1.4E10 vg/cochlea, or rAAVAnc80-bevacizumab-PC (construct according to SEQ ID NO: 93) particles at 1.2E10 vg/cochlea. Anti-VEGF protein (ranibizumab or bevacizumab) was detected using MSD in the CSF of mice administered rAAVAnc80-antiVEGF particles, but not in the CSF of mice administered vehicle. Open circles indicate an anti-VEGF protein concentration in individual samples (vehicle, n=10; ranibizumab, n=9; bevacizumab, n=4), while bars represent the mean.

Confirmation that this expression in cochlear tissues led to production and secretion of anti-VEGF protein (ranibizumab or bevacizumab) was determined. CSF (sampled from cisterna magna) and serum samples were collected and analyzed from animals (FIGS. 23 and 24). Anti-VEGF protein concentrations in the perilymph can also be measured to better understand the ratio of anti-VEGF protein exposure between perilymph and CSF. Perilymph sample collection in mice can be technically challenging. In the present example, one perilymph sample was collected. Anti-VEGF protein (ranibizumab or bevacizumab) was detected in CSF of rAAV particle-injected animals compared to no detection in vehicle-injected controls (FIG. 24). Detection of secreted anti-VEGF protein by an MSD assay was limited to qualitative comparisons between ranibizumab and bevacizumab, owing to use of a similar polyclonal secondary as used in detecting expression in cochlear tissues (as described above), where a stronger signal is observed for samples from ears receiving rAAVAnc80-bevacizumab-PC particles due to greater availability of epitopes. Without wishing to be bound to any particular theory, clear detection of anti-VEGF protein in the CSF may be due to communication between perilymph and CSF in this species via the patent cochlear aqueduct.

Mouse serum was assessed for anti-VEGF protein (ranibizumab) via an MSD assay with an anti-κ light-chain (pAb) antibody that detects ranibizumab (described above and in Example 7). Compared to vehicle-injected animals, mice that received intracochlear delivery of rAAV-ranibizumab-PC particles demonstrated higher levels of anti-VEGF protein (ranibizumab) in serum at 4 to 5 weeks following delivery (FIG. 23).

Serum from mice that received intracochlear delivery of rAAV-ranibizumab, rAAV-ranibizumab-GFP, rAAV-bevacizumab-PC, rAAV-bevacizumab, rAAV-bevacizumab-GFP, rAAV-aflibercept-PC, or rAAV-aflibercept particles (e.g., comprising ranibizumab, bevacizumab, or aflibercept) can be evaluated.

Study 2 was also performed using the same parameters: e.g., mouse strain, age, rAAV capsid, ranibizumab encoding construct, and intracochlear administration procedure to address emerging data indicating possible surgical challenges. The study utilized rAAVAnc80-ranibizumab-PC particles (as described in Example 1), as in certain embodiments, ranibizumab may have different features when compared to bevacizumab, e.g., a higher binding capacity and higher binding affinity, no Fc domain, and a smaller molecular mass. rAAVAnc80-ranibizumab-PC particles (as described in Example 1) were administered at 1.4E10 vg/cochlea via unilateral intracochlear injection through the round window membrane with posterior semicircular canal fenestration (as described herein). Uninjected ears of vehicle-injected mice served as controls. Upon study termination, animals were transcardially perfused and cochleae were harvested, decalcified, and microdissected for confocal microscopy imaging using the following labels: anti-ranibizumab (mAb) to detect transgene expression; anti-Myosin VIIa to label hair cells; and anti-Tuj1 to label projections of cochlear nerve fibers (e.g., radial nerve fibers).

TABLE 4

Study 2 Group Assignments

| Group | Number of Animals* | Test Article | Concentration (vector genome [vg]/mL) | Dose (vg/ cochlea) | Survival Period |
|---|---|---|---|---|---|
| 1 | 3 | rAAV-ranibizumab-PC particle | 1.4E13 | 1.4E10 | 4 weeks |
| 2 | 2 | Uninjected | n/a | n/a | 4 weeks* |

*From place-holder surgery date based on age of mice (no sham surgery).
Abbreviations: n/a = not applicable.

Cochlear histology of the sensory epithelium in this study depicted broad distribution of anti-VEGF protein (ranibizumab) expression across the length of the cochlea (FIG. 22) in multiple cell types, including inner and outer hair cells, lateral supporting cells, and interdental cells of the spiral limbus. In general, hair cells were present in the analyzed regions of the cochleae, with the exception that some IHC loss was observed in the apical-most region of the cochlea of Mouse 1.

Example 9.2: Phenotypic Analysis of In-Vivo Ranibizumab and Bevacizumab Delivery and Production in Mice rAAV-antiVEGF particles as described herein were evaluated for cochlear tolerability in mice. As part of a study conducted to evaluate transduction and subsequent protein secretion in mice following intracochlear delivery of exemplary rAAVAnc80-ranibizumab-PC particles, or rAAVAnc80-bevacizumab-PC particles (as described in Example 1), overall tolerability, auditory function, and cochlear hair cell survival were also assessed to evaluate cochlear tolerability of the surgical administration and transgene expression. No deleterious change in body weight or body condition score was detected throughout the 4 to 5 weeks post-intracochlear delivery, with the exception of one animal that died 1 week post-delivery for an unidentified reason (no surgical complications or aberrant findings on health observations were noted). No indication of damage to the vestibular system, as evidenced by circling or head-bobbing, was detected.

Figure 25:
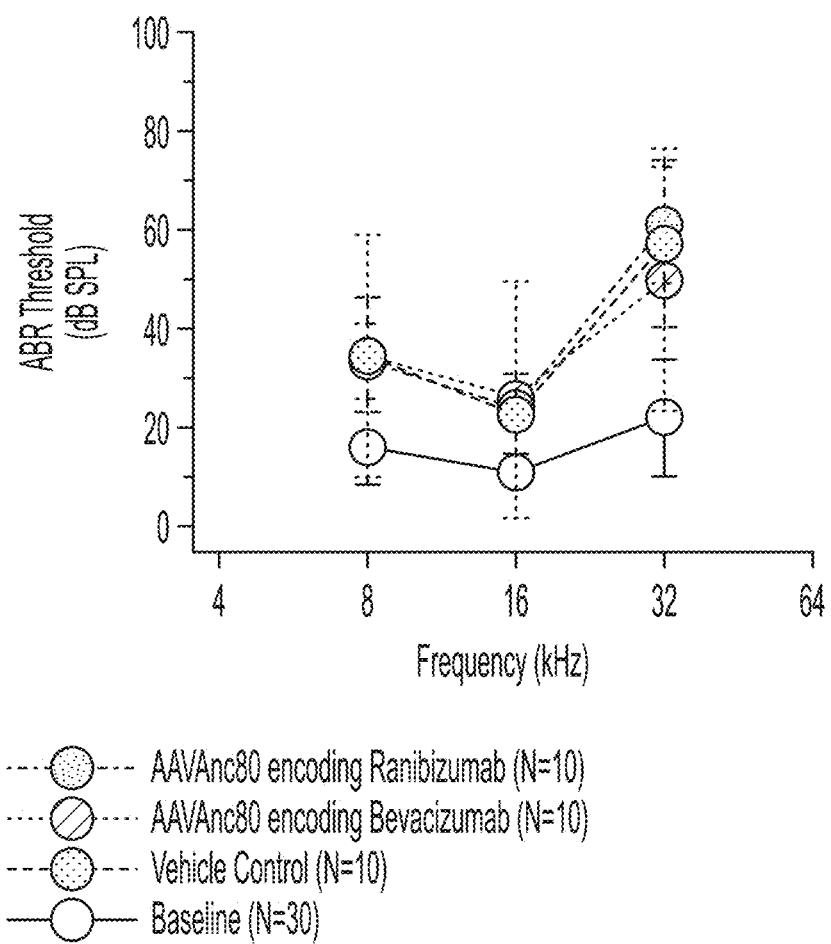
FIG. 25 is a graphical representation of Study 1 mice auditory brainstem response (ABR) thresholds pre- and post-intracochlear delivery of rAAVAnc80-ranibizumab-PC (construct according to SEQ ID NO: 90) particles at 1.4E10 vg/cochlea, or rAAVAnc80-bevacizumab-PC (construct according to SEQ ID NO: 93) particles at 1.2E10 vg/cochlea. Mean ABR thresholds were elevated in all groups following intracochlear surgery, including vehicle- and rAAVAnc80 particle-injected mice. Mean ABR thresholds were elevated relative to baseline ABRs measured prior to surgery in rAAVAnc80 particle- and vehicle-injected ears. Error bars represent standard deviation.
Figure 26B:
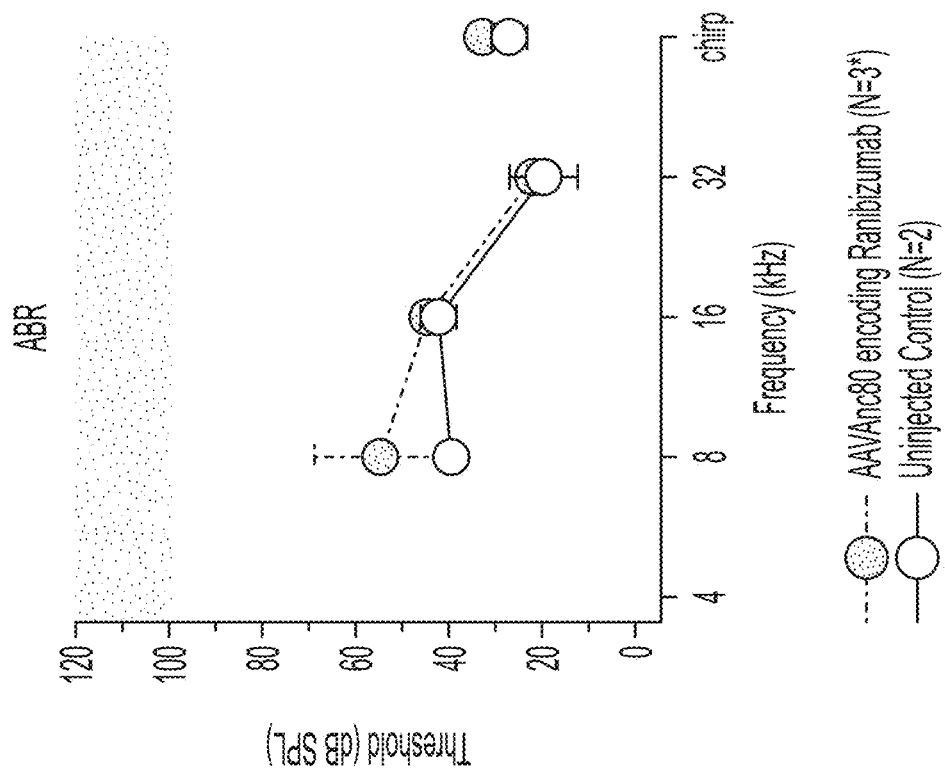
FIGS. 26A-26B are graphical representations of Study 2 mice Distortion Product Otoacoustic Emissions (DPOAE) and ABR thresholds post-intracochlear delivery of rAAVAnc80-ranibizumab-PC particles (construct according to SEQ ID NO: 90). Cochlear and auditory function (DPOAEs, FIG. 26A, and ABR, FIG. 26B, respectively) demonstrated normal mean thresholds in mice administered with exemplary rAAVAnc80-ranibizumab-PC particles when compared with uninjected mice. The * indicates that one mouse administered rAAVAnc80-ranibizumab-PC particles died during the function tests, thus only DPOAEs and chirp-evoked ABRs were measured in this animal before that time; therefore, N=2 for 8, 16, and 32 kHz ABRs. Error bars represent standard deviation.
Figure 26A:
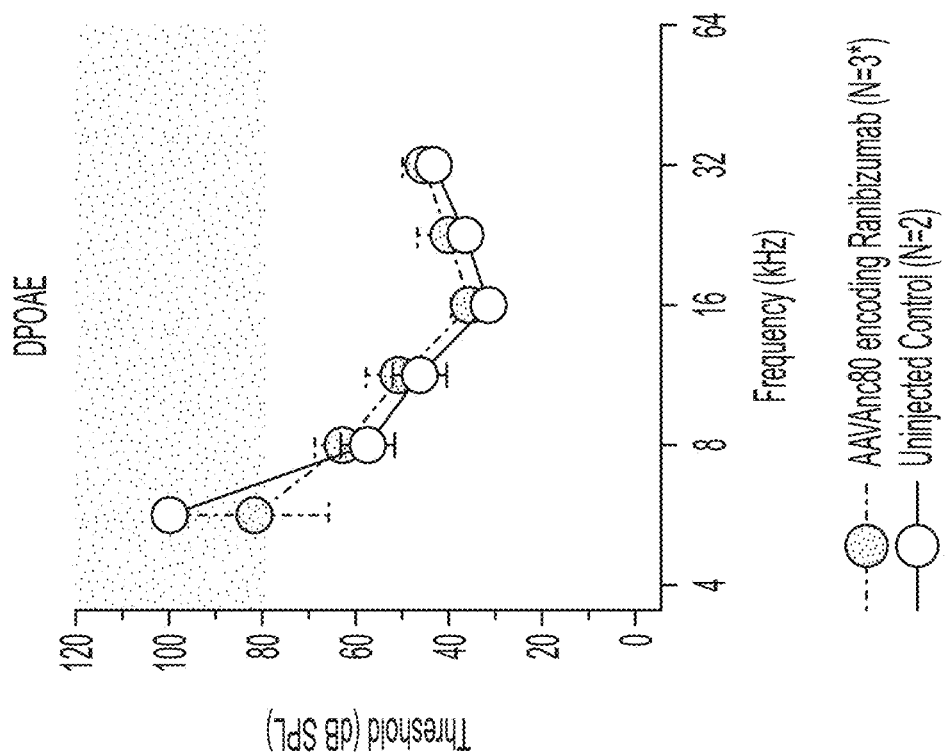

Assessment of auditory function via ABRs was performed prior to surgery and 4 to 5 weeks post-surgery (immediately prior to euthanasia). Threshold shifts were observed in groups that received rAAVAnc80-ranibizumab-PC particles, or rAAVAnc80-bevacizumab-PC particles, as well as in the group that received vehicle. Threshold shifts were of similar magnitude across groups, suggesting potential damage to the cochlea due to the surgical procedure and not due to transgene expression (FIG. 25).

Consistent with the functional assessments (ABRs; FIG. 25), hair cell loss was detected in groups that received rAAVAnc80-ranibizumab-PC particles, or rAAVAnc80-bevacizumab-PC particles, as well as the group that received vehicle, but not in the uninjected (contralateral) control ears. Damage to the basilar membrane at the base of the cochlea was detected in 16 of 19 ears that received rAAVAnc80-antiVEGF particles and in 9 of 10 ears that received vehicle, and a subsequent loss of outer hair cells in these damaged regions was prominent at 16 and 32 kHz (FIG. 18). Overall, IHC loss was not significant; sporadic IHC loss was only detected in the 8 kHz frequency region of 2 of 19 ears that received rAAVAnc80-antiVEGF particles (FIG. 18). While the route of administration resulted in hair cell damage in this particular study (referred to herein as "Study 1"), consistency between functional assessments and cell survival across ears, whether receiving rAAVAnc80-antiVEGF particles or vehicle, suggests that cell loss may have been due to the surgical procedure rather than from rAAV capsid toxicity, transgene expression, or subsequent protein secretion.

Figure 22:
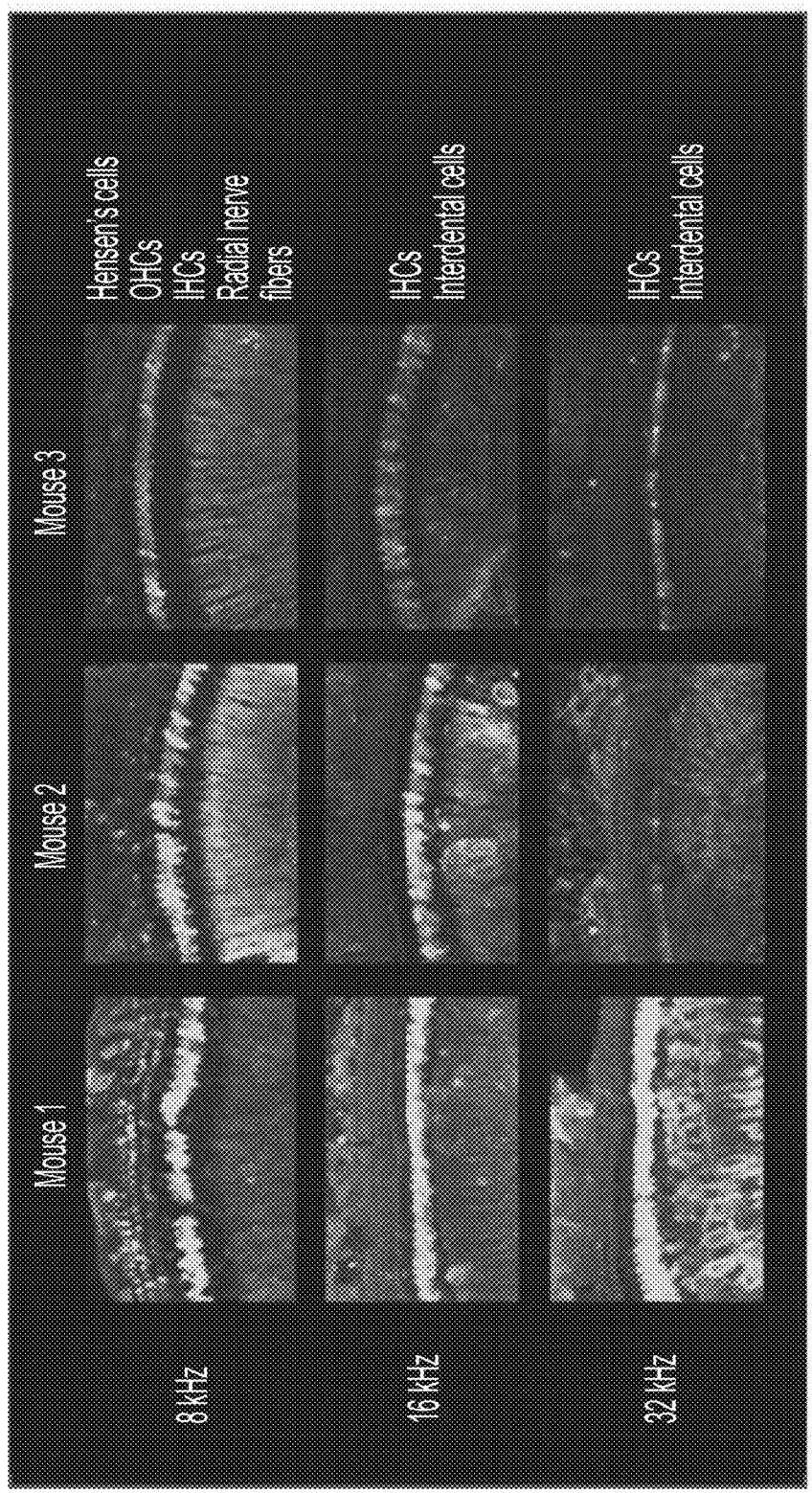
FIG. 22 includes representative high-magnification images from Study 2, depicting florescent staining of cochlear transduction by rAAVAnc80-ranibizumab-PC (construct according to SEQ ID NO: 90) particles at 1.4E10 vg/cochlea. Cochlear micrographs from three regions of injected cochleae (63×) showing anti-ranibizumab (mAb) labeling are shown. Each column represents maximum projections through confocal image stacks acquired from an injected mouse, and each row represents a frequency region from the apex (8 kHz), middle (16 kHz), and base (32 kHz) of the cochlea. Listed to the right of each row are the primary cell types that immunostained positive. Substantial background staining was detected in the nerve fiber region of the cochlea (e.g., labeling of neuronal fibers was apparent for both the injected and uninjected cochleae [uninjected cochleae not shown]), preventing reliable expression assessment in this particular area. Color images of the panels provided in this figure with anti-ranibizumab labeling in green are shown in FIG. 22 of U.S. Provisional patent application 63/152,832, the entire contents of which is incorporated herein by reference.

In light of the findings that surgical procedure may result in cell loss, Study 2 was conducted. This study showed no systematic damage to the basilar membrane and subsequent loss of OHC, and only sporadic loss at the extreme apex and base, at 4 weeks following intracochlear delivery of rAAVAnc80-ranibizumab-PC particles (as described in Example 1) (FIG. 22). Consistent with the qualitative assessment of overall hair cell survival in the corresponding regions, assessments of cochlear function (DPOAEs) and auditory function (ABRs) revealed normal thresholds at 4 weeks post-administration as compared to uninjected controls (FIG. 26, Panels (A) and (B)).

The combined data reveal delivery of rAAVAnc80-antiVEGF particles (such as rAAVAnc80-ranibizumab-PC particles, or rAAVAnc80-bevacizumab-PC particles (as described in Example 1), when introduced to mice, resulted in transgene expression in multiple cell types, including both hair cells and various supporting cells, as well as detection of the secreted anti-VEGF protein (ranibizumab or bevacizumab) in CSF. In mouse, anti-VEGF protein was present in the CSF, without wishing to be bound to any particular theory, this may potentially occur through active fluidic exchange of perilymph and CSF via the patent cochlear aqueduct in this species. These results depict 1) robust anti-VEGF protein expression in cochlear cells and 2) detection of secreted anti-VEGF protein in CSF, supporting advancement of programs to more anatomically relevant and translatable species such as non-human primates.

Example 10: Phenotypic Analysis of Transgenic Expression of Anti-VEGF Protein Encoding mRNA and Protein Expression in Murine Models of Vestibular Schwannoma (VS)

The present example pertains to an analysis of phenotypes related to VS in murine models (e.g., models as described in Chen et al., Nature Protocols 2019, which is incorporated herein in its entirety by reference). Model mice are prepared as described in Chen et al., mice are allowed to recover from surgery for an appropriate period of time (e.g., approximately 1 week), and then are anesthetized to prepare for introduction of compositions described herein. Mock rAAV particles or rAAV constructs (e.g., such as those described in Example 1) encapsidated by Anc80 capsids are prepared and introduced to the mouse inner ear through the round window membrane. Introduction of rAAV-antiVEGF particles is performed through the following steps: A) preauricular incision to expose the cochlear bulla, B) glass micropipettes (e.g., cat #4878—WPI) pulled with a micropipette puller (e.g., cat #P87—Sutter instruments) to a final OD of ~10 µm are used to manually deliver (e.g., micropipettes held by a Nanoliter 2000 micromanipulator—WPI) compositions containing rAAV particles into the scala tympanic, which allows access to inner ear cells, C) 1 µL of a composition described herein (e.g., rAAV constructs described herein at approximately $4.5 \times 10^9$ to $5 \times 10^{10}$ vg/per cochlea in 1×PBS with pluronic acid F68) is injected into each tested cochlea at a release rate of 0.3 µl/min (e.g., controlled by MICRO4 microinjection controller—WPI). Sham surgeries are performed as above with vehicle as a negative control. Mice are allowed to recover from surgery without additional intervention.

At appropriate intervals post-surgery (e.g., 2 weeks, 3 weeks, 4 weeks, 5 weeks, 6 weeks, 7 weeks, and 8 weeks), VS murine models which have undergone unilateral or bilateral composition or sham injections are anesthetized with sodium pentobarbital (e.g., 35 mg/kg) delivered intraperitoneally. Mice are then placed and maintained in a head-holder within a grounded and acoustically and electrically insulated test room. An evoked potential detection system (e.g., Smart EP 3.90, Intelligent Hearing Systems, Miami, FL, USA) is used to measure the thresholds of the auditory brainstem response (ABR) in mice. Click sounds as well as 8, 16, and 32 kHz tone bursts at varying intensity (e.g., from 10 to 130 dB SPL) are used to evoke ABRs in test mice. The response signals are recorded with a subcutaneous needle electrode inserted ventrolaterally into the ears of the mice. This example confirms that the introduction of exemplary constructs as described herein (e.g., as described in Example 1) can reduce and/or prevent VS induced symptoms, further analysis may assist in determining the exact administration timing window and how anti-VEGF protein expression acts to inhibit VS induced symptoms. Results are depicted as ABR traces, and test animals and/or ears are compared to controls, which may include non-injected animals or non-injected ears. Improvements in ABR performance are observed in test ears when compared to control ears, or in test animals when compared to control animals. Improvements in response to stimuli may also be observed in non-injected ears due to crossover from the injected ear to the non-injected ear.

At appropriate intervals post-surgery (e.g., 2 weeks, 3 weeks, 4 weeks, 5 weeks, 6 weeks, 7 weeks, and 8 weeks), VS murine models which have undergone unilateral or bilateral composition or sham injections are anesthetized (e.g., with sodium pentobarbital (35 mg/kg) delivered intraperitoneally). Mice are subsequently euthanized, and VS tumors are harvested. Tumors volume, transcriptional pattern, protein composition, and/or histology are compared. Test mice injected with exemplary compositions as described herein display reduced tumor volume, altered transcriptional patterns, altered protein composition, and/or altered histology when compared to control non-injected VS model mice.

To evaluate the potential for inner ear toxicity, following gross examination, a cochleae can be processed, dissected, and stained, and a cytocochleogram analysis can be performed to evaluate loss of IHCs and/or OHCs. The opposite cochlea/ear can be processed for middle- and inner-ear histopathology and microscopic evaluation (e.g., by a board-certified pathologist) to evaluate any gross and microscopic lesions.

Example 11: Analysis of Transgenic Expression of Anti-VEGF mRNA and Protein Expression in Non-Human Primate Animal Models The present example provides in-vivo studies of rAAVAnc80-antiVEGF particles in non-human primates (NHP). These studies can determine among other things, the tolerability, toxicology, and phenotypic response following administration of methods and/or compositions as described herein. Appropriate NHP models (e.g., *Cynomolgus* macque aka *Macaca fascicularis*) are utilized for this purpose as the inner-ear physiological similarities between NHP and humans are more pronounced than those found in murine models. The NHP animal model macaque has an inner-ear morphology that is largely representative of primate inner-ear morphology, where the lack of patent cochlear aqueduct facilitates the predictable and quantitative assessment of injectate volume dosed into the perilymph. Because of the relatively narrow diameter of the external auditory canal in NHPs compared with humans, the required surgical approach for this animal model is more invasive (entry through the mastoid/facial recess rather than through the external auditory canal). Without wishing to be bound to any particular theory, for the foregoing reasons, this approach may result in an overestimate of expected conductive loss, surgical trauma, or both. Despite having about one third the total inner ear volume of humans, the macaque cochlea is anatomically similar and the proposed drug delivery process (e.g., round window membrane injection) itself is conducted in the manner previously outlined. For analyzing and investigating the intracochlear administration of rAAV-antiVEGF particles as described herein, the macaque represents the most practical anatomically correct animal model to evaluate both safety and tolerability as well as the dose of rAAV particles needed to result in effective anti-VEGF protein exposure levels in close proximity to VS and/or related tumors.

Example 11.1: In-Vivo Expression, and Analysis of Anti-VEGF Protein Ranibizumab in NHPs In NHPs, rAAV-antiVEGF particles as described herein (e.g., rAAVAnc80-antiVEGF) were delivered as follows: a postauricular incision was made and dissection of the soft tissue was performed down to the level of the periosteum. The periosteum was incised and elevated to expose the mastoid bone. A cortical mastoidectomy was performed with a combination of high-speed cutting and diamond drill burs. The facial recess was then opened, allowing for adequate round window and oval window (OW) visualization. Fenestration of the stapes footplate in the OW was performed using a Rosen needle. As with other models, the fenestration allows for injection of a larger volume without damage to the inner ear; additionally, venting allows solution comprising rAAV-antiVEGF particles to flow toward the apex of the cochlea. Thirty µL of solution comprising viral particles (approximately 40 to 50% of the total inner ear volume) was delivered through the round window membrane at a rate of 30 µL/min.

Compositions and methods described herein were evaluated for local and systemic tolerability using simultaneous bilateral intracochlear administration of rAAVAnc80-ranibizumab particles (as described in Example 1) in NHPs (*cynomolgus* macaques) followed for 2-month or 6-month recovery periods. Among other things, this evaluation: 1) demonstrated local and systemic tolerability and 2) permitted evaluation of expression levels of anti-VEGF protein in perilymph, CSF, serum, and other tissues after intracochlear administration of an rAAVAnc80-antiVEGF particle. Both low- and high-dose groups were used. The low- and high-dose groups were based on previous platform and supportive studies in NHPs in which doses around the corresponding concentration of the higher dose (1.0E13 vg/mL corresponding to 3.0E11 vg/cochlea; with a human equivalent of 9.0E11 vg/cochlea) were not associated with pathology in NHP hair cells, whereas a higher concentration (3.7E13 vg/mL corresponding to 1.1E12 vg/cochlea; human equivalent 3.3E12 vg/cochlea) was associated with potentially capsid-related pathology in hair cells of some animals. Studies conducted herein included an additional high-dose group and vehicle group with the primary objective of collecting perilymph to ensure sample availability in which to measure anti-VEGF protein levels (e.g., by MSD); these separate groups were needed, as perilymph collection almost invariably damages the surrounding cochlea.

The results obtained from these experiments show that anti-VEGF protein (Ranibizumab) was detected in the perilymph of NHPs. No anti-VEGF protein was detected in the perilymph of the vehicle-injected control NHP, and no anti-VEGF protein was detected in terminal CSF of any NHP, regardless of post-administration duration (2 or 6 months).

Figure 27B:
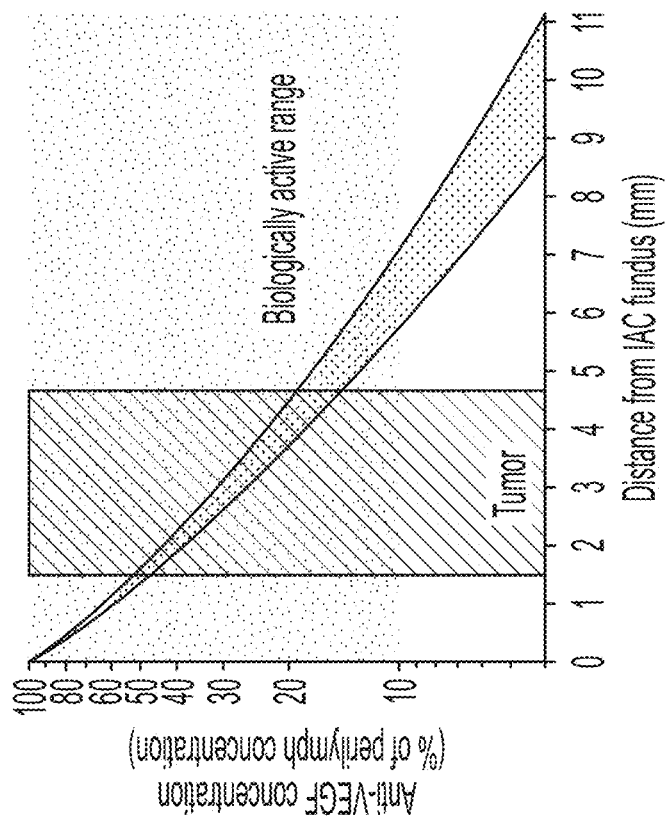
FIGS. 27A-27B provide a schematic description and graphical model depicting anti-VEGF protein concentration (modeled using measured concentrations from NHPs provided rAAVAnc80-ranibizumab particles (construct according to SEQ ID NO: 91) compared to distance to VS.
Figure 27A:
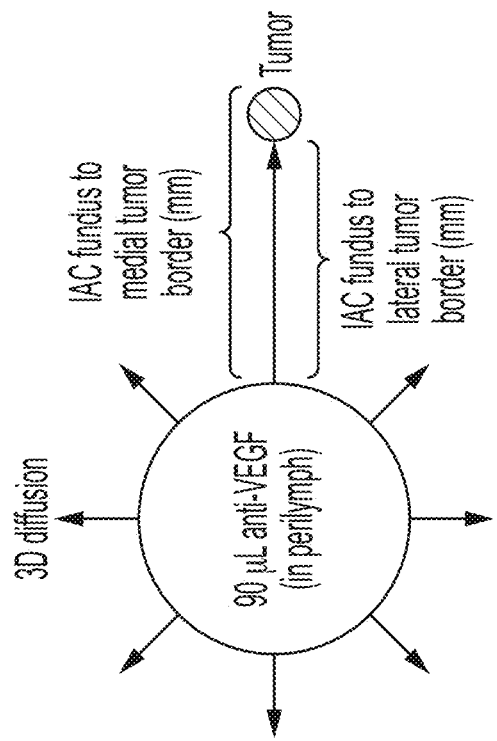

FIG. 27 demonstrates a computational model which incorporates perilymph exposure levels to estimate diffusion properties from the inner ear to the typical VS site. Computational modeling (as depicted in FIG. 27) of diffusion of anti-VEGF protein through the internal auditory canal predicted that anti-VEGF levels in the perilymph exceeded the biologically active threshold concentration (IC 50 of Ranibizumab) within the reported range of early VS locations. The concentration necessary to inhibit biological activity of VEGF-A by 50% in an in-vitro cellular proliferation assay is 11 to 27 ng/mL as described in Genentech 2017, incorporated herein in its entirety by reference.

Serum anti-VEGF protein levels were evaluated in NHPs and the level of anti-VEGF protein detected was minimal to undetectable in all NHPs. Anti-VEGF protein was also not detected in any non-cochlear tissue lysate of any NHP including liver, spleen, brainstem, left and right auditory cortex, and left and right mandibular lymph node.

Taken together with clinical data demonstrating efficacy of systemic anti-VEGF protein in controlling VS tumor growth and alleviating VS tumor symptoms, these experiments highlighted the feasibility of producing an inner-ear depot of anti-VEGF protein for the purposes of potentially shrinking tumor size, and/or controlling tumor growth and its sequelae through local exposure to anti-VEGF proteins, thereby limiting adverse effects related to repeated systemic anti-VEGF protein administration.

Example 12: Phenotypic Analysis of NHPs Delivered rAAVAnc80-Ranibizumab

As described above, an exposure and tolerability study in NHPs (*cynomolgus* macaques) using rAAVAnc80-ranibizumab particles (as described in Example 1) was performed, where particles were delivered bilaterally into the cochlea, to assess local and systemic effects of rAAVAnc80-antiVEGF particles in NHPs. Among other things, this study provided data to inform cochlear tolerability (serial ABR measurements up to 6 months post-administration; cytocochleograms at 2- and 6-months post-administration; and otic histopathology at 2- and 6-months post-administration).

Bilateral intracochlear administrations of rAAVAnc80-ranibizumab particles (as described in Example 1) with two exemplary doses (Dose 1 and Dose 2) or vehicle were performed using a transmastoid/facial recess surgical approach to access the round and oval windows as described above. Dose 1 was lower than Dose 2.

Following administration, there were no documented significant clinical observations related to intracochlear administration and/or the test rAAVAnc80-antiVEGF particle. Minor neurological signs were considered to be related to surgical maneuvers that potentially affect the vestibular system, and the NHPs recovered without medical intervention. Overall, clinical observations for all NHPs, with 2- and 6-month recoveries, were mainly expected temporary findings following inner ear surgery.

Example 13: Human Administration

This example discloses treatment of a subject having hearing loss and/or additional symptoms associated with VS arising either incidentally or as associated with a syndrome (e.g., Neurofibromatosis-2).

In humans, a less invasive approach for delivery of agents as described herein can be utilized when compared to that utilized in model organisms as described above, e.g., through the external auditory canal; as in some embodiments, it is more practical since relevant structures are relatively large in humans, even at birth. In brief, a clinical administration method described herein can comprise a transcanal exploratory tympanotomy and laser-assisted microstapedotomy (using a potassium titanyl phosphate [KTP] or CO2 otologic laser to place a small vent hole [approximately 0.25 mm] in the stapes footplate), followed by a round window injection to deliver about 0.09 mL (or about 90 µL, approximately 40 to 50% of the total inner ear volume) of solution containing rAAV-antiVEGF particles as described herein through the round window membrane within a three-minute period. As with nonclinical and cadaveric models, venting serves to prevent a potential deleterious rise in intralabyrinthine pressure. Additional information regarding the clinical administration procedure and a delivery device can be found throughout the present disclosure.

A patient can be diagnosed as having Unilateral or Bilateral VS (e.g., as determined by MRI). A clinical administration procedure can be a transcanal exploratory tympanotomy and laser-assisted microstapedotomy, followed by a round window injection to deliver an appropriate volume of solution containing rAAV-antiVEGF particles as described herein at an appropriate titer through the round window over a short period of time. Prior to surgery, an ear to be operated on can be identified and a mark placed above an ear with an indelible marker for confirmation in keeping with institutional requirements. Availability of an rAAV particle as described herein can be confirmed prior to anesthesia being administered. After induction with general anesthesia, subjects are positioned in the supine position with the head turned to the side and the operative ear facing up. An ear can be prepped with betadine and draped in the usual fashion. With use of an operating microscope or endoscope, a four-quadrant block of the external auditory canal meatus is performed with anesthesia (e.g., 1% lidocaine with epinephrine). A posterior tympanomeatal flap is developed and the middle ear entered to expose both the oval and the round window. This may require the removal of a small amount of bone at the junction of the bony canal and tympanic membrane using a micro-curette or drill. Using an appropriate laser (e.g., a KTP or CO2 otologic laser), a small hole (e.g., approximately 0.25 mm) is made in the stapes footplate. Such a hole can serve as a vent during injection to prevent a potential deleterious rise in intralabyrinthine pressure. An injection catheter can then be passed through the round window membrane to an appropriate depth (e.g., not to exceed 1 mm), as determined by a stopper near the tip of the injection device. Exposure of a round window may require removal of a pseudomembrane or ledge of overhanging bone. A delivery device can be held in place while an appropriate volume of solution is instilled. Upon removal of a catheter, a blood/tissue patch and/or drop of sealant (e.g., sodium hyaluronate, e.g., Healon®) is placed over the round window membrane and stapes footplate to create a functional seal of both fenestrae while biological healing occurs over the next 24 to 48 hours. A tympanomeatal flap is then returned to its anatomic position and held in place with antibiotic-soaked absorbable gelatin sponge.

At appropriate intervals, a subject may undergo follow-up imaging analysis (e.g., MRI analysis) to measure tumor volume and/or tumor growth rate. Subjects that are treated with exemplary methods and/or compositions as described herein may exhibit decreased tumor volume and/or a reduced tumor growth rate when compared to subjects that are not treated with exemplary methods and/or compositions as described herein.

A sterile, one-time use delivery device is utilized for delivery. Such a device is designed to allow for safe and effective delivery of product candidate rAAV-antiVEGF particles described herein, through the round window membrane into the cochlea. A delivery device is intended for use in delivery of gene therapy product candidates described herein, often in conjunction with an intracochlear route of administration. A one-time use device can be developed to deliver test articles to perilymph fluid of the inner ear through the round window membrane with a vent located in the stapes footplate; a form factor of a device optimizes the approach to the round window membrane through the external auditory canal. A custom device affords advantages over commercially available materials, both with respect to safety and the potential for efficacy of a therapeutic agent, as such a device is specifically designed for this intracochlear route of administration (FIG. 4). Certain design elements of a device include but are not limited to: maintenance of sterility of injected fluid; minimization of air bubbles introduced to an inner ear; ability to precisely deliver small volumes at a controlled flow rate (coupled with the use of a standard pump); allowance for visualization of round window membrane and delivery through an external auditory canal by a surgeon; minimization of damage to a round window membrane, or to cochlear structures beyond a round window membrane; and/or minimization of efflux back out through round window membrane.

EXEMPLARY EMBODIMENTS

Embodiment 1. A construct comprising a coding sequence operably linked to a promoter, wherein the coding sequence encodes a vascular endothelial growth factor (VEGF) binding agent or a portion thereof.

Embodiment 2. The construct of embodiment 1, wherein the promoter is an inducible promoter, a constitutive promoter, or a tissue-specific promoter.

Embodiment 3. The construct of embodiment 1 or 2, wherein the promoter is a CAG promoter, a CBA promoter, a CMV promoter, or a CB7 promoter.

Embodiment 4. The construct of any one of embodiments 1-3, wherein the promoter comprises a nucleic acid sequence according to SEQ ID NO: 64, SEQ ID NO: 49, and/or SEQ ID NO: 65.

Embodiment 5. The construct of any one of embodiments 1-4, wherein the coding sequence is or comprises a primate coding sequence.

Embodiment 6. The construct of any one of embodiments 1-5, wherein the VEGF binding agent or portion thereof is a primate VEGF binding agent.

Embodiment 7. The construct of any one of embodiments 1-4, wherein the coding sequence is or comprises a human coding sequence.

Embodiment 8. The construct of any one of embodiments 1-4 or 6, wherein the VEGF binding agent is or comprises a human VEGF binding agent.

Embodiment 9. The construct of any one of embodiments 1-4, wherein the coding sequence is or comprises an engineered coding sequence.

Embodiment 10. The construct of any one of embodiments 1-4 or 9, wherein the VEGF binding agent is or comprises a humanized VEGF binding agent.

Embodiment 11. The construct of any one of embodiments 1-10, wherein the VEGF binding agent is capable of binding to at least one VEGF protein or a fragment thereof.

Embodiment 12. The construct of embodiment 11, wherein the at least one VEGF protein is VEGF-A, VEGF-B, VEGF-C, VEGF-D, or a combination thereof.

Embodiment 13. The construct of embodiment 11, wherein the at least one VEGF protein is or comprises VEGF-A.

Embodiment 14. The construct of any one of embodiments 1-13, wherein the VEGF binding agent comprises at least one polypeptide.

Embodiment 15. The construct of any one of embodiments 1-14, wherein the VEGF binding agent is or comprises an antibody or a fragment thereof.

Embodiment 16. The construct of embodiment 15, wherein the antibody fragment is a Fab fragment, a Fab' fragment, a F(ab')2 fragment, a Fd fragment, a Fd' fragment, a complementarity determining region (CDR), a single chain Fv, or an Fc domain.

Embodiment 17. The construct of any one of embodiments 1-15, wherein the VEGF binding agent is or comprises an immunoglobulin heavy chain, an immunoglobulin light chain, or a combination thereof.

Embodiment 18. The construct of any one of embodiments 1-15 or 17, wherein the VEGF binding agent comprises:
  (i) a polypeptide that comprises an amino sequence according to SEQ ID NO: 16,
  (ii) a polypeptide that comprises an amino sequence according to SEQ ID NO: 20, or
  (iii) a combination thereof.

Embodiment 19. The construct of embodiment 18, wherein the VEGF binding agent is or comprises ranibizumab.

Embodiment 20. The construct of any one of embodiments 1-15 or 17-19, wherein the coding sequence comprises:
  (i) a nucleic acid sequence comprising SEQ ID NO: 13,
  (ii) a nucleic acid sequence comprising SEQ ID NO: 19, or
  (iii) a combination thereof.

Embodiment 21. The construct of any one of embodiments 1-20, wherein the coding sequence comprises one or more nucleic acid sequences that each encode a signal peptide.

Embodiment 22. The construct of embodiment 21, wherein at least one nucleic acid sequence encodes an interleukin 2 (IL2) signal peptide.

Embodiment 23. The construct of any one of embodiments 1-22, wherein the coding sequence comprises one or more sequences encoding a self-cleaving peptide.

Embodiment 24. The construct of embodiment 23, wherein the self-cleaving peptide is a *Thosea asigna* virus 2A (T2A) peptide.

Embodiment 25. The construct of any one of embodiments 1-15 or 17-24, wherein the coding sequence is or comprises a nucleic acid sequence according to SEQ ID NO: 21.

Embodiment 26. The construct of any one of embodiments 1-15 or 17, wherein the VEGF binding agent comprises:
(i) a polypeptide that comprises an amino sequence according to SEQ ID NO: 24,
(ii) a polypeptide that comprises an amino sequence according to SEQ ID NO: 25, or
(iii) a combination thereof.

Embodiment 27. The construct of embodiment 26, wherein the VEGF binding agent is or comprises bevacizumab.

Embodiment 28. The construct of any one of embodiments 1-15, 17, 26, or 27, wherein the coding sequence comprises:
(i) a nucleic acid sequence comprising SEQ ID NO: 108,
(ii) a nucleic acid sequence comprising SEQ ID NO: 109, or
(iii) a combination thereof.

Embodiment 29. The construct of any one of embodiments 26-28, wherein the coding sequence comprises one or more sequences that each encode a signal peptide.

Embodiment 30. The construct of embodiment 29, wherein at least one nucleic acid sequence encodes an IL2 signal peptide.

Embodiment 31. The construct of any one of embodiments 26-30, wherein the coding sequence comprises one or more sequences encoding a self-cleaving peptide.

Embodiment 32. The construct of embodiment 31, wherein the self-cleaving peptide is a T2A peptide.

Embodiment 33. The construct of any one of embodiments 1-15, 17, or 26-32 wherein the coding sequence is or comprises the nucleic acid sequence according to SEQ ID NO: 22.

Embodiment 34. The construct of any one of embodiments 1-15, wherein the VEGF binding agent comprises an Fc domain.

Embodiment 35. The construct of any one of embodiments 1-15, or 34, wherein the Fc domain comprises the amino acid sequence according to SEQ ID NO: 111.

Embodiment 36. The construct of any one of embodiments 1-15, 34, or 35, wherein the coding sequence comprises the nucleic acid sequence according to SEQ ID NO: 110.

Embodiment 37. The construct of any one of embodiments 1-15, or 34-36, wherein the VEGF binding agent comprises one or more extracellular domains of a VEGF receptor.

Embodiment 38. The construct of embodiment 37, wherein the one or more extracellular domains of the VEGF receptor comprises the amino sequence according to SEQ ID NO: 112.

Embodiment 39. The construct of any one of embodiments 1-15, or 34-38, wherein the VEGF binding agent comprises two extracellular domains of a VEGF receptor.

Embodiment 40. The construct of any one of embodiments 34-39, wherein the coding sequence comprises one or more nucleic acid sequences each encoding a signal peptide.

Embodiment 41. The construct of embodiment 40, wherein at least one nucleic acid sequence encodes an IL2 signal peptide.

Embodiment 42. The construct of any one of embodiments 1-41, further comprising two AAV inverted terminal repeats (ITRs), wherein the two AAV ITRs flank the coding sequence and promoter.

Embodiment 43. The construct of embodiment 42, wherein the two AAV ITRs are or are derived from AAV2 ITRs.

Embodiment 44. The construct of embodiment 42 or 43, wherein the two AAV ITRs comprise a 5' ITR comprising a nucleic acid sequence according to SEQ ID NO: 45 or 47, and a 3' ITR comprising a nucleic acid sequence according to SEQ ID NO: 46 or 48.

Embodiment 45. The construct of embodiment 1, wherein the construct comprises a nucleic acid sequence according to any of SEQ ID NOs: 90, 91, 92, 93, 94, 106, or 107.

Embodiment 46. The construct of embodiment 1, wherein the construct comprises a nucleic acid sequence according to any of SEQ ID NOs: 95, or 96.

Embodiment 47. An AAV particle comprising the construct of any one of embodiments 1-46.

Embodiment 48. The AAV particle of embodiment 47, further comprising an AAV capsid, wherein the AAV capsid is or is derived from an AAV2, AAV3, AAV4, AAV5, AAV6, AAV7, AAV8, AAV9, AAV10, AAV-rh8, AAV-rh10, AAV-rh39, AAV-rh43 or AAV Anc80 capsid.

Embodiment 49. The AAV particle of embodiment 48, wherein the AAV capsid is an AAV Anc80 capsid.

Embodiment 50. A composition comprising the construct of any one of embodiments 1-46.

Embodiment 51. A composition comprising the AAV particle of any one of embodiments 47-50.

Embodiment 52. The composition of embodiment 51, wherein the AAV particle comprises an AAV capsid, wherein the AAV capsid is or is derived from an AAV2, AAV3, AAV4, AAV5, AAV6, AAV7, AAV8, AAV9, AAV10, AAV-rh8, AAV-rh10, AAV-rh39, AAV-rh43 or AAV Anc80 capsid.

Embodiment 53. The composition of embodiment 52, wherein the AAV capsid of the AAV particle is an AAV Anc80 capsid.

Embodiment 54. The composition of embodiment 53, wherein the AAV Anc80 capsid is an AAV Anc80L65 capsid.

Embodiment 55. The composition of any one of embodiments 50-54, wherein the composition is a pharmaceutical composition.

Embodiment 56. The composition of embodiment 55, further comprising a pharmaceutically acceptable carrier.

Embodiment 57. The composition of embodiment 55 or 56, which is formulated at a dose of about $1 \times 10^{11}$ vg/mL to about $1 \times 10^{15}$ vg/mL.

Embodiment 58. The composition of any one of embodiments 55-57, which is formulated at a dose of about $1 \times 10^{10}$ to about $1 \times 10^{13}$ vg/cochlea.

Embodiment 59. The composition of any one of embodiments 55-58, which is administered at a volume of about 0.01 mL to 0.1 mL.

Embodiment 60. A cell comprising the composition of any one of embodiments 50-59.

Embodiment 61. The cell of embodiment 60, wherein the cell is in vivo, ex vivo, or in vitro.

Embodiment 62. The cell of embodiment 60 or 61, wherein the cell is a mammalian cell.

Embodiment 63. The cell of embodiment 62, wherein the mammalian cell is a human cell.

Embodiment 64. The cell of embodiment 60, wherein the cell is immortalized to generate a stable cell line.

Embodiment 65. The cell of embodiment 63, wherein the human cell is in the ear of a subject.

Embodiment 66. The cell of embodiment 63, wherein the human cell is an inner ear cell.

Embodiment 67. The cell of embodiment 66, wherein the inner ear cell is an inner hair cell, an outer hair cell, or both.

Embodiment 68. A system comprising the composition of any one of embodiments 50-59.

Embodiment 69. A method comprising contacting an inner ear cell with the construct of any one of embodiments 1-46.

Embodiment 70. A method comprising contacting an inner ear cell with the AAV particle of any one of embodiments 47-49.

Embodiment 71. A method comprising contacting an inner ear cell with the composition of any one of embodiments 50-59.

Embodiment 72. The method of any one of embodiments 69-71, where the inner ear cell is an outer hair cell.

Embodiment 73. The method of any one of embodiments 69-71, where the inner ear cell is an inner hair cell.

Embodiment 74. The method of any one of embodiments 69-73, wherein the inner ear cell is in the ear of a subject.

Embodiment 75. The method of any one of embodiments 69-73, wherein the inner ear cell is in vitro or ex vivo.

Embodiment 76. A method comprising, contacting a cell with:
(i) the construct of any one of embodiments 1-46; and
(ii) one or more constructs comprising an AAV Rep gene, AAV Cap gene, AAV VA gene, AAV E2a gene, and AAV E4 gene.

Embodiment 77. The method of embodiment 76, where the cell is an inner ear cell.

Embodiment 78. The method of embodiment 77, wherein the inner ear cell is an outer hair cell.

Embodiment 79. The method of embodiment 77, wherein the inner ear cell is an inner hair cell.

Embodiment 80. The method of any one of embodiments 77-79, wherein the inner ear cell is in vitro or ex vivo.

Embodiment 81. A method comprising introducing the construct of any one of embodiments 1-46 into the inner ear of a subject.

Embodiment 82. A method comprising introducing the AAV particle of any one of embodiments 47-49 into the inner ear of a subject.

Embodiment 83. A method comprising introducing the composition of any one of embodiments 50-59 into the inner ear of a subject.

Embodiment 84. The method of any one of embodiments 81-83, wherein the construct, AAV particle, or composition is introduced into the cochlea of the subject.

Embodiment 85. The method of any one of embodiments 81-84, wherein the construct, AAV particle, or composition is introduced via a round window membrane injection.

Embodiment 86. The method of any one of embodiments 69-75 and 81-85, further comprising measuring a hearing level of the subject.

Embodiment 87. The method of embodiment 86, a hearing level is measured by performing an auditory brainstem response (ABR) test.

Embodiment 88. The method of embodiment 86 or 87, further comprising comparing the hearing level of the subject to a reference hearing level.

Embodiment 89. The method of embodiment 88, wherein the reference hearing level is a published or historical reference hearing level.

Embodiment 90. The method of embodiment 89, wherein the hearing level of the subject is measured after the construct of any one of embodiments 1-46, the AAV particle of any one of embodiments 47-49, or the composition of any one of embodiments 50-59 is introduced, and the reference hearing level is a hearing level of the subject that was measured before the construct of any one of embodiments 1-46, the AAV particle of any one of embodiments 47-49, or the composition of any one of embodiments 50-59 was introduced.

Embodiment 91. The method of any one of embodiments 69-75 and 81-90, further comprising measuring a level of a vascular endothelial growth factor (VEGF) binding agent or a portion thereof in a subject.

Embodiment 92. The method of embodiment 91, wherein the level of the vascular endothelial growth factor (VEGF) binding agent or portion thereof is measured in the inner ear of the subject.

Embodiment 93. The method of embodiment 91 or 92, wherein the level of the vascular endothelial growth factor (VEGF) binding agent or portion thereof is measured in the cochlea of the subject.

Embodiment 94. The method of any one of embodiments 69-75 and 81-93, further comprising comparing the level of the vascular endothelial growth factor (VEGF) binding agent or a portion thereof in the subject to a reference level of vascular endothelial growth factor (VEGF) binding agent or a portion thereof.

Embodiment 95. The method of embodiment 94, wherein the reference level of vascular endothelial growth factor (VEGF) binding agent or a portion thereof is a published or historical reference level of vascular endothelial growth factor (VEGF) binding agent or a portion thereof.

Embodiment 96. The method of any one of embodiments 91-95, wherein the level of the vascular endothelial growth factor (VEGF) binding agent or a portion thereof in the subject is measured after the construct of any one of embodiments 1-46, the AAV particle of any one of embodiments 47-49, or the composition of any one of embodiments 50-59 is introduced, and the reference level of vascular endothelial growth factor (VEGF) binding agent or a portion thereof is the level the vascular endothelial growth factor (VEGF) binding agent or a portion thereof in the subject that was measured before the construct of any one of embodiments 1-46, the AAV particle of any one of embodiments 47-49, or the composition of any one of embodiments 50-59 was introduced.

Embodiment 97. The method of any one of embodiments 69-75 and 81-96, further comprising measuring a volume of a tumor in a subject.

Embodiment 98. The method of embodiments 97, further comprising comparing a volume of a tumor in the subject to a reference tumor volume.

Embodiment 99. The method of embodiment 98, wherein the reference tumor volume is a published or historical reference tumor volume.

Embodiment 100. The method of any one of embodiments 97-99, wherein the volume of a tumor in the subject is measured after the construct of any one of embodiments 1-46, the AAV particle of any one of embodiments 47-49, or the composition of any one of embodiments 50-59 is introduced, and the reference tumor volume is the volume of the tumor in the subject that was measured before the construct of any one of embodiments 1-46, the AAV particle of any one of embodiments 47-49, or the composition of any one of embodiments 50-59 was introduced.

Embodiment 101. A method of treating hearing loss or treating an inner ear disorder, comprising administering the construct of any one of embodiments 1-46, the AAV particle of any one of embodiments 47-49, or the composition of any one of embodiments 50-59 to a subject in need thereof.

Embodiment 102. The method of any one of embodiments 74 and 81-101, wherein the subject is suffering from or is at risk of an otological disease characterized by neovascularization.

Embodiment 103. The method of embodiment 102, wherein the otological disease is or comprises an acoustic neuroma.

Embodiment 104. The method of embodiment 102, wherein the otological disease is or comprises a vestibular schwannoma.

Embodiment 105. The method of embodiment 104, wherein the subject having vestibular schwannoma has neurofibromatosis type 2 (NF2), Embodiment 106. The method of any one of embodiments 102-105, wherein one or more symptoms associated with the otological disease is alleviated or ameliorated.

Embodiment 107. The method of embodiment 106, wherein the one or more symptoms comprises hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, death, or a combination thereof.

Embodiment 108. The method of any one of embodiments 69-75, 81-102, and 104-107, wherein the method is a method of treating vestibular schwannoma.

Embodiment 109. The method of any one of embodiments 69-75 and 81-107, wherein the method is a method of modulating the level of VEGF.

Embodiment 110. The method of any one of embodiments 69-75 and 81-107, wherein the method is a method of modulating the level of active VEGF.

Embodiment 111. The method of any one of embodiments 69-75 and 81-107, wherein the method is a method of decreasing the activity of VEGF.

Embodiment 112. A construct of any one of embodiments 1-46 for use in the treatment of an otological disease characterized by neovascularization and/or one or more symptoms associated with the otological disease.

Embodiment 113. An AAV particle of any one of embodiments 47-49 for use in the treatment of an otological disease characterized by neovascularization and/or one or more symptoms associated with the otological disease.

Embodiment 114. A composition of any one of embodiments 50-59 for use in the treatment of an otological disease characterized by neovascularization and/or one or more symptoms associated with the otological disease.

Embodiment 115. The construct of embodiment 112, the AAV particle of embodiment 113, or the composition of embodiment 114, wherein the one or more symptoms associated with the otological disease comprise hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, death, or a combination thereof.

Embodiment 116. Use of a construct of any one of embodiments 1-46 for the manufacture of a medicament to treat an otological disease characterized by neovascularization and/or one or more symptoms associated with the otological disease.

Embodiment 117. Use of a particle of any one of embodiments 47-49 for the manufacture of a medicament to treat an otological disease characterized by neovascularization and/or one or more symptoms associated with the otological disease.

Embodiment 118. Use of a composition of any one of embodiments 50-59 for the manufacture of a medicament to treat an otological disease characterized by neovascularization and/or one or more symptoms associated with the otological disease.

Embodiment 119. The use of any one of embodiments 116-118, wherein the one or more symptoms associated with the otological disease comprise hearing loss, degeneration of hair cells, alteration of biochemical milieu of inner ear fluids, elevated intralabyrinthine protein, endolymphatic hydrops, cochlear aperture obstruction, intralabyrinthine hemorrhage, disruption of cochlear vascular supply, tinnitus, dizziness, intractable headache, facial neuropathy, trigeminal neuropathy, facial paralysis, facial paresthesia, hydrocephalus, cerebellar herniation, death, or a combination thereof.

Embodiment 120. A population of cells comprising one or more cells according to any one of embodiments 60-67, wherein the population is or comprises a stable cell line.

Embodiment 121. A kit comprising a composition of any one of embodiments 50-59.

Embodiment 122. The kit of embodiment 121, wherein the composition is pre-loaded in a device.

Embodiment 123. The kit of embodiment 122, wherein the device is a microcatheter.

Embodiment 124. The kit of embodiment 123, wherein the microcatheter is shaped such that it can enter the middle ear cavity via the external auditory canal and contact the end of the microcatheter with the RWM.

Embodiment 125. The kit of embodiment 123 or 124, wherein a distal end of the microcatheter is comprised of at least one microneedle with a diameter of between 10 and 1,000 microns.

Embodiment 126. The kit of any one of embodiments 121-125, further comprising a device.

Embodiment 127. The kit of embodiment 126, wherein the device is a device described in any one of FIGS. 29-32.

Embodiment 128. The kit of any one of embodiments 122-127, wherein the device comprises a needle comprising a bent portion and an angled tip.

The invention claimed is:

1. An adeno-associated virus (AAV) particle comprising: (i) a nucleic acid construct that comprises the nucleotide sequence set forth in SEQ ID NO: 91, and (ii) an AAV Anc80 capsid.

2. The AAV particle of claim 1, wherein the AAV Anc80 capsid is an AAV Anc80L65 capsid.

3. The AAV particle of claim 1, wherein the AAV Anc80 capsid comprises the amino acid sequence set forth in SEQ ID NO: 113.

4. A kit comprising the AAV particle of claim 1.

5. A composition comprising the AAV particle of claim 1.

6. A pharmaceutical composition comprising a composition comprising the AAV particle of claim 1 and a pharmaceutically acceptable carrier.

7. The AAV particle of claim 1, wherein the AAV Anc80 capsid comprises the amino acid sequence set forth in SEQ ID NO: 114.

8. An adeno-associated virus (AAV) particle comprising: (i) a nucleic acid construct that comprises the nucleotide sequence set forth in SEQ ID NO: 92, and (ii) an AAV Anc80 capsid.

9. The AAV particle of claim 8, wherein the AAV Anc80 capsid is an AAV Anc80L65 capsid.

10. The AAV particle of claim 8, wherein the AAV Anc80 capsid comprises the amino acid sequence set forth in SEQ ID NO: 113.

11. A kit comprising the AAV particle of claim 8.

12. A composition comprising the AAV particle of claim 8.

13. A pharmaceutical composition comprising a composition comprising the AAV particle of claim 8 and a pharmaceutically acceptable carrier.

14. The AAV particle of claim 8, wherein the AAV Anc80 capsid comprises the amino acid sequence set forth in SEQ ID NO: 114.

* * * * *

SEQUENCE LISTING

```
Sequence total quantity: 117
SEQ ID NO: 1                moltype = AA  length = 412
FEATURE                     Location/Qualifiers
source                      1..412
                            mol_type = protein
                            organism = Homo sapiens
SEQUENCE: 1
MTDRQTDTAP SPSYHLLPGR RRTVDAAASR GQGPEPAPGG GVEGVGARGV ALKLFVQLLG   60
CSRFGGAVVR AGEAEPSGAA RSASSGREEP QPEEGEEEEE KEEERGPQWR LGARKPGSWT  120
GEAAVCADSA PAARAPQALA RASGRGGRVA RRGAEESGPP HSPSRRGSAS RAGPGRASET  180
MNFLLSWVHW SLALLLYLHH AKWSQAAPMA EGGGQNHHEV VKFMDVYQRS YCHPIETLVD  240
IFQEYPDEIE YIFKPSCVPL MRCGGCCNDE GLECVPTEES NITMQIMRIK PHQGQHIGEM  300
SFLQHNKCEC RPKKDRARQE KKSVRGKGKG QKRKRKKSRY KSWSVYVGAR CCLMPWSLPG  360
PHPCGPCSER RKHLFVQDPQ TCKCSCKNTD SRCKARQLEL NERTCRCDKP RR         412

SEQ ID NO: 2                moltype = AA  length = 395
FEATURE                     Location/Qualifiers
source                      1..395
                            mol_type = protein
                            organism = Homo sapiens
SEQUENCE: 2
MTDRQTDTAP SPSYHLLPGR RRTVDAAASR GQGPEPAPGG GVEGVGARGV ALKLFVQLLG   60
CSRFGGAVVR AGEAEPSGAA RSASSGREEP QPEEGEEEEE KEEERGPQWR LGARKPGSWT  120
GEAAVCADSA PAARAPQALA RASGRGGRVA RRGAEESGPP HSPSRRGSAS RAGPGRASET  180
MNFLLSWVHW SLALLLYLHH AKWSQAAPMA EGGGQNHHEV VKFMDVYQRS YCHPIETLVD  240
IFQEYPDEIE YIFKPSCVPL MRCGGCCNDE GLECVPTEES NITMQIMRIK PHQGQHIGEM  300
SFLQHNKCEC RPKKDRARQE KKSVRGKGKG QKRKRKKSRY KSWSVPCGPC SERRKHLFVQ  360
DPQTCKCSCK NTDSRCKARQ LELNERTCRC DKPRR                            395

SEQ ID NO: 3                moltype = AA  length = 137
FEATURE                     Location/Qualifiers
source                      1..137
                            mol_type = protein
                            organism = Homo sapiens
SEQUENCE: 3
MNFLLSWVHW SLALLLYLHH AKWSQAAPMA EGGGQNHHEV VKFMDVYQRS YCHPIETLVD   60
IFQEYPDEIE YIFKPSCVPL MRCGGCCNDE GLECVPTEES NITMQIMRIK PHQGQHIGEM  120
SFLQHNKCEC RCDKPRR                                                137

SEQ ID NO: 4                moltype = AA  length = 147
FEATURE                     Location/Qualifiers
source                      1..147
                            mol_type = protein
                            organism = Homo sapiens
SEQUENCE: 4
MNFLLSWVHW SLALLLYLHH AKWSQAAPMA EGGGQNHHEV VKFMDVYQRS YCHPIETLVD   60
IFQEYPDEIE YIFKPSCVPL MRCGGCCNDE GLECVPTEES NITMQIMRIK PHQGQHIGEM  120
SFLQHNKCEC RPKKDRARQE KCDKPRR                                     147

SEQ ID NO: 5                moltype = AA  length = 171
FEATURE                     Location/Qualifiers
source                      1..171
                            mol_type = protein
                            organism = Homo sapiens
SEQUENCE: 5
MNFLLSWVHW SLALLLYLHH AKWSQAAPMA EGGGQNHHEV VKFMDVYQRS YCHPIETLVD   60
IFQEYPDEIE YIFKPSCVPL MRCGGCCNDE GLECVPTEES NITMQIMRIK PHQGQHIGEM  120
SFLQHNKCEC RPKKDRARQE KKSVRGKGKG QKRKRKKSRY KSWSVCDKPR R           171

SEQ ID NO: 6                moltype = AA  length = 191
FEATURE                     Location/Qualifiers
source                      1..191
                            mol_type = protein
                            organism = Homo sapiens
SEQUENCE: 6
MNFLLSWVHW SLALLLYLHH AKWSQAAPMA EGGGQNHHEV VKFMDVYQRS YCHPIETLVD   60
IFQEYPDEIE YIFKPSCVPL MRCGGCCNDE GLECVPTEES NITMQIMRIK PHQGQHIGEM  120
SFLQHNKCEC RPKKDRARQE NPCGPCSERR KHLFVQDPQT CKCSCKNTDS RCKARQLELN  180
ERTCRCDKPR R                                                      191

SEQ ID NO: 7                moltype = AA  length = 215
FEATURE                     Location/Qualifiers
source                      1..215
                            mol_type = protein
                            organism = Homo sapiens
SEQUENCE: 7
MNFLLSWVHW SLALLLYLHH AKWSQAAPMA EGGGQNHHEV VKFMDVYQRS YCHPIETLVD   60
IFQEYPDEIE YIFKPSCVPL MRCGGCCNDE GLECVPTEES NITMQIMRIK PHQGQHIGEM  120
```

```
SFLQHNKCEC RPKKDRARQE KKSVRGKGKG QKRKRKKSRY KSWSVPCGPC SERRKHLFVQ    180
DPQTCKCSCK NTDSRCKARQ LELNERTCRC DKPRR                              215

SEQ ID NO: 8             moltype = AA  length = 232
FEATURE                  Location/Qualifiers
source                   1..232
                         mol_type = protein
                         organism = Homo sapiens
SEQUENCE: 8
MNFLLSWVHW SLALLLYLHH AKWSQAAPMA EGGGQNHHEV VKFMDVYQRS YCHPIETLVD    60
IFQEYPDEIE YIFKPSCVPL MRCGGCCNDE GLECVPTEES NITMQIMRIK PHQGQHIGEM   120
SFLQHNKCEC RPKKDRARQE KKSVRGKGKG QKRKRKKSRY KSWSVYVGAR CCLMPWSLPG   180
PHPCGPCSER RKHLFVQDPQ TCKCSCKNTD SRCKARQLEL NERTCRCDKP RR           232

SEQ ID NO: 9             moltype = AA  length = 188
FEATURE                  Location/Qualifiers
source                   1..188
                         mol_type = protein
                         organism = Homo sapiens
SEQUENCE: 9
MSPLLRRLLL AALLQLAPAQ APVSQPDAPG HQRKVVSWID VYTRATCQPR EVVVPLTVEL    60
MGTVAKQLVP SCVTVQRCGG CCPDDGLECV PTGQHQVRMQ ILMIRYPSSQ LGEMSLEEHS   120
QCECRPKKKD SAVKPDSPRP LCPRCTQHHQ RPDPRTCRCR CRRRSFLRCQ GRGLELNPDT   180
CRCRKLRR                                                            188

SEQ ID NO: 10            moltype = AA  length = 207
FEATURE                  Location/Qualifiers
source                   1..207
                         mol_type = protein
                         organism = Homo sapiens
SEQUENCE: 10
MSPLLRRLLL AALLQLAPAQ APVSQPDAPG HQRKVVSWID VYTRATCQPR EVVVPLTVEL    60
MGTVAKQLVP SCVTVQRCGG CCPDDGLECV PTGQHQVRMQ ILMIRYPSSQ LGEMSLEEHS   120
QCECRPKKKD SAVKPDRAAT PHHRPQPRSV PGWDSAPGAP SPADITHPTP APGPSAHAAP   180
STTSALTPGP AAAAADAAAS SVAKGGA                                       207

SEQ ID NO: 11            moltype = AA  length = 419
FEATURE                  Location/Qualifiers
source                   1..419
                         mol_type = protein
                         organism = Homo sapiens
SEQUENCE: 11
MHLLGFFSVA CSLLAAALLP GPREAPAAAA AFESGLDLSD AEPDAGEATA YASKDLEEQL    60
RSVSSVDELM TVLYPEYWKM YKCQLRKGGW QHNREQANLN SRTEETIKFA AAHYNTEILK   120
SIDNEWRKTQ CMPREVCIDV GKEFGVATNT FFKPPCVSVY RCGGCCNSEG LQCMNTSTSY   180
LSKTLFEITV PLSQGPKPVT ISFANHTSCR CMSKLDVYRQ VHSIIRRSLP ATLPQCAAN    240
KTCPTNYMWN NHICRCLAQE DFMFSSDAGD DSTDGFHDIC GPNKELDEET CQCVCRAGLR   300
PASCGPHKEL DRNSCQCVCK NKLFPSQCGA NREFDENTCQ CVCKRTCPRN QPLNPGKCAC   360
ECTESPQKCL LKGKKFHHQT CSCYRRPCTN RQKACEPGFS YSEEVCRCVP SYWKRPQMS    419

SEQ ID NO: 12            moltype = AA  length = 354
FEATURE                  Location/Qualifiers
source                   1..354
                         mol_type = protein
                         organism = Homo sapiens
SEQUENCE: 12
MYREWVVVNV FMMLYVQLVQ GSSNEHGPVK RSSQSTLERS EQQIRAASSL EELLRITHSE    60
DWKLWRCRLR LKSFTMDSR SASHRSTRFA ATFYDIETLK VIDEEWQRTQ CSPRETCVEV   120
ASELGKSTNT FFKPPCVNVF RCGGCCNEES LICMNTSTSY ISKQLFEISV PLTSVPELVP   180
VKVANHTGCK CLPTAPRHPY SIIRRSIQIP EEDRCSHSKK LCPIDMLWDS NKCKCVLQEE   240
NPLAGTEDHS HLQEPALCGP HMMFDEDRCE CVCKTPCPKD LIQHPKNCSC FECKESLETC   300
CQKHKLFHPD TCSCEDRCPF HTRPCASGKT ACAKHCRFPK EKRAAQGPHS RKNP          354

SEQ ID NO: 13            moltype = DNA  length = 699
FEATURE                  Location/Qualifiers
misc_feature             1..699
                         note = source = /note="Description of Artificial Sequence:
                           Synthetic polynucleotide"
source                   1..699
                         mol_type = other DNA
                         organism = synthetic construct
SEQUENCE: 13
gaggtgcagc tggtggaatc tggcggcgga cttgttcaac tggcggctc tctgagactg      60
agctgtgccg cttctggcta cgacttcacc cactacgca tgaactgggt ccgacaggcc    120
cctggcaaag cccttgaatg ggtcggatgg atcaacacct acaccggcga gccaacatac   180
gccgccgact tcaagcggag attcaccttc agcctggaca ccagcaagag caccgcctac   240
ctgcagatga acagcctgag agccgaggac accgccgtgt actactgcgc caagtatccc   300
tactactacg gcaccagcca ctggtacttt gacgtgtggg gacagggcac actggtcaca   360
gtgtctagcg ccctctacaa agggcccagc gttttccac tggctcctag cagcaagtct   420
```

```
accagcggag gaacagccgc tctgggctgt ctggtcaagg actactttcc cgagcctgtg   480
accgtgtcct ggaattctgg cgctctgaca agcggcgtgc acacctttcc agctgtgctg   540
caaagcagcg gcctgtactc tctgagcagc gtcgtgacag tgccaagcag ctctctgggc   600
acccagacct acatctgcaa tgtgaaccac aagcctagca acaccaaggt ggacaagaag   660
gtggaaccca agagctgcga caagacccac accggcaag                         699

SEQ ID NO: 14           moltype = DNA   length = 693
FEATURE                 Location/Qualifiers
misc_feature            1..693
                        note = source = /note="Description of Artificial Sequence:
                         Synthetic polynucleotide"
source                  1..693
                        mol_type = other DNA
                        organism = synthetic construct
SEQUENCE: 14
gaggtgcagc tggtggaatc tggcggcgga cttgttcaac ctggcggctc tctgagactg   60
agctgtgccg cttctggcta cgacttcacc cactacggca tgaactgggt ccgacaggcc   120
cctggcaaag gccttgaatg ggtcggatgg atcaacacct acaccggcga gccaacatac   180
gccgccgact tcaagcggag attcaccttc agcctggaca ccagcaagag caccgcctac   240
ctgcagatga acagcctgag agccgaggac accgccgtgt actactgcgc caagtatccc   300
tactactacg gcaccagcca ctggtacttt gacgtgtggg gacagggcac actggtcaca   360
gtgtctagcg cctctacaaa gggccccagc gttttcccac tggctcctag cagcaagtct   420
accagcggag gaacagccgc tctgggctgt ctggtcaagg actactttcc cgagcctgtg   480
accgtgtcct ggaattctgg cgctctgaca agcggcgtgc acacctttcc agctgtgctg   540
caaagcagcg gcctgtactc tctgagcagc gtcgtgacag tgccaagcag ctctctgggc   600
acccagacct acatctgcaa tgtgaaccac aagcctagca acaccaaggt ggacaagaag   660
gtggaaccca agagctgcga caagacccac aag                               693

SEQ ID NO: 15           moltype = DNA   length = 675
FEATURE                 Location/Qualifiers
misc_feature            1..675
                        note = source = /note="Description of Artificial Sequence:
                         Synthetic polynucleotide"
source                  1..675
                        mol_type = other DNA
                        organism = synthetic construct
SEQUENCE: 15
gaggtgcagc tggtggaatc tggcggcgga cttgttcaac ctggcggctc tctgagactg   60
agctgtgccg cttctggcta cgacttcacc cactacggca tgaactgggt ccgacaggcc   120
cctggcaaag gccttgaatg ggtcggatgg atcaacacct acaccggcga gccaacatac   180
gccgccgact tcaagcggag attcaccttc agcctggaca ccagcaagag caccgcctac   240
ctgcagatga acagcctgag agccgaggac accgccgtgt actactgcgc caagtatccc   300
tactactacg gcaccagcca ctggtacttt gacgtgtggg gacagggcac actggtcaca   360
gtgtctagcg cctctacaaa gggccccagc gttttcccac tggctcctag cagcaagtct   420
accagcggag gaacagccgc tctgggctgt ctggtcaagg actactttcc cgagcctgtg   480
accgtgtcct ggaattctgg cgctctgaca agcggcgtgc acacctttcc agctgtgctg   540
caaagcagcg gcctgtactc tctgagcagc gtcgtgacag tgccaagcag ctctctgggc   600
acccagacct acatctgcaa tgtgaaccac aagcctagca acaccaaggt ggacaagaag   660
gtggaaccca agagc                                                    675

SEQ ID NO: 16           moltype = AA   length = 233
FEATURE                 Location/Qualifiers
REGION                  1..233
                        note = source = /note="Description of Artificial Sequence:
                         Synthetic polypeptide"
source                  1..233
                        mol_type = protein
                        organism = synthetic construct
SEQUENCE: 16
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TGK          233

SEQ ID NO: 17           moltype = AA   length = 231
FEATURE                 Location/Qualifiers
REGION                  1..231
                        note = source = /note="Description of Artificial Sequence:
                         Synthetic polypeptide"
source                  1..231
                        mol_type = protein
                        organism = synthetic construct
SEQUENCE: 17
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH L            231

SEQ ID NO: 18           moltype = AA   length = 225
```

```
FEATURE                  Location/Qualifiers
REGION                   1..225
                         note = source = /note="Description of Artificial Sequence:
                           Synthetic polypeptide"
source                   1..225
                         mol_type = protein
                         organism = synthetic construct
SEQUENCE: 18
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKS                  225

SEQ ID NO: 19            moltype = DNA   length = 642
FEATURE                  Location/Qualifiers
misc_feature             1..642
                         note = source = /note="Description of Artificial Sequence:
                           Synthetic polynucleotide"
source                   1..642
                         mol_type = other DNA
                         organism = synthetic construct
SEQUENCE: 19
gacatccagc tgacacagag ccccagcagc ctgtctgcct ctgtgggaga cagagtgacc   60
atcacctgta gcgccagcca ggacatctcc aactacctga actggtatca gcaaaagccc  120
ggcaaggccc ctaaggtgct gatctacttc acaagcagcc tgcactccgg cgtgcccagc  180
agatttctg gctctggcag cggcaccgac ttcaccctga ccatatctag cctgcagcct   240
gaggacttcg ccacctacta ctgccagcag tacagcaccg tgccttggac atttggccag  300
ggcacaaagg tggaaatcaa gcggactgtg gccgctccta gcgtgttcat cttccacct   360
agcgacgagc agctgaagtc tggcacagcc tctgtcgtgt gcctgctgaa caacttctac  420
cccagagaag ccaaggtgca gtggaaagtg gacaatgcc tgcagagcgg caacagccaa   480
gagagcgtga cagagcagga ctccaaggat agcacctata gcctgagcag caccctgaca  540
ctgagcaagg ccgactacga aagcacacaa gtgtacgcct gcgaagtgac ccaccagggc  600
cttctctagcc ctgtgaccaa gagcttcaac cggggcgaat gt                    642

SEQ ID NO: 20            moltype = AA   length = 214
FEATURE                  Location/Qualifiers
REGION                   1..214
                         note = source = /note="Description of Artificial Sequence:
                           Synthetic polypeptide"
source                   1..214
                         mol_type = protein
                         organism = synthetic construct
SEQUENCE: 20
DIQLTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 21            moltype = AA   length = 512
FEATURE                  Location/Qualifiers
REGION                   1..512
                         note = source = /note="Description of Artificial Sequence:
                           Synthetic polypeptide"
source                   1..512
                         mol_type = protein
                         organism = synthetic construct
SEQUENCE: 21
MYRMQLLSCI ALSLALVTNS EVQLVESGGG LVQPGGSLRL SCAASGYDFT HYGMNWVRQA   60
PGKGLEWVGW INTYTGEPTY AADFKRRFTF SLDTSKSTAY LQMNSLRAED TAVYYCAKYP  120
YYYGTSHWYF DVWGQGTLVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TGKRKRRGSG EGRGSLLTCG DVEENPGPMY RMQLLSCIAL SLALVTNSDI  300
QLTQSPSSLS ASVGDRVTIT CSASQDISNY LNWYQQKPGK APKVLIYFTS SLHSGVPSRF  360
SGSGSGTDFT LTISSLQPED FATYYCQQYS TVPWTFGQGT KVEIKRTVAA PSVFIFPPSD  420
EQLKSGTASV VCLLNNFYPR EAKVQWKVDN ALQSGNSQES VTEQDSKDST YSLSSTLTLS  480
KADYEKHKVY ACEVTHQGLS SPVTKSFNRG EC                                512

SEQ ID NO: 22            moltype = DNA   length = 2196
FEATURE                  Location/Qualifiers
misc_feature             1..2196
                         note = source = /note="Description of Artificial Sequence:
                           Synthetic polynucleotide"
source                   1..2196
                         mol_type = other DNA
                         organism = synthetic construct
SEQUENCE: 22
atgtaccgga tgcagctgct gagctgtatc gccctgtctc tggccctggt caccaattct   60
gaggtgcagc tggtggaatc tggcggcgga cttgttcaac tggcggctc tctgagactg  120
agctgtgcc cttctggcta caccttcacc aactacggca tgaactgggt ccgacaggcc  180
```

```
cctggcaaag gccttgaatg ggtcggatgg atcaacacct acaccggcga gccaacatac    240
gccgccgact tcaagcggag attcaccttc agcctggaca ccagcaagag caccgcctac    300
ctgcagatga acagcctgag agccgaggac accgccgtgt actactgcgc caagtatccc    360
cactactacg gcagcagcca ctggtacttt gacgtgtggg gacagggcac actggtcaca    420
gtgtctagcg cctctacaaa gggccccagc gttttcccac tggctcctag cagcaagtct    480
accagcggag gaacagccgc tctgggctgt ctggtcaagg actactttcc cgagcctgtg    540
accgtgtcct ggaattctgg cgctctgaca agcggcgtgc acacctttcc agctgtgctg    600
caaagcagcg gcctgtactc tctgagcagc gtcgtgacag tgccaagcag ctctctgggc    660
acccagacct acatctgcaa tgtgaaccac aagcctagca acaccaaggt ggacaagaag    720
gtggaaccca gagctgcgca caagaccacc acctgtcctc catgtcctgc tccagaactg    780
ctcggcggac cttccgtgtt cctgtttcct ccaaagccta aggacaccct gatgatcagc    840
agaaccctg aagtgacctg cgtggtggtg gatgtgtccc acgaggatcc cgaagtgaag    900
ttcaattggt acgtggacgg cgtggaagtg cacaacgcca agacaaagcc tagagaggaa    960
cagtacaaca gcacctacag agtggtgtcc gtgctgaccg tgctcacca ggattggctg   1020
aacggcaaag agtacaagtg caaggtgtcc aacaaggccc tgcctgctcc tatcgagaaa   1080
accatcagca aggccaaggg ccagcctagg gaacccagg tttacacact gcctccaagc   1140
cgggaagaga tgaccaagaa ccaggtgtcc ctgacctgcc tcgtgaaggg cttctaccct   1200
tccgatatcg ccgtggaatg ggagagcaat ggccagccag agaacaacta caagacaacc   1260
cctcctgtgc tggacagcga cggctcattc ttcctgtaca gcaagctgac agtggacaag   1320
tccagatggc agcagggcaa cgtgttcagc tgcagcgtga tgcacgaggc cctgcacaac   1380
cactacaccc agaagtctct gagcctgtct cctggcaagc ggaagagaag aggctctggc   1440
gaaggcagag gcagcctgct tacatgtggc gacgtggaag agaaccccgg acctatgtat   1500
agaatgcagc tcctgtcctg cattgccctg agcctggctc tcgtgaccaa cagcgacatc   1560
cagatgacac agagccccag cagcctgtct gcctctgtgg gagacagagt gaccatcacc   1620
tgtagcgcca gccaggacat ctccaactac ctgaactggt atcagcaaaa gcccggcaag   1680
gcccctaagg tgctgatcta cttcacaagc agcctgcacc cggcgtgcc cagcagattt   1740
tctggctctg gcagcggcac cgacttcacc ctgaccatat ctagcctgca gcctgaggac   1800
ttcgccacct actactgcca gcagtacagc accgtgcctt ggacatttgg ccagggcaca   1860
aaggtggaaa tcaagcggac tgtggccgct cctagcgtgt tcatctttcc acctagcgac   1920
gagcagctga agtctggcac agcctctgtc gtgtgcctgc tgaacaactt ctaccccaga   1980
gaagccaagg tgcagtggaa agtggacaat gccctgcaga gcggcaacag ccaagagagc   2040
gtgacagagc aggactccaa ggatagcacc tatagcctga gcagcaccct gacactgagc   2100
aaggccgact acgagaagca caaagtgtac gcctgcgaag tgacccacca gggcctttct   2160
agccctgtga ccaagagctt caaccggggc gaatgt                              2196

SEQ ID NO: 23        moltype = AA  length = 732
FEATURE              Location/Qualifiers
REGION               1..732
                     note = source = /note="Description of Artificial Sequence:
                     Synthetic polypeptide"
source               1..732
                     mol_type = protein
                     organism = synthetic construct
SEQUENCE: 23
MYRMQLLSCI ALSLALVTNS EVQLVESGGG LVQPGGSLRL SCAASGYTFT NYGMNWVRQA    60
PGKGLEWVGW INTYTGEPTY AADFKRRFTF SLDTSKSTAY LQMNSLRAED TAVYYCAKYP   120
HYYGSSHWYF DVWGQGTLVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIEK   360
TISKAKGQPR EPQVYTLPPS REEMTKNQVS LTCLVKGFYP SDIAVEWESN GQPENNYKTT   420
PPVLDSDGSF FLYSKLTVDK SRWQQGNVFS CSVMHEALHN HYTQKSLSLS PGKRKRRGSG   480
EGRGSLLTCG DVEENPGPMY RMQLLSCIAL SLALVTNSDI QMTQSPSSLS ASVGDRVTIT   540
CSASQDISNY LNWYQQKPGK APKVLIYFTS SLHSGVPSRF SGSGSGTDFT LTISSLQPED   600
FATYYCQQYS TVPWTFGQGT KVEIKRTVAA PSVFIFPPSD EQLKSGTASV VCLLNNFYPR   660
EAKVQWKVDN ALQSGNSQES VTEQDSKDST YSLSSTLTLS KADYEKHKVY ACEVTHQGLS   720
SPVTKSFNRG EC                                                      732

SEQ ID NO: 24        moltype = AA  length = 453
FEATURE              Location/Qualifiers
REGION               1..453
                     note = source = /note="Description of Artificial Sequence:
                     Synthetic polypeptide"
source               1..453
                     mol_type = protein
                     organism = synthetic construct
SEQUENCE: 24
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 25        moltype = AA  length = 214
FEATURE              Location/Qualifiers
REGION               1..214
```

```
                        note = source = /note="Description of Artificial Sequence:
                        Synthetic polypeptide"
source                  1..214
                        mol_type = protein
                        organism = synthetic construct
SEQUENCE: 25
DIQMTQSPSS  LSASVGDRVT  ITCSASQDIS  NYLNWYQQKP  GKAPKVLIYF  TSSLHSGVPS  60
RFSGSGSGTD  FTLTISSLQP  EDFATYYCQQ  YSTVPWTFGQ  GTKVEIKRTV  AAPSVFIFPP  120
SDEQLKSGTA  SVVCLLNNFY  PREAKVQWKV  DNALQSGNSQ  ESVTEQDSKD  STYSLSSTLT  180
LSKADYEKHK  VYACEVTHQG  LSSPVTKSFN  RGEC                                214

SEQ ID NO: 26           moltype = DNA   length = 7123
FEATURE                 Location/Qualifiers
source                  1..7123
                        mol_type = other DNA
                        organism = Homo sapiens
SEQUENCE: 26
atcgaggtcc gcgggaggct cggagcgcgc caggcggaca ctcctctcgg ctcctccccg   60
gcagcggcgg cggctcggag cgggctccgg ggctcgggtg cagcggccag cgggcgcctg  120
gcggcgagga ttacccgggg aagtggttgt ctcctggctg gagccgcgag acgggcgctc  180
agggcgcggg gccggcggcg gcgaacgaga ggacggactc tggcggccgg gtcgttggcc  240
gcgggggagcg cgggcaccgg gcgagcaggc cgcgtcgcgc tcaccatggt cagctactgg  300
gacaccgggg tcctgctgtg cgcgctgctc agctgtctgc ttctcacagg atctagttca  360
ggttcaaaat taaagatcc tgaactgagt ttaaaaggca cccagcacat catgcaagca  420
ggccagacac tgcatctcca atgcaggggg gaagcagccc ataaatggtc tttgcctgaa  480
atggtgagta aggaaagcga aaggctgagc ataactaaat ctgcctgtgg aagaaatggc  540
aaacaattct gcagtacttt aaccttgaac acagctcaag caaaccacac tggcttctac  600
agctgcaaat atctagctgt acctacttca aagaagaagg aaacagaatc tgcaatctat  660
atatttatta gtgatacagg tagacctttc gtagagatgt acagtgaaat ccccgaaatt  720
atacacatga ctgaaggaag ggagctcgtc attccctgcc gggttacgtc acctaacatc  780
actgttactt aaaaaagtt tccacttgac actttgatcc ctgatgaaa acgcataatc  840
tgggacagta gaaagggctt catcatatca aatgcaacgt acaaagaaat agggcttctg  900
acctgtgaag caacagtcaa tgggcatttg tataagacaa actatctcac acatcgacaa  960
accaataacaa tcatagatgt ccaaataagc acaccacgcc cagtcaaatt acttagaggc 1020
catactcttg tcctcaattg tactgctacc actcccttga cacagagagt tcaaatgacc 1080
tggagttacc ctgatgaaaa aaataagaga gcttccgtaa ggcgacgaat tgaccaaagc 1140
aattcccatg ccaacatatt ctacagtgtt cttactattg acaaaatgca gaacaaagac 1200
aaaggactt tacttgtcg tgtaaggagt ggaccatcat tcaaatctgt taacacctca 1260
gtgcatatat atgataaagc attcatcact gtgaaacatc gaaaacagca ggtgcttgaa 1320
accgtagctg gcaagcggtc ttaccggctc tctatgaaag tgaaggcatt tcctctgccg 1380
gaagttgtat ggttaaaaga tgggttacct gcgactgaga atctgctcg ctatttgact 1440
cgtggcgact cgttaattat caaggacgta actgaagagg atgcagggaa ttatacaatc 1500
ttgctgagca taaacagtc aaatgtgttt aaaaacctca ctgccactct aattgtcaat 1560
gtgaaacccc agatttacga aaaggccgtg tcatcgttt cagacccggc tctctaccca 1620
ctgggcagca gacaaatcct gacttgtacc gcatatggta tccctcaacc tacaatcaag 1680
tggttctggc accctgtaa ccataatcat tccgaagcaa ggtgtgactt tgttccaat 1740
aatgaagagt cctttatct ggatgctgac agcaacatgc gaaacagaat tgagagcatc 1800
actcagcgca tggcaataat agaaggaaag aataagatgg ctagcacctt ggttgtggct 1860
gactctagaa tttctggaat ctacatttgc atagcttcca ataaagttgg gactgtggga 1920
agaaacataa gcttttatat cacagatgtg ccaaatgggt tcatgttaa cttggaaaaa 1980
atgccagcgg aaggagagga cctgaaactg tcttgcacag ttaacaagtt cttatacaga 2040
gacgttactt ggatttact gcggacagtt aataacagaa caatgcacta cagtattagc 2100
aagcaaaaaa tggccatcac taaggagcac tccatcactc ttaatcttac catcatgaat 2160
gtttccctgc aagattcagg cacctatgcc tgcagagcca ggaatgtata cacagggaa  2220
gaaatcctcc agaagaaaga aattacaatc agagatcagg aagcaccata cctcctgcga 2280
aacctcagtg atcacacagt ggccatcagc agttccacca ctttagactg tcatgctaat 2340
ggtgtccccg agcctcagat cacttggttt aaaaacaacc acaaaataca caagagcct  2400
ggaattattt taggaccagg aagcagcacg ctgtttattg aaagagtcac agaagaggat 2460
gaaggtgtct atcactgcaa agccaccaac cagaagggct ctgtggaaag ttcagctac  2520
ctcactgttc aaggaacctc ggacaagtct aatctgtgc tgatcactct aacatgcacc 2580
tgtgtgctg cgactctctt ctggctccta ttaaccctct ttatccgaaa atgaaaagg  2640
tcttcttctg aaataaagac tgactaccta tcaattataa tggacccaga tgaagttcct 2700
ttggatgagc agtgtgagcg gctcccttat gatgccagca gtgggagtt tgcccgggag 2760
agacttaaac tgggcaaatc acttggaaga ggggcttttg gaaagtggt tcaagtcaca 2820
gcatttggca ttaagaaatc acctacgtgc cggactgtgg ctgtgaaaat gctgaaagag 2880
ggggccacgg ccagcgagta caaagctctg atgactgagc taaaaatctt gacccacatt 2940
ggccaccatc tgaacgtggt taacctgctg ggagcctgca ccaagcaagg agggcctctg 3000
atggtgattg ttgaatactg caaatatgga aatctctcca actacctgaa gagcaaacgt 3060
gacttatttt tctcaacaa ggatgcagca ctacacatgg agcctaagaa agaaaaatg  3120
gagccaggcc tggaacaagg caagaaacca agactagata gcgtcaccag cagcgaaagc 3180
tttgcgagct ccggctttca ggaagataaa agtctgagtg atgttgagga gaggaggat  3240
tctgacggtt tctacaagga gcccatcact atggaagatc tgatttctta cagttttcaa 3300
gtggccagag gcatggagtt cctgtcttcc agaaagtgca ttcatcggga cctggcagcg 3360
agaaacatc ttttatctga gaacaacgtg gtgaagattt gtgattttgg ccttgcccg 3420
gatatttata agaaccccga ttatgtgaga aaaggagata tcgacttcc tctgaaatgg 3480
atggctcctg aatctatctt tgacaaaatc tacagcacca aagcgacgt gtggtcttac 3540
ggagtattgc tgtgggaaat cttctcctta ggtgggtctc cataccagg agtacaaatg 3600
gatgaggact tttgcagtcg cctgagggaa ggcatgagga tgagagctcc tgagtactct 3660
actcctgaaa tctatcagat catgctggac tgctggcaca gagacccaaa agaaaggcca 3720
```

```
agatttgcag aacttgtgga aaaactaggt gatttgcttc aagcaaatgt acaacaggat    3780
ggtaaagact acatcccaat caatgccata ctgacaggaa atagtgggtt tacatactca    3840
actcctgcct tctctgagga cttcttcaag gaaagtattt cagctccgaa gtttaattca    3900
ggaagctctg atgatgtcag atacgtaaat gctttcaagt tcatgagcct ggaaagaatc    3960
aaaaccttTg aagaacTTtt accgaatgcc acctccactg ttgatgacta ccagggcgac    4020
agcagcactc tgttggcctc tcccatgctg aagcgcttca cctggactga cagcaaaccc    4080
aaggcctcgc tcaagattga cttgagagta accagtaaaa gtaaggagtc ggggctgtct    4140
gatgtcagca ggcccagttt ctgccattcc agctgtgggc acgtcagcga aggcaagcgc    4200
aggttcacct acgaccacgc tgagctgaaa aggaaaatcg cgtgctgctc cccgccccca    4260
gactacaact cggtggtcct gtactccacc ccacccatct agagtttgac acgaagcctt    4320
atttctagaa gcacatgtgt atttataccc caggaaact agcttttgcc agtattatgc    4380
atatataagt ttacacctTT atctttccat gggagccagc tgcttttTgt gatttttTta    4440
atagtgcttt ttttttTTtg actaacaaga atgtaactcc agatagagaa atagtgacaa    4500
gtgaagaaca ctactgctaa atcctcatgt tactcagtgt tagagaaatc cttcctaaac    4560
ccaatgactt ccctgctcca acccccgcca cctcagggca cgcaggacca gtttgattga    4620
ggagctgcac tgatcaccca atgcatcacg taccccactg ggccagccct gcagcccaaa    4680
acccagggca acaagcccgt tagccccagg gatcactggc tggcctgagc aacatctcgg    4740
gagtcctcta gcaggcctaa gacatgtgag gaggaaaagg aaaaaaagca aaaagcaagg    4800
gagaaaagag aaaccgggag aaggcatgag aaagaatttg agacgcacca tgtgggcacg    4860
gaggggggacg gggctcagca atgccatttc agtggcttcc cagctctgac ccttctacat    4920
ttgagggccc agccaggagc agatggacag cgatgagggg acattttctg gattctggga    4980
ggcaagaaaa ggacaaatat cttttttgga actaaagcaa attttagaac tttacctatg    5040
gaagtggttc tatgtccatt ctccattcgtg gcatgttttg atttgtagca ctgagggtgg    5100
cactcaactc tgagcccata ctttTggctc tctcagTaag atgcactgaa aacttagcca    5160
gagttaggtt gtctccaggc catgatggcc ttacactgaa aatgtcacat tctatttTgg    5220
gtattaatat atagtccaga cacttaactc aatttcttgg tattattctg ttttgcacag    5280
ttagttgtga agaaagctg agaagaatga aatgcagtc ctgaggagag gagttttctc    5340
catatcaaaa cgagggctga tggaggaaaa aggtcaataa ggtcaaggga aaaccccgtc    5400
tctataccaa ccaaaccaat tcaccaacac agttgggacc caaaacacag gaagtcagtc    5460
acgtttcctt ttcatttaat ggggattcca ctatctcaca ctaatctgaa aggatgtgga    5520
agagcattag ctgcgcata ttaagcactt taagctcctt gagtaaaaag gtggtatgta    5580
atttatgcaa ggtattttctc cagttgggac tcaggatatt agttaatgag ccatcactag    5640
aagaaaagcc catttttcaac tgctttgaaa cttgcctggg gtctgagcat gatgggaata    5700
gggagacagg gtaggaaagg gcgcctactc ttcagggtct aaagatcaag tgggccttgg    5760
atcgctaagc tggctctgtt tgatgctatt tatgcaagtt agggtctatg tattTtatgat    5820
gtctgcacct tctgcagcca gtcagaagct ggagaggcaa cagtggattg ctgcttcttg    5880
gggagaaagag tatgcttcct tTtatccatg taatttaact gtagaacctg agctctaagt    5940
aaccgaagaa tgtatgcctc tgttcttatg tgccacatcc ttgttTaaag gctctctgta    6000
tgaagagatg ggaccgtcat cagcacattc cctagtgagc ctactggctc ctggcagcgg    6060
cttttgtgga agactcacta gccagaagag aggagtggga cagtcctctc caccaagatc    6120
taaatccaaa caaagcagg ctagagccag aagagaggac aaatctttgt tcttcctctt    6180
cttTacatac gcaaaccacc tgtgacagct ggcaatttta taaatcaggt aactggaagg    6240
aggttaaaca cagaaaaaag aagacctcag tcaattctct actTttTttT tTttttTtcaa    6300
atcagataat agcccagcaa atagtgataa caaataaaac cttagctatt catgtctTga    6360
tttcaataat taattcttaa tcattaagag accataataa atactccttT tcaagagaaa    6420
agcaaaacca ttagaattgt tactcagctc cttcaaactc aggtttgtag catacatgag    6480
tccatccatc agtcaaagaa tggtTccatc tggagtctta atgtagaaag aaaaatggag    6540
acttgtaata atgagctagt tacaaagtgc ttgttcatta aaatagcact gaaaattgaa    6600
acatgaatta actgataata ttccaatcat ttgccattTa tgacaaaaat ggttggcact    6660
aacaaagaac gagcacttcc tttcagagtt tctgagataa tgtacgtgga acagtctggg    6720
tggaatgggg ctgaaaccat gtgaagtct gtgtcttgtc agtccaagaa gtgacaccga    6780
gatgttaatt ttagggaccc gtgccttgtt tcctagccca caagaatgca aacatcaaac    6840
agatactcgc tagcctcatt taaattgatt aaaggaggag tgcatctttg gccgacagtg    6900
gtgtaactgt atgtgtgtgt gtgtgtgtgt gtgtgtgtgt gtgtgtgggt gtatgtgtgt    6960
tttgtgcata actatttaag gaaactggaa ttttaaagtt acttttatac aaaccaagaa    7020
tatatgctac agatataaga cagacatggt ttggtccatat atttctagtc atgatgaatg    7080
tatTtTgtat accatcttca tataataaac ttccaaaaac aca                      7123

SEQ ID NO: 27          moltype = AA   length = 1338
FEATURE                Location/Qualifiers
source                 1..1338
                       mol_type = protein
                       organism = Homo sapiens
SEQUENCE: 27
MVSYWDTGVL LCALLSCLLL TGSSSGSKLK DPELSLKGTQ HIMQAGQTLH LQCRGEAAHK     60
WSLPEMVSKE SERLSITKSA CGRNGKQFCS TLTLNTAQAN HTGFYSCKYL AVPTSKKKET    120
ESAIYIFISD TGRPFVEMYS EIPEIIHMTE GRELVIPCRV TSPNITVTLK KFPLDTLIPD    180
GKRIIWDSRK GFIISNATYK EIGLLTCEAT VNGHLYKTNY ILTHRQTNTI I DVQISTPRPV    240
KLLRGHTLVL NCTATTPLNT RVQMTWSYPD EKNKRASVRR RIDQSNSHAN IFYSVLTIDK    300
MQNKDKGLYT CRVRSGPSFK SVNTSVHIYD KAFITVKHRK QQVLETVAGK RSYRLSMKVK    360
APPSPEVVWL KDGLPATEKS ARYLTRGYSL IIKDVTEEDA GNYTILLSIK QSNVFKNLTA    420
TLIVNVKPQI YEKAVSSFPD PALYPLGSRQ ILTCTAYGIP QPTIKWFWHP CNHNHSEARC    480
DFCSNNEESF ILDADSNMGN RIESITQRMA IIEGKNKMAS TLVVADSRIS GIYICIASNK    540
VGTVGRNISF YITDVPNGFH VNLEKMPTEG EDLKLSCTVN KFLYRDVTWI LLRTVNNRTM    600
HYSISKQKMA ITKEHSITLN LTIMNVSLQD SGTYACRARN VYTGEEILQK KEITIRDQEA    660
PYLLRNLSDH TVAISSSTTL DCHANGVPEP QITWFKNNHK IQQEPGIILG PGSSTLFIER    720
VTEEDEGVYH CKATNQKGSV ESSAYLTVQG TSDKSNLELI TLTCTCVAAT LFWLLLTLFI    780
RKMKRSSSEI KTDYLSIIMD PDEVPLDEQC ERLPYDASKW EFARERLKLG KSLGRGAFGK    840
VVQASAFGIK KSPTCRTVAV KMLKEGATAS EYKALMTELK ILTHIGHHLN VVNLLGACTK    900
```

```
QGGPLMVIVE YCKYGNLSNY LKSKRDLFFL NKDAALHMEP KKEKMEPGLE QGKKPRLDSV   960
TSSESFASSG FQEDKSLSDV EEEEDSDGFY KEPITMEDLI SYSFQVARGM EFLSSRKCIH  1020
RDLAARNILL SENNVVKICD FGLARDIYKN PDYVRKGDTR LPLKWMAPES IFDKIYSTKS  1080
DVWSYGVLLW EIFSLGGSPY PGVQMDEDFC SRLREGMRMR APEYSTPEIY QIMLDCWHRD  1140
PKERPRFAEL VEKLGDLLQA NVQQDGKDYI PINAILTGNS GFTYSTPAFS EDFFKESISA  1200
PKFNSGSSDD VRYVNAFKFM SLERIKTFEE LLPNATSMFD DYQGDSSTLL ASPMLKRFTW  1260
TDSKPKASLK IDLRVTSKSK ESGLSDVSRP SFCHSSCGHV SEGKRRFTYD HAELERKIAC  1320
CSPPPDYNSV VLYSTPPI                                               1338

SEQ ID NO: 28           moltype = DNA   length = 6502
FEATURE                 Location/Qualifiers
source                  1..6502
                        mol_type = other DNA
                        organism = Homo sapiens
SEQUENCE: 28
atcgaggtcc gcgggaggct cggagcgcgc caggcggaca ctcctctcgg ctcctccccg    60
gcagcggcgg cggctcggag cgggctccgg ggctcgggtg cagcggccag cgggcgcctg   120
gcggcgagga ttacccgggg aagtggttgt ctcctggccg gaccgcgcga acgggcgctc   180
agggcgcggg gccggcggcg gcgaacgaga ggacggactc tggccggcgg gtcgttggcc   240
gcggggagcg cgggcaccgg gcgagcaggc cgcgtcgcgc tcaccatggt cagctactgg   300
gacaccgggg tcctgctgtg cgcgctgctc agctgtctgc ttctcacagg atctagttca   360
ggttcaaaat taaaagatcc tgaactgagt ttaaaagcca ccagcacat catgcaagca   420
ggccagacac tgcatctcca atgcaggggg gaagcagccc ataaatggtc tttgcctgaa   480
atggtgagta aggaaagcga aaggctgagc ataactaaat ctgcctgtgg aagaaatggc   540
aaacaattct gcagtacttt aaccttgaac acagctcaag caaaccacac tggcttctac   600
agctgcaaat atcagctgt acctacttca aagaagaaga acagaatc tgcaatctat   660
atatttatta gtgatacagg tagacccttc gtagagatgt acagtgaaat ccccgaaatt   720
atacacatga ctgaaggaag ggagctcgtc attccctgcc gggttacgtc acctaacatc   780
actgttactt taaaaaagtt tccacttgac actttgatcc ctgatggaaa acgcataatc   840
tgggacagta gaaagggctt catcatatca aatgcaacgt acaaagaaat agggcttctg   900
acctgtgaag caacagtcaa tgggcatttg tataagcaa actatctcac acatcgacaa   960
accaatacaa tcatagatgt ccaaataagc acaccacgcc cagtcaaatt acttagaggc  1020
catactcttg tcctcaattg tactgctacc actcccttga acacgagagt tcaaatgacc  1080
tggagttacc ctgatgaaaa aaataagaga gcttccgtaa ggcgacgaat tgaccaaagc  1140
aattcccatg ccaacatatt ctacagtgtt cttactattg acaaaatgca gaacaaagac  1200
aaaggacttt atacttgtcg tgtaaggagt ggaccatcat tcaaatctgt taacacctca  1260
gtgcatatat atgataaagc attcatcact gtgaaacatc gaaaacagca ggtgcttgaa  1320
accgtagctg gcaagcggtc ttaccggctc tctatgaaag tgaaggcatt tccctcgccg  1380
gaagttgtat ggttaaaaga tgggtacct gcgactgaga aatctgctcg ctatttgact  1440
cgtggctact cgttaattat caaggacgta actgaagagg atgcagggaa ttatacaatc  1500
ttgctgagca taaaacagtc aaatgtgttt aaaaaacctca ctgccactct aattgtcaat  1560
gtgaaacccc agatttacga aaaggccgtg tcatcgtttc cagacccggc tctctaccca  1620
ctgggacgca gacaaatcct gacttgtacc gcatatgcta tccctcaacc tacaatcaag  1680
tggttctggc acccctgtaa ccataatcat tccgaagcaa ggtgtgactt tgttccaat  1740
aatgaagagt cctttatcct ggatgctgac agcaacatgg gaaacagaat tgagagcatc  1800
actcagcgca tggcaataat agaaggaaag aataagatgg ctagcacctt ggttgtggct  1860
gactctagaa tttctggaat ctacatttgc atagcttcca taaagttggg gactgtggga  1920
agaaacataa gcttttatat cacagatgtg ccaaatgggt ttcatgttaa cttgaaaaa  1980
atgccgacgg aaggagagga cctgaaactg tcttgcacag ttaacaagtt cttatacaga  2040
gacgttactt ggatttact gcggacagtt aataacagaa caatgcacta cagtattagc  2100
aagcaaaaaa tggccatcac taaggagcac tccatcactc ttaatcttac catcatgaat  2160
gtttccctgc aagattcagg cacctatgcc tgcagagcca ggaatgtata cacaggggaa  2220
gaaatcctcc agaagaaga aattacaatc agaggtgagc actgcaacaa aaaggctgtt  2280
ttctctcgga tctccaaatt taaaagcaca aggaatgatt gtaccacaca agtaatgta  2340
aaacattaaa ggactcatta aaaagtaaca gttgtctcat atcatcttga tttattgtca  2400
ctgttgctaa ctttcaggct cggaggagat gctcctccca aaatgagttc ggagatgata  2460
gcagtaataa tgagaccccc gggcccagc tctgggcccc ccattcaggc cgagggggct  2520
gctccggggg gccgacttgg tgcacgtttg gatttggagg atccctgcac tgccttctct  2580
gtgtttgttg ctcttgctgt tttctcctgc ctgataaaca acaacttggg atgatccttt  2640
ccttccattt tgatgccaac ctcttttat tttaagtgt tgaagctgca caaactgaat  2700
aatttaaaca aatgctggtt tctgccaaag atggacacga ataagttaat tttccagctc  2760
agaatgagta cagttgaatt tgagactctg tcggacttct gcctggtttt atttgggact  2820
atttcatctg ctcttgattt gtaaatagca cctggatagc aagttataat gcttatttat  2880
ttgaaaatgc tttttttttt tttacgttaa gcacatttat cttgaactgg agcttctaaa  2940
atgggcccca ggggtgcaag atgttggtgt aattcagaga tagtaaaggt ttatcgcagt  3000
gtgaattata agagtccatc caaatcaacg tccctctcct cctctcatgc gatccaggta  3060
attatgcagt tagtgccaca gtagactagc ctagcaaagg gtttgctcct tgctgtctct  3120
gactgcacca cacagctatt gatggcagct gaaagaaagt ggatcatgcc ttaattttaa  3180
atattcctgt cctctggtta ttattttaag gaacttcatc atgttaaaat gacagcattc  3240
aaaggtgtac cacaatcaat ttatcaagga aataaaggct attgtaacca gagatttaat  3300
gcattcttct aaatgtaaat ttaaaatttg cccctttaaaa aagtccactt tccccatatg  3360
caaatgttaa taggattttt atggggatta agaagcggca aaactacaga agcagaattc  3420
aaagtaattt aaaaaataca caccagtttt aaatcaagag aagttgtaat ctcttgtttt  3480
aagctgcgt ttgagggaaa atgacttttt caccaattta atatgcattg ttctgttgtt  3540
tttatttatg attgatcatt atatgtgact tgcataaact atttaaaaaa aaaaactata  3600
atgaccaaaa tagccatggc tgagaaacac agtggctggg cagttcaata ggaggtgaca  3660
atatgacaac ttctcaagct tgggaactca ccagactgtt tcctccttta ggtaacagat  3720
tctgtcccac ggctaaactt gtctttcacg tgggaattgc ttttgtcaaa cgtgaaagag  3780
taaacaatag catttcccca gaatgccagt tttatggagc cccaaatgct ctgaaaacaa  3840
```

```
ttagtaacct ggaagttgtc agcccaaagg aaagaaaaat caattgtatc ttgaaatttt   3900
acctatggct ctttggcctg gcttctttgt tcattataag ttagtgtgtt ccttcaggaa   3960
acaatgcctt aataccatag aacatggggg ccttaatagt tgctaacatt aaaaaagcaa   4020
acagaatgat tgagggatcc ttatgaaaac aaaatggtga attggacatg cagaacctac   4080
catttccttc ccctgtttgc aattttttgtg gggaggggag gatgttagta tttacaaaag   4140
atgattttaa gaacttccaa gagatgagtt taagaattcc atagagtatt agttgttcac   4200
tgtgtaatta atccttccgg agagtctttt tttttttttt taaagaaact tttgggtggg   4260
ttttgttttt tattagttac cctaggggta tgttaccctg gggtatgaag ggaggtgaag   4320
ataacggagg ggggagaaaa aaaaaaggag aaaaaaggag cctaaaatgg ggataattg    4380
aaatggaaca ggggtgtga ggctggttcc tcagtcccca ttccaaacgg aggatagaag    4440
ctgtgtattt atgtgacctg gcagatctct ggggccataa cactgaaaag tgaaagaacc   4500
tggtgggcag ctatctttgg ctactgataa ccagcagaaa tgtctgttaa ttctgatttt   4560
ctcaatttga agggatcagc tacactgtta aattttggaa agccactacc tacttccatc   4620
aagtaactta ggtttcgaaa tatgggttca acgcacctcc cttattcaaa atgtcaaaat   4680
agattattat aatgtataaa gtaagaattg acaaaatatg attcttgggt tgattggtca   4740
tttagaaact agccaaaagt gagactttta atgtagaaca ttttttcagaa atgggtacaa   4800
agaaaaatgc atattactgt atatttcaga gtgtttatgt gaaccttgta tttaattgag   4860
agtcccatgt acgttctgca gccttttgc tgcttctatc atctgaagtt tgtgtagtac    4920
aaataaggcc tttgggattc ttaatgacat ttatgttaaa atgttctctt ctctttaaac   4980
accgttttcc aatccacctg tcagggagtc caaatcgtgt ctgtgttgat gatgctatac   5040
tttgtagcta gaaaaacaat tttagtgttg tgggctctgt attcagactt cctttttaca   5100
agaccgatgg gcagtgatag attatttat catatttaat gcatgggaaa tagtgtgctg    5160
aggaagctat taaaagtata actcagtgaa ttgggtctga gttttaaatg agatatttca   5220
aaattggctt gccactgtaa aagcgactaa ataataatat gatactgttc tttatgatct   5280
tgtcatgttt cactgatatg tttggggtct tcactatgta aaaaatgtca aaattgtaat   5340
gagcaagcat gtacaagtag tcgtaaatca aaggttttaa acaggactgc attttcaatt   5400
aggaaaagct gttttggcaga tagcatccaa tgcaaaaaca gaaatatcgt aacgttctgc   5460
ttagtgggca agataagata ggaaagacat gctcaaagag gcaaaagaat cattgctatc   5520
attcattcta cactagttg aagaagtttt tgtacatcag agcacttcct tcagcacact    5580
ttttgcctt cagatttcat ttttataaa atgagaagc taatgataaa ctgtagaaat    5640
caaaatttat tgagaaatct gtttctccta acagatagta accctgccat gatatactac   5700
ttcaacaatg ttataaaatt tatgtgataa tatacatttt aacctgggat ttctaaattg   5760
ctttaacaaa tgctaatcct gagagttgcc ctgcaggact caaaagggaa aggttttggg   5820
acgtggcaga accctgcagg gacatggaat taaggccatt gcaatgtatc atcttttgtag  5880
cattgtcatc actccttaagc tgccttcaca gttttagtac actaagatga ggaaatcgaa   5940
aatgggcaga gaaagctcat actgtataat tgaagacagt gacagagaac gtgtcagtta   6000
tgccaaaact cttttgattt ctgttccagg atttccaaca agaggggaaa ggaatgactt   6060
gggagggtgg gaaagacatt aggagttgtt tttatttttt accttggaag ctttagctac   6120
caatccagta ccctcctaac tagaatgtat acacatcagc aggactgact gactacttca   6180
ttagagatat actgtactca ttggggggcct tgggggtact gctgttctta tgtgggatt    6240
taatgttgta atgtattgca tcttaatgta ttgaattcat tttgttgtac tatattggtt   6300
ggcattttat taaaataaat tgtattgtat catatttgta tgttttaaga gaaaataata   6360
taaaatacaa tatttgtact attatatagt gcaaaaacta caaatctgtg cctctgcctc   6420
ttgaattaat tctttggttg cttgcatttg ggaagggaat ggagaaagga aagaaccaat   6480
aaagcttttca aagttcaaga aa                                           6502

SEQ ID NO: 29           moltype = AA   length = 687
FEATURE                 Location/Qualifiers
source                  1..687
                        mol_type = protein
                        organism = Homo sapiens
SEQUENCE: 29
MVSYWDTGVL LCALLSCLLL TGSSSGSKLK DPELSLKGTQ HIMQAGQTLH LQCRGEAAHK   60
WSLPEMVSKE SERLSITKSA CGRNGKQFCS TLTLNTAQAN HTGFYSCKYL AVPTSKKKET   120
ESAIYIFISD TGRPFVEMYS EIPEIIHMTE GRELVIPCRV TSPNITVTLK KFPLDTLIPD   180
GKRIIWDSRK GFIISNATYK EIGLLTCEAT VNGHLYKTNY LTHRQTNTII DVQISTPRPV   240
KLLRGHTLVL NCTATTPLNT RVQMTWSYPD EKNKRASVRR RIDQSNSHAN IFYSVLTIDK   300
MQNKDKGLYT CRVSGPSFK SVNTSVHIYD KAFITVKHRK QQVLETVAGK RSYRLSMKVK    360
APPSPEVVWL KDGLPATEKS ARYLTRGYSL IIKDVTEEDA GNYTILLSIK QSNVFKNLTA   420
TLIVNVKPQI YEKAVSSFPD PALYPLGSRQ ILTCTAYGIP QPTIKWFWHP CNHNHSEARC   480
DFCSNNEESF ILDADSNMGN RIESITQRMA IIEGKNKMAS TLVVADSRIS GIYICIASNK   540
VGTVGRNISF YITDVPNGFH VNLEKMPTEG EDLKLSCTVN KFLYRDVTWI LLRTVNNRTM   600
HYSISKQKMA ITKEHSITLN LTIMNVSLQD SGTYACRARN VYTGEEILQK KEITIRGEHC  660
NKKAVFSRIS KFKSTRNDCT TQSNVKH                                      687

SEQ ID NO: 30           moltype = DNA   length = 2973
FEATURE                 Location/Qualifiers
source                  1..2973
                        mol_type = other DNA
                        organism = Homo sapiens
SEQUENCE: 30
atcgaggtcc gcgggaggct cggagcgcgc caggcggaca ctcctctcgg ctcctccccg   60
gcagcggcgg cggctcggag cgggctccgg ggctcgggtg cagcggccag cgggcgcctg   120
gcggcgagga ttacccgggg aagtggttgt tcctggctg gagccgcagg acgggcgtc    180
agggcgcggg gccggcggcg gcgaacgaga ggacggactc tggccgcgg gtcgttggcc   240
gcggggagcg cgggcaccgg gcgagcaggc cgcgtcgcgc tcaccatggt cagctactgg   300
gacacccggg tcctgctgtg cgcgctgctc agctgtctgc ttctcacagg atctagttca   360
ggttcaaaat taaaagatcc tgaactgagt ttaaaaggca cccagcacat catgcaagca   420
ggccagacac tgcatctcca atgcaggggg gaagcagccc ataaatggtc tttgcctgaa   480
```

```
atggtgagta aggaaagcga aaggctgagc ataactaaat ctgcctgtgg aagaaatggc   540
aaacaattct gcagtacttt aaccttgaac acagctcaag caaaccacac tggcttctac   600
agctgcaaat atctagctgt acctacttca aagaagaagg aaacagaatc tgcaatctat   660
atatttatta gtgatacagg tagacctttc gtagagatgt acagtgaaat ccccgaaatt   720
atacacatga ctgaaggaag ggagctcgtc attccctgcc gggttacgtc acctaacatc   780
actgttactt taaaaaagtt tccacttgac actttgatcc ctgatggaaa acgcataatc   840
tgggacagta gaaagggctt catcatatca aatgcaacgt acaaagaaat agggcttctg   900
acctgtgaag caacagtcaa tgggcatttg tataagacaa actatctcac acatcgacaa   960
accaataacaa tcatagatgt ccaaataagc acaccacgcc cagtcaaatt acttagaggc  1020
catactcttg tcctcaattg tactgctacc actcccttga cacgagagt tcaaatgacc  1080
tggagttacc ctgatgaaaa aaataagaga gcttccgtaa ggcgacgaat tgaccaaagc  1140
aattcccatg ccaacatatt ctacagtgtt cttactattg acaaaatgca gaacaaagac  1200
aaaggacttt acttgtcg tgtaaggagt ggaccatcat tcaaatctgt taacacctca  1260
gtgcatatat atgataaagc attcatcact gtgaaacatc gaaaacagca ggtgcttgaa  1320
accgtagctg gcaagcggtc ttaccggctc tctatgaaag tgaaggcatt tccctcgccg  1380
gaagttgtat ggtaaaaga tgggttacct gcgactgaga atctgctcg ctatttgact  1440
cgtggctact cgttaattat caaggacgta actgaagagg atgcagggaa ttatacaatc  1500
ttgctgagca taaaacagtc aaatgtgttt aaaaacctca ctgccactct aattgtcaat  1560
gtgaaaccc agatttacga aaaggccgtg tcatcgtttc cagaccccgg ctctctaccca  1620
ctgggcagca gacaaatcct gacttgtacc gcatatggta tccctcaacc tacaatcaag  1680
tggttctggc accctgtaa ccataatcat tccgaagcaa ggtgtgactt tgttccaat  1740
aatgaagagt ccttatcct ggatgctgac agcaacatgg gaaacagaat tgagagcatc  1800
actcagcgca tggcaataat agaaggaaag aataagatgg ctagcacctt ggttgtggct  1860
gactctagaa tttctggaat ctacatttgc atagcttcca ataaagttgg gactgtggga  1920
agaaacataa gcttttatat cacagatgtg ccaaatgggt tcatgttaa cttggaaaaa  1980
atgccgacgg aaggagga cctgaaactg tcttgcgtaa ttaacaagtt cttatacaga  2040
gacgttactt ggatttttact gcggacagtt aataacagaa caatgcacta cagtattagc  2100
aagcaaaaaa tggccatcac taaggagcac tccatcactc ttaatcttac catcatgaat  2160
gtttccctgc aagattcagg cacctatgcc tgcagagcca ggaatgtata cacaggggaa  2220
gaaatcctcc agaagaaaga aattacaatc agagatcagg aagcaccata cctcctgcga  2280
aacctcagtg atcacacagt ggccatcagc agttccacca ctttagactg tcatgctaat  2340
ggtgtccccg agcctcagat cacttggttt aaaaacaacc acaaaataca caagagcct  2400
gaactgtata catcaacgtc accatcgtca tcgtcatcat caccattgtc atcatcatca  2460
tcatcgtcat catcatcatc atcatagcta tcatcattat catcatcatc atcatcatca  2520
tcatagctac catttattga aactattat gtgtcaactt caaagaactt atcctttagt  2580
tggagagcca agacaatcat aacaataaca aatggccggg catggtggct cacgcctgta  2640
atcccagcac tttgggaggc caaggcaggt ggatcatttg aggtcaggag ttcaagacca  2700
gcctgaccaa gatggtgaaa tgctgtctct attaaaaata caaaattagc caggcatggt  2760
ggctcatgcc tgtaatgcca gctactcggg aggctgagac aggagaatca cttgaaccca  2820
ggaggcagag gttgcaggga gccgagatcg tgtactgcac tccagcctgg gcaacaagag  2880
cgaaactccg tctcaaaaaa caaataaata aataaataaa taaacagaca aaattcactt  2940
tttattctat taaacttaac atacatgcat taa                                2973

SEQ ID NO: 31         moltype = AA  length = 733
FEATURE               Location/Qualifiers
source                1..733
                      mol_type = protein
                      organism = Homo sapiens
SEQUENCE: 31
MVSYWDTGVL LCALLSCLLL TGSSSGSKLK DPELSLKGTQ HIMQAGQTLH LQCRGEAAHK    60
WSLPEMVSKE SERLSITKSA CGRNGKQFCS TLTLNTAQAN HTGFYSCKYL AVPTSKKKET   120
ESAIYIFISD TGRPFVEMYS EIPEIIHMTE GRELVIPCRV TSPNITVTLK KFPLDTLIPD   180
GKRIIWDSRK GFIISNATYK EIGLLTCEAT VNGHLYKTNY LTHRQTNTII DVQISTPRPV   240
KLLRGHTLVL NCTATTPLNT RVQMTWSYPD EKNKRASVRR RIDQSNSHAN IFYSVLTIDK   300
MQNKDKGLYT CVRSGPSFK SVNTSVHIYD KAFITVKHR QQVLETVAGK RSYRLSMKVK    360
AFPSPEVVWL KDGLPATEKS ARYLTRGYSL IIKDVTEEDA GNYTILLSIK QSNVFKNLTA   420
TLIVNVKPQI YEKAVSSFPD PALYPLGSRQ ILTCTAYGIP QPTIKWFWHP CNHNHSEARC   480
DFCSNNEESF ILDADSNMGN RIESITQRMA IIEGKNKMAS TLVVADSRIS GIYICIASNK   540
VGTVGRNISF YITDVPNGFH VNLEKMPTEG EDLKLSCTVN KFLYRDVTWI LLRTVNNRTM   600
HYSISKQKMA ITKEHSITLN LTIMNVSLQD SGTYACRARN VYTGEEILQK KEITIRDQEA   660
PYLLRNLSDH TVAISSSTTL DCHANGVPEP QITWFKNNHK IQQEPELYTS TSPSSSSSSP   720
LSSSSSSSSS SSS                                                     733

SEQ ID NO: 32         moltype = DNA  length = 1911
FEATURE               Location/Qualifiers
source                1..1911
                      mol_type = other DNA
                      organism = Homo sapiens
SEQUENCE: 32
atcgaggtcc gcgggaggct cggagcgcgc caggcggaca ctcctctcgg ctcctccccg    60
gcagcggcgg cggctcggag cgggctccgg ggctcgggtg cagcggccag cgggcgcctg   120
gcggcgagga ttacccgggg aagtggttgt ctcctggctg gagccgcgag acgggcgctc   180
agggcgcggg gccggcggcg gcgaacgaga ggacggactc tggcggccgg gtcgttggcc   240
gcggggacgg cgggcaccgg ggcgagcaggc cgcgtcggtg tcaccatggt cagctactgg   300
gacaccgggg tcctgctgtg cgcgctgctc agctgtctgc ttctcacagg atctagttca   360
ggttcaaaat taaagatcc tgaactgagt ttaaaaggca cccagcacat catgcaagca   420
ggccagacac tgcatctcca atgcaggggg gaagcagccc ataaatgtc tttgcctgaa   480
atggtgagta aggaaagcga aaggctgagc ataactaaat ctgcctgtgg aagaaatggc   540
aaacaattct gcagtacttt aaccttgaac acagctcaag caaaccacac tggcttctac   600
```

```
agctgcaaat atctagctgt acctacttca aagaagaagg aaacagaatc tgcaatctat   660
atatttatta gtgatacagg tagacctttc gtagagatgt acagtgaaat ccccgaaatt   720
atacacatga ctgaaggaag ggagctcgtc attccctgcc gggttacgtc acctaacatc   780
actgttactt taaaaaagtt tccacttgac actttgatcc ctgatggaaa acgcataatc   840
tgggacagta gaaagggctt catcatatca aatgcaacgt acaaagaaat agggcttctg   900
acctgtgaag caacagtcaa tgggcatttg tataagacaa actatctcac acatcgacaa   960
accaatacaa tcatagatgt ccaaataagc acaccacgcc cagtcaaatt acttagaggc  1020
catactcttg tcctcaattg tactgctacc actcccttga acacgagagt tcaaatgacc  1080
tggagttacc ctgatgaaaa aaataagaga gcttccgtaa ggcgacagat tgaccaaagc  1140
aattcccatg ccaacatatt ctacagtgtt cttactattg acaaaatgca gaacaaagac  1200
aaaggacttt atacttgtcg tgtaaggagt ggaccatcat tcaaatctgt taacacctca  1260
gtgcatatat atgataaagc attcatcact gtgaaacatc gaaaacagca ggtgcttgaa  1320
accgtagctg gcaagcggtc ttaccggctc tctatgaaag tgaaggcatt tccctcgccg  1380
gaagttgtat ggttaaaaga tgggttacct gcgactgaga aatctgctcg ctatttgact  1440
cgtggctact cgttaattat caaggacgta actgaagagg atgcagggaa ttatacaatc  1500
ttgctgagca taaaacagtc aaatgtgttt aaaaaacctca ctgccactct aattgtcaat  1560
gtgaaacccc agatttacga aaaggccgtg tcatcgtttc cagacccggc tctctaccca  1620
ctgggcagca gacaaatcct gacttgtacc gcatatggta tccctcaacc tacaatcaag  1680
tggttctggc accctgtaa ccataatcat tccgaagcaa ggtgtgactt ttgttccaat  1740
aatgaagagt cctttatcct ggatgctgac agcaacatgg gaaacagaat tgagagcatc  1800
actcagcgca tggcaataat agaaggaaag aataagcttc caccagctaa cagttctttc  1860
atgttgccac ctacaagctt ctcttccaac tacttccatt tccttccgtg a           1911

SEQ ID NO: 33         moltype = AA    length = 541
FEATURE               Location/Qualifiers
source                1..541
                      mol_type = protein
                      organism = Homo sapiens
SEQUENCE: 33
MVSYWDTGVL LCALLSCLLL TGSSSGSKLK DPELSLKGTQ HIMQAGQTLH LQCRGEAAHK    60
WSLPEMVSKE SERLSITKSA CGRNGKQFCS TLTLNTAQAN HTGFYSCKYL AVPTSKKKET   120
ESAIYIFISD TGRPFVEMYS EIPEIIHMTE GRELVIPCRV TSPNITVTLK KFPLDTLIPD   180
GKRIIWDSRK GFIISNATYK EIGLLTCEAT VNGHLYKTNY LTHRQTNTII DVQISTPRPV   240
KLLRGHTLVL NCTATTPLNT RVQMTWSYPD EKNKRASVRR RIDQSNSHAN IFYSVLTIDK   300
MQNKDKGLYT CRVRSGPSFK SVNTSVHIYD KAFITVKHRK QQVLETVAGK RSYRLSMKVK   360
APPSPEVVWL KDGLPATEKS ARYLTRGYSL IIKDVTEEDA GNYTILLSIK QSNVFKNLTA   420
TLIVNVKPQI YEKAVSSFPD PALYPLGSRQ ILTCTAYGIP QPTIKWFWHP CNHNHSEARC   480
DFCSNNEESF ILDADSNMGN RIESITQRMA IIEGKNKLPP ANSSFMLPPT SFSSNYFHFL   540
P                                                                  541

SEQ ID NO: 34         moltype = DNA    length = 5849
FEATURE               Location/Qualifiers
source                1..5849
                      mol_type = other DNA
                      organism = Homo sapiens
SEQUENCE: 34
actgagtccc gggaccccgg gagagcggtc aatgtgtggt cgctgcgttt cctctgcctg    60
cgccgggcat cacttgcgcg ccgcagaaag tccgtctggc agcctggata tcctctccta   120
ccggcacccg cagacgcccc tgcagccgcg gtcggcgccc gggctcccta gcccgtgcg   180
ctcaactgtc ctgcgctgcg gggtgccgcg agttccacct ccgcgcctcc ttctctagac   240
aggcgctggg agaaagaacc ggctcccgag ttctgggcat ttcgcccggc tcgaggtgca   300
ggatgcagag caaggtgctg ctggccgtcg ccctgtggct ctgcgtggag acccgggccg   360
cctctgtggg tttgcctagt gttctcttg atctgcccag gctcagcata caaaaagaca   420
tacttacaat taaggctaat acaactcttc aaattacttg caggggacag agggacttgg   480
actgcttttg gcccaataat cagagtggca gtgagcaaag ggtggaggtg actgagtgca   540
gcgatggcct cttctgtaag acactcacaa ttccaaaagt gatcggaaat gacactggag   600
cctacaagtg cttctaccgg gaaactgact tggcctcgt catttatgtc tatgttcaag   660
attacagatc tccatttatt gcttctgtta gtgaccaaca tggagtcgtg tacattactg   720
agaacaaaaa caaactgtg gtgattccat gtctcgggtc catttcaaat ctcaacgtgg   780
cactttgtgc aagatacca gaaaagagat ttgttcctga tggtaacaga atttcctgga   840
acagcaagaa gggctttact attcccagct acatgatcag ctatgctggc atggtcttct   900
gtgaagcaaa aattaatgat gaaagttacc agtctattat gtacatagtt gtcgttgtag   960
ggtataggat ttatgatgtg ttctgagtc cgtctcatgg aattgaacta tctgttggag  1020
aaaagcttgt cttaaattgt acagcaagaa ctgaactaa tgtgggatt gacttcaact  1080
gggaatacccc ttcttcgaag catcagcata agaaacttgt aaaccgagac ctaaaaaccc  1140
agtctgggag tgagatgaag aaattttga gcaacttaaac tatagatggt gtaacccgga  1200
gtgaccaagg attgtacacc tgtgcagcat ccagtgggct gatgaccaag aagaacagca  1260
catttgtcag ggtccatgaa aaaccttttg ttgctttggg aagtggcatg gaatctctg  1320
tggaagccac ggtggggag cgtgtcagaa tccctgcgaa gtaccttggt tacccaccc  1380
cagaaataaa atggtataa aatgaatac cccttgagtc caatcacaca attaagcgg  1440
ggcatgtact gacgattatg gaagtgagtg aaagagacac aggaaattac actgtcatcc  1500
ttaccaatcc catttcaaag gagaagcaga gccatgtggt ctctctggtt gtgtatgtcc  1560
cacccccagat tggtgagaaa tctctaatct ctcctgtgga ttcctaccag tacggcacca  1620
ctcaaacgct gacatctacg gtctatgcca tcacatc cactggtatt  1680
ggcagttgga ggaagagtgc gccaacgagc ccagccaagc tgtctcagtg acaaacccat  1740
acccttgtga agaatggaga agtgtggagg acttccaggg aggaaataaa attgaagtta  1800
ataaaatca atttgctcta attgaaggaa aaacaaaac tgtaagtacc cttgttatcc  1860
aagcggcaaa tgtgtcagct ttgtacaaat gtgaagcggg caacaaagtc gggagaggag  1920
agagggtgat ctccttccac gtgaccaggg gtcctgaaat tactttgcaa cctgacatgc  1980
```

-continued

```
agcccactga gcaggagagc gtgtctttgt ggtgcactgc agacagatct acgtttgaga 2040
acctcacatg gtacaagctt ggcccacagc ctctgccaat ccatgtggga gagttgccca 2100
cacctgtttg caagaacttg gatactcttt ggaaattgaa tgccaccatg ttctctaata 2160
gcacaaatga cattttgatc atggagctta agaatgcatc cttgcaggac caaggagact 2220
atgtctgcct tgctcaagac aggaagacca agaaaagaca ttgcgtggtc aggcagctca 2280
cagtcctaga gcgtgtggca cccacgatca caggaaacct ggagaatcag acgacaagta 2340
ttggggaaag catcgaagtc tcatgcacgg catctgggaa tccccctcca cagatcatgt 2400
ggtttaaaga taatgagacc cttgtagaag actcaggcat tgtattgaag gatgggaacc 2460
ggaacctcac tatccgcaga gtgaggaagg aggacgaagg cctctacacc tgccaggcaa 2520
gcagtgttct tggctgtgca aaagtggagg cattttcatt aatagaaggt gcccaggaaa 2580
agacgaactt ggaaatcatt attctagtag gcacggcggt gattgccatg ttcttctggc 2640
tacttcttgt catcatccta cggaccgtta agcgggccaa tggaggggaa ctgaagacag 2700
gctacttgtc catcgtcatg gatccagatg aactcccatt ggatgaacat tgtgaacgac 2760
tgccttatga tgccagcaaa tgggaattcc ccagaaccg gctgaagcta ggtaagcctc 2820
ttggccgtgg tgcctttggc caagtgattg aagcagatgc cttggaatt gacaagacag 2880
caacttgcag gacagtagca gtcaaaatgt gaaagaagg agcaacacac agtgagcatc 2940
gagctctcat gtctgaactc aagatcctca ttcatattgg tcaccatctc aatgtggtca 3000
accttctagg tgcctgtacc aagccaggag ggccactcat ggtgattgtg gaattctgca 3060
aatttggaaa cctgtccact tacctgagga gcaagagaaa tgaatttgtc ccctacaaga 3120
ccaaagggc acgattccgt caagggaaag actacgttgg agcaatccct gtggatctga 3180
aacggcgctt ggacagcatc accagtagcc agagctcagc cagctctgga tttgtggagg 3240
agaagtccct cagtgatgta gaagaagagg aagctcctga agatctgtat aaggacttcc 3300
tgaccttgga gcatctcatc tgttacagct tccaagtggc taagggcatg gagttcttgg 3360
catcgcgaaa gtgtatccac agggacctgg cggcacgaaa tatcctctta tcggagaaga 3420
acgtggttaa aatctgtgac tttggcttgg cccgggatat ttataaagat ccagattatg 3480
tcagaaaagg agatgctcgc ctccctttga aatggatggc cccagaaaca atttttgaca 3540
gagtgtacac aatccagagt gacgtctggt cttttggtgt tttgctgtgg gaaatatttt 3600
ccttaggtgc ttctccatat cctggggtaa agattgatga agaattttgt aggcgattga 3660
aagaaggaac tagaatgagg gccctgatt atactacacc agaaatgtac cagaccatgc 3720
tggactgctg gcacggggag cccagtcaga gacccacgtt ttcagagttg gtggaacatt 3780
tgggaaatct cttgcaagct aatgctcagc aggatggcaa agactacatt gttcttccga 3840
tatcagagac tttgagcatg gaagaggatt ctggactctc tctgcctacc tcacctgttt 3900
cctgtatgga ggaggaggaa gtatgtgacc ccaaattcca ttatgacaac acagcaggaa 3960
tcagtcagta tctgcagaca agtaagcgaa agagccggcc tgtgagtgta aaaacatttg 4020
aagtatccc gttagaagaa ccagaagtaa aagtaatccc agtagacaac agacgggaca 4080
gtggtatggt tcttgcctca gaagagctga aacttttgga agacagaacc aaattatctc 4140
catcttttgg tggaatggtg cccagcaaaa gcagggagtc tgtggcatct gaaggctcaa 4200
accagacaag cggctaccag tccggatatc actccgatga cacagcacc accgtgtact 4260
ccagtgagga agcagaactt ttaaagctga tagagattgg agtgcaaacc ggtagcacag 4320
cccagattct ccagcctgac tcggggacca cactgagctg tcctcctgtt taaaaggaag 4380
catccacacc cccaactcct ggacatcaca tgagaggtgc tgctcagatt tcaagtgtt 4440
gttctttcca ccagcaggaa gtagccgcat ttgatttca tttcgacaac agaaaaagga 4500
cctcggactg caggagcca gtcttctagg catatcctgg aagaggcttg tgacccaaga 4560
atgtgtctgt gtcttctccc agtgttgacc tgatcctctt tttcattcat ttaaaaagca 4620
tttatcatgc ccctgctgc gggtctcacc atgggtttag aacaaagacg ttcaagaaat 4680
ggccccatcc tcaaagaagt agcagtacct ggggagctga cacttctgta aaactagaag 4740
ataaaccagg caatgtaagt gttcgaggtg ttgaagatgg gaaagattg cagggctgag 4800
tctatccaag aggctttgtt taggacgtgg gtcccaagcc aagccttaag tgtgaattc 4860
ggattgatag aaaggaagac taacgttacc ttgctttgga gagtactgga gcctgcaaat 4920
gcattgtgtt tgctctggtg gaggtgggca tggggtctgt tctgaaatgt aaagggttca 4980
gacgggttt ctggttttag aaggttgcgt gttcttcgag ttgggctaaa gtagagttca 5040
ttgtgctgtt tctgactcct aatgagagtt ccttccagac cgttacgtgt ctcctgccca 5100
agccccagga aggaaatgat gcagctcgg ctccttgtct cccaggctga tcctttattc 5160
agaataccac aaagaaagga cattcagctc aaggctccct gccgtgttga agagttctga 5220
ctgcacaaac cagcttctgg tttcttctgg aatgaatacc ctcatatctg tcctgatgtg 5280
atatgtctga gactgaatgc gggaggttca atgtgaagct gtgtgtggtg tcaaagtttc 5340
aggaaggatt ttaccctttt gttcttcccc ctgtccccaa cccactctca ccccgcaacc 5400
catcagtatt ttagttattt ggcctctact ccagtaaacc tgattgggtt tgttcactct 5460
ctgaatgatt attagccaga cttcaaaatt attttatagc ccaaattata acatctattg 5520
tattatttag acttttaaca tatagagcta tttctactga ttttttgccct tgttctgtcc 5580
ttttttttcaa aaaagaaaat gtgtttttg tttggtacca tagtgtgaaa tgctgggaac 5640
aatgactata agacatgcta tggcacatat atttatagtc tgtttatgta gaaacaaatg 5700
taatatatta aagcctttata tataatgaac tttgtactat tcacattttg tatcagtatt 5760
atgtagcata acaaaggtca taatgctttc agcaattgat gtcattttat taagaacat 5820
tgaaaaactt gaaaaaaaaa aaaaaaaaa 5849
```

| SEQ ID NO: 35 | moltype = AA   length = 1356 |
|---|---|
| FEATURE | Location/Qualifiers |
| source | 1..1356 |
|  | mol_type = protein |
|  | organism = Homo sapiens |

SEQUENCE: 35

```
MQSKVLLAVA LWLCVETRAA SVGLPSVSLD LPRLSIQKDI LTIKANTTLQ ITCRGQRDLD    60
WLWPNNQSGS EQRVEVTECS DGLFCKTLTI PKVIGNDTGA YKCFYRETDL ASVIYVYVQD   120
YRSPFIASVS DQHGVVYITE NKNKTVVIPC LGSISNLNVS LCARYPEKRF VPDGNRISWD   180
SKKGFTIPSY MISYAGMVFC EAKINDESYQ SIMYIVVVVG YRIYDVVLSP SHGIELSVGE   240
KLVLNCTART ELNVGIDFNW EYPSSKHQHK KLVNRDLKTQ SGSEMKKFLS TLTIDGVTRS   300
DQGLYTCAAS SGLMTKKNST FVRVHEKPFV AFGSGMESLV EATVGERVRI PAKYLGYPPP   360
EIKWYKNGIP LESNHTIKAG HVLTIMEVSE RDTGNYTVIL TNPISKEKQS HVVSLVVYVP   420
```

```
PQIGEKSLIS PVDSYQYGTT QTLTCTVYAI PPPHHIHWYW QLEEEECANEP SQAVSVTNPY  480
PCEEWRSVED FQGGNKIEVN KNQFALIEGK NKTVSTLVIQ AANVSALYKC EAVNKVGRGE  540
RVISFHVTRG PEITLQPDMQ PTEQESVSLW CTADRSTFEN LTWYKLGPQP LPIHVGELPT  600
PVCKNLDTLW KLNATMFSNS TNDILIMELK NASLQDQGDY VCLAQDRKTK KRHCVVRQLT  660
VLERVAPTIT GNLENQTTSI GESIEVSCTA SGNPPPQIMW FKDNETLVED SGIVLKDGNR  720
NLTIRRVRKE DEGLYTCQAC SVLGCAKVEA FFIIEGAQEK TNLEIIILVG TAVIAMFFWL  780
LLVIILRTVK RANGGELKTG YLSIVMDPDE LPLDEHCERL PYDASKWEFP RDRLKLGKPL  840
GRGAFGQVIE ADAFGIDKTA TCRTVAVKML KEGATHSEHR ALMSELKILI HIGHHLNVVN  900
LLGACTKPGG PLMVIVEFCK FGNLSTYLRS KRNEFVPYKT KGARFRQGKD YVGAIPVDLK  960
RRLDSITSSQ SSASSGFVEE KSLSDVEEEE APEDLYKDFL TLEHLICYSF QVAKGMEFLA 1020
SRKCIHRDLA ARNILLSEKN VVKICDFGLA RDIYKDPDYV RKGDARLPLK WMAPETIFDR 1080
VYTIQSDVWS FGVLLWEIFS LGASPYPGVK IDEEFCRRLK EGTRMRAPDY TTPEMYQTML 1140
DCWHGEPSQR PTFSELVEHL GNLLQANAQQ DGKDYIVLPI SETLSMEEDS GLSLPTSPVS 1200
CMEEEEVCDP KFHYDNTAGI SQYLQNSKRK SRPVSVKTFE DIPLEEPEVK VIPDDNQTDS 1260
GMVLASEELK TLEDRTKLSP SFGGMVPSKS RESVASEGSN QTSGYQSGYH SDDTDTTVYS 1320
SEEAELLKLI EIGVQTGSTA QILQPDSGTT LSSPPV                          1356

SEQ ID NO: 36           moltype = DNA   length = 5833
FEATURE                 Location/Qualifiers
source                  1..5833
                        mol_type = other DNA
                        organism = Homo sapiens
SEQUENCE: 36
actttcagcc ccgagccgcg gccgctcggg tcggacccac gcgcagcggc cggagatgca   60
gcggggcgcc gcgctgtgcc tgcgactgtg gctctgcctg ggactcctgg acggcctggt  120
gagtgcgctac tccatgaccc ccccgacctt gaacatcgac gaggagtcac acgtcatcga  180
caccggtgac agcctgtcca tctcctgcag gggacagcgc cccctcgagt gggcttggcc  240
aggagctcag gaggcgccag ccaccggaga caaggacagc gaggacacgg gggtggtgcg  300
agactgcgag ggcacagacg ccaggcccta ctgcaaggtg ttgctgctgc acgaggtaca  360
tgccaacgac acaggcagct acgtctgcta ctacaagtac atcaaggcac gcatcgaggg  420
caccacggcc gccagctcct acgtgttcgt gagagacttt gagcagccat tcatcaacaa  480
gcctgacacg ctcttggtca acaggaagga cgccatgtgg gtgccctgtc tggtgtccat  540
ccccggcctc aatgtcacgc tgcgctcgca agctcggtg ctgtggccag acgggcagga  600
ggtggtgtgg gatgaccggc ggggcatgct cgtgtccacg ccactgctgc acgatgccct  660
gtacctgcag tgcgagacca cctggaggaga caggacttc ctttccaacc ccttcctggt  720
gcacatcaca gcaacgagc tctatgacat ccagctgttg cccaggaagt cgctggagct  780
gctggtaggg gagaagctgg tcctgaactg accgtgtgg gctgagttta actcaggtgt  840
caccttttgac tgggactacc cagggaagca ggcagacgcg gggtaagtggg tgcccgagcg  900
acgctcccag cagacccaca cagaactctc cagcatcctg accatccaca acgtcagcca  960
gcacgacctg ggctcgtatg tgtgcaaggc caacaacggc atccagcgat tcgggagag 1020
caccgaggtc attgtgcatg aaaatccctt catcagcgtc gagtggctca aaggacccat 1080
cctggaggcc acggcaggag acgagctggt gaagctgccc gtgaagctgg cagcgtaccc 1140
cccgagag ttccagtggt acaaggatgg aaaggcactg tccgggcgcc acagtccaca 1200
tgccctggtg ctcaaggagg tgacagaggc cagcacaggc acctacaccc tcgccctgtg 1260
gaactccgct gctggcctga ggcgaacat cagcctggac ctggtggtga atgtgccccc 1320
ccagatacat gagaaggagg cctcctcccc cagcatctac tcgcgtcaca gccgccaggc 1380
cctcacctgc acggcctacg gggtgccct gcctctcagc atccagtggc actggggcca 1440
ctggacaccc tgcaagatgt tgcccagcg tagtctccgg cggcggcagc agcaagacct 1500
catgccacag tgccgtgact ggagggcggt gaccacgcag gatgccgtga cccccatcga 1560
gagcctggac acctggaccg agtttgtgga gggaaagaat aagactgtga gcaagctggt 1620
gatccagaat gccaacgtgt ctgccatgta caagtgtgtg gtctccaaca aggtgggcca 1680
ggatgagcgg ctcatctact ctatgtgac caccatcccc gacggcttca ccatcgaatc 1740
caagccatcc gaggagctac tagagggcca gccggtgctc ctgagctgcc aagccgacag 1800
ctacaagtac gagcatctgc gctggtaccg cctcaacctg tccacgctgc acgatgcgca 1860
cgggaacccg cttctgctcg actgcaagaa cgtgcatctg ttcgccacc ctctggccgc 1920
cagcctggag gaggtggcac ctggggcgcg ccacgccacg ctcagcctga gtatccccg 1980
cgtcgcgccc gagcacgagg ccactatgt gtgcgaagtg caagaccggc gcagccatga 2040
caagcactgc cacaagaagt acctgtcggt gcaggccctg gaagcccctc ggctcacgca 2100
gaacttgacc gacctcctgg tgaacgtgag cgactcgctg gagatgcagt gcttggtggc 2160
cggagcgcac gcgcccagca tcgtgtggta caaagacgag aggctgctgg aggaaaagtc 2220
tggagtcgac ttggcggact ccaaccagaa gctgagcatc cagcgcgtgc gcgaggagga 2280
tgcgggacgc tatctgtgca gcgtgtgcaa cgccaagggc tgcgtcaact cctccgccag 2340
cgtggccgtg aaggctccg aggataaggg cagcatggag atcgtgatcc ttgtcggtac 2400
cggccgtcatc gctgtcttct tctgggtcct cctcctcctc atcttcgta acatgagag 2460
gccggcccac gcagacatca agacgggcta cctgtccatc atcatgacc ccggggaggt 2520
gcctctggag gagcaatgcg aatacctgtc ctacgatgcc agcagtgggg aattccccg 2580
agagcggctg cacctgggga gagtctcgg ctacggcgcc ttcggaaggt ggtggaagc 2640
ctccgctttc ggcatccaca agggcagcag ctgtgacacc gtggccgtga aatgctgaa 2700
agagggcgcc acggccagcg agcaccgcgc gctagttgca gccttcaaga tcctcattca 2760
catcggcaac cacctcaacg tggtcaacct cctcggggcg tgcaccaagc cgcagggcc 2820
cctcatggtg atcgtggagt tctgcaagta cggcaacctc tccaacttcc tgcgcgccaa 2880
gcgggacgcc ttcagccct gcggcgagaa gtctcccgag cagcgcggac gcttccgcgc 2940
catggtggag ctgccaggc tggatcgag gcggccggga gcagcgaca gggtcctctt 3000
cgcgcgcttc tcgaagaccg agggcgagg gaggcggct tctccagacc agaagctga 3060
ggacctgtgg ctgagcccgc tgaccatgga agatcttgtc tgctacagct tccaggtggc 3120
cagagggatg gagttcctgg cttcccgaaa gtgcatccac agagacctgg ctgctcggaa 3180
cattctgctg tcgaaagcg acgtggtgaa gatctgtgac tttggccttg cccgggacat 3240
ctacaaagac cccgactacg tccgcaaggg cagtgcccgg ctgcccctga gtggatggc 3300
ccctgaaagc atcttcgaca aggtgtacac cacgcagagt gacgtgtggt cctttgggt 3360
```

-continued

```
gcttctctgg gagatcttct ctctgggggc ctccccgtac cctggggtgc agatcaatga   3420
ggagttctgc cagcggctga gagacggcac aaggatgagg gccccggagc tggccactcc   3480
cgccatacgc cgcatcatgc tgaactgctg gtccggagac cccaaggcga gacctgcatt   3540
ctcggagctg gtggagatcc tgggggacct gctccagggc aggggcctgc aagaggaaga   3600
ggaggtctgc atggcccgc gcagctctca gagctcagaa gagggcagct tctcgcaggt   3660
gtccaccatg gccctacaca tcgcccaggc tgacgctgag gacagccgc caagcctgca   3720
gcgccacagc ctgccgcca ggtattacaa ctgggtgtcc tttcccgggt gcctggccag   3780
aggggctgag acccgtggtt cctccaggat gaagacattt gaggaattcc ccatgacccc   3840
aacgacctac aaaggctctg tggacaacca gacagacagt gggtggtgc tggcctcgga   3900
ggagtttgag cagatagaga gcaggcatag acaagaaagc ggcttcagct gtaaaggacc   3960
tggccagaat gtggctgtga ccagggcaca ccctgactcc caaggggaggc ggcggcggcc   4020
tgagcggggg gcccgaggag gccaggtgtt ttacaacagc gagtatgggg agctgtcgga   4080
gccaagcgag gaggaccact gctccccgtc tgcccgcgtg actttcttca cagacaacag   4140
ctactaagca gcatcggaca agaccccag cacttgggg ttcaggcccg gcagggcggg   4200
cagagggctg gaggcccagg ctgggaactc atctggttga actctggtcgg cacaggagtg   4260
tcctcttccc tctctgcaga cttccagct aggaagagca ggactccagg cccaaggctc   4320
ccggaattcc gtcaccacga ctggccaggg ccacgctcca gctgccccgg ccctccccc   4380
tgagattcag atgtcattta gttcagcatc cgcaggtgct ggtcccgggg ccagcacttc   4440
catgggaatg tctctttggc gacctccttt catcacactg ggtggtggcc tggtccctgt   4500
tttcccacga ggaatctgtg ggtctgggag tcacacagtg ttggaggtta aggcatacga   4560
gagcagaggt ctcccaaacg ccctttcctc ctcaggcaca cagctactct ccccacgagg   4620
gctggctggc ctcacccacc cctgcacagt tgaagggagg ggctgtgttt ccatctcaaa   4680
gaaggcattt gcagggtcct cttctgggcc tgaccaaaca gccaactagc ccctggggtg   4740
gccaccagta tgacagtatt atacgctgga acacagagg cagcccgcac acctgcgcct   4800
gggtgttgag agccatcctg caagtctttt tcaacagaac ttcacagact gttagagctg   4860
ctgagaagaa tttgctttcc gaattcagcc tggaaggcgc ccagggacag ctgtactgag   4920
tctagatgac tctgacccc ccccaggtc aaggccagca gagcagtcag tgcctctgga   4980
gaaggccctt gctctcccac ctggcccaga ctccgaggag cctgggtctg gagctgccgg   5040
tctggttctt ccctttagag cccggatctg ccacctgcgg cccctcccaa gccgtgaacc   5100
agctcatgag agatgaacac tgtgggatcc actccaaggag gctcgggggct ggacaaaagg   5160
accaccagc attgccctgt gccaccagc actcagtgga cattctgggg acctgccttc   5220
agccttttcc tgccctgtgc ctgacatcag caccctggct ggtcagaatg ccgccctccc   5280
agaggagcag ccgagagatc ccctgaaggc tggaggcatt ctgctcagga cccctatccc   5340
agctcacagt gcccaaccat ctcaccagga gaaagagcca catccccacg ttaggaccac   5400
ggagactgac caccaccctg acccccccaaa cccacgcacc agacgcttgc aggacaggcg   5460
ccgcgcagcg ggcaggggct tgcccggccg accctcccct cccaccctcc cccactgcgc   5520
gttactccag gatatgccga gtgcacgtat aaggtcatct tcgtcgtccc cgtggacctc   5580
cccttcctc tgcacgtcgt ccaacgtggg actggcgtgt caggcttccc tgggaggatc   5640
tggaggttgt tctctgcaga gaaccagcct ggctcctggc gcgcacctct gctccctct   5700
cctcactacc cacccacgca tgtaccggga aaaaaactac tatgcccttc tagaccatgt   5760
tctgagaaaa gatcgaaaat atttaacaag agataataat aaatctgatg ccggtctttg   5820
tgtgtgttgc gga                                                      5833
```

| SEQ ID NO: 37 | moltype = AA  length = 1363 |
|---|---|
| FEATURE | Location/Qualifiers |
| source | 1..1363 |
| | mol_type = protein |
| | organism = Homo sapiens |

SEQUENCE: 37

```
MQRGAALCLR LWLCLGLLDG LVSGYSMTPP TLNITEESHV IDTGDSLSIS CRGQHPLEWA    60
WPGAQEAPAT GDKDSEDTGV VRDCEGTDAR PYCKVLLLHE VHANDTGSYV CYYKYIKARI   120
EGTTAASSYV FVRDFEQPFI NKPDTLLVNR KDAMWVPCLV SIPGLNVTLR SQSSVLWPDG   180
QEVVWDDRRG MLVSTPLLHD ALYLQCETTW GDQDFLSNPF LVHITGNELY DIQLLPRKSL   240
ELLVGEKLVL NCTVWAEFNS GVTFDWDYPG KQAERGKWVP ERRSQQTHTE LSSILTIHNV   300
SQHDLGSYVC KANNGIQRFR ESTEVIVHEN PFISVEWLKG PILEATAGDE LVKLPVKLAA   360
YPPPEFQWYK DGKALSGRHS PHALVLKEVT EASTGTYTLA LWNSAAGLRR NISLELVVNV   420
PPQIHEKEAS SPSIYSRHSR QALTCTAYGV PLPLSIQWHW RPWTPCKMFA QRSLRRRQQQ   480
DLMPQCRDWR AVTTQDAVNP IESLDTWTEF VEGKNKTVSK LVIQNANVSA MYKCVVSNKV   540
GQDERLIYFY VTTIPDGFTI ESKPSEELLE GQPVLLSCQA DSYKYEHLRW YRLNLSTLHD   600
AHGNPLLLDC KNVHLFATPL AASLEEVAPG ARHATLSLSI PRVAPEHEGH YVCEVQDRRS   660
HDKHCHKKYL SVQALEAPRL TQNLTDLLVN VSDSLEMQCL VAGAHAPSIV WYKDERLLEE   720
KSGVDLADSN QKLSIQRVRE EDAGRYLCSV CNAKGCVNSS ASVAVEGSED KGSMEIVILV   780
GTGVIAVFFW VLLLLIFCNM RRPAHADIKT GYLSIIMDPG EVPLEEQCEY LSYDASQWEF   840
PRERLHLGRV LGYGAFGKVV EASAFGIHKG SSCDTVAVKM LKEGATASEH RALMSELKIL   900
IHIGNHLNVV NLLGACTKPQ GPLMVIVEFC KYGNLSNFLR AKRDAFSPCA EKSPEQRGRF   960
RAMVELARLD RRRPGSSDRV LFARFSKTEG GARRASPDQE AEDLWLSPLT MEDLVCYSFQ  1020
VARGMEFLAS RKCIHRDLAA RNILLSESDV VKICDFGLAR DIYKDPDYVR KGSARLPLKW  1080
MAPESIFDKV YTTQSDVWSF GVLLWEIFSL GASPYPGVQI NEEFCQRLRD GTRMRAPELA  1140
TPAIRRIMLN CWSGDPKARP AFSELVEILG DLLQGRGLQE EEEVCMAPRS SQSSEEGSFS  1200
QVSTMALHIA QADAEDSPPS LQRHSLAARY YNWVSFPGCL ARGAETRGSS RMKTFEEFPM  1260
TPTTYKGSVD NQTDSGMVLA SEEFEQIESR HRQESGFSCK GPGQNVAVTR AHPDSQGRRR  1320
RPERGARGGQ VFYNSEYGEL SEPSEEDHCS PSARVTFFTD NSY                   1363
```

| SEQ ID NO: 38 | moltype = DNA  length = 4484 |
|---|---|
| FEATURE | Location/Qualifiers |
| source | 1..4484 |
| | mol_type = other DNA |
| | organism = Homo sapiens |

SEQUENCE: 38

```
actttcagcc ccgagccgcg gccgctcggg tcggacccac gcgcagcggc cggagatgca    60
gcggggcgcc gcgctgtgcc tgcgactgtg gctctgcctg ggactcctgg acggcctggt   120
gagtggctac tccatgaccc ccccgacctt gaacatcacg gaggagtcac acgtcatcga   180
caccggtgac agcctgtcca tctcctgcag gggacagcac cccctcgagt gggcttggcc   240
aggagctcag gaggcgccag ccaccggaga caaggacagc gaggacacgg gggtggtgcg   300
agactgcgag ggcacagacg ccaggcccta ctgcaaggtg ttgctgctgc acgaggtaca   360
tgccaacgac acaggcagct acgtctgcta ctacaagtac atcaaggcac gcatcgaggg   420
caccacggcc gccagctcct acgtgttcgt gagagacttt gagcagccat tcatcaacaa   480
gcctgacacg ctcttggtca acaggaagga cgccatgtgt gtgccctgtc tggtgtccat   540
ccccggcctc aatgtcacgc tgcgctcgca aagctggtg ctgtggccag acgggcagga   600
ggtggtgtgg gatgaccggc ggggcatgct cgtgtccacg ccactgctgc acgatgccct   660
gtacctgcag tgcgagacca cctggggaga ccaggacttc ctttccaacc ccttcctggt   720
gcacatcaca ggcaacgagc tctatgacat ccagctgttg cccaggaagt cgctggagct   780
gctggtaggg gagaagctgg tcctgaactg caccgtgtgg ctgagttta actcaggtgt   840
cacctttgac tgggactacc cagggaagca ggcagagcgg ggtaagtggg tgcccgagcg   900
acgctcccag cagacccaca cagaactctc cagcatcctg accatccaca acgtcagcca   960
gcacgacctg ggctcgtatg tgtgcaaggc caacaacggc atccagcgat ttcgggagag  1020
caccgaggtc attgtgcatg aaaatccctt catcagcgtc gagtgctca aaggacccat  1080
cctggaggcc acggcaggag acgagctggt gaagctgccc gtgaagctgg cagcgtaccc  1140
cccgcccgag ttccagtggt acaaggatgg aaaggcactg tccggcgcc acagtccaca  1200
tgccctggtg ctcaaggagg tgacagaggc cagcacaggc acctacaccc tcgccctgtg  1260
gaactccgct gctggcctga ggcgcaacat cagcctggtg ctggtggtga atgtgcccc  1320
ccagatacat gagaaggagg cctcctcccc cagcatctac tcgcgtcaca gccgccaggc  1380
cctcacctgc acggcctacg gggtgcccct gcctctcagc atccagtggc actggcggcc  1440
ctggacaccc tgcaagatgt tgcccagcg tagtctccgg cggcggcagc agcaagacct  1500
catgccacag tgccgtgact ggagggcggt gaccacgcag gatgccgtga acccgatggc  1560
gagcctggac acctgaccg agttggtgga gggaaagaat aagactgtga gcaagctggt  1620
gatccagaat gccaacgtgt ctgccatgta caagtgtgtg gtctccaaca aggtgggcca  1680
ggatgagcgg ctcatctact tctatgtgac caccatcccc gacggcttca ccatcgaatc  1740
caagccatcc gaggagctac tagaggggca gccggtcctc ctgaacgcca aagccgacag  1800
ctacaagtac gagcatctgc gctggtaccg cctcaacctg tccacgctgc acgatgcgca  1860
cgggaacccg cttctgctcg actgcaagaa cgtgcatctg ttcgcaccc ctctggccgc  1920
cagcctggag gaggtggcac ctggggcgcg ccacgccacg ctcagcctga gtatcccccg  1980
cgtcgcgccc gagcacgagg gccactatgt gtgcgaagtc caagaccggc gcagcgcatga  2040
caagcactgc cacaagaagt acctgtcggt gcaggccctg gaagcccctc ggctcacgca  2100
gaacttgacc gacctcctgg tgaacgtgag cgactcgctg gagatgcagt gcttggtggc  2160
cggagcgcac gcgcccagca tcgtgtggta caaagacgag aggctgctgg aggaaaagtc  2220
tggagtcgac ttggcggact ccaaccagaa gctgagcatc cagcgcgtgc gcgaggagga  2280
tgcgggacgc tatctgtgca gcgtgtgcaa cgccaaggc tgcgtcaact cctccgccag  2340
cgtggccgtg gaaggctccg aggataaggg cagcatggga atcgtgatcc ttgtcggtac  2400
cggcgtcatc gctgtcttct tctgggtcct cctcctcctc atcttctgta acatgaggag  2460
gccggcccac ccagacatca agacgggcta cctgtccatc atcatggacc ccgggaggt  2520
gcctctggag gagcaatgcg aatacctgtc ctacgatgcc agcagtgga aattcccccg  2580
agagcggctg cacctgggga gagtgctcgg ctacggcgcc ttcggaaggg tggtggaagc  2640
ctccgctttc ggcatccaca agggcagcag ctgtgacacc gtggccgtga aaatgctgaa  2700
agagggcgcc acggccagcg agcaccgcgc gctgatgtcg gagctcaaga tcctcattca  2760
catccgcaac cacctcaacg tggtcaacct cctcggggcg tgcaccaagc cgcagggccc  2820
cctcatggtg atcgtggagt ctgcaagta cggcaacctc tccaacttcc tgcgcgccaa  2880
gcgggacgcc ttcagcccct gcgcggagaa gtctcccgag cagcgcggac gcttccgcgc  2940
catggtggag ctcgccaggc tggatcgagg cggccggggg agcagcgaca gggtcctctt  3000
cgcgcggttc tcgaagaccg agggcgggac gaggcgggct tctccagacc aagaagctga  3060
ggacctgtgg ctgagcccgc tgaccatgga agatcttgtc tgctacagct tccaggtggc  3120
cagagggatg gagttcctgg cttcccgaaa gtgcatccac agagacctgg ctgctcggaa  3180
cattctgctg tcgaaagcg acgtggtgaa gatctgtgac tttggccttg cccgggacat  3240
ctacaaagac cccgactacg tccgcaaggg cagtgcccgg ctgcccctga agtggatggc  3300
ccctgaaagc atcttcgaca aggtgtacac cacgcagagt gacgtgtggt cctttgggt  3360
gcttctctgg gagatcttct ctctgggggc ctccccgtac cctggggtgc agatcaatga  3420
ggagttctgc cagcggctga gagacggcac aaggatgagg ccccggagc tggccactcc  3480
cgccatacgc cgcatcatgc tgaactgctg gtccggagac cccaaggcga gacctgcatt  3540
ctcggagctg gtggagatcc tgggggacct gctccagggc agggtgctgc aagaggaaga  3600
ggaggtctgc atgccccgc gcagctctca gagctcagaa gagggcagct ctctcgcaggt  3660
gtccaccatg gccctacaca tcgcccaggc tgacgctgag gacagcccgc caagcctgca  3720
gcgccacagc ctggccgcca ggtattacaa ctgggtgtcc tttcccgggt gcctggccag  3780
aggggctgag acccgtggtt cctccaggat gaagacattg aggaattcc ccatgacccc  3840
aacgacctac aaaggctctg tggacaacca gacagacagt gggatggtgc tggcctcgga  3900
ggagtttgag cagatagaga gcaggcatag acaagaaagc ggcttcaggt agctgaagca  3960
gagagagaga aggcagcata cgtcagcatt ttcttctctg cacttataag aaagatcaaa  4020
gactttaaga ctttcgctat ttcttctact gctatctact acaaacttca aagaggaacc  4080
aggaggacaa gaggagcatg aaagtggaca aggagtgtga ccactgagca accacaggga  4140
gggttaggc ctccggatga ctgcgggcag gcctggataa tatccagcct cccacaagaa  4200
gctggtggag cagagtgttc cctgactcct ccaaggaaag ggagacgcc tttcatggtc  4260
tgctgagtaa caggtgcctt cccagacact ggcgttactg cttgaccaaa gagccctcaa  4320
gcggccctta tgcagcgtg acagagggct caccctcttgc cttctaggtc acttctcaca  4380
atgtcccttc agcacctgac cctgtgccca ccagttattc cttggtaata tgagtaatac  4440
atcaaagagt agtattaaaa gctaattaat catgtttata ctaa                 4484

SEQ ID NO: 39        moltype = AA   length = 1298
FEATURE              Location/Qualifiers
source               1..1298
```

```
                        mol_type = protein
                        organism = Homo sapiens
SEQUENCE: 39
MQRGAALCLR LWLCLGLLDG LVSGYSMTPP TLNITEESHV IDTGDSLSIS CRGQHPLEWA    60
WPGAQEAPAT GDKDSEDTGV VRDCEGTDAR PYCKVLLLHE VHANDTGSYV CYYKYIKARI   120
EGTTAASSYV FVRDFEQPFI NKPDTLLVNR KDAMWVPCLV SIPGLNVTLR SQSSVLWPDG   180
QEVVWDDRRG MLVSTPLLHD ALYLQCETTW GDQDFLSNPF LVHITGNELY DIQLLPRKSL   240
ELLVGEKLVL NCTVWAEFNS GVTFDWDYPG KQAERGKWVP ERRSQQTHTE LSSILTIHNV   300
SQHDLGSYVC KANNGIQRFR ESTEVIVHEN PFISVEWLKG PILEATAGDE LVKLPVKLAA   360
YPPPEFQWYK DGKALSGRHS PHALVLKEVT EASTGTYTLA LWNSAAGLRR NISLELVVNV   420
PPQIHEKEAS SPSIYSRHSR QALTCTAYGV PLPLSIQWHW RPWTPCKMFA QRSLRRRQQQ   480
DLMPQCRDWR AVTTQDAVNP IESLDTWTEF VEGKNKTVSK LVIQNANVSA MYKCVVSNKV   540
GQDERLIYFY VTTIPDGFTI ESKPSEELLE GQPVLLSCQA DSYKYEHLRW YRLNLSTLHD   600
AHGNPLLLDC KNVHLFATPL AASLEEVAPG ARHATLSLSI PRVAPEHEGH YVCEVQDRRS   660
HDKHCHKKYL SVQALEAPRL TQNLTDLLVN VSDSLEMQCL VAGAHAPSIV WYKDERLLEE   720
KSGVDLADSN QKLSIQRVRE EDAGRYLCSV CNAKGCVNSS ASVAVEGSED KGSMEIVILV   780
GTGVIAVFFW VLLLLIFCNM RRPAHADIKT GYLSIIMDPG EVPLEEQCEY LSYDASQWEF   840
PRERLHLGRV LGYGAFGKVV EASAFGIHKG SSCDTVAVKM LKEGATASEH RALMSELKIL   900
IHIGNHLNVV NLLGACTKPQ GPLMVIVEFC KYGNLSNFLR AKRDAFSPCA EKSPEQRGRF   960
RAMVELARLD RRRPGSSDRV LFARFSKTEG GARRASPDQE AEDLWLSPLT MEDLVCYSFQ  1020
VARGMEFLAS RKCIHRDLAA RNILLSESDV VKICDFGLAR DIYKDPDYVR KGSARLPLKW  1080
MAPESIFDKV YTTQSDVWSF GVLLWEIFSL GASPYPGVQI NEEFCQRLRD GTRMRAPELA  1140
TPAIRRIMLN CWSGDPKARP AFSELVEILG DLLQGRGLQE EEEVCMAPRS SQSSEEGSFS  1200
QVSTMALHIA QADAEDSPPS LQRHSLAARY YNWVSFPGCL ARGAETRGSS RMKTFEEFPM  1260
TPTTYKGSVD NQTDSGMVLA SEEFEQIESR HRQESGFR                         1298

SEQ ID NO: 40           moltype = DNA   length = 4359
FEATURE                 Location/Qualifiers
source                  1..4359
                        mol_type = other DNA
                        organism = Homo sapiens
SEQUENCE: 40
actttcagcc ccgagccgcg gccgctcggg tcggacccac gcgcagcggc cggagatgca    60
gcggggcgcc gcgctgtgcc tgcgactgtg gctctgcctg ggactcctgg acggcctggt   120
gagtggctac tccatgaccc ccccgacctt gaacatcgaa gaggagtcac acgtcatcga   180
caccggtgac agcctgtcca tctcctgcag gggacagcac cccctcgagt gggcttggcc   240
aggagctcag gaggcgccag ccaccggaga caaggacagc gaggacacgg gggtggtgcg   300
agactgcgag ggcacagacg ccaggcccta ctgcaaggtg ttgctgctgc acgaggtaca   360
tgccaacgac acaggcagct acgtctgcta ctacaagtac atcaaggcac gcatcgaggg   420
caccacggcc gccagctcct acgtgttcgt gagagacttt gagcagccat tcatcaacaa   480
gcctgacacg ctcttggtca acaggaagga cgccatgtgg gtgccctgtc tggtgtccat   540
ccccggcctc aatgtcacgc tgcgctcgca aagctcggtg ctgtggccag acgggcagga   600
ggtggtgtgg gatgaccggc ggggcatgct cgtgtccacg ccactgctgc acgatgcctt   660
gtacctgcag tgcgagacca cctgggggag ccaggacttc cttttccaac ccttcctggt   720
gcacatcaca ggcaacgagc tctatgacat ccagctgttg cccaggaagt cgctggagct   780
gctggtaggg gagaagctgg tcctgaactg caccgtgtgg gctgagttta actcaggtgt   840
cacctttgac tgggactacc cagggaagca ggcagagcgg ggtaagtggg tgccccaggg   900
acgctcccag cagacccaca cagaactctc cagcatcctg accatccaca acgtcagcca   960
gcacgacctg ggctcgtatg tgtgcaaggc caacaacggc atccagcgat tcgggagag  1020
caccgaggtc attgtgcatg aaaatccctt catcagcgtc gagtggctca aggaccat   1080
cctggagccc acggcaggag acgagctggt gaagctgccc gtgaagctgg cagcgtaca   1140
cccgccgag ttccagtggt acaaggatgg aaaaggcactg tccggggcgc acagtccaca  1200
tgccctggtg ctcaaggagg tgacagaggc agcacaggc acctacaccc tgcccctgtg  1260
gaactccgct gctggcctga gcgcaacat cagcctggag ctggtggtga atgtgccccc  1320
ccagatacat gagaaggagg cctcctcccc cagcatctac tcgcgtcaca gccgccaggc  1380
cctcacctgc acggcctacg gggtgcccct gcctctcagc atccagtggc actggcggcc  1440
ctggacaccc tgcaagatgt ttgcccagcg tagtctccgg cggcggcagc agcaagacct  1500
catgccacag tgccgtgact ggagggcggt gaccacgcag gatgccgtga cccccatcga  1560
gagcctggac acctggaccg agtttgtgga gggaaagaat aagactgtga gcaagctggt  1620
gatccagaat gccaacgtgt ctgccatgta caagtgtgtg gtctccaaca aggtgggcca  1680
ggatgagcgg ctcatctact ctatgtgac caccatcccc gacggcttca ccatcgaatc  1740
caagccatcc gaggagctac tagagggcca gccggtgctc ctgagctgcc aagccgacag  1800
ctacaagtac gagcatctgc gctggtaccg cctcaacctg tccacgctgc acgatgcgca  1860
cgggaacccg cttctgctcg actgcaagaa cgtgcatctg ttcgccaccc ctctggccag  1920
cagcctggag gaggtggcac ctgggggcgc ccacgccacg ctcagcctga gtatcccccg  1980
cgtcgcgccc gagcacgagg gccactatgt gtgcgaagtg caagaccggc gcagccatga  2040
caagcactgc cacaagaagt acctgtcggt gcaggccctg gaagcccctc ggctcacgca  2100
gaacttgacc gacctcctgg tgaacgtgag cgactgctgg agatgcagt gcttggtggc  2160
cggagcgcac gcgccagca tcgtgttggta caaagacgaa gggctgctgg agcaaaagtc  2220
tggagtcgac ttggcggact ccaaccagaa gctgagcatc cagcgcgtgc gcgaggagga  2280
tgcgggacgc tatctgtgca gcgtgtgcaa cgccaagggc tgcgtcaact cctccgccag  2340
cgtggccgtg gaaggctccg aggataaggg cagcatggaa atcgtgatcc ttgtcggtac  2400
cggcgtcatc gctgtcttct tctgggtcct cctcctcctc atcttctgta acatgaggag  2460
gccgccccac gcagacatca gacgggcta cctgtccatc atcatggacc ccgggaggt  2520
gcctctggag gagcaatgcg aatacctgtc ctacgatgcc agccagtggg aattccccg  2580
agagcggctg cacctgggga gagtgctcgg ctacggcgcc ttcgggaagg tggtggaagc  2640
ctccgctttc ggcatccaca agggcagcag ctgtgacacc gtggccgtga aaatgctgaa  2700
agagggcgcc acgccagcg agcaccgcgc gctgatgtcg gagctcaaga tcctcattca  2760
catcggcaac caccctcaacg tggtcaacct cctcggggcg tgcaccaagc cgcagggccc  2820
```

-continued

```
cctcatggtg atcgtggagt tctgcaagta cggcaacctc tccaacttcc tgcgcgccaa 2880
gcgggacgcc ttcagcccct gcgcggagaa gtctcccgag cagcgcgac gcttccgcgc 2940
catggtggag ctcgccaggc tggatcggag gcggccgggg agcagcgaca gggtcctctt 3000
cgcgcggttc tcgaagaccg agggcggagc gaggcgggct tctccagacc aagaagctga 3060
ggacctgtgg ctgagcccgc tgaccatgga agatcttgtc tgctacagct tccaggtggc 3120
cagagggatg gagttcctgg cttcccgaaa gtgcatccac agagacctgg ctgctcggaa 3180
cattctgctg tcggaaagcg acgtggtgaa gatctgtgac tttggccttg cccgggacat 3240
ctacaaagac cccgactacg tccgcaaggg cagtgcccgg ctgcccctga gtggatggc 3300
ccctgaaagc atcttcgaca aggtgtacac cacgcagagt gacgtgtggt cctttgggt 3360
gcttctctgg gagatcttct ctctggggc ctccccgtac cctggggtgc agatcaatga 3420
ggagttctgc cagcggctga gagacgggca aaggatgagg gccccggagc tggccactcc 3480
cgccatacgc cgcatcatgc tgaactgctg gtccggagac cccaaggcga gacctgcatt 3540
ctcggagctg gtggagatcc tggggacct gctccagggc aggggcctgc aagaggaaga 3600
ggaggtctgc atggcccgc gcagctctca gagctcagaa gagggcagct tctcgcaggt 3660
gtccaccatg gccctacaca tcgcccagc tgacgctgag gacagcccgc caagcctgca 3720
gcgccacagc ctggccgcca ggtattacaa ctgggtgtcc tttcccgggt gcctggccag 3780
aggggctgag acccgtggtt cctccaggat gaagacattt gaggaattcc ccatgacccc 3840
aacgacctac aaaggctctg tggacaacca gacagacgt gggatggtgc tggcctcgga 3900
ggagtttgag cagatagaga gcaggcatag acaagaaagc ggcttcagag gaaccaggag 3960
gacaagagga gcatgaaagt ggacaaggag tgtgaccact gaagcaccac agggaggggt 4020
taggcctccg gatgactgcg ggcaggcctg gataatatcc agcctccac aagaagctgg 4080
tggagcagag tgttccctga ctcctccaag gaaagggag cgcccttca tggtctgctg 4140
agtaacaggt gccttcccag acactggcgt tactgcttga ccaaagagcc ctcaagcggc 4200
ccttatgcca gcgtgacaga gggctcacct cttgccttct aggtcacttc tcacaatgtc 4260
ccttcagcac ctgaccctgt gcccaccagt tattccttgg taatatgagt aatacatcaa 4320
agagtagtat taaaagctaa ttaatcatgt ttatactaa 4359

SEQ ID NO: 41        moltype = AA  length = 1306
FEATURE              Location/Qualifiers
source               1..1306
                     mol_type = protein
                     organism = Homo sapiens
SEQUENCE: 41
MQRGAALCLR LWLCLGLLDG LVSGYSMTPP TLNITEESHV IDTGDSLSIS CRGQHPLEWA   60
WPGAQEAPAT GDKDSEDTGV VRDCEGTDAR PYCKVLLLHE VHANDTGSYV CYYKYIKARI  120
EGTTAASSYV FVRDFEQPFI NKPDTLLVNR KDAMWVPCLV SIPGLNVTLR SQSSVLWPDG  180
QEVVWDDRRG MLVSTPLLHD ALYLQCETTW GDQDFLSNPF LVHITGNELY DIQLLPRKSL  240
ELLVGEKLVL NCTVWAEFNS GVTFDWDYPG KQAERGKWVP ERRSQQTHTE LSSILTIHNV  300
SQHDLGSYVC KANNGIQRFR ESTEVIVHEN PFISVEWLKG PILEATAGDE LVKLPVKLAA  360
YPPPEFQWYK DGKALSGRHS PHALVLKEVT EASTGTYTLA LWNSAAGLRR NISLELVVNV  420
PPQIHEKEAS SPSIYSRHSR QALTCTAYGV PLPLSIQWHW RPWTPCKMFA QRSLRRRQQQ  480
DLMPQCRDWR AVTTQDAVNP IESLDTWTEF VEGKNKTVSK LVIQNANVSA MYKCVVSNKV  540
GQDERLIYFY VTTIPDGFTI ESKPSEELLE GQPVLLSCQA DSYKYEHLRW YRLNLSTLHD  600
AHGNPLLLDC KNVHLFATPL AASLEEVAPG ARHATLSLSI PRVAPEHEGH YVCEVQDRRS  660
HDKHCHKKYL SVQALEAPRL TQNLTDLLVN VSDSLEMQCL VAGAHAPSIV WYKDERLLEE  720
KSGVDLADSN QKLSIQRVRE EDAGRYLCSV CNAKGCVNSS ASVAVEGSED KGSMEIVILV  780
GTGVIAVFFW VLLLLIFCNM RRPAHADIKT GYLSIIMDPG EVPLEEQCEY LSYDASQWEF  840
PRERLHLGRV LGYGAFGKVV EASAFGIHKG SSCDTVAVKM LKEGATASEH RALMSELKIL  900
IHIGNHLNVV NLLGACTKPQ GPLMVIVEFC KYGNLSNFLR AKRDAFSPCA EKSPEQRGRF  960
RAMVELARLD RRRPGSSDRV LFARFSKTEG GARRASPDQE AEDLWLSPLT MEDLVCYSFQ 1020
VARGMEFLAS RKCIHRDLAA RNILLSESDV VKICDFGLAR DIYKDPDYVR KGSARLPLKW 1080
MAPESIFDKV YTTQSDVWSF GVLLWEIFSL GASPYPGVQI NEEFCQRLRD GTRMRAPELA 1140
TPAIRRIMLN CWSGDPKARP AFSELVEILG DLLQGRGLQE EEEVCMAPRS SQSSEEGSFS 1200
QVSTMALHIA QADAEDSPPS LQRHSLAARY YNWVSFPGCL ARGAETRGSS RMKTFEEFPM 1260
TPTTYKGSVD NQTDSGMVLA SEEFEQIESR HRQESGFRGT RRTRGA                1306

SEQ ID NO: 42        moltype = DNA  length = 1353
FEATURE              Location/Qualifiers
misc_feature         1..1353
                     note = source = /note="Description of Artificial Sequence:
                     Synthetic polynucleotide"
source               1..1353
                     mol_type = other DNA
                     organism = synthetic construct
SEQUENCE: 42
atgtaccgga tgcagctgct gagctgtatc gccctgtctc tggccctggt caccaattct   60
agcgataccg gcagaccctt cgtggaaatg tacagcgaga tccccgagat catccacatg  120
accgagggca gagagctggt catccctgc agagtgacaa gccccaacac caccgtgact  180
ctgaagaagt tccctctgga cactgatc ccgacgtca agagaatcat ctgggacag  240
cggaagggct tcatcatcag caacgccacc tacaaagaga tcggcctgct gacctgtgaa  300
gccaccgtga atgccaccct gtacaagacc aactacctga cacacagaca gaccaacacc  360
atcatcgacg tggtgctgag ccctagccac ggcattgaac tgtctgtggg cgagaagctg  420
gtgctgaact gtaccgccag aaccgagctg aacgtgggca tcgacttcaa ctgggagtac  480
cccagcagca gcaaccagca caagaaactg cagtgaaaac ccagagcgtg  540
agcgagatga agaaattcct gagcaccctg accatcgacg gcgtgaccag atctgaccag  600
ggcctgtaca catgtgccgc cagctctggc ctgatgacca gaaaaacag caccttcgtg  660
cgggtgcacg agaaggacaa gacccacacc tgtcctccat gtcctgctcc agaactgctc  720
gcggaccttt ccgtgttcct gtttcctcca agcctaagg acaccctgat gatcagcaga  780
accccttgaag tgacctgcgt ggtggtggat gtgtcccacg aggatccga agtgaagttc  840
```

```
aattggtacg tggacggcgt ggaagtgcac aacgccaaga ccaagcctag agaggaacag   900
tacaatagca cctacagagt ggtgtccgtg ctgaccgtgc tgcaccagga ttggctgaac   960
ggcaaagagt acaagtgcaa ggtgtccaac aaggccctgc ctgctcctat cgagaaaacc  1020
atctccaagg ccaggggcca gcctaggaa ccccaggttt acacactgcc tccaagcagg  1080
gacgagctga caaagaacca ggtgtccctg acctgcctgg tcaagggctt ctacccttcc  1140
gatatcgccg tggaatggga gagcaatggc cagcctgaga caactacaa gacaacccct  1200
cctgtgctgg acagcgacgg ctcattcttc ctgtacagca agctgacagt ggacaagagc  1260
agatggcagc agggcaacgt gttcagctgc agcgtgatgc acgaggccct gcacaaccac  1320
tacacccaga agtccctgag cctgtctcct gga                                1353

SEQ ID NO: 43          moltype = AA   length = 451
FEATURE                Location/Qualifiers
REGION                 1..451
                       note = source = /note="Description of Artificial Sequence:
                       Synthetic polypeptide"
source                 1..451
                       mol_type = protein
                       organism = synthetic construct
SEQUENCE: 43
MYRMQLLSCI ALSLALVTNS SDTGRPFVEM YSEIPEIIHM TEGRELVIPC RVTSPNITVT    60
LKKFPLDTLI PDGKRIIWDS RKGFIISNAT YKEIGLLTCE ATVNGHLYKT NYLTHRQTNT   120
IIDVVLSPSH GIELSVGEKL VLNCTARTEL NVGIDFNWEY PSSKHQHKKL VNRDLKTQSG   180
SEMKKFLSTL TIDGVTRSDQ GLYTCAASSG LMTKKNSTFV RVHEKDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP G                                  451

SEQ ID NO: 44          moltype = AA   length = 431
FEATURE                Location/Qualifiers
REGION                 1..431
                       note = source = /note="Description of Artificial Sequence:
                       Synthetic polypeptide"
source                 1..431
                       mol_type = protein
                       organism = synthetic construct
SEQUENCE: 44
SDTGRPFVEM YSEIPEIIHM TEGRELVIPC RVTSPNITVT LKKFPLDTLI PDGKRIIWDS    60
RKGFIISNAT YKEIGLLTCE ATVNGHLYKT NYLTHRQTNT IIDVVLSPSH GIELSVGEKL   120
VLNCTARTEL NVGIDFNWEY PSSKHQHKKL VNRDLKTQSG SEMKKFLSTL TIDGVTRSDQ   180
GLYTCAASSG LMTKKNSTFV RVHEKDKTHT CPPCPAPELL GGPSVFLFPP KPKDTLMISR   240
TPEVTCVVVD VSHEDPEVKF NWYVDGVEVH NAKTKPREEQ YNSTYRVVSV LTVLHQDWLN   300
GKEYKCKVSN KALPAPIEKT ISKAKGQPRE PQVYTLPPSR DELTKNQVSL TCLVKGFYPS   360
DIAVEWESNG QPENNYKTTP PVLDSDGSFF LYSKLTVDKS RWQQGNVFSC SVMHEALHNH   420
YTQKSLSLSP G                                                        431

SEQ ID NO: 45          moltype = DNA   length = 145
FEATURE                Location/Qualifiers
misc_feature           1..145
                       note = source = /note="Description of Artificial Sequence:
                       Synthetic polynucleotide"
source                 1..145
                       mol_type = other DNA
                       organism = synthetic construct
SEQUENCE: 45
ttggccactc cctctctgcg cgctcgctcg ctcactgagg ccgccgggc aaagcccggg     60
cgtcgggcga cctttggtcg cccggcctca gtgagcgagc gagcgcgcag agagggagtg   120
gccaactcca tcactagggg ttcct                                          145

SEQ ID NO: 46          moltype = DNA   length = 145
FEATURE                Location/Qualifiers
misc_feature           1..145
                       note = source = /note="Description of Artificial Sequence:
                       Synthetic polynucleotide"
source                 1..145
                       mol_type = other DNA
                       organism = synthetic construct
SEQUENCE: 46
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120
gagcgcgcag agagggagtg gccaa                                          145

SEQ ID NO: 47          moltype = DNA   length = 119
FEATURE                Location/Qualifiers
misc_feature           1..119
                       note = source = /note="Description of Artificial Sequence:
                       Synthetic polynucleotide"
source                 1..119
                       mol_type = other DNA
```

```
                           organism = synthetic construct
SEQUENCE: 47
ctgcgcgctc gctcgctcac tgaggccgcc cgggcgtcgg gcgacctttg gtcgcccggc    60
ctcagtgagc gagcgagcgc gcagagaggg agtggccaac tccatcacta ggggttcct    119

SEQ ID NO: 48              moltype = DNA   length = 130
FEATURE                    Location/Qualifiers
misc_feature               1..130
                           note = source = /note="Description of Artificial Sequence:
                             Synthetic polynucleotide"
source                     1..130
                           mol_type = other DNA
                           organism = synthetic construct
SEQUENCE: 48
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120
gagcgcgcag                                                           130

SEQ ID NO: 49              moltype = DNA   length = 279
FEATURE                    Location/Qualifiers
misc_feature               1..279
                           note = source = /note="Description of Artificial Sequence:
                             Synthetic polynucleotide"
source                     1..279
                           mol_type = other DNA
                           organism = synthetic construct
SEQUENCE: 49
gtcgaggtga gccccacgtt ctgcttcact ctccccatct ccccccctc cccaccccca     60
attttgtatt tatttatttt ttaattattt tgtgcagcga tggggcggg gggggggggg    120
gggcgcgcgc caggcgggc ggggcggggc gaggggcggg gcggggcgag gcggagaggt    180
gcggcggcag ccaatcagag cggcgcgctc cgaaagtttc cttttatggc gaggcggcgg   240
cggcggcggc cctataaaaa gcgaagcgcg cggcgggcg                          279

SEQ ID NO: 50              moltype = DNA   length = 277
FEATURE                    Location/Qualifiers
misc_feature               1..277
                           note = source = /note="Description of Artificial Sequence:
                             Synthetic polynucleotide"
source                     1..277
                           mol_type = other DNA
                           organism = synthetic construct
SEQUENCE: 50
gtcgaggtga gccccacgtt ctgcttcact ctccccatct ccccccctc cccaccccca     60
attttgtatt tatttatttt ttaattattt tgtgcagcga tggggcggg gggggggggg    120
gcgcgcgcca ggcggggcgg ggcggggcga gggcggggc gggcgaggc ggagaggtgc    180
ggcggcagcc aatcagagcg gcgcgctccg aaagtttcct tttatggcga ggcggcgcg   240
gcggcggccc tataaaagc gaagcgcgcg gcgggcg                             277

SEQ ID NO: 51              moltype = DNA   length = 660
FEATURE                    Location/Qualifiers
misc_feature               1..660
                           note = source = /note="Description of Artificial Sequence:
                             Synthetic polynucleotide"
source                     1..660
                           mol_type = other DNA
                           organism = synthetic construct
SEQUENCE: 51
gacattgatt attgactagt tattaatagt aatcaattac ggggtcatta gttcatagcc    60
catatatgga gttccgcgtt acataactta cggtaaatgg cccgcctggc tgaccgccca   120
acgaccccg cccattgacg tcaatgaatga cgtatgttcc catagtaacg ccaataggga  180
ctttccattg acgtcaatgg gtggactatt tacggtaaac tgcccacttg gcagtacatc   240
aagtgtatca tatgccaagt acgccccta ttgacgtcaa tgacggtaaa tggcccgcct    300
ggcattatgc ccagtacatg accttatggg acttcctac ttggcagtac atctacgtat   360
tagtcatcgc tattaccatg gtcgaggtg agccccacgt tctgcttcac tctccccatc   420
tccccccct ccccacccc aattttgtat tatttatttt ttaattatt ttgtgcagcg    480
atggggcgg ggggggggg gggcgcgcgc caggcgggg cggggcgggg cgaggggcgg    540
ggcggggcga ggcggagagg tgcggcggca gccaatcaga gcggcgcgct ccgaaagttt   600
cctttatgg cgaggcggcg gcggcggcgg ccctataaaa agcgaagcgc gcggcgggcg   660

SEQ ID NO: 52              moltype = DNA   length = 658
FEATURE                    Location/Qualifiers
misc_feature               1..658
                           note = source = /note="Description of Artificial Sequence:
                             Synthetic polynucleotide"
source                     1..658
                           mol_type = other DNA
                           organism = synthetic construct
SEQUENCE: 52
gacattgatt attgactagt tattaatagt aatcaattac ggggtcatta gttcatagcc    60
```

```
catatatgga gttccgcgtt acataactta cggtaaatgg cccgcctggc tgaccgccca    120
acgaccccg  cccattgacg tcaataatga cgtatgttcc catagtaacg ccaataggga    180
ctttccattg acgtcaatgg gtggactatt tacggtaaac tgcccacttg gcagtacatc    240
aagtgtatca tatgccaagt acgccccta  ttgacgtcaa tgacggtaaa tggcccgcct    300
ggcattatgc ccagtacatg accttatggg actttcctac ttggcagtac atctacgtat    360
tagtcatcgc tattaccatg gtcgaggtg  agccccacgt tctgcttcac tctccccatc    420
tccccccct  ccccacccc  aattttgtat ttatttattt tttaattatt ttgtgcagcg    480
atggggggcgg gggggggggg ggcgcgcgcc aggcggggcg gggcggggcg aggggcgggg    540
cggggcgagg cggagaggtg cggcggcagc caatcagagc ggcgcgctcc gaaagtttcc    600
ttttatggca aggcggcggc ggcggcggcc ctataaaaag cgaagcgcgc ggcgggcg      658

SEQ ID NO: 53            moltype = DNA   length = 1673
FEATURE                  Location/Qualifiers
misc_feature             1..1673
                         note = source = /note="Description of Artificial Sequence:
                         Synthetic polynucleotide"
source                   1..1673
                         mol_type = other DNA
                         organism = synthetic construct
SEQUENCE: 53
gacattgatt attgactagt tattaatagt aatcaattac ggggtcatta gttcatagcc     60
catatatgga gttccgcgtt acataactta cggtaaatgg cccgcctggc tgaccgccca    120
acgaccccg  cccattgacg tcaataatga cgtatgttcc catagtaacg ccaataggga    180
ctttccattg acgtcaatgg gtggactatt tacggtaaac tgcccacttg gcagtacatc    240
aagtgtatca tatgccaagt acgccccta  ttgacgtcaa tgacggtaaa tggcccgcct    300
ggcattatgc ccagtacatg accttatggg actttcctac ttggcagtac atctacgtat    360
tagtcatcgc tattaccatg gtcgaggtg  agccccacgt tctgcttcac tctccccatc    420
tccccccct  ccccacccc  aattttgtat ttatttattt tttaattatt ttgtgcagcg    480
atggggggcgg gggggggggg ggggcgcgcg ccaggcgggg cggggcgggg cgaggggcgg    540
ggcggggcga ggcggagagg tgcggcggca gccaatcaga gcggcgcgct ccgaaagttt    600
ccttttatgg cgaggcggcg gcgcggcggcg ccctataaaa agcgaagcgc gcggcgggcg    660
ggagtcgctg cgttgccttc gccccgtgcc ccgctccgcg ccgcctcgcg ccgcccgccc    720
cggctctgac tgaccgcgtt actcccacag gtgagcgggc gggacggccc ttctcctccg    780
ggctgtaatt agcgcttggt ttaatgacgg ctcgtttctt ttctgtggct gcgtgaaagc    840
cttaaagggc tccggagggc ccctttgtgc ggggggagcg ggctcgggg tgcgtgcgt     900
gtgtgtgtgc gtggggagcg ccgcgtgcg  cccgcgctgc ccgcggcgct gagcgctgc    960
gggcgcggcg cggggcttg  tgcgctccgc gtgtgcgcga gggagcgcg  gccggggcg    1020
gtgccccgcg gtgcgggggg gctgcgaggg gaacaaaggc tgcgtgcggg gtgtgtgcgt   1080
ggggggcgtga gcagggggtg tgggcggcgg gtcggccgg  taaccccccc ctgcacccc   1140
ctccccgagt tgctgagcac ggcccggctt cgggtgcggg gctccgtgcg gggcgtggcg   1200
cggggctcgc cgtgccgggc gggggtggc  ggcaggtggg ggtgccgggc ggggcggggc   1260
cgcctcgggc cggagggc   tcggggagg  ggcgcggcg  ccccggagc gccggcggct   1320
gtcgaggcgc ggcgagccgc agccattgcc ttttatggta atcgtgcgga agggcgcagg   1380
gacttcctttt gtcccaaatc tgtgcggagc cgaaatctgg gaggcgccgc cgcacccct   1440
ctagcgggcg cggggcgaag cggtgcggcg ccggcaggaa ggaaatgggc ggggagggcc   1500
ttcgtgcgtc gccgcgccgc cgtccccttc tccctctcca gcctcgggc  tgtccgcggg   1560
gggacggctg ccttcggggg gacgggggca gggcggggtt cggcttctgg cgtgtgaccg   1620
gcggctctag agcctctgct aaccatgttc atgccttctt cttttcccta cag         1673

SEQ ID NO: 54            moltype = DNA   length = 1671
FEATURE                  Location/Qualifiers
misc_feature             1..1671
                         note = source = /note="Description of Artificial Sequence:
                         Synthetic polynucleotide"
source                   1..1671
                         mol_type = other DNA
                         organism = synthetic construct
SEQUENCE: 54
gacattgatt attgactagt tattaatagt aatcaattac ggggtcatta gttcatagcc     60
catatatgga gttccgcgtt acataactta cggtaaatgg cccgcctggc tgaccgccca    120
acgaccccg  cccattgacg tcaataatga cgtatgttcc catagtaacg ccaataggga    180
ctttccattg acgtcaatgg gtggactatt tacggtaaac tgcccacttg gcagtacatc    240
aagtgtatca tatgccaagt acgccccta  ttgacgtcaa tgacggtaaa tggcccgcct    300
ggcattatgc ccagtacatg accttatggg actttcctac ttggcagtac atctacgtat    360
tagtcatcgc tattaccatg gtcgaggtg  agccccacgt tctgcttcac tctccccatc    420
tccccccct  ccccacccc  aattttgtat ttatttattt tttaattatt ttgtgcagcg    480
atggggggcgg gggggggggg ggcgcgcgcc aggcggggcg gggcggggcg aggggcgggg    540
cggggcgagg cggagaggtg cggcggcagc caatcagagc ggcgcgctcc gaaagtttcc    600
ttttatggca aggcggcggc ggcggcggcc ctataaaaag cgaagcgcgc ggcgggcg      660
agtcgctgcg ttgccttcgc cccgtgcccc gctccgcgcc gcctcgcgcc ccgcccc      720
gctctgactg accgcgttac tcccacaggt gagcgggcgg gacggccctt ctcctcgggg    780
ctgtaattag cgcttggttt aatgacggct cgtttctttt ctgtggctgc gtgaaagcct    840
taaagggctc cggagggccc tttgtgcggg gggagcgctc ggggggtgcgt gcgtgt       900
gtgtgtgcgt ggggagcgcc gcgtgcggcc cgcgctgccc gcggcgctga gcgctgcg      960
gcgcggcgcg gggctttgtc gctccgcgtg tgcgagggag cgcggccggg gcggt        1020
gccccgcgtg cgggggggct gcagggggac aaaaggctgc gtgcgggtgt gtgcgtgg     1080
ggggtgagca gggggtgtgg gcgcggcggt cggctgtaa cccccccctg cacccccct    1140
ccccgagttg ctgagcacgg cccggcttcg ggtgcgggcc tccgtgcggg gcggtggcgcg   1200
gggctcgccc tgccgggcgg ggggtggcgg caggtggggg tgccggggcg ggcggggccg   1260
```

```
cctcgggccg gggagggctc ggggagggg cgcggcggcc cccggagcgc cggcggctgt   1320
cgaggcgcgg cgagccgcag ccattgcctt ttatggtaat cgtgcgagag ggcgcaggga   1380
cttcctttgt cccaaatctg tgcggagccg aaatgtggga ggcgccgccg cacccctct    1440
agcgggcgcg gggcgaagcg gtgcggcgcc ggcaggaagg aaatgggcgg ggagggcctt   1500
cgtgcgtcgc cgcgccgccg tccccttctc cctctccagc ctcggggtcg tccgcggggg   1560
gacggctgcc ttcgggggg acggggcagg gcggggttcg gcttctggcg tgtgaccggc    1620
ggctctagag cctctgctaa ccatgttcat gccttcttct tttcctaca g             1671

SEQ ID NO: 55          moltype = DNA   length = 1725
FEATURE                Location/Qualifiers
source                 1..1725
                       mol_type = other DNA
                       organism = Homo sapiens
SEQUENCE: 55
ctatggagtt tgcataacaa acgtttggca gctcgctctc ttacactcca ttaacaagct     60
gtaacatata gctgcaggtt gctataatct cattaatatt ttggaaactt gaatattgag    120
tatttctgag tgctcattcc ccatatgcca gccacttctg ccatgctgac tggttccttt    180
ctctccatta ttagcaatta gcttcttacc ttccaaagtc agatccaagg tatccaagat    240
actagcaaag gaatcaacta tgtgtgcaag ttaagcatgc ttaatatcac ccaaacaaac    300
aaaagaggcag catttcttaa agtaatgaag atagataaat cgggtagtc ctttgcgaca    360
ctgctggtgc tttctagagt tttatatatt ttaagcagct tgctttatat tctgtctttg    420
cctcccaccc caccagcact tttatttgtg gagggtttg gctcgccaca ctttgggaaa     480
cttatttgat ttcacggaga gctgaaggaa gatcattttt ggcaacagac aagtttaaac    540
acgatttcta tgggacattg ctaactgggg cccctaaagga gaaagggaa actgagcgga    600
gaatgggtta aatccttgga agcagggag aggcaggga ggagagaagt cggaggagta     660
taaagaaaag gacaggaacc aagaagcgtg ggggtggtt gccgtaatgt gagtgtttct    720
taattagaga acgttgaca atagagggtc tggcagagc tcctggccgc ggtgcggagc     780
gtctggagcg gagcacgcgc tgtcagctgg tgagcgcact ctcctttcag gcagctcccc    840
ggggagctgt gcgccacat ttaacaccat catcaccct ccccggcctc ctcaacctcg     900
gcctcctcct cgtcgacagc cttccttggc ccccaccagc agagctcaca gtagcgacgc    960
tctctcgccg tctcccgcac tcggccgggg cctctctcct cccccagctg cgcagcggga   1020
gccgccactg cccactgcac ctccagcaa ccagcccagc acgcaaagaa gctgcgcaaa   1080
gttaaagcca agcaatgcca aggggagggg aagctggagg cgggctttga gtggcttctg   1140
ggcgcctggc gggtccagaa tcgcccagag ccgcccgcgg tcgtgcacat ctgaccgag    1200
tcagcttggg caccagccga gagccggctc cgcaccgctc ccgcaccca gcgcgcgggg   1260
tggtgacaca caccggagtc gaattacagc cctgcaatta acatatgaat ctgacgaatt   1320
taaaagaagg aaaaaaaaaa aaaacctga gcaggcttgg gagtcctctg cacacaagaa   1380
cttttctcgg ggtgtaaaaa ctctttgatt ggctgctcgc acgcgcctgc ccgcgccctc   1440
cattgctgca gaagacacgc gaccggcgcg aggagggt tgggagagga acgggggag    1500
actgagtggc gcgtgccgct ttttaaaggg gcgcagcgcc ttcagcaacc ggagaagcat   1560
agttgcacgc gacctggtgt gtgatctccg agtgggtggg ggagggtcga ggagggaaaa   1620
aaaaataaga cgttgcagaa gagacccgga aagggccttt ttttggttg agctggtgtc    1680
ccagtgctgc ctccgatcct gagcctccga gcctttgcag tgcaa                   1725

SEQ ID NO: 56          moltype = DNA   length = 60
FEATURE                Location/Qualifiers
source                 1..60
                       mol_type = other DNA
                       organism = Homo sapiens
SEQUENCE: 56
ctgccttctg agagcgctat aaaggcagcg gaagggtagt ccgcggggca ttccgggcgg    60

SEQ ID NO: 57          moltype = DNA   length = 60
FEATURE                Location/Qualifiers
source                 1..60
                       mol_type = other DNA
                       organism = Homo sapiens
SEQUENCE: 57
ctctaggcgg gctctgctct tctttaagga gtcccacagg gcctggcccg cccctgacct    60

SEQ ID NO: 58          moltype = DNA   length = 2000
FEATURE                Location/Qualifiers
source                 1..2000
                       mol_type = other DNA
                       organism = Homo sapiens
SEQUENCE: 58
taaagagttg tgagttgtgt aggtgagttg ccatggagct acaaatatga gttgatattc     60
tgaaatccta gacagccatc tccaaggtta agaaaaatcc ttatgcactc acttgcaaag    120
atatccacag catgctctta atggagaaaa acaaagcctt agatcaaata tgtaaagtaa    180
ttttttagttt tttgaaaagg tatgtttggg ctatagataa atctgttcaa aaaacatgag   240
agaagataat aatggttgaa aggagacaca gtgcttgccc tcaagaagtt tttgtctagt    300
gagggagaga gaacttgtat gtaaataaaa ttgtgttact aaggtagata gtgagaagta    360
acttaagaga ggatcagata aggtattaag agaaatacaga aagggtctg gattaattct    420
gaacagcatc aaagaatgtt cttgcaagag atagtgtttt caccagatct tgaaggtatg    480
gatgagggta tacagagtga gtatattcag attctacttt aaaacaaata ctttcctctg    540
ttgtagtgga gttgagctat acatccaaca ataatgaaaa aatacacgca tatatacata    600
tatgagagag gatacatatt ttagtacatg tagcaattga ttaataaatg tacagtttaa    660
gtcgcatgca aaaccttgga gtgatagcaa acttcattgt aggatgttta gcagcatctc    720
tggtctctac tcactagatc ccaatagcat ctccctaggt gtgacaacca aaatgtctc     780
```

```
caggcattga cctctggagg caaaaaaagc cctttattaa gaaccagtgg tatacataag    840
taaaacatac acaagagatt cctccctct tctctgtatg tgaataaaaa ttgcaaagtt    900
catgacctgg attttccttt taggtttctt ctttagtggt tcttaacttc attgggtgaa    960
gtaagccttt gaagatctgt tgaaagctgt tgactcattc acttctcagg aaaacgcaca   1020
tgctgactac catttcagag aatttgcatc agggttctct ggggaggagt tctgagttct   1080
gtttccagga gctcgtagaa ttgtcatggt ctgcatatgc aaggcaggtg gattacggaa   1140
ggttgatgta cagaggtctg tattttggag cctcttctgt atttacttca gaacactaac   1200
aatcaggcga gaatgttctg gtttatcaaa cccttccttc tgcctttcat cttaaccatg   1260
cattagtttt aacaaagttc atcccaacag aagacaaaac actgatgagg taggatagct   1320
ccagctcctc ctccctctct tctagtcttg atttccatgt agtccagttt attccttccc   1380
tgattgtcca ggagaatgag aaaaagaaaa aacagagtct agtgggtaag aaagggccac   1440
ctggacggct tgatttggat tgtgaaataa acacacaca catgcacacg tagaataagt   1500
ggctaaaatc tgagtaaatc gtgaactctc tgtatcctcc acccattgaa tactcctaaa   1560
agactttcta gaaattcaag gacttattaa tatagaaacc tggccattgt tcctcttctc   1620
ctccccatgt ggtatgagag cacctgtggc aggctcccag agaccacgga cctcttcctc   1680
taggcgggct ctgctcttct ttaaggagtc ccacagggcc tggcccgccc ctgacctcgc   1740
aaccccttgag attagtaacg ggatgagtga ggatccgggt ggccctgcg tggcagccag    1800
taagagtctc agccttcccg gttcgggaaa ggggaagaat gcaggagggg taggatttct   1860
ttcctgatag gatcggttgg gaaagaccgc agcctgtgtg tgtctttccc ttcgaccaag   1920
gtgtctgttg ctccgtaaat aaaacgtccc actgccttct gagagcgcta taaaggcagc   1980
ggaagggtag tccgcggggc                                              2000

SEQ ID NO: 59          moltype = DNA   length = 1400
FEATURE                Location/Qualifiers
source                 1..1400
                       mol_type = other DNA
                       organism = Homo sapiens
SEQUENCE: 59
ggctgctcgg aaaacaggac gaggggagag acttgctcaa taagctgaaa gttctgcccc    60
cgagagggct gcgacagctg ctggaatgtg cctgcagcgt ccgcctcttg gggaccgcg    120
gagcgcgccc tgacggttcc acgcctggcc cggggtctg cacctctcct ccagtgctga   180
cctggagctg cgtcccgggt caggtgcggg gagggaggga atctcagtgt cccccttccag   240
ccttgcaagc gcctttggcc cctgccccag cccctcggtt tggggagat ttcagaacgc    300
ggacagcgcc ctggctgcgg gccataggg actgggtgga actcgggagg cccccagagc   360
aggggcttac tcgcttcaag tttggggaac cccgggcagc gggtgcaggc cacgagaccg   420
gaaggttctc aggtgccccc ctgcaggctg gccgtgcgcg ccgtggggcg cttgtcgcga   480
gcgccgaggc ctgcaggacg cggaccagac tcgcggtgca ggggggcctg gctgcagcta   540
acaggtgatc ccgttctttc tgttcctcgc tcttcccctc cgatcgtcct cgcttaccgc   600
gtgtcctccc tcctcgctgt cctctggctc gcaggtcatg gcagcgccag gcggcaggtc   660
ggagccgccg cagctccccg agtacagctg cagctacatg gtgtcgcggc cggtctacag   720
cgagctcgct ttccagcaac agcacgagcg gcgcctgcag gagcgcaaga cgctgcggga   780
gagcctggcc aagtgctgca ggtagcggcc gcgcgggcct gcgtagagag aagcggagcg   840
gggcgtccac gccttgggga gggaaggggcg tccccagagg agtcagtgtgg ggtgcgggcg   900
gcggagcccc tgggcgccag ctgcttctcc cagaggcccg actttcggtc tccggtcctc   960
cacgccgccc ttctggtggg agggtggctc catcagtctc gggcccgaaa tgaacttacc   1020
tgggaaactc gcctttgggg agagtgggtt ctaggagccc cgtctctctt tttcctctct   1080
gaaggaaact tggagtgcct cttggggtac agtgggtccc tgttgccttc ttgggagctt   1140
gtttaaatga aatgaatagg gaaacccagc tcttgaccag gaggagtcct tgaaacactc   1200
aagctaagta ggcgggctac cattcagtta gagaccagga tgcaagctag aacccagggg   1260
agcgcggggt gtgccaagta cttcatcagc aggctgtggg acccctgggg aaagccaccc   1320
tcagtctcta aacccaaaca tgccgtaact agatgtcaca aacataaaga aattagagtt   1380
tctaaaacct ttcattatag                                              1400

SEQ ID NO: 60          moltype = DNA   length = 900
FEATURE                Location/Qualifiers
source                 1..900
                       mol_type = other DNA
                       organism = Homo sapiens
SEQUENCE: 60
cggaaggttg atgtacagag gtctgtattt tggagcctct tctgtattta cttcagaaca    60
ctaacaatca ggcgagaatg ttctggttta tcaaaccctt ccttctgcct ttcatcttaa   120
ccatgcatta gttttaacaa agttcatccc aacagaagac aaaacactga tgaggtagga   180
tagctccagc tcctcctccc tctcttctag tcttgatttc catgtagtcc agtttattcc   240
ttccctgatt gtccaggaga atgagaaaaa gaaaaaacac agagtctagt gggtaagaagg   300
gccacctgga cggcttgatt tggattgtga aataaaacac acacatgc acacgtagaa   360
taagtggcta aaatctgagt aaatcgtgaa ctctctgtat cctcacccca ttgaatactc   420
ctaaaagact ttctagaaat tcaaggactt attaatatag aaacctggcc attgttcctc   480
ttctcctccc catgtggtat gagagcacct gtggcaggct cccagagacc acggacctct   540
tcctctaggc gggctctgct cttctttaag gagtcccaca gggcctggcc cgcccgctgac   600
ctcgcaaccc ttgagattag taacgggatg agtgaggatc cgggtggccc ctgcgtggca   660
gccagtaaga gtctcagcct tcccggttcg ggaaagggga agaatgcagg aggggtagga   720
tttctttcct gataggatcg gttgggaaag accgcagcct gtgtgtgtct ttcccttcga   780
ccaaggtgtc tgttgctccg taaataaaac gtccactgc cttctgagag cgctataaag    840
gcagcggaag ggtagtccgc ggggcattcc gggcggggc cgagcagaga caggtgagtt    900

SEQ ID NO: 61          moltype = DNA   length = 1269
FEATURE                Location/Qualifiers
source                 1..1269
                       mol_type = other DNA
```

```
                    organism = Homo sapiens
SEQUENCE: 61
agggctattt gtacctcaac gagggcttct ctccaagaaa gccctgaatc ctttccctcc    60
tttttcctgc agattcacta taggacactt tttgaagcaa gagcatgcat tttcccctg    120
gcgctctgca gcggttctca gagcccagtg tcactcacat aggtgggagt gctctcagtt   180
cagagagcgc tgggacactt aagatgaaaa gtccctggaa gttagcaaac agccatctgt   240
cactctggca tcgatttact aaaagtgact tctagggtat tctaaaccac ttttaaaaaa   300
caaatgagtc acttcgactt cctcaccccg caagagatag gaaggcagca gtggagtgct   360
cgctcaggag ctgtatttgt ttagcgatta gcctagagct ttgattttag ggcaaaagcg   420
agccagacag tgcggcagac gtaaggatca aaaaggccac ctatccattcg ccggggacgc   480
ctgcctcctt accctgataa cgtaactatt tctctgcata ggattttagt ttttgtgttt   540
ttgttttgtt ttattctgtt taatcacttc aagtatctca tccattattt gaagcgggct   600
cggaggaaac gtgccgcatc ctccagtcct tgtgcgtctg tttaggtctc tccgaagcag   660
gtccctctcg actcttagat ctgggtctcc agcacgcatg aagggtaag ggtggggggg    720
tcccctattc cggcgcgcgg cgttgagcac tgaatcttcc aggcggaggc tcagtggag    780
cgccgagaac tcgccagtac cgcgcgctgc ctgctgcctg ctgcctccca gcccaggact   840
tgggaaagga gggaggggac aagtggaggg aaagtggggc cgggcggggg gtgcctggga   900
agccaggctg cgctgacgtc actgggcgcg caattccggc tggagcgctt taaaaaacga   960
gcgtgcaagc agatgctgc ctccacaccg ctcaggccgc gagcagcagc aaggcgcacc   1020
gccactgtcg ccgctgcagc cagggctgct ccgaaggccg gcgtggcggc aaccggcacc   1080
tctgtccccg ccgcgcttct cctcgccgcc cacgccgtgg ggtcaggaac gcggcgtctg   1140
gcgctgcaga cgcccgctga gttgcagaag cccacggagc ggcgcccggc gcgccacggc   1200
ccgtagcagt ccggtgctgc tctccgcccg cgtccggctc gtggccccct acttcgggca   1260
ccgaccggt                                                          1269

SEQ ID NO: 62          moltype = DNA  length = 463
FEATURE                Location/Qualifiers
source                 1..463
                       mol_type = other DNA
                       organism = Homo sapiens
SEQUENCE: 62
tgcgtatgag tgcaagtggg ttttaggacc aggatgaggc ggggtggggg tgcctacctg    60
acgaccgacc ccgacccact ggacaagcac ccaacccca ttccccaaat tgcgcatccc    120
ctatcagaga gggggagggg aaacaggatg cggcgaggcg cgtgcgcact gccagcttca   180
gcaccgcgga cagtgccttc gccccgcct ggcggcgcgc gccaccgccg cctcagcact    240
gaaggcgcgc tgacgtcact cgccggtccc ccgcaaactc cccttccgg ccaccttggt    300
cgcgtccgcg ccgccgccgg cccagccgga ccgcaccacg cgaggcgcga datagggggg   360
cacgggcgcg accatctgcg ctgcggcgcc ggcgactcag cgctgcctca gtctgcggtg   420
ggcagcggag gagtcgtgtc gtgcctgaga gcgcagtcga gaa                     463

SEQ ID NO: 63          moltype = DNA  length = 2204
FEATURE                Location/Qualifiers
source                 1..2204
                       mol_type = other DNA
                       organism = Homo sapiens
SEQUENCE: 63
cccacctccc tctctgtgct gggactcaca gagggagacc tcaggaggca gtctgtccat    60
cacatgtcca aatgcagagc ataccctggg ctgggcgcag tggcgcacaa ctgtaattcc   120
agcactttgg gaggctgatg tggaaggatc acttgagccc agaagttcta gaccagcctg   180
ggcaacatgg caagaccta tctctacaaa aaaagttaaa aaatcagcca cgtgtggtga    240
cacacacctg tagtcccagc tattcaggag gctgaggtga ggggatcact taaggctgga   300
aggttgaggc tgcagtgagt cgtggttgcg ccactgcact ccagcctggg caacagtgag   360
accctgtctc aaaagacaaa aaaaaaaaa aaaaaaaaa gaacatatcc tggtgtggag    420
taggggacgc tgctctgaca gaggctcggg ggcctgagct ggctctgtga gctggggagg    480
aggcacagag ccaggccttg tctgcaagca gacctggcag cattgggctg gccgccccca   540
agggcctcct cttcatgccc agtgaatgac tcaccttggc acagacacaa tgttcggggt   600
gggcacagtg cctgcttccc gccgcacccc agcccccctc aaatgccttc cgagaagccc   660
attgagcagg gggcttgcat tgcacccag cctgacagcc tggcatcttg ggataaaagc     720
agcacagccc cctaggggct gcccttgctg tgtggcgcca ccggcggtgg agaacaaggc   780
tctattcagc ctgtgcccag gaaagggat caggggatgc ccaggcatgg acagtgggtg    840
gcagggggg agaggagggc tgtctgcttc ccagaagtcc aaggcacaa atgggtgagg    900
ggactgggca gggttctgac cctgtgggac cagagtggag ggcgtagatg gacctgaagt   960
ctccaggac aacagggccc aggtctcagg ctcctagttg gcccagtgg ctccagcgtt   1020
tccaaaccca tccatcccca gaggttcttc ccatctctcc agctgatgt gtgggaactc   1080
gaggaaataa atctccagtg gggagacgag gggtggccag ggaaacgggg cgctgcagga   1140
ataaagacga gccagcacag ccagctcatg tgtaacggct ttgtggagct gtcaaggcct   1200
ggtctctggg agagaggcac agggaggcca gacaaggaag gggtgacctg gagggacaga   1260
tccagggggct aaagtcctga taaggcaaga gagtgccggc cccctcttgc cctatcagga   1320
cctccactgc cacatagagg ccatgattga cccttagaca aagggctggt gtccaatctg   1380
agccccagc cccagaactc cagggaatga atgggcagag agcaggaatg tgggacatct   1440
gtgttcaagg gaaggactcc aggagtctgc tgggaatgag gcctagtagg aaatgaggtg    1500
gcccttgagg gtacagaaca ggttcattct tcgccaaatt cccagcacct tgcaggcact    1560
tacagctgag tgagataatg cctgggttat gaaatcaaaa agttggaaag caggtcagag   1620
gtcatctggt acagcccttc cttcccttt tttttttttt ttttgtgaga caaggtctca   1680
ctctgttgcc caggctggag tggcgcaaac acagctcact gcagcctcaa cctactgggc    1740
tcaagcaatc ctccagcctc agcctcccaa agtgctggga ttacaagcat gagccacccc   1800
actcagccct ttccttcctt tttaattgat gcataataat tgtaagtatt catcatggtc   1860
caaccaaccc tttcttgacc caccttccta gagagagggg cctcttgctt cagcggtcag    1920
ggccccagac ccatggtctg gctccaggta ccacctgcct catgcaggag ttggcgtgcc   1980
```

```
caggaagctc tgcctctggg cacagtgacc tcagtggggt gaggggagct ctccccatag    2040
ctgggctgcg gcccaacccc accccctcag gctatgccag ggggtgttgc caggggcacc    2100
cgggcatcgc cagtctagcc cactccttca taaagccctc gcatcccagg agcgagcaga    2160
gccagagcag gttggagagg agacgcatca cctccgctgc tcgc                     2204

SEQ ID NO: 64           moltype = DNA  length = 381
FEATURE                 Location/Qualifiers
misc_feature            1..381
                        note = source = /note="Description of Artificial Sequence:
                        Synthetic polynucleotide"
source                  1..381
                        mol_type = other DNA
                        organism = synthetic construct
SEQUENCE: 64
gacattgatt attgactagt tattaatagt aatcaattac ggggtcatta gttcatagcc    60
catatatgga gttccgcgtt acataactta cggtaaatgg cccgcctggc tgaccgccca    120
acgacccccg cccattgacg tcaataatga cgtatgttcc catagtaacg ccaataggga    180
ctttccattg acgtcaatgg gtggactatt tacggtaaac tgcccacttg gcagtacatc    240
aagtgtatca tatgccaagt acgcccccta ttgacgtcaa tgacggtaaa tggcccgcct    300
ggcattatgc ccagtacatg accttatggg actttcctac ttggcagtac atctacgtat    360
tagtcatcgc tattaccatg g                                              381

SEQ ID NO: 65           moltype = DNA  length = 1013
FEATURE                 Location/Qualifiers
misc_feature            1..1013
                        note = source = /note="Description of Artificial Sequence:
                        Synthetic polynucleotide"
source                  1..1013
                        mol_type = other DNA
                        organism = synthetic construct
SEQUENCE: 65
ggagtcgctg cgttgccttc gccccgtgcc ccgctccgcg ccgcctcgcg ccgcccgccc    60
cggctctgac tgaccgcgtt actcccacag gtgagcgggc gggacggccc ttctcctccg    120
ggctgtaatt agcgcttggt ttaatgacgg ctcgtttctt ttctgtggct gcgtgaaagc    180
cttaaagggc tccggagggc ccctttgtgc ggggggagcc ggctcggggg gtgcgtgcgt    240
gtgtgtgtgc gtggggagcg ccgcgtgcgg cccgcgctgc ccgcggcgctg tgagcgctgc    300
gggcgcggcg cggggctttg tgcgctccgc gtgtgcgcga gggagcgcg gccggggggcg    360
gtgccccgcg gtgcggggg gctgcgaggg gaacaaaggc tgcgtgcggg gtgtgtgcgt    420
gggggggtga gcaggggtg tgggcgcggc ggtcgggctg taaccccccc ctgcaccccc    480
ctccccgagt tgctgagcac ggcccggctt cgggtgcggg gctccgtgcg gggcgtggcg    540
cggggctcgc cgtgccgggc gggggtggc ggcaggtggg ggtgccgggc gggggggggc    600
cgcctcgggc cgggggagggc tcggggggagg ggcgcggcgg ccccccggagc gccggcggct    660
gtcgaggcgc ggcgagccgc agccattgcc ttttatggta atcgtgcgag agggcgcagg    720
gacttcctttt gtcccaaatc tgtgcggagc cgaaatctgg gaggcgccgc cgcaccccct    780
ctagcggggcg cggggcgaag cggtgcggcg ccggcaggaa ggaaatgggc ggggagggcc    840
ttcgtgcgtc gccgcgccgc cgtcccccttc tccctctcca gcctcgggggc tgtccgcggg    900
gggacgcgctg ccttcggggg ggacggggca gggcggggtt cggcttctgg cgtgtgaccgg    960
gcggctctag agcctctgct aaccatgttc atgccttctt cttttttccta cag            1013

SEQ ID NO: 66           moltype = DNA  length = 60
FEATURE                 Location/Qualifiers
misc_feature            1..60
                        note = source = /note="Description of Artificial Sequence:
                        Synthetic oligonucleotide"
source                  1..60
                        mol_type = other DNA
                        organism = synthetic construct
SEQUENCE: 66
atgtaccgga tgcagctgct gagctgtatc gccctgtctc tggccctggt caccaattct    60

SEQ ID NO: 67           moltype = DNA  length = 60
FEATURE                 Location/Qualifiers
misc_feature            1..60
                        note = source = /note="Description of Artificial Sequence:
                        Synthetic oligonucleotide"
source                  1..60
                        mol_type = other DNA
                        organism = synthetic construct
SEQUENCE: 67
atgtatagaa tgcagctcct gtcctgcatt gccctgagcc tggctctcgt gaccaacagc    60

SEQ ID NO: 68           moltype = AA  length = 20
FEATURE                 Location/Qualifiers
REGION                  1..20
                        note = source = /note="Description of Artificial Sequence:
                        Synthetic peptide"
source                  1..20
                        mol_type = protein
                        organism = synthetic construct
```

```
SEQUENCE: 68
MYRMQLLSCI ALSLALVTNS                                              20

SEQ ID NO: 69           moltype = DNA  length = 63
FEATURE                 Location/Qualifiers
misc_feature            1..63
                        note = source = /note="Description of Artificial Sequence:
                        Synthetic oligonucleotide"
source                  1..63
                        mol_type = other DNA
                        organism = synthetic construct
SEQUENCE: 69
ggctctggcg aaggcagagg cagcctgctt acatgtggcg acgtggaaga gaacccgga   60
cct                                                                63

SEQ ID NO: 70           moltype = AA  length = 21
FEATURE                 Location/Qualifiers
REGION                  1..21
                        note = source = /note="Description of Artificial Sequence:
                        Synthetic peptide"
source                  1..21
                        mol_type = protein
                        organism = synthetic construct
SEQUENCE: 70
GSGEGRGSLL TCGDVEENPG P                                            21

SEQ ID NO: 71           moltype = DNA  length = 33
FEATURE                 Location/Qualifiers
misc_feature            1..33
                        note = source = /note="Description of Artificial Sequence:
                        Synthetic oligonucleotide"
source                  1..33
                        mol_type = other DNA
                        organism = synthetic construct
SEQUENCE: 71
gacaagaccc acaccggcaa gcggaagaga aga                               33

SEQ ID NO: 72           moltype = AA  length = 11
FEATURE                 Location/Qualifiers
REGION                  1..11
                        note = source = /note="Description of Artificial Sequence:
                        Synthetic peptide"
source                  1..11
                        mol_type = protein
                        organism = synthetic construct
SEQUENCE: 72
DKTHTGKRKR R                                                       11

SEQ ID NO: 73           moltype = DNA  length = 82
FEATURE                 Location/Qualifiers
misc_feature            1..82
                        note = source = /note="Description of Artificial Sequence:
                        Synthetic oligonucleotide"
source                  1..82
                        mol_type = other DNA
                        organism = synthetic construct
SEQUENCE: 73
gtaagtatca aggttacaag acaggtttaa ggagaccaat agaaactggg cttgtcgaga   60
cagagaagac tcttgcgttt ct                                           82

SEQ ID NO: 74           moltype = DNA  length = 51
FEATURE                 Location/Qualifiers
misc_feature            1..51
                        note = source = /note="Description of Artificial Sequence:
                        Synthetic oligonucleotide"
source                  1..51
                        mol_type = other DNA
                        organism = synthetic construct
SEQUENCE: 74
gataggcacc tattggtctt actgacatcc actttgcctt tctctccaca g           51

SEQ ID NO: 75           moltype = DNA  length = 225
FEATURE                 Location/Qualifiers
misc_feature            1..225
                        note = source = /note="Description of Artificial Sequence:
                        Synthetic polynucleotide"
source                  1..225
                        mol_type = other DNA
                        organism = synthetic construct
```

```
SEQUENCE: 75
ctgtgccttc tagttgccag ccatctgttg tttgcccctc ccccgtgcct tccttgaccc   60
tggaaggtgc cactcccact gtcctttcct aataaaatga ggaaattgca tcgcattgtc  120
tgagtaggtg tcattctatt ctgggggtg gggtggggca ggacagcaag ggggaggatt   180
gggaagacaa tagcaggcat gctggggatg cggtgggctc tatgg                  225

SEQ ID NO: 76            moltype = DNA   length = 122
FEATURE                  Location/Qualifiers
misc_feature             1..122
                         note = source = /note="Description of Artificial Sequence:
                         Synthetic polynucleotide"
source                   1..122
                         mol_type = other DNA
                         organism = synthetic construct
SEQUENCE: 76
aacttgttta ttgcagctta taatggttac aaataaagca atagcatcac aaatttcaca   60
aataaagcat ttttttcact gcattctagt tgtggtttgt ccaaactcat caatgtatct  120
ta                                                                 122

SEQ ID NO: 77            moltype = DNA   length = 22
FEATURE                  Location/Qualifiers
misc_feature             1..22
                         note = source = /note="Description of Artificial Sequence:
                         Synthetic oligonucleotide"
source                   1..22
                         mol_type = other DNA
                         organism = synthetic construct
SEQUENCE: 77
ttgtcgacgc ggccgcacgc gt                                            22

SEQ ID NO: 78            moltype = DNA   length = 39
FEATURE                  Location/Qualifiers
misc_feature             1..39
                         note = source = /note="Description of Artificial Sequence:
                         Synthetic oligonucleotide"
source                   1..39
                         mol_type = other DNA
                         organism = synthetic construct
SEQUENCE: 78
ctcctgggca acgtgctggt tattgtgacc ggtgccacc                          39

SEQ ID NO: 79            moltype = DNA   length = 24
FEATURE                  Location/Qualifiers
misc_feature             1..24
                         note = source = /note="Description of Artificial Sequence:
                         Synthetic oligonucleotide"
source                   1..24
                         mol_type = other DNA
                         organism = synthetic construct
SEQUENCE: 79
taagagctcg ctgatcagcc tcga                                          24

SEQ ID NO: 80            moltype = DNA   length = 38
FEATURE                  Location/Qualifiers
misc_feature             1..38
                         note = source = /note="Description of Artificial Sequence:
                         Synthetic oligonucleotide"
source                   1..38
                         mol_type = other DNA
                         organism = synthetic construct
SEQUENCE: 80
aagcttgaat tcagctgacg tgcctcggac cgcctagg                           38

SEQ ID NO: 81            moltype = DNA   length = 14
FEATURE                  Location/Qualifiers
misc_feature             1..14
                         note = source = /note="Description of Artificial Sequence:
                         Synthetic oligonucleotide"
source                   1..14
                         mol_type = other DNA
                         organism = synthetic construct
SEQUENCE: 81
gcggccgcac gcgt                                                     14

SEQ ID NO: 82            moltype = DNA   length = 34
FEATURE                  Location/Qualifiers
misc_feature             1..34
                         note = source = /note="Description of Artificial Sequence:
                         Synthetic oligonucleotide"
```

```
                        source          1..34
                                        mol_type = other DNA
                                        organism = synthetic construct
SEQUENCE: 82
aagcttgaat tcagctgacg tgcctcggac cgct                                       34

SEQ ID NO: 83           moltype = AA   length = 159
FEATURE                 Location/Qualifiers
REGION                  1..159
                        note = source = /note="Description of Artificial Sequence:
                          Synthetic polypeptide"
source                  1..159
                        mol_type = protein
                        organism = synthetic construct
SEQUENCE: 83
MISLIAALAV DYVIGMENAM PWNLPADLAW FKRNTLNKPV IMGRHTWESI GRPLPGRKNI        60
ILSSQPSTDD RVTWVKSVDE AIAACGDVPE IMVIGGGRVI EQFLPKAQKL YLTHIDAEVE       120
GDTHFPDYEP DDWESVFSEF HDADAQNSHS YCFEILERR                              159

SEQ ID NO: 84           moltype = DNA   length = 483
FEATURE                 Location/Qualifiers
misc_feature            1..483
                        note = source = /note="Description of Artificial Sequence:
                          Synthetic polynucleotide"
source                  1..483
                        mol_type = other DNA
                        organism = synthetic construct
SEQUENCE: 84
ggtaccatca gtctgattgc ggcgttagcg gtagattacg ttatcggcat ggaaaacgcc        60
atgccgtgga acctgcctgc cgatctcgcc tggtttaaac gcaacacctt aaataaaccc       120
gtgattatgg gccgccatac ctgggaatca atccggtcgt cgttgccagg acgcaaaaat       180
attatcctca gcagtcaacc gagtacggac gatcgcgtaa cgtgggtgaa gtcggtggat       240
gaagccatcg cggcgtgtgg tgacgtacca gaaatcatgg tgattggcgg cggtcgcgtt       300
attgaacagt tcttgccaaa agcgcaaaaa ctgtatctga cgcatatcga cgcagaagtg       360
gaaggcgaca cccatttccc ggattacgag ccggatgact gggaatcggt attcagcgaa       420
ttccacgatg ctgatgcgca gaactctcac agctattgct ttgagattct ggagcggcga       480
taa                                                                     483

SEQ ID NO: 85           moltype = DNA   length = 474
FEATURE                 Location/Qualifiers
misc_feature            1..474
                        note = source = /note="Description of Artificial Sequence:
                          Synthetic polynucleotide"
source                  1..474
                        mol_type = other DNA
                        organism = synthetic construct
SEQUENCE: 85
atcagtctga ttgcggcgtt agcggtagat tacgttatcg gcatggaaaa cgccatgccg        60
tggaacctgc ctgccgatct cgcctggttt aaacgcaaca ccttaaataa acccgtgatt       120
atgggccgcc atacctggga atcaatcggt cgtccgttgc caggacgcaa aaatattatc       180
ctcagcagtc aaccgagtac ggacgatcgc gtaacgtcgg tgaagtcggt ggatgaagcc       240
atcgcggcgt gtggtgacgt accagaaatc atggtgattg gcggcggtcg cgttattgaa       300
cagttcttgc caaaagcgca aaaactgtat ctgacgcata tcgacgcaga gtggaaggc       360
gacacccatt tcccggatta cgagccggat gactgggaat cggtattcag cgaattccac       420
gatgctgatg cgcagaactc tcacagctat tgctttgaga ttctggagcg gcga            474

SEQ ID NO: 86           moltype = AA   length = 112
FEATURE                 Location/Qualifiers
REGION                  1..112
                        note = source = /note="Description of Artificial Sequence:
                          Synthetic polypeptide"
source                  1..112
                        mol_type = protein
                        organism = synthetic construct
SEQUENCE: 86
MGVEKQVIRP GNGPKPAPGQ TVTVHCTGFG KDGDLSQKFW STKDEGQKPF SFQIGKGAVI        60
KGWDEGVIGM QIGEVARLRC SSDYAYGAGG FPAWGIQPNS VLDFEIEVLS VQ               112

SEQ ID NO: 87           moltype = DNA   length = 78
FEATURE                 Location/Qualifiers
misc_feature            1..78
                        note = source = /note="Description of Artificial Sequence:
                          Synthetic oligonucleotide"
source                  1..78
                        mol_type = other DNA
                        organism = synthetic construct
SEQUENCE: 87
ggatcccggg ctgactacaa agaccatgac ggtgattata agatcatga catcgactac         60
aaggatgacg atgacaag                                                      78
```

| SEQ ID NO: 88 | moltype = DNA  length = 2208 |
|---|---|
| FEATURE | Location/Qualifiers |
| misc_feature | 1..2208 |
| | note = source = /note="Description of Artificial Sequence: Synthetic polynucleotide" |
| source | 1..2208 |
| | mol_type = other DNA |
| | organism = synthetic construct |

SEQUENCE: 88

```
atggctgccg atggttatct tccagattgg ctcgaggaca acctctctga gggcattcgc   60
gagtggtggg acttgaaacc tggagccccg aaacccaaag ccaaccagca aaagcaggac  120
gacggccggg gtctggtgct tcctggctac aagtacctcg gacccttcaa cggactcgac  180
aaggggggagc ccgtcaacgc ggcggacgca gcggccctcg agcacgacaa ggcctacgac  240
cagcagctca aagcgggtga caatccgtac ctgcggtata accacgccga cgccgagttt  300
caggagcgtc tgcaagaaga tacgtctttt ggggggcaacc tcgggcgagc agtcttccag  360
gccaagaagc gggttctcga acctctcggt ctggttgagg aaggcgctaa gacggctcct  420
ggaaagaaga gaccggtaga gcaatcaccc caggaaccag actcctcctc gggcatcggt  480
aagaaaggcc agcagcccgc gaagaagaga ctcaactttg gcagacaggg cgactcagag  540
tcagtgcccg accctcaacc actcggagaa cccccgcag cccctctgg tgtgggatct  600
aatacaatgc agcaggcgg tggcgctcca atggcagaca taacgaagg cgccgacgga  660
gtgggtaacg cctcaggaaa ttggcattgc gattccacat ggctgggcga cagagtcatc  720
accaccagca cccgaacctg ggccctcccc acctacaaca accacctcta caagcaaatc  780
tccagccaat cgggagcaag caccaacgac aacacctact cggctacag cacccctgg  840
gggtatttg actttaacag attccactgc cacttctcac cacgtgactg gcagcgactc  900
atcaacaaca actgggggat tccggcccaag agactcaagt tcaagctctt caacatccag  960
gtcaaggagg tcacgacgaa tgatggcacc acgaccatcg ccaataacct taccagcacg 1020
gttcaggtct ttacggactc ggaataccag ctcccgtacg tcctcggctc tgcgcaccag 1080
ggctgcctgc ctccgttccc ggcggacgtc ttcatgattc ctcagtacgg gtacctgact 1140
ctgaacaatg gcagtcaggc cgtggccgt tcctccttct actgcctgga gtactttcct 1200
tctcaaatgc tgagaacggg caacaacttt gagttcagct acacgtttga ggacgtgcct 1260
tttcacagca gctacgcgca cagccaaagc ctggaccggc tgatgaaccc cctcatcgac 1320
cagtacctgt actacctgtc tcggactcag accacgagtg gtaccgcagg aaatcggacg 1380
ttgcaatttt ctcaggccgg gcctagtagc atggcgaatc aggcgaaaaa ctggctaccc 1440
gggccctgct accggcagca acgcgtctcc aagacagcga atcaaaataa caacagcaac 1500
tttgcctgga ccggtgccac caagtatcat ctgaatggca gagactctct ggtaaatccc 1560
ggtcccgcta tggcaaccca caaggacgac gaagacaaat ttttccgat gagcggagtc 1620
ttaatatttg ggaaacaggg agctggaaat agcaacgtgg accttgacaa cgttatgata 1680
accagtgagg aagaaattaa aaccaccaac ccagtgccca gaaacagta cggcacggtg 1740
gccactaacc tgcaatcgtc aaacaccgct cctgctacag ggaccgtcaa cagtcaagga 1800
gccttacctg gcatggtctg gcagaaccgg gacgtgtacc tgcagggtcc tatctgggcc 1860
aagattcctc acacggacgg acactttcat ccctcgccgc tgatgggagg ctttggactg 1920
aaacaccccg ctcctcagat cctgattaag aatacacctg ttcccgcgaa tcctccaact 1980
accttcagtc cagctaagtt tgcgtcgttc atcacgcagt acagcaccgg acaggtcagc 2040
gtggaaattg aatgggagct gcagaaagaa aacagcaaac gctggaaccc agagattcaa 2100
tacacttcca actacaacaa atctacaaat gtggactttg ctgttgacac aaatggcgtt 2160
tattctgagc ctcgccccat cggcacccgt tacctcaccc gtaatctg             2208
```

| SEQ ID NO: 89 | moltype = AA  length = 736 |
|---|---|
| FEATURE | Location/Qualifiers |
| REGION | 1..736 |
| | note = source = /note="Description of Artificial Sequence: Synthetic polypeptide" |
| source | 1..736 |
| | mol_type = protein |
| | organism = synthetic construct |

SEQUENCE: 89

```
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPAKKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SSQSGASTND NTYFGYSTPW GYFDFNRFHC HFSPRDWQRL  300
INNNWGFRPK RLNFKLFNIQ VKEVTTNDGT TTIANNLFST VQVFTDSEYQ LPYVLGSAHQ  360
GCLPPFPADV FMIPQYGYLT LNNGSQAVGR SSFYCLEYFP SQMLRTGNNF EFSYTFEDVP  420
FHSSYAHSQS LDRLMNPLID QYLYYLSRTQ TTSGTAGNRT LQFSQAGPSS MANQAKNWLP  480
GPCYRQQRVS KTANQNNNSN FAWTGATKYH LNGRDSLVNP GPAMATHKDD EDKFFPMSGV  540
LIFGKQGAGN SNVDLDNVMI TSEEEIKTTN PVATEQYGTV ATNLQSSNTA PATGTVNSQG  600
ALPGMVWQNR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                 736
```

| SEQ ID NO: 90 | moltype = DNA  length = 3792 |
|---|---|
| FEATURE | Location/Qualifiers |
| misc_feature | 1..3792 |
| | note = source = /note="Description of Artificial Sequence: Synthetic polynucleotide" |
| source | 1..3792 |
| | mol_type = other DNA |
| | organism = synthetic construct |

```
SEQUENCE: 90
ctgcgcgctc gctcgctcac tgaggccgcc cgggcgtcgg gcgacctttg gtcgcccggc    60
ctcagtgagc gagcgagcgc gcagagaggg agtggccaac tccatcacta ggggttcctg   120
cggccgcacg cgtgacattg attattgact agttattaat agtaatcaat tacgggtca    180
ttagttcata gcccatatat ggagttccgc gttacataac ttacggtaaa tggcccgcct   240
ggctgaccgc ccaacgaccc cgcccattg acgtcaataa tgacgtatgt tcccatagta   300
acgccaatag ggactttcca ttgacgtcaa tgggtggact atttacggta aactgcccac   360
ttggcagtac atcaagtgta tcatatgcca agtacgcccc ctattgacgt caatgacggt   420
aaatggcccg cctggcatta tgcccagtac atgaccttat gggactttcc tacttggcag   480
tacatctacg tattagtcat cgctattacc atgggtcgag gtgagcccca cgttctgctt   540
cactctcccc atctccccc cctcccacc cccaattttg tatttattta ttttttaatt    600
attttgtgca gcgatggggg cggggggggg ggggcgcgc gccaggcggg gcggggcggg   660
gcgagggcg gggcggggcg aggcggagag gtgcggcggc agccaatcag agcggcgcgc   720
tccgaaagtt tccttttatg gcgaggcggc ggcggccggc gccctataaa aagcgaagcg   780
cgcggcgggc gggagtcgct gcgttgcctt cgcccgtgc cccgctccgc gccgcctcgc   840
gccgcccgcc ccggctctga ctgaccgcgt tactcccaca ggtgagcggg cgggacggcc   900
cttctcctcc gggctgtaat tagcgcttgg tttaatgacg gctcgtttct tttctgtggc   960
tgcgtgaaag ccttaaaggg ctccgggagg gcccttgtg cggggggag cggctcgggg  1020
ggtgcgtgcg tgtgtgtgtg cgtggggagc gccgcgtgcg gccgcgctg cccggcggct  1080
gtgagcgctg cgggcgcggc gcggggcttt gtgcgctccg cgtgtgcgcg agggagcgc   1140
ggccggggc ggtgccccgc ggtgcggggg gctgcgagg ggaacaaagg ctgcgtgcgg  1200
ggtgtgtcg tggggggtg agcagggggt gtgggccgg cggtcgggct gtaaccccgg    1260
cctgcacccc cctccccgag ttgctgagca cggcccggct tcgggtgcgg ggctccgtgc  1320
ggggcgtggc gcggggctcg ccgtgccggg cgggggtgg cggcaggtgg gggtgccggg   1380
cggggcgggg ccgcctcggg ccggggaggg ctcggggag gggcgcggcg gccccggag   1440
cgccggcgc tgtcgaggcg cggcgagccg cagccattgc cttttatggt aatcgtgga   1500
gagggcgcag ggacttcctt tgtcccaaat ctgtgcggga ccgaaatctg ggaggcgccg  1560
ccgcaccccc tctagcgggc gcggggcgaa gcggtgcggc gccggcagga aggaaatggg   1620
cggggagggc cttcgtgcgt cgccgcgccg ccgtcccctt ctccctctcc agcctcgggg   1680
ctgtccgcgg ggggacggct gccttcgggg gggacggggc agggcggggt tcggcttctg   1740
gcgtgtgacc ggcggctcta gagcctctgc taaccatgtt catgccttct tcttttttcct  1800
acagctcctg ggcaacgtgc tggttattgt gaccggtgcc accatgtacc ggatgcagct   1860
gctgagctgt atcgccctgt ctctggccct ggtcaccaat tctgaggtgc agctggtgga   1920
atctggcggc ggacttgttc aacctggcgg ctctctgaga ctgagctgtg ccgcttctgg   1980
ctacgacttc acccactacg gcatgaactg gtccgacag gccctggca aaggccttga    2040
atgggtcgga tggatcaaca cctacaccgg cgagccaaca tacgccgccg acttcaagcg   2100
gagattcacc ttcagcctgg acaccagcaa gagcaccgcc tacctgcaga tgaacagcct   2160
gagagccgag gacaccgccg tgtactactg cgccaagtat ccctactact acggcaccag   2220
ccactggtac tttgacgtgt ggggacaggg cacactgtcta acagtgtcta gcgcctctac   2280
aaagggcccc agcgttttcc cactggctct agcagcaag tctaccgcg gaggaacagc    2340
cgctctgggc tgtctggtca aggactactt tcccgagcct gtgaccgtgt cctggaattc   2400
tggcgctctg acaagcggcg tgcacacctt tccagctgtg ctgcaaagca gcggcctgta   2460
ctctctgagc agcgtcgtga cagtgccaag cagctctctg ggcacccaga cctacatctg   2520
caatgtgaac cacaagccta gcaacaccaa ggtggacaag aaggtggaac ccaagactg    2580
cgacaagacc cacaccggca gcggaagag aagaggctct ggcgaaggca gagcagcct    2640
gcttacatgt ggcgacgtgg aagagaaccc cggacctatg tatagaatgc agctcctgtc   2700
ctgcattgcc ctgagcctgg ctctcgtgac caacagcgac atccagctga cacagagccc   2760
cagcagcctg tctgcctctg tgggagacag agtgaccatc acctgtagcg ccagccagga   2820
catctccaac tacctgaact ggtatcagca aaagcccggc aaggcccta aggtgctgat    2880
ctacttcaca agcagcctgc actccggcgt gccagcagga ttttctggct ctggcagcgg   2940
caccgacttc accctgacca tatctagcct gcagcctgag gacttcgcca cctactactg   3000
ccagcagtac agcaccgtgc cttggacatt tggccagggc acaaaggtgg aaatcaagcg   3060
gactgtggcc gctcctagcg tgttcatctt tccacctagc gacgagcagc tgaagtctgg   3120
cacagcctct gtcgtgtgcc tgctgaacaa cttctacccc agagaagcca aggtgcagtg   3180
gaaagtggac aatgccctgc agagcggcaa cagccaagag acgtgacag agcaggactc   3240
caaggatagc acctatagcc tgagcagcac cctgacactg agcaaggccg actacgagaa   3300
gcacaaagtg tacgcctgcg aagtgaccca ccagggcctt tctagccctg tgaccaagag   3360
cttcaaccgg ggcgaatgtt aagagctcgc tgatcagcct cgactgtgcc ttctagttgc   3420
cagccatctg ttgtttgccc ctcccccgtg ccttccttga ccctggaagg tgccactcct   3480
actgtccttt cctaataaaa tgaggaaatt gcatcgcatt gtctgagtag gtgtcattct   3540
attctggggg gtggggtggg gcaggacagc aaggggagg attggaaga caatagcagg   3600
catgctgggg atgcggtggg ctctatgaa gcttgaattc agctgacgtg cctcggaccg   3660
ctaggaaccc ctagtgatgg agttggccac tccctctctg cgcgctcgct cgctcactga   3720
ggccgggcga ccaaaggtcg cccgacgccc gggctttgcc cggcggcct cagtgagcga   3780
gcgagcgcgc ag                                                      3792
SEQ ID NO: 91          moltype = DNA  length = 3847
FEATURE                Location/Qualifiers
misc_feature           1..3847
                       note = source = /note="Description of Artificial Sequence:
                       Synthetic polynucleotide"
source                 1..3847
                       mol_type = other DNA
                       organism = synthetic construct
SEQUENCE: 91
ttggccactc cctctctgcg cgctcgctcg ctcactgagg ccgcccggc aaagcccggg     60
cgtcgggcga ccttttggtcg cccggcctca gtgagcgagc gagcgcgcag agagggagtg   120
gccaactcca tcactagggg ttcctttgtc gacgcggccg cacgcgtgac attgattatt   180
gactagttat taatagtaat caattacggg gtcattagtt catagcccat atatggagtt    240
```

```
ccgcgttaca taacttacgg taaatggccc gcctggctga ccgcccaacg accccgccc    300
attgacgtca ataatgacgt atgttcccat agtaacgcca atagggactt tccattgacg    360
tcaatgggtg gactatttac ggtaaactgc ccacttggca gtacatcaag tgtatcatat    420
gccaagtacg cccctattg acgtcaatga cggtaaatgg cccgcctggc attatgccca    480
gtacatgacc ttatgggact ttcctacttg gcagtacatc tacgtattag tcatcgctat    540
taccatggt cgaggtgagc cccacgttct gcttcactct ccccatctcc cccctccc    600
cacccccaat tttgtattta tttatttttt aattattttg tgcagcgatg ggggcggggg    660
ggggggggg gcgcgcgcca ggcggggcgg ggcggggcga ggggcggggc ggggcgaggc    720
ggagaggtgc ggcggcagcc aatcagagcg gcgcgctccg aaagtttcct ttatggcga    780
ggcggcggcg gcggcggccc tataaaaagc gaagcgcgcg gcgggcggga gtcgctgcgt    840
tgccttcgcc ccgtgccccg ctccgcgccg cctcgcgccg cccgccggg ctctgactga    900
ccgcgttact cccacaggtg agcgggcggg acggccttc tcctccggc tgtaattagc    960
gcttggttta atgacggctc gttttctttc tgtggctgcg tgaaagcctt aaagggctcc   1020
gggagggcc tttgtgcggg ggagaggcc tcggggggtg cgtgcgtgtg tgtgtgcgtg   1080
gggagcgccg cgtgcggccc gcgctgcccg gcggctgtga gcgctgcgcg gcgcgcgg    1140
ggctttgtgc gctccgcgtg tgcgcgaggg gagcgcggcc ggggcggtg ccccgcggtg   1200
cgggggggct gcgaggggaa caaaggctgc gtgcgggtg tgtgcgtggg ggggtgagca   1260
gggggtgtgg gcgcggcggt cgggctgtaa ccccccctg cacccccctc cccgagttgc   1320
tgagcacggc ccggcttcgg gtgcggggct ccgtgcgggg cgtgcggcgg ggctcgccgt   1380
gccgggcggg gggtggcggc aggtgggggt gccgggcggg gcggggccgc ctcgggccgg   1440
ggagggctcg ggggagggc gcggcggccc cggagcgcc ggcggctgtc gaggcgcggc    1500
gagccgcgc cattgccttt tatggtaatc gtgcgagagg gcgcagggac ttcctttgtc    1560
ccaaatctgt gcggagccga aatctggag gcgccgccgc acccctcta gcgggcgcgg   1620
ggcgaagcgg tgcggcgccg gcaggaagga aatgggcggg gagggccttc gtgcgtcgcc   1680
gcgccgccgt cccttctcc ctctccagcc tcggggctgt ccgcgggggg acggctgcct   1740
tcgggggga cgggcaggg gggttcgg ctttgtgcg gtgaccggcg gctctagagc    1800
ctctgctaac catgttcatg ccttcttctt tttcctacag ctcctgggca acgtgctggt   1860
tattgtgacc ggtgccacca tgtaccggat gcagctgctg agctgtatcg ccctgtctct   1920
ggccctggtc accaattctg aggtgcagct ggtggaatct ggcggcggac ttgttcaacc   1980
tggcggctct ctgagactga gctgtgccgc ttctggcat gacttcaccc actacggcat   2040
gaactgggtc cgacaggccc ctggcaaagg ccttgaatgg gtcggatgga tcaacaccta   2100
caccggcgag ccaacatacg ccgccgactt caagcggaga ttcaccttca gcctggacac   2160
cagcaagagc accgcctacc tgcagatgaa cagcctgaga gccgaggaca ccgccgtgta   2220
ctactgcgcc aagtatccct actactacgg caccagccac tggtactttg acgtgtgggg   2280
acagggcaca ctggtcacag tgtctagcgc ctctacaaag ggcccagcg ttttcccact   2340
ggctcctagc agcaagtcta ccagcggagg aacagccgct ctgggctgtc tggtcaagga   2400
ctactttccc gagcctgtga ccgtgtcctg aattctggc gctctgacaa gcggcgtgca   2460
cacctttcca gctgtgctgc aaagcagcgg cctgtactct ctgagcagcg tcgtgacagt   2520
gccaagcagc tctctgggca cccagaccta catctgcaat gtgaaccaca agcctagcaa   2580
caccaaggtg gacaagaagg tggaacccaa gagctgcgac aagacccaca ccggcaagcc   2640
gaagagaaga ggctctggcg aaggcagagg cagcctgctt acatgtgcg acgtggaaga   2700
gaaccccgga cctatgtata aatgcagct cctgtcctgc attgccctga gcctggctct   2760
cgtgaccaac agcgacatcc agctgacaca gagccccagc agcctgtctg cctctgtggg   2820
agacagagtg accatcacct gtagcgccag ccaggacatc tccaactacc tgaactggta   2880
tcagcaaaag cccggcaagg cccctaaggt gctgatctac ttcacaagca gcctgcactc   2940
cggcgtgccc agcagatttt ctggctctgg cagcggcacc gacttcaccc tgaccatatc   3000
tagcctgcag cctgaggact cgccaccta ctactgcag cagtacagca ccgtgccttg   3060
gacatttggc cagggcacaa aggtggaaat caagcggact gtggccgctc tagcgtgtt   3120
catctttcca cctagcacg agcagctgaa gtctggcaca gcctctgtcg tgtgcctgct   3180
gaacaacttc taccccagag aagccaaggt gcagtggaaa gtggacaatg ccctgcagag   3240
cggcaacagc caagagagcg tgacagagca ggactccaag atagcacct atagcctgag   3300
cagcaccctg acactgagca aggccgacta cgagaagcac aaagtgtacg cctgcgaagt   3360
gacccaccag ggccttttcta gccctgtgac aagagcttc aaccgggcg aatgttaaga   3420
gctcgctgat cagcctcgac tgtgccttct agttgccagc catctgttgt ttgccctcc   3480
cccgtgcctt ccttgaccct ggaaggtgcc actcccactg tcctttccta ataaaatgag   3540
gaaattgcat cgcattgtct gagtaggtgt cattctattc tgggggtgg ggtggcag    3600
gacagcaagg gggaggattg ggaagacaat agcaggcatg ctgggatgc ggtggctct    3660
atggaagctt gaattcagct gacgtgcctc ggaccgccta ggaggaaccc ctagtgatgg   3720
agttggccac tccctctctg cgcgctcgct cgctcactga ggccgggcga ccaaaggtcg   3780
cccgacgccc gggctttgcc cgggcggcct cagtgagcga gcgagcgcgc agagagggag   3840
tggccaa                                                              3847
SEQ ID NO: 92           moltype = DNA   length = 3845
FEATURE                 Location/Qualifiers
misc_feature            1..3845
                        note = source = /note="Description of Artificial Sequence:
                        Synthetic polynucleotide"
source                  1..3845
                        mol_type = other DNA
                        organism = synthetic construct
SEQUENCE: 92
ttggccactc cctctctgcg cgctcgctcg ctcactgagg ccgcccgggc aaagcccggg     60
cgtcgggcga ccttggtcg cccggcctca gtgagcgagc gagcgcgcag agagggagtg    120
gccaactcca tcactagggg ttcctttgtc gacgcggccg cacgcgtgac attgattatt    180
gactagttat taatagtaat caattacggg gtcattagtt catagcccat atatggagtt    240
ccgcgttaca taacttacgg taaatggccc gcctggctga ccgcccaacg accccgccc    300
attgacgtca ataatgacgt atgttcccat agtaacgcca atagggactt tccattgacg    360
tcaatgggtg gactatttac ggtaaactgc ccacttggca gtacatcaag tgtatcatat    420
gccaagtacg cccctattg acgtcaatga cggtaaatgg cccgcctggc attatgccca    480
```

```
gtacatgacc ttatgggact ttcctacttg gcagtacatc tacgtattag tcatcgctat    540
taccatgggt cgaggtgagc cccacgttct gcttcactct ccccatctcc cccccctccc    600
caccccccaat tttgtattta tttatttttt aattattttg tgcagcgatg ggggcggggg   660
gggggggggc gcgcgccagg cggggcgggg cgggcgagg ggcggggcgg ggcgaggcgg     720
agaggtgcgg cggcagccaa tcagagcggc gcgctccgaa agtttccttt tatggcgagg    780
cggcggcggc ggcggcccta taaaaagcga agcgcgcggc gggcgggagt cgctgcgttg    840
ccttcgcccc gtgccccgct ccgcgccgcc tcgcgccgcc cgccccggct ctgactgacc    900
gcgttactcc cacaggtgag cgggcgggac ggccttctc ctccgggctg taattagcgc     960
ttggttaat gacggctcgt ttcttttctg tggctgcgtg aaagccttaa agggctccgg    1020
gagggcccttt tgtgcggggg ggagcggctc gggggggtgcg tgcgtgtgtg tgtgcgttga  1080
gagcgccgcg tgcggcccgc gctgcccggc ggctgtgagc gctgcgggcg cggcgcgggg   1140
ctttgtgcgc tccgcgtgtg cgcgagggga gcgcggccgg gggcggtgcc ccgcggtgcg   1200
gggggggctgc gaggggaaca aaggctgcgt gcgggtgtg tgcgtggggg ggtgagcagg   1260
gggtgtgggc gcggcggtcg ggctgtaacc ccccccctgca cccccctccc cgagttgctg  1320
agcacggccc ggcttcgggt gcggggctcc gtgcgggcg tggcgcgggg ctcgccgtgc    1380
cgggcgggg gtggcggcag gtgggggtgc cgggcgggc ggggccgcct cgggccgggg     1440
agggctcggg ggaggggcgc ggcggccccc ggagcgccgg cggctgtcga ggcgcggcga   1500
gccgcagcca ttgccttta tggtaatcgt gcgagagggc gcagggactt cctttgtccc    1560
aaatctgtgc ggagccgaaa tctgggaggc gccgccgcac cccctctagc ggggcgcgggg  1620
cgaagcggtg cggcgccggc aggaaggaaa tgggcggga gggccttcgt gcgtcgccgc    1680
gccgccgtcc ccttctccct ctccagcctc ggggctgtcc gcggggggac ggctgccttc   1740
ggggggggacg gggcaggggc gggttcggct tctggcggtgt gaccggcctg tctagagcct  1800
ctgctaacca tgttcatgcc ttcttctttt tcctacagct cctgggcaac gtgctggtta   1860
ttgtgaccgg tgccaccatg taccggatgc agctgctgag ctgtatcgcc ctgtctctgg   1920
ccctggtcac caattctgag gtgcagctgg tggaatctgg cggcggactt gttcaacctg   1980
gcggctctct gagactgagc tgtgccgctt ctggcacgca cttcacccac tacggcatga   2040
actgggtccg acaggcccct ggcaaaggcc ttgaatgggt cggatggatc aacacctaca   2100
ccggcgagcc aacatacgcc gccgacttca agcggagatt caccttcagc ctggacacca   2160
gcaagagcac cgcctacctg cagatgaaca gcctgagagc cgaggacacc gccgtgtact   2220
actgcgccaa gtatccctac tactacggca ccagccactg gtactttgac gtgtggggac   2280
agggcacact ggtcacagtg tctagcgcct ctacaaaggg ccccagcgtt ttcccactgt   2340
ctcctagcag caagtctacc agcggaggaa cagccgctct gggctgtctg gtcaaggact   2400
actttcccga gcctgtgacc gtgtcctgga attctggcgc tctgacaagc ggcgtgcaca   2460
ccttccagc tgtgctgcaa agcagcggcc tgtactctct gagcagcgtc gtgacagtgc    2520
caagcagctc tctgggcacc cagacctaca tctgcaatgt gaaccacaag cctagcaaca   2580
ccaaggtgga caagaaggtg gaacccaaga gctgcgacaa gacccacacc ggcaagcgga   2640
agagaagagg ctctggcgaa ggcagaggca gcctgcttac atgtggcgac gtggaagaga   2700
acccccggacc tatgtataga atgcagctcc tgtcctgcat tgccctgagc ctggctctcg   2760
tgaccacaag cgacatccag ctgacacaga gcccccagcc cctgtctgcc tctgtgggga   2820
acagagtgac catcacctgt agcgccagcc aggacatctc caactacctg aactggtatc   2880
agcaaaagcc cggcaaggcc cctaaggtgc tgatctactt cacaagcagc ctgcactccg   2940
gcgtgcccag cagattttct ggctctggca gcggcaccga cttcacccctg accatatcta   3000
gcctgcagcc tgaggacttc gccaccctact actgccaggc tattacgcag acgctgccttga  3060
catttggcca gggcacaaag gtggaaatca gcggactgt ggccgctcct agcgtgttca    3120
tctttccacc tagcgacgag cagctgaagt ctggcacagc ctctgtcgtg tgcctgctga   3180
acaacttcta ccccagagaa gccaaggtgc agtggaaagt ggacaatgcc ctgcagagcg   3240
gcaacagcca agagagcgtg acagagcagg actccaagga tagcacctat agcctgagca   3300
gcaccctgac actgagcaag gccgactacg agaagcacaa agtgtacgcc tgcgaagtga   3360
cccaccaggg cctttctagc cctgtgacca gagcttcaa ccggggcgaa tgttaagagc     3420
tcgctgatca gcctcgactg tgccttctag ttgccagcca tctgttgttt gccctccc     3480
cgtgccttcc ttgaccctgg aaggtgccac tcccactgtc ctttcctaat aaaatgagga   3540
aattgcatcg cattgtctga gtaggtgtca ttctattctg ggggtgggg tgggcagga     3600
cagcaagggg gaggattggg aagacaatag caggcatgct ggggatgcgg tgggctctat   3660
ggaagcttga attcagctga cgtgcctcgg accgcctagg aggaaccctc agtgatggag   3720
ttggccactc cctctctgcg cgctcgctcg ctcactgagg ccgggcgacc aaaggtcgcc   3780
cgacgcccgg gctttgcccg ggcggcctca gtgagcgagc gagcgcgcag agagggagtg   3840
gccaa                                                              3845
```

SEQ ID NO: 93          moltype = DNA    length = 4452
FEATURE                Location/Qualifiers
misc_feature           1..4452
                       note = source = /note="Description of Artificial Sequence:
                       Synthetic polynucleotide"
source                 1..4452
                       mol_type = other DNA
                       organism = synthetic construct
SEQUENCE: 93

```
ctgcgcgctc gctcgctcac tgaggccgcc cgggcgtcgg gcgacctttg gtcgcccggc     60
ctcagtgagc gagcgagcgc gcagagaggg agtggccaac tccatcacta ggggttcctg    120
cggccgcacg cgtgacattg attattgact agttattaat agtaatcaat tacgggggtca   180
ttagttcata gcccatatat ggagttccgc gttacataac ttacggtaaa tggcccgcct    240
ggctgaccgc ccaacgaccc ccgcccattg acgtcaataa tgacgtatgt tcccatagta    300
acgccaatag ggactttcca ttgacgtcaa tgggtggact atttacggta aactgcccac    360
ttggcagtac atcaagtgta tcatatgcca agtacgccc ctattgacgt caatgacggt     420
aaatggcccg cctggcatta tgcccagtac atgaccttat gggactttcc tacttggcag    480
tacatctacg tattagtcat cgctattacc atggtcgag gtgagcccca cgttctgctt     540
cactctcccc atctccccc cctcccacc ccaatttttg tatttattta ttttttaatt      600
attttgtgca gcgatgggg ggggggggg gggggcgcgc gccaggcggg gcggggcggg      660
gcgagggggcg gggcggggcg aggcggagag gtgcggcggc agccaatcag agcggcgcgc   720
```

```
tccgaaagtt tccttttatg gcgaggcggc ggcggcggcg gccctataaa aagcgaagcg    780
cgcggcgggc gggagtcgct gcgttgcctt cgccccgtgc cccgctccgc gccgcctcgc    840
gccgcccgcc ccggctctga ctgaccgcgt tactcccaca ggtgagcggg cgggacggcc    900
cttctcctcc gggctgtaat tagcgcttgg tttaatgacg gctcgtttct tttctgtggc    960
tgcctgaaag ccttaaaggg ctccgtgaag gccctttgtg cggggggag cggctcgggg    1020
ggtgcgtgcg tgtgtgtgtg cgtggggagc gccgcgtgcg gcccgcgctg cccggcggct   1080
gtgagcgctg cgggcgcggc gcggggcttt gtgcgctccg cgtgtgcgcg aggggagcgc   1140
ggccggggc ggtgccccgc ggtgcggggg ggctgcgagg ggaacaaagg ctgcgtgcgg    1200
ggtgtgtgcg tgggggggtg agcagggggt gtgggcgcgg cggtcgggct gtaaccccc    1260
cctgcacccc cctccccgag ttgctgagca cggcccggct tcgggtgcgg ggctccgtgc   1320
ggggcgtggc gcggggctcg ccgtgccggg cgggggtgg cggcaggtgg gggtgccggg    1380
cggggcgggg ccgcctcggg ccggggaggg ctcgggggag gggcgcggcg gccccggag   1440
cgccggcggc tgtcgaggcg cggcgagccg cagccattgc cttttatggt aatcgtgcga   1500
gagggcgcag ggacttcctt tgtcccaaat ctgtgcggga ccgaaatctg ggaggcgccg   1560
ccgcacccc tctagcgggc gcggggcgaa gcggtgcggc gccggcagga aggaaatggg   1620
cggggagggc cttcgtgcgt cgccgcgccg ccgtccccctt ctccctctcc agcctcgggg   1680
ctgtccgcgg ggggacgggct gccttcgggg gggacggggc agggcggggt tcggcttctg   1740
gcgtgtgacc ggcggctcta gagcctctgc taaccatgtt catgccttct tctttttcct   1800
acagctcctg ggcaacgtgc tggttattgt gaccggtgcc accatgtacc ggatgcagct   1860
gctgagctgt atcgccctgt ctctggccct ggtcaccaat tctgaggtgc agctggtgga   1920
atctggcggc ggacttgttc aacctggcgg ctctctgaga ctgagctgtg ccgcttctgg   1980
ctacaccttc accaactacg gcatgaactg ggtccgacag gccctggca aaggccttga   2040
atgggtcgga tggatcaaca cctacaccgg cgagccaaca tacgccgccg acttcaagcg   2100
gagattcacc ttcagcctgg acaccagcaa gagcaccgcc tacctgcaga tgaacagcct   2160
gagagccgag gacaccgccg tgtactactg cgccaagtat ccccactact acggcagcag   2220
ccactggtac tttgacgtgt ggggacaggg cacactggtca acagtgtcta gcgcctctac   2280
aaagggcccc agcgttttcc cactggctcc tagcagcaag tctaccgcg gaggaacagc   2340
cgctctgggc tgtctggtca aggactactt tcccgagcct gtgaccgtgt cctggaattc   2400
tggcgctctg acaagcggcg tgcacacctt tccagctgtg ctgcaaagca gcggcctgta   2460
ctctctgagc agcgtcgtga cagtgccaag cagctctctg ggcacccaga cctacatctg   2520
caatgtgaac cacaagccta gcaaccacca ggtggacaa aaggtggaac ccaagagctg   2580
cgacaagacc cacacctgtc ctccatgtcc tgctccagaa ctgctcggcg gacctttccgt   2640
gttcctgttt cctccaaagc ctaaggcacc cctgatgatc agcagaaccc ctgaagtgac   2700
ctgcgtggtg gtggatgtgt cccacgagga tcccgaagtg aagttcaatt ggtacgtgga   2760
cggcgtggaa gtgcacaacg ccaagaccaa gcctagagag gaacagtaca acagcaccta   2820
cagagtggtg tccgtgctga ccgtgctgca ccaggattgg ctgaacggca aagagtacaa   2880
gtgcaaggtg tccaacaagg ccctgcctgc tcctatcgag aaaaccatca gcaaggccaa   2940
gggccagcct agggaacccc aggtttacac actgcctcca agcccggaag atgaccaa    3000
gaaccaggtg tccctgacct gcctcgtgaa ggcttctac ccttccgata tcgccgtgga   3060
atgggagagc aatggccagc cagagaacaa ctacaagaca cccctcctg tgctggacag   3120
cgacggctca ttcttcctgt acagcaagct gacagtggac aagtccagat ggcagcaggg   3180
caacgtgttc agctgcagcg tgatgcacga ggccctgcac aaccactaca cccagaagtc   3240
tctgagcctg tctcctggca gcggaaagag aaggctct ggcgaaggca gggcagcct    3300
gcttacatgt ggcgacgtgg aagagaaccc cggacctatg tatagaatgc agctcctgtc   3360
ctgcattgcc ctgagcctgg ctctcgtgac caacagcgac atccagatga cacagagccc   3420
cagcagcctg tctgcctctg tgggagacag agtgaccatc acctgtagcg ccagccagga   3480
catctccaac tacctgaact ggtatcagca aagcccgga aggccccta aggtgctgat   3540
ctacttcaca agcagcctgc actccggcgt gcccagcaga ttttctggct ctggcagcgg   3600
caccgacttc accctgacca tatctagcct gcagcctgag gacttcgcca cctactactg   3660
ccagcagtac agcaccgtgc cttggacatt tggccaggc acaaaggtgg aaatcaagcg   3720
gactgtggcc gctcctagcg tgttcatctt tccacctagc gacgagcgc tgaagtctga   3780
cacagcctct gtcgtgtgcc tgctgaacaa cttctacccc agagaagcca aggtgcagtg   3840
gaaagtggac aatgccctgc agagcggcaa cagccaagag agcgtgacag agcaggactc   3900
caaggatagc acctataccg ccagcagcac cctgacactg agcaaggcg actacgagaa   3960
gcacaaagtg tacgcctgcg aagtgaccca ccagggcctt tctagccctg tgaccaagag   4020
cttcaaccgg ggcgaatgtt aagagctcgc tgatcagcct cgactgtgcc ttctagttgc   4080
cagccatctg ttgtttgccc ctcccccgtg ccttccttga ccctgaaggg tgccactccc   4140
actgtccttt cctaataaaa tgaggaaatt gcatcgcatt gtctgagtag gtgtcattct   4200
attctggggg gtgggtggg gcaggacagc aaggggggagg attgggaaga caatagcagg   4260
catgctgggg atgcggtggg ctctatgaa gcttgaattc agctgacgtg cctcggaccg   4320
ctaggaaccc ctagtgatgg agttggccac tccctctctg cgcgctcgct cgctcactga   4380
ggccgggcga ccaaaggtcg cccgacgccc gggctttgcc cgggcggcct cagtgagcga   4440
gcgagcgcgc ag                                                       4452
```

SEQ ID NO: 94   moltype = DNA  length = 4507  
FEATURE      Location/Qualifiers  
misc_feature   1..4507  
          note = source = /note="Description of Artificial Sequence:  
          Synthetic polynucleotide"  
source       1..4507  
          mol_type = other DNA  
          organism = synthetic construct  
SEQUENCE: 94

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg   120
gccaactcca tcactagggg ttcctttgtc gacgcgccg cacgcgtgac attgattatt    180
gactagttat taatagtaat caattacggg gtcattagtt catagcccat atatggagtt   240
ccgcgttaca taacttacgg taaatggccc gcctggctga ccgcccaacg acccccgccc   300
attgacgtca ataatgacgt atgttcccat agtaacgcca atagggactt tccattgacg   360
```

```
tcaatgggtg gactatttac ggtaaactgc ccacttggca gtacatcaag tgtatcatat    420
gccaagtacg cccctattg acgtcaatga cggtaaatgg cccgcctggc attatgccca    480
gtacatgacc ttatgggact ttcctacttg gcagtacatc tacgtattag tcatcgctat    540
taccatgggt cgaggtgagc cccacgttct gcttcactct cccatctcc cccctccc      600
cacccccaat tttgtattta tttattttt aattattttg tgcagcgatg ggggcgggg     660
ggggggggggg gcgcgcgcca ggcggggcgg ggcggggcga ggggcgggc ggggcgaggc   720
ggagaggtgc ggcggcagcc aatcagagcg gcgcgctccg aaagtttcct tttatggcga   780
ggcggcggcg gcggcggccc tataaaaagc gaagcgcgcg gcgggcggga gtcgctgcgt   840
tgccttcgcc ccgtgcccg ctccgcgccg cctcgccgcg cccgccccgg ctctgactga    900
ccgcgttact cccacaggtg agcggccggg acggcccttc tcctccgggc tgtaattagc   960
gcttggtttta atgacggctc gtttcttttc tgtggctgcg tgaaagcctt aaagggctcc 1020
gggagggccc tttgtgcggg ggggagcggc tcggggggtg cgtgcgtgtg tgtgtgcgtg  1080
gggagcgccg cgtgcggccc gcgctgcccg gcggctgtga gcgctgcggg cgcggcgcgg  1140
ggctttgtgc gctccgcgtg tgcgcgaggg gagcgcgcg cccgcgcgtg                1200
cggggggggct gcgaggggaa caaaggctgc gtgcgggtg tgtgcgtggg gggtgagca    1260
gggggtgtgg gcgcggcgt cgggctgtaa ccccccctg caccccctc cccgagttgc     1320
tgagcacggc ccggcttcgg gtgcggggct ccgtgcgggg cgtggcgcgg ggctcgccgt  1380
gccggggcggg gggtggcggc aggtggggt gccgggcggg gcggggcgc ctcggggcgg   1440
ggagggctcg ggggagggc gcggcggccc ccggagcgcc ggcggctgtc gaggcgcggc   1500
gagccgcagc cattgccttt tatggtaatc gtgcgagagg gcgcagggac ttcctttgtc  1560
ccaaatctgt gcggagccga aatctgggag gcgccgccgc ccccctcta gcgggcgcgg   1620
ggcgaagcgg tgcggcgccg gcaggaagga aatgggcggg agggccttc gtgcgtcgcc   1680
gcgccgccgt cccttctcc ctctccagcc tcggggctgt ccgcgggggg acggctgcct   1740
tcgggggga cggggcaggg cgggttcgg cttctggcgt gtgaccggcg gctctagagc   1800
ctctgctaac catgttcatg ccttcttctt tttcctacag ctcctgggca acgtgctggt  1860
tattgtgacc ggtgccacca tgtaccggat gcagctgctg agctgtatcg ccctgtctct  1920
ggccctggtc accaattctg aggtgcagct ggtggaatct ggcggcggac ttgttcaacc  1980
tggcggctct ctgagactga gctgtgccgc ttctggctac accttcacca actacggcat  2040
gaactgggtc cgacaggccc ctggcaaagg ccttgaatgg gtcggatgga tcaacaccta  2100
caccggcgag ccaacatacg ccgccgactt caagcggaga ttcaccttca gcctggacac  2160
cagcaagagc accgcctacc tgcagatgaa cagcctgaga gccgaggaca ccgccgtgta  2220
ctactgcgcc aagtatcccc actactacgg cagcagccac tggtactttg acgtgtgggg  2280
acagggcaca ctggtcacag tgtctagcgc ctctacaaag ggccccagcg ttttcccact  2340
ggctcctagc agcaagtcta ccagcggagg aacagccgct ctgggctgtc tggtcaagga  2400
ctactttccc gagcctgtga ccgtgtcctg gaattctggc gctctgacaa gcggcgtgca  2460
cacctttcca gctgtgctgc aaagcagcgg cctgtactct ctgagcagcg tcgtgacagt  2520
gccaagcagc tctctgggca cccagaccta catctgcaat gtgaaccaca agcctagcaa  2580
caccaaggtg gacaagaagg tggaacccaa gagctgcgac aagacccaca cctgtcctcc  2640
atgtcctgct ccagaactgc tcggcggacc ttccgtgttc ctgtttcctc caaagcctaa  2700
ggacaccctg atgatcagca gaacccctga agtgacctgc gtggtggtgg atgtgtccca  2760
cgaggatccc gaagtgaagt tcaattggta cgtggacggc gtgaagtgc acaacgccaa   2820
gaccaagcct agagaggaac agtacaacag cacctacaga gtggtgtccg tgctgaccgt  2880
gctgcaccag gattggctga acggcaaaga gtacaagtgc aaggtgctcc acaaggccct  2940
gcctgctcct atcgagaaaa ccatcagcaa ggccaagggc cagcctaggg aacccccagg  3000
ttacacactg cctccaagcc gggaagagat gaccaagaac caggtgtccc tgacctgcct  3060
cgtgaagggc ttctaccctt ccgatatcgc cgtggaatgg gagagcaatg ccagccaga   3120
gaacaactac aagacaaccc ctcctgtgct ggacagcgac ggctcattct tcctgtacag  3180
caagctgaca gtggacaagt ccagatggca gcagggcaac gtgttcagct gcagcgtgat  3240
gcacgaggcc ctgcacaacc actacaccca gaagtctctg agcctgtctc ctggcaagcg  3300
gaagagaaga ggctctggcg aaggcagagg cagcctgctt acatgtggcg acgtggaaga  3360
gaaccccgga cctatgtata gaatgcagct cctgtcctgc attgccctga gctggctct   3420
cgtgaccaac agcgacatcc agatgacaca gagcccagc agcctgtctg cctctgtggg   3480
agacagagtg accatcacct gtagcgccag ccaggacatc tccaactacc tgaactggta  3540
tcagcaaaag cccggcaagg cccctaaggt gctgatctac ttcacaagca gcctgcactc  3600
cggcgtgccc agcagatttt ctggctctgg cagcggcacc gacttcaccc tgaccatatc  3660
tagcctgcag cctgaggact tcgccaccta ctactgccag cagtacagca ccgtgccttg  3720
gacatttggc cagggcacaa aggtggaaat caagcggact gtggccgctc tagcgtgtt   3780
catcttttcca cctagcgacg agcagctgaa gtctggcaca gcctctgtcg tgtgcctgct  3840
gaacaacttc taccccagag aagccaaggt gcagtggaaa gtggacaatg ccctgcagag  3900
cggcaacagc caagagagcg tgacagagca ggactccaag gatagcacct atagcctgag  3960
cagcaccctg acactgagca aggccgacta cgagaagcac aaagtgtacg cctgcgaagt  4020
gacccaccag ggcctttcta gccctgtgac caagagcttc aaccggggcg aatgttaaga  4080
gctcgctgat cagcctcgac tgtgccttct agttgccagc catctgttgt ttgccctcc   4140
cccgtgcctt ccttgaccct ggaaggtgcc actcccactg tccttctcctacta ataaatgag  4200
gaaattgcat cgcattgtct gagtaggtgt cattctattc tggggggtgg ggtggggcag  4260
gacagcaagg gggaggattg ggaagacaat agcaggcatg ctgggatgc ggtgggctct   4320
atggaagctt gaattcagct gacgtgcctc ggaccgccta ggaggaaccc ctagtgatgg  4380
agttggccac tccctctctg cgcgctcgct cgctcactga ggccgggcga ccaaaggtcg  4440
cccgacgccc gggctttgcc cgggcggcct cagtgagcga gcgagcgcgc agagagggag  4500
tggccaa                                                              4507
```

SEQ ID NO: 95      moltype = DNA    length = 3609
FEATURE            Location/Qualifiers
misc_feature       1..3609
                   note = source = /note="Description of Artificial Sequence:
                   Synthetic polynucleotide"
source             1..3609
                   mol_type = other DNA
                   organism = synthetic construct

SEQUENCE: 95

```
ctgcgcgctc gctcgctcac tgaggccgcc cgggcgtcgg gcgacctttg gtcgcccggc    60
ctcagtgagc gagcgagcgc gcagagaggg agtggccaac tccatcacta ggggttcctg   120
cggccgcacg cgtgacattg attattgact agttattaat agtaatcaat tacgggtca    180
ttagttcata gcccatatat ggagttccgc gttacataac ttacggtaaa tggcccgcct   240
ggctgaccgc ccaacgaccc cgcccattg acgtcaataa tgacgtatgt tcccatagta    300
acgccaatag ggactttcca ttgacgtcaa tgggtggact atttacggta aactgcccac   360
ttggcagtac atcaagtgta tcatatgcca agtacgcccc ctattgacgt caatgacggt   420
aaatggcccg cctggcatta tgcccagtac atgaccttat gggactttcc tacttggcag   480
tacatctacg tattagtcat cgctattacc atgggtcgag gtgagcccca cgttctgctt   540
cactctcccc atctccccc cctccccacc cccaattttg tatttattta ttttttaatt   600
attttgtgca gcgatggggg cgggggggg ggggcgcgc gccaggcggg gcggggcggg   660
gcgagggcg gggcggggcg aggcggagag gtgcggcgg agccaatcag agcggcgcgc   720
tccgaaagtt tccttttatg gcgaggcggc ggcggccggg gccctataaa aagcgaagcg   780
cgcggcgggc gggagtcgct gcgttgcctt cgccccgtgc cccgctccgc gccgcctcgc   840
gccgcccgcc ccggctctga ctgaccgcgt tactcccaca ggtgagcggg cgggacggcc   900
cttctcctcc gggctgtaat tagcgcttgg tttaatgacg gctcgtttct tttctgtggc   960
tgcgtgaaag ccttaaaggg ctccgggagg gccctttgg gcggggggag cggctcgggg  1020
ggtgcgtgcg tgtgtgtgtg cgtggggagc gccgcgtgcg gcccgcgctg cccggcggct  1080
gtgagcgctg cgggcgcggc gcgggggcttt gtgcgctccg cgtgtgcgcg aggggagcgc  1140
ggccggggc ggtgccccgc ggtgcggggg ggctgcgagg gaacaaagg ctgcgtgcgg   1200
ggtgtgtcg tgggggggt agcagggggt gtgggccgg cggtcgggct gtaaccccc    1260
cctgcacccc cctccccgag ttgctgagca cggcccggct tcgggtgcgg ggctccgtgc  1320
ggggcgtggc gcggggctcg ccgtgccggg cgggggtgg cggcaggtgg gggtgccggg   1380
cggggcgggg ccgcctcggg ccggggaggg ctcggggag gggcgcggcg gccccggag   1440
cgccggcggc tgtcgaggcg cggcgagccg cagccattgc cttttatggt aatcgtgcga   1500
gagggcgcag ggacttcctt tgtcccaaat ctgtgcggga ccgaaatctg ggaggcgccg   1560
ccgcacccc tctagcgggc gcggggcgaa gcggtgcggc gccggcagga aggaaatggg   1620
cggggagggc cttcgtgcgt cgccgcgccg ccgtcccctt ctccctctcc agcctcgggg   1680
ctgtccgcgg gggacggct gccttcgggg gggacggggc agggcgggt tcggcttctg   1740
gcgtgtgacc ggcggctcta gagcctctgc taaccatgtt catgccttct tcttttttcct  1800
acagctcctg ggcaacgtgc tggttattgt gaccggtgcc accatgtacc ggatgcagct   1860
gctgagctgt atcgccctgt ctctggccct ggtcaccaat tctagcgata ccggcagacc   1920
cttcgtggaa atgtacagcg agatcccga gatcatccac atgaccgagg gcagagagct   1980
ggtcatccc tgcagagtga caagcccaa catcaccgtg actctgaaga agttccctct   2040
ggacacactg atccccgacg gcaagagaat catctgggac agccggaagg gcttcatcat   2100
cagcaacgcc acctacaaag agatcggcct gctgacctgt gaagccaccg tgaatgccca   2160
cctgtacaag accaactacc tgacacacag acagaccaac accatcatcg acgtggtgct   2220
gagccctagc cacggcattg aactgtctgt gggcgagaag ctggtgctga actgtaccgc   2280
cagaaccgag ctgaacgtgg gcatcgactt caactgggag tacccccagca gcaagcacca   2340
gcacaagaaa ctggtcaacc gggacctgaa acccagagc ggcagcgaga tgaagaaatt   2400
cctgagcacc ctgaccatcg acggcgtgac cagatctgac cagggcctgt acacatgtgc   2460
cgccagctct ggcctgatga ccaagaaaaa cagcaccttc gtgcgggtgc acgagaagtg   2520
caagacccac acctgtcctc catgtcctgc tccagaactg ctcggcgac cttccgtgtt   2580
cctgtttcct ccaaagccta aggacaccct gatgatcagc agaacccctg aagtgacctg   2640
cgtggtggtg gatgtgtccc acgaggatcc cgaagtgaag ttcaattggt acgtggacgg   2700
cgtggaggtg cacaacgcca agaccaagcc tagagaggaa cagtacaata gcacctacag   2760
agtggtgtcc gtgctgaccg tgctgcacca ggattggctg aacggcaaag agtacaagtg   2820
caaggtgtcc aacaaggccc tgcctgctcc tatcgagaaa accatctcca aggccaaggg   2880
ccagcctagg gaacccccagg tttacacact gcctccaagc agggacgagc tgacaaagaa   2940
ccaggtgtcc ctgacctgcc tggtcaaggg ctttctaccct tccgatatcg ccgtggaatg   3000
ggagagcaat ggccagcctg agaacaacta caagacaacc cctcctgtgc tggacagcga   3060
cggctcattc ttcctgtaca gcaagctgac agtggacaag agcagatggc agcagggcaa   3120
cgtgttcagc tgcagcgtga tgcacgaggc cctgcacaac cactacaccc agaagtcct   3180
gagcctgtct cctggataag agctcgctga tcagcctcga ctgtgccttc tagttgccag   3240
ccatctgttg tttgcccctc ccccgtgcct tccttgaccc tggaaggtgc cactcccact   3300
gtcctttcct aataaaatga ggaaattgca tcgcattgtc tgagtaggtg tcattctatt   3360
ctggggggtg ggtggggca ggacagcaag ggggaggatt gggaagacaa tagcaggcat   3420
gctggggatg cggtgggctc tatggaagct tgaattcagc tgacgtgcct cggaccgcta   3480
ggaacccta gtgatggagt tggccactcc ctctctgcgc gctcgctcgc tcactgaggc   3540
cgggcgacca aaggtcgccc gacgcccggg cttttgcccgg gcggcctcag tgagcgagcg   3600
agcgcgcag                                                         3609
```

| SEQ ID NO: 96 | moltype = DNA    length = 3664 |
|---|---|
| FEATURE | Location/Qualifiers |
| misc_feature | 1..3664 |
| | note = source = /note="Description of Artificial Sequence: Synthetic polynucleotide" |
| source | 1..3664 |
| | mol_type = other DNA |
| | organism = synthetic construct |

SEQUENCE: 96

```
ttggccactc cctctctgcg cgctcgctcg ctcactgagg ccgcccgggc aaagcccggg    60
cgtcggggcga cctttggtcg cccggcctca gtgagcgagc gagcgcgcag agagggagtg   120
gccaactcca tcactagggg ttcctttgtc gacgcggccg cacgcgtgac attgattatt   180
gactagttat taatagtaat caattacggg gtcattagtt catagcccat atatggagtt   240
ccgcgttaca taacttacgg taaatggccc gcctggctga ccgcccaacg accccgccc    300
attgacgtca ataatgacgt atgttccat agtaacgcca atagggactt tccattgacg   360
tcaatgggtg gactatttac ggtaaactgc ccacttggca gtacatcaag tgtatcatat   420
```

```
gccaagtacg cccctattg acgtcaatga cggtaaatgg cccgcctggc attatgccca    480
gtacatgacc ttatgggact ttcctacttg gcagtacatc tacgtattag tcatcgctat    540
taccatgggt cgaggtgagc cccacgttct gcttcactct cccatctcc cccctccc      600
cacccccaat tttgtattta tttattttt aattattttg tgcagcgatg ggggcggggg    660
gggggggggg gcgcgcgcca ggcggggcgg ggcggggcga gggggcgggc gggcgaggc    720
ggagaggtgc ggcggcagcc aatcagagcg gcgcgctccg aaagtttcct tttatggcga    780
ggcggcggcg gcggcggccc tataaaaagc gaagcgcgcg gcgggcggga gtcgctgcgt    840
tgccttcgcc ccgtgcccg ctccgcgccg cctcgcgccg cccgcccgg ctctgactga     900
ccgcgttact cccacaggtg agcgggcggg acggcccttc tcctccgggc tgtaattagc    960
gcttggttta atgacggctc gttttctttc tgtggctgcg tgaaagcctt aaagggctcc   1020
gggagggccc tttgtgcggg ggggagcggc tcgggggtg cgtgcgtgtg tgtgtgcgtg    1080
gggagcgccg cgtgcggccc gcgctgcccg cggctgtga gcgctgcggg cgcggcgcgg   1140
ggctttgtgc gctccgcgtg tgcgcgaggg gagcgcggcc ggggcggtg cccgcggtg     1200
cgggggcgtg gcgagggaaa caaaggctgc gtgcgggggc tgtgcgtggg gggtgagca    1260
gggggtgtgg gcgcggcggt cgggctgtaa ccccccctg caccccctc cccgagttgc    1320
tgagcacggc ccggcttcgg gtgcggggct ccgtgcgggg cgtggcgcgg ggctcgccgt   1380
gccgggcggg gggtggcggc aggtgggggt gccgggcggg gcggggccgc ctcgggccgg   1440
gggagggctcg ggggagggc gcggcggcc ccggagcgcc ggcggctgtc gaggcgcgc    1500
gagccgcagc cattgccttt tatggtaatc gtgcgagagg gcgcagggac ttccttttgc   1560
ccaaatctgt gcggagccga aatctgggag gcgccgccgc accccctcta gcgggcgcgg   1620
ggcgaagcgg tgcggcgccg gcaggaagga aatgggcggg gagggccttc gtgcgtcgcc   1680
gcgccgccgt cccttctcc ctctccagcc tcggggctgt ccgcggggg acggctgcct    1740
tcggggggga cggggcaggg cggggttcgg cttctggcgt gtgaccggcg gctctagagc   1800
ctctgctaac catgttcatg ccttcttctt tttcctacag ctcctgggca acgtgctggt   1860
tattgtgacc ggtgccacca tgtaccggat gcagctgctg agctgtatcg ccctgtctct   1920
ggccctggtc accaattcta gcgataccgg cagaccttc gtggaaatgt acagcgagat   1980
ccccgagatc atccacatga ccgagggcag agagctggtc atccctgca gagtgacaag   2040
ccccaacatc accgtgactc tgaagaagtt ccctctggac acactgatcc ccgacggcaa   2100
gagaatcatc tgggacagcc ggaagggctt catcatcagc aacgccacct acaaagagat   2160
cggcctgctg acctgtgaag ccaccgtgaa tggccacctg tacaagacca actacctgac   2220
acacagacag accaacacca tcatcgacgt ggtgctgagc cctagccacg gcattgaact   2280
gtctgtgggc gagaagctgg tgctgaactg taccgccaga accgagctga acgtgggcat   2340
cgacttcaac tgggagtacc ccagcagcaa gcaccagcac aagaaactgg tcaacgggga   2400
cctgaaaacc cagagcggca gcgagatgaa gaaattcctg agcaccctga ccatcgacgg   2460
cgtgaccaga tctgaccagg gcctgtacac atgtgccgcc agctctggcc tgatgaccaa   2520
gaaaacagc accttcgtgc gggtgcacga aaggacaag acccacacct gtcctccatg    2580
tcctgctcca gaactgctcg gcggaccttc cgtgttcctg tttcctccaa agcctaagga   2640
caccctgatg atcagcagaa ccccctgaagt gacctgcgtg gtggtggatg tgtcccacga   2700
ggatcccgaa gtgaagttca attggtacgt ggacggcgtg gaagtgcaca acgccaagac   2760
caagcctaga gaggaacagt acaatagcac ctacagagtg gtgtccgtgc tgaccgtgct   2820
gcaccaggat tggctgaacg gcaaagagta caagtgcaag gtgtccaaca aggccctgcc   2880
tgctcctatc gagaaaacca tctccaaggc caagggccag cctagggaac ccagggttta   2940
cacactgcct ccaagcaggg acgagctgac aaagaaccag gtgtccctga cctgcctggt   3000
caagggcttc tacccttccg atatcgccgt ggaatgggag agcaatggcc agcctgagaa   3060
caactacaag acaacccctc ctgtgctgga cagcgacggc tcattcttcc tgtacagcaa   3120
gctgacagtg gacaagagca gatggcagca gggcaacgtg ttcagctgca gcgtgatgca   3180
cgaggccctg cacaaccact acacccgaaa gtccctgagc ctgtctccttg gataagagct   3240
cgctgatcag cctcgactgt gccttctagt tgccagccat ctgttgtttg ccctcccccc   3300
gtgccttcct tgaccctgga aggtgccact cccactgtcc tttcctaata aaatgaggaa   3360
attgcatcgc attgtctgag taggtgtcat tctattctgg ggggtggggt ggggcaggac   3420
agcaaggggg aggattggga agacaatagc aggcatgctg gggatgcggt gggctctatg   3480
gaagcttgaa ttcagctgac gtgcctcgga ccgcctagga ggaaccccta gtgatggagt   3540
tggccactcc ctctctgcgc gctcgctcgc tcactgagc cgggcgacca aaggtcgccc     3600
gacgcccggg ctttgcccgg gcggcctcag tgagcgagcg agcgcgcaga gagggagtgg   3660
ccaa                                                                3664

SEQ ID NO: 97           moltype = DNA  length = 16
FEATURE                 Location/Qualifiers
misc_feature            1..16
                        note = source = /note="Description of Artificial Sequence:
                        Synthetic probe"
source                  1..16
                        mol_type = other DNA
                        organism = synthetic construct
SEQUENCE: 97
ccagcagagt cagggc                                                      16

SEQ ID NO: 98           moltype = DNA  length = 23
FEATURE                 Location/Qualifiers
misc_feature            1..23
                        note = source = /note="Description of Artificial Sequence:
                        Synthetic primer"
source                  1..23
                        mol_type = other DNA
                        organism = synthetic construct
SEQUENCE: 98
gatacagcta gagtcctgat tgc                                              23

SEQ ID NO: 99           moltype = DNA  length = 23
```

```
FEATURE                 Location/Qualifiers
misc_feature            1..23
                        note = source = /note="Description of Artificial Sequence:
                        Synthetic primer"
source                  1..23
                        mol_type = other DNA
                        organism = synthetic construct
SEQUENCE: 99
gatctgccaa gtacctcact atg                                                    23

SEQ ID NO: 100          moltype = DNA  length = 21
FEATURE                 Location/Qualifiers
misc_feature            1..21
                        note = source = /note="Description of Artificial Sequence:
                        Synthetic primer"
source                  1..21
                        mol_type = other DNA
                        organism = synthetic construct
SEQUENCE: 100
ccgatttcgg cctattggtt a                                                      21

SEQ ID NO: 101          moltype = DNA  length = 21
FEATURE                 Location/Qualifiers
misc_feature            1..21
                        note = source = /note="Description of Artificial Sequence:
                        Synthetic primer"
source                  1..21
                        mol_type = other DNA
                        organism = synthetic construct
SEQUENCE: 101
ctgtggagag aaaggcaaag t                                                      21

SEQ ID NO: 102          moltype = DNA  length = 26
FEATURE                 Location/Qualifiers
misc_feature            1..26
                        note = source = /note="Description of Artificial Sequence:
                        Synthetic probe"
source                  1..26
                        mol_type = other DNA
                        organism = synthetic construct
SEQUENCE: 102
ggcacctatt ggtcttactg acatcc                                                 26

SEQ ID NO: 103          moltype = DNA  length = 1536
FEATURE                 Location/Qualifiers
misc_feature            1..1536
                        note = source = /note="Description of Artificial Sequence:
                        Synthetic polynucleotide"
source                  1..1536
                        mol_type = other DNA
                        organism = synthetic construct
SEQUENCE: 103
atgtaccgga tgcagctgct gagctgtatc gccctgtctc tggccctggt caccaattct    60
gaggtgcagc tggtggaatc tggcggcgga cttgttcaac ctggcggctc tctgagactg   120
agctgtgccg cttctggcta cgacttcacc cactacggca tgaactgggt ccgacaggcc   180
cctggcaaag gccttgaatg ggtcggatgg atcaacacct acaccggcga gccaacatac   240
gccgccgact tcaagcggag attcaccttc agcctggaca ccagcaagag caccgcctac   300
ctgcagatga acagcctgag agccgaggac accgccgtgt actactgcgc caagtatccc   360
tactactacg gcaccagcca ctggtacttt gacgtgtggg gacagggcac actggtcaca   420
gtgtctagcg cctctacaaa gggcccagc gttttcccac tggctcctag cagcaagtct   480
accagcggag aacagccgc tctgggctgt ctggtcaagg actactttcc cgagcctgtg   540
accgtgtcct ggaattctgg cgctctgaca agcggcgtgc acacctttcc agctgtgctg   600
caaagcagcg gcctgtactc tctgagcagc gtcgtgacag tgccaagcag ctctctgggc   660
acccagacct acatctgcaa tgtgaaccac aagcctagca accaaggt ggacaagaag   720
gtggaaccca gagctgcga caagacccac accggcaagc ggaagagaag aggctctggc   780
gaaggcagag gcagcctgct tacatgtggc gactgtgaag agaacccgg acctatgtat   840
agaatgcagc tcctgtcctg cattgccctg agcctggctc tcgtgaccaa cagcgacatc   900
cagctgacac agagccccag cagcctgtct gcctctgtgg gagacagagt gaccatcacc   960
tgtagcgcca gccaggacat ctccaactac ctgaactggt atcagcaaaa gcccggcaag  1020
gcccctaagg tgctgatcta cttcacaagc agcctgcact ccggcgtgcc cagcagattt  1080
tctggctctg gcagcggcac cgacttcacc ctgaccatat ctagcctgca gcctgaggac  1140
ttcgccacct actactgcca gcagtacagc accgtgcctt ggacatttgg ccagggcaca  1200
aaggtggaaa tcaagcggac tgtggccgct cctagcgtgt tcatctttcc acctagcgac  1260
gagcagctga gtctgtccac agcctctgtc gtgtgcctgc tgaacaactt ctaccccaga  1320
gaagccaagg tgcagtggaa agtggacaat gccctgcaga gcggcaacag ccaagagagc  1380
gtgacagagc aggactccaa ggatagcacc tatagcctga gcagcaccct gacactgagc  1440
aaggccgact acgagaagca caaagtgtac gcctgcgaag tgacccacca gggcctttct  1500
agccctgtga ccaagagctt caaccggggc gaatgt                              1536
```

```
SEQ ID NO: 104           moltype = AA   length = 239
FEATURE                  Location/Qualifiers
REGION                   1..239
                         note = source = /note="Description of Artificial Sequence:
                         Synthetic polypeptide"
source                   1..239
                         mol_type = protein
                         organism = synthetic construct
SEQUENCE: 104
MVSKGEELFT GVVPILVELD GDVNGHKFSV SGEGEGDATY GKLTLKFICT TGKLPVPWPT   60
LVTTLTYGVQ CFSRYPDHMK QHDFFKSAMP EGYVQERTIF FKDDGNYKTR AEVKFEGDTL  120
VNRIELKGID FKEDGNILGH KLEYNYNSHN VYIMADKQKN GIKVNFKIRH NIEDGSVQLA  180
DHYQQNTPIG DGPVLLPDNH YLSTQSALSK DPNEKRDHMV LLEFVTAAGI TLGMDELYK   239

SEQ ID NO: 105           moltype = DNA   length = 717
FEATURE                  Location/Qualifiers
misc_feature             1..717
                         note = source = /note="Description of Artificial Sequence:
                         Synthetic polynucleotide"
source                   1..717
                         mol_type = other DNA
                         organism = synthetic construct
SEQUENCE: 105
atggtgagca agggcgagga gctgttcacc ggggtggtgc ccatcctggt cgagctggac   60
ggcgacgtaa acgccacaa gttcagcgtg tccggcgagg gcgagggcga tgccacctac  120
ggcaagctga cccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaag     717

SEQ ID NO: 106           moltype = DNA   length = 4509
FEATURE                  Location/Qualifiers
misc_feature             1..4509
                         note = source = /note="Description of Artificial Sequence:
                         Synthetic polynucleotide"
source                   1..4509
                         mol_type = other DNA
                         organism = synthetic construct
SEQUENCE: 106
ctgcgcgctc gctcgctcac tgaggccgcc cgggcgtcgg gcgacctttg gtcgcccggc   60
ctcagtgagc gagcgagcgc gcagagaggg agtggccaac tccatcacta gggttcctg  120
cggccgcacg cgtgacattg attattgact agttattaat agtaatcaat tacgggtca  180
ttagttcata gcccatatat ggagttccgc gttacataac ttacggtaaa tggcccgcct  240
ggctgaccgc ccaacgaccc ccgcccattg acgtcaataa tgacgtatgt tcccatagta  300
acgccaatag ggactttcca ttgacgtcaa tgggtggat atttacggta aactgcccac  360
ttggcagtac atcaagtgta tcatatgcca agtacgcccc ctattgacgt caatgacggt  420
aaatggcccg cctggcatta tgcccagtac atgaccttat gggactttcc tacttggcag  480
tacatctacg tattagtcat cgctattacc atgggtcgag gtgagcccca cgttctgctt  540
cactctcccc atctccccc cctccccacc cccaattttg tatttattta ttttttaatt  600
attttgtgca gcgatggggg cgggggggg gggggcgcg gccaggcggg gcggggcggg  660
gcgaggggcg gggcggggcg aggcggagag gtgcggcggc agccaatcag agcggcgcgc  720
tccgaaagtt cccttttatg gcgaggcggc ggcggcggcg gccctataaa aagcgaagcg  780
cgcggcgggc gggagtcgct gcgttgcctt cgccccgtgc cccgctccgc gccgcctcgc  840
gccgcccgcc ccggctctga ctgaccgcgt tactcccaca ggtgagcggg cgggacggcc  900
cttctcctcc gggctgtaat tagcgcttgg tttaatgacg gctcgtttct ttctgtggc  960
tgcgtgaaag ccttaaaggg ctccggggagg gccctttgtg cggggggag cggctcgggg 1020
ggtgcgtgcg tgtgtgtgtg cgtggggagc gccgcgtgcg gcccgcgctg ccgggcggct 1080
gtgagcgctg cgggcgcggc gcggggcttt gtgcgctccg cgtgtgcgcg aggggagcgc 1140
ggccgggggc ggtgccccgc ggtgcggggg ggctgcgagg gaacaaaggg ctgcgtgcgg 1200
ggtgtgtgcg tgggggggtg agcaggggt gtgggcgcgg cggtcgggct gtaaccccc 1260
cctgcacccc cctccccgag ttgctgagca cggcccggct tcgggtgcgg ggctccgtgc 1320
ggggcgtggc gcggggctcg ccgtgccggg cggggggtgg cggcaggtgg gggtgccggg 1380
cggggcgggg ccgcctcggg ccgggaggg ctcggggagg gggcgcggcg ggccccggag 1440
cgccggcggc tgtcgaggcg cggcgagccg cagccattgc cttttatggt aatcgtgcga 1500
gagggcgcag ggacttcctt tgtcccaaat ctgtgcggag ccgaaatctg ggaggcgccg 1560
ccgcacccc tctagcgggc gcggggcgaa gcggtgcggc gccggcagga aggaaatggg 1620
cggggagggc cttcgtgcgt cgccgcgccg ccgtcccctt ctccctctcc agcctcgggg 1680
ctgtccgcgg gggacggct gccttcgggt gggacggggg agggcggggt tcggcttctg 1740
gcgtgtgacc ggcggctcta gagcctctgt taaccatgtt catgccttct tctttttcct 1800
acagctcctg gcaacgtgc tggttattgt gaccggtgcc accatgtacc ggatgcagct 1860
gctgagctgt atcgccctgt ctctggccct ggtcaccaat tctgaggtgc agctggtgga 1920
atctggcggc ggacttgttc aacctggcgg ctctctgaga ctgagctgtg ccgcttctg 1980
ctacgacttc acccactacg gcatgaactg ggtccgacag gcccctggca aaggcctgga 2040
```

```
atgggtcgga tggatcaaca cctacaccgg cgagccaaca tacgccgccg acttcaagcg 2100
gagattcacc ttcagcctgg acaccagcaa gagcaccgcc tacctgcaga tgaacagcct 2160
gagagccgag gacaccgccg tgtactactg cgccaagtat ccctactact acggcaccag 2220
ccactggtac tttgacgtgt ggggacaggg cacactggtc acagtgtcta gcgcctctac 2280
aaagggcccc agcgttttcc cactggctcc tagcagcaag tctaccagcg gaggaacagc 2340
cgctctgggc tgtctggtca aggactactt tcccgagcct gtgaccgtgt cctggaattc 2400
tggcgctctg acaagcggcg tgcacacctt tccagctgtg ctgcaaagca gcggcctgta 2460
ctctctgagc agcgtcgtga cagtgccaag cagctctctg ggcacccaga cctacatctg 2520
caatgtgaac cacaagccta gcaacaccaa ggtggacaag aaggtggaac ccaagagctg 2580
cgacaagacc cacaccggca gcggaagag gcgaaggca gaggcagcct 2640
gcttacatgt ggcgacgtgg aagagaaccc cggacctatg tatagaatgc agctcctgtc 2700
ctgcattgcc ctgagcctgg ctctcgtgac caacagcgac atccagctga cacagagccc 2760
cagcagcctg tctgcctctg tgggagacag agtgaccatc acctgtagcg ccagccagga 2820
catctccaac tacctgaact ggtatcagca aaagcccagc aaggccccta aggtgctgat 2880
ctacttcaca agcagcctgc actccggcgt gcccagcaga ttttctggct ctggcagcgg 2940
caccgacttc accctgacca tatctagcct gcagcctgag gacttcgcca cctactactg 3000
ccagcagtac agcaccgtgc cttggacatt tggccagggc acaaaggtgg aaatcaagcg 3060
gactgtggcc gctcctagcg tgttcatctt tccacctagc gacgagcagc tgaagtctgg 3120
cacagcctct gtcgtgtgcc tgctgaacaa cttctacccc agagaagcca aggtgcagtg 3180
gaaagtggac aatgccctgc agagcggcaa cagccaagag agcgtgacag agcaggactc 3240
caaggatagc acctatagcc tgagcagcac cctgacactg agcaaggccg actacgagaa 3300
gcacaaagtg tacgcctgcg aagtgaccca ccagggcctt tctagccctg tgaccaagag 3360
cttcaaccgg ggcgaatgta tggtgagcaa gggcgaggag ctgttcaccg gggtggtgcc 3420
catcctggtc gagctggacg gcgacgtaaa cggccacaag ttcagcgtgt ccggcgaggg 3480
cgagggcgat gccacctacg gcaagctgac cctgaagttc atctgcacca ccggcaagct 3540
gcccgtgccc tggcccaccc tcgtgaccac cctgacctac ggcgtgcagt gcttcagccg 3600
ctaccccgac cacatgaagc agcacgactt cttcaagtcc gccatgcccg aaggctacgt 3660
ccaggagcgc accatcttct tcaaggacga cggcaactac aagacccgcg ccgaggtgaa 3720
gttcgagggc gacaccctgg tgaaccgcat cgagctgaag ggcatcgact tcaaggagga 3780
cggcaacatc ctggggcaca agctggagta caactacaac agccacaacg tctatatcat 3840
ggccgacaag cagaagaacg gcatcaaggt gaacttcaag atccgccaca acatcgagga 3900
cggcagcgtg cagctcgccg accactacca gcagaacacc cccatcggcg acggccccgt 3960
gctgctgccc gacaaccact acctgagcac ccagtccgcc ctgagcaaag ccccaacga 4020
gaagcgcgat cacatggtcc tgctggagtt cgtgaccgcc gcgggatca ctctcggcat 4080
ggacgagctg tacaagtaag agctcgctga tcagcctcga ctgtgccttc tagttgccag 4140
ccatctgttg tttgccccct ccccgtgcct tccttgaccc tggaaggtgc cactcccact 4200
gtcctttcct aataaaatga ggaaattgca tcgcattgtc tgagtaggtg tcattctatt 4260
ctgggggggtg gggtggggca ggacagcaag ggggaggatt gggaagacaa tagcaggcat 4320
gctgggatg cggtgggctc tatggaagct tgaattcagc tgacgtgcct cggaccgcta 4380
ggaacccta gtgatggagt tggccactcc ctctctgcgc gctcgctcgc tcactgaggc 4440
cgggcgacca aagtcgccc gacgcccggg cttttgcccgg gcggcctcag tgagcgagcg 4500
agcgcgcag 4509
```

SEQ ID NO: 107      moltype = DNA  length = 5169
FEATURE             Location/Qualifiers
misc_feature       1..5169
                    note = source = /note="Description of Artificial Sequence:
                    Synthetic polynucleotide"
source               1..5169
                    mol_type = other DNA
                    organism = synthetic construct
SEQUENCE: 107

```
ctgcgcgctc gctcgctcac tgaggccgcc cgggcgtcgg gcgacctttg gtcgcccggc 60
ctcagtgagc gagcgagcgc gcagagaggg agtggccaac tccatcacta ggggttcctg 120
cggccgcacg cgtgacattg attattgact agttattaat agtaatcaat tacggggtca 180
ttagttcata gcccatatat ggagttccgc gttacataac ttacggtaaa tggcccgcct 240
ggctgaccgc ccaacgaccc ccgcccattg acgtcaataa tgacgtatgt tcccatagta 300
acgccaatag ggactttcca ttgacgtcaa tgggtggact atttacggta aactgcccac 360
ttggcagtac atcaagtgta tcatatgcca agtacgcccc ctattgacgt caatgacggt 420
aaatggcccg cctggcatta tgcccagtac atgaccttat gggactttcc tacttggcag 480
tacatctacg tattagtcat cgctattacc atggtcgag gtgagcccca cgttctgctt 540
cactctcccc atctccccccc cctccccacc ccaatttttg tatttattta ttttttaatt 600
attttgtgca gcgatggggg cggggggggg ggggcgcgc gccaggcggg gcggggcggg 660
gcgagggcg gggcgggcg aggcgagag gtgcggccgc agccaatcag agcggcgcgc 720
tccgaaagtt tccttttatg gcgaggcggc ggcggcggcg gccctataaa agcgaagcgc 780
gcggcgggc gggagtcgct gcgttgcctt cgccccgtgc cccgctccgc gccgcctcgc 840
gccgcccgcc ccggctctga ctgaccgcgt tactcccaca ggtgagcggg cgggacggcc 900
cttctcctcc gggctgtaat tagcgcttgg tttaatgacg gctcgtttct tttctgtggc 960
tgcgtgaaag ccttaaaggg ctccgggagg gccctttgtg cggggggaag cggctcggga 1020
ggtgcgtgcg tgtgtgtgtg cgtggggagc gccgcgtgcg gccgcgctg cccggcgget 1080
gtgagcgctg cgggcgcggc gcggggcttt gtgcgctccg cgtgtgcgcg aggggagcgc 1140
ggccggggc ggtgccccgc ggtgcggggg gctgcgagg gaacaaagg ctgcgtgcgg 1200
ggtgtgtgcg tggggggtg agcagggggt gtgggcgcgg cggtcgggct gtaacccccc 1260
cctgcaccc cctccccgag ttgctgagca cggcccggct tcgggtgcgg ggctccgtgc 1320
ggggcgtggc gcggggctcg ccgtgccggg cgggggaggg cggcaggtgg ggtgccctgc 1380
cggggcgggg ccgcctcggg ccggggaggg ctcggggaag gggcgcggcg ccccccggag 1440
cgccggcggc tgtcgaggcg cggcgagccg cagccattgc ctttttatggt aatcgtgcga 1500
gagggcgcag gacttccttt gtcccaaat ctgtgcggag ccgaaatctg ggaggcgccg 1560
ccgcaccccc tctagcgggc gcggggcgaa gcggtgcggc gccggcagga aggaaatggg 1620
```

```
cggggagggc cttcgtgcgt cgccgcgccg ccgtcccctt ctccctctcc agcctcgggg    1680
ctgtccgcgg gggacggct gccttcgggg gggacggggc agggcggggt tcggcttctg    1740
gcgtgtgacc ggcggctcta gagcctctgc taaccatgtt catgccttct tcttttttcct  1800
acagctcctg ggcaacgtgc tggttattgt gaccggtgcc accatgtacc ggatgcagct   1860
gctgagctgt atcgccctgt ctctggccct ggtcaccaat tctgaggtgc agctggtgga   1920
atctggcggc ggacttgttc aacctggcgg ctctctgaga ctgagctgtg ccgcttctgt   1980
ctacaccttc accaactacg gcatgaactg ggtccgacag gccctggca aaggccttga    2040
atgggtcgga tggatcaaca cctacaccgg cgagccaaca tacgccgccg acttcaagcg   2100
gagattcacc ttcagcctgg acaccagcaa gagcaccgcc tacctgcaga tgaacagcct   2160
gagagccgag gacaccgccg tgtactactg cgccaagtat ccccactact acggcagcag   2220
ccactggtac tttgacgtgt ggggacaggg cacactggtc acagtgtcta gcgcctctac   2280
aaagggcccc agcgttttcc cactggctcc tagcagcaag tctaccagcg gaggaacagc   2340
cgctctgggc tgtctggtca aggactactt tcccgagcct gtgaccgtgt cctggaattc   2400
tggcgctctg acaagcggcg tgcacacctt tccagctgtc ctgcaaagca gcggcctgta   2460
ctctctgagc agcgtcgtga cagtgccaag cagctctctg ggcacccaga cctacatctg   2520
caatgtgaac cacaagccta gcaacaccaa ggtggacaag aagtggaac ccaagagctg    2580
cgacaagacc cacacctgtc ctccatgtcc tgctccagaa ctgctcggcg gacccttccgt 2640 
gttcctgttt cctccaaagc ctaaggacac cctgatgatc agcagaaccc ctgaagtgac   2700
ctgcgtggtg gtggatgtgt cccacgagga tcccgaagtg aagttcaatt ggtacgtgga   2760
cggcgtggaa gtgcacaacg ccaagaccaa gcctagagtg gaacagtaca acagcaccta   2820
cagagtggtg tccgtgctga ccgtgctgca ccaggattgg ctgaacggca agagtacaa    2880
gtgcaaggtg tccaacaagg ccctgcctgc tcctatcgaa aaaccatca gcaaggccaa    2940
gggccagcct agggaacccc aggtttacac actgcctcca agcccggaag agatgaccaa   3000
gaaccaggtg tccctgacct gcctcgtgaa gggcttctac ccttccgata tcgccgtgga   3060
atgggagagc aatggccagc cagagaacaa ctacaagaca cccctcctg tgctggacag    3120
cgacggctca ttcttcctgt acagcaagct gacagtggac aagtccagat ggcagcaggg   3180
caacgtgttc agctgcagcg tgatgcacga ggccctgcac aaccactaca cccgaagtgc   3240
tctgagcctg tctcctggca gcggaagag aaaggctct ggcgaaggca gagcagcct     3300
gcttacatgt ggcgacgtgg aagagaaccc cggacctatg tatagaatgc agctcctgtc   3360
ctgcattgcc ctgagcctgg ctcctcgtgac caacagcgac atccagatga cacagagccc   3420
cagcagcctg tctgcctctg tgggacagg agtgaccatc acctgtagcg ccagccagga   3480
catctccaac tacctgaact ggtatcagca aaagcccggc aaggcccta aggtgctgat    3540
ctacttcaca agcagcctgc actccggcgt gccccagaga ttttctggct ctggcagcgg   3600
caccgacttc accctgacca tatctagcct gcagcctgag gacttcgcca cctactactg   3660
ccagcagtac agcaccgtgc cttggacatt tggccaggc acaaaggtgg aaatcaagcg   3720
gactgtggcc gctcctagcg tgttcatctt tccacctagc gacgagcagc tgaagtctgg   3780
cacagcctct gtcgtgtgcc tgctgaacaa cttctacccc agagaagcca aggtgcagtg   3840
gaaagtggac aatgccctgc agagcggcaa cagccaagag agcgtgacag agcaggactc   3900
caaggatagc acctatagcc tgagcagcac cctgacactg agcaaggccg actacgagaa   3960
gcacaaagtg tacgcctgcg aagtgaccca ccagggcctt tctagccctg tgaccaagag   4020
cttcaaccgg ggcgaatgta tggtgagcaa gggcgaggag ctgttcaccg gggtggtgcc   4080
catcctggtc gagctggacg gcgacgtaaa cggccacaag ttcagcgtgt ccggcgaggg   4140
cgagggcgat gccacctacg gcaagctgac cctgaagttc atctgcacca ccggcaagct   4200
gcccgtgccc tggcccaccc tcgtgaccac cctgacctac ggcgtgcagt gcttcagccg   4260
ctaccccgac cacatgaagc agcacgactt cttcaagtcc gccatgcccg aaggctacgt   4320
ccaggagcgc accatcttct tcaaggacga cggcaactac aagacccgcg ccgaggtgaa   4380
gttcgagggc gacaccctgg tgaaccgcat cgagctgaag ggcatcgact tcaaggagga   4440
cggcaacatc ctggggcaca gctggagta caactacaac agccacaacg tctatatcat    4500
ggccgacaag cagaagaacg gcatcaaggt gaacttcaag atccgccaca acatcgagga   4560
cggcagcgtg cagctcgccg accactacca gcagaacacc cccatcggcg acggccccgt   4620
gctgctgccc gacaaccact acctgagcac ccagtccgcc ctgagcaaag acccaacga    4680
gaagcgcgat cacatggtcc tgctggagtt cgtgaccgcc gccgggatca ctctcggcat   4740
ggacgagctg tacaagtaag agctcgctga tcagcctcga ctgtgccttc tagttgccag   4800
ccatctgttg tttgcccctc ccccgtgcct tccttgaccc tggaaggtgc cactcccact   4860
gtcctttcct aataaaatga ggaaattgca tcgcattgtc tgagtaggtg tcattctatt   4920
ctgggggtg gggtgggca ggacagcaag ggggaggatt gggaagacaa tagcaggcat    4980
gctggggatg cggtgggctc tatggaagct tgaattcagc tgacgtgcct cggaccgcta   5040
ggaaccccta gtgatggagt tggccactcc ctctctgcgc gctcgctcgc tcactgaggc   5100
cgggcgacca aggtcgccc gacgcccggg ctttgcccgg gcggcctcag tgagcgagcg   5160
agcgcgcag                                                          5169
```

SEQ ID NO: 108         moltype = DNA   length = 1419
FEATURE                Location/Qualifiers
misc_feature           1..1419
                       note = source = /note="Description of Artificial Sequence:
                       Synthetic polynucleotide"
source                 1..1419
                       mol_type = other DNA
                       organism = synthetic construct
SEQUENCE: 108

```
atgtaccgga tgcagctgct gagctgtatc gccctgtctc tggccctggt caccaattct    60
gaggtgcagc tggtggaatc tggcggcgga cttgttcaac ctggcggctc tctgagactg   120
agctgtgccg cttctggcta caccttcacc aactacggca tgaactgggt ccgacaggcc   180
cctggcaaag gccttgaatg ggtcggatgg atcaacacct acaccggcga gccaacatac   240
gccgccgact tcaagcggag attcaccttc agcctggaca ccagcaagag caccgcctac   300
ctgcagatga acagcctgag agccgaggac accgccgtgt actactgcgc caagtatccc   360
cactactacg gcagcagcca ctggtacttt gacgtgtggg gacagggcac actggtcaca   420
gtgtctagcc cctctacaaa gggccccagc gttttcccac tggctcctag cagcaagtct   480
accagcggag gaacagccgc tctgggctgt ctggtcaagg actactttcc cgagcctgtg   540
```

-continued

```
accgtgtcct ggaattctgg cgctctgaca agcggcgtgc acacctttcc agctgtgctg    600
caaagcagcg gcctgtactc tctgagcagc gtcgtgacag tgccaagcag ctctctgggc    660
acccagacct acatctgcaa tgtgaaccac aagcctagca acaccaaggt ggacaagaag    720
gtggaaccca gagctgcga caagacccac acctgtcctc catgtcctgc tccagaactg    780
ctcggcggac cttccgtgtt cctgtttcct ccaaagccta aggacaccct gatgatcagc    840
agaaccctg aagtgacctg cgtggtggtg gatgtgtccc acgaggatcc cgaagtgaag    900
ttcaattggt acgtggacgg cgtggaagtg cacaacgcca agaccaagcc tagagaggaa    960
cagtacaaca gcacctacag agtggtgtcc gtgctgaccg tgctgcacca ggattggctg   1020
aacggcaaag agtacaagtg caaggtgtcc aacaaggccc tgcctgctcc tatcgagaaa   1080
accatcagca aggccaaggg ccagcctagg gaaccccagg tttacacact gcctccaagc   1140
cgggaagaga tgaccaagaa ccaggtgtcc ctgacctgcc tcgtgaaggg cttctaccct   1200
tccgatatcg ccgtggaatg ggagagcaat ggccagccag agaacaacta caagacaacc   1260
cctcctgtgc tggacagcga cggctcattc ttcctgtaca gcaagctgac agtggacaag   1320
tccagatggc agcagggcaa cgtgttcagc tgcagcgtga tgcacgaggc cctgcacaac   1380
cactacaccc agaagtctct gagcctgtct cctggcaag                          1419
```

| SEQ ID NO: 109 | moltype = DNA length = 642 |
|---|---|
| FEATURE | Location/Qualifiers |
| misc_feature | 1..642 |
| | note = source = /note="Description of Artificial Sequence: Synthetic polynucleotide" |
| source | 1..642 |
| | mol_type = other DNA |
| | organism = synthetic construct |

SEQUENCE: 109
```
gacatccaga tgacacagag cccccagcagc ctgtctgcct ctgtgggaga cagagtgacc     60
atcacctgta gcgccagcca ggacatctcc aactacctga actggtatca gcaaaagccc    120
ggcaaggccc ctaaggtgct gatctacttc acaagcagcc tgcactccgg cgtgcccagc    180
agattttctg gctctggcag cggcaccgac ttcaccctga ccatatctag cctgcagcct    240
gaggacttcg ccacctacta ctgccagcag tacagcaggc tgcctttggac atttggcacg    300
ggcacaaagg tggaaatcaa gcggactgtg gccgctccta gcgtgttcat cttttccacct    360
agcgacgagc agctgaagtc tggcacagcc tctgtcgtgt gcctgctgaa caacttctac    420
cccagagaag ccaaggtgca gtggaaagtg gacaatgccc tgcagagcgg caacagccaa    480
gagagcgtga cagagcagga ctccaaggat agcacctata gctgagcag cacccctgaca    540
ctgagcaagg ccgactacga gaagcacaaa gtgtacgcct aagaagtgac ccaccagggc    600
ctttctagcc ctgtgaccaa gagcttcaac cggggcgaat gt                        642
```

| SEQ ID NO: 110 | moltype = DNA length = 678 |
|---|---|
| FEATURE | Location/Qualifiers |
| misc_feature | 1..678 |
| | note = source = /note="Description of Artificial Sequence: Synthetic polynucleotide" |
| source | 1..678 |
| | mol_type = other DNA |
| | organism = synthetic construct |

SEQUENCE: 110
```
gacaagaccc acacctgtcc tccatgtcct gctccagaac tgctcggcgg acccttccgtg     60
ttcctgtttc ctccaaagcc taaggacacc ctgatgatca gcagaacccc tgaagtgacc    120
tgcgtggtgg tggatgtgtc ccacgaggat cccgaagtga agttcaattg gtacgtggac    180
ggcgtggaag tgcacaacgc caagaccaag cctagagagg aacagtacaa cagcacctac    240
agagtggtgt ccgtgctgac cgtgctgcac caggattgg tgaacggcaa agagtacaag    300
tgcaaggtgt ccaacaaggc cctgcctgct cctatcgaga aaaccatcag caaggccaag    360
ggccagccta gggaaccca ggtttacaca ctgcctccaa gccggggaaga gatgaccaag    420
aaccaggtgt ccctgacctg cctcgtgaag ggcttctacc cttccgatat cgccgtggaa    480
tgggagagca atggccagcc agagaacaac tacaagacaa cccctcctgt gctggacagc    540
gacggctcat tcttcctgta cagcaagctg acagtggaca agtccagatg gcagcagggc    600
aacgtgttca gctgcagcgt gatgcacgag gccctgcaca accactacac ccagaagtct    660
ctgagcctgt ctcctggc                                                  678
```

| SEQ ID NO: 111 | moltype = AA length = 226 |
|---|---|
| FEATURE | Location/Qualifiers |
| REGION | 1..226 |
| | note = source = /note="Description of Artificial Sequence: Synthetic polypeptide" |
| source | 1..226 |
| | mol_type = protein |
| | organism = synthetic construct |

SEQUENCE: 111
```
DKTHTCPPCP APELLGGPSV FLFPPKPKDT LMISRTPEVT CVVVDVSHED PEVKFNWYVD     60
GVEVHNAKTK PREEQYNSTY RVVSVLTVLH QDWLNGKEYK CKVSNKALPA PIEKTISKAK    120
GQPREPQVYT LPPSRDELTK NQVSLTCLVK GFYPSDIAVE WESNGQPENN YKTTPPVLDS    180
DGSFFLYSKL TVDKSRWQQG NVFSCSVMHE ALHNHYTQKS LSLSPG                   226
```

| SEQ ID NO: 112 | moltype = AA length = 225 |
|---|---|
| FEATURE | Location/Qualifiers |
| REGION | 1..225 |
| | note = source = /note="Description of Artificial Sequence: Synthetic polypeptide" |
| source | 1..225 |

```
                        mol_type = protein
                        organism = synthetic construct
SEQUENCE: 112
MYRMQLLSCI ALSLALVTNS SDTGRPFVEM YSEIPEIIHM TEGRELVIPC RVTSPNITVT   60
LKKFPLDTLI PDGKRIIWDS RKGFIISNAT YKEIGLLTCE ATVNGHLYKT NYLTHRQTNT  120
IIDVVLSPSH GIELSVGEKL VLNCTARTEL NVGIDFNWEY PSSKHQHKKL VNRDLKTQSG  180
SEMKKFLSTL TIDGVTRSDQ GLYTCAASSG LMTKKNSTFV RVHEK                  225

SEQ ID NO: 113          moltype = AA  length = 736
FEATURE                 Location/Qualifiers
VARIANT                 168
                        note = /replace="R"
VARIANT                 204
                        note = /replace="S"
VARIANT                 266
                        note = /replace="G"
VARIANT                 311
                        note = /replace="K"
VARIANT                 411
                        note = /replace="Q"
VARIANT                 460
                        note = /replace="E"
VARIANT                 493
                        note = /replace="T"
VARIANT                 562
                        note = /replace="N"
VARIANT                 576
                        note = /replace="E"
VARIANT                 587
                        note = /replace="A"
VARIANT                 609
                        note = /replace="D"
SITE                    1..736
                        note = /note="Variant residues given in the sequence have
                         no preference with respect to those in the annotations for
                         variant positions"
REGION                  1..736
                        note = source = /note="Description of Artificial Sequence:
                         Synthetic polypeptide"
source                  1..736
                        mol_type = protein
                        organism = synthetic construct
SEQUENCE: 113
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPAKKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SSQSGASTND NTYFGYSTPW GYFDFNRFHC HFSPRDWQRL  300
INNNWGFRPK RLNFKLFNIQ VKEVTTNDGT TTIANNLTST VQVFTDSEYQ LPYVLGSAHQ  360
GCLPPFPADV FMIPQYGYLT LNNGSQAVGR SSFYCLEYFP SQMLRTGNNF EFSYTFEDVP  420
FHSSYAHSQS LDRLMNPLID QYLYYLSRTQ TTSGTAGNRT LQFSQAGPSS MANQAKNWLP  480
GPCYRQQRVS KTANQNNNSN FAWTGATKYH LNGRDSLVNP GPAMATHKDD EDKFFPMSGV  540
LIFGKQGAGN SNVDLDNVMI TSEEEIKTTN PVATEQYGTV ATNLQSSNTA PATGTVNSQG  600
ALPGMVWQNR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                  736

SEQ ID NO: 114          moltype = AA  length = 736
FEATURE                 Location/Qualifiers
REGION                  1..736
                        note = source = /note="Description of Artificial Sequence:
                         Synthetic polypeptide"
source                  1..736
                        mol_type = protein
                        organism = synthetic construct
SEQUENCE: 114
MAADGYLPDW LEDNLSEGIR EWWDLKPGAP KPKANQQKQD DGRGLVLPGY KYLGPFNGLD   60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KKGQQPARKR LNFGQTGDSE  180
SVPDPQPLGE PPAAPSGVGS NTMAAGGGAP MADNNEGADG VGNASGNWHC DSTWLGDRVI  240
TTSTRTWALP TYNNHLYKQI SSQSGGSTND NTYFGYSTPW GYFDFNRFHC HFSPRDWQRL  300
INNNWGFRPK KLNFKLFNIQ VKEVTTNDGT TTIANNLTST VQVFTDSEYQ LPYVLGSAHQ  360
GCLPPFPADV FMIPQYGYLT LNNGSQAVGR SSFYCLEYFP SQMLRTGNNF QFSYTFEDVP  420
FHSSYAHSQS LDRLMNPLID QYLYYLSRTQ TTSGTAGNRT LQFSQAGPSS MANQAKNWLP  480
GPCYRQQRVS KTTNQNNNSN FAWTGATKYH LNGRDSLVNP GPAMATHKDD EDKFFPMSGV  540
LIFGKQGAGN SNVDLDNVMI TNEEEIKTTN PVATEEYGTV ATNLQSANTA PATGTVNSQG  600
ALPGMVWQDR DVYLQGPIWA KIPHTDGHFH PSPLMGGFGL KHPPPQILIK NTPVPANPPT  660
TFSPAKFASF ITQYSTGQVS VEIEWELQKE NSKRWNPEIQ YTSNYNKSTN VDFAVDTNGV  720
YSEPRPIGTR YLTRNL                                                  736
```

```
SEQ ID NO: 115          moltype = AA  length = 8
FEATURE                 Location/Qualifiers
VARIANT                 2
                        note = Any amino acid
VARIANT                 4
                        note = Any amino acid
REGION                  1..8
                        note = source = /note="Description of Unknown: 2A peptide
                         motif sequence"
source                  1..8
                        mol_type = protein
                        organism = unidentified
SEQUENCE: 115
DXEXNPGP                                                                    8

SEQ ID NO: 116          moltype = DNA  length = 17
FEATURE                 Location/Qualifiers
misc_feature            1..17
                        note = source = /note="Description of Artificial Sequence:
                         Synthetic oligonucleotide"
source                  1..17
                        mol_type = other DNA
                        organism = synthetic construct
SEQUENCE: 116
aaataaaata cgaaatg                                                         17

SEQ ID NO: 117          moltype = RNA  length = 5000
FEATURE                 Location/Qualifiers
misc_feature            1..5000
                        note = /note="This sequence may encompass 50-5000
                         nucleotides"
misc_feature            1..5000
                        note = source = /note="Description of Artificial Sequence:
                         Synthetic polynucleotide"
misc_feature            1..5000
                        note = source = /note="See specification as filed for
                         detailed description of substitutions and preferred
                         embodiments"
source                  1..5000
                        mol_type = other RNA
                        organism = synthetic construct
SEQUENCE: 117
aaaaaaaaaa aaaaaaaaaa aaaaaaaaaa aaaaaaaaaa aaaaaaaaaa aaaaaaaaaa          60
aaaaaaaaaa aaaaaaaaaa aaaaaaaaaa aaaaaaaaaa aaaaaaaaaa aaaaaaaaaa         120
aaaaaaaaaa aaaaaaaaaa aaaaaaaaaa aaaaaaaaaa aaaaaaaaaa aaaaaaaaaa         180
aaaaaaaaaa aaaaaaaaaa aaaaaaaaaa aaaaaaaaaa aaaaaaaaaa aaaaaaaaaa         240
aaaaaaaaaa aaaaaaaaaa aaaaaaaaaa aaaaaaaaaa aaaaaaaaaa aaaaaaaaaa         300
aaaaaaaaaa aaaaaaaaaa aaaaaaaaaa aaaaaaaaaa aaaaaaaaaa aaaaaaaaaa         360
aaaaaaaaaa aaaaaaaaaa aaaaaaaaaa aaaaaaaaaa aaaaaaaaaa aaaaaaaaaa         420
aaaaaaaaaa aaaaaaaaaa aaaaaaaaaa aaaaaaaaaa aaaaaaaaaa aaaaaaaaaa         480
aaaaaaaaaa aaaaaaaaaa aaaaaaaaaa aaaaaaaaaa aaaaaaaaaa aaaaaaaaaa         540
aaaaaaaaaa aaaaaaaaaa aaaaaaaaaa aaaaaaaaaa aaaaaaaaaa aaaaaaaaaa         600
aaaaaaaaaa aaaaaaaaaa aaaaaaaaaa aaaaaaaaaa aaaaaaaaaa aaaaaaaaaa         660
aaaaaaaaaa aaaaaaaaaa aaaaaaaaaa aaaaaaaaaa aaaaaaaaaa aaaaaaaaaa         720
aaaaaaaaaa aaaaaaaaaa aaaaaaaaaa aaaaaaaaaa aaaaaaaaaa aaaaaaaaaa         780
aaaaaaaaaa aaaaaaaaaa aaaaaaaaaa aaaaaaaaaa aaaaaaaaaa aaaaaaaaaa         840
aaaaaaaaaa aaaaaaaaaa aaaaaaaaaa aaaaaaaaaa aaaaaaaaaa aaaaaaaaaa         900
aaaaaaaaaa aaaaaaaaaa aaaaaaaaaa aaaaaaaaaa aaaaaaaaaa aaaaaaaaaa         960
aaaaaaaaaa aaaaaaaaaa aaaaaaaaaa aaaaaaaaaa aaaaaaaaaa aaaaaaaaaa        1020
aaaaaaaaaa aaaaaaaaaa aaaaaaaaaa aaaaaaaaaa aaaaaaaaaa aaaaaaaaaa        1080
aaaaaaaaaa aaaaaaaaaa aaaaaaaaaa aaaaaaaaaa aaaaaaaaaa aaaaaaaaaa        1140
aaaaaaaaaa aaaaaaaaaa aaaaaaaaaa aaaaaaaaaa aaaaaaaaaa aaaaaaaaaa        1200
aaaaaaaaaa aaaaaaaaaa aaaaaaaaaa aaaaaaaaaa aaaaaaaaaa aaaaaaaaaa        1260
aaaaaaaaaa aaaaaaaaaa aaaaaaaaaa aaaaaaaaaa aaaaaaaaaa aaaaaaaaaa        1320
aaaaaaaaaa aaaaaaaaaa aaaaaaaaaa aaaaaaaaaa aaaaaaaaaa aaaaaaaaaa        1380
aaaaaaaaaa aaaaaaaaaa aaaaaaaaaa aaaaaaaaaa aaaaaaaaaa aaaaaaaaaa        1440
aaaaaaaaaa aaaaaaaaaa aaaaaaaaaa aaaaaaaaaa aaaaaaaaaa aaaaaaaaaa        1500
aaaaaaaaaa aaaaaaaaaa aaaaaaaaaa aaaaaaaaaa aaaaaaaaaa aaaaaaaaaa        1560
aaaaaaaaaa aaaaaaaaaa aaaaaaaaaa aaaaaaaaaa aaaaaaaaaa aaaaaaaaaa        1620
aaaaaaaaaa aaaaaaaaaa aaaaaaaaaa aaaaaaaaaa aaaaaaaaaa aaaaaaaaaa        1680
aaaaaaaaaa aaaaaaaaaa aaaaaaaaaa aaaaaaaaaa aaaaaaaaaa aaaaaaaaaa        1740
aaaaaaaaaa aaaaaaaaaa aaaaaaaaaa aaaaaaaaaa aaaaaaaaaa aaaaaaaaaa        1800
aaaaaaaaaa aaaaaaaaaa aaaaaaaaaa aaaaaaaaaa aaaaaaaaaa aaaaaaaaaa        1860
aaaaaaaaaa aaaaaaaaaa aaaaaaaaaa aaaaaaaaaa aaaaaaaaaa aaaaaaaaaa        1920
aaaaaaaaaa aaaaaaaaaa aaaaaaaaaa aaaaaaaaaa aaaaaaaaaa aaaaaaaaaa        1980
aaaaaaaaaa aaaaaaaaaa aaaaaaaaaa aaaaaaaaaa aaaaaaaaaa aaaaaaaaaa        2040
aaaaaaaaaa aaaaaaaaaa aaaaaaaaaa aaaaaaaaaa aaaaaaaaaa aaaaaaaaaa        2100
aaaaaaaaaa aaaaaaaaaa aaaaaaaaaa aaaaaaaaaa aaaaaaaaaa aaaaaaaaaa        2160
```

```
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680
aaaaaaaaaa aaaaaaaaaa aaaaaaaaaa aaaaaaaaaa aaaaaaaaaa aaaaaaaaaa 4740
aaaaaaaaaa aaaaaaaaaa aaaaaaaaaa aaaaaaaaaa aaaaaaaaaa aaaaaaaaaa 4800
aaaaaaaaaa aaaaaaaaaa aaaaaaaaaa aaaaaaaaaa aaaaaaaaaa aaaaaaaaaa 4860
aaaaaaaaaa aaaaaaaaaa aaaaaaaaaa aaaaaaaaaa aaaaaaaaaa aaaaaaaaaa 4920
aaaaaaaaaa aaaaaaaaaa aaaaaaaaaa aaaaaaaaaa aaaaaaaaaa aaaaaaaaaa 4980
aaaaaaaaaa aaaaaaaaaa                                            5000
```